(12) United States Patent
Nagano et al.

(10) Patent No.: US 9,156,827 B2
(45) Date of Patent: Oct. 13, 2015

(54) ANTICANCER AGENT

(75) Inventors: Tetsuo Nagano, Tokyo (JP); Takayoshi Okabe, Ibaraki (JP); Hirotatsu Kojima, Tokyo (JP); Nae Saito, Tokyo (JP); Hirofumi Nakano, Tokyo (JP); Masanao Abe, Tokyo (JP); Akiko Tanaka, Tokyo (JP); Teruki Honma, Kanagawa (JP); Shigeyuki Yokoyama, Tokyo (JP); Keiko Tsuganezawa, Kanagawa (JP); Hitomi Yuki, Kanagawa (JP)

(73) Assignees: THE UNIVERSITY OF TOKYO, Tokyo (JP); RIKEN, Saitama (JP)

(*) Notice: Subject to any disclaimer, the term of this patent is extended or adjusted under 35 U.S.C. 154(b) by 85 days.

(21) Appl. No.: 13/643,002

(22) PCT Filed: Apr. 28, 2011

(86) PCT No.: PCT/JP2011/060356
§ 371 (c)(1),
(2), (4) Date: Jan. 7, 2013

(87) PCT Pub. No.: WO2011/136319
PCT Pub. Date: Mar. 11, 2011

(65) Prior Publication Data
US 2013/0102776 A1    Apr. 25, 2013

(30) Foreign Application Priority Data

Apr. 30, 2010  (JP) .................................. 2010-105280
Apr. 30, 2010  (JP) .................................. 2010-105281

(51) Int. Cl.
| | | |
|---|---|---|
| *C07D 405/14* | (2006.01) |
| *A61K 31/36* | (2006.01) |
| *A61K 31/454* | (2006.01) |
| *A61K 31/496* | (2006.01) |
| *A61K 31/5377* | (2006.01) |
| *C07D 405/06* | (2006.01) |
| *C07D 493/04* | (2006.01) |
| *C07D 413/14* | (2006.01) |
| *C07D 417/14* | (2006.01) |
| *C07D 471/04* | (2006.01) |

(52) U.S. Cl.
CPC .............. *C07D 405/14* (2013.01); *A61K 31/36* (2013.01); *A61K 31/454* (2013.01); *A61K 31/496* (2013.01); *A61K 31/5377* (2013.01); *C07D 405/06* (2013.01); *C07D 413/14* (2013.01); *C07D 417/14* (2013.01); *C07D 471/04* (2013.01); *C07D 493/04* (2013.01)

(58) Field of Classification Search
CPC .............................. C07D 405/14; A61K 31/36
See application file for complete search history.

(56) References Cited

U.S. PATENT DOCUMENTS

| | | |
|---|---|---|
| 2008/0125590 A1 | 5/2008 | Lee et al. |
| 2008/0261988 A1 | 10/2008 | Bearss et al. |
| 2009/0042918 A1 | 2/2009 | Kearney et al. |
| 2009/0298820 A1 | 12/2009 | Tsou et al. |
| 2010/0227861 A1 | 9/2010 | Bearss et al. |
| 2011/0281863 A1 | 11/2011 | Bearss et al. |

FOREIGN PATENT DOCUMENTS

| | | |
|---|---|---|
| CA | 2 264 220 A | 2/1998 |
| CA | 2 717 388 A1 | 9/2009 |
| JP | 2001-503736 A | 3/2001 |
| JP | 2007-84494 A | 4/2007 |

(Continued)

OTHER PUBLICATIONS

Nawjin "For better or for worse: the role of Pim oncogenes in tumorigenesis" Nature Reviews Cancer vol. 11 Jan. 2011.*

(Continued)

*Primary Examiner* — David K O Dell
(74) *Attorney, Agent, or Firm* — Greenblum & Bernstein, P.L.C.

(57) ABSTRACT

An anticancer agent comprising a compound represented by the formula (I) [$R^1$ represents hydrogen atom, hydroxyl group, a $C_{1-6}$ alkoxy group and the like; $R^2$ and $R^3$ represents hydrogen atom, a halogen atom, a $C_{1-6}$ alkyl group and the like; $R^4$ represents hydrogen atom, a $C_{1-6}$ alkyl group, a $C_{1-6}$ alkylsulfonyl group and the like; $R^5$ represents hydrogen atom or a substituent; ⋯ represents a single bond or a double bond; $R^6$ and $R^7$ represents hydrogen atom, a $C_{1-6}$ alkyl group and the like; $R^8$ represents hydrogen atom, a $C_{1-6}$ alkyl group and the like; A represents —O—, —S—, or —CH$_2$—; D represents —C= or —N=; X represents methylene group, —O—, or —CO—; Q represents —N= or —C(R$^8$)=; and Y represents a heterocyclic group or amino group], which shows a superior inhibitory activity against pim-1 kinase.

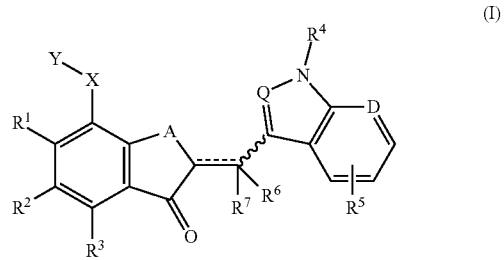

(I)

6 Claims, 2 Drawing Sheets

(56) References Cited

FOREIGN PATENT DOCUMENTS

| | | |
|---|---|---|
| JP | 2008-133274 A | 6/2008 |
| JP | 2009-511499 A | 3/2009 |
| WO | 98/30556 A1 | 7/1998 |
| WO | 00/75139 A2 | 12/2000 |
| WO | 2007/044724 | 4/2007 |
| WO | 2008/080015 A2 | 3/2008 |
| WO | 2008/058126 A2 | 5/2008 |
| WO | 2009/109576 A1 | 9/2009 |
| WO | 2009/155052 A1 | 12/2009 |

OTHER PUBLICATIONS

STN-Chemical database registry #RN 896066-95-8 for 3(2H)-Benzofuranone, 6-hydroxy-2-(1H-indol-3-ylmethylene)-7-(4-morpholinylmethyl)- Entered STN: Jul. 25, 2006.*

Trisha Gura "Cancer Models: Systems for Identifying New Drugs Are Often Faulty" Science Nov. 7, 1997: vol. 278. No. 5340, pp. 1041-1042.*

Simone, Oncology: Introduction, Cecil Textbook of Medicine, 20th Edition, 1996 vol. 1, pp. 1004-1010.*

IBS Products and Services "http://web.archive.org/web/20070529094927/http://www.ibscreen.com/products.shtml" dated May 29, 2007, accessed Aug. 27, 2014.*

Johnson, A. W. Invitation to Organic Chemistry 1999 Jones and Bartlett: Mississauga, Canada, p. 24.*

Johnson, et. al. "Relationships between drug activity in NCI preclinical in vitro and in vivo models and early clinical trials." British Journal of Cancer 2001, 84, 1424-1431.*

Lin "Acute Myeloid Leukemia: Focus on Novel Therapeutic Strategies" Clinical Medicine Insights: Oncology 2012:6 205-217.*

Database PubChem Compound [Online], Database Accession No. CID 1832884, XP002711575, Jul. 13, 2005.

Database PubChem Compound [Online], Database Accession No. CID 1847947, XP002711576, Jul. 13, 2005.

Database PubChem Compound [Online], Database Accession No. CID 1850985, XP002711577, Jul. 13, 2005.

Database PubChem Compound [Online], Database Accession No. CID 1833986, XP002711578, Jul. 13, 2005.

Database PubChem Compound [Online], Database Accession No. CID 1846018, XP002711579, Jul. 13, 2005.

Supplemental European Search Report issued with respect to EP Patent App. No. 11775100.8, dated Sep. 13, 2013.

Cuypers et al., "Murine Leukemia Virus-Induced T-Cell Lymphomagenesis: Integration of Proviruses in a Distinct Chromosomal Region", Cell, vol. 37, pp. 141-150, 1984.

Selton et al., "Proviral activation of the putative oncogene Pim-1 in MuLV induced T-cell lymphomas", The EMBO Journal, vol. 4, No. 7, pp. 1793-1798, 1985.

Bachmann et al., "Molecules in focus: the serine/threonine kinase Pim-1", The International Journal of Biochemistry & Cell Biology, vol. 37, pp. 726-730, 2005.

Shah et al., "Potential roles for the PIM1 kinase in human cancer—A molecular and therapeutic appraisal", European Journal of Cancer, vol. 44, pp. 2144-2151, 2008.

Schoepfer et al., "Structure-Based Design and Synthesis of 2-Benzylidene-benzofuran-3-ones as Flavopiridol Mimics", Journal of Medicinal Chemistry, vol. 45, pp. 1741-1747, 2002.

Lange et al., "Regioselective Aminomethylations of Bicyclic Phenols", Heterocycles, vol. 53, No. 1, pp. 197-204, 2000.

Wahlstrom et al., "Synthesis and purification of aggregation-prone hydrophobic peptides by the incorporation of an Fmoc dipeptide with the peptide bond protected with a modified 2-hydroxy-4-methoxybenzyl (Hmb) group", Tetrahedron Letters, vol. 49, pp. 3921-3924, 2008.

Still et al., "The Structures of the Trihydroxyflavans from the Acid-catalyzed Rearrangement and Dimerization of 3-Carene-2,5-dione", Canadian Journal of Chemistry, vol. 50, pp. 1276-1282, 1972.

Hadj-esfandiari et al., "Synthesis, antibacterial activity, and quantitative structure-activity relationships of new (Z)-2-(nitroimidazolylmethylene)-3(2H)-benzofuranone derivatives" Bioorganic & Medicinal Chemistry Letters, vol. 17, pp. 6354-6363, 2007.

Saran et al., "A Versatile Photocleavable Bifunctional Linker for Facile Synthesis of Substrate—DNA Conjugates for the Selection of Nucleic Acid Catalysts", Bioconjugate Chemistry, vol. 18, pp. 275-279, 2007.

Conway et al., "Synthesis of 1-(Phenylsulfonyl)Indol-3-yl Trifluoromethanesulfonate", Heterocycles, vol. 30, No. 1, pp. 627-633, 1990.

Hanaya et al.,"Synthesis of 2-Amino-2,5,6-trideoxy-5-phenylphosphinyl-L-galactopyranose. The P-in-the-Ring Analogue of L-Fucosamine", Bulletin of Chemical Society of Japan, vol. 65, No. 11, pp. 2922-2925, 1992.

STN File Accession No. 0019769179, CAS Registry No. 1206448-72-7, Apr. 6, 2011.

STN File Accession No. 0066467343, CAS Registry No. 951997-60-7, Apr. 11, 2011.

STN File Accession No. 0067285417, CAS Registry No. 929961-73-9, Apr. 11, 2011.

STN File Accession No. 2083467064, CAS Registry No. 896838-55-4, May 11, 2010.

STN File Accession No. 2083466010, CAS Registry No. 929440-31-3, May 11, 2010.

STN File Accession No. 2083464898, CAS Registry No. 900269-11-6, May 11, 2010.

STN File Accession No. 2083463379, CAS Registry No. 929512-63-0, May 11, 2010.

International Preliminary Report on Patentability for PCT/JP2011/060356, mailed Nov. 15, 2012, along with an English language translation.

International Search Report for PCT/JP2011/060356, mailed Jul. 12, 2011.

* cited by examiner

ANTICANCER AGENT

TECHNICAL FIELD

The present invention relates to an anticancer agent comprising an indole compound or an indazole compound, or a physiologically acceptable salt thereof that has a selective inhibitory action against pim-1 kinase as an active ingredient.

BACKGROUND ART

Pim-1 kinase, which is overexpressed in certain kinds of leukemia and prostate cancer, is a serine/threonine kinase that promotes or enhances canceration of cells, exacerbation of cancer cells, resistance to an anticancer agent, and the like by phosphorylating proteins involved in apoptosis or cell cycle control (Cell, 37, pp. 141-150, 1984; EMBO J., 4, pp. 1793-1798, 1985; The International Journal of Biochemistry & Cell Biology, 37, pp. 726-730, 2005; European Journal of Cancer, 44, pp. 2144-2151, 2008). Because of the aforementioned characteristic actions of pim-1 kinase, usefulness of a substance having an inhibitory action against pim-1 kinase as an anticancer agent or the like is expected (refer to Japanese Patent Unexamined Publication (KOKAI) No. 2007-84494, Japanese Patent Unexamined Publication (KOHYO) No. 2009-511499 and the like).

From the aforementioned point of view, several pim-1 kinase inhibitors useful as an anticancer agent have been proposed. Among them, an example of compounds containing a bicyclic nitrogen-containing heteroaryl ring in a fundamental structure includes the 1,2-imidazo[b]pyridazine compounds disclosed in International Patent Publication WO2008/58126. SGI-1776, a typical compound among those disclosed in the aforementioned publication, has been under a clinical trial (phase I) for use as an anticancer agent. Although developments of compounds having the inhibitory activity against pim-1 kinase have been actively conducted as mentioned above, no medicament has yet been launched into the market, and in view of the circumstances, developments of novel compounds having superior activity have still been desired.

As compounds having the indole or 7-azaindole structure, the compounds disclosed in International Patent Publications WO2009/155052 are known. However, as for these compounds, inhibitory action against pim-1 kinase has not been reported. Although this publication discloses compounds having a benzofuran-3-one ring, and also discloses several compounds having hydroxyl group at the 7-position of the benzofuran-3-one ring, it does not disclose any compound having a substituent other than hydroxyl group at the 7-position of the benzofuran-3-one ring. Compounds having the benzofuran-3-one ring with a substituent at the 7-position are disclosed in Journal of Medicinal Chemistry, 45, pp. 1741-1'747, 2002. However, these compounds do not contain a bicyclic nitrogen-containing heteroaryl ring in the fundamental structure.

PRIOR ART REFERENCES

Patent Documents

Patent document 1: International Patent Publication WO2008/58126
Patent document 2: International Patent Publication WO2009/155052

Non-Patent Documents

Non-patent document 1: Cell, 37, pp. 141-150, 1984
Non-patent document 2: EMBO J., 4, pp. 1793-1798, 1985
Non-patent document 3: The International Journal of Biochemistry & Cell Biology, 37, pp. 726-730, 2005
Non-patent document 4: European Journal of Cancer, 44, pp. 2144-2151, 2008
Non-patent document 5: Journal of Medicinal Chemistry, 45, pp. 1741-1747, 2002

SUMMARY OF THE INVENTION

Object to be Achieved by the Invention

An object of the present invention is to provide an anticancer agent comprising a compound or a physiologically acceptable salt thereof having superior inhibitory action against pim-1 kinase as an active ingredient.

Means for Achieving the Object

The inventors of the present invention conducted various researches to achieve the aforementioned object. As a result, they found that the compounds represented by the following general formula (I), which contain an indole ring or an indazole ring in the fundamental structure, had a potent and selective inhibitory action against pim-1 kinase, and that the aforementioned compounds were useful as an active ingredient of an anticancer agent. The present invention was accomplished on the basis of the aforementioned findings.

The present invention thus provided an anticancer agent comprising a compound represented by the following general formula (I):

[Formula 1]

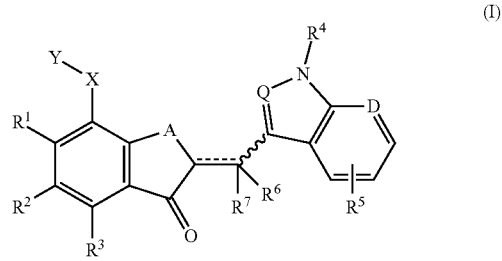

(I)

[wherein, $R^1$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^2$ represents hydrogen atom, a halogen atom, a $C_{1-6}$ alkyl group, a $C_{1-6}$ alkoxy group, an aryl group, amino group, hydroxyl group, or a heterocyclic group, wherein $R^1$ and $R^2$ may bind together to form a $C_{1-6}$ alkylenedioxy group; $R^8$ represents hydrogen atom, a halogen atom, a $C_{1-6}$ alkyl group, a $C_{1-6}$ alkoxy group, an aryl group, amino group, hydroxyl group, or a heterocyclic group; $R^4$ represents hydrogen atom, a $C_{1-6}$ alkyl group, a $C_{1-6}$ alkylsulfonyl group, or an arylsulfonyl group; $R^5$ represents hydrogen atom, or one to four substituents substituting on the benzene ring or the pyridine ring; ⋯ represents a single bond or a double bond; $R^8$ and $R^7$ independently represent hydrogen atom, a $C_{1-6}$ alkyl group, or a halogen-substituted $C_{1-6}$ alkyl group, wherein when ⋯ represents a double bond, $R^7$ does not exist, and in this instance, the wavy line represents a bond in the Z-configuration or the E-configuration, or a mixture thereof with reference to the double bond; A represents —O—, —S—, or —CH$_2$—; D represents —C= or —N=; Q represents —N= or —C(R⁸)= (R⁸ represents hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group); X represents a single bond, or a $C_{1-6}$ alkylene group, a $C_{2-6}$ alkenylene group, or a $C_{2-6}$ alkynylene group (these alkylene group, alkenylene group, and alkynylene group may be substituted with hydroxyl group), or —O— or —CO—; and Y represents a heterocyclic group or amino group (these groups may have one to three substituents)], or a physiologically acceptable salt thereof as an active ingredient.

According to a preferred embodiment of the aforementioned invention, there is provided the anticancer agent comprising a compound represented by the following general formula (IA):

[Formula 2]

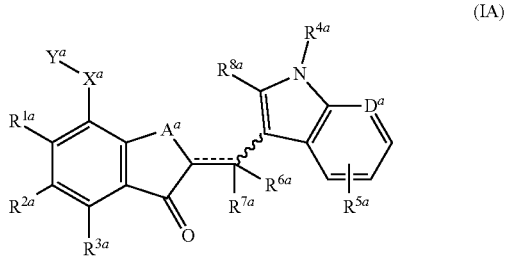

(IA)

[wherein, $R^{1a}$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{2a}$ represents hydrogen atom, a halogen atom, a $C_{1-6}$ alkyl group, a $C_{1-6}$ alkoxy group, an aryl group, amino group, hydroxyl group, or a heterocyclic group, wherein $R^{1a}$ and $R^{2a}$ may bind together to form a $C_{1-6}$ alkylenedioxy group; $R^{3a}$ represents hydrogen atom, a halogen atom, a $C_{1-6}$ alkyl group, a $C_{1-6}$ alkoxy group, an aryl group, amino group, hydroxyl group, or a heterocyclic group; $R^{4a}$ represents hydrogen atom, a $C_{1-6}$ alkyl group, a $C_{1-6}$ alkylsulfonyl group, or an arylsulfonyl group; $R^{5a}$ represents hydrogen atom, or one to four substituents substituting on the benzene ring or the pyridine ring; ⋯ represents a single bond or a double bond; $R^{6a}$ and $R^{7a}$ independently represent hydrogen atom, a $C_{1-6}$ alkyl group, or a halogen-substituted $C_{1-6}$ alkyl group, wherein when ⋯ represents a double bond, $R^{7a}$ does not exist, and in this instance, the wavy line represents a bond in the Z-configuration or the E-configuration, or a mixture thereof with reference to the double bond; $R^{8a}$ represents hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group; $A^a$ represents —O—, —S—, or —CH₂—; $D^a$ represents —C= or —N=; $X^a$ represents methylene group (this methylene group may be substituted with one or two alkyl groups or hydroxyl groups), —O—, or —CO—; and $Y^a$ represents a heterocyclic group or amino group (these groups may have one to three substituents)], or a physiologically acceptable salt thereof as an active ingredient.

According to a preferred embodiment of the aforementioned invention, there is provided the anticancer agent comprising the aforementioned compound or a physiologically acceptable salt thereof, wherein $R^{1a}$ is hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{2a}$ is hydrogen atom, a halogen atom, a $C_{1-6}$ alkyl group, a $C_{1-6}$ alkoxy group, an aryl group, amino group, hydroxyl group, or a heterocyclic group, wherein $R^{1a}$ and $R^{2a}$ may bind together to form a $C_{1-6}$ alkylenedioxy group; $R^{3a}$ is hydrogen atom, a halogen atom, a $C_{1-6}$ alkyl group, a $C_{1-6}$ alkoxy group, an aryl group, amino group, hydroxyl group, or a heterocyclic group; $R^{4a}$ is hydrogen atom, a $C_{1-6}$ alkyl group, an alkylsulfonyl group, or an arylsulfonyl group; $R^{5a}$ is hydrogen atom, or one to four substituents substituting on the benzene ring or the pyridine ring (the substituent(s) is (are) selected from the group consisting of a halogen atom, a $C_{1-6}$ alkyl group, a $C_{2-6}$ alkenyl group, a $C_{2-6}$ alkynyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group); ⋯ is a single bond or a double bond; $R^{6a}$ and $R^{7a}$ are independently hydrogen atom, a $C_{1-6}$ alkyl group, or a halogen-substituted $C_{1-6}$ alkyl group, wherein when ⋯ represents a double bond, $R^{7a}$ does not exist, and in this instance, the wavy line represents a bond in the Z-configuration or the E-configuration, or a mixture thereof with reference to the double bond; $R^{8a}$ is hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group; $A^a$ is —S—, or —CH₂—; $D^a$ is —C= or —N=; $X^a$ is methylene group (this methylene group may be substituted with one or two $C_{1-6}$ alkyl groups or hydroxyl groups), —O—, or —CO—; and $Y^a$ is a 5- to 7-membered saturated heterocyclic group (the ring of this heterocyclic group contains one or two heteroatoms) or amino group (the heterocyclic group or amino group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group) as an active ingredient.

According to further preferred embodiments of the present invention, there are provided the aforementioned anticancer agent, wherein $R^{1a}$ is hydrogen atom, hydroxyl group, or a $C_{1-6}$ alkoxy group; the aforementioned anticancer agent, wherein $R^{2a}$ is hydrogen atom, a halogen atom, a $C_{1-6}$ alkoxy group, or an aryl group; the aforementioned anticancer agent, wherein $R^{3a}$ is hydrogen atom; the aforementioned anticancer agent, wherein $R^{4a}$ is hydrogen atom, an alkylsulfonyl group, or an arylsulfonyl group; the aforementioned anticancer agent, wherein $R^{5a}$ is hydrogen atom, or one or two substituents substituting on the benzene ring or the pyridine ring (the substituent(s) is (are) selected from the group consisting of a halogen atom, a $C_{1-6}$ alkyl group, a $C_{2-6}$ alkenyl group, a $C_{2-6}$ alkynyl group, an amino-substituted $C_{1-6}$ alkyl group, hydroxyl group, a $C_{1-6}$ alkoxy group, a $C_{1-6}$ alkoxycarbonyl group, amino group, nitro group, an aralkyloxy group, and a heterocyclic group-substituted $C_{1-6}$ alkoxy group); the aforementioned anticancer agent, wherein $R^{6a}$ and $R^{7a}$ are hydrogen atoms; the aforementioned anticancer agent, wherein $R^{8a}$ is hydrogen atom or a $C_{1-6}$ alkyl group; the aforementioned anticancer agent, wherein $D^a$ is —C=; the aforementioned anticancer agent, wherein $X^a$ is methylene group; and the aforementioned anticancer agent, wherein $Y^a$ is 1-piperazinyl group, morpholino group, thiomorpholino group, 1-piperidinyl group, 4-piperidinyl group, 4-tetrahydropyranyl group, 1-homopiperazinyl group, 1-pyrrolidinyl group, hexamethyleneimin-1-yl group, or amino group (these groups may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group).

According to more preferred embodiments of the aforementioned invention, there are provided the aforementioned anticancer agent, wherein $R^{1a}$ is hydroxyl group or a $C_{1-6}$ alkoxy group, $R^{2a}$ and $R^{3a}$ are hydrogen atoms, $R^{4a}$ is hydrogen atom, an alkylsulfonyl group, or an arylsulfonyl group, $R^{5a}$ is hydrogen atom, or one halogen atom substituting on the benzene ring, ⋯ is a double bond, $R^{6a}$ is hydrogen atom, $R^{8a}$ is hydrogen atom, $D^a$ is —C=, $X^a$ is methylene group, and $Y^a$ is 1-piperazinyl group (this piperazinyl group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group); and the aforementioned anticancer agent, wherein $R^{1a}$ is hydroxyl group or a $C_{1-6}$ alkoxy group, $R^{2a}$ and $R^{1a}$ are hydrogen atoms, $R^{4a}$ is hydrogen atom, $R^{5a}$ is hydrogen atom, or one halogen atom substituting on the pyridine ring, ⋯ is a double bond, $R^{6a}$ is hydrogen atom, $R^{8a}$ is hydrogen atom, $D^a$ is —N=, $X^a$ is methylene group (this methylene group may be substituted with one or two $C_{1-6}$ alkyl groups), and $Y^a$ is 1-piperazinyl group or morpholinyl group (the piperazinyl group or morpholinyl group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group).

According to another preferred embodiment of the aforementioned invention, there is provided the aforementioned anticancer agent comprising a compound represented by the following general formula (IB):

[Formula 3]

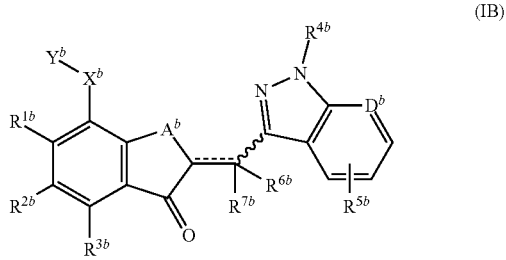

(IB)

[wherein, $R^{1b}$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{2b}$ represents hydrogen atom, a halogen atom, a $C_{1-6}$ alkyl group, a $C_{1-6}$ alkoxy group, an aryl group, amino group, hydroxyl group, or a heterocyclic group, wherein $R^{1b}$ and $R^{2b}$ may bind together to form a $C_{1-6}$ alkylenedioxy group; $R^{8b}$ represents hydrogen atom, a halogen atom, a $C_{1-6}$ alkyl group, a $C_{1-6}$ alkoxy group, an aryl group, amino group, hydroxyl group, or a heterocyclic group; $R^{4b}$ represents hydrogen atom, a $C_{1-6}$ alkyl group, or sulfonyl group; $R^{5b}$ represents hydrogen atom, or one to four substituents substituting on the benzene ring or the pyridine ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, sulfonyl group, or a heterocyclic group); ⋯ represents a single bond or a double bond; $R^{6b}$ and $R^{7b}$ independently represent hydrogen atom, a $C_{1-6}$ alkyl group, or a halogen-substituted $C_{1-6}$ alkyl group, wherein when ⋯ represents a double bond, $R^{7b}$ does not exist; $A^b$ represents —O—, —S—, or —CH$_2$—; $D^b$ represents —C= or —N=; $X^b$ represents a single bond, or a $C_{1-6}$ alkylene group, a $C_{2-6}$ alkenylene group, or a $C_{2-6}$ alkynylene group (these alkylene group, alkenylene group, and alkynylene group may be substituted with hydroxyl group), or —O— or —CO—; and $Y^b$ represents a heterocyclic group or amino group (these groups may have one or two or more substituents)], or a physiologically acceptable salt thereof as an active ingredient.

According to a preferred embodiment of the aforementioned invention, there is provided the aforementioned anticancer agent comprising the compound or a physiologically acceptable salt thereof as an active ingredient, wherein $R^{1b}$ is hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{2b}$ is hydrogen atom, a halogen atom, a $C_{1-6}$ alkoxy group, wherein $R^{1b}$ and $R^{2b}$ may bind together to form a $C_{1-6}$ alkylenedioxy group; $R^{3b}$ is hydrogen atom, a halogen atom, or hydroxyl group; $R^{4b}$ is hydrogen atom, a $C_{1-6}$ alkyl group, or sulfonyl group; $R^{5b}$ is hydrogen atom, or one to three substituents substituting on the benzene ring or the pyridine ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, and a halogen-substituted $C_{1-6}$ alkoxy group); ⋯ is a single bond or a double bond; $R^{6b}$ and $R^{7b}$ are hydrogen atoms, wherein when ⋯ represents a double bond, $R^{7b}$ does not exist; $A^b$ is —O—, —S—, or —CH$_2$—; $D^b$ is —C= or —N=; $X^b$ is methylene group (this methylene group may be substituted with a $C_{1-6}$ alkyl group or hydroxyl group), —O—, or —CO—; and $Y^b$ is a 5- to 7-membered saturated heterocyclic group containing one to three ring-constituting heteroatoms (for example, 1-piperazinyl group, morpholino group, 4-piperidinyl group, 4-tetrahydropyranyl group, 1-homopiperazinyl group, or 1-pyrrolidinyl group), or amino group (these groups may have one or two or more substituents selected from the group consisting of a $C_{1-6}$ alkyl group, hydroxyl group, amino group, an alkylsulfonyl group, and oxo group) as an active ingredient.

According to further preferred embodiments of the aforementioned invention, there are provided the aforementioned compound or a salt thereof, wherein $R^{3b}$ is hydrogen atom; the aforementioned anticancer agent comprising the compound or a physiologically acceptable salt thereof, wherein $R^{4b}$ is hydrogen atom as an active ingredient; the aforementioned compound or a salt thereof, wherein ⋯ is a double bond; the aforementioned anticancer agent comprising the compound or a physiologically acceptable salt thereof, wherein $A^b$ is —O— as an active ingredient; the aforementioned anticancer agent comprising the compound or a physiologically acceptable salt thereof, wherein $D^b$ is —C= as an active ingredient; and the aforementioned anticancer agent comprising the compound or a physiologically acceptable salt thereof, wherein $R^{3b}$ is hydrogen atom, $R^{4b}$ is hydrogen atom, ⸺ is a double bond, $A^b$ is —O—, $D^b$ is —C═, and $Y^b$ is 1-piperazinyl group, morpholino group, or 4-piperidinyl group (these groups may have one or two or more substituents selected from the group consisting of a $C_{1-6}$ alkyl group, hydroxyl group, and oxo group) as an active ingredient.

According to particularly preferred embodiments, there are provided the aforementioned anticancer agent comprising the compound or a physiologically acceptable salt thereof, wherein $R^{1b}$ is hydroxyl group or a $C_{1-6}$ alkoxy group as an active ingredient; the aforementioned anticancer agent comprising the compound or a physiologically acceptable salt thereof, wherein $R^{2b}$ is hydrogen atom or a halogen atom as an active ingredient; the aforementioned anticancer agent comprising the compound or a physiologically acceptable salt thereof, wherein $X^b$ is methylene group as an active ingredient; and the aforementioned anticancer agent comprising the compound or a physiologically acceptable salt thereof, wherein $R^{5b}$ is hydrogen atom, one halogen atom, one $C_{1-6}$ alkoxy group, or one fluoro-substituted $C_{1-6}$ alkoxy group as an active ingredient.

From another aspect of the present invention, there is provided a pim-1 kinase inhibitor comprising a compound represented by the aforementioned general formula (I) or a physiologically acceptable salt thereof.

The present invention also provides the aforementioned anticancer agent, which is for suppressing canceration of a cell and/or malignant alteration of a cancer cell; and the aforementioned anticancer agent, which is for suppressing acquisition of resistance against an anticancer agent by a cancer cell. The present invention also provides use of a compound represented by the aforementioned general formula (I) or a physiologically acceptable salt thereof for manufacture of the aforementioned anticancer agent.

From further aspects of the present invention, there are provided a method for inhibiting pim-1 kinase, which comprises contacting a compound represented by the aforementioned general formula (I) or a physiologically acceptable salt thereof with pim-1 kinase; and a method for inhibiting pim-1 kinase of a mammal including human in vivo, which comprises administering an effective amount of a compound represented by the aforementioned general formula (I) or a physiologically acceptable salt thereof to a mammal including human.

The present invention also provides a method for therapeutic treatment of cancer, which comprises the step of administering a therapeutically effective amount of a compound represented by the aforementioned general formula (I) or a physiologically acceptable salt thereof to a mammal including human; a method for suppressing canceration of a cell in vivo, which comprises the step of administering an effective amount of a compound represented by the aforementioned general formula (I) or a physiologically acceptable salt thereof to a mammal including human; a method for suppressing malignant alteration of a cancer cell in vivo, which comprises the step of administering an effective amount of a compound represented by the aforementioned general formula (I) or a physiologically acceptable salt thereof to a mammal including human; a method for prophylactic treatment of cancer, which comprises the step of administering a prophylactically effective amount of a compound represented by the aforementioned general formula (I) or a physiologically acceptable salt thereof to a mammal including human; and a method for suppressing acquisition of resistance against an anticancer agent by a cancer cell in vivo, which comprises the step of administering an effective amount of a compound represented by the aforementioned general formula (I) or a physiologically acceptable salt thereof to a mammal including human.

From still another aspect of the present invention there is provided the compound represented by the following general formula (IB):

[Formula 4]

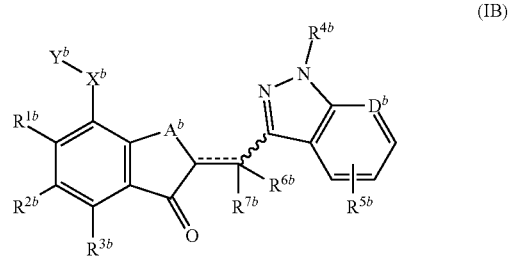

(IB)

[wherein, $R^{1b}$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{2b}$ represents hydrogen atom, a halogen atom, a $C_{1-6}$ alkyl group, a $C_{1-6}$ alkoxy group, an aryl group, amino group, hydroxyl group, or a heterocyclic group, wherein $R^{1b}$ and $R^{2b}$ may bind together to form a $C_{1-6}$ alkylenedioxy group; $R^{3b}$ represents hydrogen atom, a halogen atom, a $C_{1-6}$ alkyl group, a $C_{1-6}$ alkoxy group, an aryl group, amino group, hydroxyl group, or a heterocyclic group; $R^{4b}$ represents hydrogen atom, a $C_{1-6}$ alkyl group, or sulfonyl group; $R^{5b}$ represents hydrogen atom, or one to four substituents substituting on the benzene ring or the pyridine ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, and a heterocyclic group); ⸺ represents a single bond or a double bond; $R^{6b}$ and $R^{7b}$ independently represent hydrogen atom, a $C_{1-6}$ alkyl group, or a halogen-substituted $C_{1-6}$ alkyl group, wherein when ⸺ represents a double bond, $R^{7b}$ does not exist; $A^b$ represents —O—, —S—, or —CH$_2$—; $D^b$ represents —C═ or —N═; $X^b$ represents methylene group (this methylene group may be substituted with a $C_{1-6}$ alkyl group or hydroxyl group), —O—, or —CO—; and $Y^b$ represents a heterocyclic group or amino group (these groups may have one or two or more substituents)], or a salt thereof.

From still further aspect of the present invention, there is provided a compound represented by the following general formula (II):

[Formula 5]

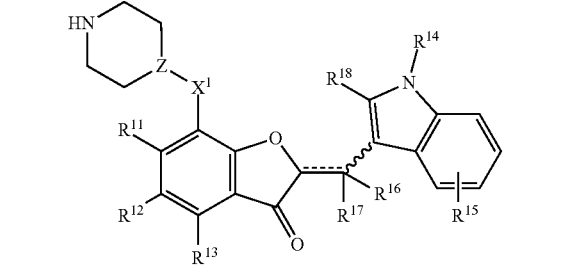

(II)

[wherein, $R^{11}$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{12}$ represents hydrogen atom, a halogen atom, a $C_{1-6}$ alkyl group, a $C_{1-6}$ alkoxy group, an aryl group, amino group, hydroxyl group, or a heterocyclic group, wherein $R^{11}$ and $R^{12}$ may bind together to form a $C_{1-6}$ alkylenedioxy group; $R^{13}$ represents hydrogen atom, a halogen atom, a $C_{1-6}$ alkyl group, a $C_{1-6}$ alkoxy group, an aryl group, amino group, hydroxyl group, or a heterocyclic group; $R^{14}$ represents hydrogen atom, a $C_{1-6}$ alkyl group, an alkylsulfonyl group, or an arylsulfonyl group; $R^{15}$ represents hydrogen atom, or one to four substituents substituting on the benzene ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group); ⸺ represents a single bond or a double bond; $R^{16}$ and $R^{17}$ independently represent hydrogen atom, a $C_{1-6}$ alkyl group, or a halogen-substituted $C_{1-6}$ alkyl group, wherein when ⸺ represents a double bond, $R^{17}$ does not exist, and in this instance, the wavy line represents a bond in the Z-configuration or the E-configuration, or a mixture thereof with reference to the double bond; $R^{18}$ represents hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group; $X^1$ represents methylene group (this methylene group may be substituted with one or two $C_{1-6}$ alkyl groups or hydroxyl groups), —O—, or —CO—; and Z represents nitrogen atom or CH], or a salt thereof.

As a preferred embodiment of the compound represented by the aforementioned general formula (II), there is provided the aforementioned compound or a salt thereof, wherein $R^{11}$ is hydroxyl group or a $C_{1-6}$ alkoxy group, $R^{12}$ is hydrogen atom, a halogen atom, a $C_{1-6}$ alkyl group, a $C_{1-6}$ alkoxy group, or an aryl group, $R^{13}$ is hydrogen atom, $R^{14}$ is hydrogen atom, $R^{15}$ is hydrogen atom, or one to four substituents substituting on the benzene ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group), ⸺ is a double bond, $R^{16}$ is hydrogen atom, $R^{18}$ is hydrogen atom, $X^1$ is methylene group (this methylene group may be substituted with one or two $C_{1-6}$ alkyl groups or hydroxyl groups), and Z is nitrogen atom or CH.

From still furthermore aspect of the present invention, there is provided a compound represented by the following general formula (III):

[Formula 6]

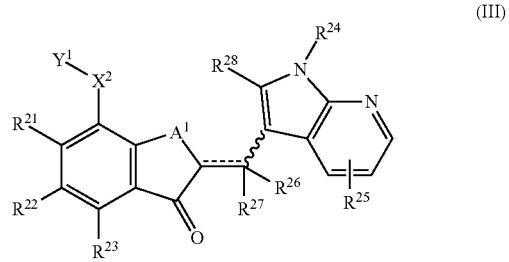

(III)

[wherein $R^{21}$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group; $R^{22}$ represents hydrogen atom, a halogen atom, a $C_{1-6}$ alkyl group, a $C_{1-6}$ alkoxy group, an aryl group, amino group, hydroxyl group, or a heterocyclic group, wherein $R^{21}$ and $R^{22}$ may bind together to form a $C_{1-6}$ alkylenedioxy group; $R^{23}$ represents hydrogen atom, a halogen atom, a $C_{1-6}$ alkyl group, a $C_{1-6}$ alkoxy group, an aryl group, amino group, hydroxyl group, or a heterocyclic group; $R^{24}$ represents hydrogen atom, a $C_{1-6}$ alkyl group, an alkylsulfonyl group, or an arylsulfonyl group; $R^{25}$ represents hydrogen atom, or one to four substituents substituting on the benzene ring or the pyridine ring (the substituent(s) is (are) selected from the group consisting of a halogen atom, a $C_{1-6}$ alkyl group, a $C_{2-6}$ alkenyl group, a $C_{2-6}$ alkynyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group); ⸺ represents a single bond or a double bond; $R^{26}$ and $R^{27}$ independently represent hydrogen atom, a $C_{1-6}$ alkyl group, or a halogen-substituted $C_{1-6}$ alkyl group, wherein when ⸺ represents a double bond, $R^{27}$ does not exist, and in this instance, the wavy line represents a bond in the Z-configuration or the E-configuration, or a mixture thereof with reference to the double bond; $R^{28}$ represents hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group; $A^1$ represents —O—, —S—, or —CH$_2$—; $X^2$ represents methylene group (this methylene group may be substituted with one or two $C_{1-6}$ alkyl groups or hydroxyl groups), —O—, or —CO—; and $Y^1$ represents a 5- to 7-membered saturated heterocyclic group (the ring of this heterocyclic group contains one or two heteroatoms) or amino group (the heterocyclic group or amino group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group)], or a salt thereof.

As a preferred embodiment of the compound represented by the aforementioned general formula (III), there is provided the aforementioned compound or a salt thereof, wherein $R^{21}$ is hydroxyl group or a $C_{1-6}$ alkoxy group, $R^{22}$ is hydrogen atom, a halogen atom, a $C_{1-6}$ alkyl group, a $C_{1-6}$ alkoxy group, or an aryl group, $R^{23}$ is hydrogen atom, $R^{24}$ is hydrogen atom, $R^{25}$ is hydrogen atom or one to four substituents substituting on the benzene ring (the substituent(s) is (are) selected from the group consisting of a halogen atom, a $C_{1-6}$ Alkyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group), ⋯ is a double bond, $R^{26}$ is hydrogen atom, $R^{25}$ is hydrogen atom, $X^2$ is methylene group (this methylene group may be substituted with one or two $C_{1-6}$ alkyl groups or hydroxyl groups), and $Y^1$ is 1-piperazinyl group, morpholino group, thiomorpholino group, 1-piperidinyl group, 4-piperidinyl group, 4-tetrahydropyranyl group, 1-homopiperazinyl group, 1-pyrrolidinyl group, hexamethyleneimin-1-yl group, or amino group (these groups may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group).

The compounds represented by the aforementioned general formula (IB), (II) or (III) and salts thereof have has a selective inhibitory action against pim-1 kinase, and are useful as an active ingredient of anticancer agent and the like Therefore, the present invention provides a pim-1 kinase inhibitor comprising a compound represented by the aforementioned general formula (IB), (II) or (III), or a physiologically acceptable salt thereof.

The present invention further provides a medicament containing a compound represented by the general formula (IB), (II), or (III), or a physiologically acceptable salt thereof, and as preferred embodiments thereof, there are provided the aforementioned medicament, which is an anticancer agent; the aforementioned medicament, which is for suppressing canceration of a cell and/or malignant alteration of a cancer cell; and the aforementioned medicament, which is for suppressing acquisition of resistance against an anticancer agent by a cancer cell. The present invention also provides use of a compound represented by the general formula (IB), (II), or (III), or a physiologically acceptable salt thereof for manufacture of the aforementioned medicament, preferably the aforementioned anticancer agent.

From still other aspects of the present invention, there are provided a method for inhibiting pim-1 kinase, which comprises contacting a compound represented by the aforementioned general formula (IB), (II), or (III), or a physiologically acceptable salt thereof with pim-1 kinase; and a method for inhibiting pim-1 kinase in a mammal including human in vivo, which comprises administering an effective amount of a compound represented by the aforementioned general formula (IB), (II), or (III), or a physiologically acceptable salt thereof to a mammal including human.

The present invention also provides a method for therapeutic treatment of cancer, which comprises the step of administering a therapeutically effective amount of a compound represented by the aforementioned general formula (IB), (II), or (III), or a physiologically acceptable salt thereof to a mammal including human; a method for suppressing canceration of a cell in vivo, which comprises the step of administering an effective amount of a compound represented by the aforementioned general formula (IB), (II), or (III), or a physiologically acceptable salt thereof to a mammal including human; a method for suppressing malignant alteration of a cancer cell in vivo, which comprises the step of administering an effective amount of a compound represented by the aforementioned general formula (IB), (II), or (III), or a physiologically acceptable salt thereof to a mammal including human; a method for prophylactic treatment of cancer, which comprises the step of administering a prophylactically effective amount of a compound represented by the aforementioned general formula (IB), (II), or (III), or a physiologically acceptable salt thereof to a mammal including human; and a method for suppressing acquisition of resistance against an anticancer agent by a cancer cell in vivo, which comprises the step of administering an effective amount of a compound represented by the aforementioned general formula (IB), (II), or (III), or a physiologically acceptable salt thereof to a mammal including human.

Effect of the Invention

The anticancer agent of the present invention comprising a compound represented by the general formula (I), or a physiologically acceptable salt thereof as an active ingredient has a superior inhibitory action against pim-1 kinase which promotes or enhances canceration of a cell, exacerbation of a cancer cell, resistance against an anticancer agent, and the like, and has a selective inhibitory action against pim-1 kinase. Therefore the agent is useful as an anticancer agent having strong selective toxicity against a cancer cell, and less side reactions.

Moreover, the compounds represented by the general formula (IB), (II), or formula (III) and salts thereof have a superior inhibitory action against pim-1 kinase and have a selective inhibitory action against pim-1 kinase. Therefore the compounds are useful as an active ingredient of a medicament such as an anticancer agent.

MODES FOR CARRYING OUT THE INVENTION

Figure 1:
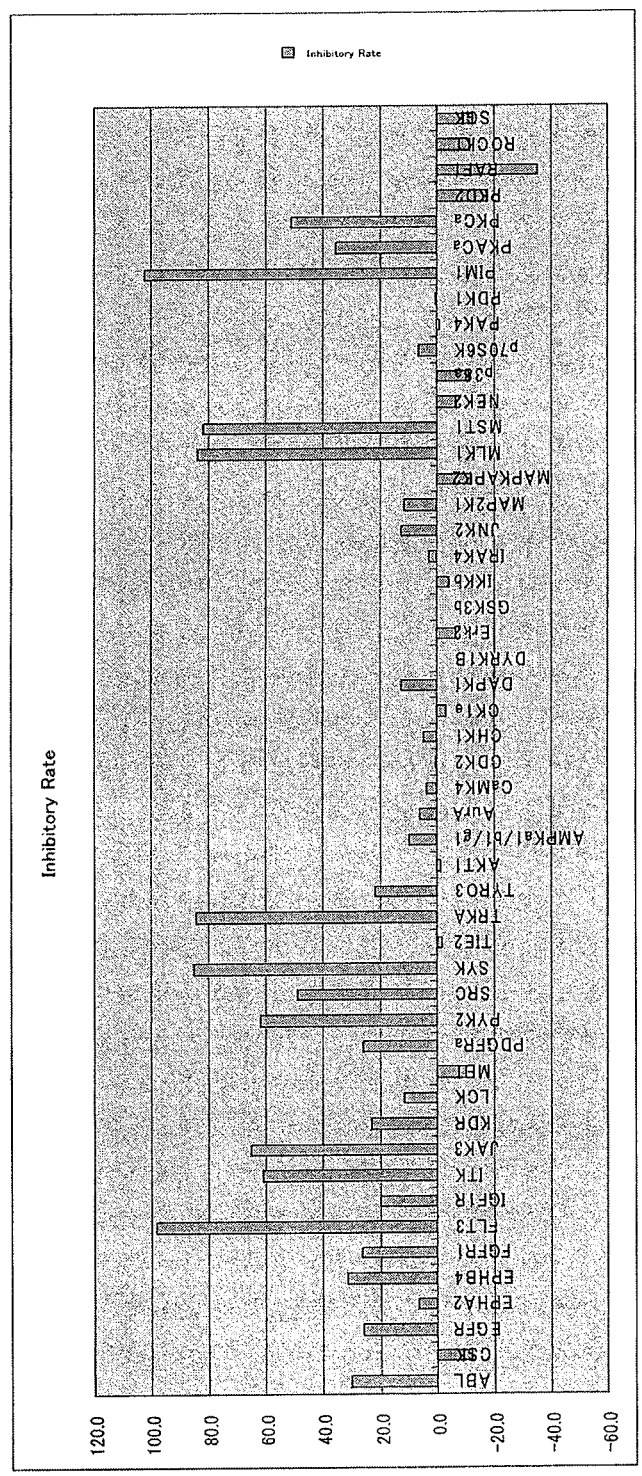
FIG. 1 This figure depicts results of study on inhibitory activity of Compound A42 (concentration of compound: 2 μM) against 50 kinds of kinases including pim-1 kinase.

In the specification, an alkyl group or an alkyl moiety of a substituent having the alkyl moiety (for example, alkoxy group and the like) may be a linear alkyl, a branched alkyl or a cyclic alkyl, or an alkyl consisting of a combination of the foregoing alkyls. The $C_{1-6}$ alkyl group means an alkyl group having 1 to 6 carbon atoms, and the same shall apply to the other substituents. Examples of the $C_{1-6}$ alkyl group include, for example, methyl group, ethyl group, n-propyl group, isopropyl group, cyclopropyl group, n-butyl group, sec-butyl group, tert-butyl group, isobutyl group, cyclopropylmethyl group, n-pentyl group, n-hexyl group, cyclohexyl group and the like, but are not limited to these examples.

Examples of the halogen-substituted $C_{1-6}$ alkyl group include, for example, a $C_{1-6}$ alkyl group substituted with one or two or more halogen atoms such as fluorine atom and chlorine atom, and when the group has two or more halogen atoms, they may be the same or different. The halogen-substituted $C_{1-6}$ alkyl group may be a perhalogenated alkyl group, for example, trifluoromethyl group, pentafluoroethyl group, or the like. As the halogen-substituted $C_{1-6}$ alkyl group, trifluoromethyl group is preferred. As the halogen-substituted $C_{1-6}$ alkoxy group, trifluoromethoxy group is preferred.

In the specification, an aryl group or an aryl moiety of a substituent having the aryl moiety (for example, aryl-substituted alkoxy group and the like) may be a monocyclic or a condensed polycyclic aromatic hydrocarbon group. As the aryl group, for example, phenyl group, naphthyl group, and the like can be used, but the group is not limited to these examples. The aryl group or the aryl moiety may contain one or two or more ring-constituting heteroatoms such as nitrogen atom, oxygen atom and sulfur atom. For example, the aryl group may be pyridyl group containing one ring-constituting nitrogen atom. The aryl group or the aryl moiety may have one or two or more substituents selected from, for example, a halogen atom, a $C_{1-6}$ alkyl group, a $C_{2-6}$ alkenyl group, a $C_{2-6}$ alkynyl group, a $C_{1-6}$ alkoxy group, a $C_{1-6}$ alkoxycarbonyl group, carboxyl group, amino group, carbamoyl group, hydroxyl group, an aralkyl group, an aralkyloxy group and the like, on the ring.

In the specification, the halogen atom includes fluorine atom, chlorine atom, bromine atom, and iodine atom. Further, in the specification, the amino group may have one or two substituents, such as a $C_{1-6}$ alkyl group, an amino-substituted $C_{1-6}$ alkyl group, and an acyl group. When it has two substituents, they may be the same or different. The heterocyclic group means a non-aromatic cyclic group containing one or two or more ring-constituting heteroatoms such as nitrogen atom, oxygen atom and sulfur atom, and for example, a heterocyclic group having a 3- to 8-membered ring can be used. The ring may contain one or two unsaturated bonds. Examples include, for example, pyrrolidinyl group, piperazinyl group, morpholinyl group, dihydropyranyl group, tetrahydropyranyl group, hexamethyleneimin-1-yl group and the like. The heterocyclic group may have, for example, one or four or more substituents selected from a halogen atom, a $C_{1-12}$ alkyl group, an amino-substituted $C_{1-12}$ alkyl group, a $C_{1-6}$ alkoxy-substituted $C_{1-6}$ alkyl group, a $C_{2-12}$ alkenyl group, a $C_{2-12}$ alkynyl group, a $C_{1-12}$ alkoxy group, a $C_{1-6}$ alkoxycarbonyl group, carboxyl group, amino group, carbamoyl group, hydroxyl group, an aralkyl group, an aralkyloxy group, oxo group, a $C_{1-12}$ alkylsulfonyl group, and the like. When the group has two or more substituents, they may be the same or different.

$R^1$ represents hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group. Examples of the $C_{1-6}$ alkoxy group as $R^1$ include, for example, methoxy group, ethoxy group, n-propoxy group, isopropoxy group, n-butoxy group, cyclopropylmethyloxy group, and the like, but are not limited to these examples. As the aryl-substituted $C_{1-6}$ alkoxy group as $R^1$, a group consisting of the above-explained alkoxy group further having about one or two, preferably one, aryl group at arbitrary positions of the alkyl moiety can be used, and more specifically, for example, benzyloxy group, phenethyloxy group, naphthylmethyloxy group, and the like can be used, but the group is not limited to these examples.

As the aryloxy-substituted $C_{1-6}$ alkoxy group as $R^1$, a group consisting of the above-explained alkoxy group further having about one or two, preferably one, aryloxy group at an arbitrary position of the alkyl moiety can be used, and more specifically, for example, phenoxymethyloxy group, phenoxyethyloxy group, naphthoxymethyloxy group, and the like can be used, but the group is not limited to these examples. As the $C_{1-6}$ alkoxy-substituted $C_{1-6}$ alkoxy group as $R^1$, a group consisting of the above-explained alkoxy group further having about one or two, preferably one, $C_{1-6}$ alkoxy group at an arbitrary position of the alkyl moiety can be used, and more specifically, methoxyethyloxy group, ethoxyethyloxy group, and the like can be used, but the group is not limited to these examples. As the hydroxy-substituted $C_{1-6}$ alkoxy group as $R^1$, a group consisting of the above-explained alkoxy group further having about one or two, preferably one, hydroxyl group at an arbitrary position of the alkyl moiety can be used, and more specifically, hydroxyethyloxy group, hydroxypropyloxy group, and the like can be used, but the group is not limited to these examples. The $C_{1-6}$ alkoxy-substituted $C_{1-6}$ alkoxy group as $R^1$ may form a ring, and it may be, for example, tetrahydropyranyloxy group, or the like. As $R^1$, hydroxyl group or a $C_{1-6}$ alkoxy group is preferred, and a $C_{1-6}$ alkoxy group is more preferred.

$R^2$ represents hydrogen atom, a halogen atom, a $C_{1-6}$ alkyl group, a $C_{1-6}$ alkoxy group, an aryl group, amino group, hydroxyl group, or a heterocyclic group. The halogen atom as $R^2$, chlorine atom is preferred, but it may also be fluorine atom, bromine atom, or iodine atom. Examples of the $C_{1-6}$ alkoxy group as $R^2$ include, for example, methoxy group, ethoxy group, n-propoxy group, isopropoxy group, n-butoxy group, cyclopropylmethyloxy group, and the like, but are not limited to these examples. As the $C_{1-6}$ alkyl group as $R^2$, for example, methyl group, ethyl group, and the like can be used, as the aryl group, phenyl group, and the like can be used, as the amino group, unsubstituted amino group, methylamino group, dimethylamino group, ethylamino group, and the like can be used, and examples of the heterocyclic group include, for example, piperazinyl group, pyrrolidinyl group, morpholinyl group, and the like, but are not limited to these examples. The same shall apply to the $C_{1-6}$ alkyl group, the aryl group, and the like as the other substituents such as $R^3$. Further, $R^1$ and $R^2$ may bind together to form a $C_{1-6}$ alkylenedioxy group, for example, methylenedioxy group, or the like. As $R^2$, hydrogen atom, a halogen atom, a $C_{1-6}$ alkoxy group, or an aryl group is preferred, hydrogen atom or chlorine atom is more preferred, and hydrogen atom is particularly preferred.

$R^3$ represents hydrogen atom, a halogen atom, a $C_{1-6}$ alkyl group, a $C_{1-6}$ alkoxy group, an aryl group, amino group, hydroxyl group, or a heterocyclic group, preferably hydrogen atom, a halogen atom, or hydroxyl group, more preferably hydrogen atom. $R^4$ represents hydrogen atom, a $C_{1-6}$ alkyl group, a $C_{1-6}$ alkylsulfonyl group, or an arylsulfonyl group. Examples include, for example, methylsulfonyl group, benzenesulfonyl group, and the like. The benzenesulfonyl group may have one or two or more substituents, for example, a $C_{1-6}$ alkyl group, a halogen-substituted $C_{1-6}$ alkyl group, a halogen atom, and the like on the ring, and for example, methylbenzenesulfonyl group, trifluoromethylbenzenesulfonyl group, chlorobenzenesulfonyl group, dichlorobenzenesulfonyl group, and the like can be used. As $R^4$, hydrogen atom is preferred.

$R^5$ represents hydrogen atom, or one to four, preferably one to three, substituents substituting on the benzene ring or the pyridine ring, and the substituents can be selected from, for example, the group consisting of a halogen atom, a $C_{1-6}$ alkyl group, a $C_{2-6}$ alkenyl group, a $C_{2-6}$ alkynyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, sulfonyl group, a heterocyclic group, and a heterocyclic group-substituted $C_{1-6}$ alkoxy group, and can be preferably selected from the group consisting of a halogen atom, a $C_{1-6}$ alkyl group, a $C_{2-6}$ alkenyl group, a $C_{2-6}$ alkynyl group, an amino-substituted $C_{1-6}$ alkyl group, hydroxyl group, a $C_{1-6}$ alkoxy group, a $C_{1-6}$ alkoxycarbonyl group, amino group, nitro group, an aralkyloxy group, sulfonyl group, and a heterocyclic group-substituted $C_{1-6}$ alkoxy group. When there are two or three substituents as $R^5$, they may be the same or different. Further, positions of the substituents on the benzene ring are not particularly limited, and a substituent may or may not exist on —C= or —N= as D. $R^5$ preferably represents hydrogen atom. However, when $R^5$ is a substituent, number of the substituent is preferably one or two, more preferably one. As the substituent, for example, a halogen atom is preferred, and the substituent is more preferably fluorine atom, chlorine atom, or bromine atom.

The symbol ---- represents a single bond or a double bond, and it is preferably a double bond. $R^6$ and $R^7$ independently represent hydrogen atom, a $C_{1-6}$ alkyl group, or a halogen-substituted $C_{1-6}$ alkyl group, wherein when ---- represents a double bond, $R^7$ does not exist. It is preferred that $R^6$ and $R^7$ are hydrogen atoms, and it is preferred that ---- is a double bond, and $R^6$ is hydrogen atom. When ---- is a double bond, the wavy line represents a bond in the Z-configuration or the E-configuration, or a mixture thereof with reference to the double bond.

The symbol "A" represents —O—, —S—, or —CH$_2$—, and it is preferably —O—. D represents —C= or —N=, and it is preferably —C=. X represents a single bond, or represents a $C_{1-6}$ alkylene group, a $C_{2-6}$ alkenylene group, a $C_{2-6}$ alkynylene group, —O—, or —CO—. These alkylene group, alkenylene group, and alkynylene group may be linear or branched, and may be substituted with one or two hydroxyl group. Although number of unsaturated bonds contained in the alkenylene group or the alkynylene group is not particularly limited, the number is preferably about one or two.

Q represents —N= or —C(R$^8$)=, and $R^8$ represents hydrogen atom, a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, a halogen-substituted $C_{1-6}$ alkoxy group, amino group, an aryl group, or a heterocyclic group. It is preferred that $R^8$ is hydrogen atom or a $C_{1-6}$ alkyl group, and it is more preferred that $R^8$ is hydrogen atom. Examples of the methylene group as X having a $C_{1-6}$ alkyl group include —CH(CH$_3$)—, and the like, but are not limited to these examples. It is preferred that X represents methylene group.

The symbol "Y" represents a heterocyclic group or amino group, preferably a 5- to 7-membered saturated heterocyclic group (the ring of this heterocyclic group contains one or two heteroatoms) or amino group. This heterocyclic group or amino group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group. Examples of the heterocyclic group include, for example, 1-piperazinyl group, morpholino group, thiomorpholino group, 1-piperidinyl group, 4-piperidinyl group, 4-tetrahydropyranyl group, 1-homopiperazinyl group, 1-pyrrolidinyl group, hexamethyleneimin-1-yl group, and the like. Preferred examples of the substituent of the heterocyclic group or amino group include one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group.

Examples of 1-piperazinyl group having a substituent include, for example, 3,5-dimethyl-1-piperazinyl group, 2-methyl-1-piperazinyl group, 4-methyl-1-piperazinyl group, 3-oxo-1-piperazinyl group, 4-methylsulfonyl-1-piperazinyl group, 4-(2-methoxyethyl)-1-piperazinyl group, 4-dimethylcarbamoyl-1-piperazinyl group, and the like, but are not limited to these examples. Examples of morpholino group having a substituent include, for example, 3-methylmorpholino group, 2-hydroxymorpholino group, 3-oxomorpholino group, and the like, but are not limited to these examples. Examples of 1-pyrrolidinyl group having a substituent include 3-aminopyrrolidinyl group, 3-dimethylaminopyrrolidinyl group, 3-hydroxypyrrolidinyl group, and the like, but are not limited to these examples. Examples of 1-piperidinyl group having a substituent include 4-hydroxy-1-piperidinyl group, 3-ethoxycarbonyl-1-piperidinyl group, and the like, but are not limited to these examples. Examples of amino group having a substituent as Y include, for example, those having a substituent selected from the group consisting of an amino-substituted $C_{1-6}$ alkyl group and a $C_{1-6}$ alkyl group, and the like, and more specifically, examples of such amino group as Y include (methylaminoethyl)(methyl)amino group, (dimethylaminoethyl)(methyl)amino group, and the like.

$R^{1a}$, $R^{2a}$, $R^{3a}$, $R^{4a}$, $R^{5a}$, $R^{6a}$, $R^{7a}$, ----, $R^{8a}$, $A^a$, $D^a$, $X^a$, and $Y^a$ in the aforementioned general formula (IA), and $R^{1b}$, $R^{2b}$, $R^{3b}$, $R^{4b}$, $R^{5b}$, $R^{6b}$, $R^{7b}$, ----, $R^{8b}$, $A^b$, $D^b$, $X^b$, and $Y^b$ in the aforementioned general formula (IB) have the same meanings as those of $R^1$, $R^2$, $R^3$, $R^4$, $R^5$, $R^6$, $R^7$, ----, $R^8$, A, D, X, and Y in the aforementioned general formula (I), respectively. As compounds falling within the scope of the aforementioned general formula (I), compounds represented by the aforementioned general formula (IA) or (IB) are also preferred.

A compound represented by the aforementioned general formula (I), wherein
$R^1$ is hydrogen atom, hydroxyl group, or a $C_{1-6}$ alkoxy group;
$R^2$ is hydrogen atom, a halogen atom, a $C_{1-6}$ alkoxy group, or an aryl group;
$R^3$ is hydrogen atom;
$R^4$ is hydrogen atom, an alkylsulfonyl group, or an arylsulfonyl group;
$R^5$ is hydrogen atom, or one or two substituents substituting on the benzene ring or the pyridine ring (the substituent(s) is (are) selected from the group consisting of a halogen atom, a $C_{1-6}$ alkyl group, a $C_{2-6}$ alkenyl group, a $C_{2-6}$ alkynyl group, an amino-substituted $C_{1-6}$ alkyl group, hydroxyl group, a $C_{1-6}$ alkoxy group, a $C_{1-6}$ alkoxycarbonyl group, amino group, nitro group, an aralkyloxy group, and a heterocyclic group-substituted $C_{1-6}$ alkoxy group);
$R^6$ and $R^7$ are hydrogen atoms;
$R^8$ is hydrogen atom or a $C_{1-6}$ alkyl group;
D is —C=;
Q is —C(R$^8$)=;
X is methylene group; and
Y is 1-piperazinyl group, morpholino group, thiomorpholino group, 1-piperidinyl group, 4-piperidinyl group, 4-tetrahydropyranyl group, 1-homopiperazinyl group, 1-pyrrolidinyl group, hexamethyleneimin-1-yl group, or amino group (these groups may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group) is preferred.

Further, a compound represented by the aforementioned general formula (I), wherein
$R^1$ is hydroxyl group or a $C_{1-6}$ alkoxy group;
$R^2$ and $R^3$ are hydrogen atoms;
$R^4$ is hydrogen atom, an alkylsulfonyl group, or an arylsulfonyl group;
$R^5$ is hydrogen atom, or one halogen atom substituting on the benzene ring;

⋯ is a double bond;
$R^6$ is hydrogen atom;
$R^8$ is hydrogen atom;
D is —C═;
Q is —C═;
X is methylene group; and
Y is 1-piperazinyl group (this piperazinyl group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group)
is more preferred.

As another embodiment, a compound represented by the aforementioned general formula (I), wherein
$R^1$ is hydroxyl group or a $C_{1-6}$ alkoxy group;
$R^2$ and $R^3$ are hydrogen atoms;
$R^4$ is hydrogen atom;
$R^5$ is hydrogen atom, or one halogen atom substituting on the pyridine ring;
⋯ is a double bond;
$R^6$ is hydrogen atom;
$R^8$ is hydrogen atom;
D is —N═;
Q is —C═;
X is methylene group (this methylene group may be substituted with one or two $C_{1-6}$ alkyl groups); and
Y is 1-piperazinyl group or morpholinyl group (this piperazinyl group or morpholinyl group may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group)
is also more preferred.

As another embodiment, a compound represented by the aforementioned general formula (I), wherein
$R^1$ is hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group;
$R^2$ is hydrogen atom, a halogen atom, a $C_{1-6}$ alkoxy group, wherein $R^1$ and $R^2$ may bind together to form a $C_{1-6}$ alkylenedioxy group;
$R^3$ is hydrogen atom, a halogen atom, or hydroxyl group;
$R^4$ is hydrogen atom, a $C_{1-6}$ alkyl group, or sulfonyl group;
$R^5$ is hydrogen atom or one to three substituents substituting on the benzene ring or the pyridine ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, and a halogen-substituted $C_{1-6}$ alkoxy group);
⋯ is a single bond or a double bond;
$R^6$ and $R^7$ are hydrogen atoms, wherein when ⋯ represents a double bond, $R^7$ does not exist;
A is —O—, —S—, or —CH$_2$—;
D is —C═ or —N═;
Q is —N═;
X is methylene group (this methylene group may be substituted with one or two $C_{1-6}$ alkyl groups or hydroxyl groups), —O—, or —CO—; and
Y is 1-piperazinyl group, morpholino group, or 4-piperidinyl group (these groups may have one or two or more substituents selected from the group consisting of a $C_{1-6}$ alkyl group, hydroxyl group, and oxo group) is preferred.

Further, it is preferred that Q is —N═, and (a) $R^3$ is hydrogen atom, (b) $R^4$ is hydrogen atom, (c) ⋯ is a double bond, (d) A is —O—, or (e) D is —C═. A compound satisfying two or more of the aforementioned conditions (a) to (e) is more preferred, a compound satisfying three or more of the aforementioned conditions (a) to (e) is still more preferred, and a compound satisfying four or more of the aforementioned conditions (a) to (e) is particularly preferred. A compound satisfying all of the aforementioned conditions (a) to (e) is most preferred.

Furthermore, a compound wherein Q is —N═, and (f) $R^1$ is hydroxyl group or a $C_{1-6}$ alkoxy group, (g) $R^2$ is hydrogen atom or a halogen atom, (h) X is methylene group, (i) $R^6$ is hydrogen atom, one halogen atom, one $C_{1-6}$ alkoxy group, or one fluoro-substituted $C_{1-6}$ alkoxy group is also preferred. A compound satisfying two or more of the aforementioned conditions (f) to (i) is more preferred, a compound satisfying three or more of the aforementioned conditions (f) to (i) is still more preferred, and a compound satisfying all of the aforementioned conditions (f) to (i) is particularly preferred. A compound satisfying all of the aforementioned conditions (a) to (e) and the aforementioned conditions (f) to (i) is most preferred.

The compounds represented by the general formula (I) may form an acid addition salt. Examples of physiologically acceptable acid addition salts include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, but are not limited to these examples. Arbitrary physiologically acceptable salts can be used as the active ingredient of the anticancer agent of the present invention. Further, the compounds represented by the general formula (I) in free form and salts thereof may exist as a hydrate or a solvate, and arbitrary hydrates and solvates can also be used as the active ingredient of the anticancer agent of the present invention. Although the solvent that forms the solvate is not particularly limited, physiologically acceptable organic solvents such as ethanol, dioxane, ethyl acetate and n-hexane are preferred.

Further, the compounds represented by the general formula (I) may have one or two or more asymmetric carbons depending on type of substituent. One or two or more asymmetric carbons in the compounds represented by the general formula (I) may be in an arbitrary steric configuration. Stereoisomers such as optical isomers and diastereoisomers in pure forms based on these asymmetric carbons, arbitrary mixtures of stereoisomers, racemates, and the like all can be used as the active ingredient of the anticancer agent of the present invention. When the compounds represented by the general formula (I) have a double bond, geometrical isomers thereof based on the double bond exist. It should be understood that any geometrical isomers in pure forms and arbitrary mixtures of geometrical isomers can also be used as the active ingredient of the anticancer agent of the present invention.

Specific examples of the compound represented by the general formula (I) or salt thereof are shown below. However, the scope of the compound represented by the general formula (I) is not limited to the following compounds and salts thereof. The compound numbers mentioned below correspond to the example numbers. Among them, Compound A40, Compound A53, and salts thereof are particularly preferred.
[Formula 7]
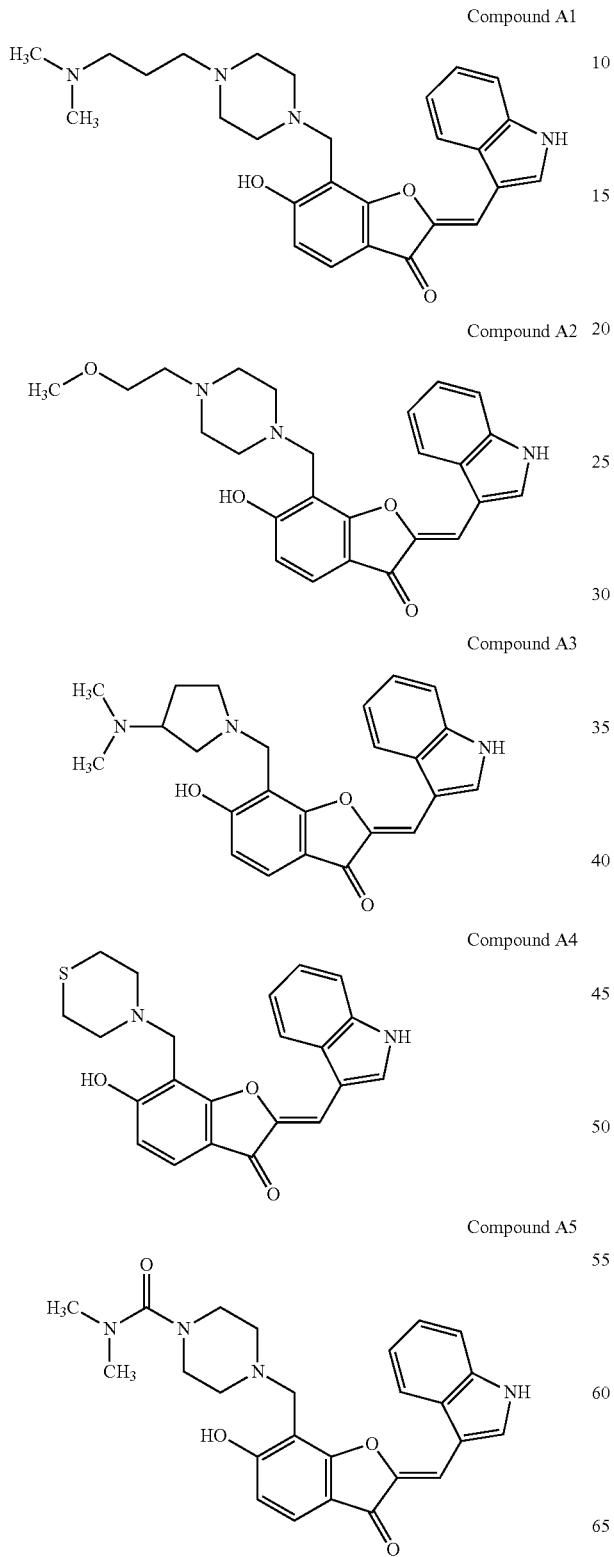
Compound A1
Compound A2
Compound A3
Compound A4
Compound A5
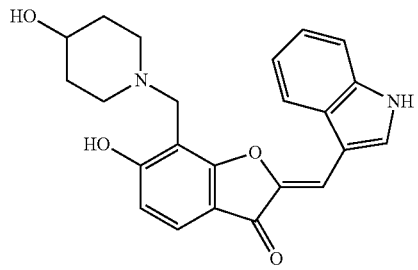
Compound A6
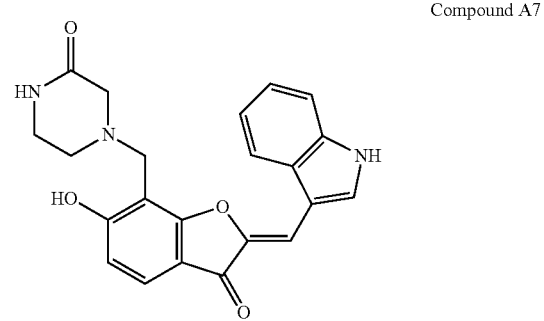
Compound A7
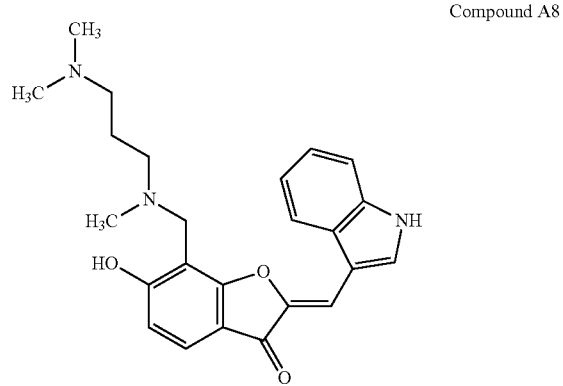
Compound A8
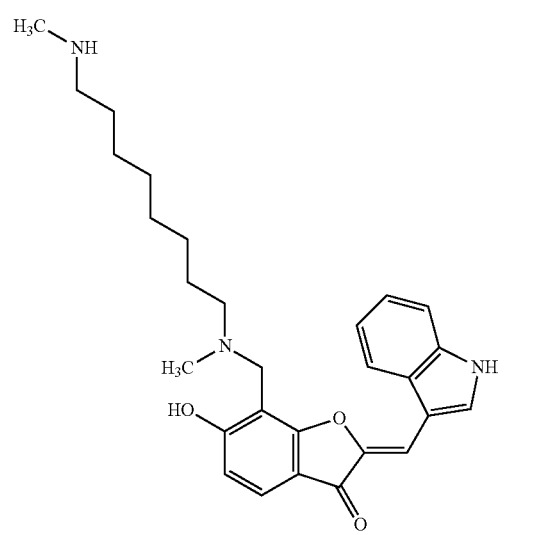
Compound A9

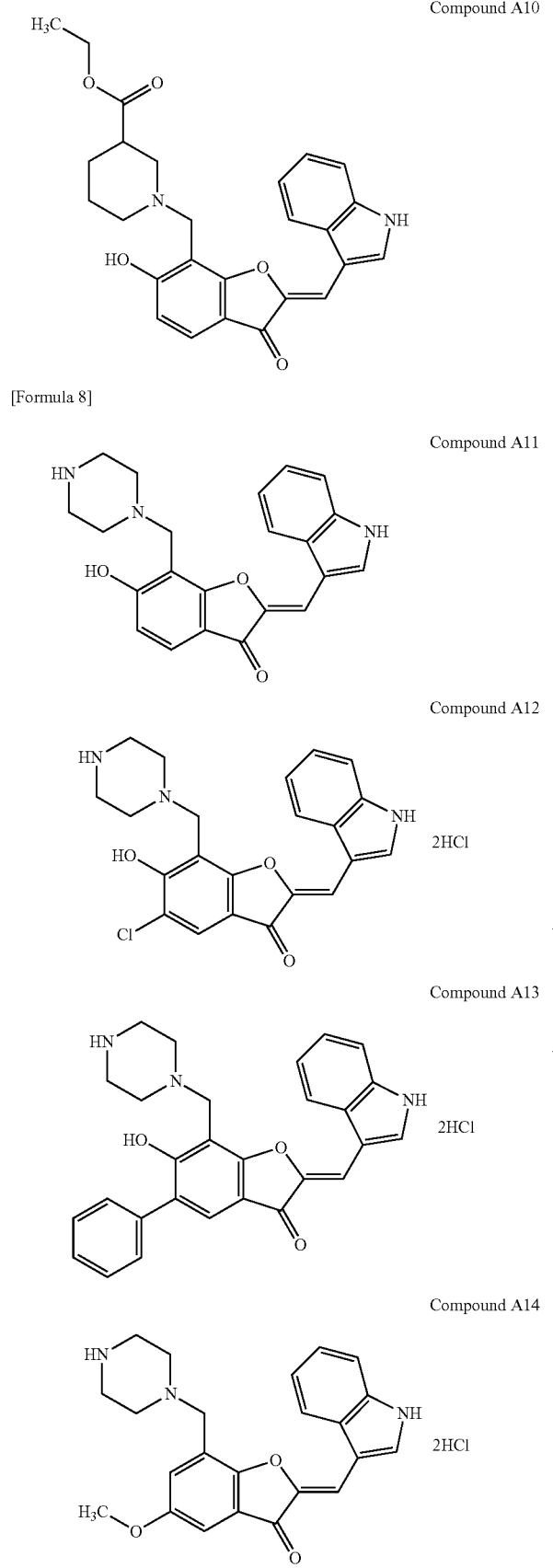

-continued
Compound A20
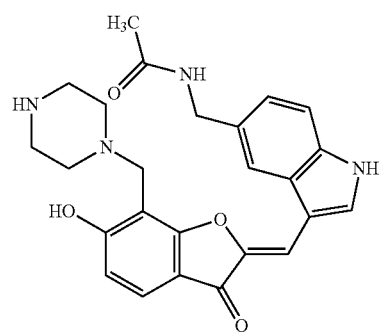
2HCl
[Formula 9]
Compound A21
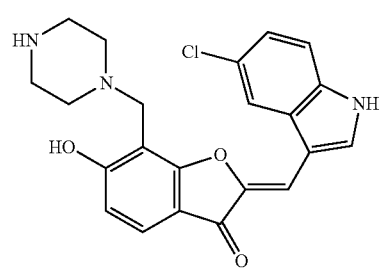
2HCl
Compound A22
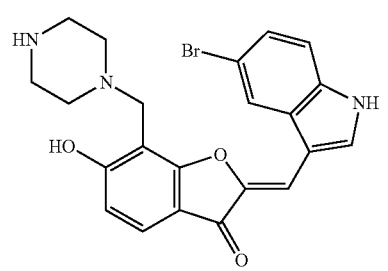
2HCl
Compound A23
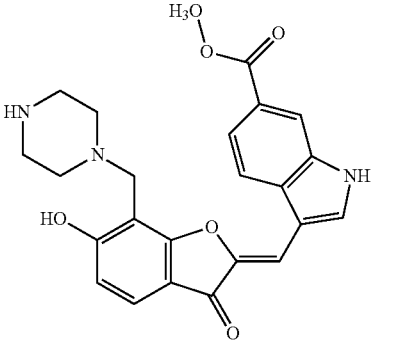
Compound A24
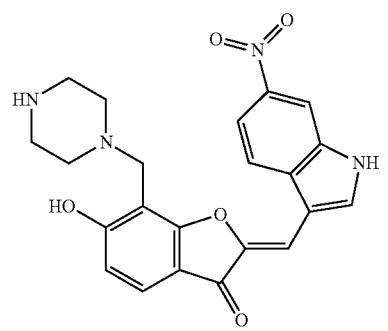
2HCl
-continued
Compound A25
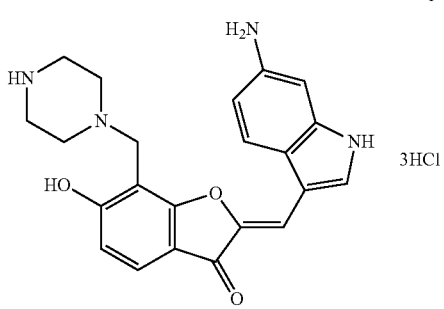
3HCl
Compound A26
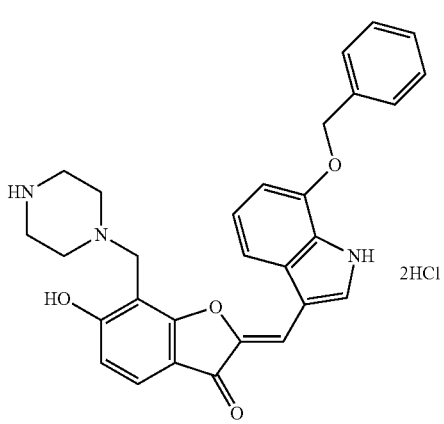
2HCl
Compound A27
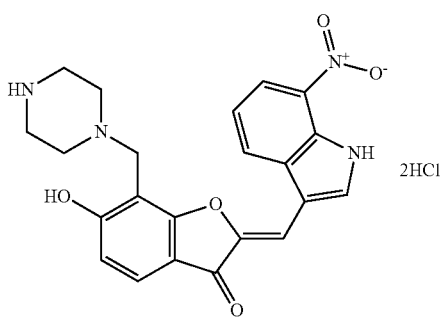
2HCl
Compound A28
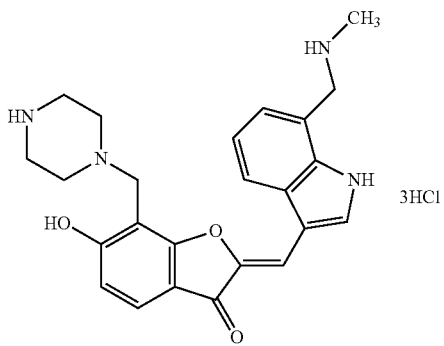
3HCl Compound A29
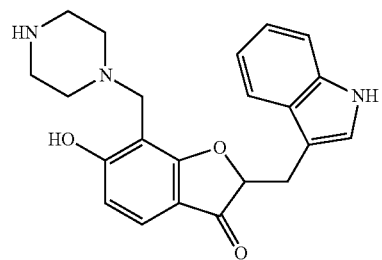
Compound A30
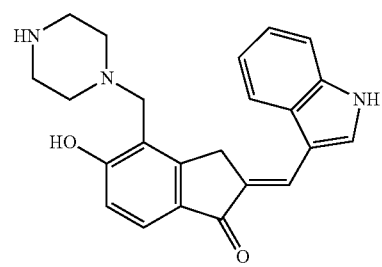
2HCl
[Formula 10]
Compound A31
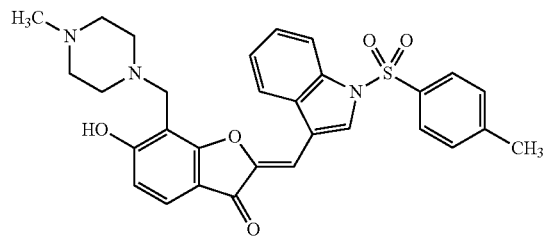
Compound A32
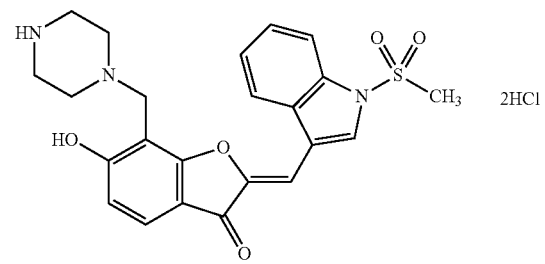
2HCl
Compound A33
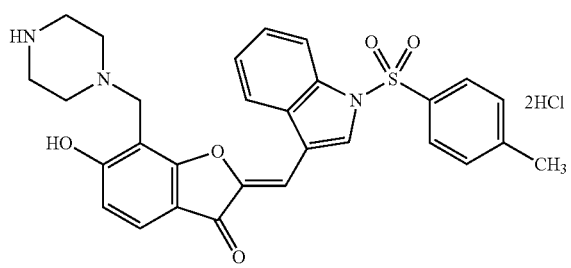
2HCl
Compound A34
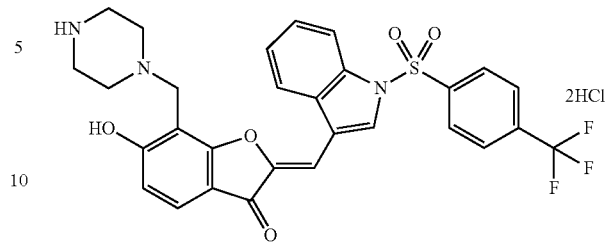
2HCl
Compound A35
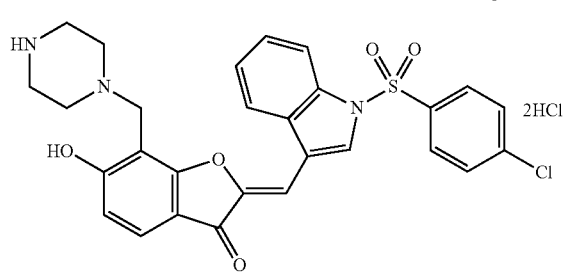
2HCl
Compound A36
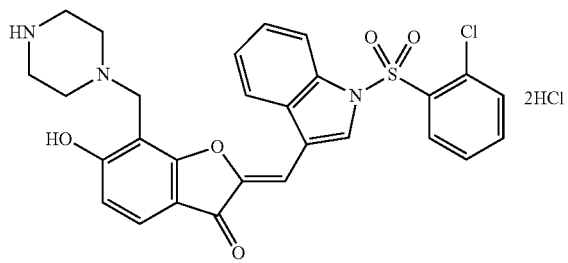
2HCl
Compound A37
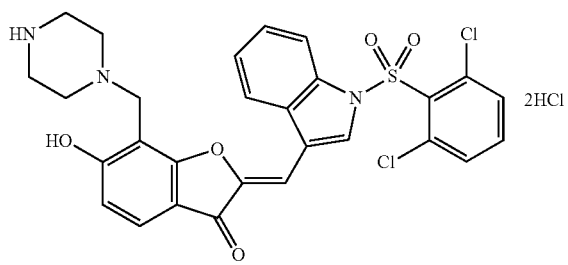
2HCl
Compound A38
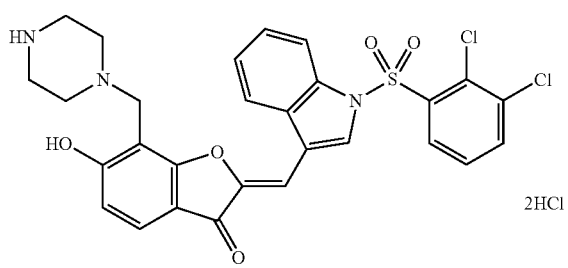
2HCl Compound A39

Compound A40

[Formula 11]

Compound A41

Compound A42

Compound A43

Compound A44

Compound A45

Compound A46

Compound A47

Compound A48

Compound A49
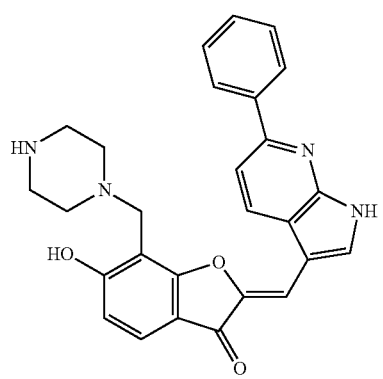
3HCl
Compound A50
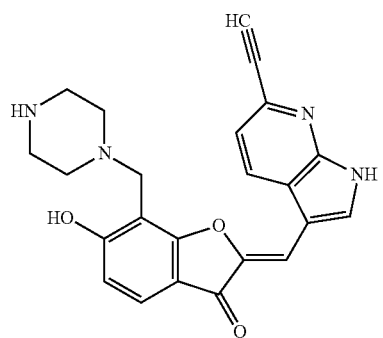
3HCl
[Formula 12]
Compound A51
3HCl
Compound A52
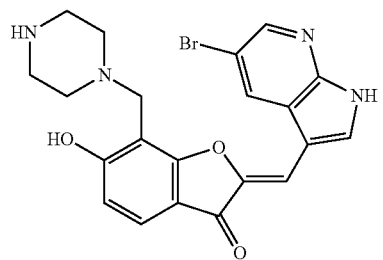
3HCl
Compound A53
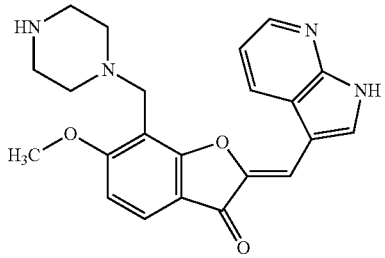
Compound A54
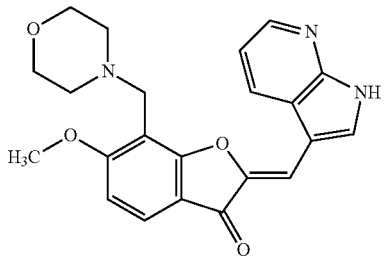
[Formula 13]
Compound A55
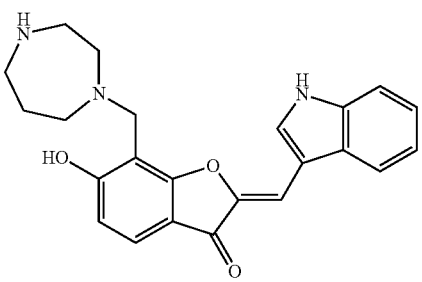
Compound A56
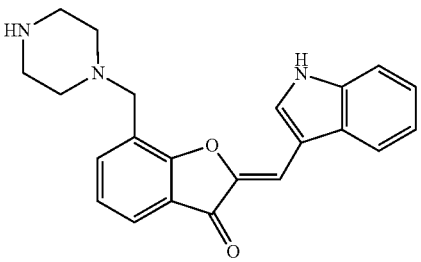
Compound A57
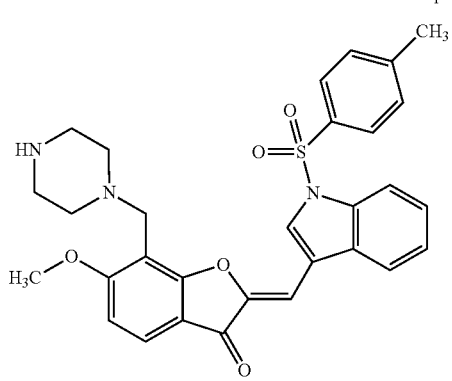

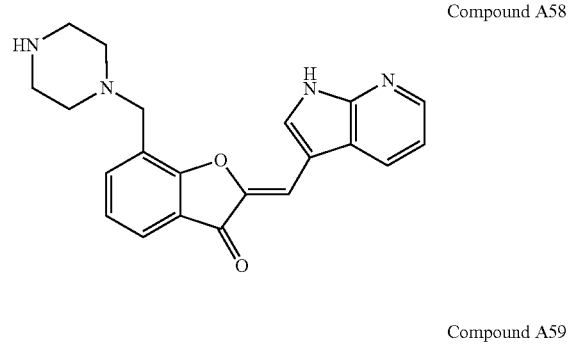
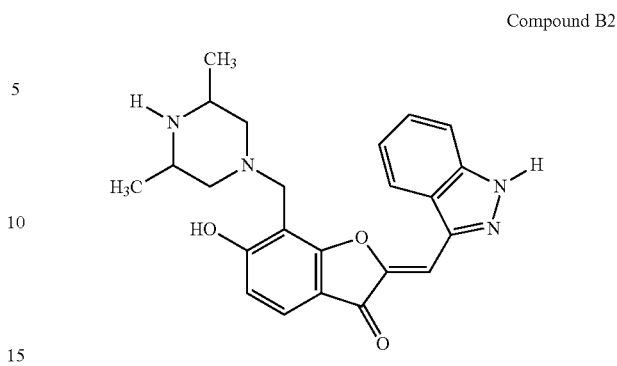

Compound B7
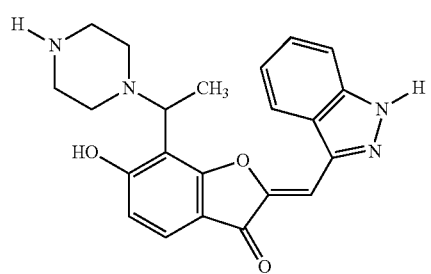
Compound B12
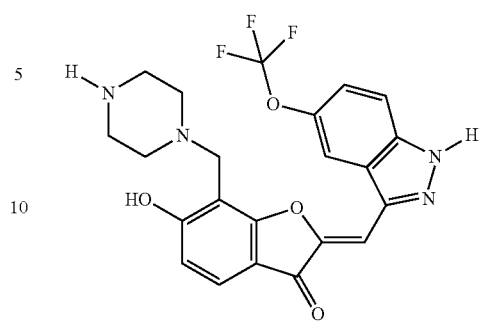
Compound B8
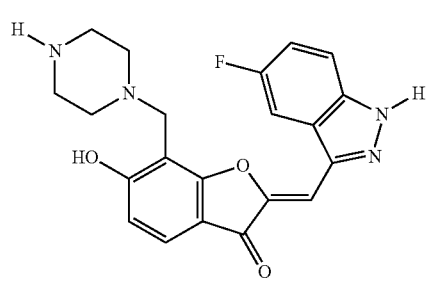
Compound B13
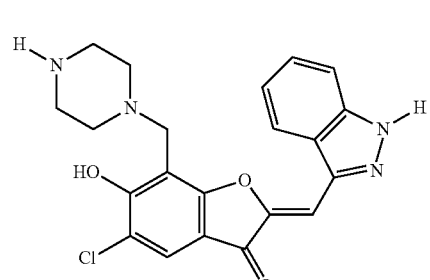
Compound B9
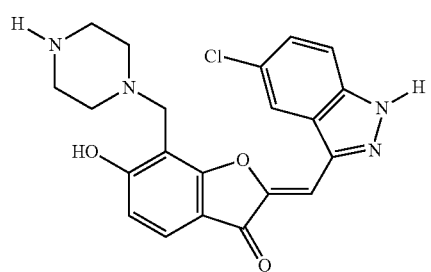
Compound B14
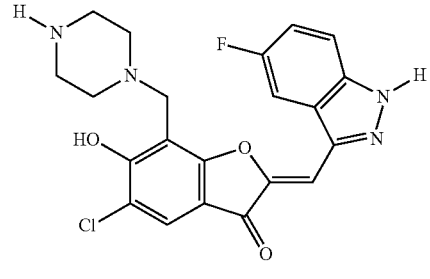
Compound B10
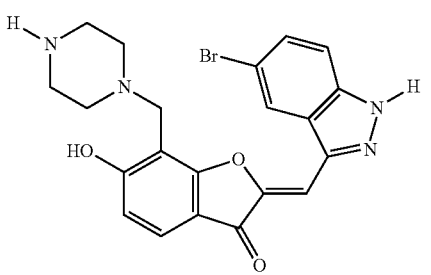
Compound B15
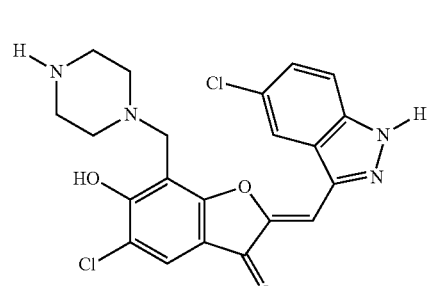
[Formula 15]
Compound B11
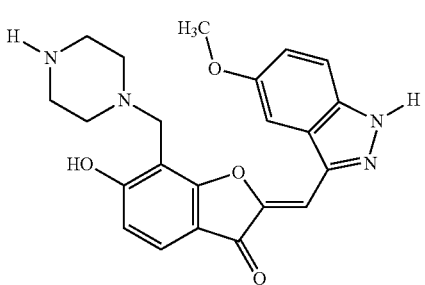
Compound B16
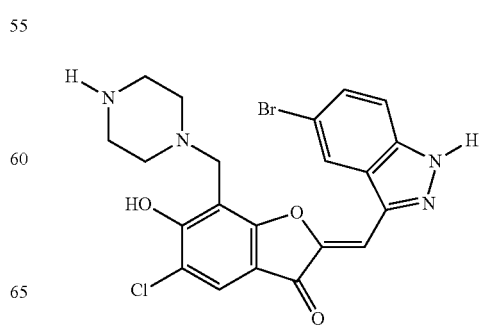

Compound B17
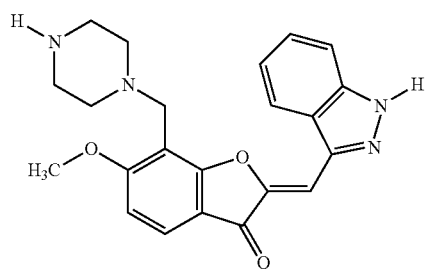
Compound B18
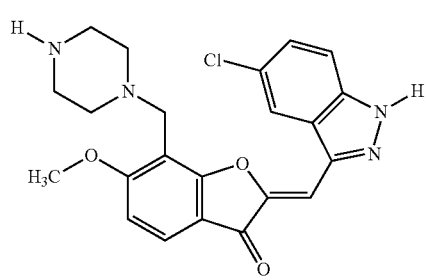
Compound B19
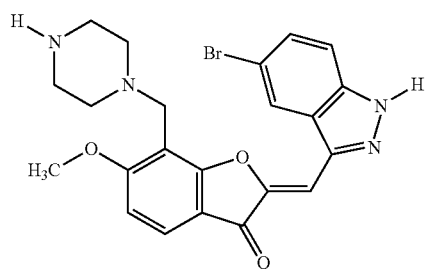
Compound B20
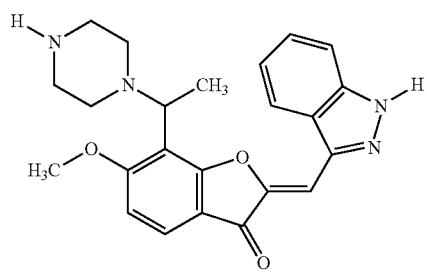
[Formula 16]
Compound B21
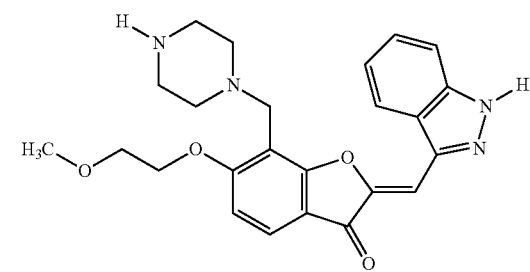
Compound B22
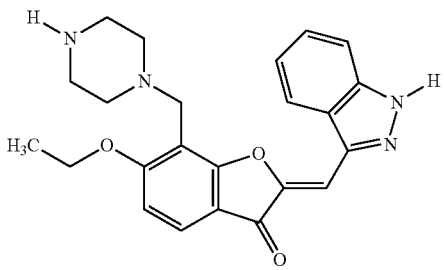
Compound B23
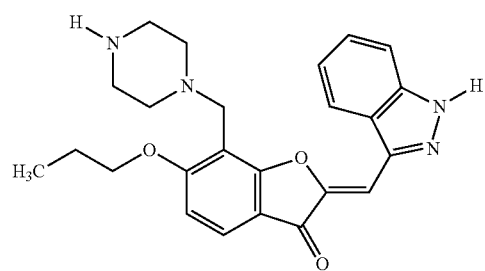
Compound B24
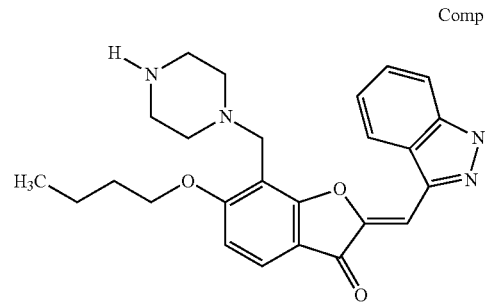
Compound B25
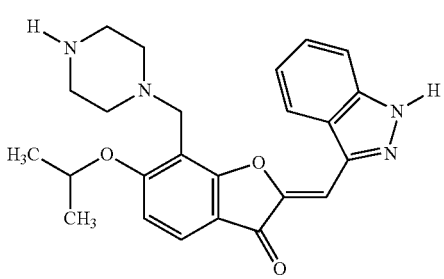
Compound B26
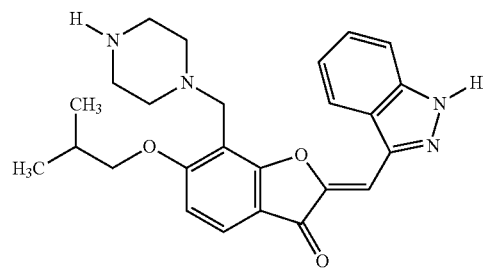

Compound B27
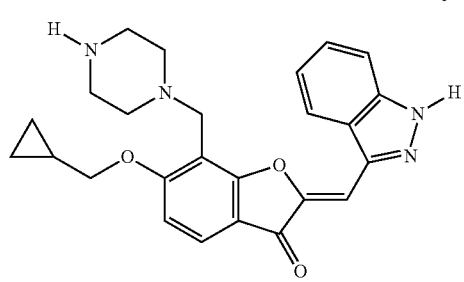
Compound B28
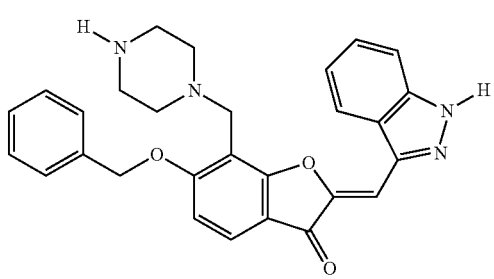
Compound B29
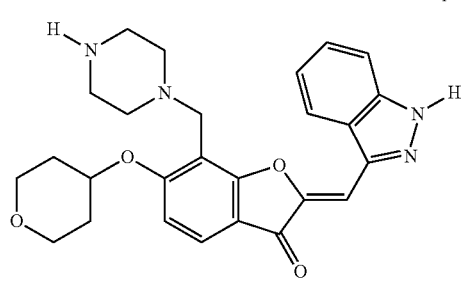
Compound B30
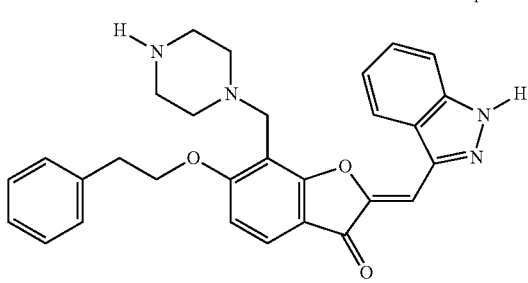
[Formula 17]
Compound B31
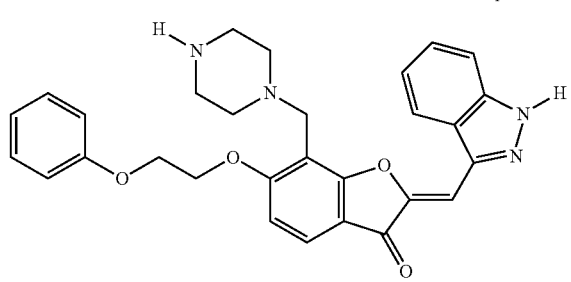
Compound B32
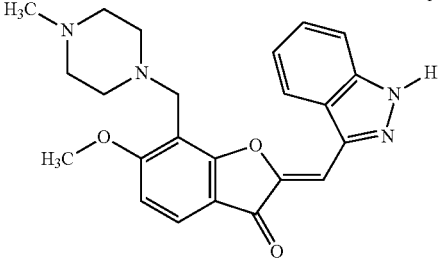
Compound B33
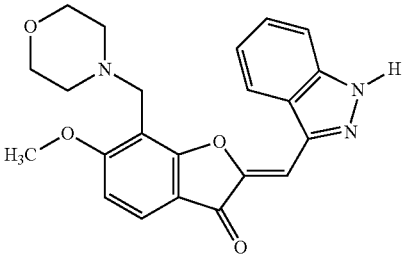
Compound B34
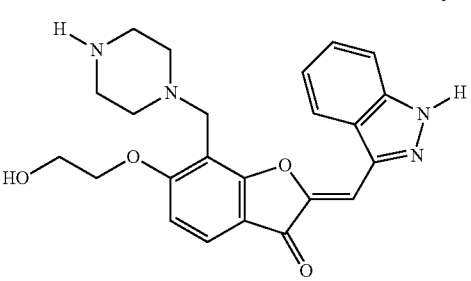
Compound B35
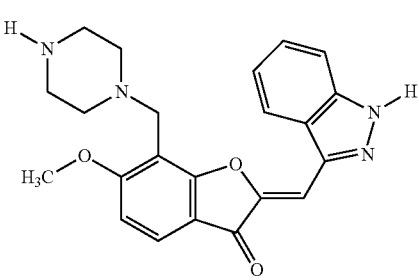
Compound B36
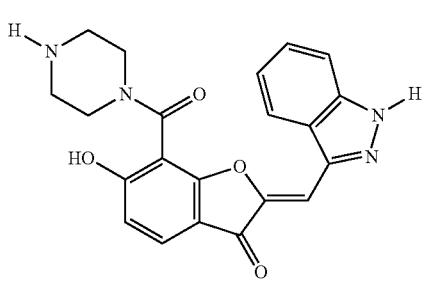

-continued
Compound B37
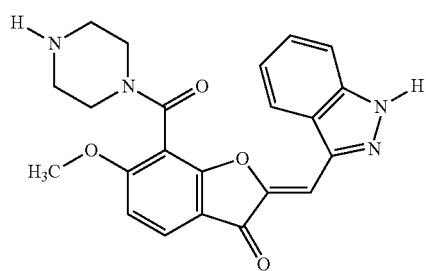
Compound B38
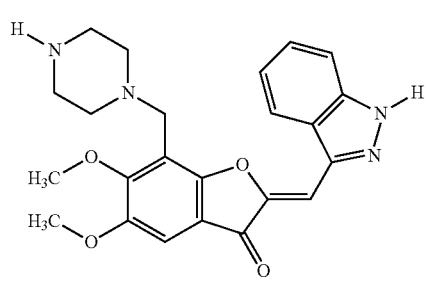
Compound B39
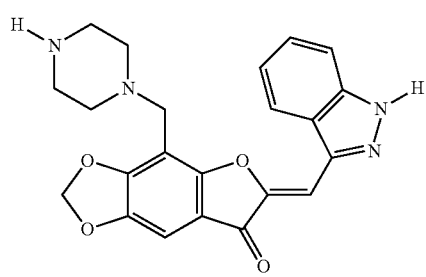
Compound B40
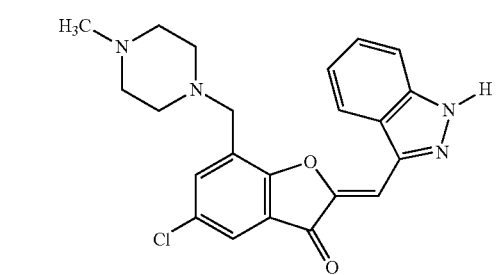
[Formula 18]
Compound B41
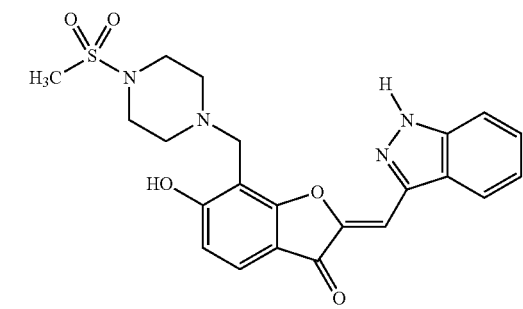
-continued
Compound B42
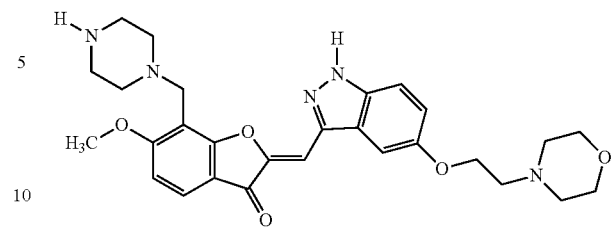
Compound B43
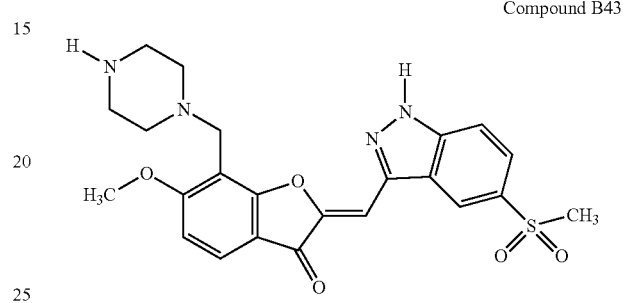
Compound B44
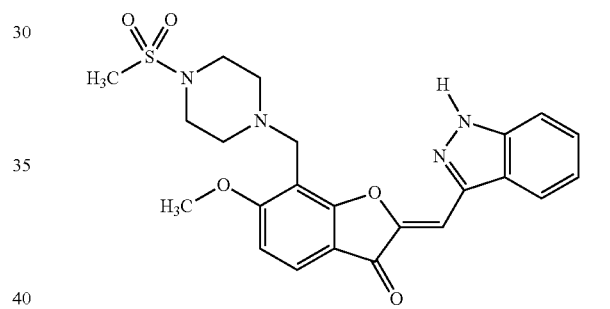
Compound B45
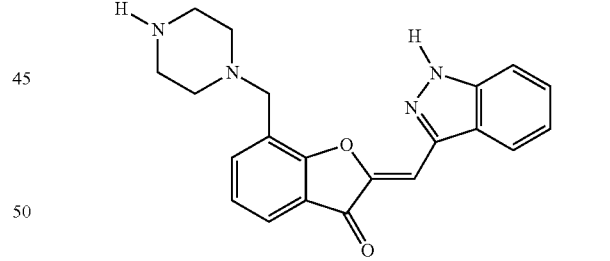
Compound B46
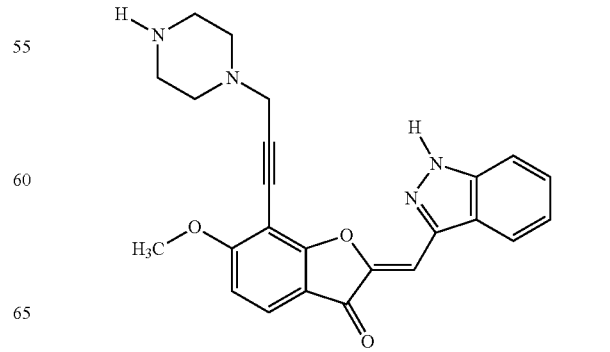

Compound B47
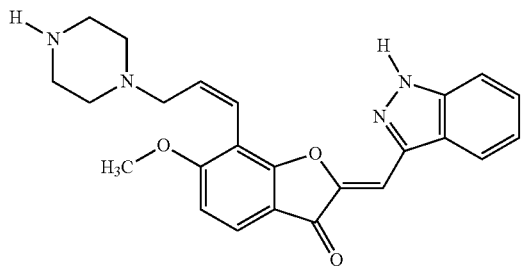
Compound B48
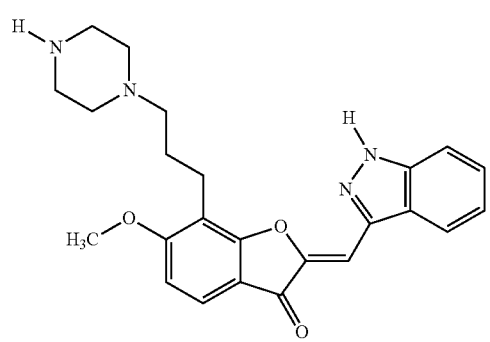
Compound B49
Compound B50
Compound B51
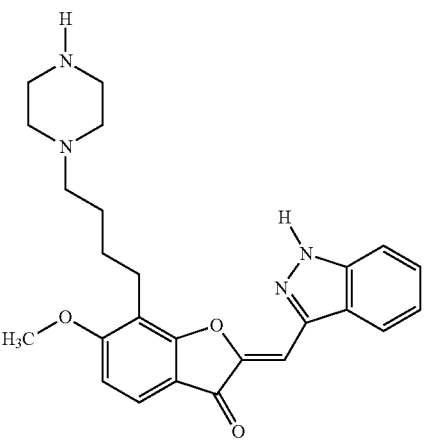
Compound B52
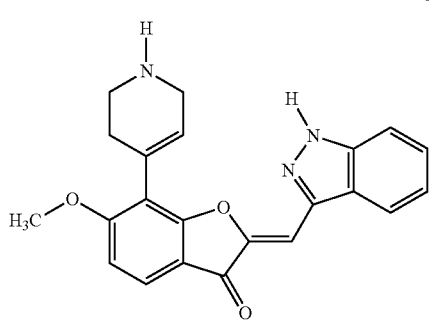
Compound B53
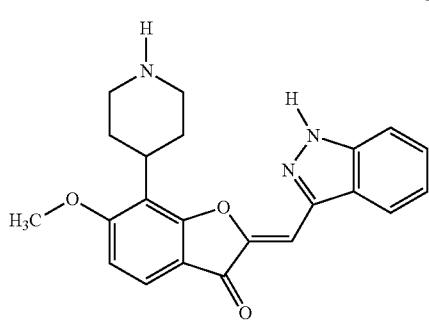
Compound B54
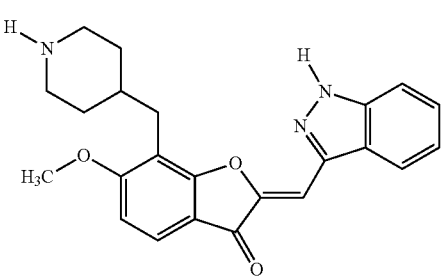

Compound B55
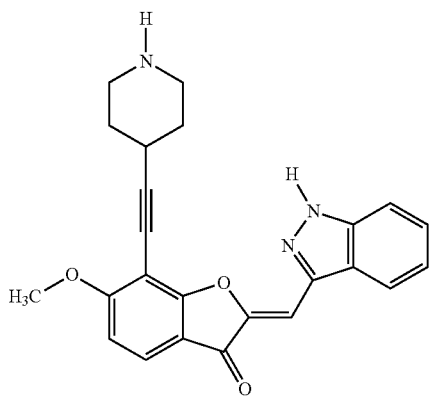
Compound B59
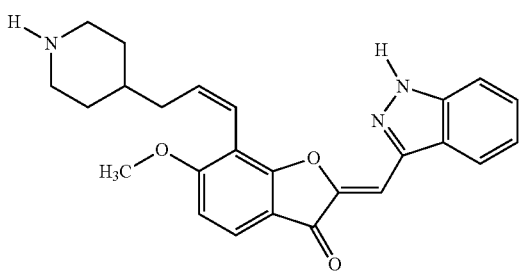
Compound B60
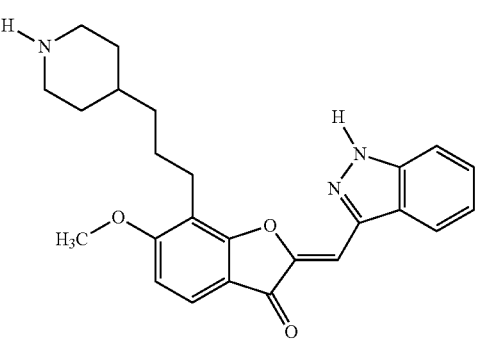
Compound B56
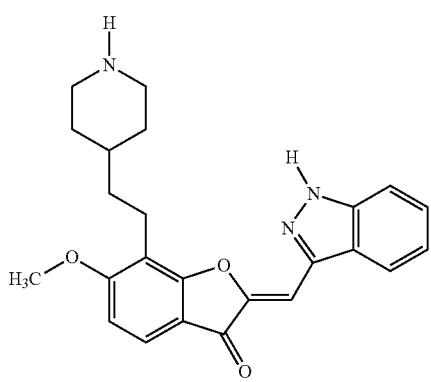
[Formula 20]
Compound B57
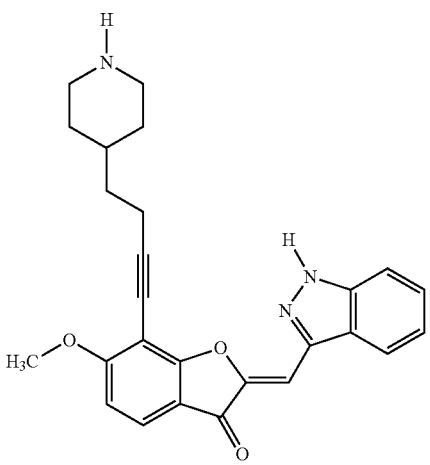
Compound B61
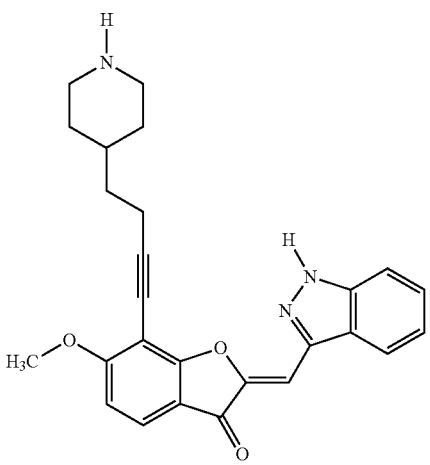
Compound B58
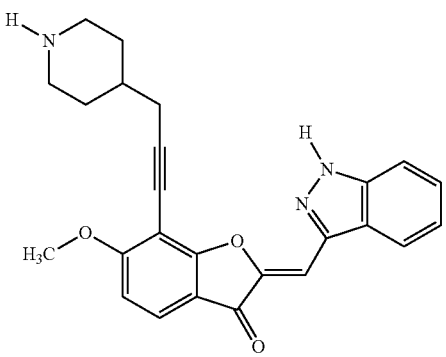
Compound B62
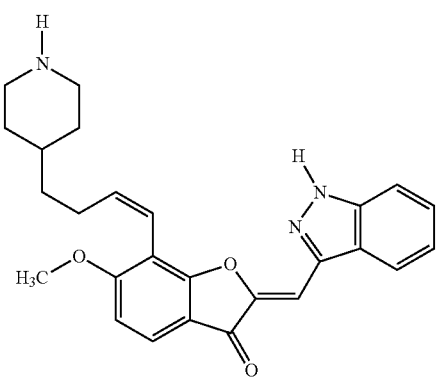

Compound B63
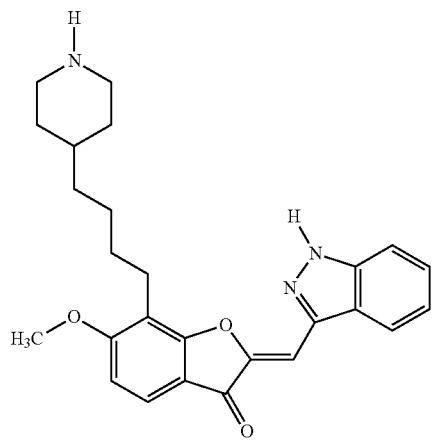
Compound B64
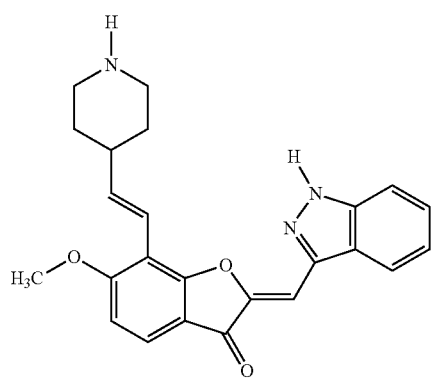
Compound B65
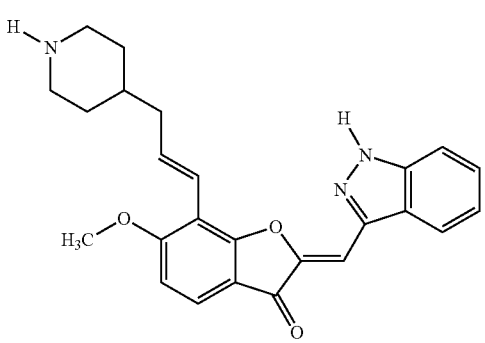
Compound B66
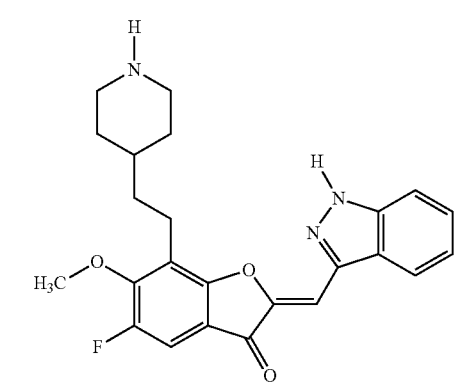
Compound B67
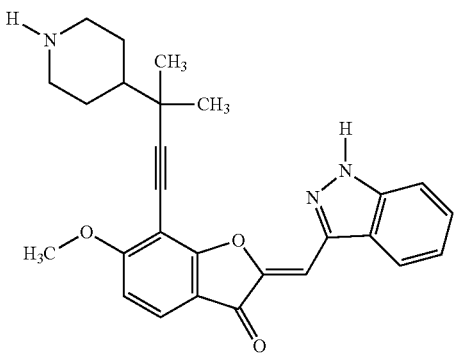
Compound B68
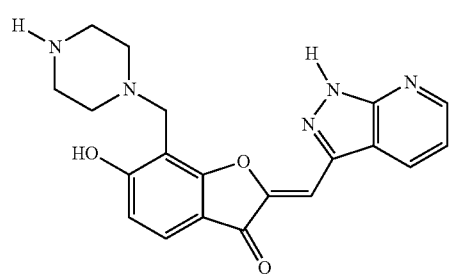
Compound B69
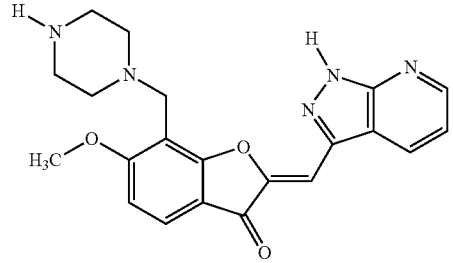
Compound B70
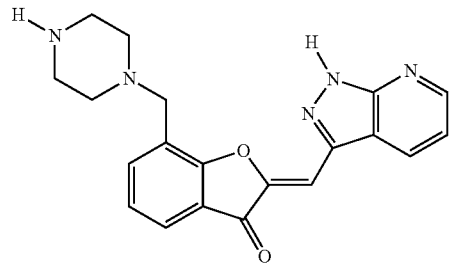
[Formula 21]
Compound B71
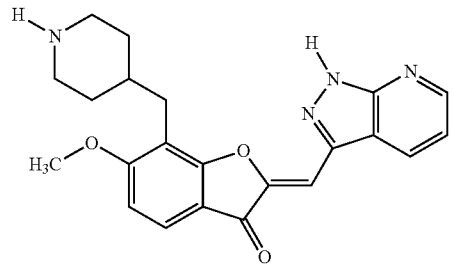

Compound B72

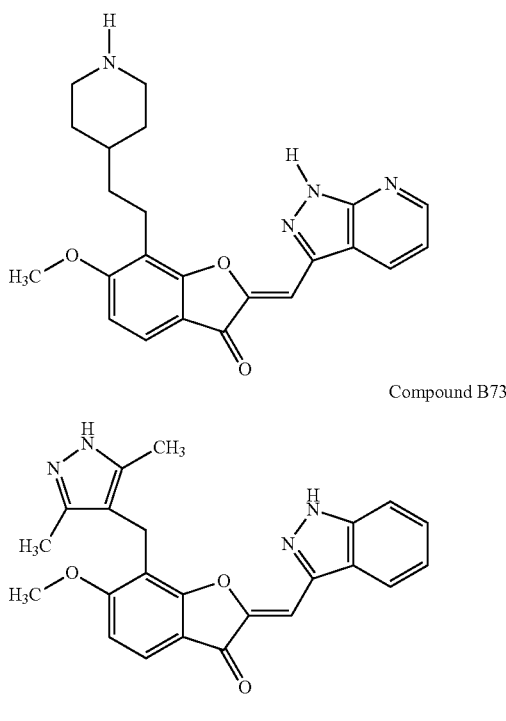

Compound B73

Scheme A1 (Compound A1)

[Formula 22]

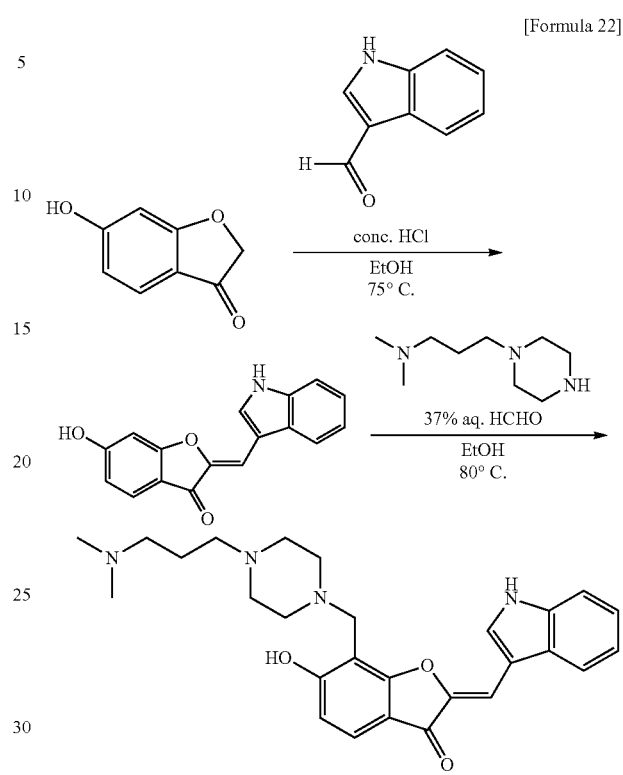

Methods for preparing the compounds represented by the general formula (I) are not particularly limited. Method for preparing novel compounds, among typical compounds falling within the scope of the general formula (I), are specifically described in the examples included in the specification. Further, general synthetic methods corresponding to the examples are shown in the following schemes. By referring to the examples of the specification and also to the following schemes, and appropriately modifying starting materials, reagents, reaction conditions, and the like as required, those skilled in the art will be able to easily prepare the compounds falling within the scope of the general formula (I).

In the schemes, Me stands for methyl group, Et for ethyl group, Pr for propyl group, Ac for acetyl group, Boc for tert-butoxycarbonyl group, Ph for phenyl group, TFA for trifluoroacetic acid, THF for tetrahydrofuran, DMF for dimethylformamide, DMSO for dimethyl sulfoxide, DMAP for dimethylaminopyridine, Tos for p-toluenesulfonyl group, DME for 1,2-dimethoxyethane, NBS for N-bromosuccinimide, Bz for benzoyl group, DEAD for diethyl azodicarboxylate, Bn for benzyl group, WSCD for 1-ethyl-3-(3-dimethylaminopropyl)-carbodiimide hydrochloride, HOBt for 1-hydroxybenzotriazole, DIBAL-H for diisobutylaluminum hydride, SEM-Cl for 2-(trimethylsilyl)ethoxymethyl chloride, TBAF for tetrabutylammonium fluoride, rt for room temperature, NBS for N-bromosuccinimide, mW for microwave, dppf for 1,1'-bis-(diphenylphosphino)ferrocene group, and Cp for cyclopentadienyl group.

Scheme A2 (Compounds A2-A8 & A10)

[Formula 23]

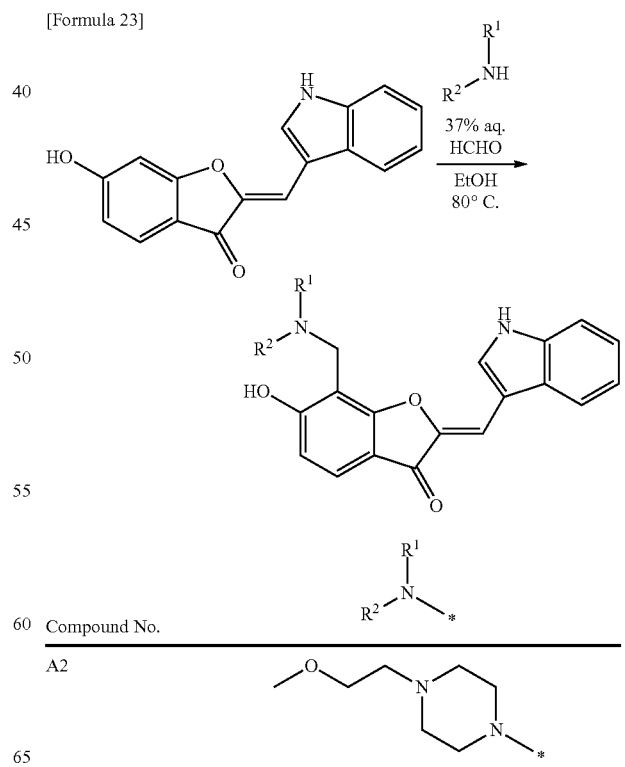

| Compound No. | |
|---|---|
| A2 | |

Scheme A2 (Compounds A2-A8 & A10)
[Formula 23]
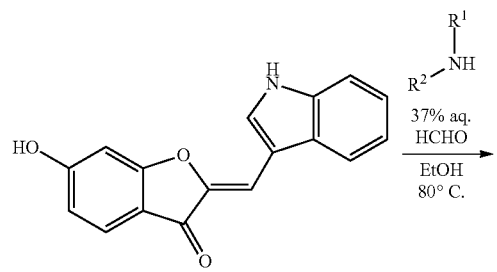
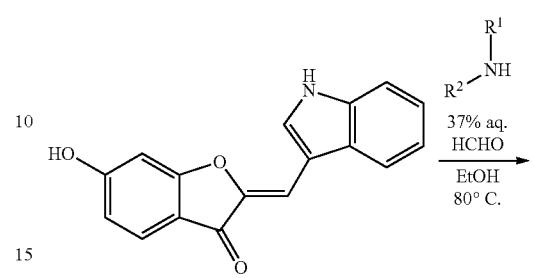
| Compound No. | $R^1R^2N-*$ | Compound No. | $R^1R^2N-*$ |
|---|---|---|---|
| A3 | 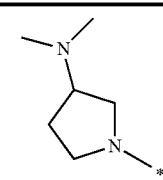 | A7 | 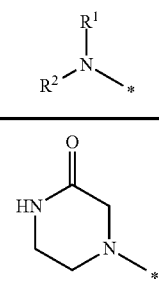 |
| A4 | 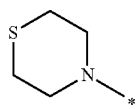 | A8 | 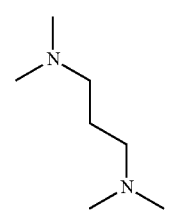 |
| A5 | 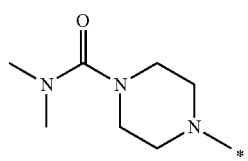 | A10 | 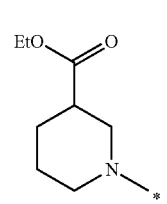 |
| A6 | 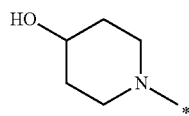 | | |
Scheme A3 (Compound A9)
[Formula 24]
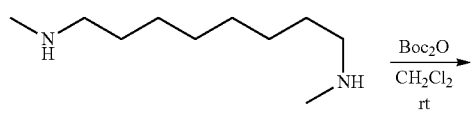

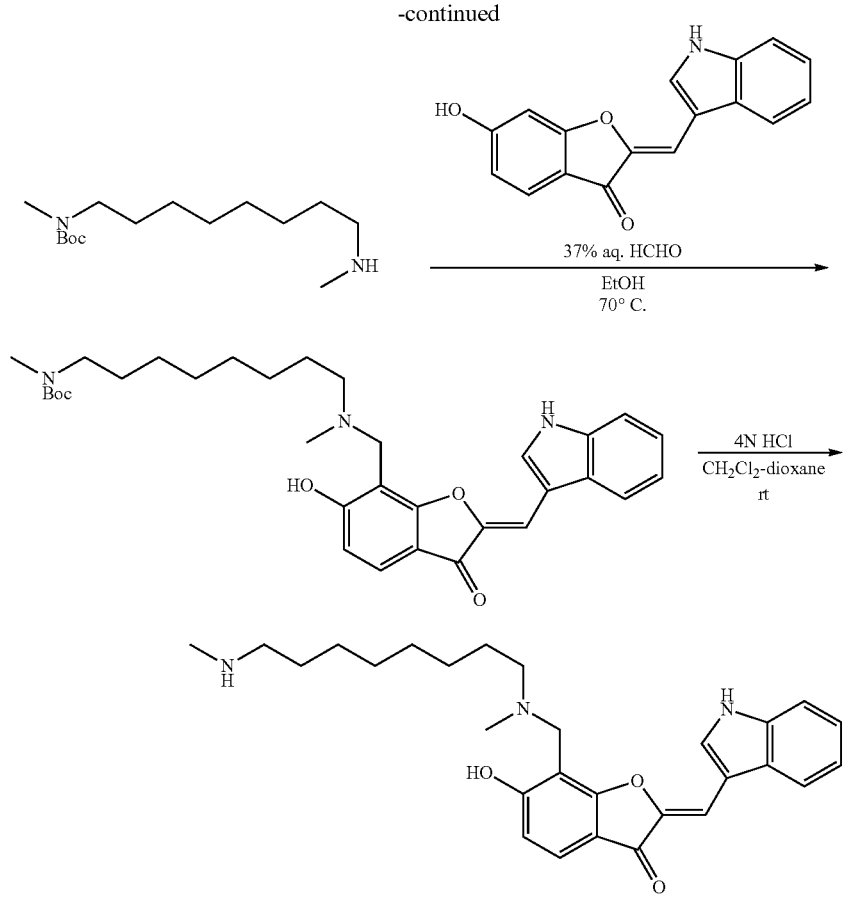
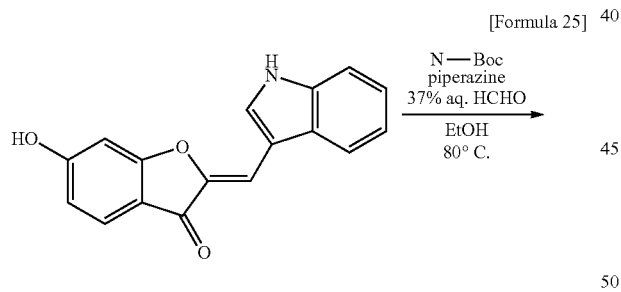
Scheme A4 (Compound A11)
[Formula 25]
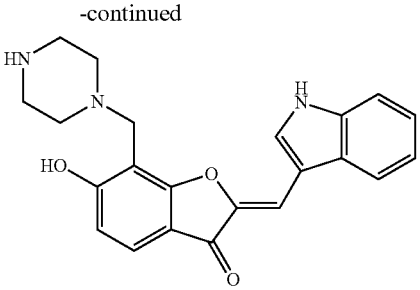
Scheme A5 (Compound A12)
[Formula 26]
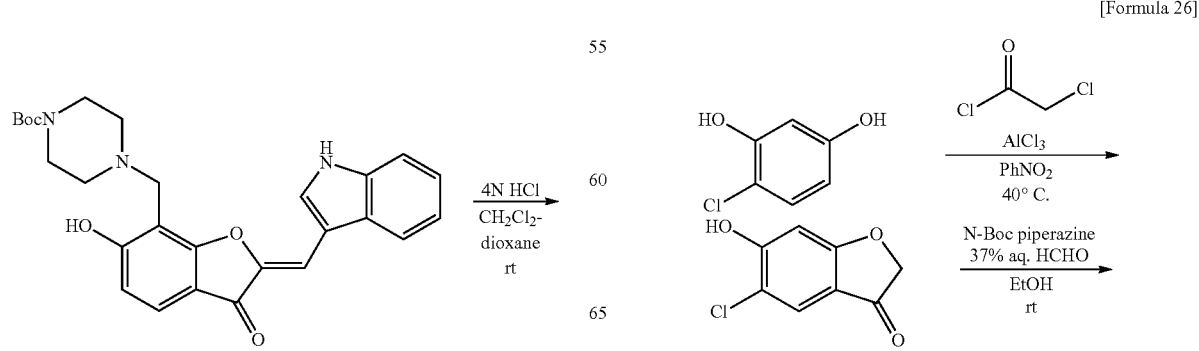

53
-continued
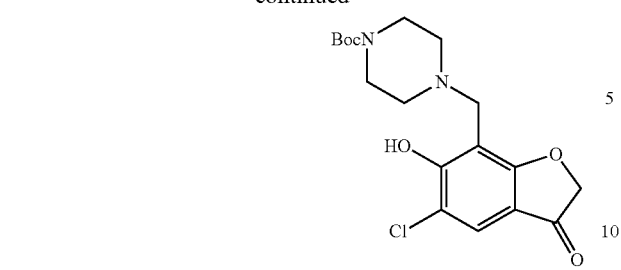
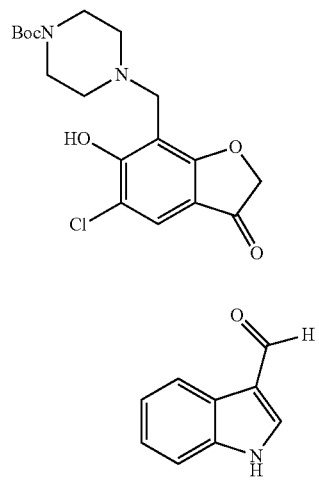
54
-continued
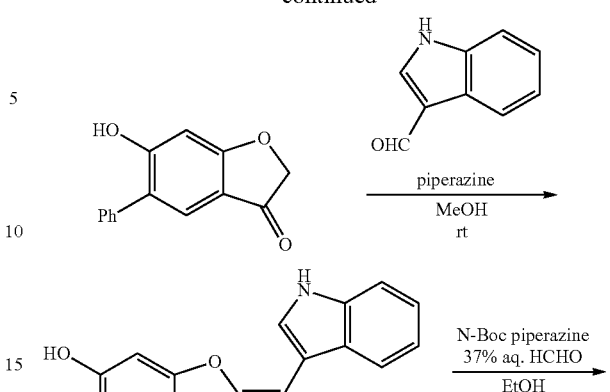
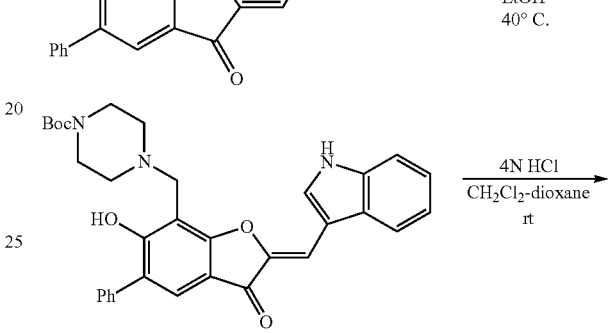
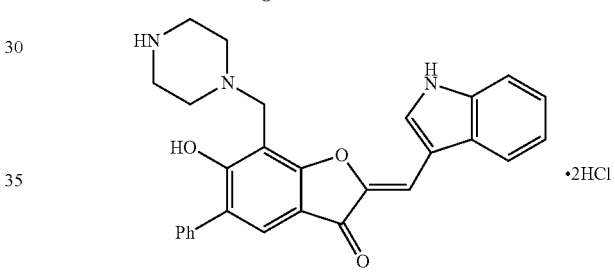
Scheme A7 (Compound A14)
[Formula 28]
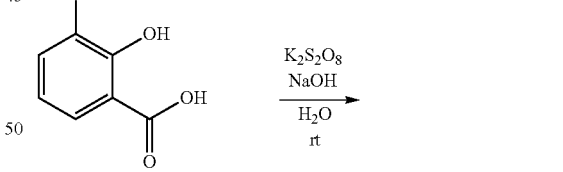
Scheme A6 (Compoound A13)
[Formula 27]
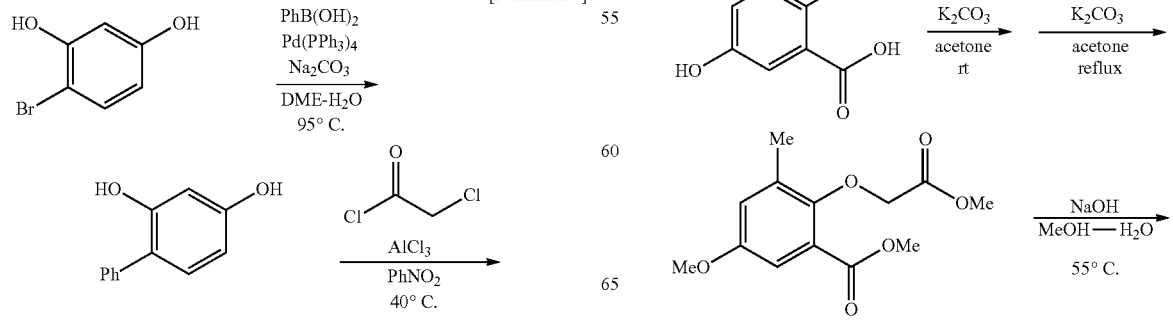

55
-continued
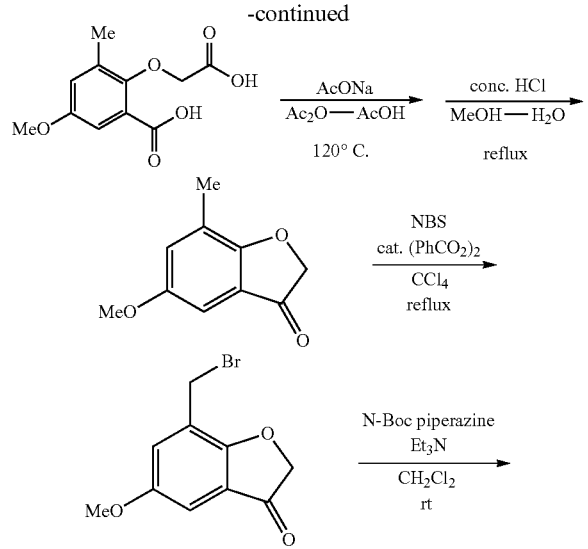
56
-continued
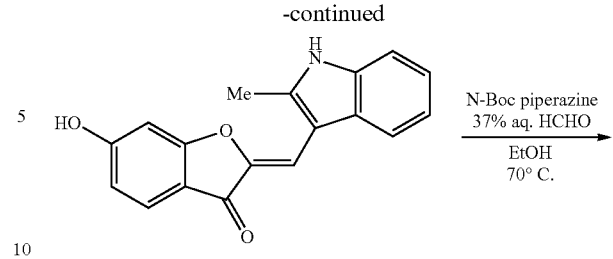
Scheme A9 (Compound A16)
[Formula 30]
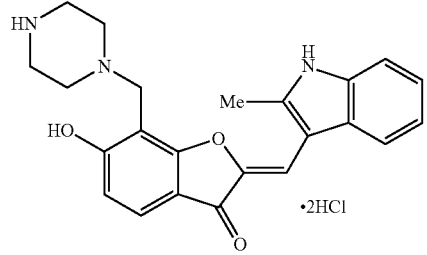
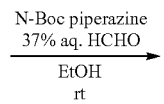
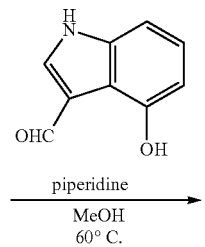
Scheme A8 (Compound A15)
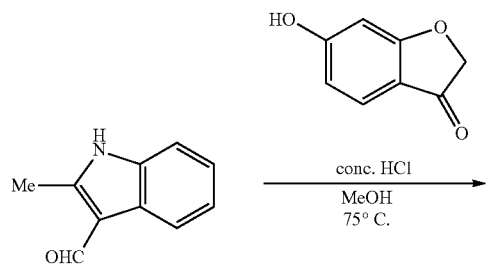
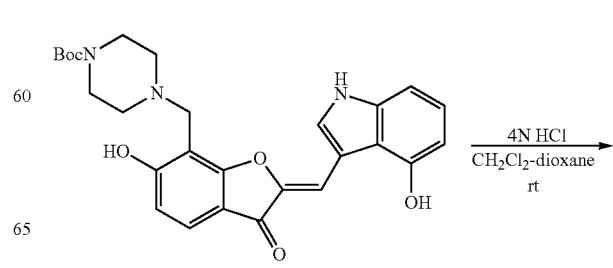

57
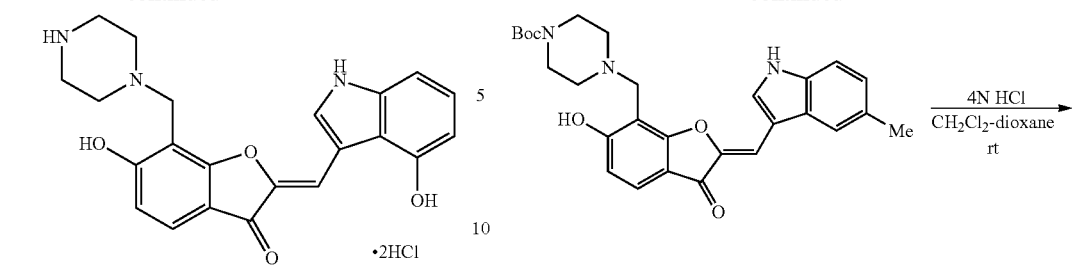
Scheme A10 (Compound A17)
[Formula 31]
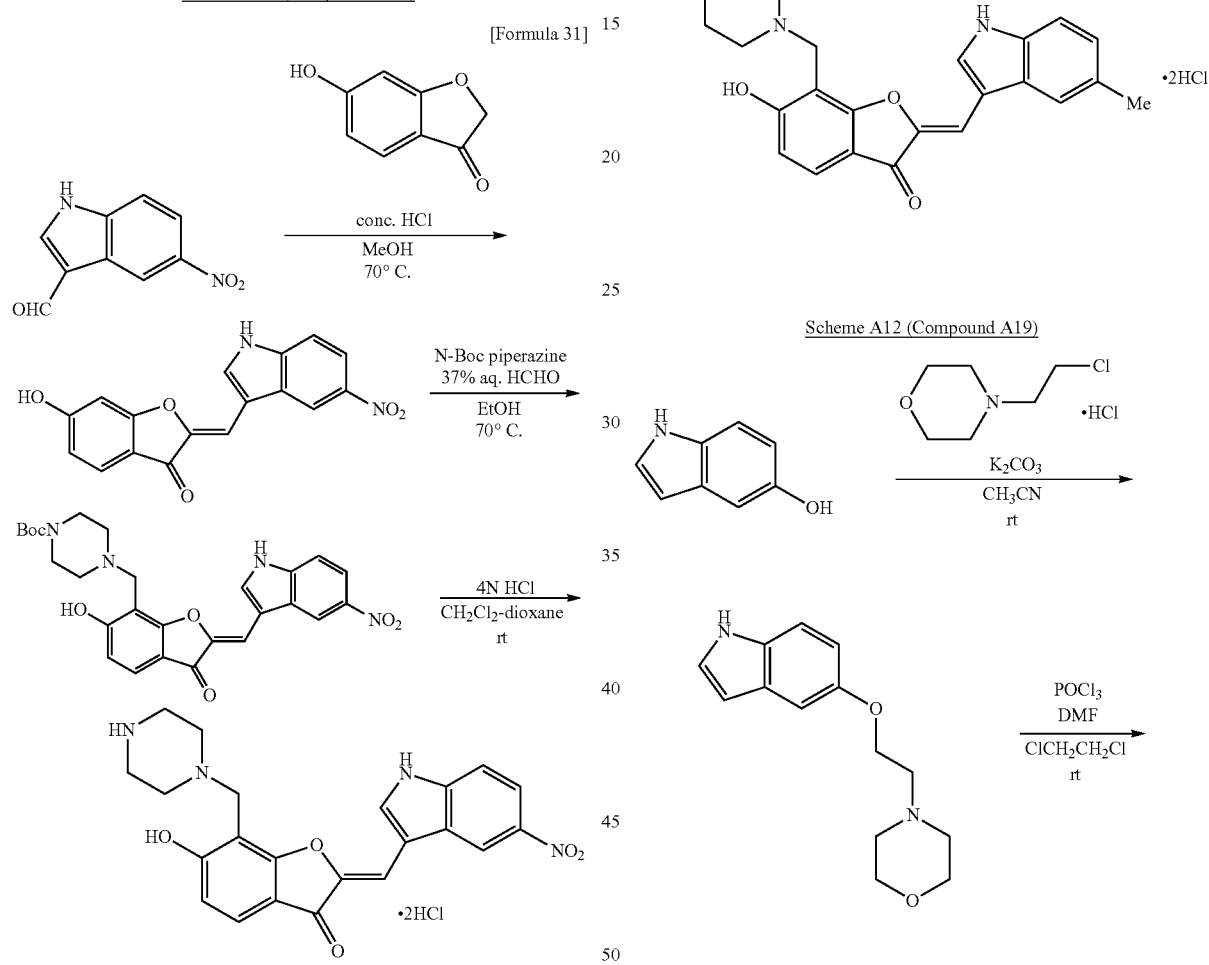
Scheme A11 (Compound A18)
[Formula 32]
58
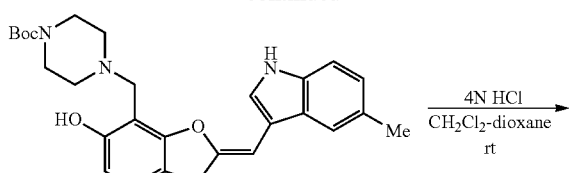
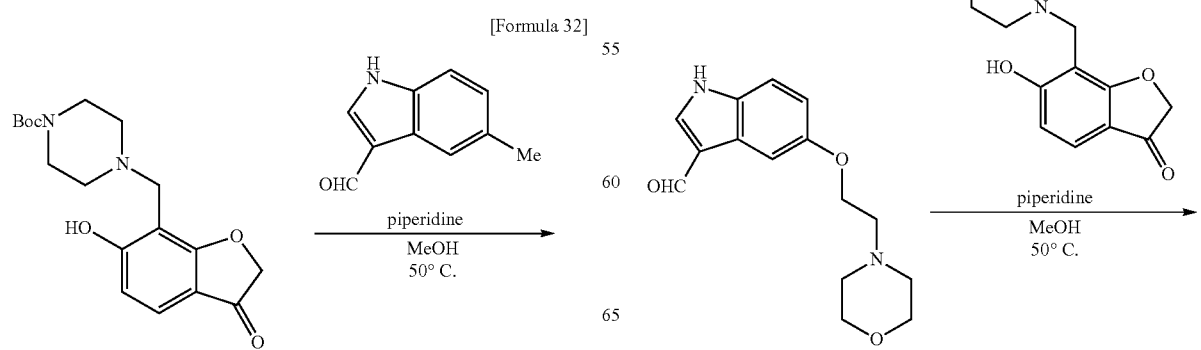
Scheme A12 (Compound A19)

59
-continued
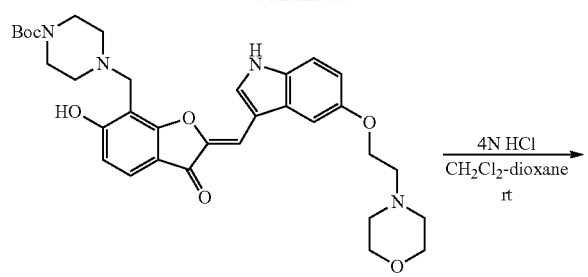
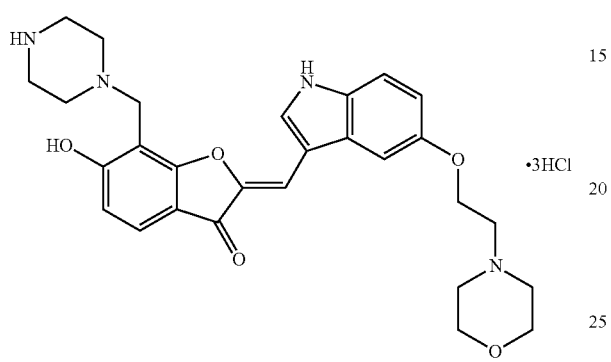
60
-continued
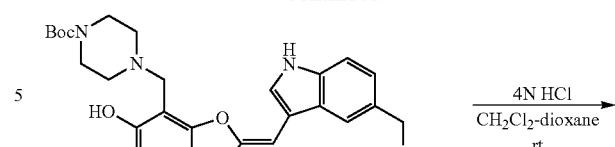
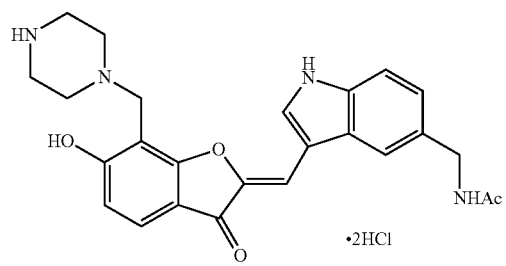
Scheme A14 (Compound A21)
[Formula 35]
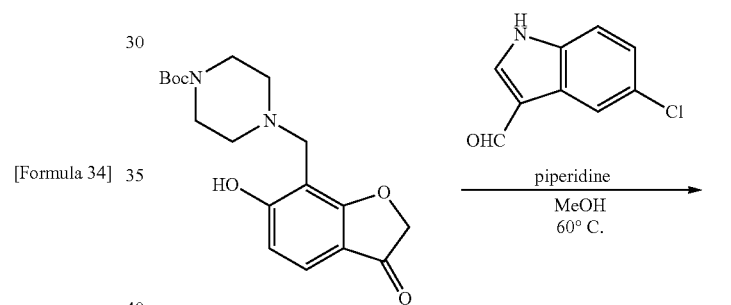
Scheme A13 (Compound A20)
[Formula 34]
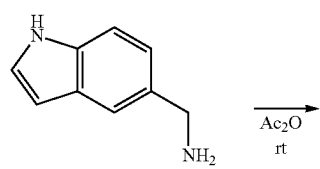
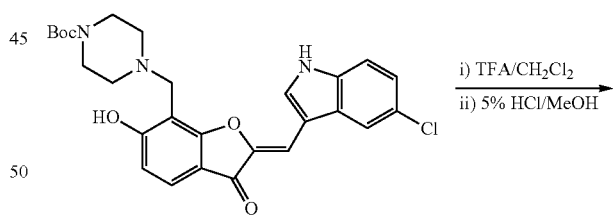
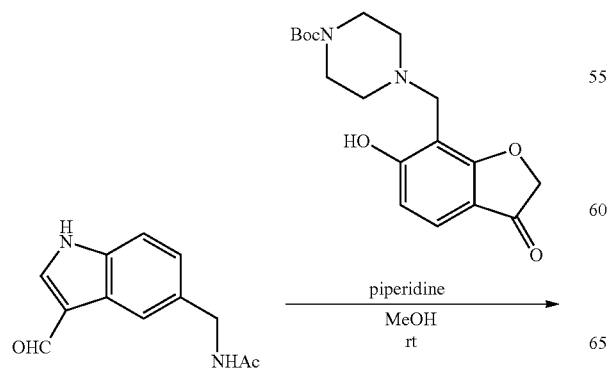
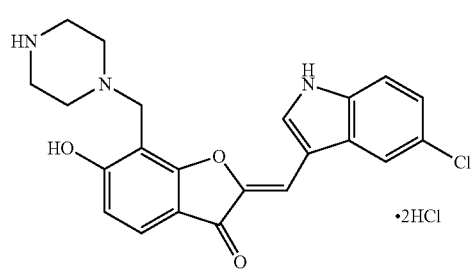

Scheme A15 (Compound A22)
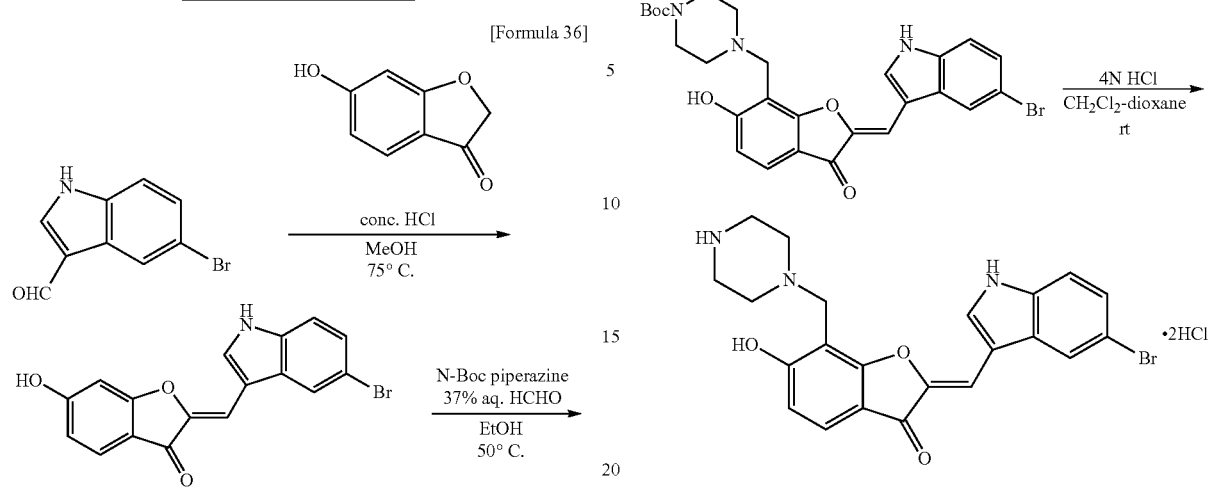
Scheme A16 (Compound A23)
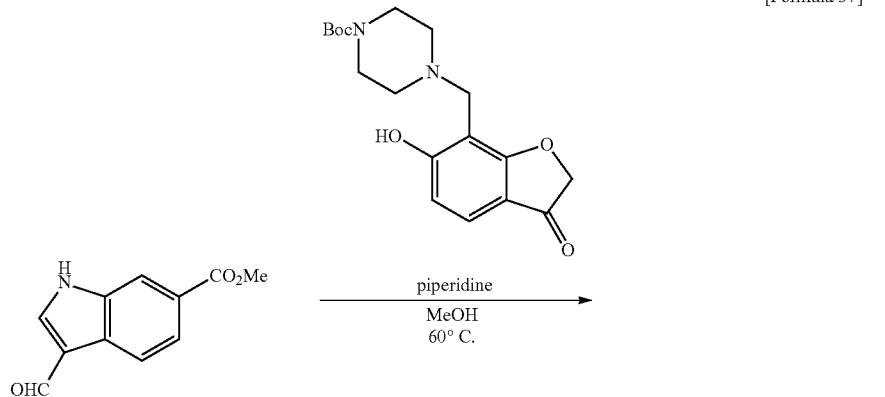
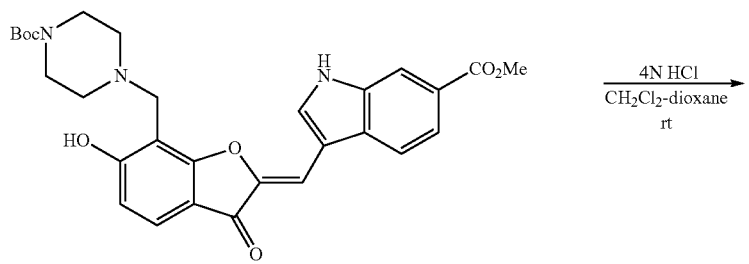
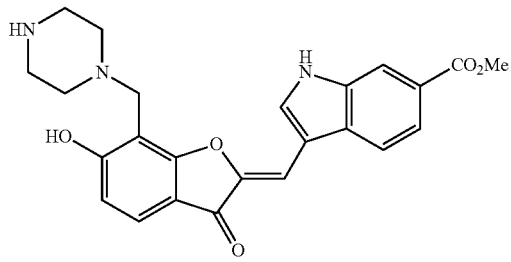

Scheme A17 (Compound A24)
[Formula 38]
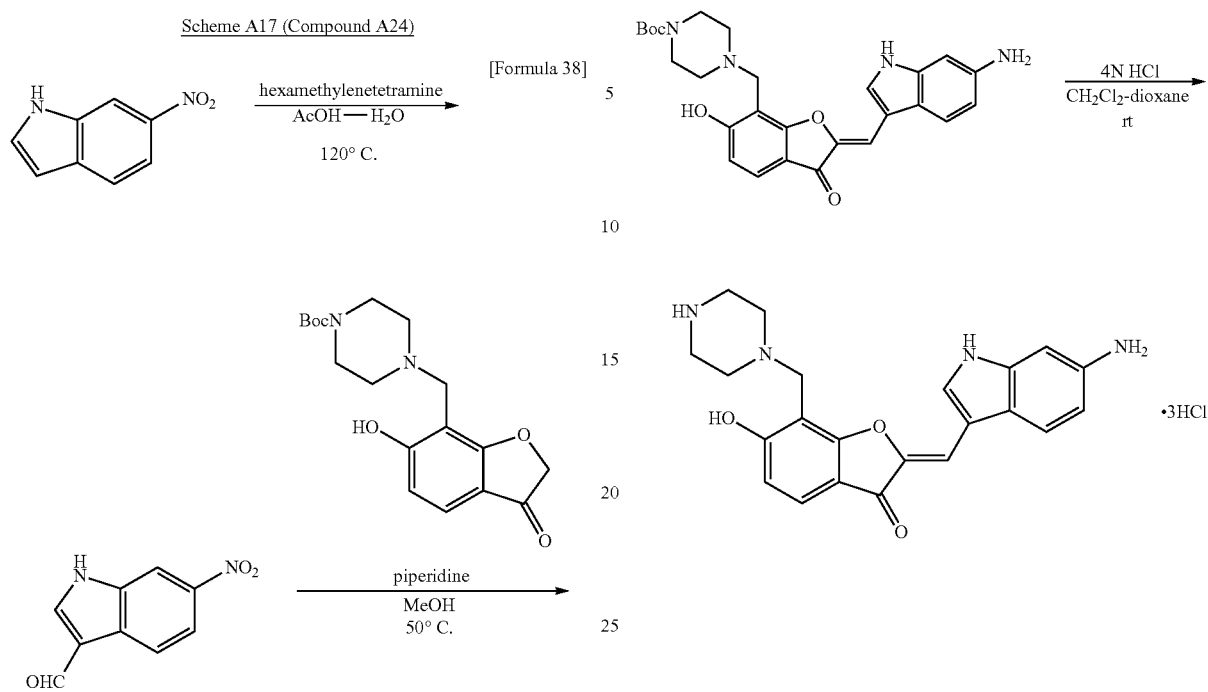
Scheme A18 (Compound A25)
[Formula 39]
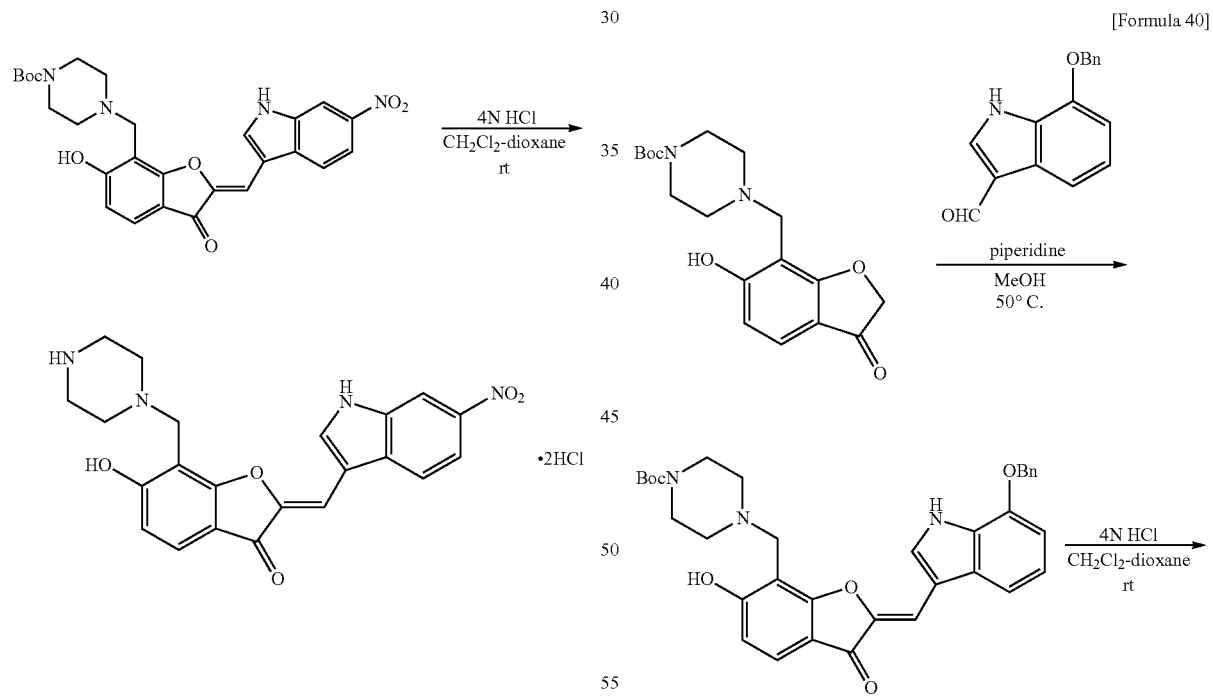
Scheme A19 (Compound A26)
[Formula 40]
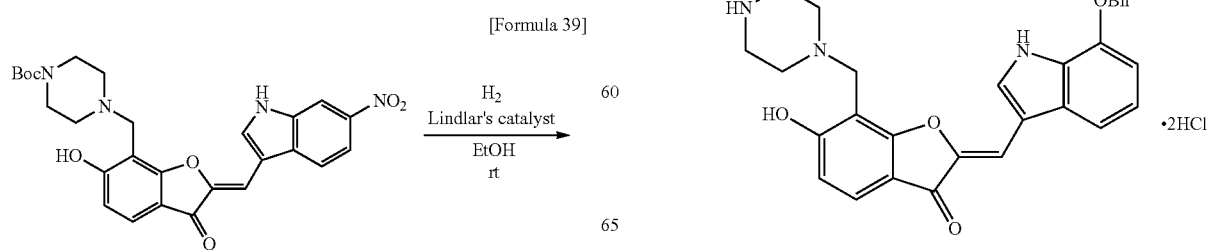

Scheme A20 (Compound A27)
[Formula 41]
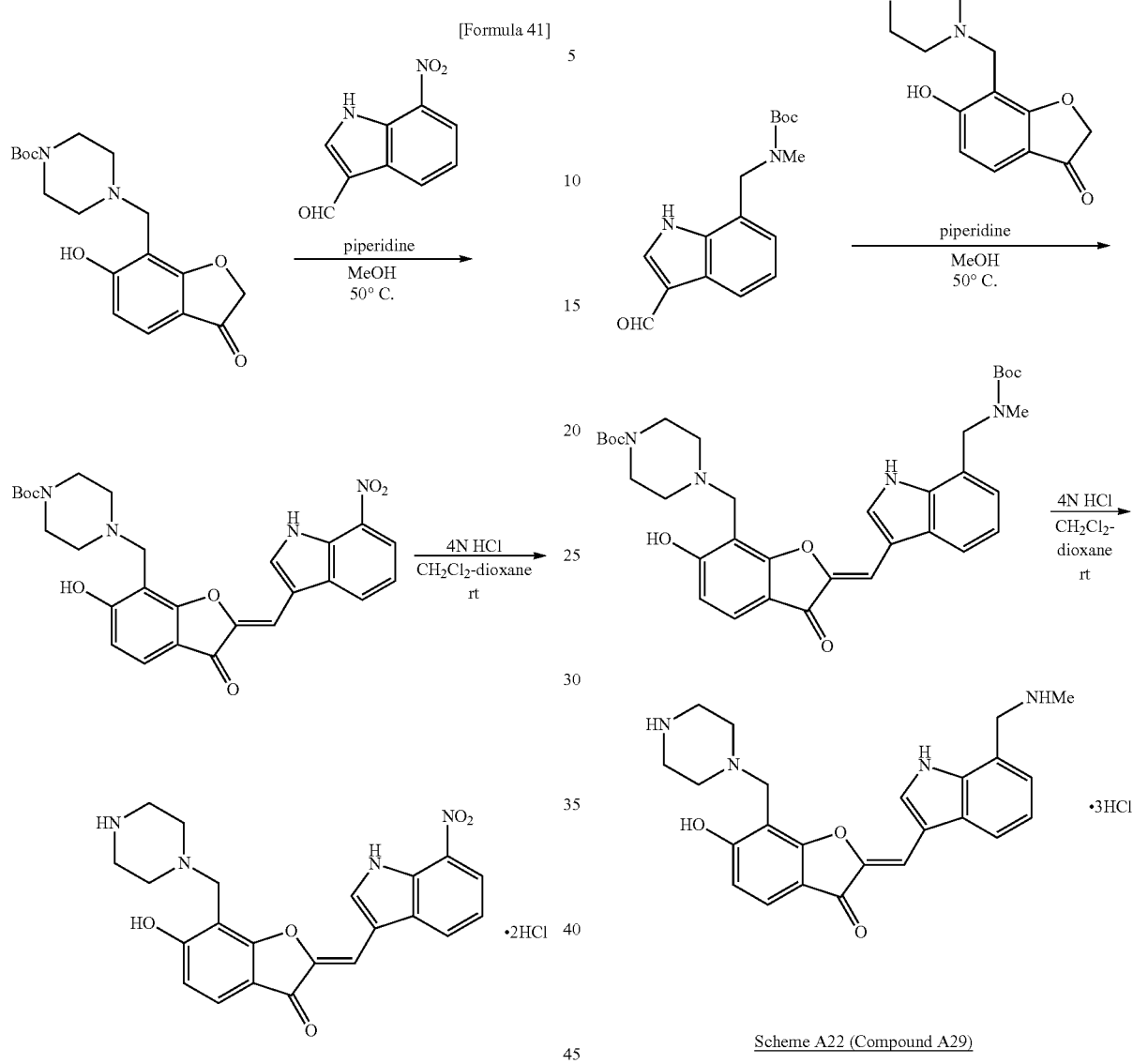
Scheme A21 (Compound A28)
Scheme A22 (Compound A29)
[Formula 43]
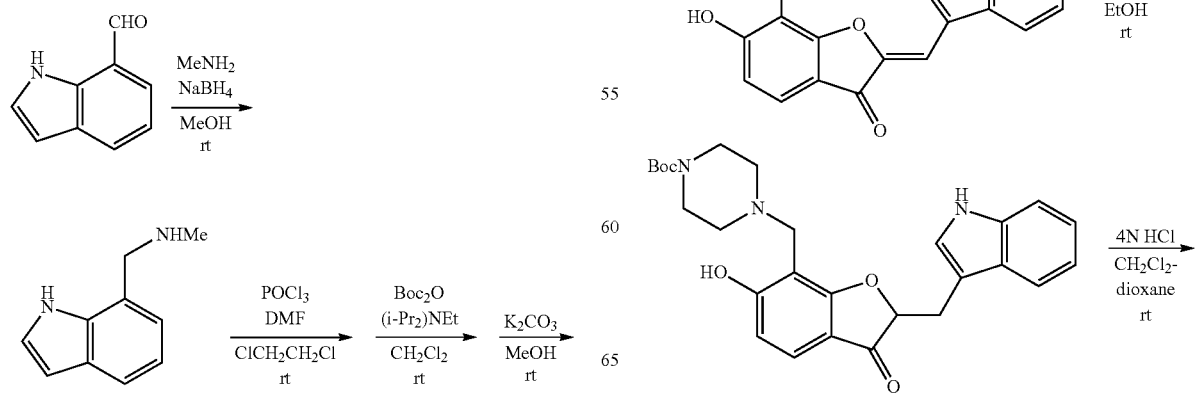

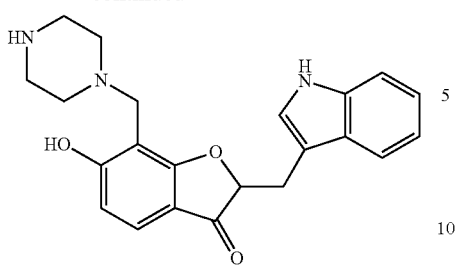
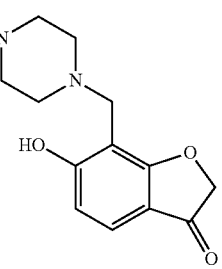
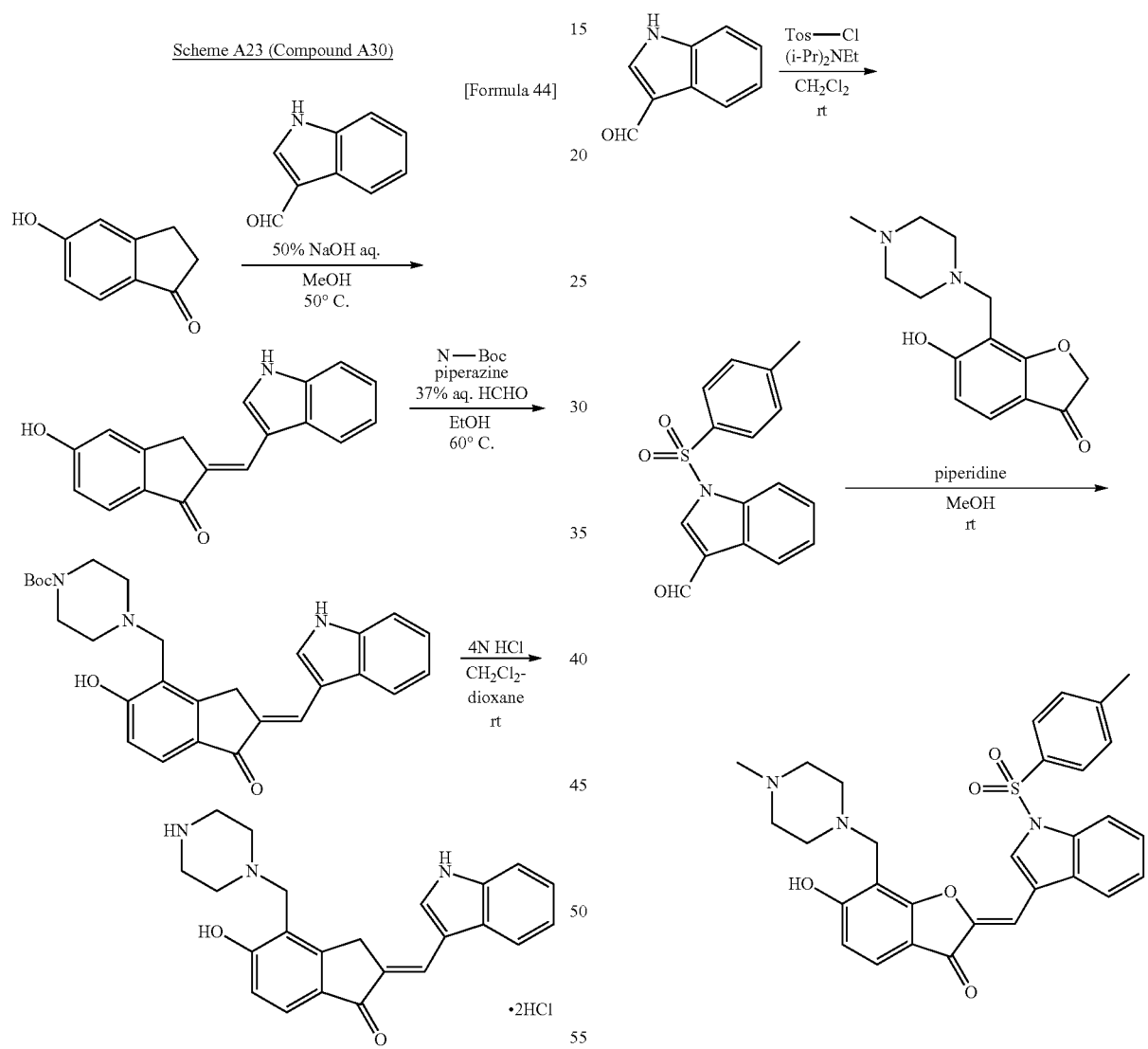

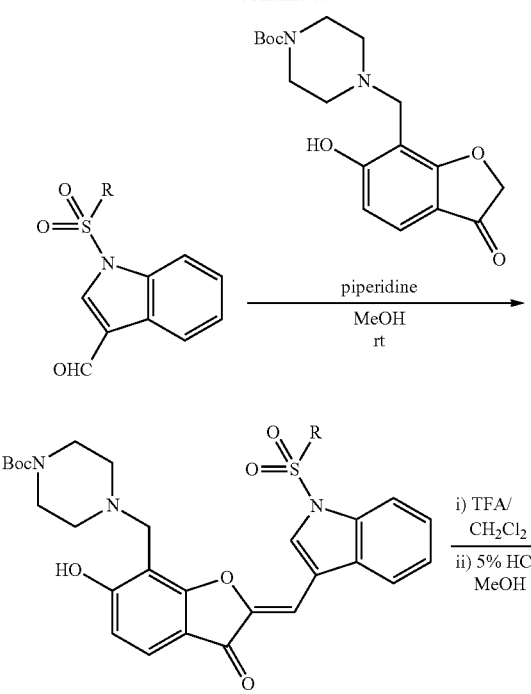
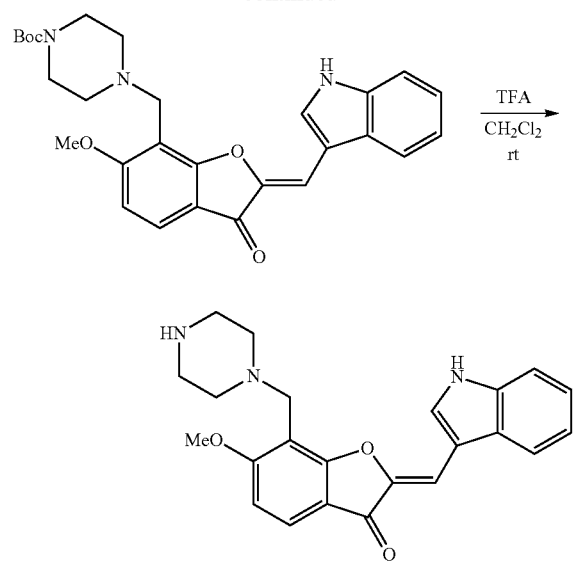
Scheme A26 (Compound A40)
[Formula 47]
Scheme A27 (Compound A41)
[Formula 48]
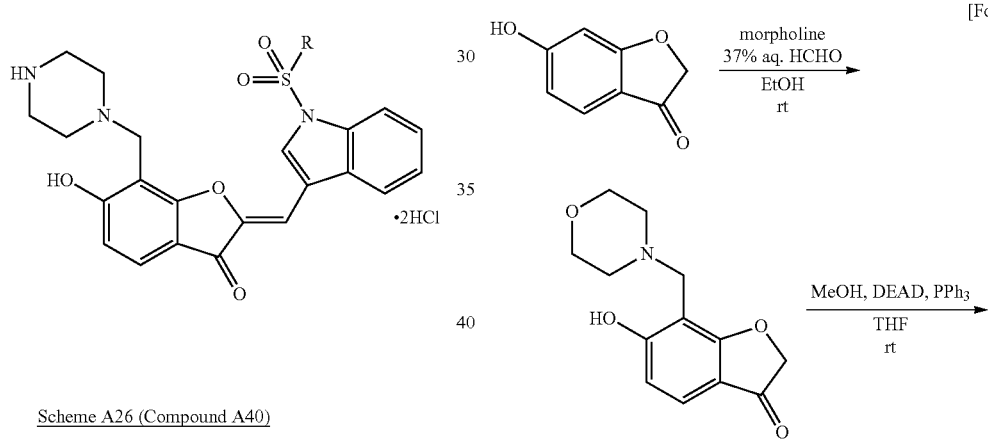
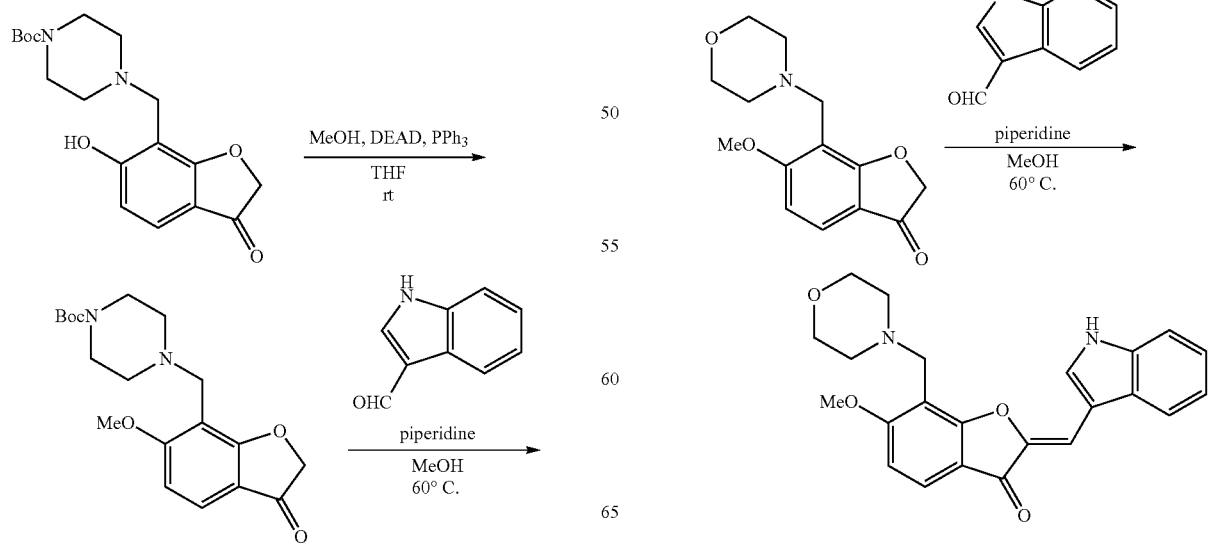

Scheme A28 (Compound A42)
[Formula 49]
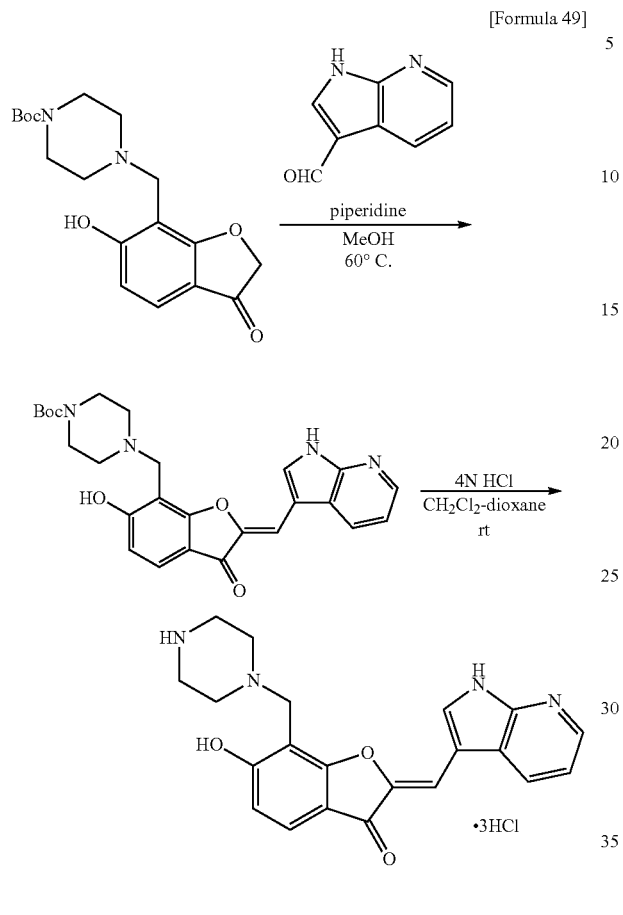
Scheme A29 (Compounds A43 & A44)
[Formula 50]
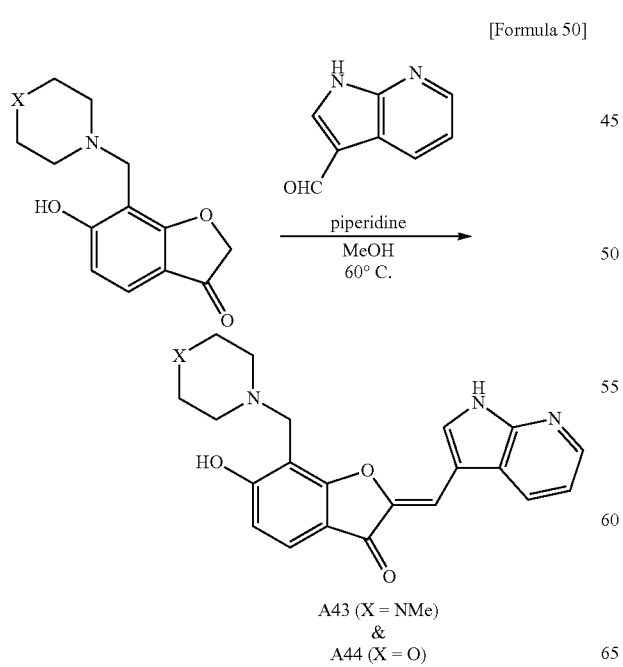
A43 (X = NMe) & A44 (X = O)
Scheme A30 (Compound A45)
[Formula 51]
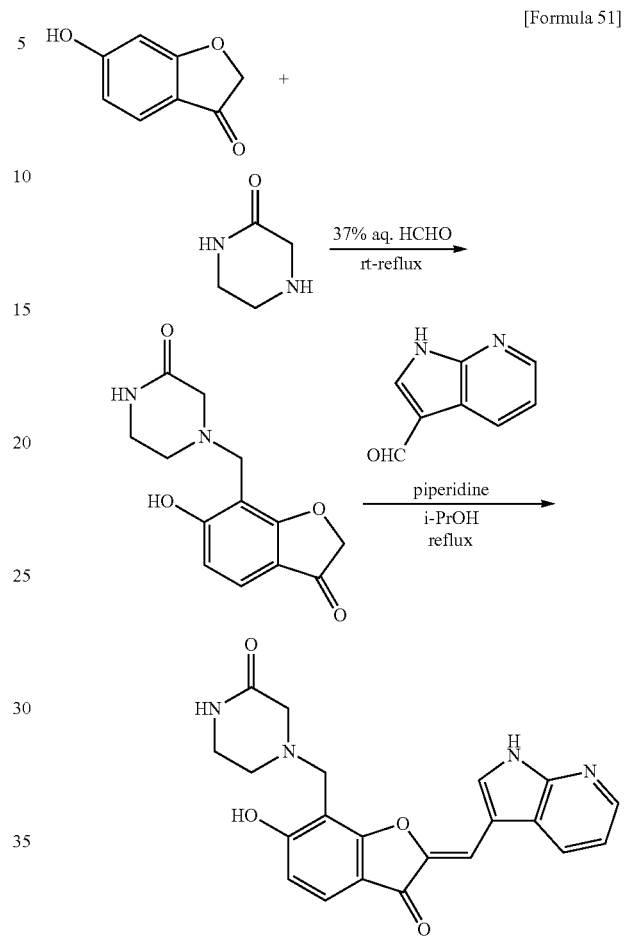
Scheme A31 (Compounds A46 & A47)
[Formula 52]
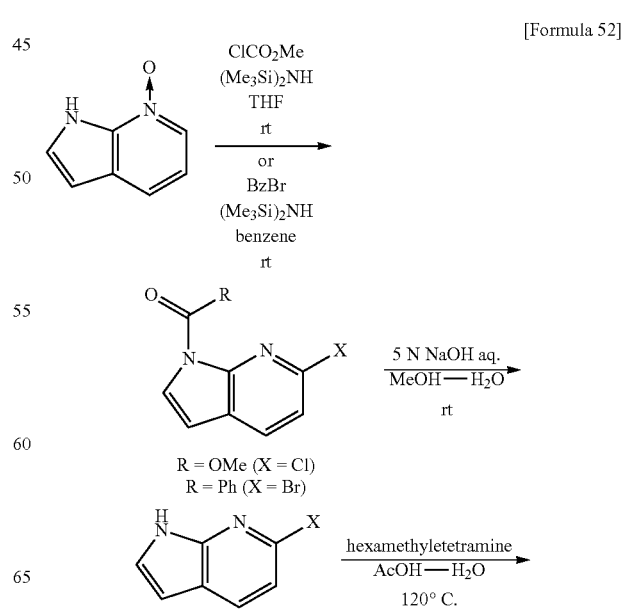

Scheme A32 (Compound A48)

Scheme A33 (Compound A50)

[Formula 53]

[Formula 54]

A46 (X = Cl)
&
A47 (X = Br)

75
-continued
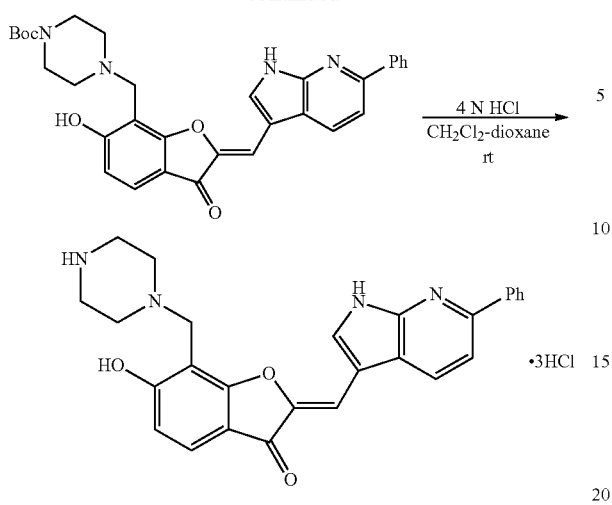
Scheme A34 (Compound A50)
[Formula 55]
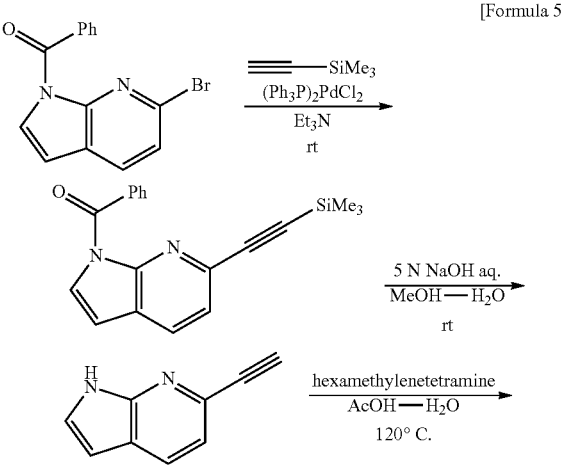
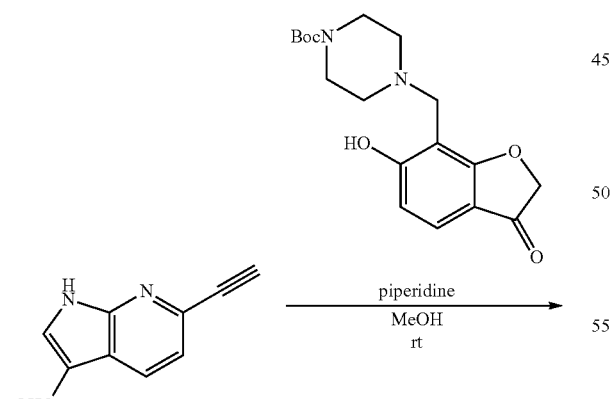
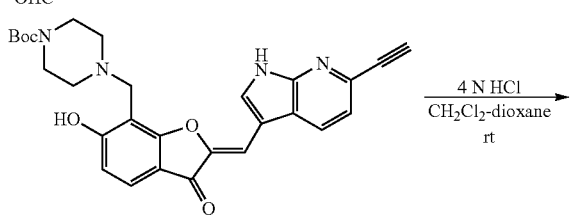
76
-continued
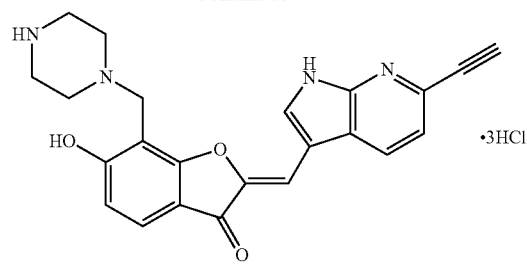
Scheme A35 (Compound A51)
[Formula 56]
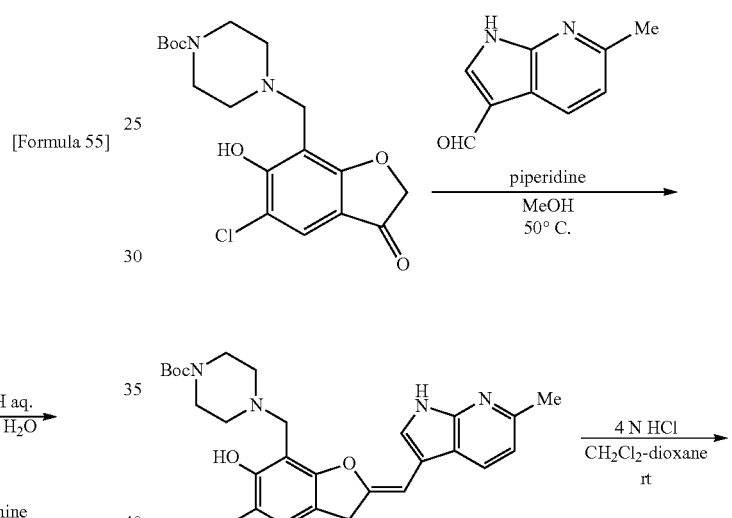
Scheme A36 (Compound A52)
[Formula 57]
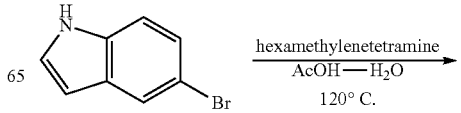

77
-continued
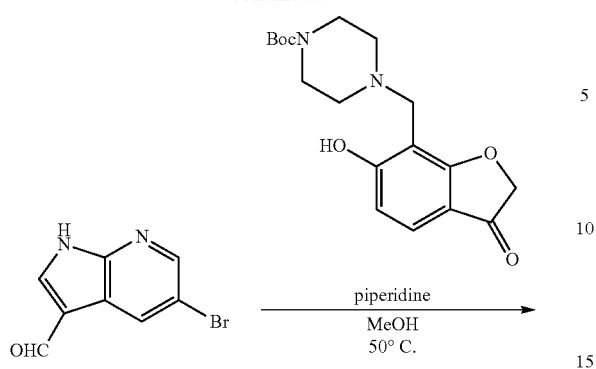
78
-continued
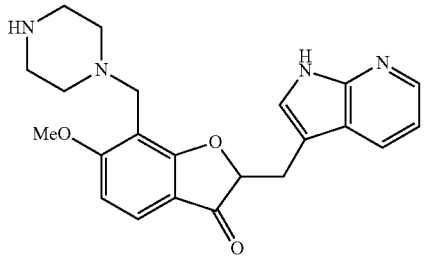
Scheme A38 (Compound A54)
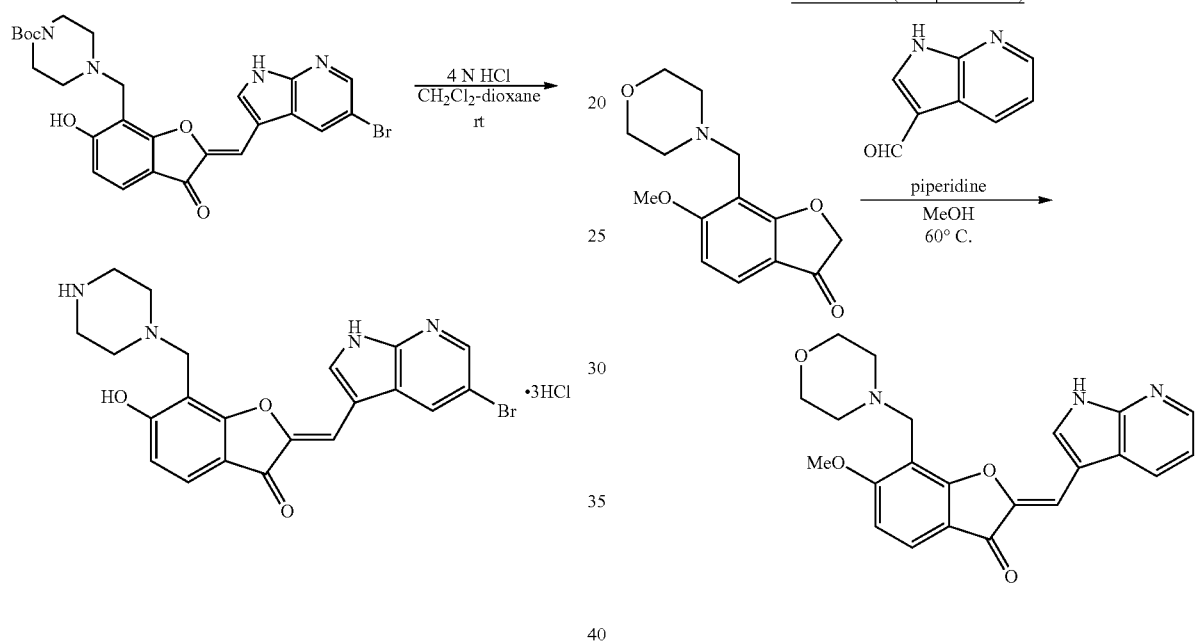
Scheme A37 (Compound A53)
[Formula 58]
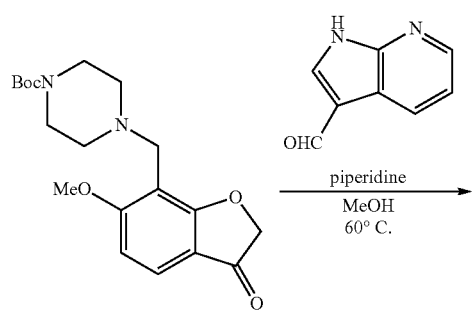
Scheme A39 (Compound A55)
[Formula 59]
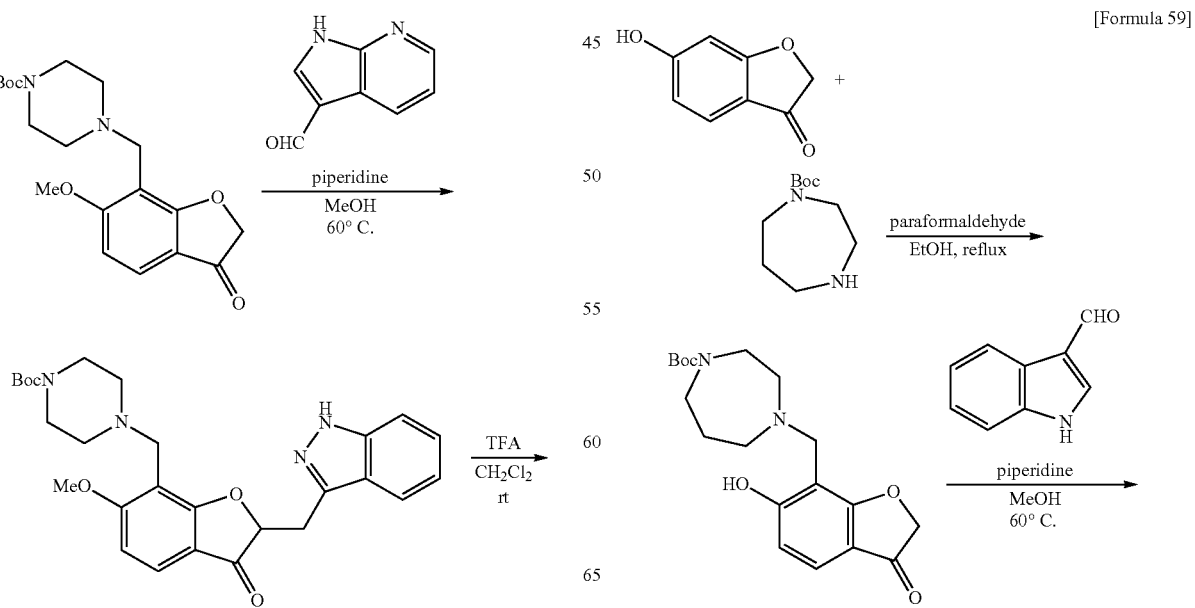

79
-continued
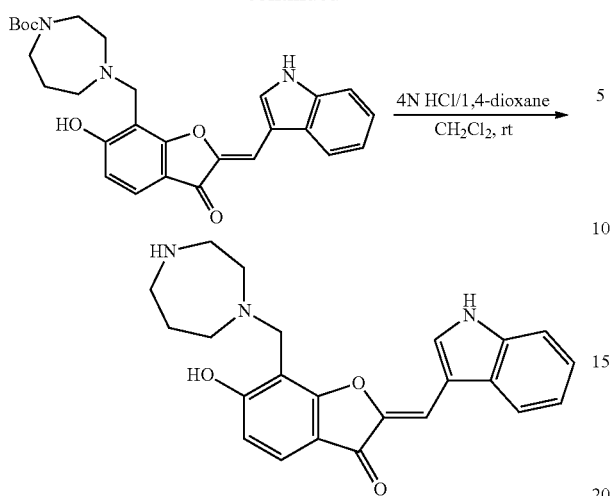
Scheme A40 (Compound A56)
[Formula 60]
80
-continued
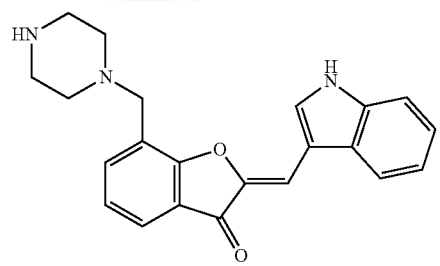
Scheme A41 (Compound A57)
[Formula 61]
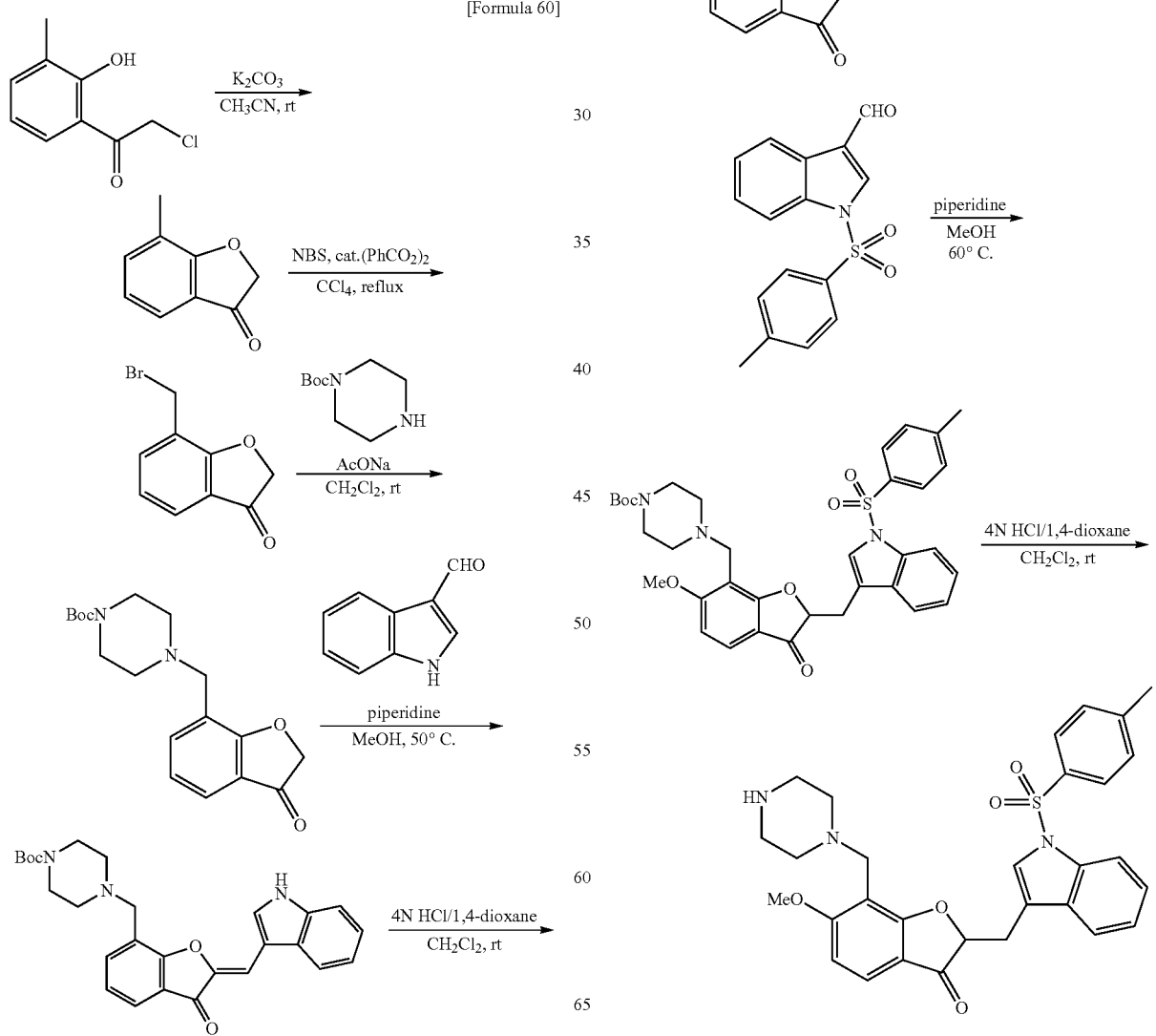

81
Scheme A42 (Compound A58)
[Formula 62]
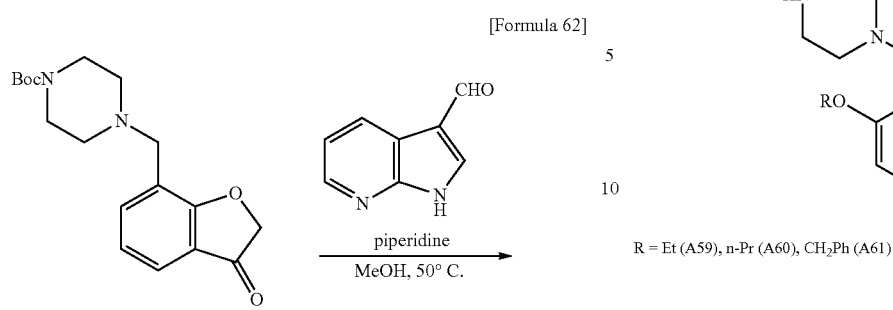
Scheme A43 (Compounds A59-A61)
[Formula 63]
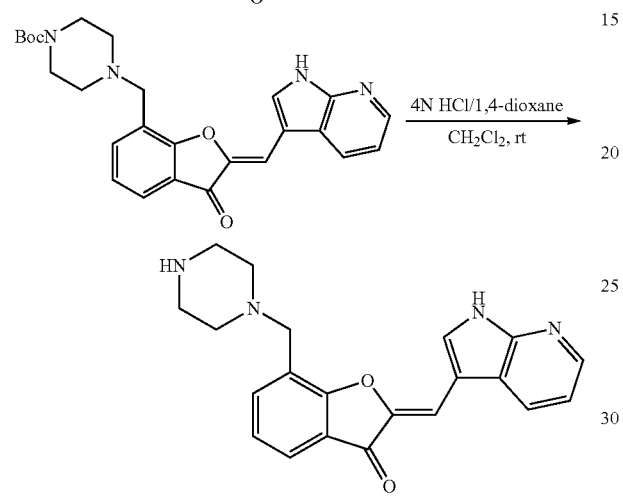
82
-continued
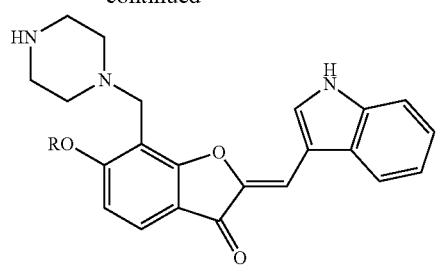
R = Et (A59), n-Pr (A60), CH$_2$Ph (A61)
Scheme B1 (Compounds B1-B6)
[Formula 64]
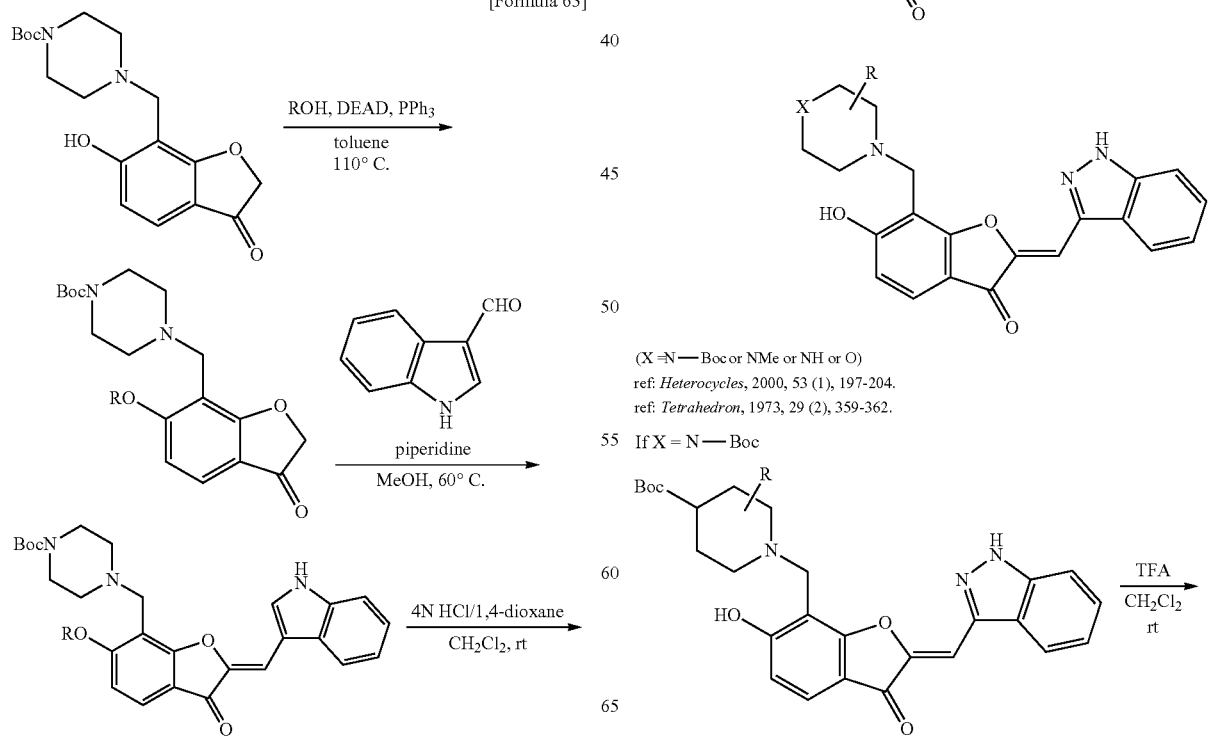
(X = N—Boc or NMe or NH or O)
ref: *Heterocycles*, 2000, 53 (1), 197-204.
ref: *Tetrahedron*, 1973, 29 (2), 359-362.
If X = N—Boc -continued
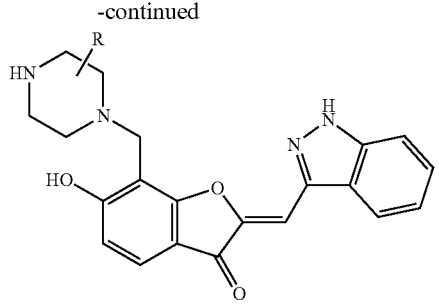
ref: 'Protective Groups in Organic Synthesis: Fourth Edition', Wiley-Interscience, 2007
Scheme B2 (Compound B7)
[Formula 65]
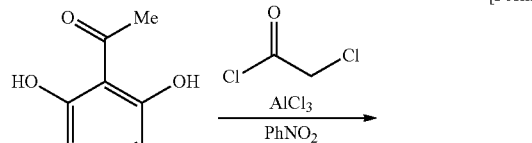
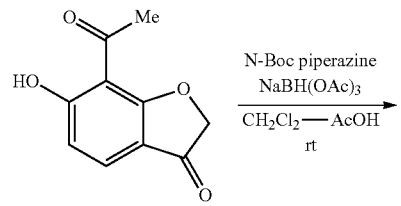
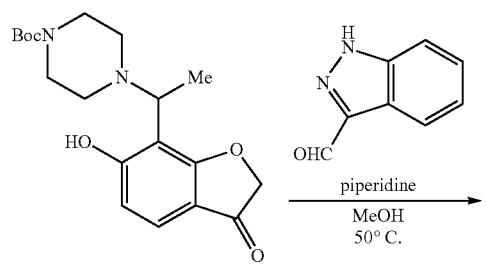
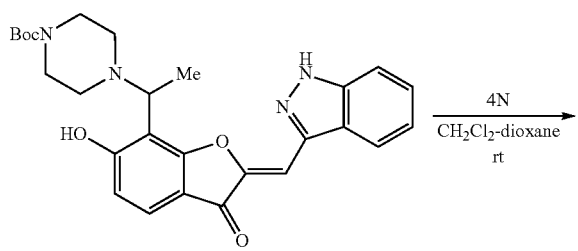
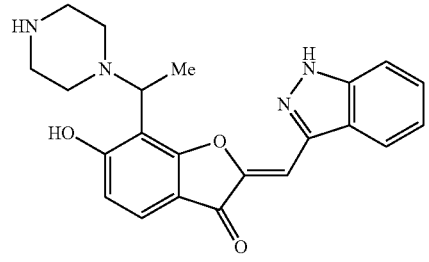
ref: Yakugaku Zasshi, 1968, 88 (5), 589-592.
Scheme B3 (Compounds B8-B12)
[Formula 66]
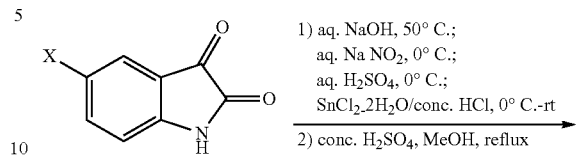
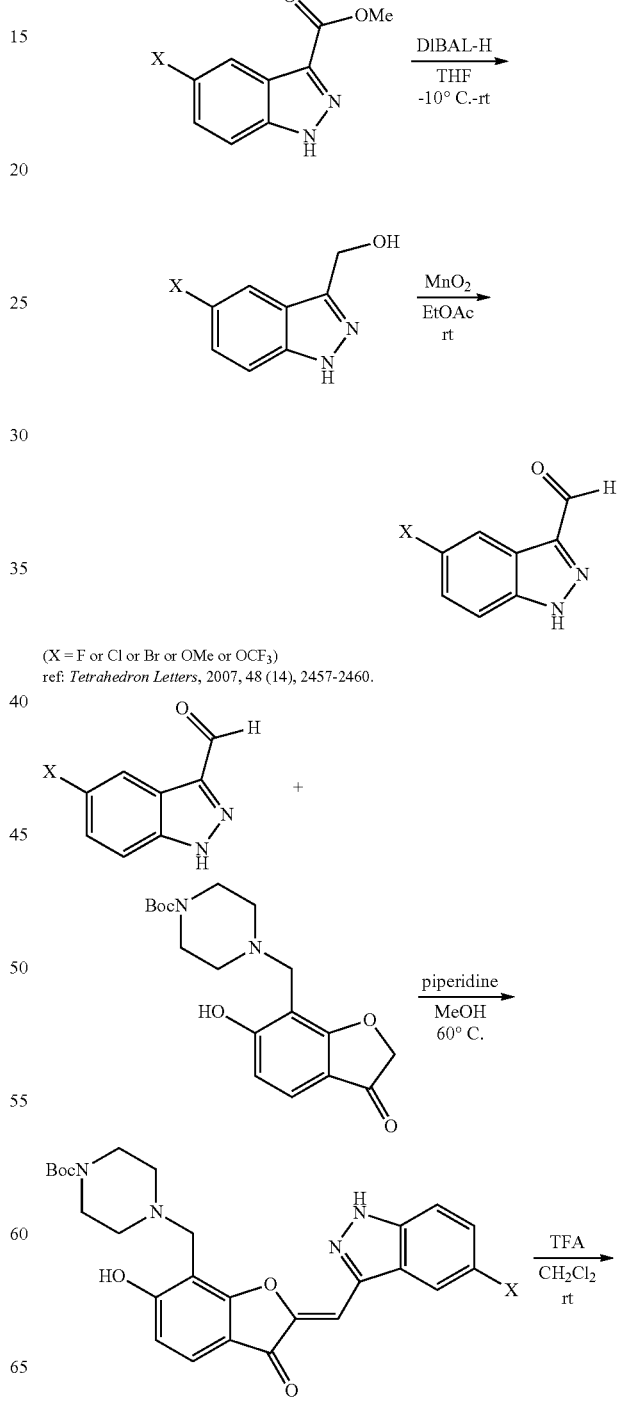
(X = F or Cl or Br or OMe or $OCF_3$)
ref: Tetrahedron Letters, 2007, 48 (14), 2457-2460.

85
-continued
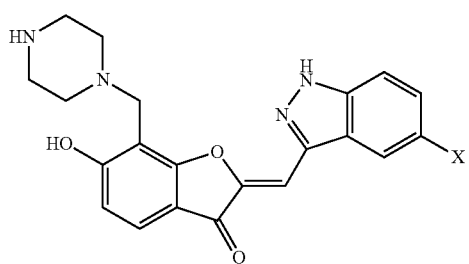
86
-continued
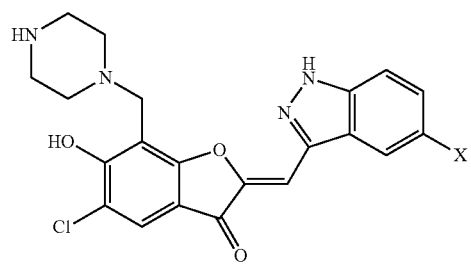
(X = H or F or Cl or Br)
Scheme B4 (Compounds B13-B16)
[Formula 67]
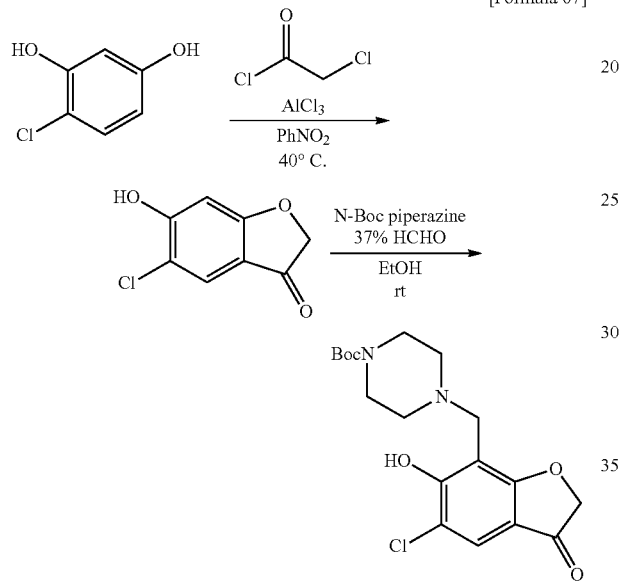
Scheme B5 (Compounds B17-B33)
[Formula 68]
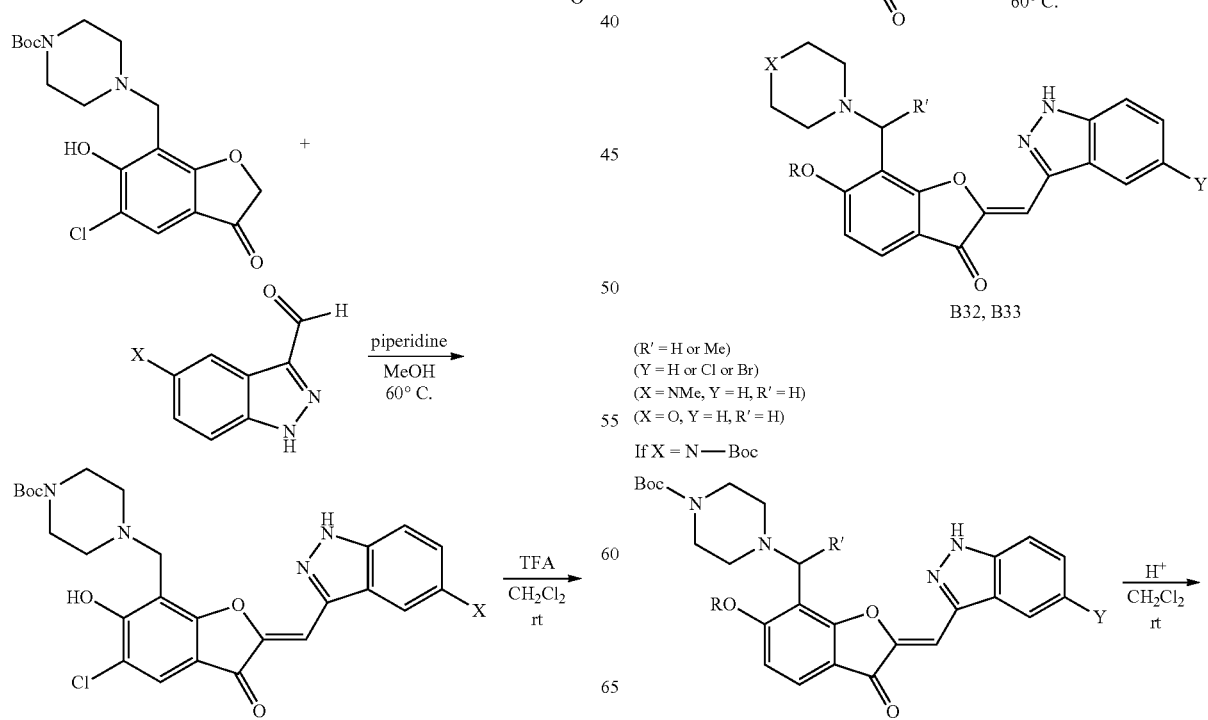
B32, B33
(R' = H or Me)
(Y = H or Cl or Br)
(X = NMe, Y = H, R' = H)
(X = O, Y = H, R' = H)
If X = N—Boc

87
-continued
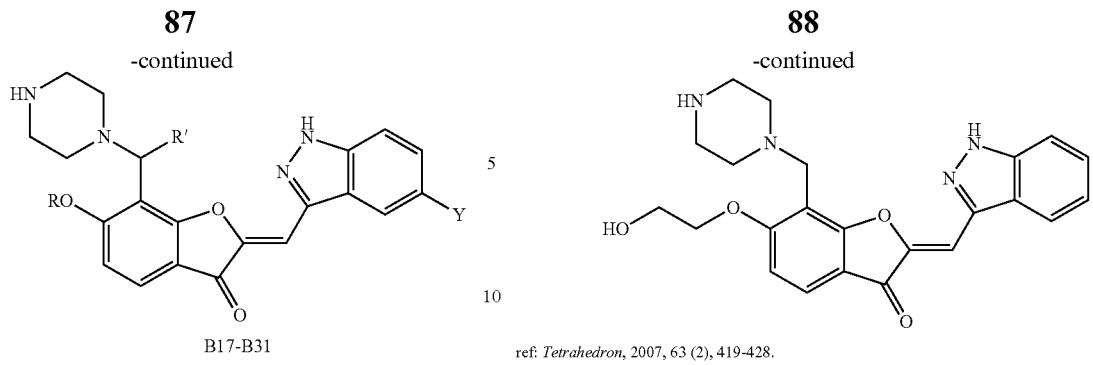
B17-B31
88
-continued
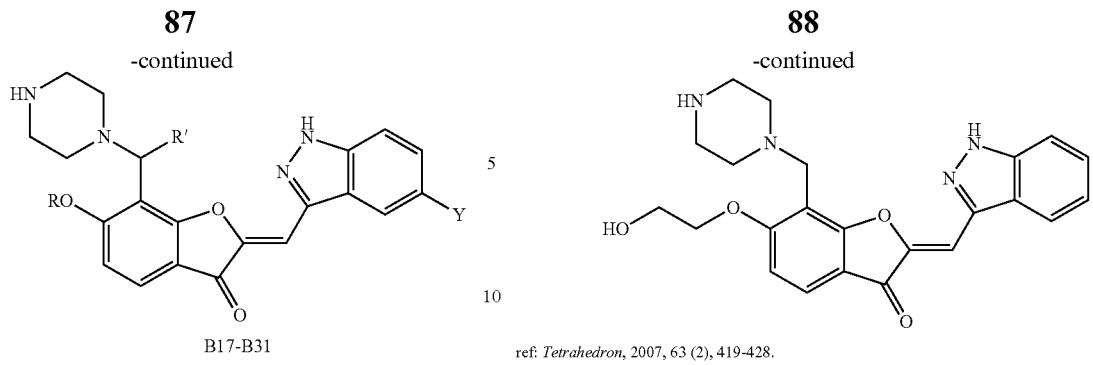
ref: *Tetrahedron*, 2007, 63 (2), 419-428.
Scheme B6 (Compound B34)
[Formula 69]
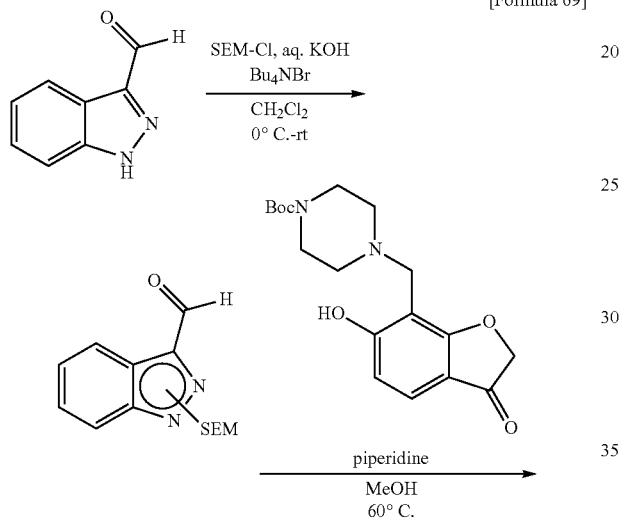
Scheme B7 (Compound B35)
[Formula 70]
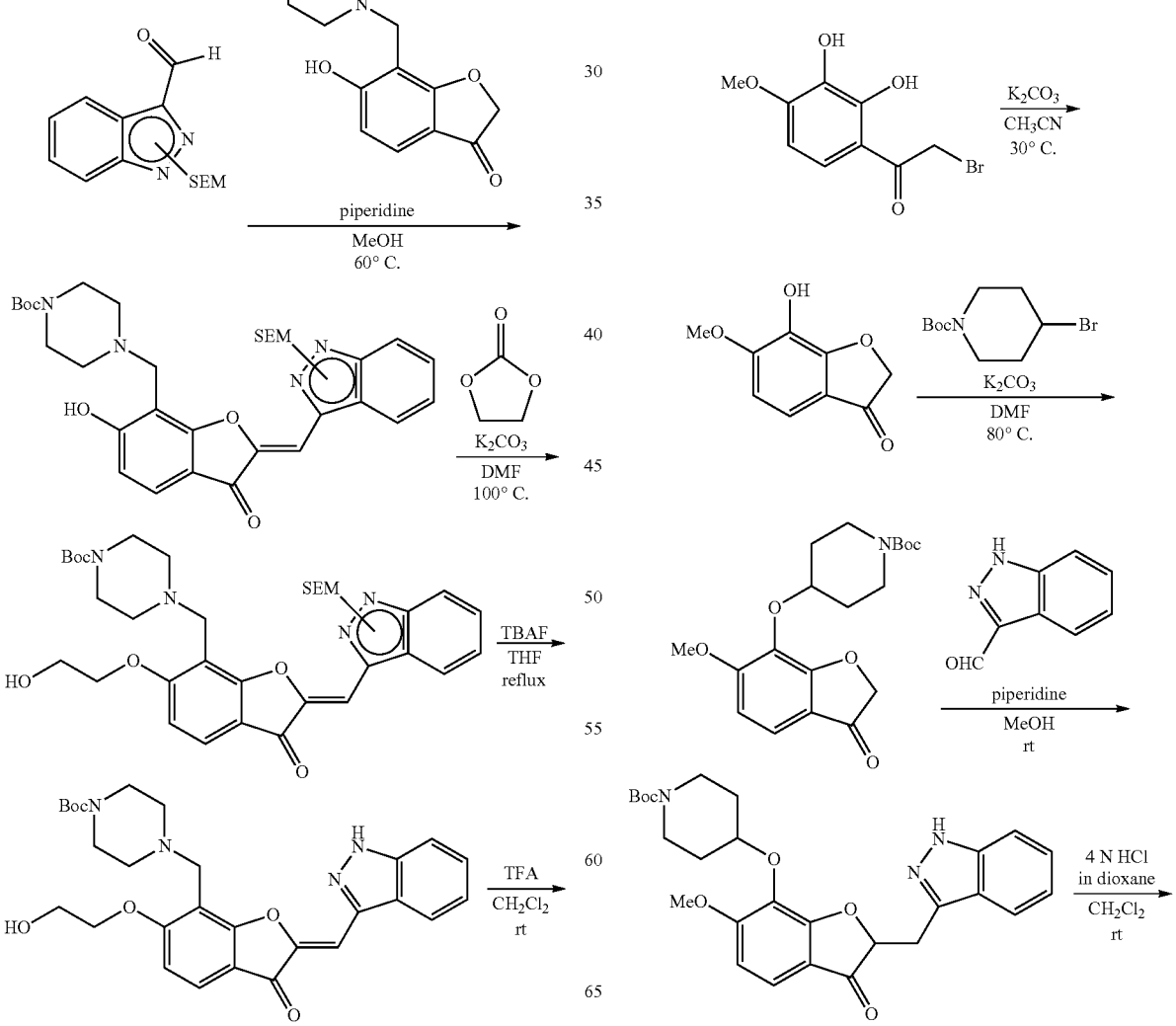

89
-continued
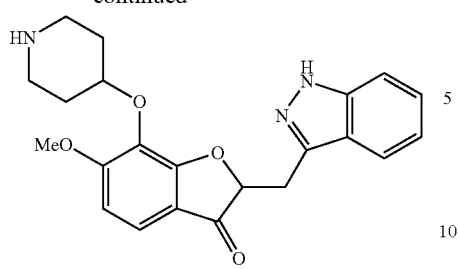
90
-continued
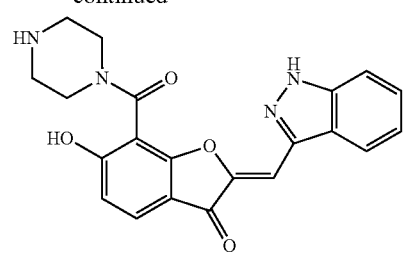
Scheme B8 (Compound B36)
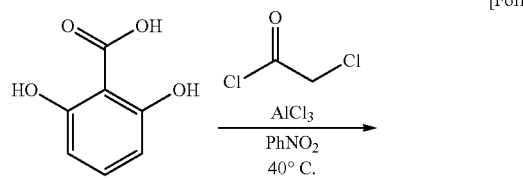
[Formula 71]
Scheme B9 (Compound B37)
[Formula 72]
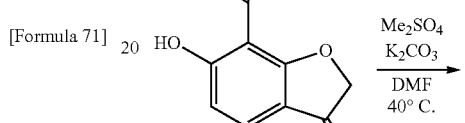
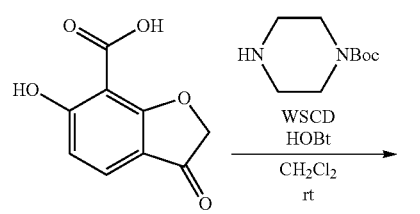
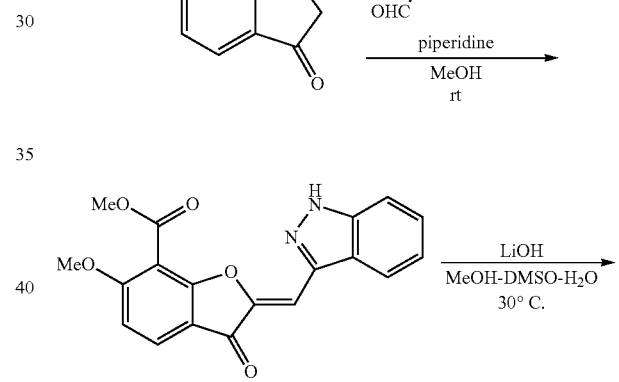
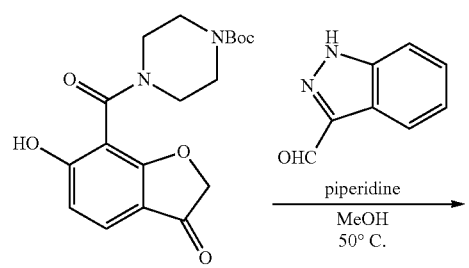
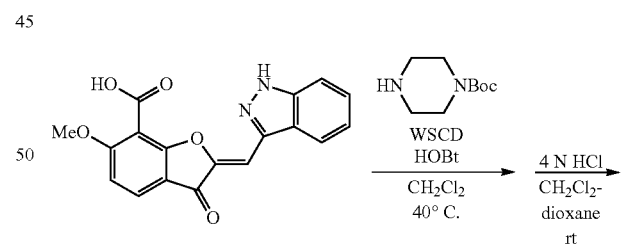
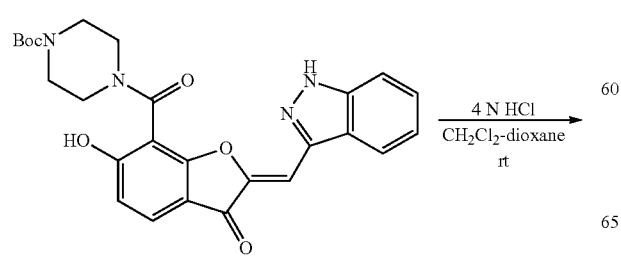
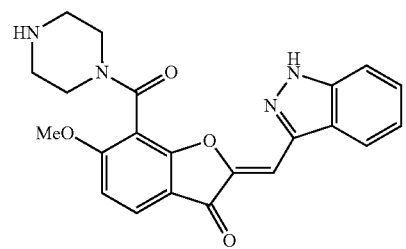

Scheme B10 (Compound B38)
[Formula 73]
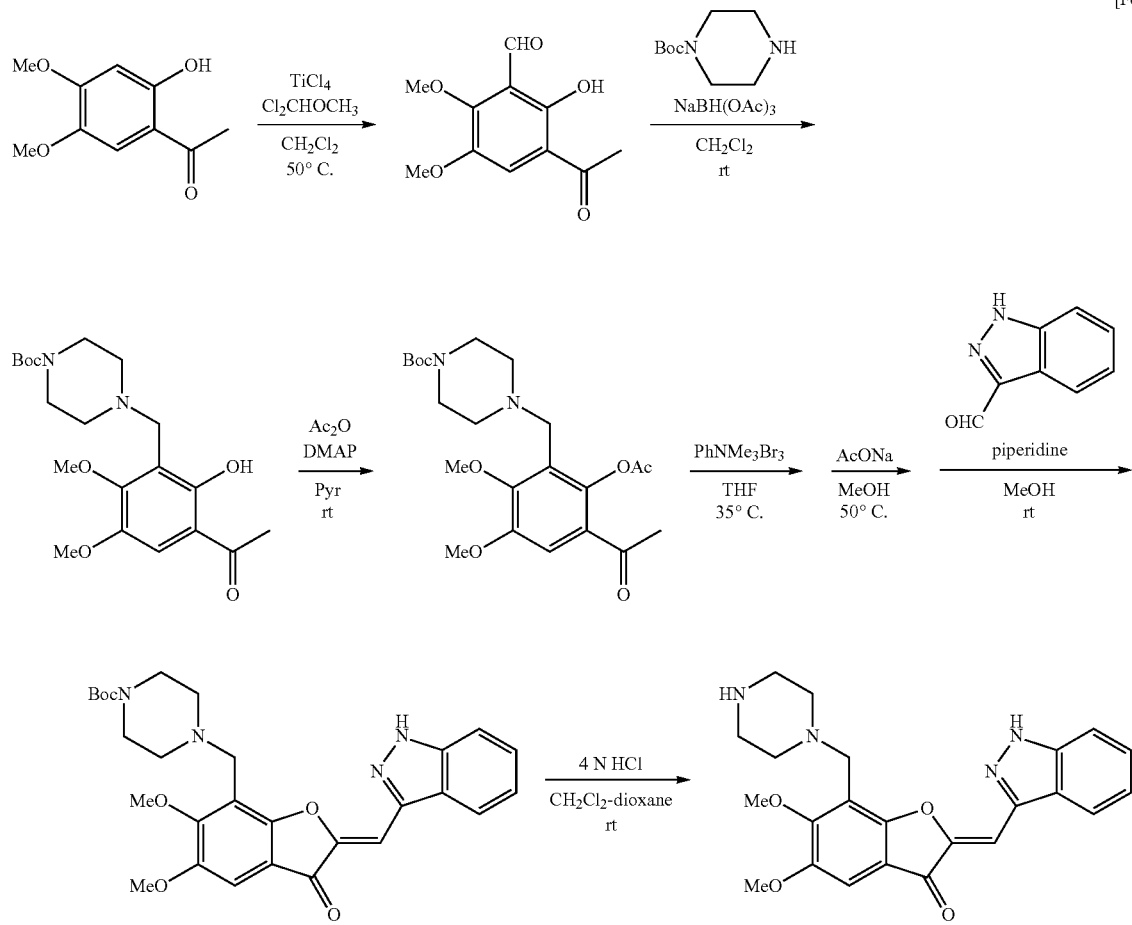
40
Scheme B11 (Compound B39)
[Formula 74]
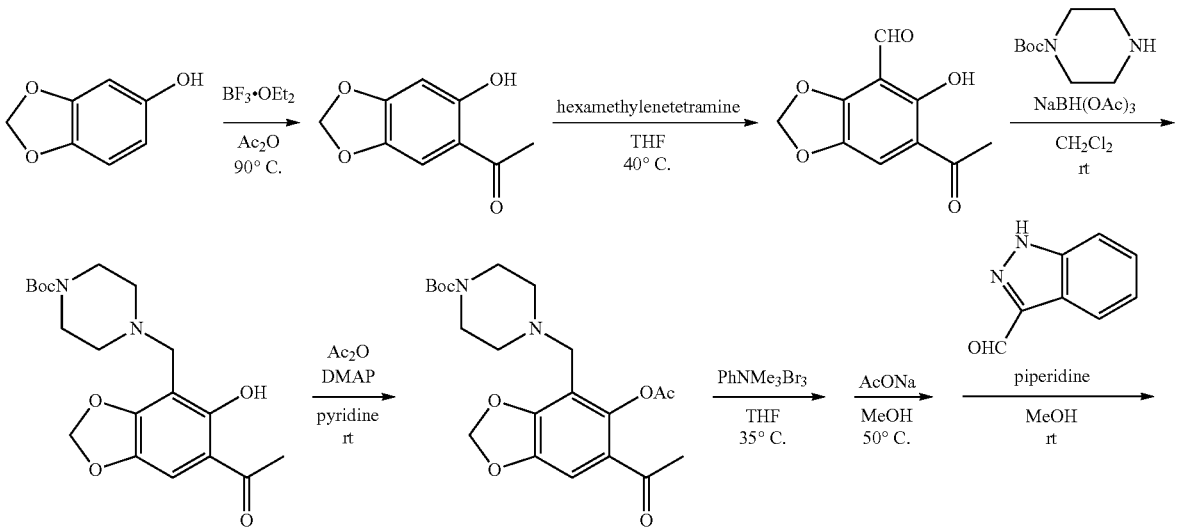

93 94
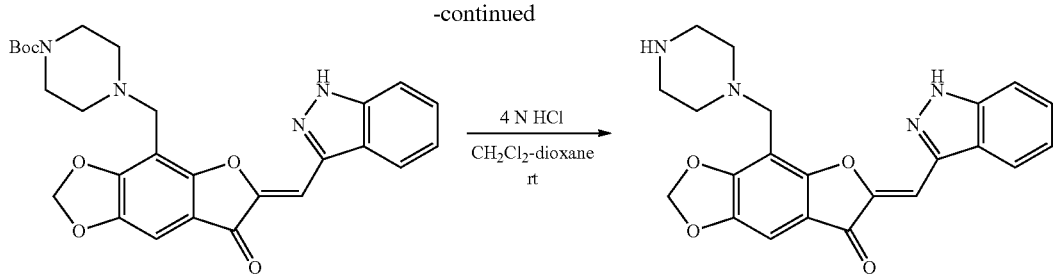
-continued
Scheme B12 (Compound B40)
[Formula 75]
-continued
Scheme B13 (Compound B41)
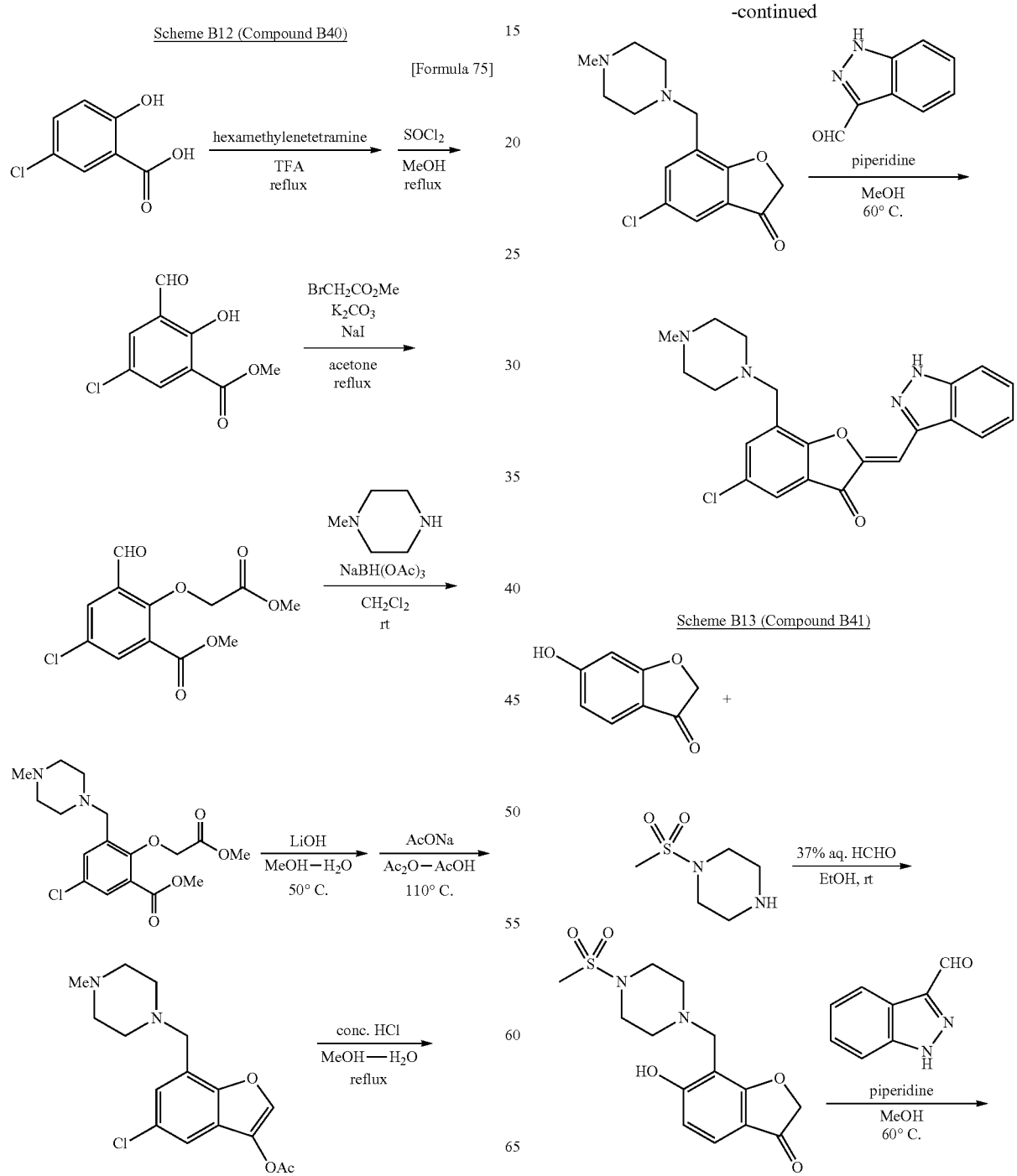

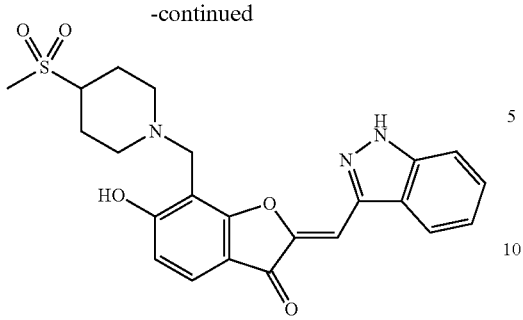
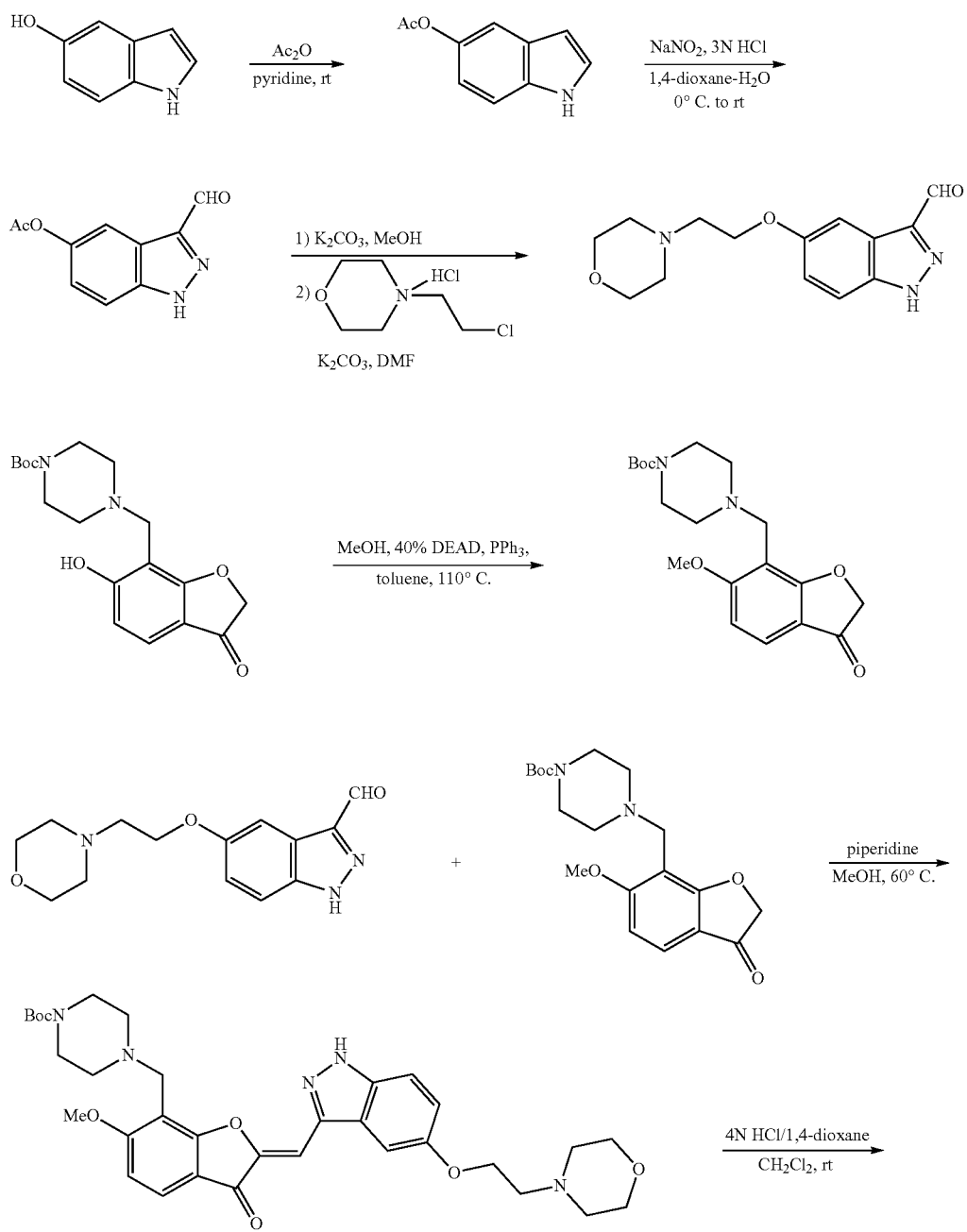

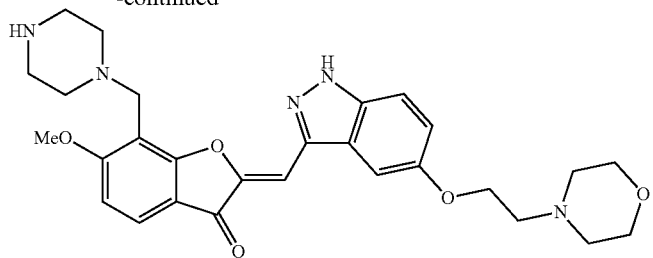
Scheme B15 (Compound B43)
[Formula 78]
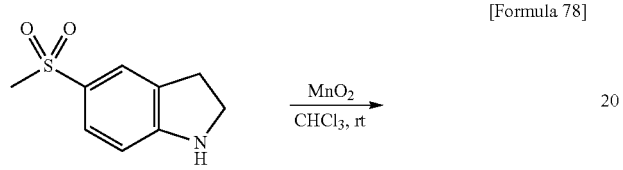
MnO₂
CHCl₃, rt
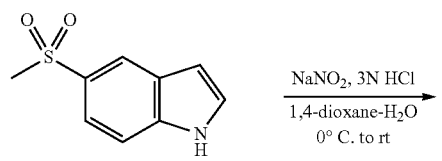
NaNO₂, 3N HCl
1,4-dioxane-H₂O
0° C. to rt
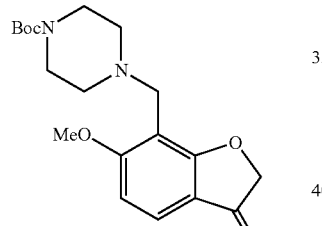
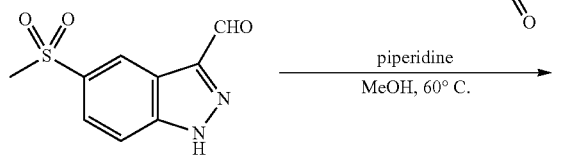
piperidine
MeOH, 60° C.
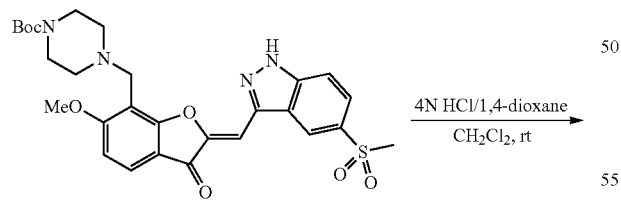
4N HCl/1,4-dioxane
CH₂Cl₂, rt
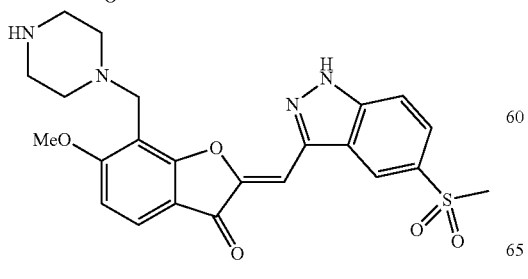
Scheme B16 (Compound B44)
MeOH, 40% DEAD, PPh₃
toluene, 110° C.
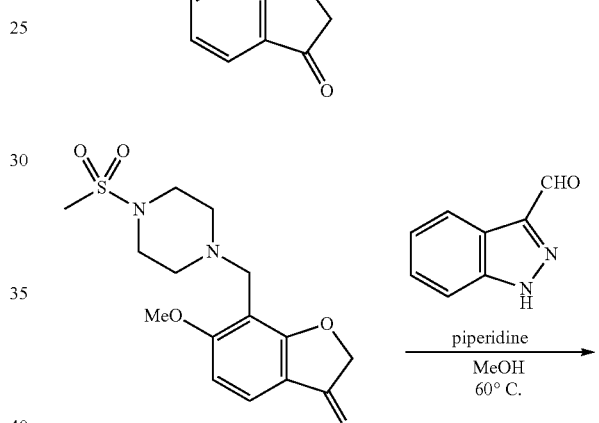
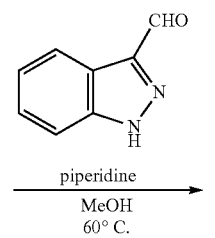
piperidine
MeOH
60° C.
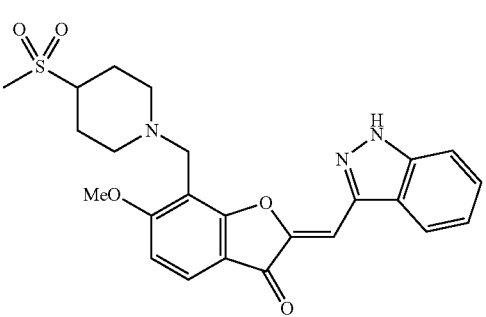
Scheme B17 (Compound B45)
[Formula 79]
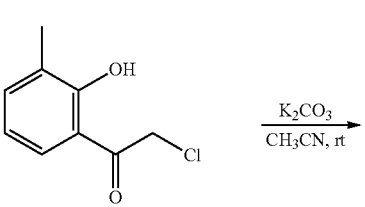
K₂CO₃
CH₃CN, rt

99
-continued
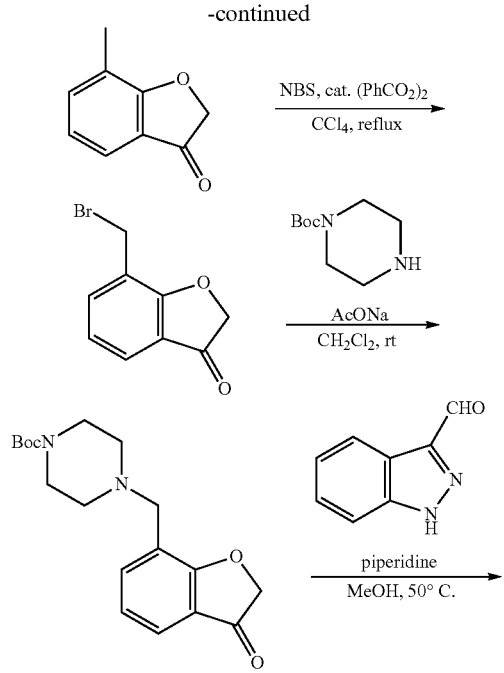
100
-continued
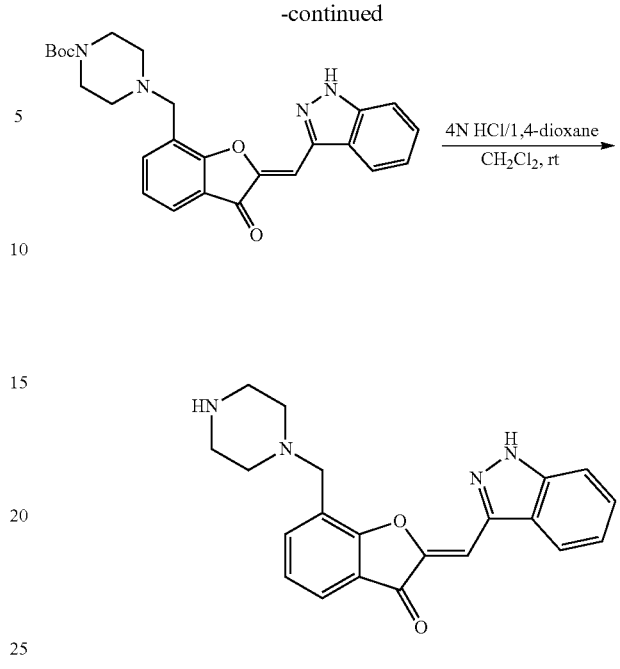

[Formula 80]
Scheme B18 (Compounds B46-B51)
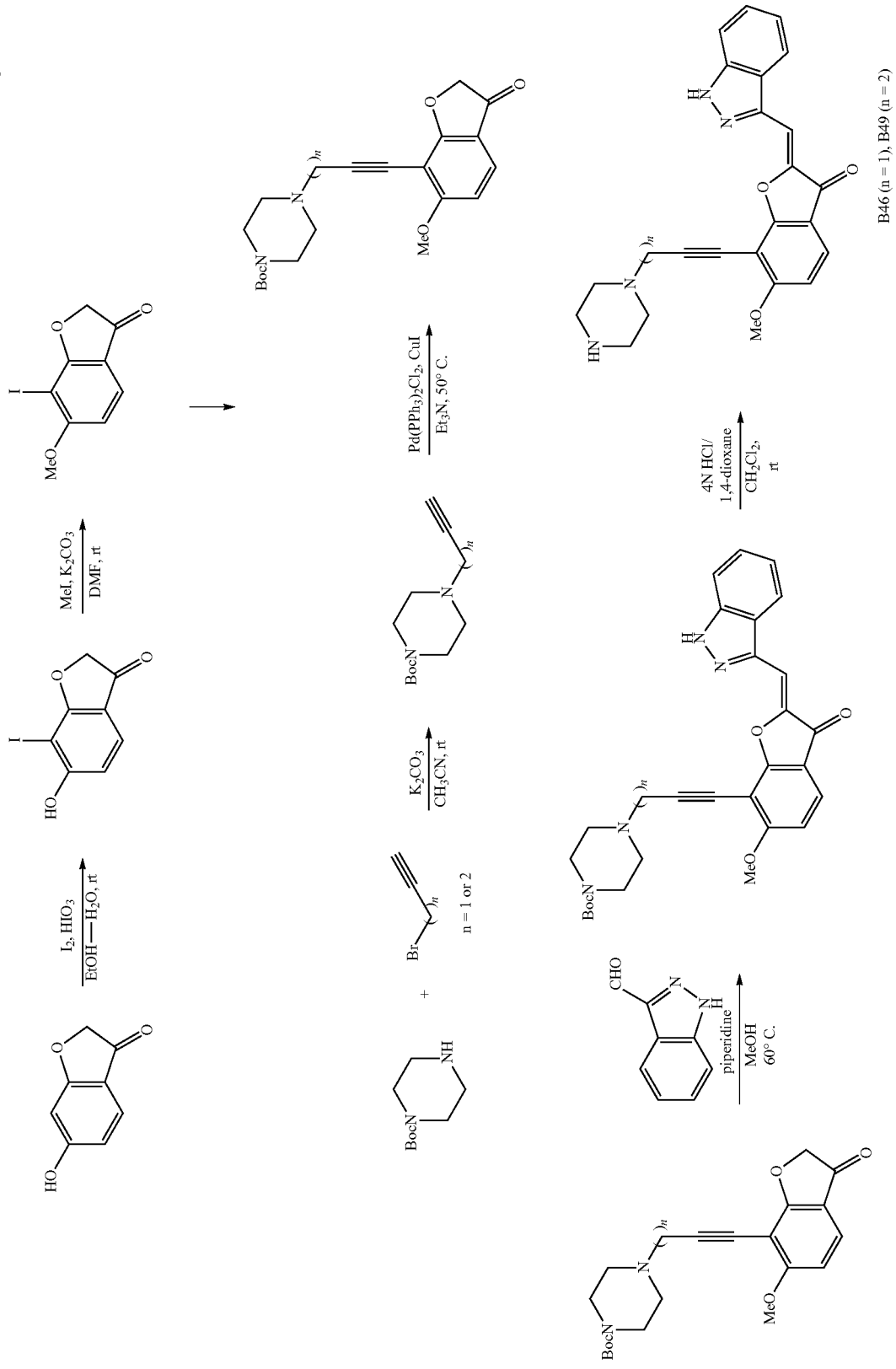
B46 (n = 1), B49 (n = 2)

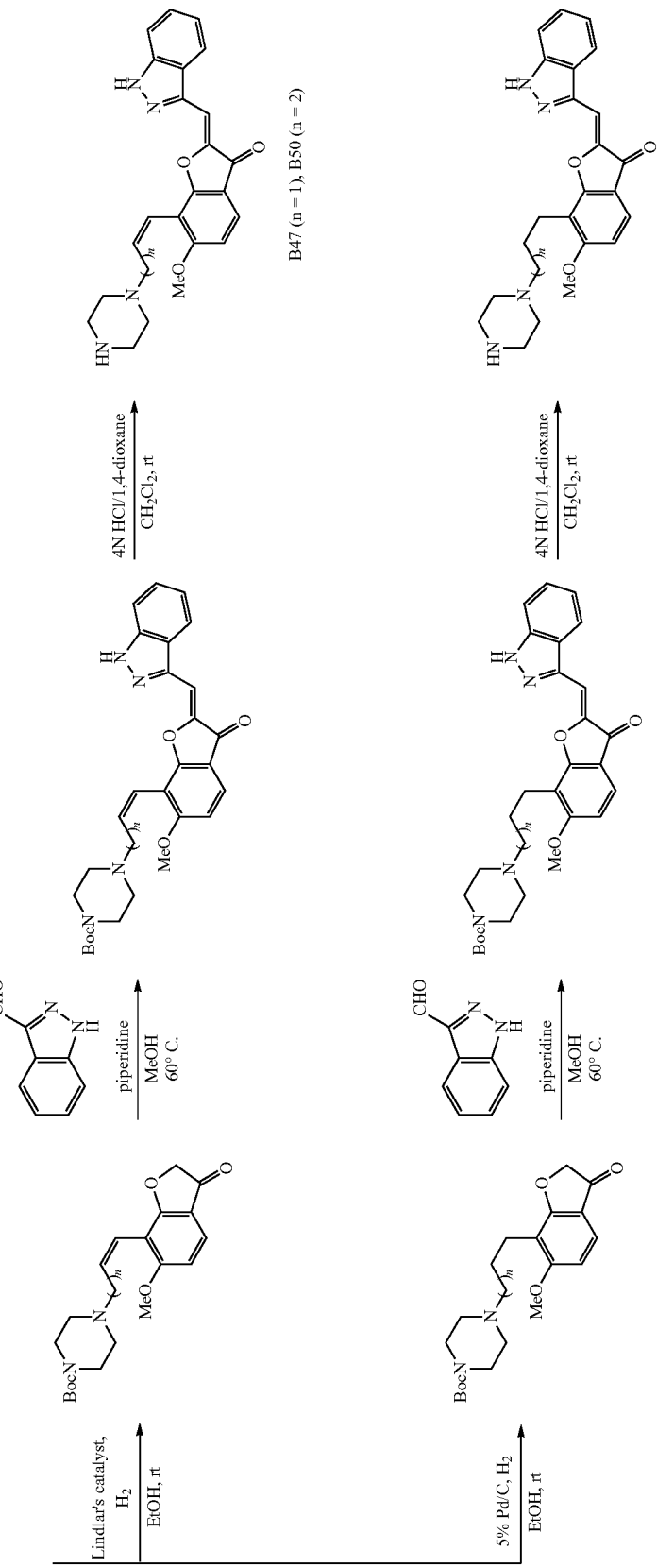

Scheme B19 (Compounds B52 & B53)
[Formula 81]
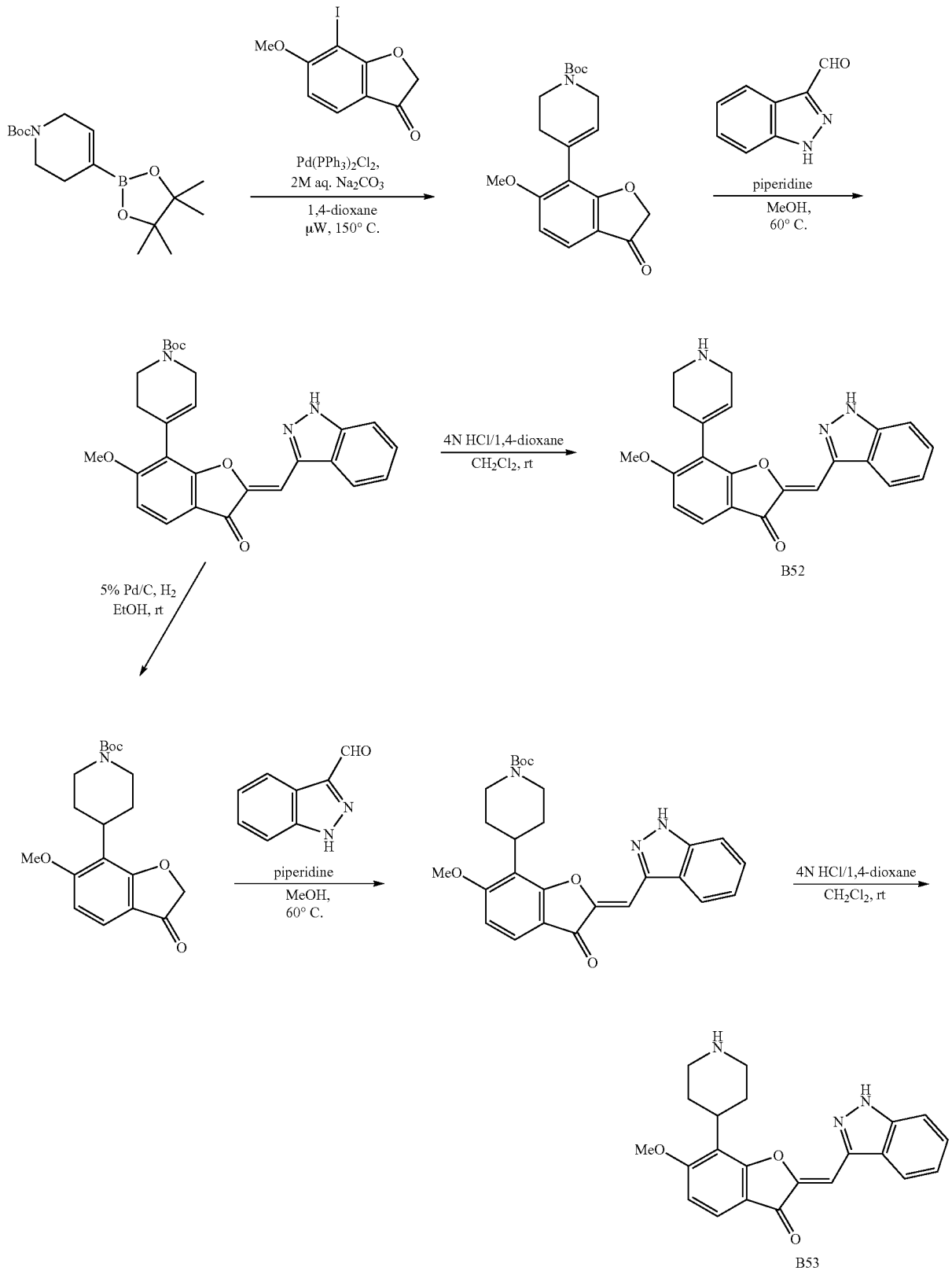

Scheme B20 (Compound B54)
[Formula 82]
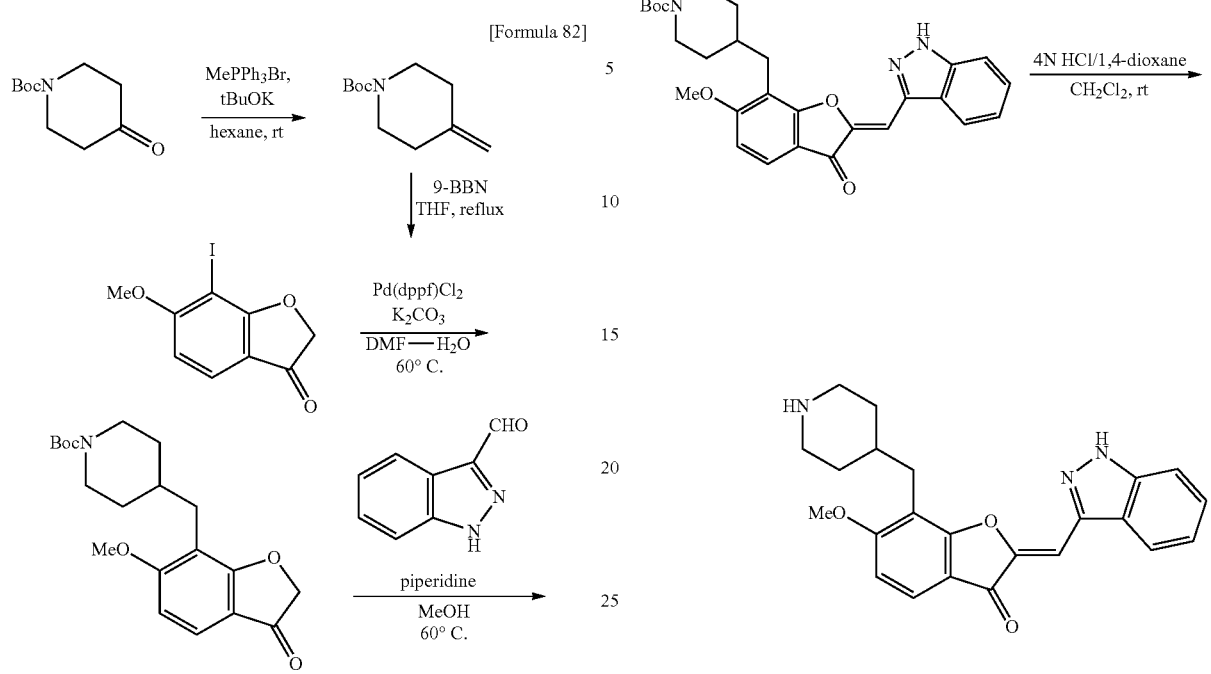

[Formula 83]
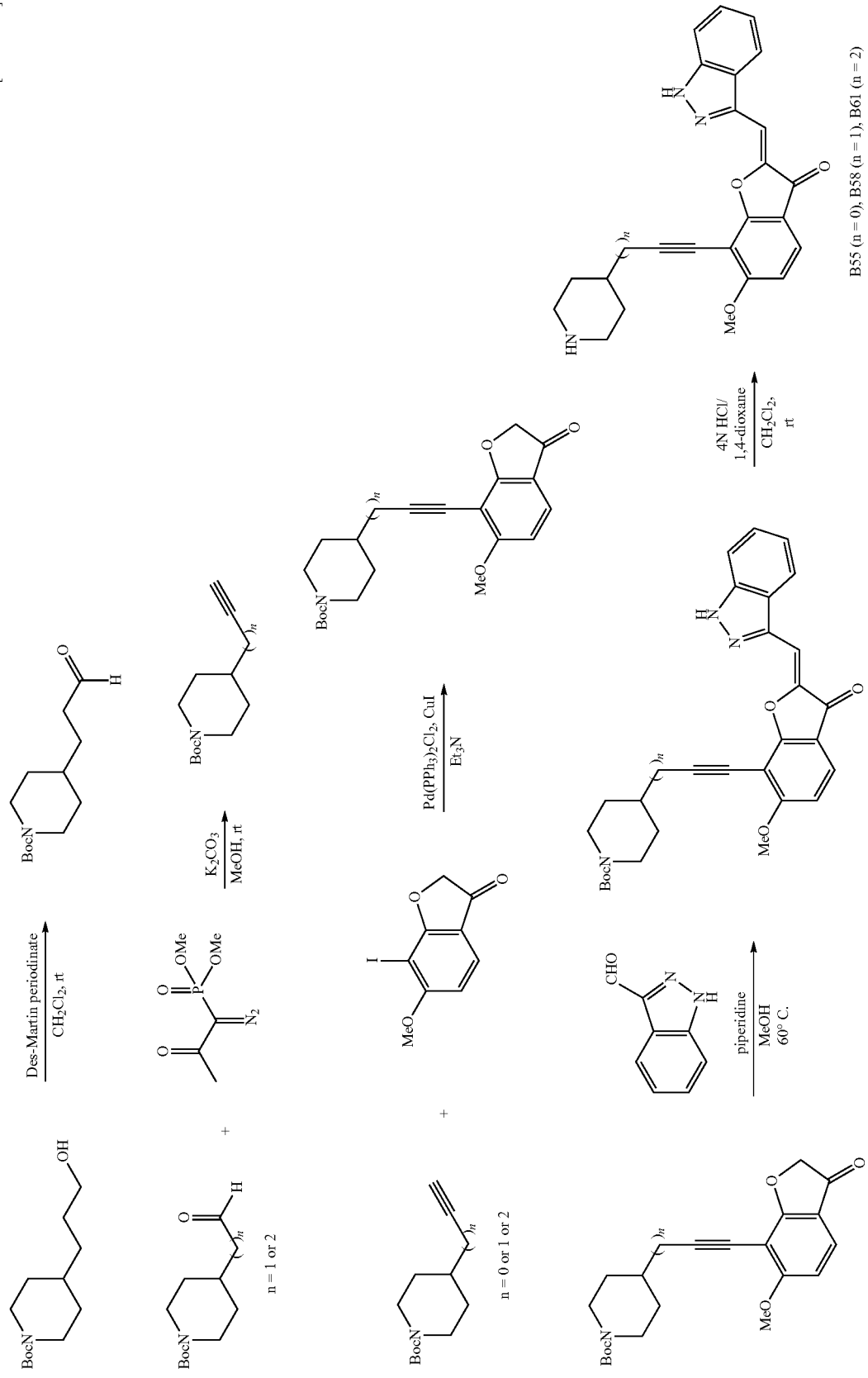

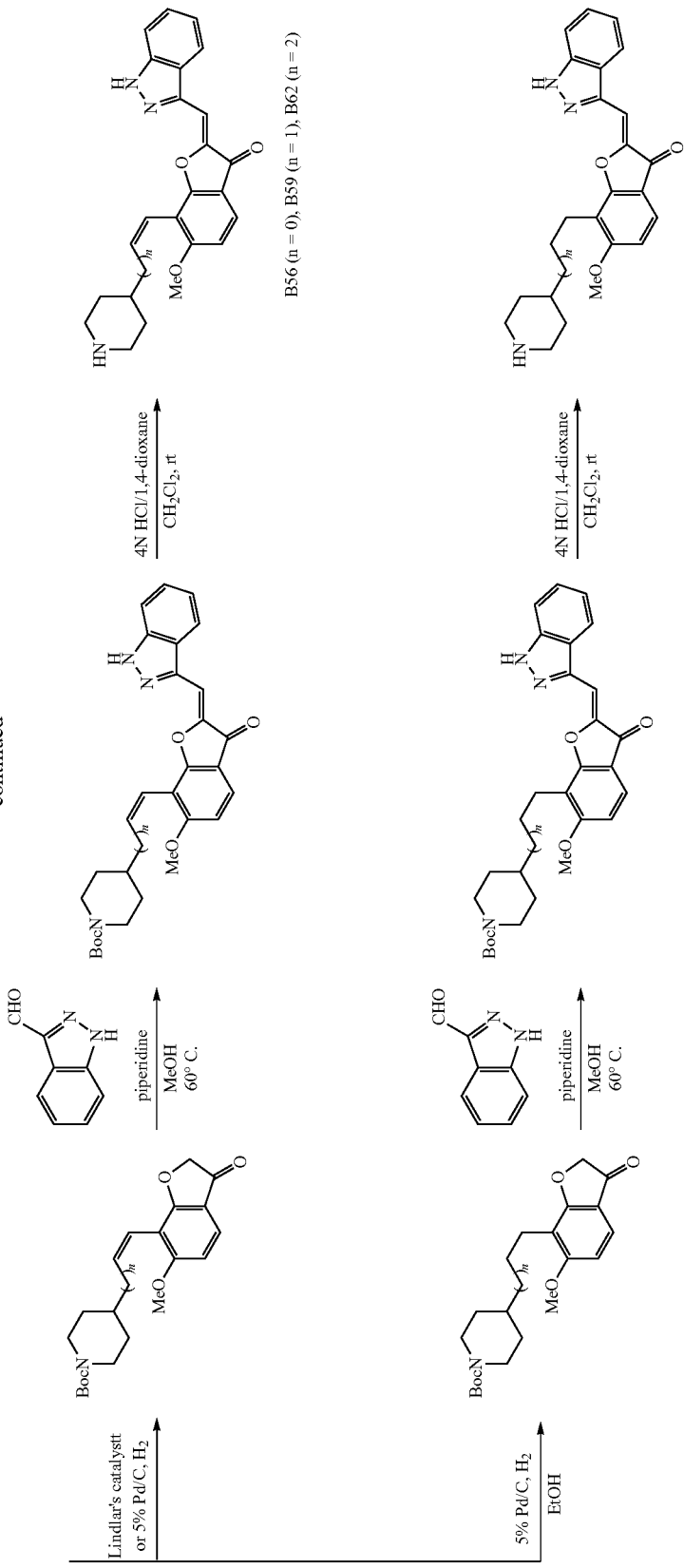

Scheme B22 (Compounds B64 & B65)
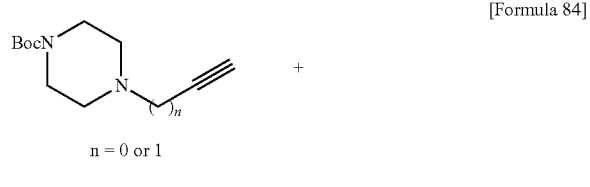
Scheme B23 (Compound B66)
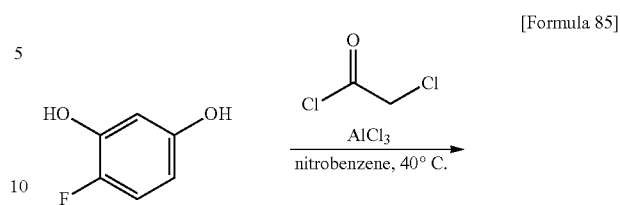
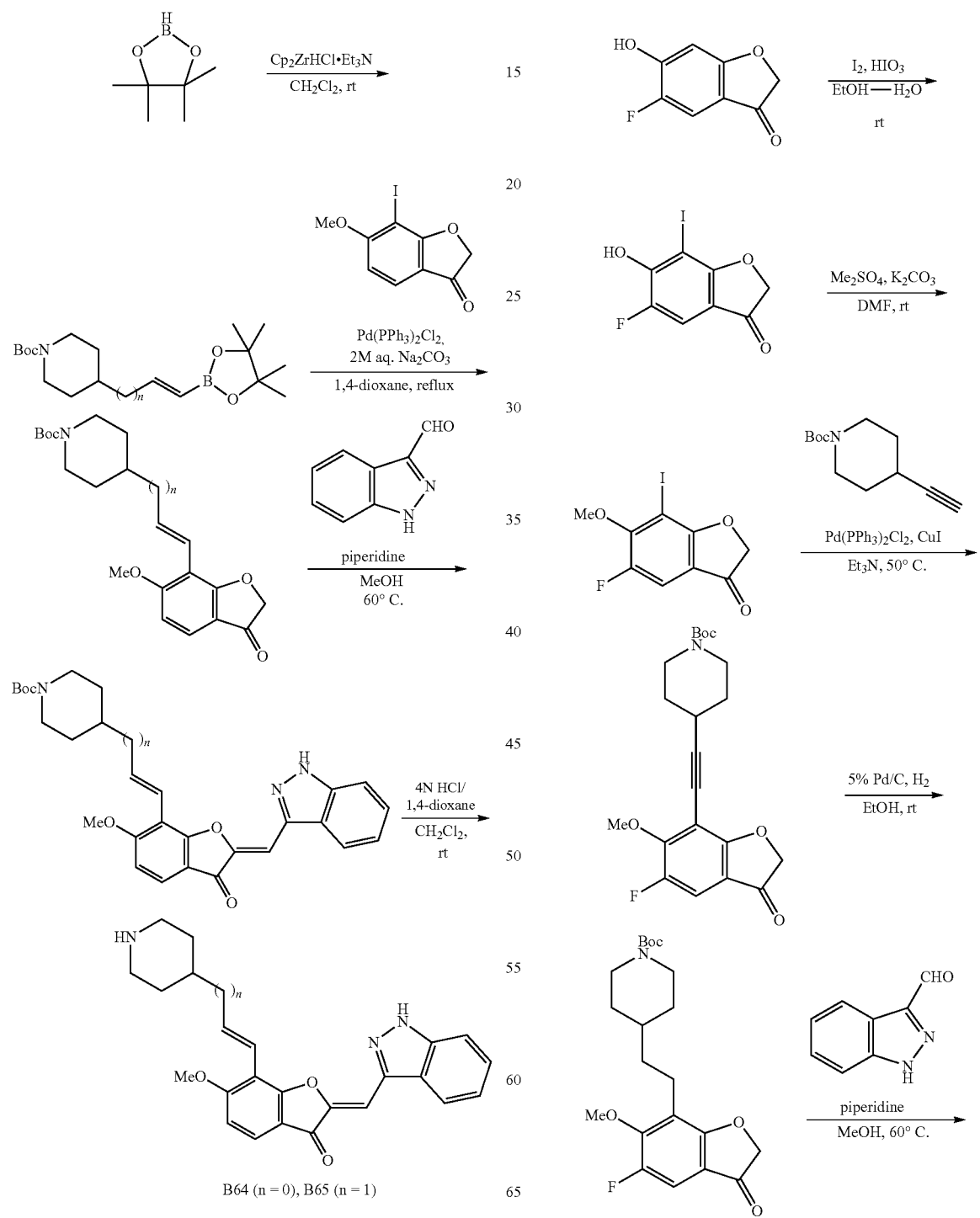

115
-continued
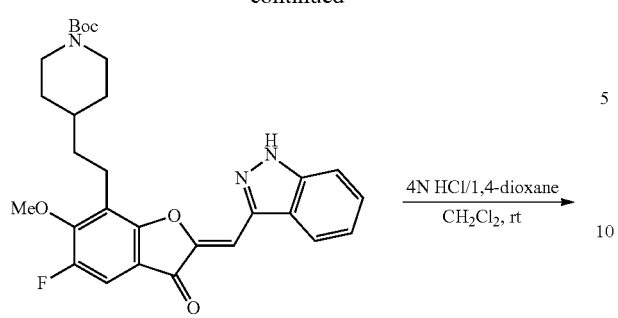
116
-continued
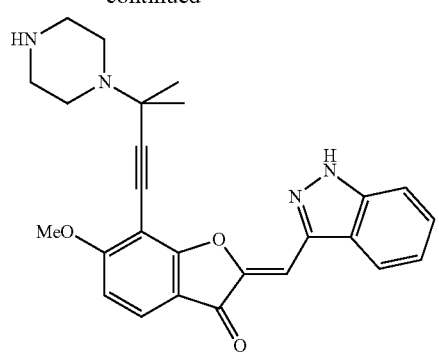
Scheme B25 (Compound B68-B70)
Scheme B24 (Compound B67)
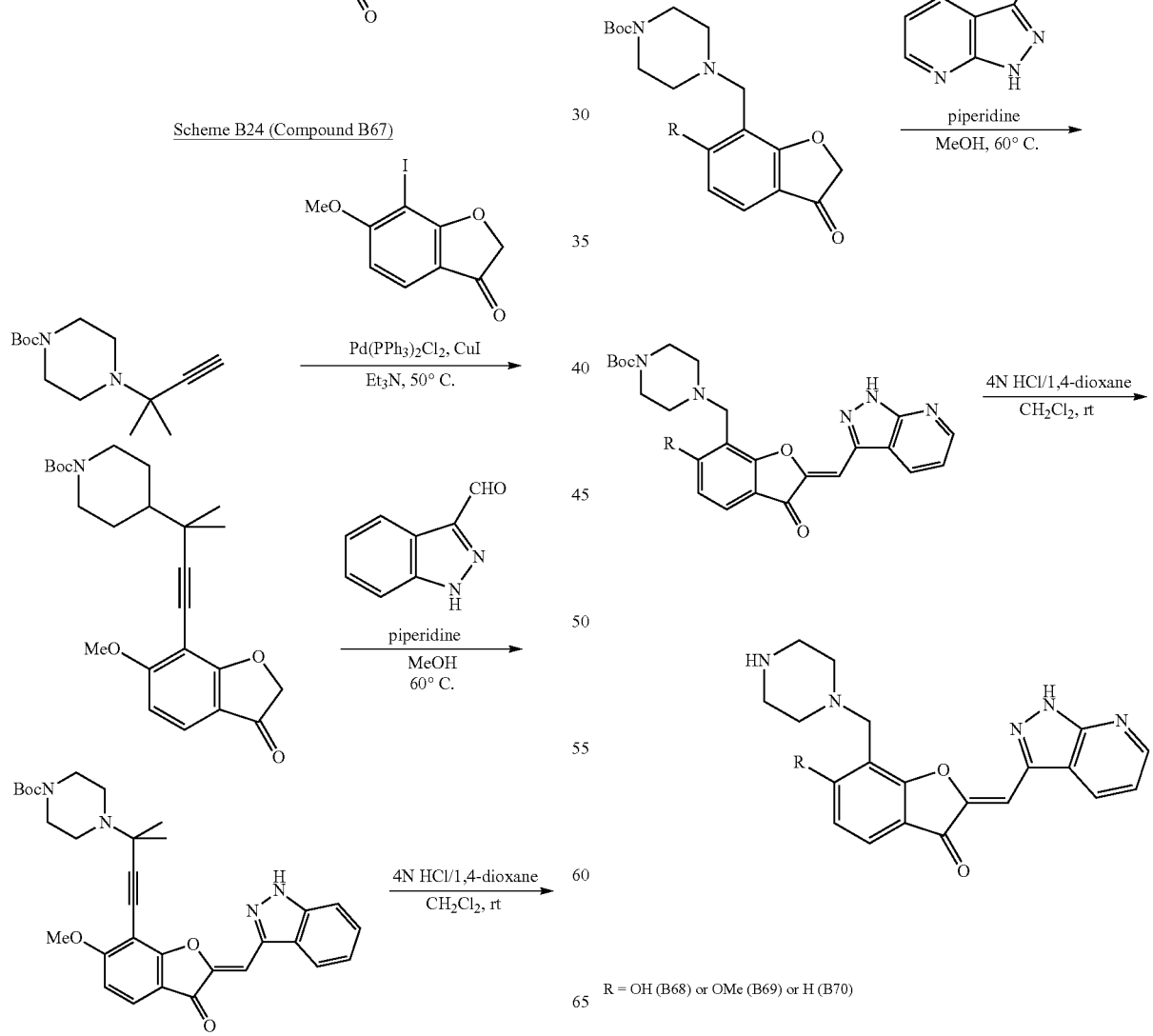
R = OH (B68) or OMe (B69) or H (B70)

Scheme B26 (Compound B71 & B72)

[Formula 88]

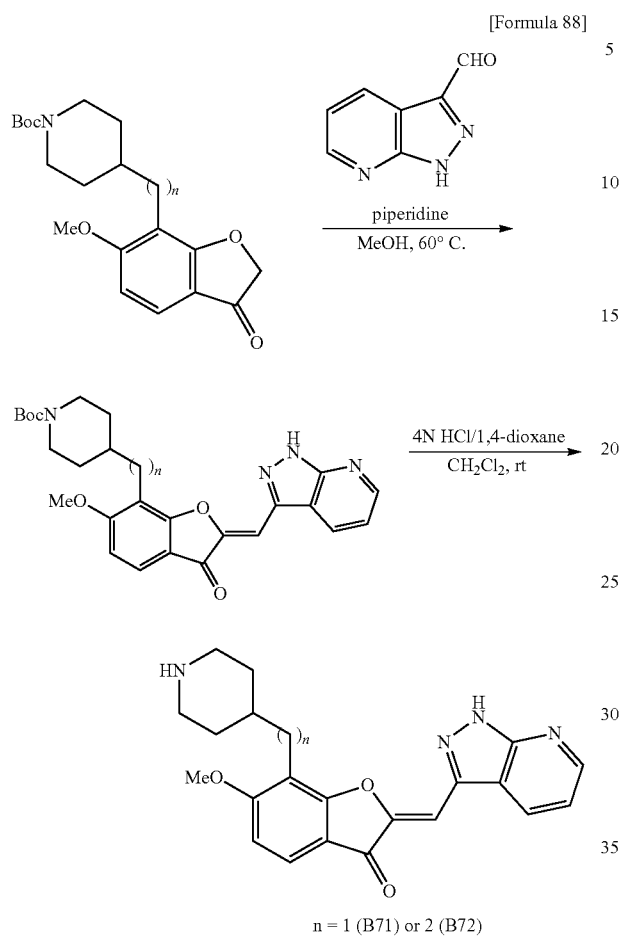

n = 1 (B71) or 2 (B72)

Scheme B27 (Compound B73)

[Formula 89]

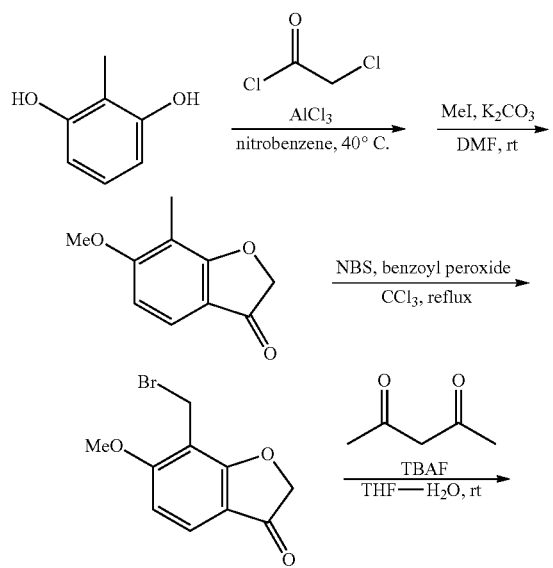

The compounds represented by the aforementioned general formula (I) have an inhibitory action against pim-1 kinase, and are useful as an active ingredient of a medicament, preferably an anticancer agent. The action of the anticancer agent of the present invention should be construed in the broadest sense thereof so that it includes action of suppressing proliferation of cancer cells as well as actions of suppressing canceration of a cell, suppressing malignant alteration of a cancer cell, and the like, and should not be construed in any limitative way. Further, the anticancer agent of the present invention can inhibit a process of acquiring resistance against various kinds of anticancer agents by a cancer cell, and can also be used as an agent for enhancing an action of another anticancer agent, or an agent for inhibiting acquisition of resistance by a cancer cell against another anticancer agent. Type of cancer as a target of the anticancer agent of the present invention is not particularly limited, and arbitrary cancers such as solid cancers and non-solid cancers can be an object of the application. Since it is known that pim-1 kinase is highly expressed in leukemia patients and prostate cancer, leukemia and prostate cancer are particularly preferred objects of the application of the anticancer agent of the present invention.

As the active ingredient of the anticancer agent of the present invention, one or two or more kinds of substances selected from the group consisting of the compounds represented by the general formula (I), pharmacologically acceptable salts thereof, hydrates of them and solvates of them can be used. Although the aforementioned substances, per se, may be used as the anticancer agent of the present invention, the anticancer agent of the present invention is preferably provided in the form of a pharmaceutical composition containing the aforementioned substances as the active ingredient, and one or two or more kinds of pharmaceutically acceptable pharmaceutical additives. Although a ratio of the active ingredient to the pharmaceutical additives in the aforementioned pharmaceutical composition is not particularly limited, the ratio may be generally about 1 to 90% by weight.

Administration route of the anticancer agent of the present invention is not particularly limited, and the agent can be administered orally or parenterally. Examples of the pharmaceutical composition suitable for oral administration include, for example, granules, subtilized granules, powders, hard capsules, soft capsules, syrups, emulsions, suspensions, solutions, and the like. Examples of the pharmaceutical composition suitable for parenteral administration include, for example, injections for intravenous administration, intramuscular administration, or subcutaneous administration, fusion drips, suppositories, transdermal preparations, transmucosal preparations, nose drops, ear drops, eye drops, inhalants, and the like. A preparation prepared as the pharmaceutical composition in the form of dry powder such as a lyophilized product may be dissolved before use, and used as an injection or fusion drip.

For manufacture of the pharmaceutical composition, solid or liquid pharmaceutical additives can be used. The pharmaceutical additives may be organic substances or inorganic substances. When a solid preparation for oral administration is prepared, for example, after an excipient is added to a substance selected from the group consisting of the compounds represented by the aforementioned general formula (I), pharmacologically acceptable salts thereof, hydrates thereof, and solvates thereof, and binder, disintegrating agent, lubricant, colorant, corrigent and the like are added to the mixture as required, a preparation in the form of tablet, coated tablet, granule, powder, capsule, or the like can be prepared from the resulting mixture in a conventional manner.

Examples of the excipient include, for example, lactose, saccharose, sucrose, glucose, cornstarch, starch, talc, sorbit, crystalline cellulose, dextrin, kaoline, calcium carbonate, silicon dioxide, and the like. Examples of the binder include, for example, polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, dextrin, pectin, and the like. Examples of the lubricant include, for example, magnesium stearate, talc, polyethylene glycol, silica, hardened vegetable oil, and the like. As the colorant, any of those of which addition to pharmaceutical products is approved can be used. As the corrigent, cocoa powder, menthol, aromatic acids, peppermint oil, borneol, powdered cinnamon bark, and the like can be used. Tablets or granules may be optionally coated with sugar coating, gelatin coating, or others as required. A preservative, an anti-oxidant, and the like can also be added, as required.

For manufacture of a liquid preparation for oral administration, such as emulsions, syrups, suspensions, or solutions, a generally used inert diluent such as water or vegetable oil can be used. To a liquid preparation, an auxiliary agent, for example, wetting agent, suspension auxiliary agent, sweetener, aromatic, colorant, preservative, and the like can be added. A resulting liquid preparation may be filled in capsules such as gelatin capsules.

Examples of solvent or suspending agent used for manufacture of the pharmaceutical composition for parenteral administration such as injections and suppositories include, for example, water, propylene glycol, polyethylene glycol, benzyl alcohol, ethyl oleate, lecithin and the like. Examples of base used for manufacture of suppository include, for example, cacao butter, emulsified cacao butter, laurin butter, and Witepsol. Method for manufacturing a dosage form is not particularly limited, and any of the methods widely used in this field can be used.

When the pharmaceutical composition in the form of an injection is prepared, there can be used, for example, as a carrier, diluent such as water, ethyl alcohol, macrogol, and propylene glycol; pH adjustor or buffering agent such as sodium citrate, sodium acetate, and sodium phosphate; stabilizer such as sodium pyrosulfite, ethylenediaminetetraacetic acid, thioglycolic acid, and thiolactic acid, and the like. Glucose, mannitol, glycerol or the like may be blended into the pharmaceutical composition in an amount sufficient for preparing an isotonic solution, and dissolving aid, soothing agent, local anesthetic, and the like can also be added.

When the pharmaceutical composition in the form of an ointment such as paste, cream or gel is prepared, usually used bases, stabilizers, wetting agents, preservatives and the like can be used as required, and the components can be mixed in a conventional manner to prepare the pharmaceutical composition. As the base, for example, white petrolatum, polyethylene, paraffin, glycerol, cellulose derivative, polyethylene glycol, silicon, bentonite, and the like can be used. As the preservative, for example, methyl paraoxybenzoate, ethyl paraoxybenzoate, propyl paraoxybenzoate, and the like can be used. When the pharmaceutical composition in the form of patch is prepared, the aforementioned ointment, cream, gel, paste or the like can be applied to a surface of a usual support in a conventional manner. As the support, for example, fabric or nonwoven fabric consisting of cotton, rayon or chemical fibers, a film such as those consisting of plasticized vinyl chloride, polyethylene or polyurethane, or a foam sheet can be preferably used.

A dose of the anticancer agent of the present invention is not particularly limited. In the case of oral administration, the dose can usually be chosen so as to be in the range of about 0.01 to 5,000 mg in terms of weight of the aforementioned substances as the active ingredient as a daily dose for an adult. It is preferred that the dose is appropriately increased or decreased depending on the age, body weight, or sex of the patient, purpose of administration, symptoms, and the like. The aforementioned daily dose can be administered by one to four times a day of administration, or by a single administration in several days to several weeks with appropriate intervals. Further, when the agent is used as an injection or a fusion drip, the daily dose for adults is about 0.001 to 500 mg in terms of weight of the aforementioned substances as the active ingredient.

The compounds represented by the general formula (IB), (II), or (III) provided from other aspects of the present invention are novel compounds encompassed within the scope of the aforementioned general formula (I). In the same manner as the compounds represented by the aforementioned general formula (I), these compounds also have the pim-1 kinase inhibitory action, and are useful as an active ingredient of a medicament such as an anticancer agent.

The substituents in the aforementioned general formulas (IB), (II) and (III) are the same as the substituents in the aforementioned general formula (I) at corresponding positions.

For example, a compound represented by the general formula (IB), wherein:
$R^{1b}$ is hydrogen atom, hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group;

$R^{2b}$ is hydrogen atom, a halogen atom, a $C_{1-6}$ alkoxy group, wherein $R^{1b}$ and $R^{2b}$ may bind together to form a $C_{1-6}$ alkylenedioxy group;

$R^{3b}$ is hydrogen atom, a halogen atom, or hydroxyl group;

$R^{4b}$ is hydrogen atom, a $C_{1-6}$ alkyl group, or sulfonyl group;

$R^{5b}$ is hydrogen atom or one to three substituents substituting on the benzene ring or the pyridine ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, hydroxyl group, a $C_{1-6}$ alkoxy group, and a halogen-substituted $C_{1-6}$ alkoxy group);

⋯ is a single bond or a double bond;

$R^{6b}$ and $R^{7b}$ are hydrogen atoms, wherein when ⋯ represents a double bond, $R^{7b}$ does not exist;

$A^b$ is —O—, —S—, or —CH$_2$—;

$D^b$ is —C= or —N=;

$X^b$ is methylene group (this methylene group may be substituted with one or two $C_{1-6}$ alkyl groups or hydroxyl groups), —O—, or —CO—; and $Y^b$ is 1-piperazinyl group, morpholino group, or 4-piperidinyl group (these groups may have one or two or more substituents selected from the group consisting of a $C_{1-6}$ alkyl group, hydroxyl group, and oxo group) is preferred.

Further, it is preferred that (a) $R^{3b}$ is hydrogen atom, (b) $R^{4b}$ is hydrogen atom, (c) ⋯ is a double bond, (d) $A^b$ is —O—, or (e) $D^b$ is —C=. A compound satisfying two or more of the aforementioned conditions (a) to (e) is more preferred, a compound satisfying three or more of the aforementioned conditions (a) to (e) is still more preferred, and a compound satisfying four or more of the aforementioned conditions (a) to (e) is particularly preferred. A compound satisfying all of the aforementioned conditions (a) to (e) is most preferred.

From another aspect, a compound wherein (f) $R^{1b}$ is hydroxyl group or a $C_{1-6}$ alkoxy group, (g) $R^{2b}$ is hydrogen atom or a halogen atom, (h) $X^b$ is methylene group, or (i) $R^{5b}$ is hydrogen atom, one halogen atom, one $C_{1-6}$ alkoxy group, or one fluoro-substituted $C_{1-6}$ alkoxy group is also preferred. A compound satisfying two or more of the aforementioned conditions (f) to (i) is more preferred, a compound satisfying three or more of the aforementioned conditions (f) to (i) is still more preferred, and a compound satisfying all of the aforementioned conditions (f) to (i) is particularly preferred. A compound satisfying all of the aforementioned conditions (a) to (e) and the aforementioned conditions (f) to (i) is most preferred.

Further, a compound represented by the general formula (II), wherein:

$R^{11}$ is hydroxyl group or a $C_{1-6}$ alkoxy group;

$R^{12}$ is hydrogen atom, a halogen atom, a $C_{1-6}$ alkyl group, a $C_{1-6}$ alkoxy group, or an aryl group;

$R^{13}$ is hydrogen atom;

$R^{14}$ is hydrogen atom;

$R^{15}$ is hydrogen atom, or one to four substituents substituting on the benzene ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group);

⋯ is a double bond;

$R^{16}$ is hydrogen atom;

$R^{18}$ is hydrogen atom;

$X^1$ is methylene group (this methylene group may be substituted with one or two $C_{1-6}$ alkyl groups or hydroxyl groups); and Z is nitrogen atom or a CH is preferred.

Further, a compound represented by the general formula (III), wherein:

$R^{21}$ is hydroxyl group or a $C_{1-6}$ alkoxy group;

$R^{22}$ is hydrogen atom, a halogen atom, a $C_{1-6}$ alkyl group, a $C_{1-6}$ alkoxy group, or an aryl group;

$R^{23}$ is hydrogen atom;

$R^{24}$ is hydrogen atom;

$R^{26}$ is hydrogen atom, or one to four substituents substituting on the benzene ring (the substituent(s) is (are) selected from the group consisting of a halogen atom, a $C_{1-6}$ alkyl group, a halogen-substituted $C_{1-6}$ alkyl group, a hydroxy-substituted $C_{1-6}$ alkyl group, an amino-substituted $C_{1-6}$ alkyl group, hydroxyl group, a $C_{1-6}$ alkoxy group, a halogen-substituted $C_{1-6}$ alkoxy group, a $C_{1-6}$ alkoxycarbonyl group, amino group, nitro group, an aryl group, an aralkyloxy group, a heterocyclic group, and a heterocyclic group-substituted $C_{1-6}$ alkoxy group);

⋯ is a double bond;

$R^{26}$ is hydrogen atom;

$R^{28}$ is hydrogen atom;

$X^2$ is methylene group (this methylene group may be substituted with one or two $C_{1-6}$ alkyl groups or hydroxyl groups); and $Y^1$ is 1-piperazinyl group, morpholino group, thiomorpholino group, 1-piperidinyl group, 4-piperidinyl group, 4-tetrahydropyranyl group, 1-homopiperazinyl group, 1-pyrrolidinyl group, hexamethyleneimin-1-yl group, or amino group (these groups may have one or two or more substituents selected from the group consisting of a $C_{1-12}$ alkyl group, hydroxyl group, amino group, an amino-substituted $C_{1-12}$ alkyl group, an alkylsulfonyl group, a $C_{1-6}$ alkoxy-substituted $C_{1-6}$ alkyl group, a $C_{1-6}$ alkoxycarbonyl group, carbamoyl group, and oxo group)

is preferred.

Methods for preparing these compounds are not particularly limited. Methods for preparation of typical compounds are specifically described in the examples included in the specification. Further, general synthetic methods corresponding to the examples are shown in the aforementioned schemes. Therefore, by referring to the examples of the specification and also to the aforementioned schemes, and appropriately modifying starting materials, reagents, reaction conditions, and the like as required, those skilled in the art will be able to easily prepare the compounds represented by the aforementioned general formula (IB), (II) or (III).

The compounds represented by the general formula (IB), (II) or (III) may form an acid addition salt. Examples of the acid addition salt include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, but are not limited to these examples. Among them, physiologically acceptable salts are preferred. Further, the compounds represented by general formula (IB), (II) or (III) in free form and salts thereof may exist as a hydrate or a solvate, and arbitrary hydrates and solvates also fall within the scope of the present invention. Although the solvent that forms the solvate is not particularly limited, physiologically acceptable organic solvents such as ethanol, dioxane, ethyl acetate and n-hexane are preferred.

Further, the compounds represented by the general formula (IB), (II) or (III) may have one or more asymmetric carbons depending on type of substituent, and one or two or more asymmetric carbons existing in the compounds of the present invention may be in an arbitrary steric configuration. Stereoisomers such as optical isomers and diastereoisomers in pure forms based on these asymmetric carbons, arbitrary mixtures of stereoisomers, racemates, and the like all fall within the scope of the present invention. When the compounds represented by the general formula (IB), (II) or (III) have a double bond, geometrical isomers thereof based on the double bond exist. It should be understood that any geometrical isomers in pure forms or arbitrary mixtures of such geometrical isomers also fall within the scope of the present invention.

EXAMPLES

Hereafter, the present invention will be more specifically explained with reference to examples. However, the scope of the present invention is not limited to the following examples. The compound numbers used in the examples correspond to those of the compounds mentioned above. Unless specifically mentioned, the reactions were performed under an argon atmosphere.

Example A1

(Z)-2-[(1H-Indol-3-yl)methylene]-7-({4-[3-(dimethylamino)propyl]piperazin-1-yl}methyl)-6-hydroxybenzofuran-3(2H)-one (a) Step 1

The synthesis was performed with reference to the known literature (International Patent Publication WO1998/30556). A solution of 6-hydroxybenzofuran-3(2H)-one (2.0 g, 13 mmol) and 1H-indole-3-carboxaldehyde (2.3 g, 16 mmol) in ethanol (100 mL) was added with concentrated hydrochloric acid (10 mL), and the mixture was stirred at 75° C. for 5 hours. The reaction mixture was cooled to room temperature, and then the solid was collected by filtration, and washed with methanol and water to obtain (Z)-2-[(1H-indol-3-yl)methylene]-6-hydroxybenzofuran-3(2H)-one (3.8 g, 100%).
$^1$H NMR (300 MHz, DMSO-$d_6$) δ 6.72 (dd, J=2.2 Hz, J=8.8 Hz, 1H), 6.86 (d, J=2.2 Hz, 1H), 7.07-7.28 (m, 2H), 7.18 (s, 1H), 7.50 (d, J=8.1 Hz, 1H), 7.61 (d, J=8.8 Hz, 1H), 8.01 (d, J=7.3 Hz, 1H), 8.20 (d, J=2.9 Hz, 1H), 12.05 (s, 1H).

(b) Step 2

The synthesis was performed with reference to the known literature (Heterocycles, Vol. 53, p. 197, 2000). A solution of (Z)-2-[(1H-indol-3-yl)methylene]-6-hydroxybenzofuran-3(2H)-one (0.028 g, 0.10 mmol) in ethanol (2.0 mL) was added with 1-[3-(dimethylamino)propyl]piperazine (0.022 g, 0.13 mmol), and 37% aqueous formaldehyde (0.011 g, 0.13 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-7-({4-[3-(dimethylamino)propyl]piperazin-1-yl}methyl)-6-hydroxybenzofuran-3(2H)-one (0.020 g, 43%).
$^1$H NMR (300 MHz, CD$_3$OD) δ 1.60-1.82 (m, 2H), 2.28 (s, 6H), 2.33-2.49 (m, 4H), 2.49-2.72 (m, 4H), 2.74-3.01 (m, 4H), 4.08 (s, 2H), 6.65 (d, J=8.8 Hz, 1H), 7.14-7.34 (m, 2H), 7.33 (s, 1H), 7.44-7.51 (m, 1H), 7.58 (d, J=8.8 Hz, 1H), 7.88-7.98 (m, 1H), 8.09 (s, 1H).

Example A2

(Z)-2-[(1H-Indol-3-yl)methylene]-6-hydroxy-7-{[4-(2-methoxyethyl)piperazin-1-yl]methyl}benzofuran-3(2H)-one A solution of (Z)-2-[(1H-indol-3-yl)methylene]-6-hydroxybenzofuran-3(2H)-one (0.051 g, 0.19 mmol) obtained in Example A1, Step 1 in ethanol (2.0 mL) was added with 1-(2-methoxyethyl)piperazine (0.036 g, 0.25 mmol), and 37% aqueous formaldehyde (0.021 g, 0.25 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-6-hydroxy-7-{[4-(2-methoxyethyl)piperazin-1-yl]methyl}benzofuran-3(2H)-one (0.027 g, 33%).
$^1$H NMR (300 MHz, CDCl$_3$) δ 2.37-3.12 (m, 8H), 2.65 (m, 2H), 3.38 (s, 3H), 3.54 (m, 2H), 3.99 (s, 2H), 6.65 (d, J=8.8 Hz, 1H), 7.23-7.35 (m, 3H), 7.47 (d, J=8.1 Hz, 1H), 7.63 (d, J=8.8 Hz, 1H), 7.94 (d, J=8.1 Hz, 1H), 7.97 (s, 1H).

Example A3

(Z)-2-[(1H-Indol-3-yl)methylene]-7-{[3-(dimethylamino)pyrrolidin-1-yl]methyl}-6-hydroxybenzofuran-3(2H)-one A solution of (Z)-2-[(1H-indol-3-yl)methylene]-6-hydroxybenzofuran-3(2H)-one (0.050 g, 0.18 mmol) obtained in Example A1, Step 1 in ethanol (3.0 mL) was added with 3-(dimethylamino)pyrrolidine (0.025 g, 0.22 mmol), and 37% aqueous formaldehyde (0.020 g, 0.24 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-7-{[3-(dimethylamino)pyrrolidin-1-yl]methyl}-6-hydroxybenzofuran-3(2H)-one (0.015 g, 21%).
$^1$H NMR (300 MHz, CD$_3$OD) δ 1.83-1.98 (m, 1H), 2.09-2.23 (m, 1H), 2.26 (s, 6H), 2.85-2.97 (m, 1H), 2.97-3.15 (m, 3H), 3.20-3.25 (m, 1H), 4.26 (s, 2H), 6.59 (d, J=8.8 Hz, 1H), 7.16-7.30 (m, 2H), 7.27 (s, 1H), 7.42-7.50 (m, 1H), 7.54 (d, J=8.8 Hz, 1H), 7.89-7.95 (m, 1H), 8.13 (s, 1H).

Example A4

(Z)-2-[(1H-Indol-3-yl)methylene]-6-hydroxy-7-(thiomorpholinomethyl)benzofuran-3(2H)-one A solution of (Z)-2-[(1H-indol-3-yl)methylene]-6-hydroxybenzofuran-3(2H)-one (0.050 g, 0.18 mmol) obtained in Example A1, Step 1 in ethanol (2.0 mL) was added with thiomorpholine (0.023 g, 0.22 mmol), and 37% aqueous formaldehyde (0.020 g, 0.24 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-6-hydroxy-7-(thiomorpholinomethyl)benzofuran-3(2H)-one (0.031 g, 44%).

$^1$H NMR (400 MHz, DMSO-$d_6$) δ 2.67 (m, 4H), 2.86 (m, 4H), 3.91 (s, 2H), 6.72 (d, J=8.3 Hz, 1H), 7.19 (s, 1H), 7.24 (m, 2H), 7.51 (d, J=8.3 Hz, 1H), 7.54 (d, J=8.3 Hz, 1H), 8.09 (d, J=8.3 Hz, 1H), 8.17 (d, J=2.4 Hz, 1H), 12.00 (d, J=2.4 Hz, 1H).

Example A5

(Z)-4-({2-[(1H-Indol-3-yl)methylene]-6-hydroxy-3-oxo-2,3-dihydrobenzofuran-7-yl}methyl)-N,N-dimethylpiperazine-1-carboxamide A solution of (Z)-2-[(1H-indol-3-yl)methylene]-6-hydroxybenzofuran-3(2H)-one (0.050 g, 0.18 mmol) obtained in Example A1, Step 1 in ethanol (2.0 mL) was added with piperazine-1-carboxylic acid dimethylamide (0.035 g, 0.22 mmol), and 37% aqueous formaldehyde (0.020 g, 0.24 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-4-({2-[(1H-indol-3-yl)methylene]-6-hydroxy-3-oxo-2,3-dihydrobenzofuran-7-yl}methyl)-N,N-dimethylpiperazine-1-carboxamide (0.044 g, 55%).

$^1$H NMR (400 MHz, DMSO-$d_6$) δ 2.60 (m, 4H), 2.72 (s, 6H), 3.15 (m, 4H), 3.91 (s, 2H), 6.73 (d, J=8.3 Hz, 1H), 7.18 (m, 1H), 7.19 (s, 1H), 7.24 (m, 1H), 7.50 (d, J=8.3 Hz, 1H), 7.54 (d, J=8.3 Hz, 1H), 8.10 (d, J=8.3 Hz, 1H), 8.17 (d, J=2.9 Hz, 1H), 11.98 (s, 1H).

Example A6

(Z)-2-[(1H-Indol-3-yl)methylene]-6-hydroxy-7-[(4-hydroxypiperidin-1-yl)methyl]benzofuran-3(2H)-one A solution of (Z)-2-[(1H-indol-3-yl)methylene]-6-hydroxybenzofuran-3(2H)-one (0.050 g, 0.18 mmol) obtained in Example A1, Step 1 in ethanol (2.0 mL) was added with 4-hydroxypiperidine (0.024 g, 0.22 mmol), and 37% aqueous formaldehyde (0.020 g, 0.24 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-6-hydroxy-7-[(4-hydroxypiperidin-1-yl)methyl]benzofuran-3(2H)-one (0.034 g, 48%).

$^1$H NMR (300 MHz, CD$_3$OD) δ 1.64-1.90 (m, 2H), 1.90-2.12 (m, 2H), 2.80-3.05 (m, 2H), 3.16-3.41 (m, 2H), 3.76-3.94 (m, 1H), 4.24 (s, 2H), 6.54 (d, J=8.8 Hz, 1H), 7.15-7.29 (m, 2H), 7.25 (s, 1H), 7.41-7.46 (m, 1H), 7.53 (d, J=8.8 Hz, 1H), 7.86-7.90 (m, 1H), 8.11 (s, 1H).

Example A7

(Z)-4-({2-[(1H-Indol-3-yl)methylene]-6-hydroxy-3-oxo-2,3-dihydrobenzofuran-7-yl}methyl)piperazin-2-one A solution of (Z)-2-[(1H-indol-3-yl)methylene]-6-hydroxybenzofuran-3(2H)-one (0.030 g, 0.11 mmol) obtained in Example A1, Step 1 in ethanol (3.0 mL) was added with 2-oxopiperazine (0.013 g, 0.13 mmol), and 37% aqueous formaldehyde (0.011 g, 0.13 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-4-({2-[(1H-indol-3-yl)methylene]-6-hydroxy-3-oxo-2,3-dihydrobenzofuran-7-yl}methyl)piperazin-2-one (0.012 g, 28%).

$^1$H NMR (300 MHz, CD$_3$OD) δ 2.87-2.96 (m, 2H), 3.38-3.49 (m, 4H), 4.08 (s, 2H), 6.73 (d, J=8.1 Hz, 1H), 7.21-7.33 (m, 2H), 7.40 (s, 1H), 7.47-7.52 (m, 1H), 7.65 (d, J=8.1 Hz, 1H), 7.91-8.00 (m, 1H), 8.06 (s, 1H).

Example A8

(Z)-2-[(1H-Indol-3-yl)methylene]-7-({[3-(dimethylamino)propyl](methyl)amino}methyl)-6-hydroxybenzofuran-3(2H)-one A solution of (Z)-2-[(1H-indol-3-yl)methylene]-6-hydroxybenzofuran-3(2H)-one (0.030 g, 0.11 mmol) obtained in Example A1, Step 1 in ethanol (2.0 mL) was added with N,N,N'-trimethylpropane-1,3-diamine (0.015 g, 0.13 mmol), and 37% aqueous formaldehyde (0.011 g, 0.13 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain (Z)-2-[(1H-indol-3-yl)methylene]-7-({[3-(dimethylamino)propyl](methyl)amino}methyl)-6-hydroxybenzofuran-3(2H)-one (0.024 g, 54%).

$^1$H NMR (300 MHz, CD$_3$OD) δ 1.80-1.95 (m, 2H), 2.36 (s, 6H), 2.55-2.71 (m, 2H), 2.62 (s, 3H), 2.89-3.02 (m, 2H), 4.03 (s, 2H), 6.47 (d, J=8.8 Hz, 1H), 7.13-7.27 (m, 2H), 7.17 (s, 1H), 7.41-7.48 (m, 1H), 7.49 (d, J=8.8 Hz, 1H), 7.85-7.94 (m, 1), 8.06 (s, 1H).

Example A9

(Z)-2-[(1H-Indol-3-yl)methylene]-6-hydroxy-7-({methyl[8-(methylamino)octyl]amino}methyl)benzofuran-3(2H)-one (a) Step 1

The synthesis was performed with reference to the known literature (Tetrahedron Letters, Vol. 49, p. 3921, 2008). A solution of N,N'-dimethyl-1,8-octanediamine (0.50 g, 2.9 mmol) in methylene chloride (10 mL) was added dropwise with di-tert-butyl dicarbonate (0.33 g, 1.5 mmol), and then the mixture was stirred at room temperature for 4 hours. The reaction mixture was added with water, the mixture was extracted with methylene chloride, and then the organic layer was washed with saturated brine, and dried over anhydrous magnesium sulfate. The solvent was evaporated under reduced pressure, and the residue was subjected to silica gel column chromatography (eluted with chloroform/methanol (90:10→80:20)) to obtain tert-butyl methyl[8-(methylamino)octyl]carbamate (0.21 g, 51%).

$^1$H NMR (300 MHz, CDCl$_3$) δ 1.16-1.39 (m, 8H), 1.39-1.59 (m, 4H), 1.45 (s, 9H), 2.45 (s, 3H), 2.58 (m, 2H), 2.83 (s, 3H), 3.18 (m, 2H).

(b) Step 2

A solution of (Z)-2-[(1H-indol-3-yl)methylene]-6-hydroxybenzofuran-3(2H)-one (0.050 g, 0.18 mmol) obtained in Example A1, Step 1 in ethanol (3.0 mL) was added with tert-butyl methyl[8-(methylamino)octyl]carbamate (0.074 g, 0.27 mmol), and 37% aqueous formaldehyde (0.017 g, 0.22 mmol), and the mixture was stirred overnight at 70° C. in a sealed tube. The solvent was evaporated under reduced pressure, and then the residue was subjected to silica gel column chromatography (aminopropyl silica was used, eluted with chloroform/methanol (90:10)) to obtain tert-butyl (Z)-8-[({2-[(1H-indol-3-yl)methylene]-6-hydroxy-3-oxo-2,3-dihydrobenzofuran-7-yl}methyl)(methyl)amino]octyl(methyl)carbamate (0.045 g, 45%).

$^1$H NMR (300 MHz, CDCl$_3$) δ 1.14-1.39 (m, 8H), 1.39-1.55 (m, 2H), 1.46 (s, 9H), 1.55-1.71 (m, 2H), 2.42 (s, 3H), 2.62 (m, 2H), 2.83 (s, 2H), 3.19 (m, 2H), 4.00 (s, 2H), 6.65 (d, J=8.8 Hz, 1H), 7.22-7.34 (m, 3H), 7.42-7.50 (m, 1H), 7.63 (d, J=8.8 Hz, 1H), 7.89-7.97 (m, 1H), 7.99 (s, 1H).

(c) Step 3

A solution of tert-butyl (Z)-8-[({2-[(1H-indol-3-yl)methylene]-6-hydroxy-3-oxo-2,3-dihydrobenzofuran-7-yl}methyl)(methyl)amino]octyl(methyl)carbamate (0.020 g, 0.036 mmol) in methylene chloride (2.0 mL) was added with a 4 M solution of hydrogen chloride in 1,4-dioxane (2.0 mL), and then the mixture was stirred at room temperature for 1 hour. The solvent was evaporated under reduced pressure, and then the residue was added with triethylamine and thereby made basic. The mixture was azeotroped with toluene, and then the residue was subjected to silica gel column chromatography (aminopropyl silica was used, eluted with chloroform/methanol (90:10)) to obtain (Z)-2-[(1H-indol-3-yl)methylene]-6-hydroxy-7-({methyl[8-(methylamino)octyl]amino}methyl)benzofuran-3(2H)-one (0.010 g, 60%).

$^1$H NMR (300 MHz, CD$_3$OD) δ 1.11-1.49 (m, 10H), 1.63-1.80 (m, 2H), 2.41 (s, 3H), 2.48-2.55 (m, 2H), 2.65 (s, 3H), 2.84-2.95 (m, 2H), 4.18 (s, 2H), 6.45 (d, J=8.8 Hz, 1H), 7.17 (s, 1H), 7.18-7.27 (m, 2H), 7.41-7.48 (m, 1H), 7.48 (d, J=8.8 Hz, 1H), 7.83-7.89 (m, 1H), 8.10 (s, 1H).

Example A10

Ethyl (Z)-1-({2-[(1H-indol-3-yl)methylene]-6-hydroxy-3-oxo-2,3-dihydrobenzofuran-7-yl}methyl)piperidine-3-carboxylate A solution of (Z)-2-[(1H-indol-3-yl)methylene]-6-hydroxybenzofuran-3(2H)-one (0.10 g, 0.36 mmol) obtained in Example A1, Step 1 in ethanol (2.0 mL) was added with ethyl nipecotate (0.068 g, 0.43 mmol), and 37% aqueous formaldehyde (0.036 g, 0.46 mmol), and the mixture was stirred overnight at 80° C. in a sealed tube. The solvent was evaporated under reduced pressure, and then the residue was subjected to silica gel column chromatography (aminopropyl silica was used, eluted with chloroform/methanol (90:10)) to obtain ethyl (Z)-1-({2-[(1H-indol-3-yl)methylene]-6-hydroxy-3-oxo-2,3-dihydrobenzofuran-7-yl}methyl)piperidine-3-carboxylate (0.056 g, 35%).

$^1$H NMR (300 MHz, CD$_3$OD) δ 1.20 (t, J=7.3 Hz, 3H), 1.56-2.06 (m, 4H), 2.47-3.00 (m, 4H), 3.00-3.23 (m, 1H), 3.94-4.26 (m, 4H), 6.62 (d, J=8.8 Hz, 1H), 7.15-7.29 (m, 2H), 7.30 (s, 1H), 7.47 (d, J=8.8 Hz, 1H), 7.56 (d, J=8.1 Hz, 1H), 7.90 (m, 1H), 8.11 (s, 1H).

Example A11

(Z)-2-[(1H-Indol-3-yl)methylene]-6-hydroxy-7-(piperazin-1-ylmethyl)benzofuran-3(2H)-one (a) Step 1

A solution of (Z)-2-[(1H-indol-3-yl)methylene]-6-hydroxybenzofuran-3(2H)-one (0.20 g, 0.72 mmol) obtained in Example A1, Step 1 in ethanol (10 mL) was added with 1-tert-butoxycarbonylpiperazine (0.16 g, 0.87 mmol), and 37% aqueous formaldehyde (0.068 g, 0.87 mmol), and the mixture was stirred overnight at 80° C. in a sealed tube. The solvent was evaporated under reduced pressure, and then the residue was subjected to silica gel column chromatography (eluted with chloroform/methanol (90:10)) to obtain tert-butyl (Z)-4-({2-[(1H-indol-3-yl)methylene]-6-hydroxy-3-oxo-2,3-dihydrobenzofuran-7-yl}methyl)piperazine-1-carboxylate (0.22 g, 63%).

$^1$H NMR (300 MHz, CD$_3$OD) δ 1.35 (s, 9H), 2.58 (m, 4H), 3.42 (m, 4H), 3.92 (s, 2H), 6.59 (d, J=8.8 Hz, 1H), 7.06-7.19 (m, 2H), 7.23 (s, 1H), 7.33-7.40 (m, 1H), 7.48 (d, J=8.8 Hz, 1H), 7.79-7.87 (m, 1H), 8.02 (s, 1H).

(b) Step 2

A solution of tert-butyl (Z)-4-({2-[(1H-indol-3-yl)methylene]-6-hydroxy-3-oxo-2,3-dihydrobenzofuran-7-yl}methyl)piperazine-1-carboxylate (0.025 g, 0.053 mmol) in methylene chloride (2.0 mL) was added with a 4 M solution of hydrogen chloride in 1,4-dioxane (2.0 mL), and then the mixture was stirred at room temperature for 2 hours. The solvent was evaporated under reduced pressure, and then the residue was added with triethylamine and thereby made basic. Then, the mixture was azeotroped with toluene, and then the residue was subjected to silica gel column chromatography (aminopropyl silica was used, eluted with chloroform/methanol (90:10)) to obtain (Z)-2-[(1H-indol-3-yl)methylene]-6-hydroxy-7-(piperazin-1-ylmethyl)benzofuran-3(2H)-one (0.012 g, 60%).

$^1$H NMR (300 MHz, CDCl$_3$) δ 2.79 (m, 4H), 3.00 (m, 4H), 4.05 (s, 2H), 6.65 (d, J=8.8 Hz, 1H), 7.18-7.31 (m, 2H), 7.34 (s, 1H), 7.44-7.54 (m, 1H), 7.59 (d, J=8.8 Hz, 1H), 7.89-8.00 (m, 1H), 8.07 (s, 1H).

Example A12

(Z)-2-[(1H-Indol-3-yl)methylene]-5-chloro-6-hydroxy-7-(piperazin-1-ylmethyl)benzofuran-3(2H)-one dihydrochloride (a) Step 1

A solution of 4-chlororesorcinol (4.34 g, 30.0 mmol) in nitrobenzene (60 mL) was added with aluminum chloride (10.2 g, 90.0 mmol) at room temperature. Then, the mixture was added with chloroacetyl chloride (2.87 mL, 36.0 mmol) under ice cooling. The mixture was stirred at 40° C. for 2 hours, and then added with 2 N aqueous sodium hydroxide (60 mL), and then the aqueous layer was separated. The separated aqueous layer was added with concentrated hydrochloric acid and thereby adjusted to pH 3, and the precipitated solid was collected by filtration to obtain the objective 5-chloro-6-hydroxybenzofuran-3(2H)-one (0.995 g, 17%).

$^1$H NMR (300 MHz, DMSO-d$_6$) δ 4.76 (s, 2H), 6.72 (s, 1H), 7.62 (s, 1H), 11.83 (s, 1H).

(b) Step 2

A solution of 5-chloro-6-hydroxybenzofuran-3(2H)-one (0.185 g, 1.00 mmol) in ethanol (20 mL) was added with 1-tert-butoxycarbonylpiperazine (0.186 g, 1.00 mmol), and 37% aqueous formaldehyde (0.0812 g, 1.00 mmol) at room temperature. The mixture was stirred overnight at room temperature, and then the precipitates formed were collected by filtration, and then washed with ethyl acetate to obtain tert-butyl 4-[(5-chloro-6-hydroxy-3-oxo-2,3-dihydrobenzofuran-7-yl)methyl]piperazine-1-carboxylate (0.216 g, 56%).

¹H NMR (300 MHz, DMSO-d₆) δ 1.40 (s, 9H), 2.85 (m, 4H), 3.48 (m, 4H), 4.00 (s, 2H), 4.66 (s, 2H), 7.44 (s, 1H).

(c) Step 3

A solution of tert-butyl 4-[(5-chloro-6-hydroxy-3-oxo-2,3-dihydrobenzofuran-7-yl)methyl]piperazine-1-carboxylate (0.014 g, 0.037 mmol) in methanol (2.0 mL) was added with 1H-indole-3-carboxaldehyde (0.013 g, 0.090 mmol). Then, the mixture was added with 5 drops of piperidine, and then the mixture was stirred at 40° C. for 2 hours. The reaction mixture was cooled to room temperature, and then the solid was collected by filtration, and washed with methanol to obtain tert-butyl (Z)-4-({2-[(1H-indol-3-yl)methylene]-5-chloro-6-hydroxy-3-oxo-2,3-dihydrobenzofuran-7-yl}methyl)piperazine-1-carboxylate (0.016 g, 85%).

¹H NMR (300 MHz, CD₃OD) δ 1.47 (s, 9H), 2.76 (m, 4H), 3.60 (m, 4H), 4.09 (s, 2H), 7.20-7.32 (m, 2H), 7.36 (s, 1H), 7.43-7.50 (m, 1H), 7.73 (s, 1H), 7.91 (d, J=8.1 Hz, 1H), 7.97 (s, 1H).

(d) Step 4

A solution of tert-butyl (Z)-4-({2-[(1H-indol-3-yl)methylene]-5-chloro-6-hydroxy-3-oxo-2,3-dihydrobenzofuran-7-yl}methyl)piperazine-1-carboxylate (0.016 g, 0.031 mmol) in methylene chloride (2.0 mL) was added with a 4 M solution of hydrogen chloride in 1,4-dioxane (2.0 mL), and then the mixture was stirred at room temperature for 1 hour. The mixture was azeotroped twice with toluene under reduced pressure, and then the residual solid was suspended in methylene chloride and thereby washed to obtain (Z)-2-[(1H-indol-3-yl)methylene]-5-chloro-6-hydroxy-7-(piperazin-1-ylmethyl)benzofuran-3(2H)-one dihydrochloride (0.011 g, 73%).

¹H NMR (300 MHz, DMSO-d₆) δ 3.00-3.72 (m, 8H), 4.51 (br s, 2H), 7.17-7.29 (m, 2H), 7.32 (s, 1H), 7.54 (d, J=7.3 Hz, 1H), 7.88 (s, 1H), 8.04 (d, J=7.3 Hz, 1H), 8.38 (d, J=2.2 Hz, 1H), 12.09 (s, 1H).

Example A13

(Z)-2-[(1H-Indol-3-yl)methylene]-6-hydroxy-5-phenyl-7-(piperazin-1-ylmethyl)benzofuran-3(2H)-one dihydrochloride (a) Step 1

The synthesis was performed with reference to the known literature (Journal of Medicinal Chemistry, Vol. 44, p. 664, 2001). A solution of 4-bromoresorcinol (0.42 g, 2.2 mmol) in 1,2-dimethoxyethane (10 mL) was successively added with phenylboronic acid (0.37 g, 3.0 mmol), and 2 M aqueous sodium carbonate (3.5 mL), and the mixture was stirred at room temperature. After the inside of the reaction vessel was replaced with argon, the reaction mixture was added with tetrakis(triphenylphosphine)palladium(0) (0.14 g, 0.12 mmol), and the mixture was stirred at 95° C. for 6 hours in a sealed tube. The reaction mixture was added with ice water, the mixture was extracted with ethyl acetate, and then the organic layer was washed successively with water and saturated brine, and dried over anhydrous magnesium sulfate. The solvent was evaporated under reduced pressure, and then the residue was subjected to silica gel column chromatography (eluted with hexane/ethyl acetate (75:25)) to obtain biphenyl-2,4-diol (0.25 g, 61%).

¹H NMR (300 MHz, DMSO-d₆) δ 6.30 (dd, J=2.2 Hz, J=8.8 Hz, 1H), 6.40 (d, J=2.2 Hz, 1H), 7.04 (d, J=8.8 Hz, 1H), 7.20 (m, 1H), 7.33 (m, 2H), 7.47 (d, J=7.3 Hz, 2H), 9.31 (s, 1H), 9.34 (s, 1H).

(b) Step 2

A solution of biphenyl-2,4-diol (0.24 g, 1.3 mmol) in nitrobenzene (1.0 mL) was added with aluminum chloride (0.60 g, 4.5 mmol) at room temperature. Then, the reaction mixture was added with chloroacetyl chloride (0.60 g, 1.7 mmol) under ice cooling. The mixture was stirred at 40° C. for 3 hours, and then added with water, and the mixture was extracted with ethyl acetate. The organic layer was washed successively with water and saturated brine, and dried over anhydrous magnesium sulfate. The solvent was evaporated under reduced pressure, and then the residue was subjected to silica gel column chromatography (eluted with chloroform/methanol (100:0→90:10)) to obtain 6-hydroxy-5-phenylbenzofuran-3(2H)-one (0.12 g, 42%).

¹H NMR (300 MHz, CDCl₃) δ 4.62 (s, 2H), 6.58 (s, 1H), 7.38-7.48 (m, 3H), 7.48-7.56 (m, 2H), 7.58 (s, 1H), 12.00 (br s, 1H).

(c) Step 3

A solution of 6-hydroxy-5-phenylbenzofuran-3(2H)-one (0.10 g, 0.46 mmol) and 1H-indole-3-carboxaldehyde (0.066 g, 0.46 mmol) in methanol (10 mL) was added with piperidine 0.2 mL), and the mixture was stirred at room temperature for 2 hours. The solid formed was collected by filtration, washed with a mixed solvent of chloroform and methanol to obtain (Z)-2-[(1H-indol-3-yl)methylene]-6-hydroxy-5-phenylbenzofuran-3(2M-one (0.10 g, 62%).

¹H NMR (300 MHz, DMSO-d₆) δ 7.02 (s, 1H), 7.15-7.28 (m, 3H), 7.30-7.37 (m, 2H), 7.38-7.47 (m, 2H), 7.48-7.61 (m, 4H), 8.03 (d, J=7.3 Hz, 1H), 8.24 (d, J=2.2 Hz, 1H), 12.01 (s, 1H).

(d) Step 4

A solution of (Z)-2-[(1H-indol-3-yl)methylene]-6-hydroxy-5-phenylbenzofuran-3(2H)-one (0.035 g, 0.10 mmol) in methanol (3.0 mL) was added with 1-tert-butoxycarbonylpiperazine (0.021 g, 0.11 mmol), and 37% aqueous formaldehyde (0.011 g, 0.15 mmol), and the mixture was stirred overnight at 40° C. The solvent was evaporated under reduced pressure, and then the residue was subjected to silica gel column chromatography (aminopropyl silica was used, eluted with chloroform/methanol (90:10)) to obtain tert-butyl (Z)-4-({2-[(1H-indol-3-yl)methylene]-6-hydroxy-3-oxo-5-phenyl-2,3-dihydrobenzofuran-7-yl}methyl)piperazine-1-carboxylate (0.031 g, 56%).

¹H NMR (300 MHz, CDCl₃) δ 1.46 (s, 9H), 2.71 (m, 4H), 3.54 (m, 4H), 4.09 (s, 2H), 7.20-7.31 (m, 2H), 7.32 (m, 1H), 7.34-7.39 (m, 2H), 7.39-7.52 (m, 3H), 7.56 (d, J=7.3 Hz, 2H), 7.92-8.01 (m, 1H), 7.99 (s, 1H).

(e) Step 5

A solution of tert-butyl (Z)-4-({2-[(1H-indol-3-yl)methylene]-6-hydroxy-3-oxo-5-phenyl-2,3-dihydrobenzofuran-7-yl}methyl)piperazine-1-carboxylate (0.031 g, 0.056 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in methylene chloride and thereby washed to obtain (Z)-2-[(1H-indol-3-yl)methylene]-6-hydroxy-5-phenyl-7-(piperazin-1-ylmethyl)benzofuran-3(2H)-one dihydrochloride (0.023 g, 78%).

$^1$H NMR (300 MHz, DMSO-$d_6$) δ 3.00-3.64 (m, 8H), 4.42 (br s, 2H), 7.15-7.27 (m, 1H), 7.29 (s, 2H), 7.33-7.41 (m, 1H), 7.41-7.50 (m, 2H), 7.50-7.66 (m, 4H), 8.07 (d, J=8.1 Hz, 1H), 8.32 (m, 1H), 9.17 (br s, 2H), 12.04 (s, 1H).

Example A14

(Z)-2-[(1H-Indol-3-yl)methylene]-5-methoxy-7-(piperazin-1-ylmethyl)benzofuran-3(2H)-one dihydrochloride (a) Step 1

The synthesis was performed with reference to the known literature (Canadian Journal of Chemistry, Vol. 50, p. 1276, 1972). 3-Methylsalicylic acid (6.0 g, 39 mmol) was added with 10% aqueous sodium hydroxide (80 mL), and the mixture was stirred at room temperature. The reaction mixture was added portionwise with a suspension of potassium peroxodisulfate (10.8 g, 40 mmol) in water (150 mL), and then the mixture was stirred at room temperature for 12 hours. The reaction mixture was made acidic with concentrated hydrochloric acid, and then extracted with diethyl ether to remove the unreacted starting material. Then, the aqueous layer was added with concentrated hydrochloric acid (40 mL), and the mixture was refluxed by heating for 2 hours. The reaction mixture was cooled to room temperature, and extracted with diethyl ether, and then the organic layer was washed successively with water and saturated brine, and dried over anhydrous magnesium sulfate. The solvent was evaporated under reduced pressure, the solid formed was suspended in ethyl acetate, and then collected by filtration to obtain 2,5-dihydroxy-3-methylbenzoic acid (4.7 g, 71%).

$^1$H NMR (300 MHz, DMSO-$d_6$) δ 2.12 (s, 3H), 6.87 (d, J=3.0 Hz, 1H), 7.00 (d, J=3.0 Hz, 1H), 9.04 (s, 1H), 10.98 (br s, 1H)

(b) Step 2

2,5-Dihydroxy-3-methylbenzoic acid (4.7 g, 29 mmol) was added successively with acetone (40 mL), dimethyl sulfate (9.0 g, 71 mmol), and potassium carbonate (10 g, 72 mmol), and the mixture was stirred at room temperature for 8 hours. The solvent was evaporated under reduced pressure, the residue was added with ethyl acetate, and then the organic layer was washed successively with water and saturated brine, and dried over anhydrous magnesium sulfate. The solvent was evaporated under reduced pressure, the residue was successively added with acetone (50 mL), potassium carbonate (1.0 g, 72 mmol), and methyl bromoacetate (6.6 g, 43 mmol), and then the mixture was refluxed for 8 hours by heating. The reaction mixture was filtered through Celite, and then the solvent was evaporated under reduced pressure. The residue was dissolved in ethyl acetate, and the organic layer was washed successively with water and saturated brine, and then dried over anhydrous magnesium sulfate. The solvent was evaporated under reduced pressure, and the residue was subjected to silica gel column chromatography (eluted with hexane/ethyl acetate (70:30→50:50)) to obtain methyl 5-methoxy-2-(2-methoxy-2-oxoethoxy)-3-methylbenzoate (4.9 g, 63%).

$^1$H NMR (300 MHz, CDCl$_3$) δ 2.32 (s, 3H), 3.79 (s, 3H), 3.83 (s, 3H), 3.88 (s, 3H), 4.54 (s, 2H), 6.91 (d, J=3.0 Hz, 1H), 7.17 (d, J=3.0 Hz, 1H)

(c) Step 3

The synthesis was performed with reference to the known literature (Bioorganic & Medicinal Chemistry Letters, Vol. 17, p. 6354, 2007). Methyl 5-methoxy-2-(2-methoxy-2-oxoethoxy)-3-methylbenzoate (4.9 g, 18.3 mmol) was added with methanol (30 mL), and water (10 mL), and then added with sodium hydroxide (2.2 g, 55 mmol), and the mixture was stirred at 55° C. for 2 hours. The solvent was evaporated under reduced pressure, the residue was made acidic with 3 N hydrochloric acid, and then extracted with ethyl acetate, and the organic layer was washed successively with water and saturated brine, and then dried over anhydrous magnesium sulfate. The solvent was evaporated under reduced pressure, and the solid formed was dried to obtain 2-(carboxymethoxy)-5-methoxy-3-methylbenzoic acid (3.9 g, 89%).

$^1$H NMR (300 MHz, DMSO-$d_6$) δ 2.30 (s, 3H), 3.79 (s, 3H), 4.65 (s, 2H), 7.00 (d, J=3.0 Hz, 1H), 7.03 (d, J=3.0 Hz, 1H)

(d) Step 4

The synthesis was performed with reference to the known literature (Bioorganic & Medicinal Chemistry Letters, Vol. 17, p. 6354, 2007). 2-(Carboxymethoxy)-5-methoxy-3-methylbenzoic acid (3.9 g, 16 mmol) was successively added with acetic acid (12 mL), acetic anhydride (20 mL), and sodium acetate (4.0 g), and the mixture was stirred at 120° C. for 4 hours. The reaction mixture was added with ethyl acetate, and the organic layer was successively washed with water, saturated aqueous sodium hydrogencarbonate, and saturated brine, and then dried over anhydrous magnesium sulfate. The solvent was evaporated under reduced pressure, the residue was successively added with methanol (40 mL), water (10 mL), and concentrated hydrochloric acid (1.0 mL), and the mixture was refluxed for 1 hour by heating. The solvent was evaporated under reduced pressure, then the residue was dissolved in ethyl acetate, and the solution was washed successively with water and saturated brine, and then dried over anhydrous magnesium sulfate. The solvent was evaporated under reduced pressure, and the solid formed was suspended in hexane/ethyl acetate (90:10) and thereby washed to obtain 5-methoxy-7-methylbenzofuran-3(2H)-one (0.25 g, 8%).

$^1$H NMR (300 MHz, CDCl$_3$) δ 2.30 (s, 3H), 3.79 (s, 3H), 4.65 (s, 2H), 6.89 (d, J=3.0 Hz, 1H), 7.07 (d, J=3.0 Hz, 1H)

(e) Step 5

The synthesis was performed with reference to the known literature (Bioconjugate Chemistry, Vol. 18, p. 275, 2007). A solution of 5-methoxy-7-methylbenzofuran-3(2H)-one (0.25 g, 1.4 mmol) in carbon tetrachloride (15 mL) was successively added with N-bromosuccinimide (0.27 g, 1.5 mmol), and benzoyl peroxide (0.025 g, 0.070 mmol), and the mixture was refluxed for 2 hours by heating. The solid in the reaction mixture was removed by filtration, and the solvent was evaporated under reduced pressure. The residue was subjected to silica gel column chromatography (eluted with hexane/ethyl acetate (75:25)) to obtain 7-(bromomethyl)-5-methoxybenzofuran-3(2H)-one (0.040 g, 11%).

$^1$H NMR (300 MHz, CDCl$_3$) δ 3.81 (s, 3H), 4.52 (s, 2H), 4.73 (s, 2H), 7.05 (d, J=3.0 Hz, 1H), 7.27 (d, J=3.0 Hz, 1H)

(f) Step 6

A solution of 7-(bromomethyl)-5-methoxybenzofuran-3(2H)-one (0.040 g, 0.16 mmol) in methylene chloride (2.0 mL) was added with 1-tert-butoxycarbonylpiperazine (0.032 g, 0.17 mmol), and triethylamine (0.021 g, 0.20 mmol), and the mixture was stirred at room temperature for 5 hours. The solvent was evaporated under reduced pressure, and then the residue was subjected to silica gel column chromatography (eluted with chloroform/methanol (95:5)) to obtain tert-butyl 4-[(5-methoxy-3-oxo-2,3-dihydrobenzofuran-7-yl)methyl]piperazine-1-carboxylate (0.008 g, 14%).

$^1$H NMR (300 MHz, CD$_3$OD) δ 1.45 (s, 9H), 2.47 (m, 4H), 3.43 (m, 4H), 3.63 (s, 2H), 3.81 (s, 3H), 4.89 (s, 2H), 7.02 (d, J=3.0 Hz, 1H), 7.34 (d, J=3.0 Hz, 1H)

(g) Step 7

A solution of tert-butyl 4-((5-methoxy-3-oxo-2,3-dihydrobenzofuran-7-yl)methyl)piperazine-1-carboxylate (0.024 g, 0.066 mmol) in methanol (2.0 mL) was added with 1H-indole-3-carboxaldehyde (0.011 g, 0.073 mmol). Then, the mixture was added with 5 drops of piperidine, and the mixture was stirred at 50° C. for 2 hours. The solvent was evaporated under reduced pressure, and then the residue was subjected to silica gel column chromatography (aminopropyl silica was used, eluted with chloroform/methanol (90:10)) to obtain tert-butyl (Z)-4-({2-[(1H-indol-3-yl)methylene]-5-methoxy-3-oxo-2,3-dihydrobenzofuran-7-yl}methyl)piperazine-1-carboxylate (0.027 g, 84%).

$^1$H NMR (300 MHz, CD$_3$OD) δ 1.44 (s, 9H), 2.57 (m, 4H), 3.47 (m, 4H), 3.82 (s, 2H), 3.84 (s, 3H), 7.17 (d, J=2.2 Hz, 1H), 7.18-7.30 (m, 2H), 7.33 (d, J=2.2 Hz, 1H), 7.44 (s, 1H), 7.48 (d, J=7.3 Hz, 1H), 8.00 (d, J=8.1 Hz, 1H), 8.18 (s, 1H).

(h) Step 8

A solution of tert-butyl (Z)-4-({2-[(1H-indol-3-yl)methylene]-5-methoxy-3-oxo-2,3-dihydrobenzofuran-7-yl}methyl)piperazine-1-carboxylate (0.025 g, 0.051 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-2-[(1H-indol-3-yl)methylene]-5-methoxy-7-(piperazin-1-ylmethyl)benzofuran-3(2H)-one dihydrochloride (0.017 g, 73%).

$^1$H NMR (300 MHz, DMSO-d$_6$) δ 3.10-3.70 (m, 8H), 3.86 (s, 3H), 4.50 (br s, 2H), 7.18-7.30 (m, 2H), 7.33 (s, 1H), 7.41 (s, 1H), 7.55 (d, J=7.3 Hz, 1H), 7.65 (m, 1H), 8.07 (d, J=7.3 Hz, 1H), 8.44 (s, 1H), 12.19 (s, 1H).

Example A15

(Z)-6-Hydroxy-2-[(2-methyl-1H-indol-3-yl)methylene]-7-(piperazin-1-ylmethyl)benzofuran-3(2H)-one dihydrochloride (a) Step 1

A solution of 6-hydroxybenzofuran-3(2H)-one (0.50 g, 3.3 mmol) and 2-methyl-1H-indole-3-carboxaldehyde (0.58 g, 3.6 mmol) in ethanol (10 mL) was added with concentrated hydrochloric acid (1.0 mL), and the mixture was stirred at 75° C. for 2 hours. The reaction mixture was cooled to room temperature, and then the solid was collected by filtration, and washed with methanol to obtain (Z)-6-hydroxy-2-[(2-methyl-1H-indol-3-yl)methylene]benzofuran-3(2H)-one (1.1 g, 95%).

$^1$H NMR (300 MHz, DMSO-d$_6$) δ 2.59 (s, 3H), 6.72 (dd, J=2.2 Hz, J=8.8 Hz, 1H), 6.82 (d, J=2.2 Hz, 1H), 6.95 (s, 1H), 7.13-7.21 (m, 2H), 7.33-7.41 (m, 1H), 7.61 (d, J=8.8 Hz, 1H), 8.28-8.37 (m, 1H), 11.95 (s, 1H).

(b) Step 2

A solution of (Z)-6-hydroxy-2-[(2-methyl-1H-indol-3-yl)methylene]benzofuran-3(2H)-one (0.052 g, 0.18 mmol) in methanol (3.0 mL) was added with 1-tert-butoxycarbonylpiperazine (0.040 g, 0.23 mmol), and 37% aqueous formaldehyde (0.019 g, 0.023 mmol), and the mixture was stirred overnight at 70° C. in a sealed tube. The solvent was evaporated under reduced pressure, and then the residue was subjected to silica gel column chromatography (eluted with chloroform/methanol (95:5)) to obtain tert-butyl (Z)-4-({6-hydroxy-2-[(2-methyl-1H-indol-3-yl)methylene]-3-oxo-2,3-dihydrobenzofuran-7-yl}methyl)piperazine-1-carboxylate (0.032 g, 36%).

$^1$H NMR (300 MHz, CDCl$_3$) δ 1.47 (s, 9H), 2.53 (m, 4H), 2.63 (s, 3H), 3.50 (m, 4H), 4.02 (s, 2H), 6.65 (d, J=8.8 Hz, 1H), 7.11 (s, 1H), 7.17-7.30 (m, 2H), 7.34-7.41 (m, 1H), 7.63 (d, J=8.8 Hz, 1H), 8.27-8.33 (m, 1H).

(c) Step 3

A solution of tert-butyl (Z)-4-({6-hydroxy-2-[(2-methyl-1H-indol-3-yl)methylene]-3-oxo-2,3-dihydrobenzofuran-7-yl}methyl)piperazine-1-carboxylate (0.031 g, 0.063 mmol) in methylene chloride (2.0 mL) was added with a 4 M solution of hydrogen chloride in 1,4-dioxane (2.0 mL), and then the mixture was stirred at room temperature for 1 hour. The mixture was azeotroped twice with toluene under reduced pressure, and then the residual solid was suspended in methylene chloride and thereby washed to obtain (Z)-6-hydroxy-2-[(2-methyl-1,1-indol-3-yl)methylene]-7-(piperazin-1-ylmethyl)benzofuran-3(2H)-one dihydrochloride (0.021 g, 78%).

$^1$H NMR (300 MHz, CDCl$_3$) δ 3.22-3.72 (m, 8H), 4.44 (s, 2H), 7.02 (d, J=8.1 Hz, 1H), 7.04 (s, 1H), 7.20 (m, 1H), 7.33 (m 1H), 7.40 (d, J=8.1 Hz, 1H), 7.76 (d, J=8.1 Hz, 1H), 8.34 (d, J=8.1 Hz, 1H), 12.11 (s, 1H).

Example A16

(Z)-6-Hydroxy-2-[(4-hydroxy-1H-indol-3-yl)methylene]-7-(piperazin-1-ylmethyl)benzofuran-3(2H)-one dihydrochloride (a) Step 1

A solution of 6-hydroxybenzofuran-3(2H)-one (3.00 g, 20.0 mmol) in ethanol (20 mL) was added with 1-tert-butoxycarbonylpiperazine (3.73 g, 20.0 mmol), and 37% aqueous formaldehyde (1.62 g, 20.0 mmol) at room temperature. The mixture was stirred overnight at room temperature, and then subjected to suction filtration, and the filtrate was concentrated. Crude product obtained by silica gel column chromatography (hexane/ethyl acetate) was recrystallized from ethyl acetate to obtain the objective tert-butyl 4-[(6-hydroxy-3-oxo-2,3-dihydrobenzofuran-7-yl)methyl]piperazine-1-carboxylate (3.51 g, 50%).

$^1$H NMR (300 MHz, DMSO-d$_6$) δ 1.38 (s, 9H), 2.44 (m, 4H), 3.27 (m, 4H), 3.66 (s, 2H), 4.73 (s, 2H), 6.59 (d, J=8.8 Hz, 1H), 7.40 (d, J=8.8 Hz, 1H).

(b) Step 2

A solution of tert-butyl 4-[(6-hydroxy-3-oxo-2,3-dihydrobenzofuran-7-yl)methyl]piperazine-1-carboxylate (0.056 g, 0.016 mmol) in methanol (2.0 mL) was added with 4-hydroxy-1H-indole-3-carboxaldehyde (0.026 g, 0.016 mmol). Then, the mixture was added with 5 drops of piperidine, and then the mixture was stirred at 60° C. for 2 hours. The solvent was evaporated under reduced pressure, and then the residue was subjected to silica gel column chromatography (aminopropyl silica was used, eluted with chloroform/methanol (90:10)) to obtain tert-butyl (Z)-4-({6-hydroxy-2-[(4-hydroxy-1H-indol-3-yl)methylene]-3-oxo-2,3-dihydrobenzofuran-7-yl}-methyl)piperazine-1H-carboxylate (0.050 g, 64%).

$^1$H NMR (300 MHz, DMSO-d$_6$) δ 1.38 (s, 9H), 2.53 (m, 4H), 3.38 (m, 4H), 3.88 (s, 2H), 6.55 (d, J=7.3 Hz, 1H), 6.72 (d, J=8.1 Hz, 1H), 6.91-7.04 (m, 2H), 7.52 (d, J=8.1 Hz, 1H), 7.69 (s, 1H), 8.06 (d, J=2.9 Hz, 1H), 11.87 (s, 1H).

(c) Step 3

A solution of tert-butyl (Z)-4-({6-hydroxy-2-[(4-hydroxy-1H-indol-3-yl)methylene]-3-oxo-2,3-dihydrobenzofuran-7-yl}methyl)piperazine-1-carboxylate (0.015 g, 0.031 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-[(4-hydroxy-1H-indol-3-yl)methylene]-7-(piperazin-1-ylmethyl)benzofuran-3(2H)-one dihydrochloride (0.010 g, 75%).

$^1$H NMR (300 MHz, DMSO-d$_6$) δ 3.25-3.74 (m, 8H), 4.57 (br s, 2H), 6.65 (dd, J=2.2 Hz, J=5.9 Hz, 1H), 6.87-7.09 (m, 3H), 7.73 (d, J=8.8 Hz, 1H), 7.79 (s, 1H), 8.33 (s, 1H), 11.89 (s, 1H).

Example A17

(Z)-6-Hydroxy-2-[(5-nitro-1H-indol-3-yl)methylene]-7-(piperazin-1-ylmethyl)benzofuran-3(2H)-one dihydrochloride (a) Step 1

A solution of 6-hydroxybenzofuran-3(2H)-one (0.400 g, 2.7 mmol) and 5-nitro-1H-indole-3-carboxaldehyde (0.56 g, 2.9 mmol) in ethanol (5.0 mL) was added with concentrated hydrochloric acid (1.0 mL), and the mixture was stirred at 70° C. for 3 hours. The reaction mixture was cooled to room temperature, and then the solid was collected by filtration, and washed with methanol to obtain (Z)-6-hydroxy-2-[(5-nitro-1H-indol-3-yl)methylene]benzofuran-3(2H)-one (0.77 g, 90%).

$^1$H NMR (300 MHz, DMSO-d$_6$) δ 6.73 (d, J=8.8 Hz, 1H), 6.84 (s, 1H), 7.33 (s, 1H), 7.63 (d, J=8.8 Hz, 1H), 7.68 (d, J=8.8 Hz, 1H), 8.11 (dd, J=2.2 Hz, J=8.8 Hz, 1H), 8.39 (d, J=2.2 Hz, 1H), 9.19 (s, 1H), 12.60 (s, 1H)

(b) Step 2

A solution of (Z)-6-hydroxy-2-[(5-nitro-1H-indol-3-yl)methylene]benzofuran-3(2H)-one (0.12 g, 0.37 mmol) in ethanol (3.0 mL) was added with 1-tert-butoxycarbonylpiperazine (0.075 g, 0.40 mmol), and 37% aqueous formaldehyde (0.040 g, 0.50 mmol), and the mixture was stirred overnight at 70° C. in a sealed tube. The reaction mixture was cooled to room temperature, and then the solid was collected by filtration, and washed with methanol to obtain tert-butyl (Z)-4-({6-hydroxy-2-[(5-nitro-1H-indol-3-yl)methylene]-3-oxo-2,3-dihydrobenzofuran-7-yl}methyl)piperazine-1-carboxylate (0.090 g, 47%).

$^1$H NMR (300 MHz, DMSO-d$_6$) δ 1.38 (s, 9H), 2.57 (m, 4H), 3.37 (m, 4H), 4.03 (s, 2H), 6.75 (d, J=8.8 Hz, 1H), 7.30 (s, 1H), 7.58 (d, J=8.8 Hz, 1H), 7.69 (d, J=8.8 Hz, 1H), 8.12 (dd, J=2.2 Hz, J=8.8 Hz, 1H), 8.35 (d, J=2.9 Hz, 1H), 9.25 (d, J=2.2 Hz, 1H), 12.53 (s, 1H).

(c) Step 3

A solution of tert-butyl (Z)-4-({6-hydroxy-2-[(5-nitro-1H-indol-3-yl)methylene]-3-oxo-2,3-dihydrobenzofuran-7-yl}methyl)piperazine-1-carboxylate (0.020 g, 0.038 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in methylene chloride and thereby washed to obtain (Z)-6-hydroxy-2-[(5-nitro-1H-indol-3-yl)methylene]-7-(piperazin-1-ylmethyl)benzofuran-3(2H)-one dihydrochloride (0.013 g, 69%).

$^1$H NMR (300 MHz, DMSO-d$_6$) δ 3.10-3.70 (m, 8H), 4.57 (br s, 2H), 7.00 (d, J=8.8 Hz, 1H), 7.43 (s, 1H), 7.72 (d, J=8.8 Hz, 1H), 7.76 (d, J=8.8 Hz, 1H), 7.75 (d, J=8.8 Hz, 1H), 8.61 (s, 1H), 9.18 (s, 1H), 12.64 (br s, 1H).

Example A18

(Z)-6-Hydroxy-2-[(5-methyl-1H-indol-3-yl)methylene]-7-(piperazin-1-ylmethyl)benzofuran-3(2H)-one dihydrochloride (a) Step 1

A solution of tert-butyl 4-[(6-hydroxy-3-oxo-2,3-dihydrobenzofuran-7-yl)methyl]piperazine-1-carboxylate (0.070 g, 0.020 mmol) in methanol (2.0 mL) was added with 5-methyl-1H-indole-3-carboxaldehyde (0.034 g, 0.021 mmol). Then, the mixture was added with 5 drops of piperidine, and the mixture was stirred at 50° C. for 2 hours. The reaction mixture was cooled to room temperature, and then filtered through Celite, and the filtrate was concentrated under reduced pressure. The residue was subjected to silica gel column chromatography (aminopropyl silica was used, eluted with chloroform/methanol (93:7)) to obtain tert-butyl (Z)-4-({6-hydroxy-2-[(5-methyl-1H-indol-3-yl)methylene]-3-oxo-2,3-dihydrobenzofuran-7-yl}methyl)piperazine-1-carboxylate (0.056 g, 55%).

$^1$H NMR (300 MHz, CD$_3$OD) δ 1.47 (s, 9H), 2.52 (s, 3H), 2.71 (m, 4H), 3.57 (m, 4H), 4.09 (s, 2H), 6.70 (d, J=8.8 Hz, 1H), 7.11 (d, J=8.1 Hz, 1H), 7.35 (s, 1H), 7.38 (d, J=8.1 Hz, 1H), 7.63 (d, J=8.8 Hz, 1H), 7.79 (s, 1H), 7.98 (s, 1H)

(b) Step 2

A solution of tert-butyl (Z)-4-({6-hydroxy-2-[(5-methyl-1H-indol-3-yl)methylene]-3-oxo-2,3-dihydrobenzofuran-7- yl}methyl)piperazine-1-carboxylate (0.030 g, 0.061 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-[(5-methyl-1H-indol-3-yl)methylene]-7-(piperazin-1-ylmethyl)benzofuran-3(2H)-one dihydrochloride (0.018 g, 64%).

$^1$H NMR (300 MHz, DMSO-$d_6$) δ 2.44 (s, 3H), 3.10-3.76 (m, 8H), 4.59 (br s, 2H), 7.00 (d, J=8.8 Hz, 1H), 7.07 (d, J=8.8 Hz, 1H), 7.24 (s, 1H), 7.41 (d, J=8.8 Hz, 1H), 7.75 (d, J=8.8 Hz, 1H), 8.40 (d, J=2.9 Hz, 1H), 11.93 (s, 1H).

Example A19

(Z)-6-Hydroxy-2-{[5-(2-morpholinoethoxy)-1H-indol-3-yl]methylene}-7-(piperazin-1-ylmethyl)benzofuran-3(2H)-one dihydrochloride (a) Step 1

A solution of 5-hydroxy-1H-indole (0.13 g, 1.0 mmol) in acetonitrile (10 mL) was successively added with N-(2-chloroethyl)morpholine hydrochloride (0.19 g, 1.0 mmol), and potassium carbonate (0.28 g, 2.0 mmol), and the mixture was stirred at room temperature for 72 hours. The solvent was evaporated under reduced pressure, then the residue was added with ethyl acetate, and the organic layer was washed successively with water and saturated brine, and dried over anhydrous magnesium sulfate. The solvent was evaporated under reduced pressure, and then the residue was subjected to silica gel column chromatography (eluted with hexane/ethyl acetate (50:50→20:80)) to obtain 4-[2-(1H-indol-5-yloxy)ethyl]morpholine (0.12 g, 50%).

$^1$H NMR (300 MHz, DMSO-$d_6$) δ 2.48 (m, 4H), 2.71 (m, 2H), 3.59 (m, 4H), 4.06 (m, 2H), 6.31 (m, 1H), 6.72 (dd, J=2.2 Hz, J=8.8 Hz, 1H), 7.05 (d, J=2.2 Hz, 1H), 7.23-7.30 (m, 1H), 10.89 (s, 1H).

(b) Step 2

Under an argon atmosphere, a solution of 4-[2-(1H-indol-5-yloxy)ethyl]morpholine (0.12 g, 0.5 mmol) in 1,2-dichloroethane (2.0 mL) was added dropwise with a solution of phosphorus oxychloride (0.1 mL) and N,N-dimethylformamide (0.1 mL) in 1,2-dichloroethane (1.0 mL). The mixture was stirred at room temperature for 1 hour, and then added with 3 N aqueous potassium hydroxide, and the mixture was stirred at 60° C. for 2 hours. The aqueous layer was adjusted to pH 7 with 3 N hydrochloric acid, and then extracted with ethyl acetate. The resulting organic layer was washed successively with water and saturated brine, and dried over anhydrous magnesium sulfate. The solvent was evaporated under reduced pressure, the residue was suspended in a mixed solvent of ethyl acetate and hexane and thereby washed to obtain 5-(2-morpholinoethoxy)-1H-indole-3-carboxaldehyde (0.068 g, 50%).

$^1$H NMR (300 MHz, DMSO-$d_6$) δ 2.47-2.53 (m, 4H), 2.72 (m, 2H), 3.58 (m, 4H), 4.10 (m, 2H), 6.93 (dd, J=2.2 Hz, J=8.8 Hz, 1H), 7.44 (d, J=8.8 Hz, 1H), 7.63 (d, J=2.2 Hz, 1H), 8.25 (d, J=2.9 Hz, 1H), 9.89 (s, 1H), 12.01 (s, 1H).

(c) Step 3

A solution of tert-butyl 4-[(6-hydroxy-3-oxo-2,3-dihydrobenzofuran-7-yl)methyl]piperazine-1-carboxylate (0.067 g, 0.19 mmol) obtained in Example A16, Step 1 in methanol (5.0 mL) was added with 5-(2-morpholinoethoxy)-1H-indole-3-carboxaldehyde (0.044 g, 0.16 mmol). Then, the mixture was added with 5 drops of piperidine, and the mixture was stirred at 50° C. for 2 hours. The solvent was evaporated under reduced pressure, and then the residue was subjected to silica gel column chromatography (eluted with chloroform/methanol (95:5)) to obtain tert-butyl (Z)-4-[(6-hydroxy-2-{[5-(2-morpholinoethoxy)-1H-indol-3-yl]methylene}-3-oxo-2,3-dihydrobenzofuran-7-yl)methyl]piperazine-1-carboxylate (0.076 g, 81%).

$^1$H NMR (300 MHz, CD$_3$OD) δ 1.48 (s, 9H), 2.68 (m, 8H), 2.89 (m, 2H), 3.56 (m, 4H), 3.78 (m, 4H), 4.04 (s, 2H), 4.24 (m, 2H), 6.69 (d, J=8.8 Hz, 1H), 7.18 (dd, J=2.2 Hz, J=8.8 Hz, 1H), 7.30-7.42 (m, 3H), 7.62 (d, J=8.8 Hz, 1H), 8.00 (s, 1H).

(d) Step 4

A solution of tert-butyl (Z)-4-[(6-hydroxy-2-{[5-(2-morpholinoethoxy)-1H-indol-3-yl]methylene}-3-oxo-2,3-dihydrobenzofuran-7-yl)methyl]piperazine-1-carboxylate (0.076 g, 0.013 mmol) in methylene chloride (2.0 mL) was added with a 4 M solution of hydrogen chloride in 1,4-dioxane (2.0 mL), and then the mixture was stirred at room temperature for 1 hour. The mixture was azeotroped twice with toluene under reduced pressure, and then the residual solid was suspended in methylene chloride and thereby washed to obtain (Z)-6-hydroxy-2-{[5-(2-morpholinoethoxy)-1H-indol-3-yl]methylene}-7-(piperazin-1-ylmethyl)benzofuran-3(2H)-one trihydrochloride (0.048 g, 60%).

$^1$H NMR (300 MHz, DMSO-$d_6$) δ 2.91-3.72 (m, 12H), 3.72-4.10 (m, 6H), 4.50 (m, 4H), 6.89-7.03 (m, 2H), 7.33 (s, 1H), 7.46 (d, J=8.8 Hz, 1H), 7.64 (s, 1H), 7.73 (d, J=8.1 Hz, 1H), 8.41 (d, J=2.9 Hz, 1H), 11.96 (s, 1H).

Example A20

(Z)—N-[(3-{[6-Hydroxy-3-oxo-7-(piperazin-1-ylmethyl)benzofuran-2(3H)-ylidene]methyl}-1H-indol-5-yl)methyl]acetamide dihydrochloride (a) Step 1

The synthesis was performed with reference to the known literature (International Patent Publication WO2000/75139). 5-Aminomethyl-1H-indole (0.50 g, 3.4 mmol) was added with acetic anhydride (2.0 mL), and the mixture was stirred at room temperature for 3 hours. The mixture was azeotroped twice with toluene under reduced pressure, and the residual solid was washed with ethyl acetate to obtain N-[(1H-indol-5-yl)methyl]acetamide (0.62 g, 96%).

$^1$H NMR (300 MHz, CDCl$_3$) δ 2.00 (s, 3H), 4.50 (d, J=5.9 Hz, 2H), 5.76 (br s, 1H), 6.52 (m, 1H), 7.12 (d, J=8.1 Hz, 1H), 7.22 (m, 1H), 7.36 (d, J=8.1 Hz, 1H), 7.55 (s, 1H), 8.41 (br s, 1H).

(b) Step 2

The synthesis was performed with reference to the known literature (International Patent Publication WO2000/75139). N,N-Dimethylformamide (2.0 mL) cooled to 0° C. was added dropwise with phosphorus oxychloride (0.54 g, 3.5 mmol), and then the mixture was stirred for 15 minutes. Then, the mixture was added with a solution of N-[(1H-indol-5-yl)methyl]acetamide (0.60 g, 3.2 mmol) in N,N-dimethylformamide (4.0 mL), and then the mixture was stirred overnight at room temperature. The reaction mixture was added with ethyl acetate, and then the organic layer was washed successively with water and saturated brine, and dried over anhydrous magnesium sulfate. The solvent was evaporated under reduced pressure, and then the residue was subjected to silica gel column chromatography (eluted with chloroform/methanol (90:10)) to obtain a solid containing the objective substance. This solid was washed with ethyl acetate to obtain N-[(3-formyl-1H-indol-5-yl)methyl]acetamide (0.12 g, 17%).

$^1$H NMR (300 MHz, DMSO-$d_6$) δ 1.86 (s, 3H), 4.33 (d, J=5.9 Hz, 2H), 7.16 (d, J=8.1 Hz, 1H), 7.44 (d, J=8.1 Hz, 1H), 7.90 (s, 1H), 8.27 (s, 1H), 8.36 (m, 1H), 9.91 (s, 1H), 12.09 (s, 1H).

(c) Step 3

A solution of tert-butyl 4-[(6-hydroxy-3-oxo-2,3-dihydrobenzofuran-7-yl)methyl]piperazine-1-carboxylate (0.083 g, 0.24 mmol) obtained in Example A16, Step 1 in methanol (5.0 mL) was added with N-[(3-formyl-1H-indol-5-yl)methyl]acetamide (0.043 g, 0.20 mmol). Then, the mixture was added with 10 drops of piperidine, and then the mixture was stirred overnight at room temperature. The solvent was evaporated under reduced pressure, and then the residue was subjected to silica gel column chromatography (eluted with chloroform/methanol (95:5)) to obtain tert-butyl (Z)-4-[(2-{[5-(acetamidemethyl)-1H-indol-3-yl]methylene}-6-hydroxy-3-oxo-2,3-dihydrobenzofuran-7-yl)methyl]piperazine-1-carboxylate (0.076 g, 70%).

$^1$H NMR (300 MHz, DMSO-$d_6$) δ 1.38 (s, 9H), 1.88 (s, 3H), 2.54 (m, 4H), 3.36 (m, 4H), 3.93 (s, 2H), 4.38 (d, J=5.9 Hz, 2H), 6.73 (d, J=8.8 Hz, 1H), 7.14 (m, 2H), 7.45 (d, J=8.1 Hz, 1H), 7.54 (d, J=8.8 Hz, 1H), 7.93 (s, 1H), 8.15 (s, 1H), 8.32 (m, 1H), 11.94 (s, 1H).

(d) Step 4

A solution of tert-butyl (Z)-4-[(2-{[5-(acetamidemethyl)-1H-indol-3-yl]methylene}-6-hydroxy-3-oxo-2,3-dihydrobenzofuran-7-yl)methyl]piperazine-1-carboxylate (0.040 g, 0.073 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in diethyl ether and thereby washed to obtain (Z)—N-[(3-{[6-hydroxy-3-oxo-7-(piperazin-1-ylmethyl)benzofuran-2(3H)-ylidene]methyl}-1H-indol-5-yl)methyl]acetamide dihydrochloride (0.029 g, 82%).

$^1$H NMR (300 MHz, DMSO-$d_6$) δ 1.89 (s, 3H), 3.10-3.75 (m, 8H), 4.37 (s, 2H), 4.53 (br s, 2H), 6.98 (d, J=8.1 Hz, a), 7.15 (d, J=8.8 Hz, 1H), 7.22 (s, 1H), 7.47 (d, J=8.1 Hz, 1H), 7.69-7.79 (m, 2H), 7.86 (s, 1H), 8.32-8.44 (m, 2H), 12.00 (s, 1H).

Example A21

(Z)-2-[(5-Chloro-1H-indol-3-yl)methylene]-6-hydroxy-7-(piperazin-1-ylmethyl)benzofuran-3(2H)-one dihydrochloride (a) Step 1

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1.2 mL) was added with 5-chloro-1H-indole-3-carboxaldehyde (0.0515 g, 0.287 mmol) and piperidine (0.00244 g, 0.0287 mmol), and the mixture was stirred at 60° C. for 3 hours. The reaction mixture was cooled to room temperature, and added with methanol (4 mL), and the solid was suspended in methanol and thereby washed to obtain tert-butyl (Z)-4-({2-[(5-chloro-1H-indol-3-yl)methylene]-6-hydroxy-3-oxo-2,3-dihydrobenzofuran-7-yl}methyl)piperazine-1-carboxylate (0.0730 g, 49%).

$^1$H NMR (300 MHz, DMSO-$d_6$) δ 1.37 (s, 9H), 2.50 (m, 4H), 3.35 (m, 4H), 3.91 (s, 2H), 6.73 (d, J=8.8 Hz, 1H), 7.20 (s, 1H), 7.23 (dd, J=2.2 Hz, 8.1 Hz, 1H), 7.51 (d, J=8.8 Hz, 1H), 7.55 (d, J=8.1 Hz, 1H), 8.20 (d, J=2.2 Hz, 1H), 8.27 (s, 1H), 12.11 (s, 1H).

(b) Step 2

A solution of tert-butyl (Z)-4-({2-[(5-chloro-1H-indol-3-yl)methylene]-6-hydroxy-3-oxo-2,3-dihydrobenzofuran-7-yl}methyl)piperazine-1-carboxylate (0.0710 g, 0.139 mmol) in methylene chloride (3.0 mL) was added with trifluoroacetic acid (3.0 mL), and then the mixture was stirred overnight at room temperature. The reaction mixture was concentrated, then a solution of the resulting residue in methanol (8 mL) was added with a 5% solution of hydrogen chloride in methanol (2 mL), and the mixture was stirred at room temperature for 2 hours. The solvent was evaporated to obtain (Z)-2-[(5-chloro-1H-indol-3-yl)methylene]-6-hydroxy-7-(piperazin-1-ylmethyl)benzofuran-3(2H)-one dihydrochloride (0.0611 g, 98%).

$^1$H NMR (300 MHz, DMSO-$d_6$) δ 3.57-3.79 (m, 8H), 4.52 (br s, 2H), 6.99 (d, J=8.8 Hz, 1H), 7.22 (dd, J=2.2 Hz, 8.8 Hz, 1H), 7.31 (s, 1H), 7.54 (d, J=8.8 Hz, 1H), 7.73 (d, J=8.8 Hz, 1H), 8.15 (d, J=2.2 Hz, 1H), 8.48 (s, 1H), 12.17 (br s, 1H).

Example A22

(Z)-2-[(5-Bromo-1H-indol-3-yl)methylene]-6-hydroxy-7-(piperazin-1-ylmethyl)benzofuran-3(2H)-one dihydrochloride (a) Step 1

A solution of 6-hydroxybenzofuran-3(2H)-one (0.50 g, 3.3 mmol) and 5-bromo-1H-indole-3-carboxaldehyde (0.90 g, 4.0 mmol) in ethanol (10 mL) was added with concentrated hydrochloric acid (1.0 mL), and the mixture was stirred at 75° C. for 2 hours. The reaction mixture was cooled to room temperature, and then the solid was collected by filtration, and washed with methanol to obtain (Z)-2-[(5-bromo-1H-indol-3-yl)methylene]-6-hydroxybenzofuran-3(2H)-one (1.1 g, 95%).

$^1$H NMR (300 MHz, DMSO-$d_6$) δ 6.73 (d, J=2.2 Hz, J=8.8 Hz, 1H), 6.83 (d, J=2.2 Hz, 1H), 7.22 (s, 1H), 7.63 (dd, J=2.2 Hz, J=8.8 Hz, 1H), 7.47 (d, J=8.8 Hz, 1H), 7.61 (d, J=8.8 Hz, 1H), 8.23 (d, J=2.9 Hz, 1H), 8.30 (s, 1H), 12.20 (s, 1H)

(b) Step 2

A solution of (Z)-2-[(5-bromo-1H-indol-3-yl)methylene]-6-hydroxybenzofuran-3(2H)-one (0.30 g, 0.84 mmol) in ethanol (3.0 mL) was added with 1-tert-butoxycarbonylpiperazine (0.17 g, 0.93 mmol), and 37% aqueous formaldehyde (0.093 g, 1.1 mmol), and the mixture was stirred overnight at 50° C. in a sealed tube. The solvent was evaporated under reduced pressure, and then the residue was subjected to silica gel column chromatography (aminopropyl silica was used, eluted with chloroform/methanol (90:10)) to obtain tert-butyl (Z)-4-({2-[(5-bromo-1H-indol-3-yl)methylene]-6-hydroxy-3-oxo-2,3-dihydrobenzofuran-7-yl}-methyl)piperazine-1-carboxylate (0.15 g, 33%).

$^1$H NMR (300 MHz, CD$_3$OD) δ 1.47 (s, 9H), 2.74 (m, 4H), 3.55 (m, 4H), 4.11 (s, 2H), 6.70 (d, J=8.1 Hz, 1H), 7.19 (s, 1H), 7.30-7.41 (m, 2H), 7.60 (d, J=8.1 Hz, 1H), 7.74 (s, 1H), 8.32 (s, 1H).

(c) Step 3

A solution of tert-butyl (Z)-4-({2-[(5-bromo-1H-indol-3-yl)methylene]-6-hydroxy-3-oxo-2,3-dihydrobenzofuran-7-yl}methyl)piperazine-1-carboxylate (0.015 g, 0.027 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in methylene chloride and thereby washed to obtain (Z)-2-[(5-bromo-1H-indol-3-yl)methylene]-6-hydroxy-7-(piperazin-1-ylmethyl)benzofuran-3(2H)-one dihydrochloride (0.012 g, 91%).

$^1$H NMR (300 MHz, DMSO-d$_6$) δ 3.10-3.70 (m, 8H), 4.53 (br s, 2H), 6.98 (d, J=8.8 Hz, 1H), 7.32 (s, 1H), 7.35 (d, J=8.8 Hz, 1H), 7.50 (d, J=8.8 Hz, 1H), 7.74 (d, J=8.8 Hz, 1H), 8.30 (s, 1H), 8.46 (s, 1H), 12.22 (br s, 1H).

Example A23

Methyl (Z)-3-{[6-hydroxy-3-oxo-7-(piperazin-1-ylmethyl)benzofuran-2(3H)-ylidene]methyl}-1H-indole-6-carboxylate (a) Step 1

A solution of tert-butyl 4-[(6-hydroxy-3-oxo-2,3-dihydrobenzofuran-7-yl)methyl]piperazine-1-carboxylate (0.060 g, 0.017 mmol) obtained in Example A16, Step 1 in methanol (2.0 mL) was added with methyl 3-formyl-1H-indole-6-carboxylate (0.040 g, 0.019 mmol). Then, the mixture was added with 5 drops of piperidine, and the mixture was stirred at 60° C. for 2 hours. The solvent was evaporated under reduced pressure, and then the residue was subjected to silica gel column chromatography (aminopropyl silica was used, eluted with chloroform/methanol (93:7)) to obtain methyl (Z)-3-[(7-{[4-(tert-butoxycarbonyl)piperazin-1-yl]methyl}-6-hydroxy-3-oxobenzofuran-2(3H)-ylidene)methyl]-1H-indole-6-carboxylate (0.071 g, 78%).

$^1$H NMR (300 MHz, CD$_3$OD) δ 1.47 (s, 9H), 2.71 (m, 4H), 3.56 (m, 4H), 3.95 (s, 3H), 4.05 (s, 2H), 6.80 (d, J=8.1 Hz, 1H), 7.28 (s, 1H), 7.60 (d, J=8.1 Hz, 1H), 7.69 (s, 1H), 7.88 (d, J=8.8 Hz, 1H), 7.96 (d, J=8.1 Hz, 1H), 8.18 (s, 2H).

(b) Step 2

A solution of methyl (Z)-3-[(7-{[4-(tert-butoxycarbonyl)piperazin-1-yl]methyl}-6-hydroxy-3-oxobenzofuran-2(3H)-ylidene)methyl]-1H-indole-6-carboxylate (0.020 g, 0.037 mmol) in methylene chloride (2.0 mL) was added with a 4 M solution of hydrogen chloride in 1,4-dioxane (2.0 mL), and then the mixture was stirred at room temperature for 2 hours. The solvent was evaporated under reduced pressure, then the residue was added with an excessive amount of triethylamine, and the mixture was azeotroped with toluene. The resulting residue was subjected to silica gel column chromatography (aminopropyl silica was used, eluted with chloroform/methanol (90:10)) to obtain methyl (Z)-3-{[6-hydroxy-3-oxo-7-(piperazin-1-ylmethyl)benzofuran-2(3H)-ylidene]methyl}-1H-indole-6-carboxylate (0.007 g, 43%).

$^1$H NMR (300 MHz, CDCl$_3$) δ 2.79 (m, 4H), 3.00 (m, 4H), 3.94 (s, 3H), 4.04 (s, 2H), 6.64 (d, J=8.8 Hz, 1H), 7.24 (s, 1H), 7.58 (d, J=8.8 Hz, 1H), 7.87 (d, J=8.1 Hz, 1H), 7.94 (d, J=8.1 Hz, 1H), 8.17 (s, 2H).

Example A24

(Z)-6-Hydroxy-2-[(6-nitro-1H-indol-3-yl)methylene]-7-(piperazin-1-ylmethyl)benzofuran-3(2H)-one dihydrochloride (a) Step 1

6-Nitroindole (1.0 g, 6.2 mmol) was successively added with acetic acid (2.5 mL), water (5.0 mL), and hexamethylenetetramine (1.2 g, 8.4 mmol), and then the mixture was stirred overnight at 120° C. in a sealed tube. The reaction mixture was added with water, and the precipitated solid was collected by filtration, and then dried to obtain 6-nitro-1H-indole-3-carboxaldehyde (0.91 g, 77%).

$^1$H NMR (300 MHz, DMSO-d$_6$) δ 8.12 (d, J=8.8 Hz, 1H), 8.27 (d, J=8.8 Hz, 1H), 8.44 (s, 1H), 8.66 (s, 1H), 10.02 (s, 1H).

(b) Step 2

A solution of tert-butyl 4-[(6-hydroxy-3-oxo-2,3-dihydrobenzofuran-7-yl)methyl]piperazine-1-carboxylate (0.050 g, 0.14 mmol) obtained in Example A16, Step 1 in methanol (2.0 mL) was added with 6-nitro-1H-indole-3-carboxaldehyde (0.026 g, 0.14 mmol). Then, the mixture was added with 5 drops of piperidine, and the mixture was stirred at 50° C. for 2 hours. The solvent was evaporated under reduced pressure, and then the residue was washed with a mixed solvent of chloroform and methanol to obtain tert-butyl (Z)-4-({6-hydroxy-2-[(6-nitro-1H-indol-3-yl)methylene]-3-oxo-2,3-dihydrobenzofuran-7-yl}methyl)piperazine-1-carboxylate (0.049 g, 67%).

$^1$H NMR (300 MHz, CDCl$_3$) δ 1.48 (s, 9H), 2.70 (m, 4H), 3.58 (m, 4H), 4.04 (s, 2H), 6.70 (d, J=8.1 Hz, 1H), 7.25 (s, 1H), 7.66 (d, J=8.1 Hz, 1H), 7.99 (d, J=8.8 Hz, 1H), 8.06 (dd, J=2.2 Hz, J=8.8 Hz, 1H), 8.19 (s, 1H), 8.42 (d, J=2.2 Hz, 1H).

(c) Step 3

A solution of tert-butyl (Z)-4-({6-hydroxy-2-[(6-nitro-1H-indol-3-yl)methylene]-3-oxo-2,3-dihydrobenzofuran-7-yl}methyl)piperazine-1-carboxylate (0.020 g, 0.038 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-[(6-nitro-1H-indol-3-yl)methylene]-7-(piperazin-1-ylmethyl)benzofuran-3(2H)-one dihydrochloride (0.014 g, 75%).

$^1$H NMR (300 MHz, DMSO-d$_6$) δ 3.15-3.75 (m, 8H), 4.56 (br s, 2H), 6.99 (d, J=8.8 Hz, 1H), 7.34 (s, 1H), 7.76 (d, J=8.8 Hz, 1H), 8.05 (dd, J=2.2 Hz, J=8.8 Hz, 1H), 8.27 (d, J=8.8 Hz, 1H), 8.47 (d, J=2.2 Hz, 1H), 8.81 (s, 1H), 12.65 (s, 1H)

Example A25

(Z)-2-[(6-Amino-1H-indol-3-yl)methylene]-6-hydroxy-7-(piperazin-1-ylmethyl)benzofuran-3(2H)-one trihydrochloride (a) Step 1

A solution of tert-butyl (Z)-4-({6-hydroxy-2-[(6-nitro-1H-indol-3-yl)methylene]-3-oxo-2,3-dihydrobenzofuran-7-yl}methyl)piperazine-1-carboxylate (0.025 g, 0.048 mmol) obtained in Example A24, Step 2 in ethanol (2.0 mL) was added with Lindlar's catalyst (0.010 mg) under an argon atmosphere, and then the inside of the reaction vessel was replaced with hydrogen. The reaction mixture was stirred at room temperature for 5 hours, and then filtered through Celite, and the solvent was evaporated under reduced pressure to obtain tert-butyl (Z)-4-({2-[(6-amino-1H-indol-3-yl)methylene]-6-hydroxy-3-oxo-2,3-dihydrobenzofuran-7-yl}methyl)piperazine-1-carboxylate (0.023 g, 97%).

$^1$H NMR (300 MHz, CD$_3$OD) δ 1.45 (s, 9H), 2.64 (m, 4H), 3.50 (m, 4H), 3.99 (s, 2H), 6.67 (d, J=8.8 Hz, 1H), 6.75 (d, J=8.8 Hz, 1H), 6.82 (s, 1H), 7.23 (s, 1H), 7.55 (d, J=8.8 Hz, 1H), 7.72 (d, J=8.8 Hz, 1H), 7.87 (s, 1H).

(b) Step 2

A solution of tert-butyl (Z)-4-({2-[(6-amino-1H-indol-3-yl)methylene]-6-hydroxy-3-oxo-2,3-dihydrobenzofuran-7-yl}methyl)piperazine-1-carboxylate (0.023 g, 0.047 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-2-[(6-amino-1H-indol-3-yl)methylene]-6-hydroxy-7-(piperazin-1-ylmethyl)benzofuran-3(2H)-one trihydrochloride (0.010 g, 43%).

$^1$H NMR (300 MHz, DMSO-d$_6$) δ 3.20-3.75 (m, 8H), 4.52 (br s, 2H), 7.00 (d, J=8.8 Hz, 1H), 7.18 (d, J=8.8 Hz, 1H), 7.27 (s, 1H), 7.64 (s, 1H), 7.74 (d, J=8.8 Hz, 1H), 8.14 (d, J=8.8 Hz, 1H), 8.53 (s, 1H), 12.25 (s, 1H).

Example A26

(Z)-2-{[7-(Benzyloxy)-1H-indol-3-yl]methylene}-6-hydroxy-7-(piperazin-1-ylmethyl)benzofuran-3(2M-one dihydrochloride (a) Step 1

A solution of tert-butyl 4-[(6-hydroxy-3-oxo-2,3-dihydrobenzofuran-7-yl)methyl]piperazine-1-carboxylate (0.050 g, 0.14 mmol) obtained in Example A16, Step 1 in methanol (2.0 mL) was added with 7-benzyloxy-1H-indole-3-carboxaldehyde (0.035 g, 0.14 mmol). Then, the mixture was added with 5 drops of piperidine, and the mixture was stirred at 50° C. for 2 hours. The reaction mixture was cooled to room temperature, and then the solid was collected by filtration, and washed with a mixed solvent of chloroform and methanol to obtain tert-butyl (Z)-4-[(2-{[7-(benzyloxy)-1H-indol-3-yl]methylene}-6-hydroxy-3-oxo-2,3-dihydrobenzofuran-7-yl)methyl]piperazine-1-carboxylate (0.049 g, 61%).

$^1$H NMR (300 MHz, CD$_3$OD) δ 1.47 (s, 9H), 2.67 (m, 4H), 3.54 (m, 4H), 4.01 (s, 2H), 5.24 (s, 2H), 6.67 (d, J=8.1 Hz, 1H), 6.81 (d, J=7.3 Hz, 1H), 7.13 (m, 1H), 7.32 (s, 1H), 7.33-7.45 (m, 3H), 7.51 (s, 1H), 7.52 (m, 3H), 7.60 (d, J=8.1 Hz, 1H), 7.96 (s, 1H)

(b) Step 2

A solution of tert-butyl (Z)-4-[(2-{[7-(benzyloxy)-1H-indol-3-yl]methylene}-6-hydroxy-3-oxo-2,3-dihydrobenzofuran-7-yl)methyl]piperazine-1-carboxylate (0.025 g, 0.043 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was washed with methylene chloride to obtain (Z)-2-{[7-(benzyloxy)-1H-indol-3-yl]methylene}-6-hydroxy-7-(piperazin-1-ylmethyl)benzofuran-3(2H)-one dihydrochloride (0.017 g, 71%).

$^1$H NMR (300 MHz, DMSO-d$_6$) δ 3.00-3.75 (m, 8H), 4.40 (br s, 2H), 5.32 (s, 2H), 6.89-7.00 (m, 2H), 7.10-7.21 (m, 1H), 7.25 (s, 1H), 7.32-7.51 (m, 3H), 7.56-7.78 (m, 4H), 8.24 (s, 1H), 12.21 (s, 1H).

Example A27

(Z)-6-Hydroxy-2-[(7-nitro-1H-indol-3-yl)methylene]-7-(piperazin-1-ylmethyl)benzofuran-3(2H)-one dihydrochloride (a) Step 1

A solution of tert-butyl 4-[(6-hydroxy-3-oxo-2,3-dihydrobenzofuran-7-yl)methyl]piperazine-1-carboxylate (0.077 g, 0.022 mmol) in methanol (2.0 mL) was added with 7-nitro-1H-indole-3-carboxaldehyde (0.038 g, 0.020 mmol). Then, the mixture was added with 5 drops of piperidine, and the mixture was stirred at 50° C. for 2 hours. The reaction mixture was cooled to room temperature, and then the solid was collected by filtration, and washed with methanol to obtain tert-butyl (Z)-4-({6-hydroxy-2-[(7-nitro-1H-indol-3-yl)methylene]-3-oxo-2,3-dihydrobenzofuran-7-yl}methyl)piperazine-1-carboxylate (0.054 g, 50%).

$^1$H NMR (300 MHz, DMSO-d$_6$) δ 1.38 (s, 9H), 2.53 (m, 4H), 3.35 (m, 4H), 3.80 (s, 2H), 6.76 (d, J=8.1 Hz, 1H), 7.29 (s, 1H), 7.40 (m, 1H), 7.57 (d, J=8.8 Hz, 1H), 8.22 (d, J=8.1 Hz, 1H), 8.25 (d, J=2.2 Hz, 1H), 8.64 (d, J=8.1 Hz, 1H), 12.58 (s, 1H).

(b) Step 2

A solution of tert-butyl (Z)-4-({6-hydroxy-2-[(7-nitro-1H-indol-3-yl)methylene]-3-oxo-2,3-dihydrobenzofuran-7-yl}methyl)piperazine-1-carboxylate (0.030 g, 0.058 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-[(7-nitro-1H-indol-3-yl)methylene]-7-(piperazin-1-ylmethyl)benzofuran-3(2H)-one dihydrochloride (0.018 g, 62%).

$^1$H NMR (300 MHz, DMSO-d$_6$) δ 3.10-3.76 (m, 8H), 4.40 (br s, 2H), 6.91 (d, J=8.8 Hz, 1H), 7.35 (s, 1H), 7.43 (m, 1H), 7.70 (d, J=8.8 Hz, 1H), 8.23 (d, J=7.3 Hz, 1H), 8.36 (s, 1H), 8.65 (d, J=8.1 Hz, 1H), 12.51 (s, 1H).

Example A28

(Z)-6-Hydroxy-2-({7-[(methylamino)methyl]-1H-indol-3-yl}methylene)-7-(piperazin-1-ylmethyl)benzofuran-3(2H)-one trihydrochloride (a) Step 1

A solution of 7-formyl-1H-indole (0.23 g, 1.6 mmol) in methanol (10 mL) was added with a 40% solution of methylamine in methanol (0.6 mL, 6.4 mmol), and the mixture was stirred at room temperature for 1 hour. Then, the mixture was added portionwise with sodium borohydride (0.060 g, 4.8 mmol), and the mixture was stirred at room temperature for 3 hours. The solvent was evaporated under reduced pressure, then the residue was added with ethyl acetate, and the organic layer was washed successively with water and saturated brine, and dried over anhydrous magnesium sulfate. The solvent was evaporated under reduced pressure, and then the residue was purified by silica gel column chromatography (aminopropyl silica was used, eluted with chloroform/methanol (99:1→95:5)) to obtain 1-(1H-indol-7-yl)-N-methylmethanamine (0.23 g, 89%).

$^1$H NMR (300 MHz, DMSO-$d_6$) δ 2.30 (s, 3H), 3.92 (s, 2H), 6.41 (d, J=2.9 Hz, 1H), 6.92 (m, 1H), 7.01 (d, J=7.3 Hz, 1H), 7.29 (d, J=2.9 Hz, 1H), 7.41 (d, J=7.3 Hz, 1H), 10.91 (br s, 1H).

(b) Step 2

A solution of N,N-dimethylformamide (0.16 g, 2.1 mmol) in 1,2-dichloroethane (5.0 mL) cooled to 0° C. was slowly added with phosphorus oxychloride (0.54 g, 3.5 mmol) under an argon atmosphere, and then the mixture was stirred for 15 minutes. Then, the mixture was added with a solution of 1-(1H-indol-7-yl)-N-methylmethanamine (0.22 g, 1.4 mmol) in 1,2-dichloroethane (5.0 mL), and the mixture was stirred at room temperature for 3 hours. The reaction mixture was added with ethyl acetate, and then the organic layer was successively washed with aqueous sodium hydroxide, water and saturated brine, and dried over anhydrous magnesium sulfate. The solvent was evaporated under reduced pressure, and then the mixture was subjected to silica gel column chromatography (eluted with chloroform/methanol (90:10→60:40)). A solution of the resulting mixture in methylene chloride (5.0 mL) was successively added with di-tert-butyl dicarbonate (0.61 g, 2.8 mmol), and diisopropylethylamine (0.36 g, 2.8 mmol), and the mixture was stirred at room temperature for 3 hours. The solvent was evaporated under reduced pressure, and then the residue was subjected to silica gel column chromatography (eluted with chloroform/methanol (99:1→95:5).

A solution of the resulting mixture in methanol (5.0 mL) was added with potassium carbonate (0.39 g, 2.8 mmol), and the mixture was stirred at room temperature for 1 hour. The solvent was evaporated under reduced pressure, and then the residue was subjected to silica gel column chromatography (eluted with chloroform/methanol (100:0→99:1)) to obtain tert-butyl (3-formyl-1H-indol-7-yl)methyl(methyl)carbamate (0.029 g, 7%).

$^1$H NMR (300 MHz, DMSO-$d_6$) δ 1.20-1.58 (s, 9H), 2.83 (s, 3H), 4.68 (s, 2H), 7.06 (m, 1H), 7.23 (m, 1H), 8.02 (d, J=7.3 Hz, 1H), 8.35 (s, 1H), 9.95 (s, 1H).

(c) Step 3

A solution of tert-butyl 4-[(6-hydroxy-3-oxo-2,3-dihydrobenzofuran-7-yl)methyl]piperazine-1-carboxylate (0.029 g, 0.10 mmol) obtained in Example A16, Step 1 in methanol (3.0 mL) was added with tert-butyl (3-formyl-1H-indole-7-yl)methyl(methyl)carbamate (0.038 g, 0.11 mmol). Then, the mixture was added with 5 drops of piperidine, and the mixture was stirred at 50° C. for 2 hours. The solvent was evaporated under reduced pressure, and then the residue was subjected to silica gel column chromatography (eluted with chloroform/methanol (99:1→95:5)) to obtain tert-butyl (Z)-4-({2-[(7-{[tert-butoxycarbonyl(methyl)amino]methyl}-1H-indol-3-yl)methylene]-6-hydroxy-3-oxo-2,3-dihydrobenzofuran-7-yl}methyl)piperazine-1-carboxylate (0.044 g, 71%).

$^1$H NMR (300 MHz, DMSO-$d_6$) δ 1.38 (s, 9H), 1.45 (s, 9H), 2.53 (m, 4H), 2.83 (s, 3H), 3.35 (m, 4H), 3.86 (s, 2H), 4.86 (s, 2H), 6.75 (d, J=8.1 Hz, 1H), 7.05 (m, 1H), 7.15-7.24 (m, 1H), 7.19 (s, 1H), 7.55 (d, J=8.1 Hz, 1H), 8.02 (d, J=8.1 Hz, 1H), 8.20 (s, 1H), 11.63 (s, 1H).

(d) Step 4

A solution of tert-butyl (Z)-4-({2-[(7-{[tert-butoxycarbonyl(methyl)-amino]methyl}-1H-indol-3-yl)methylene]-6-hydroxy-3-oxo-2,3-dihydrobenzofuran-7-yl}methyl)piperazine-1-carboxylate (0.044 g, 0.071 mmol) in methylene chloride (2.0 mL) was added with a 4 M solution of hydrogen chloride in 1,4-dioxane (2.0 mL), and then the mixture was stirred at room temperature for 4 hours. The mixture was azeotroped twice with toluene under reduced pressure, and then the residual solid was suspended in a mixed solvent of chloroform and methanol and thereby washed to obtain (Z)-6-hydroxy-2-({7-[(methylamino)methyl]-1H-indol-3-yl}methylene)-7-(piperazin-1-ylmethyl)benzofuran-3(2H)-one trihydrochloride (0.025 g, 72%).

$^1$H NMR (300 MHz, DMSO-$d_6$) δ 2.62 (s, 3H), 3.00-3.75 (m, 8H), 4.53 (br s, 4H), 7.02 (d, J=8.1 Hz, 1H), 7.26 (m, 2H), 7.42 (d, J=7.3 Hz, 1H), 7.73 (d, J=8.1 Hz, 1H), 8.12 (d, J=8.1 Hz, 1H), 8.51 (s, 1H), 12.62 (s, 1H).

Example A29

2-[(1H-Indol-3-yl)methyl]-7-(piperazin-1-ylmethyl)benzofuran-3,6-diol (a) Step 1

A solution of tert-butyl (Z)-4-({2-[(1H-indol-3-yl)methylene]-6-hydroxy-3-oxo-2,3-dihydrobenzofuran-7-yl}methyl)piperazine-1-carboxylate (0.030 g, 0.063 mmol) obtained in Example A11, Step 1 in ethanol (2.0 mL) was added with 5% palladium/carbon (wetted with 50% water, 0.027 g) under an argon atmosphere, and then the inside of the reaction vessel was replaced with hydrogen. The reaction mixture was stirred at room temperature for 4 hours, and then filtered through Celite, and the solvent was evaporated under reduced pressure to obtain tert-butyl 4-({2-[(1H-indol-3-yl)methyl]-6-hydroxy-3-oxo-2,3-dihydrobenzofuran-7-yl}methyl)piperazine-1-carboxylate (0.028 g, 93%).

$^1$H NMR (300 MHz, CD$_3$OD) δ 1.49 (s, 9H), 2.73-2.97 (m, 4H), 3.31 (dd, J=5.1 Hz, J=15.4 Hz, 1H), 3.48 (m, 4H), 3.56 (dd, J=5.1 Hz, J=15.4 Hz, 1H), 4.03 (d, J=13.9 Hz, 1H), 4.12 (d, J=13.9 Hz, 1H), 5.03 (t, J=5.1 Hz, 1H), 6.55 (d, J=8.8 Hz, 1H), 6.96-7.12 (m, 2H), 6.99 (s, 1H), 7.22-7.30 (m, 1H), 7.47 (d, J=8.8 Hz, 1H), 7.60-7.66 (m, 1H).

(b) Step 2

A solution of tert-butyl 4-({2-[(1H-indol-3-yl)methyl]-6-hydroxy-3-oxo-2,3-dihydrobenzofuran-7-yl}methyl)piperazine-1-carboxylate (0.020 g, 0.042 mmol) in methylene chloride (2.0 mL) was added with a 4 M solution of hydrogen chloride in 1,4-dioxane (2.0 mL), and then the mixture was stirred at room temperature for 2 hours. The solvent was evaporated under reduced pressure, and then the residue was added with triethylamine and thereby made basic. Then, the mixture was azeotroped twice with toluene under reduced pressure, and the residue was subjected to silica gel column chromatography (aminopropyl silica was used, eluted with chloroform/methanol (90:10)) to obtain 2-[(1H-indol-3-yl)methyl]-7-(piperazin-1-ylmethyl)benzofuran-3,6-diol (0.011 g, 69%).

$^1$H NMR (300 MHz, CD$_3$OD) δ 2.40-2.62 (m, 4H), 2.78 (m, 4H), 3.21 (d, J=14.7 Hz, 1H), 3.50 (d, J=14.7 Hz, 1H), 3.67 (d, J=13.9 Hz, 1H), 3.78 (d, J=13.9 Hz, 1H), 6.32 (d, J=8.8 Hz, 1H), 6.96-7.09 (m, 2H), 6.98 (s, 1H), 7.22-7.27 (m, 1H), 7.27 (d, J=8.8 Hz, 1H), 7.57-7.66 (m, 1H), 7.90 (s, 1H).

Example A30

(E)-2-[(1H-Indol-3-yl)methylene]-5-hydroxy-4-(piperazin-1-ylmethyl)-2,3-dihydro-1H-inden-1-one dihydrochloride (a) Step 1

A solution of 5-hydroxy-2,3-dihydro-1H-inden-1-one (0.30 g, 2.0 mmol) and 1H-indole-3-carboxaldehyde (0.32 g, 2.2 mmol) in methanol (10 mL) was added with 50% sodium hydroxide (0.34 mL), and the mixture was stirred at 50° C. for 2 hours. The reaction mixture was cooled to room temperature, and then added with water, and the precipitated solid was collected by filtration, and washed with methanol to obtain (E)-2-[(1H-indol-3-yl)methylene]-5-hydroxy-2,3-dihydro-1H-inden-1-one (0.45 g, 83%).

$^1$H NMR (300 MHz, DMSO-d$_6$) δ 3.87 (s, 2H), 6.85 (d, J=8.1 Hz, 1H), 6.97 (s, 1H), 7.16 (m, 1H), 7.22 (m, 1H), 7.49 (d, J=8.1 Hz, 1H), 7.61 (d, J=8.1 Hz, 1H), 7.77 (s, 1H), 7.87 (d, J=7.3 Hz, 1H), 7.94 (d, J=2.9 Hz, 1H), 10.49 (s, 1H), 11.99 (s, 1H).

(b) Step 2

A solution of (E)-2-[(1H-indol-3-yl)methylene]-5-hydroxy-2,3-dihydro-1H-inden-1-one (0.060 g, 0.22 mmol) in ethanol (3.0 mL) was added with 1-tert-butoxycarbonylpiperazine (0.049 g, 0.26 mmol), and 37% aqueous formaldehyde (0.020 g, 0.26 mmol), and the mixture was stirred overnight at 60° C. in a sealed tube. The solvent was evaporated under reduced pressure, and then the residue was subjected to silica gel column chromatography (aminopropyl silica was used, eluted with chloroform/methanol (90:10)) to obtain tert-butyl (E)-4-({2-[(1H-indol-3-yl)methylene]-5-hydroxy-1-oxo-2,3-dihydro-1H-inden-4-yl}methyl)piperazine-1-carboxylate (0.068 g, 65%).

$^1$H NMR (300 MHz, CD$_3$OD) δ 1.46 (s, 9H), 2.62 (m, 4H), 3.52 (m, 4H), 3.82 (s, 2H), 3.94 (s, 2H), 6.85 (d, J=8.1 Hz, 1H), 7.14-7.29 (m, 2H), 7.45 (d, J=7.3 Hz, 1H), 7.66 (d, J=8.1 Hz, 1H), 7.85 (d, J=7.3 Hz, 1H), 7.90 (s, 1H), 8.01 (s, 1H).

(c) Step 3

A solution of tert-butyl (E)-4-({2-[(1H-indol-3-yl)methylene]-5-hydroxy-1-oxo-2,3-dihydro-1H-inden-4-yl}methyl)piperazine-1-carboxylate (0.030 g, 0.063 mmol) in methylene chloride (2.0 mL) was added with a 4 M solution of hydrogen chloride in 1,4-dioxane (2.0 mL), and then the mixture was stirred at room temperature for 1 hour. The mixture was azeotroped twice with toluene under reduced pressure, and the residual solid was suspended in methylene chloride and thereby washed to obtain (E)-2-[(1H-indol-3-yl)-methylene]-5-hydroxy-4-(piperazin-1-ylmethyl)-2,3-dihydro-1H-inden-1-one dihydrochloride (0.024 g, 85%).

$^1$H NMR (300 MHz, DMSO-d$_6$) δ 3.20-3.86 (m, 8H), 4.25 (s, 2H), 4.53 (s, 2H), 7.13 (d, J=8.8 Hz, 1H), 7.14-7.28 (m, 2H), 7.51 (d, J=8.1 Hz, 1H), 7.74 (d, J=8.8 Hz, 1H), 7.81 (s, 1H), 7.89 (d, J=7.3 Hz, 1H), 8.22 (s, 1H), 12.16 (s, 1H).

Example A31

(Z)-6-Hydroxy-7-[(4-methylpiperazin-1-yl)methyl]-2-[(1-tosyl-1H-indol-3-yl)methylene]benzofuran-3(2H)-one (a) Step 1

A solution of 6-hydroxybenzofuran-3(2H)-one (2.00 g, 13.3 mmol) in ethanol (25 mL) was added with N-methylpiperazine (1.33 g, 13.3 mmol), and 37% aqueous formaldehyde (1.08 g, 13.3 mmol) at room temperature. The mixture was stirred overnight at room temperature, and then subjected to suction filtration, and the filtrate was concentrated. The residue was purified by silica gel column chromatography (chloroform/methanol) to obtain 6-hydroxy-7-[(4-methylpiperazin-1-yl)methyl]benzofuran-3(2H)-one (1.87 g, 54%).

$^1$H NMR (300 MHz, DMSO-d$_6$) δ 2.16 (s, 3H), 2.35 (m, 4H), 2.55 (m, 4H), 3.74 (s, 2H), 4.72 (s, 2H), 6.52 (d, J=8.8 Hz, Hp, 7.38 (d, J=8.8 Hz, 1H).

(b) Step 2

A solution of 1H-indole-3-carboxaldehyde (7.26 g, 50.0 mmol) in methylene chloride (100 mL) was added with tosyl chloride (11.4 g, 60.0 mmol) and diisopropylethylamine (7.75 g, 60.0 mmol), and the mixture was stirred overnight at room temperature. The reaction mixture was added with saturated aqueous sodium hydrogencarbonate to terminate the reaction, and then extracted three times with methylene chloride, and the organic layer was dried over anhydrous magnesium sulfate. The solvent was evaporated, and the resulting residue was purified by silica gel column chromatography (hexane/ethyl acetate) to obtain 1-tosyl-1H-indole-3-carboxaldehyde (11.8 g, 78%).

$^1$H NMR (300 MHz, CDCl$_3$) δ 2.37 (s, 3H), 7.29 (d, J=8.1 Hz, 2H), 7.33-7.44 (m, 2H), 7.85 (d, J=8.1 Hz, 2H), 7.94 (d, J=7.3 Hz, 1H), 8.23 (s, 1H), 8.25 (d, J=6.6 HZ, 1H), 10.09 (s, 1H).

(c) Step 3

A solution of 6-hydroxy-7-[(4-methylpiperazin-1-yl)methyl]benzofuran-3(2H)-one (0.525 g, 2.00 mol) in methanol (10 mL) was added with 1-tosyl-1H-indole-3-carboxaldehyde (0.599 g, 2.00 mmol) and piperidine (0.017 g, 0.200 mmol), and the mixture was stirred overnight at room temperature. The reaction mixture was added with methanol, and the solid was suspended in methanol and thereby washed to obtain the objective (Z)-6-hydroxy-7-[(4-methylpiperazin-1-yl)methyl]-2-[(1-tosyl-1H-indol-3-yl)methylene]benzofuran-3(2H)-one (0.887 g, 81%).

$^1$H NMR (300 MHz, DMSO-d$_6$) δ 2.19 (s, 3H), 2.36-2.70 (m, 4H), 2.40-2.63 (m, 4H), 3.15 (s, 3H), 3.81 (s, 2H), 6.70 (d,

J=8.8 Hz, 1H), 7.06 (s, 1H), 7.33-7.44 (m, 4H), 7.54 (d, J=8.8 Hz, 1H), 7.88-7.99 (m, 3H), 8.10 (d, J=7.3 Hz, 1H), 8.38 (s, 1H).

Example A32

(Z)-6-Hydroxy-2-{[1-(methylsulfonyl)-1H-indol-3-yl]methylene}-7-(piperazin-1-ylmethyl)benzofuran-3(2H)-one dihydrochloride (a) Step 1

A solution of 1H-indole-3-carboxaldehyde (2.90 g, 20.0 mmol) in methylene chloride (40 mL) was added with methanesulfonyl chloride (1.86 mL, 24.0 mmol) and diisopropylethylamine (3.10 g, 24.0 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain the objective 1-(methanesulfonyl)-1H-indole-3-carboxaldehyde (4.06 g, 91%).
$^1$H NMR (300 MHz, DMSO-$d_6$) δ 3.68 (s, 3H), 7.43-7.54 (m, 2H), 7.91 (d, J=8.8 Hz, 1H), 8.20 (d, J=8.0 Hz, 1H), 8.63 (s, 1H), 10.10 (s, 1H).

(b) Step 2

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (2 mL) was added with 1-(methanesulfonyl)-1H-indole-3-carboxaldehyde (0.0641 g, 0.287 mmol) and piperidine (0.00244 g, 0.0287 mmol), and the mixture was stirred overnight at room temperature. The reaction mixture was added with methanol (2 mL), and the solid was suspended in methanol and thereby washed to obtain tert-butyl (Z)-4-[(6-hydroxy-2-{[1-(methylsulfonyl)-1H-indol-3-yl]methylene}-3-oxo-2,3-dihydrobenzofuran-7-yl)methyl]piperazine-1-carboxylate (0.104 g, 66%).
$^1$H NMR (300 MHz, DMSO-$d_6$) δ 1.38 (s, 9H), 2.52 (m, 4H), 3.33 (m, 4H), 3.60 (s, 3H), 3.75 (s, 2H), 6.79 (d, J=8.8 Hz, 1H), 7.18 (s, 1H), 7.43 (m, 1H), 7.50 (t, J=7.3 Hz, 1H), 7.59 (d, J=8.8 Hz, 1H), 7.91 (d, J=7.3 Hz, 1H), 8.20 (d, J=8.0 Hz, 1H), 8.28 (s, 1H).

(c) Step 3

A solution of tert-butyl (Z)-4-[(6-hydroxy-2-{[1-(methylsulfonyl)-1H-indol-3-yl]methylene}-3-oxo-2,3-dihydrobenzofuran-7-yl)methyl]piperazine-1-carboxylate (0.0500 g, 0.0903 mmol) in methylene chloride (2 mL) was added with trifluoroacetic acid (2 mL), and the mixture was stirred overnight at room temperature. The reaction mixture was concentrated, then a solution of the resulting residue in methanol (4 mL) was added with a 5% solution of hydrogen chloride in methanol (1 mL), and the mixture was stirred at room temperature for 2 hours. The solvent was evaporated, and the resulting solid was suspended in acetonitrile and thereby washed to obtain the objective (Z)-6-hydroxy-2-{[1-(methylsulfonyl)-1H-indol-3-yl]methylene}-7-(piperazin-1-ylmethyl)benzofuran-3(2H)-one dihydrochloride (0.0421 g, 88%).
$^1$H NMR (300 MHz, DMSO-$d_6$) δ 3.57-3.69 (m, 8H), 3.66 (s, 3H), 4.36 (s, 2H), 6.99 (d, J=8.8 Hz, 1H), 7.26 (s, 1H), 7.42-7.52 (m, 2H), 7.74 (d, J=8.8 Hz, 1H), 7.92 (d, J=7.3 Hz, 1H), 8.18 (d, J=7.3 Hz, 1H), 8.46 (s, 1H).

Example A33

(Z)-6-Hydroxy-7-(piperazin-1-ylmethyl)-2-[(1-tosyl-1H-indol-3-yl)methylene]benzofuran-3(2H)-one dihydrochloride (a) Step 1

A solution of 1H-indole-3-carboxaldehyde (7.26 g, 50.0 mmol) in methylene chloride (100 mL) was added with tosyl chloride (11.4 g, 60.0 mmol) and diisopropylethylamine (7.75 g, 60.0 mmol), and the mixture was stirred overnight at room temperature. The reaction mixture was added with saturated aqueous sodium hydrogencarbonate to terminate the reaction, and then extracted three times with methylene chloride, and the organic layer was dried over anhydrous magnesium sulfate. The solvent was evaporated, and the resulting residue was purified by silica gel column chromatography (hexane/ethyl acetate) to obtain 1-tosyl-1H-indole-3-carboxaldehyde (11.8 g, 78%).
$^1$H NMR (300 MHz, CDCl$_3$) δ 2.37 (s, 3H), 7.29 (d, J=8.1 Hz, 2H), 7.33-7.44 (m, 2H), 7.85 (d, J=8.1 Hz, 2H), 7.94 (d, J=7.3 Hz, 1H), 8.23 (s, 1H), 8.25 (d, J=6.6 HZ, 1H), 10.09 (s, 1H).

(b) Step 2

A solution of tert-butyl 4-[(6-hydroxy-3-oxo-2,3-dihydrobenzofuran-7-yl)methyl]piperazine-1-carboxylate (0.697 g, 2.00 mmol) obtained in Example A16, Step 1 in methanol (10 mL) was added with 1-tosyl-1H-indole-3-carboxaldehyde (0.599 g, 2.00 mmol) synthesized in Step 1 and piperidine (0.0170 g, 0.200 mmol), and the mixture was stirred overnight at room temperature. The reaction mixture was added with methanol (2 mL), and the solid was suspended in methanol and thereby washed to obtain tert-butyl (Z)-4-({6-hydroxy-3-oxo-2-[(1-tosyl-1H-indol-3-yl)methylene]-2,3-dihydrobenzofuran-7-yl}methyl)piperazine-1-carboxylate (0.470 g, 37%).
$^1$H NMR (300 MHz, DMSO-$d_6$) δ 1.34 (s, 9H), 2.30 (s, 3H), 2.55 (m, 4H), 3.35 (m, 4H), 3.77 (s, 2H), 6.79 (d, J=8.1 Hz, 1H), 7.10 (s, 1H), 7.33-7.46 (m, 2H), 7.41 (d, J=8.1 Hz, 2H), 7.58 (d, J=8.1 Hz, 1H), 7.90 (d, J=8.1 Hz, 2H), 7.95 (d, J=8.0 Hz, 1H), 8.11 (d, J=8.1 Hz, 1H), 8.39 (s, 1H).

(c) Step 3

A solution of tert-butyl (Z)-4-({6-hydroxy-3-oxo-2-[(1-tosyl-1H-indol-3-yl)methylene]-2,3-dihydrobenzofuran-7-yl}methyl)piperazine-1-carboxylate (0.0400 g, 0.0635 mmol) in methylene chloride (2 mL) was added with trifluoroacetic acid (2 mL), and the mixture was stirred overnight at room temperature. The reaction mixture was concentrated, and then a solution of the resulting residue in methanol (4 mL) was added with a 5% solution of hydrogen chloride in methanol (1 mL), and the mixture was stirred at room temperature for 2 hours. The solvent was evaporated, and the resulting solid was suspended in acetonitrile and thereby washed to obtain the objective (Z)-6-hydroxy-7-(piperazin-1-ylmethyl)-2-[(1-tosyl-1H-indol-3-yl)methylene]benzofuran-3(2H)-one dihydrochloride (0.0344 g, 89%).

¹H NMR (300 MHz, DMSO-d₆) δ 2.33 (s, 3H), 3.47 (m, 4H), 3.77 (m, 4H), 4.4.1 (s, 2H), 6.99 (d, J=8.1 Hz, 1H), 7.20 (s, 1H), 7.35-7.46 (m, 4H), 7.75 (d, J=8.1 Hz, 1H), 7.94 (d, J=7.3 Hz, 1H), 8.09-8.11 (m, 3H), 8.64 (s, 1H)

Example A34

(Z)-6-Hydroxy-7-(piperazin-1-ylmethyl)-2-({1-[4-(trifluoromethyl)phenylsulfonyl]-1H-indol-3-yl}methylene)benzofuran-3(2H)-one dihydrochloride

(a) Step 1

A solution of 1H-indole-3-carboxaldehyde (0.290 g, 2.00 mmol) in methylene chloride (4 mL) was added with 4-(trifluoromethyl)phenylsulfonyl chloride (0.587 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-[4' (trifluoromethyl)phenylsulfonyl]-1H-indole-3-carboxaldehyde (0.650 g, 92%).

¹H NMR (300 MHz, DMSO-d₆) δ 7.40-7.52 (m, 2H), 8.00 (d, J=8.0 Hz, 1H), 8.05 (d, J=8.8 Hz, 2H), 8.13 (d, J=8.1 Hz, 1H), 8.36 (d, J=8.8 Hz, 2H), 8.96 (s, 1H), 10.10 (s, 1H).

(b) Step 2

A solution of tert-butyl 4-[(6-hydroxy-3-oxo-2,3-dihydrobenzofuran-7-yl)methyl]piperazine-1-carboxylate (0.0500 g, 0.144 mmol) obtained in Example A16, Step 1 in methanol (0.6 mL) was added with 1-[4-(trifluoromethyl)phenylsulfonyl]-1H-indole-3-carboxaldehyde (0.0509 g, 0.144 mmol) and piperidine (0.00123 g, 0.0144 mmol), and the mixture was stirred overnight at room temperature. The reaction mixture was added with methanol (1 mL), and the solid was suspended in methanol and thereby washed to obtain tert-butyl (Z)-4-([6-hydroxy-3-oxo-2-({1-[4-(trifluoromethyl)phenylsulfonyl]-1H-indol-3-yl}methylene)-2,3-dihydrobenzofuran-7-yl]methyl)piperazine-1-carboxylate (0.0759 g, 77%).

¹H NMR (300 MHz, CD₃OD) δ 1.42 (s, 9H), 2.75 (t, J=4.4 Hz, 4H), 3.54 (m, 4H), 3.99 (s, 2H), 6.73 (d, J=8.8 Hz, 1H), 7.07 (s, 1H), 7.35-7.46 (m, 2H), 7.60 (d, J=8.8 Hz, 1H), 7.87-7.90 (m, 3H), 8.01 (d, J=8.1 Hz, 1H), 8.20 (d, J=8.1 Hz, 2H), 8.44 (s, 1H).

(c) Step 3

A solution of tert-butyl (Z)-4-([6-hydroxy-3-oxo-2-({1-[4-(trifluoromethyl)phenylsulfonyl]-1H-indol-3-yl]methylene)-2,3-dihydrobenzofuran-7-yl}methyl)piperazine-1-carboxylate (0.0500 g, 0.0731 mmol) in methylene chloride (2 mL) was added with trifluoroacetic acid (2 mL), and the mixture was stirred overnight at room temperature. The reaction mixture was concentrated, then a solution of the resulting residue in methanol (4 mL) was added with a 5% solution of hydrogen chloride in methanol (1 mL), and the mixture was stirred at room temperature for 2 hours. The solvent was evaporated, and the resulting solid was suspended in acetonitrile and thereby washed to obtain the objective (Z)-6-hydroxy-7-(piperazin-1-ylmethyl)-2-({1-[4-(trifluoromethyl) phenylsulfonyl]-1H-indol-3-yl}methylene)benzofuran-3(2H)-one dihydrochloride (0.0311 g, 64%).

¹H NMR (300 MHz, DMSO-d₆) δ 3.44-3.67 (m, 8H), 4.44 (s, 2H), 6.99 (d, J=8.8 Hz, 1H), 7.19 (s, 1H), 7.38-7.49 (m, 2H), 7.75 (d, J=8.8 Hz, 1H), 7.96-8.02 (m, 3H), 8.13 (d, J=7.3 Hz, 1H), 8.47 (d, J=8.1 Hz, 2H), 8.69 (s, 1H).

Example A35

(Z)-{[1-(4-Chlorophenylsulfonyl)-1H-indol-3-yl] methylene}-6-hydroxy-7-(piperazin-1-ylmethyl) benzofuran-3(2H)-one dihydrochloride

(a) Step 1

A solution of 1H-indole-3-carboxaldehyde (0.290 g, 2.00 mmol) in methylene chloride (4 mL) was added with 4-chlorophenylsulfonyl chloride (0.507 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-(4-chlorophenylsulfonyl)-1H-indole-3-carboxaldehyde (0.575 g, 89%).

¹H NMR (300 MHz, CDCl₃) δ 7.35-7.50 (m, 4H), 7.87-7.94 (m, 3H), 8.20 (s, 1H), 8.26 (dd, J=1.4 Hz, 7.3 HZ, 1H), 10.10 (s, 1H).

(b) Step 2 tert-Butyl 4-[(6-hydroxy-3-oxo-2,3-dihydrobenzofuran-7-yl)methyl]piperazine-1-carboxylate (0.100 g, 0.287 mmol) obtained in Example A16, Step 1 and 1-(4-chlorophenylsulfonyl)-1H-indole-3-carboxaldehyde (0.0918 g, 0.287 mmol) were stirred overnight at room temperature in methanol (1.2 mL) in the presence of piperidine (0.00244 g, 0.0287 mmol). The reaction mixture was further added with methanol (1 mL), and the solid was suspended in methanol and thereby washed to obtain tert-butyl (Z)-4-[(2-{[1-(4-chlorophenylsulfonyl)-1H-indol-3-yl]methylene}-6-hydroxy-3-oxo-2,3-dihydrobenzofuran-7-yl)methyl]piperazine-1-carboxylate (0.161 g, 86%).

¹H NMR (300 MHz, DMSO-d₆) δ 1.35 (s, 9H), 2.56 (m, 4H), 3.36 (m, 4H), 3.78 (s, 2H), 6.80 (d, J=8.8 Hz, 1H), 7.12 (s, 1H), 7.37-7.49 (m, 2H), 7.60 (d, J=8.8 Hz, 1H), 7.71 (d, J=8.8 Hz, 2H), 7.96 (d, J=8.1 Hz, 1H), 8.04 (d, J=8.8 Hz, 2H), 8.15 (d, J=8.0 Hz, 1H), 8.42 (s, 1H).

(c) Step 3

A solution of tert-butyl (Z)-4-[(2-{[1-(4-chlorophenylsulfonyl)-1H-indol-3-yl]methylene}-6-hydroxy-3-oxo-2,3-dihydrobenzofuran-7-yl)methyl]piperazine-1-carboxylate (0.153 g, 0.235 mmol) in methylene chloride (6 mL) was added with trifluoroacetic acid (6 mL), and the mixture was stirred overnight at room temperature. The reaction mixture was concentrated, then a solution of the resulting residue in methanol (8 mL) was added with a 5% solution of hydrogen chloride in methanol (2 mL), and the mixture was stirred at room temperature for 2 hours. The solvent was evaporated, and the resulting solid was suspended in acetonitrile and thereby washed to obtain (Z)-2-{[1-(4-chlorophenylsulfonyl)-1H-indol-3-yl]methylene}-6-hydroxy-7-(piperazin-1-ylmethyl)benzofuran-3(2H)-one dihydrochloride (0.0878 g, 60%).

$^1$H NMR (300 MHz, DMSO-$d_6$) δ 3.34-3.55 (m, 8H), 4.38 (br s, 2H), 6.98 (d, J=8.1 Hz, 1H), 7.19 (s, 1H), 7.37-7.48 (m, 2H), 7.70 (d, J=8.8 Hz, 2H), 7.74 (d, J=8.1 HZ, 1H), 7.95 (d, J=8.1 Hz, 1H), 8.12 (d, J=5.9 Hz, 1H), 8.24 (d, J=8.8 Hz, 2H), 8.64 (s, 1H).

Example A36

(Z)-2-{[1-(2-Chlorophenylsulfonyl)-1H-indol-3-yl]methylene}-6-hydroxy-7-(piperazin-1-ylmethyl)benzofuran-3(2H)-one dihydrochloride (a) Step 1

A solution of 1H-indole-3-carboxaldehyde (0.290 g, 2.00 mmol) in methylene chloride (4 mL) was added with 2-chlorophenylsulfonyl chloride (0.507 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-(2-chlorophenylsulfonyl)-1H-indole-3-carboxaldehyde (0.580 g, 90%).

$^1$H NMR (300 MHz, CDCl$_3$) δ 7.28-7.38 (m, 2H), 7.45-7.61 (m, 4H), 8.29 (dd, J=2.2 Hz, 6.6 Hz, 1H), 8.37-8.40 (m, 1H), 8.43 (s, 1H), 10.14 (s, 1H).

(b) Step 2

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1.2 mL) was added with 1-(2-chlorophenylsulfonyl)-1H-indole-3-carboxaldehyde (0.0918 g, 0.287 mmol) and piperidine (0.00244 g, 0.0287 mmol), and the mixture was stirred overnight at room temperature. The reaction mixture was added with methanol (2 mL), and the solid was suspended in methanol and thereby washed to obtain tert-butyl (Z)-4-[(2-{[1-(2-chlorophenylsulfonyl)-1H-indol-3-yl]methylene}-6-hydroxy-3-oxo-2,3-dihydrobenzofuran-7-yl)methyl]piperazine-F carboxylate (0.0950 g, 50%).

$^1$H NMR (300 MHz, DMSO-$d_6$) δ 1.36 (s, 9H), 2.52 (m, 4H), 3.33 (m, 4H), 3.73 (s, 2H), 6.80 (d, J=8.8 Hz, 1H), 7.17 (s, 1H), 7.38 (dd, J=2.9 Hz, 5.9 Hz, 1H), 7.59-7.81 (m, 5H), 8.17 (dd, J=2.9 Hz, 5.9 Hz, 1H), 8.43 (dd, J=1.5 Hz, 8.1 Hz, 1H), 8.56 (s, 1H).

(c) Step 3

A solution of tert-butyl (Z)-4-[(2-{[1-(2-chlorophenylsulfonyl)-1H-indol-3-yl]methylene}-6-hydroxy-3-oxo-2,3-dihydrobenzofuran-7-yl)methyl]piperazine-1-carboxylate (0.0930 g, 0.143 mmol) in methylene chloride (4 mL) was added with trifluoroacetic acid (4 mL), and the mixture was stirred overnight at room temperature. The reaction mixture was concentrated, then a solution of the resulting residue in methanol (4 mL) was added with a 5% solution of hydrogen chloride in methanol (1 mL), and the mixture was stirred at room temperature for 2 hours. The solvent was evaporated, and the resulting solid was suspended in acetonitrile and thereby washed to obtain (Z)-2-{[1-(2-chlorophenylsulfonyl)-1H-indol-3-yl]methylene}-6-hydroxy-7-(piperazin-1-ylmethyl)benzofuran-3(2H)-one dihydrochloride (0.0711 g, 79%).

$^1$H NMR (300 MHz, DMSO-$d_6$) δ 3.55-3.73 (m, 8H), 4.39 (s, 2H), 7.03 (d, J=8.8 Hz, 1H), 7.25 (s, 1H), 7.34-7.43 (m, 2H), 7.62 (d, J=8.8 Hz, 1H), 7.69-7.81 (m, 4H), 8.17 (d, J=6.6 Hz, 1H), 8.46 (d, J=8.1 Hz, 1H), 8.67 (s, 1H).

Example A37

(Z)-2-{[1-(2,6-Dichlorophenylsulfonyl)-1H-indol-3-yl]methylene}-6-hydroxy-7-(piperazin-1-ylmethyl)benzofuran-3(2H)-one dihydrochloride (a) Step 1

A solution of 1H-indole-3-carboxaldehyde (0.290 g, 2.00 mmol) in methylene chloride (4 mL) was added with 2,6-dichlorophenylsulfonyl chloride (0.589 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-(2,6-dichlorophenylsulfonyl)-1H-indole-3-carboxaldehyde (0.658 g, 93%).

$^1$H NMR (300 MHz, CDCl$_3$) δ 7.32-7.38 (m, 2H), 7.41-7.45 (m, 1H), 7.48-7.51 (m, 2H), 7.63-7.67 (m, 1H), 8.28-8.31 (m, 1H), 8.41 (s, 1H), 10.18 (s, 1H).

(b) Step 2

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1.2 mL) was added with 1-(2,6-dichlorophenylsulfonyl)-1H-indole-3-carboxaldehyde (0.0918 g, 0.287 mmol) and piperidine (0.00244 g, 0.0287 mmol), and the mixture was stirred overnight at room temperature. The reaction mixture was added with methanol (2 mL), and the solid was suspended in methanol and thereby washed to obtain tert-butyl (Z)-4-[(2-{[1-(2,6-dichlorophenylsulfonyl)-1H-indol-3-yl]methylene}-6-hydroxy-3-oxo-2,3-dihydrobenzofuran-7-yl)methyl]piperazine-1-carboxylate (0.137 g, 69%).

$^1$H NMR (300 MHz, DMSO-$d_6$) δ 1.34 (s, 9H), 2.52 (m, 4H), 3.33 (m, 4H), 3.37 (s, 2H), 6.80 (d, J=8.8 Hz, 1H), 7.18 (s, 1H), 7.39-7.43 (m, 2H), 7.53-7.56 (m, 1H), 7.10 (d, J=8.8 Hz, 1H), 7.69-7.79 (m, 3H), 8.18-8.21 (m, 1H), 8.54 (s, 1H).

(c) Step 3

A solution of tert-butyl (Z)-4-[(2-{[1-(2,6-dichlorophenylsulfonyl)-1H-indol-3-yl]methylene}-6-hydroxy-3-oxo-2,3-dihydrobenzofuran-7-yl)methyl]piperazine-1-carboxylate (0.133 g, 0.194 mmol) in methylene chloride (5 mL) was added with trifluoroacetic acid (5 mL), and the mixture was stirred overnight at room temperature. The reaction mixture was concentrated, then a solution of the resulting residue in methanol (8 mL) was added with a 5% solution of hydrogen chloride in methanol (2 mL), and the mixture was stirred at room temperature for 2 hours. The solvent was evaporated, and the resulting solid was suspended in acetonitrile and thereby washed to obtain (Z)-2-{[1-(2,6-dichlorophenylsulfonyl)-1H-indol-3-yl]methylene}-6-hydroxy-7-(piperazin-1-ylmethyl)benzofuran-3(2H)-one dihydrochloride (0.0930 g, 72%).

¹H NMR (300 MHz, DMSO-d$_6$) δ 3.49 (m, 4H), 3.90 (m, 4H), 4.42 (s, 2H), 7.02 (d, J=8.8 Hz, 1H), 7.25 (s, 1H), 7.39-7.42 (m, 2H), 7.47-7.50 (m, 1H), 7.69-7.80 (m, 4H), 8.16-8.22 (m, 1H), 8.69 (s, 1H).

Example A38

(Z)-2-{[1-(2,3-Dichlorophenylsulfonyl)-1H-indol-3-yl]methylene}-6-hydroxy-7-(piperazin-1-ylmethyl)benzofuran-3(2H)-one dihydrochloride (a) Step 1

A solution of 1H-indole-3-carboxaldehyde (0.290 g, 2.00 mmol) in methylene chloride (4 mL) was added with 2,3-dichlorophenylsulfonyl chloride (0.589 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-(2,3-dichlorophenylsulfonyl)-1H-indole-3-carboxaldehyde (0.568 g, 80%).

¹H NMR (300 MHz, CDCl$_3$) δ 7.30-7.40 (m, 2H), 7.48 (t, J=8.1 Hz, 1H), 7.58 (dd, J=1.5 Hz, 7.3 Hz, 1H), 7.75 (dd, J=1.5 Hz, 8.1 Hz, 1H), 8.29-8.32 (m, 2H), 8.41 (s, 1H), 10.14 (s, 1H).

(b) Step 2

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1.2 mL) was added with 1-(2,3-dichlorophenylsulfonyl)-1H-indole-3-carboxaldehyde (0.102 g, 0.287 mmol) and piperidine (0.00244 g, 0.0287 mmol), and the mixture was stirred overnight at room temperature. The reaction mixture was added with methanol (2 mL), and the solid was suspended in methanol and thereby washed to obtain tert-butyl (Z)-4-[(2-{[1-(2,3-dichlorophenylsulfonyl)-1H-indol-3-yl]methylene}-6-hydroxy-3-oxo-2,3-dihydrobenzofuran-7-yl)methyl]piperazine-1-carboxylate (0.159 g, 80%).

¹H NMR (300 MHz, DMSO-d$_6$) δ 1.35 (s, 9H), 2.53 (m, 4H), 3.33 (m, 4H), 3.75 (s, 2H), 6.80 (d, J=8.8 Hz, 1H), 7.17 (s, 1H), 7.38-7.41 (m, 2H), 7.61 (d, J=8.8 Hz, 1H), 7.65-7.7.75 (m, 2H), 8.07 (dd, J=1.5 Hz, 8.8 Hz, 1H), 8.19 (dd, J=2.2 Hz, 5.9 Hz, 1H), 8.37 (dd, J=1.5 Hz, 8.1 Hz, 1H), 8.55 (s, 1H).

(c) Step 3

A solution of tert-butyl (Z)-4-[(2-{[1-(2,3-dichlorophenylsulfonyl)-1H-indol-3-yl]methylene}-6-hydroxy-3-oxo-2,3-dihydrobenzofuran-7-yl)methyl]piperazine-1-carboxylate (0.152 g, 0.222 mmol) in methylene chloride (6 mL) was added with trifluoroacetic acid (6 mL), and the mixture was stirred overnight at room temperature. The reaction mixture was concentrated, then a solution of the resulting residue in methanol (8 mL) was added with a 5% solution of hydrogen chloride in methanol (2 mL), and the mixture was stirred at room temperature for 2 hours. The solvent was evaporated, and the resulting solid was suspended in acetonitrile and thereby washed to obtain (Z)-2-{[1-(2,3-dichlorophenylsulfonyl)-1H-indol-3-yl]methylene}-6-hydroxy-7-(piperazin-1-ylmethyl)benzofuran-3(2H)-one dihydrochloride (0.0878 g, 60%).

¹H NMR (300 MHz, DMSO-d$_6$) δ 3.40-3.72 (m, 8H), 4.38 (s, 2H), 7.01 (d, J=8.8 Hz, 1H), 7.24 (s, 1H), 7.37-7.44 (m, 2H), 7.63 (dd, J=2.2 Hz, 6.6 Hz, 1H), 7.71-7.76 (m, 2H), 8.08 (dd, J=1.5 Hz, 8.1 Hz, 1H), 8.18 (dd, J=2.2 Hz, 6.6 Hz, 1H), 8.44 (dd, J=1.5 Hz, 8.1 Hz, 1H), 8.68 (s, 1H).

Example A39

(Z)-2-{[1-(2,4-Dichlorophenylsulfonyl)-1H-indol-3-yl]methylene}-6-hydroxy-7-(piperazin-1-ylmethyl)benzofuran-3(2H)-one dihydrochloride (a) Step 1

A solution of 1H-indole-3-carboxaldehyde (0.290 g, 2.00 mmol) in methylene chloride (4 mL) was added with 2,4-dichlorophenylsulfonyl chloride (0.589 g, 2.40 mmol) and diisopropylethylamine (0.310 g, 2.40 mmol), and the mixture was stirred overnight at room temperature. The reaction mixture was added with saturated aqueous sodium hydrogencarbonate to terminate the reaction, and then extracted three times with methylene chloride. The organic layer was dried over anhydrous magnesium sulfate, then the solvent was evaporated, and the resulting residue was purified by silica gel column chromatography (hexane/ethyl acetate) to obtain 1-(2,4-dichlorophenylsulfonyl)-1H-indole-3-carboxaldehyde (0.620 g, 87%).

¹H NMR (300 MHz, CDCl$_3$) δ 7.30-7.40 (m, 2H), 7.47-7.58 (m, 3H), 8.28-8.33 (m, 2H), 8.39 (s, 1H), 10.13 (s, 1H).

(b) Step 2

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1.2 mL) was added with 1-(2,4-dichlorophenylsulfonyl)-1H-indole-3-carboxaldehyde (0.102 g, 0.287 mmol) and piperidine (0.00244 g, 0.0287 mmol), and the mixture was stirred overnight at room temperature. The reaction mixture was added with methanol (2 mL), and the solid was suspended in methanol and thereby washed to obtain tert-butyl (Z)-4-[(2-{[1-(2,4-dichlorophenylsulfonyl)-1H-indol-3-yl]methylene}-6-hydroxy-3-oxo-2,3-dihydrobenzofuran-7-yl)methyl]piperazine-1-carboxylate (0.147 g, 74%).

¹H NMR (300 MHz, DMSO-d$_6$) δ 1.36 (s, 9H), 2.52 (m, 4H), 3.33 (m, 4H), 3.73 (s, 2H), 6.80 (d, J=8.8 Hz, 1H), 7.17 (s, 1H), 7.17-7.38 (m, 2H), 7.60 (d, J=8.8 Hz, 1H), 7.66 (dd, J=2.9 Hz, 6.6 Hz, 1H), 7.79 (dd, J=2.2 Hz, 8.8 Hz, 1H), 7.92 (d, J=2.2 Hz, 1H), 8.18 (dd, J=2.9 Hz, 5.9 Hz, 1H), 8.41 (d, J=8.8 Hz, 1H), 8.53 (s, 1H).

(c) Step 3

A solution of tert-butyl (Z)-4-[(2-{[1-(2,4-dichlorophenylsulfonyl)-1H-indol-3-yl]methylene}-6-hydroxy-3-oxo-2,3-dihydrobenzofuran-7-yl)methyl]piperazine-1-carboxylate (0.139 g, 0.203 mmol) in methylene chloride (6 mL) was added with trifluoroacetic acid (6 mL), and the mixture was stirred overnight at room temperature. The reaction mixture was concentrated, then a solution of the resulting residue in methanol (8 mL) was added with a 5% solution of hydrogen chloride in methanol (2 mL), and the mixture was stirred at room temperature for 2 hours. The solvent was evaporated, and the resulting solid was suspended in acetonitrile and thereby washed to obtain (Z)-2-{[1-(2,4-dichlorophenylsulfonyl)-1H-indol-3-yl]methylene}-6-hydroxy-7-(piperazin-1-ylmethyl)benzofuran-3(2H)-one dihydrochloride (0.0701 g, 52%).

$^1$H NMR (300 MHz, DMSO-d$_6$) δ 1.36 (s, 9H), 2.52 (m, 4H), 3.33 (m, 4H), 3.73 (s, 2H), 6.80 (d, J=8.8 Hz, 1H), 7.17 (s, 1H), 7.17-7.38 (m, 2H), 7.60 (d, J=8.8 Hz, 1H), 7.66 (dd, J=2.9 Hz, 6.6 Hz, 1H), 7.79 (dd, J=2.2 Hz, 8.8 Hz, 1H), 7.92 (d, J=2.2 Hz, 1H), 8.18 (dd, J=2.9 Hz, 5.9 Hz, 1H), 8.41 (d, J=8.8 Hz, 1H), 8.53 (s, 1H).

Example A40

(Z)-2-[(1H-Indol-3-yl)methylene]-6-methoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.400 g, 1.15 mmol) obtained in Example A16, Step 1, methanol (0.0442 g, 1.38 mmol) and triphenylphosphine (0.454 g, 1.73 mmol) in THF (8 mL) was added with a solution of a 40% solution of diethyl azodicarboxylate in toluene (0.901 g, 2.07 mmol) in THF (2 mL), and the mixture was stirred overnight at room temperature. The reaction mixture was concentrated, and the resulting residue was purified by silica gel column chromatography (chloroform/ethyl acetate) to obtain tert-butyl 4-[(6-methoxy-3-oxo-2,3-dihydrobenzofuran-7-yl)methyl]piperazine-1-carboxylate (0.107 g, 25%).

$^1$H NMR (300 MHz, DMSO-d$_6$) δ 1.44 (s, 9H), 2.48 (m, 4H), 3.42 (m, 4H), 3.70 (s, 2H), 3.93 (s, 3H), 4.64 (s, 2H), 6.70 (d, J=8.8 Hz, 1H), 7.62 (d, J=8.8 Hz, 1H).

(b) Step 2

A solution of tert-butyl 4-[(6-methoxy-3-oxo-2,3-dihydrobenzofuran-7-yl)methyl]piperazine-1-carboxylate (0.0932 g, 0.257 mmol) in methanol (1 mL) was added with 1H-indole-3-carboxaldehyde (0.0447 g, 0.308 mmol) and piperidine (0.00219 g, 0.0257 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indol-3-yl)methylene]-6-methoxy-3-oxo-2,3-dihydrofuran-7-yl}methyl)piperazine-1-carboxylate (0.0724 g, 57%).

$^1$H NMR (300 MHz, DMSO-d$_6$) δ 1.36 (s, 9H), 2.47 (m, 4H), 3.38 (m, 4H), 3.78 (s, 2H), 3.95 (s, 3H), 7.01 (d, J=8.8 Hz, 1H), 7.18 (m, 1H), 7.21-7.27 (m, 1H), 7.24 (s, 1H), 7.50 (d, J=8.1 Hz, 1H), 7.73 (d, J=8.8 Hz, 1H), 8.14 (d, J=8.1 Hz, 1H), 8.20 (d, J=2.9 Hz, 1H), 12.04 (br s, 1H).

(c) Step 3

A solution of tert-butyl (Z)-4-({2-[(1H-indol-3-yl)methylene]-6-methoxy-3-oxo-2,3-dihydrofuran-7-yl}methyl)piperazine-1-carboxylate (0.0647 g, 0.132 mmol) in methylene chloride (1 mL) was added with trifluoroacetic acid (1 mL), and the reaction mixture was stirred overnight at room temperature. The reaction mixture was concentrated, and then added with saturated aqueous sodium hydrogencarbonate (4 mL), and the precipitated solid was collected by filtration. The solid was washed with water, and then dried under reduced pressure to obtain the objective (Z)-2-[(1H-indol-3-yl)methylene]-6-methoxy-7-(piperazin-1-ylmethyl)benzofuran-3(2H)-one (0.0228 g, 44%).

$^1$H NMR (300 MHz, DMSO-d$_6$) δ 2.45 (m, 4H), 2.66 (m, 4H), 3.72 (s, 2H), 3.94 (s, 3H), 7.01 (d, J=8.8 Hz, 1H), 7.18 (t, J=7.3 Hz, 1H), 7.22-7.27 (m, 2H), 7.50 (d, J=8.0 Hz, 1H), 7.72 (d, J=8.8 Hz, 1H), 8.14 (d, J=8.0 Hz, 1H), 8.20 (s, 1H), 12.09 (br s, 1H).

Example A41

(Z)-2-[(1H-Indol-3-yl)methylene]-6-methoxy-7-(morpholinomethyl)benzofuran-3(2H)-one (a) Step 1

A solution of 6-hydroxybenzofuran-3(2H)-one (1.50 g, 10.0 mmol) in ethanol (10 mL) was added with morpholine (0.871 g, 10.0 mmol), and 37% aqueous formaldehyde (0.812 g, 10.0 mmol) at room temperature. The mixture was stirred overnight at room temperature, and then the filtrate was concentrated. The resulting residue was purified by silica gel column chromatography (hexane/ethyl acetate) to obtain the objective 6-hydroxy-7-(morpholinomethyl)benzofuran-3(2H)-one (0.987 g, 40%).

$^1$H NMR (300 MHz, DMSO-d$_6$) δ 2.57 (m, 4H), 3.60 (m, 4H), 3.68 (s, 2H), 4.73 (s, 2H), 6.58 (d, J=8.8 Hz, 1H), 7.40 (d, J=8.8 Hz, 1H).

(b) Step 2

A solution of 6-hydroxy-7-(morpholinomethyl)benzofuran-3(2H)-one (0.586 g, 2.35 mmol), methanol (0.0904 g, 2.82 mmol) and triphenylphosphine (0.923 g, 3.52 mmol) in THF (12 mL) was added with a solution of a 40% solution of diethyl azodicarboxylate in toluene (1.84 g, 4.23 mmol) in THF (6 mL), and the mixture was stirred overnight at room temperature. The reaction mixture was concentrated, and the resulting residue was purified by silica gel column chromatography (chloroform/methanol) to obtain 6-methoxy-7-(morpholinomethyl)benzofuran-3(2H)-one (0.509 g, 82%).

$^1$H NMR (300 MHz, DMSO-d$_6$) δ 2.40 (m, 4H), 3.51 (m, 4H), 3.53 (s, 2H), 3.91 (s, 3H), 4.77 (s, 2H), 6.89 (d, J=8.8 Hz, 1H), 7.60 (d, J=8.8 Hz, 1H).

(c) Step 3

A solution of 6-methoxy-7-(morpholinomethyl)benzofuran-3(2H)-one (0.079 g, 0.300 mmol) in methanol (1.2 mL) was added with 1H-indole-3-carboxaldehyde (0.0523 g, 0.300 mmol) and piperidine (0.00255 g, 0.0300 mmol), and the mixture was stirred at 60° C. for 2 hours. The reaction mixture was concentrated, and the residue was purified by silica gel column chromatography (chloroform/methanol) to obtain an orange crude product as a solid. This solid was suspended in ethyl acetate and thereby washed to obtain the objective (Z)-2-[(1H-indol-3-yl)methylene]-6-methoxy-7-(morpholinomethyl)benzofuran-3(2H)-one (0.0128 g, 10%).

$^1$H NMR (300 MHz, DMSO-d$_6$) δ 2.51 (m, 4H), 3.56 (m, 4H), 3.76 (s, 2H), 3.95 (s, 3H), 7.02 (d, J=8.8 Hz, 1H), 7.15-7.20 (m, 1H), 7.22-7.26 (m, 1H), 7.24 (s, 1H), 7.50 (d, J=8.1 Hz, 1H), 7.73 (d, J=8.8 Hz, 1H), 8.14 (d, J=8.1 Hz, 1H), 8.21 (d, J=2.9 Hz, 1H), 12.07 (br s, 1H).

Example A42

(Z)-2-[(1H-Pyrrolo[2,3-b]pyridin-3-yl)methylene]-6-hydroxy-7-(piperazin-1-ylmethyl)benzofuran-3(2H)-one trihydrochloride (a) Step 1

A solution of tert-butyl 4-[(6-hydroxy-3-oxo-2,3-dihydrobenzofuran-7-yl)methyl]piperazine-1-carboxylate (0.100 g, 0.287 mmol) obtained in Example A16, Step 1 in methanol (1 mL) was added with 7-aza-1H-indole-3-carboxaldehyde (0.0502 g, 0.344 mmol) and piperidine (0.00244 g, 0.0287 mmol), and the mixture was stirred at 60° C. for 2 hours. The reaction mixture was cooled to room temperature, and then the precipitated solid was collected by filtration to obtain tert-butyl (Z)-4-({2-[(1H-pyrrolo[2,3-b]pyridin-3-yl)methylene]-6-hydroxy-3-oxo-2,3-dihydrobenzofuran-7-yl}methyl)piperazine-1-carboxylate (0.0798 g, 58%).

$^1$H NMR (300 MHz, DMSO-$d_6$) δ 1.38 (s, 9H), 2.52 (m, 4H), 3.35 (m, 4H), 3.85 (s, 2H), 6.75 (d, J=8.8 Hz, 1H), 7.19 (s, 1H), 7.23 (dd, J=5.1 Hz, 8.1 Hz, 1H), 7.55 (d, J=8.8 Hz, 1H), 8.24 (d, J=2.2 Hz, 1H), 8.34 (dd, J=1.5 Hz, 5.1 Hz, 1H), 8.62 (d, J=1.5 Hz, 8.1 Hz, 1H), 12.50 (br s, 1H).

(b) Step 2

A solution of tert-butyl (Z)-4-({2-[(1H-pyrrolo[2,3-b]pyridin-3-yl)methylene]-6-hydroxy-3-oxo-2,3-dihydrobenzofuran-7-yl}methyl)piperazine-1-carboxylate (0.0788 g, 0.165 mmol) in methylene chloride (2 mL) was added with a 4 M solution of hydrochloric acid in dioxane (2 mL), and the mixture was stirred at room temperature for 2 hours. The reaction mixture was filtered, and the resulting solid was washed with acetonitrile to obtain the objective (Z)-2-[(1H-pyrrolo[2,3-b]pyridin-3-yl)methylene]-6-hydroxy-7-(piperazin-1-ylmethyl)benzofuran-3(2H)-one trihydrochloride (0.0518 g, 64%).

$^1$H NMR (300 MHz, DMSO-$d_6$) δ 3.39-3.53 (m, 8H), 4.60 (s, 2H), 7.03 (d, J=8.8 Hz, 1H), 7.30 (s, 1H), 7.31 (dd, J=4.4 Hz, 8.1 Hz, 1H), 7.76 (d, J=8.8 Hz, 1H), 8.37 (d, J=4.4 Hz, 1H), 8.54 (d, J=1.5 Hz, 1H), 8.58 (d, J=8.1 Hz, 1H), 12.66 (br s, 1H).

Example A43

(Z)-2-[(1H-Pyrrolo[2,3-b]pyridin-3-yl)methylene]-6-hydroxy-7-[(4-methylpiperazin-1-yl)methyl]benzofuran-3(2H)-one A solution of 6-hydroxy-7-[(4-methylpiperazin-1-yl)methyl]benzofuran-3(2H)-one (0.100 g, 0.381 mmol) obtained in Example A31, Step 1 in methanol (1.5 mL) was added with 7-aza-1H-indole-3-carboxaldehyde (0.0557 g, 0.381 mmol) and piperidine (0.00324 g, 0.0381 mmol), and the mixture was stirred at 60° C. for 2 hours. The reaction mixture was cooled to room temperature, and then the precipitated solid was collected by filtration to obtain (Z)-2-((1H-pyrrolo[2,3-b]pyridin-3-yl)methylene)-6-hydroxy-7-[(4-methylpiperazin-1-yl)methyl]benzofuran-3(2H)-one (0.109 g, 73%).

$^1$H NMR (300 MHz, DMSO-$d_6$) δ 2.17 (s, 3H), 2.38 (m, 4H), 2.63 (m, 4H), 3.91 (s, 2H), 6.68 (d, J=8.8 Hz, 1H), 7.18 (s, 1H), 7.22 (dd, J=4.4 Hz, 8.1 Hz, 1H), 7.53 (d, J=8.8 Hz, 1H), 8.24 (s, 1H), 8.34 (dd, J=1.5 Hz, 4.4 Hz, 1H), 8.60 (dd, J=1.5 Hz, 8.1 Hz, 1H), 12.50 (br s, 1H).

Example A44

(Z)-2-[(1H-Pyrrolo[2,3-b]pyridin-3-yl)methylene]-6-hydroxy-7-(morpholinomethyl)benzofuran-3(2H)-one A solution of 6-hydroxy-7-(morpholinomethyl)benzofuran-3(2H)-one (0.170 g, 0.684 mmol) obtained in Example A41, Step 1 in methanol (3 mL) was added with 7-aza-1H-indole-3-carboxaldehyde (0.100 g, 0.684 mmol) and piperidine (0.00582 g, 0.0684 mmol), and the mixture was stirred at 60° C. for 1 hour. The reaction mixture was cooled to room temperature, and then added with methanol (2 mL), and the precipitated solid was suspended in methanol and thereby washed. The solid was collected by filtration to obtain the objective (Z)-2-[(1H-pyrrolo[2,3-b]pyridin-3-yl)methylene]-6-hydroxy-7-(morpholinomethyl)benzofuran-3(2H)-one (0.135 g, 52%).

$^1$H NMR (300 MHz, DMSO-$d_6$) δ 2.58 (m, 4H), 3.61 (m, 4H), 3.85 (s, 2H), 6.74 (d, J=8.8 Hz, 1H), 7.19 (s, 1H), 7.22 (dd, J=5.1 Hz, 8.1 Hz, 1H), 7.55 (d, J=8.8 Hz, 1H), 8.25 (s, 1H), 8.34 (d, J=4.4 Hz, 1H), 8.61 (d, J=7.3 Hz, 1H), 12.49 (br s, 1H).

Example A45

(Z)-4-({2-[(1H-Pyrrolo[2,3-b]pyridin-3-yl)methylene]-6-hydroxy-3-oxo-2,3-dihydrobenzofuran-7-yl}methyl)piperazin-2-one (a) Step 1

A solution of 6-hydroxybenzofuran-3(2H)-one (0.750 g, 5.00 mmol) in ethanol (5 mL) was added with 2-oxopiperazine (0.500 g, 5.00 mmol), and 37% aqueous formaldehyde (0.406 g, 5.00 mmol) at room temperature. The mixture was stirred overnight at room temperature, and then added with 37% aqueous formaldehyde (0.406 g, 5.00 mmol) at room temperature, and the mixture was refluxed for 4 hours by heating. The reaction mixture was cooled to room temperature, and then subjected to suction filtration to obtain 4-[(6-hydroxy-3-oxo-2,3-dihydrobenzofuran-7-yl)methyl]piperazin-2-one (0.631 g, 48%) as a white solid.

$^1$H NMR (300 MHz, DMSO-$d_6$) δ 2.63 (t, J=5.1 Hz, 2H), 3.00 (s, 2H), 3.13 (m, 2H), 3.64 (s, 2H), 4.74 (s, 2H), 6.64 (d, J=8.8 Hz, 1H), 7.42 (d, J=8.8 Hz, 1H), 7.74 (s, 1H).

(b) Step 2

A solution of 4-[(6-hydroxy-3-oxo-2,3-dihydrobenzofuran-7-yl)methyl]piperazin-2-one (0.0986 g, 0.376 mmol) in isopropanol (1.5 mL) was added with 7-aza-1H-indole-3-carboxaldehyde (0.0550 g, 0.376 mmol) and piperidine (0.00320 g, 0.0376 mmol), and the mixture was refluxed by heating for 2 hours. The reaction mixture was cooled to room temperature, and then added with isopropanol (2 mL), and the precipitated solid was suspended in isopropanol and thereby washed. The solid was collected by filtration to obtain the objective (Z)-4-({2-[(1H-pyrrolo[2,3-b]pyridin-3-yl)methylene]-6-hydroxy-3-oxo-2,3-dihydrobenzofuran-7-yl}methyl)piperazin-2-one (0.106 g, 72%).

$^1$H NMR (300 MHz, DMSO-$d_6$) δ 2.59 (m, 2H), 2.97 (s, 2H), 3.03 (m, 2H), 3.71 (s, 2H), 6.65 (d, J=8.1 Hz, 1H), 7.04 (s, 1H), 7.11 (dd, J=4.4 Hz, 8.1 Hz, 1H), 7.43 (d, J=8.1 Hz, 1H), 7.65 (s, 1H), 8.11 (s, 1H), 8.21 (dd, J=1.5 Hz, 4.4 Hz, 1H), 8.54 (dd, J=1.5 Hz, 8.1 Hz, 1H), 12.36 (br s, 1H).

Example A46

(Z)-2-[(6-Chloro-1H-pyrrolo[2,3-b]pyridin-3-yl) methylene]-6-hydroxy-7-(piperazin-1-ylmethyl)benzofuran-3(2H)-one trihydrochloride

(a) Step 1

The synthesis was performed according to the known method (Synthesis, p. 661, 1992). A solution of 7-aza-1H-indole-N-oxide (0.710 g, 5.29 mmol) in THF (53 mL) was added with hexamethyldisilazane (1.10 mL, 5.29 mmol) and methyl chloro acetate (1.02 g, 13.2 mmol) under an argon atmosphere, and the mixture was stirred at room temperature for 1 hour. The solvent was evaporated, then the residue was added with saturated aqueous sodium hydrogencarbonate, and the mixture was extracted three times with ethyl acetate. The organic layer was washed with saturated brine, and dried over anhydrous magnesium sulfate. The solvent was evaporated, and the resulting residue was purified by silica gel column chromatography (hexane/ethyl acetate) to obtain methyl 6-chloro-1H-pyrrolo[2,3-b]pyridine-1-carboxylate (0.580 g, 52%).

$^1$H NMR (300 MHz, CDCl$_3$) δ 4.11 (s, 3H), 6.56 (d, J=4.4 Hz, 1H), 7.24 (d, J=8.0 Hz, 1H), 7.73 (d, J=4.4 Hz, 1H), 7.80 (d, J=8.0 Hz, 1H).

(b) Step 2

The synthesis was performed with reference to the known literature (International Patent Publication WO2008/080015). A solution of methyl 6-chloro-1H-pyrrolo[2,3-b]pyridine-1-carboxylate (0.37 g, 1.8 mmol) in methanol (10 mL) was added with 5 N aqueous sodium hydroxide (2.0 mL), and the mixture was stirred overnight at room temperature. The solvent was evaporated under reduced pressure, the residue was added with water, and the mixture was extracted with ethyl acetate. The resulting organic layer was washed with saturated brine, and dried over anhydrous magnesium sulfate. The solvent was evaporated under reduced pressure to obtain 6-chloro-1H-pyrrolo[2,3-b]pyridine (0.26 g, 95%).

$^1$H NMR (300 MHz, CDCl$_3$) δ 6.52 (m, 1H), 7.11 (d, J=8.1 Hz, 1H), 7.34 (m, 1H), 7.90 (d, J=8.1 Hz, 1H), 9.80 (br s, 1H).

(c) Step 3

6-Chloro-1H-pyrrolo[2,3-b]pyridine (0.041 g, 0.27 mmol) was successively added with acetic acid (0.1 mL), water (0.2 mL), and hexamethylenetetramine (0.053 g, 0.28 mmol), and then the mixture was stirred overnight at 120° C. in a sealed tube. The reaction mixture was added with water, and the precipitated solid was collected by filtration to obtain 6-chloro-1H-pyrrolo[2,3-b]pyridine-3-carboxaldehyde (0.031 g, 64%).

$^1$H NMR (300 MHz, DMSO-d$_6$) δ 7.36 (d, J=8.1 Hz, 1H), 8.42 (d, J=8.1 Hz, 1H), 8.52 (s, 1H), 9.93 (s, 1H), 12.88 (br s, 1H).

(d) Step 4

A solution of tert-butyl 4-[(6-hydroxy-3-oxo-2,3-dihydrobenzofuran-7-yl)methyl]piperazine-1-carboxylate (0.020 g, 0.057 mmol) obtained in Example A16, Step 1 in methanol (2.0 mL) was added with 6-chloro-1H-pyrrolo[2,3-b]pyridine-3-carboxaldehyde (0.009 g, 0.057 mmol). Then, the mixture was added with 5 drops of piperidine, and the mixture was stirred at 60° C. for 1 hour. The solvent was evaporated under reduced pressure, and then the residue was subjected to silica gel column chromatography (eluted with chloroform/methanol (95:5→90:10)) to obtain tert-butyl (Z)-4-({2-[(6-chloro-1H-pyrrolo[2,3-b]pyridin-3-yl)methylene]-6-hydroxy-3-oxo-2,3-dihydrobenzofuran-7-yl}methyl) piperazine-1-carboxylate (0.020 g, 69%).

$^1$H NMR (300 MHz, CD$_3$OD) δ 1.48 (s, 9H), 2.70 (m, 4H), 3.57 (m, 4H), 4.04 (s, 2H), 6.71 (d, J=8.8 Hz, 1H), 7.15 (s, 1H), 7.25 (d, J=8.8 Hz, 1H), 7.65 (d, J=8.1 Hz, 1H), 8.01 (s, 1H), 8.28 (d, J=8.1 Hz, 1H), 13.83 (s, 1H).

(e) Step 5

A solution of tert-butyl (Z)-4-({2-[(6-chloro-1H-pyrrolo[2,3-b]pyridin-3-yl)methylene]-6-hydroxy-3-oxo-2,3-dihydrobenzofuran-7-yl}methyl)piperazine-1-carboxylate (0.020 g, 0.039 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-2-[(6-chloro-1H-pyrrolo[2,3-b]pyridin-3-yl)methylene]-6-hydroxy-7-(piperazin-1-ylmethyl)benzofuran-3(2H)-one trihydrochloride (0.015 g, 75%).

$^1$H NMR (300 MHz, DMSO-d$_6$) δ 3.00-4.00 (m, 8H), 4.57 (br s, 2H), 7.01 (d, J=8.8 Hz, 1H), 7.28 (s, 1H), 7.35 (d, J=8.1 Hz, 1H), 7.76 (d, J=8.8 Hz, 1H), 8.51 (s, H), 8.60 (d, J=8.8 Hz, 1H), 12.74 (s, 1H).

Example A47

(Z)-2-[(6-Bromo-1H-pyrrolo[2,3-b]pyridin-3-yl) methylene]-6-hydroxy-7-(piperazin-1-ylmethyl)benzofuran-3(2H)-one trihydrochloride

(a) Step 1

The synthesis was performed with reference to the known literature (International Patent Publication WO2008/080015). A solution of 7-aza-1H-indole-N-oxide (1.0 g, 7.5 mmol) in benzene (80 mL) was slowly added with a solution of benzoyl bromide (3.4 g, 19 mmol) and hexamethyldisilazane (1.3 g, 8.3 mmol) in benzene (40 mL) under an argon atmosphere, and then the mixture was stirred at room temperature for 2 hours. The reaction mixture was added with ethyl acetate, and the organic layer was successively washed with saturated aqueous sodium hydrogencarbonate, and saturated brine, and dried over anhydrous magnesium sulfate. The solvent was evaporated under reduced pressure to obtain 1-benzoyl-6-bromo-1H-pyrrolo[2,3-b]pyridine (1.27 g, 56%).

$^1$H NMR (300 MHz, CDCl$_3$) δ 6.63 (d, J=3.7 Hz, 1H), 7.35 (d, J=8.1 Hz, 1H), 7.49 (d, J=8.1 Hz, 1H), 7.52 (d, J=7.3 Hz, 1H), 7.60-7.68 (m, 1H), 7.71-7.82 (m, 4H).

(b) Step 2

A solution of 1-benzoyl-6-bromo-1H-pyrrolo[2,3-b]pyridine (0.046 g, 0.15 mmol) in methanol (5.0 mL) was added with 5 N aqueous sodium hydroxide (1.0 mL), and the mixture was stirred at room temperature for 2 hours. The solvent was evaporated under reduced pressure, the residue was extracted with diethyl ether, and then the organic layer was washed successively with water and saturated brine, and dried over anhydrous magnesium sulfate. The solvent was evaporated under reduced pressure to obtain 6-bromo-1H-pyrrolo [2,3-b]pyridine (0.028 g, 95%).

$^1$H NMR (300 MHz, DMSO-d$_6$) δ 7.01 (d, J=8.1 Hz, 1H), 7.46 (d, J=8.1 Hz, 1H), 7.75 (d, J=8.1 Hz, 1H), 8.51 (d, J=8.1 Hz, 1H).

(c) Step 3

6-Bromo-1H-pyrrolo[2,3-b]pyridine (0.028 g, 0.14 mmol) was successively added with acetic acid (0.1 mL), water (0.2 mL), and hexamethylenetetramine (0.028 g, 0.20 mmol), and then the mixture was stirred overnight at 120° C. in a sealed tube. The reaction mixture was added with water, and the precipitated solid was collected by filtration to obtain 6-bromo-1H-pyrrolo[2,3-b]pyridine-3-carboxaldehyde (0.008 g, 25%).

$^1$H NMR (300 MHz, CDCl$_3$) δ 7.48 (d, J=8.1 Hz, 1H), 8.33 (d, J=8.1 Hz, 1H), 8.50 (s, 1H), 9.93 (s, 1H).

(d) Step 4

A solution of tert-butyl 4-[(6-hydroxy-3-oxo-2,3-dihydrobenzofuran-7-yl)methyl]piperazine-1-carboxylate (0.012 g, 0.034 mmol) obtained in Example A16, Step 1 in methanol (2.0 mL) was added with 6-bromo-1H-pyrrolo[2,3-b]pyridine-3-carboxaldehyde (0.007 g, 0.031 mmol). Then, the mixture was added with 5 drops of piperidine, and the mixture was stirred at 50° C. for 2 hours. The solvent was evaporated under reduced pressure, and the residue was purified by silica gel column chromatography (eluted with chloroform/methanol (95:5→90:10)) to obtain tert-butyl (Z)-4-({2-[(6-bromo-1H-pyrrolo[2,3-b]pyridin-3-yl)methylene]-6-hydroxy-3-oxo-2,3-dihydrofuran-7-yl}methyl)piperazine-1-carboxylate (0.012 g, 71%).

$^1$H NMR (300 MHz, CD$_3$OD) δ 1.48 (s, 9H), 2.69 (m, 4H), 3.57 (m, 4H), 4.03 (s, 2H), 6.70 (d, J=8.8 Hz, 1H), 7.13 (s, 1H), 7.38 (d, J=8.1 Hz, 1H), 7.65 (d, J=8.8 Hz, 1H), 7.98 (s, 1H), 8.17 (d, J=8.1 Hz, 1H).

(e) Step 5

A solution of tert-butyl (Z)-4-({2-[(6-bromo-1H-pyrrolo [2,3-b]pyridin-3-yl)methylene]-6-hydroxy-3-oxo-2,3-dihydrofuran-7-yl}methyl)piperazine-1-carboxylate (0.012 g, 0.022 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-2-[(6-bromo-1H-pyrrolo[2, 3-b]pyridin-3-yl)methylene]-6-hydroxy-7-(piperazin-1-ylmethyl)benzofuran-3(2H)-one trihydrochloride (0.006 g, 50%).

$^1$H NMR (300 MHz, DMSO-d$_6$) δ 3.00-3.75 (m, 8H), 4.43 (br s, 2H), 6.96 (d, J=8.1 Hz, 1H), 7.26 (s, 1H), 7.46 (d, J=8.1 Hz, 1H), 7.72 (d, J=8.1 Hz, 1H), 8.44 (s, 1H), 8.53 (d, J=8.1 Hz, 1H), 12.75 (s, 1H).

Example A48

(Z)-6-Hydroxy-2-[(6-methyl-1H-pyrrolo[2,3-b]pyridin-3-yl)methylene]-7-(piperazin-1-ylmethyl)benzofuran-3(2H)-one trihydrochloride (a) Step 1

The synthesis was performed with reference to the known literature (Heterocycles, Vol. 30, p. 627, 1990). A solution of 6-chloro-1H-pyrrolo[2,3-b]pyridine (0.21 g, 1.4 mmol) obtained in Example A46, Step 2 in methylene chloride (10 mL) was successively added with sodium hydroxide (0.17 g, 4.2 mmol), and tetrabutylammonium hydrogensulfate (0.14 g, 0.42 mmol), and the mixture was stirred at room temperature. Then, the reaction mixture was added dropwise with a solution of tosyl chloride (0.32 g, 1.7 mmol) in methylene chloride (5 mL), and then the mixture was stirred overnight. The reaction mixture was extracted with ethyl acetate, and then the resulting organic layer was successively washed with water and saturated brine, and dried over anhydrous magnesium sulfate. The solvent was evaporated under reduced pressure, and the residue was washed with a mixed solvent of ethyl acetate and hexane to obtain 6-chloro-1-tosyl-1H-pyrrolo[2,3-b]pyridine (0.39 g, 93%).

$^1$H NMR (300 MHz, DMSO-d$_6$) δ 2.36 (s, 3H), 6.85 (d, J=4.4 Hz, 1H), 7.39 (d, J=8.1 Hz, 1H), 7.45 (d, J=8.8 Hz, 2H), 7.92 (d, J=3.7 Hz, 1H), 7.99 (d, J=8.1 Hz, 2H), 8.11 (d, J=8.1 Hz, 2H).

(b) Step 2

The synthesis was performed with reference to the known literature (US 2006/0148801). A solution of 6-chloro-1-tosyl-1H-pyrrolo[2,3-b]pyridine (0.38 g, 1.2 mmol) in tetrahydrofuran (20 mL) was added with tetrakis(triphenylphosphine)palladium(0) (0.069 g, 0.060 mmol) under an argon atmosphere. Then, the mixture was added dropwise with a 2 M solution of methyl zinc chloride in THF (3.6 mL, 7.2 mmol), and then the mixture was stirred at 60° C. for 48 hours. The reaction mixture was added with water, and the mixture was extracted with ethyl acetate. The organic layer was washed with saturated brine, and then dried over anhydrous magnesium sulfate. The solvent was evaporated under reduced pressure, and then the residue was subjected to silica gel column chromatography (eluted with hexane/ethyl acetate (90:10→50:50)) to obtain 6-methyl-1-tosyl-1H-pyrrolo[2,3-b]pyridine (0.28 g, 81%).

$^1$H NMR (300 MHz, CDCl$_3$) δ 2.37 (s, 3H), 2.63 (s, 3H), 6.50 (d, J=3.7 Hz, 1H), 7.01 (d, J=8.1 Hz, 1H), 7.26 (d, J=8.1 Hz, 2H), 7.62 (d, J=4.4 Hz, 1H), 7.68 (d, J=8.1 Hz, 1H), 8.12 (d, J=8.1 Hz, 2H).

(c) Step 3

The synthesis was performed with reference to the known literature (US 2006/0148801). A solution of 6-methyl-1-tosyl-1H-pyrrolo[2,3-b]pyridine (0.17 g, 0.60 mmol) in ethanol (5.0 mL) was added with 5 N aqueous sodium hydroxide (1.0 mL), and the mixture was refluxed for 8 hours by heating. The solvent was evaporated under reduced pressure, the residue was extracted with chloroform, and then the organic layer was washed successively with water and saturated brine, and dried over anhydrous magnesium sulfate. The solvent was evaporated under reduced pressure, and then the residue was subjected to silica gel column chromatography (eluted with hexane/ethyl acetate (80:20→60:40)) to obtain 6-methyl-1H-pyrrolo[2,3-b]pyridine (0.071 g, 90%).

$^1$H NMR (300 MHz, CDCl$_3$) δ 2.67 (s, 3H), 6.46 (m, 1H), 6.97 (d, J=8.1 Hz, 1H), 7.24-7.29 (m, 1H), 7.85 (d, J=8.1 Hz, 1H), 12.50 (br s, 1H).

(d) Step 4

6-Methyl-1H-pyrrolo[2,3-b]pyridine (0.066 g, 0.50 mmol) was successively added with acetic acid (0.2 mL), water (0.4 mL), and hexamethylenetetramine (0.098 g, 0.70 mmol), and then the mixture was stirred overnight at 120° C. in a sealed tube. The reaction mixture was added with water, and then the precipitated solid was collected by filtration to obtain 6-methyl-1H-pyrrolo[2,3-b]pyridine-3-carboxaldehyde (0.054 g, 67%).

$^1$H NMR (300 MHz, DMSO-d$_6$) δ 2.55 (s, 3H), 7.16 (d, J=8.1 Hz, 1H), 8.27 (d, J=8.1 Hz, 1H), 8.36 (s, 1H), 10.28 (s, 1H).

(e) Step 5

A solution of tert-butyl 4-[(6-hydroxy-3-oxo-2,3-dihydrobenzofuran-7-yl)methyl]piperazine-1-carboxylate (0.020 g, 0.058 mmol) obtained in Example A16, Step 1 in methanol (2.0 mL) was added with 6-methyl-1H-pyrrolo[2,3-b]pyridine-3-carboxaldehyde (0.010 g, 0.063 mmol). Then, the mixture was added with 5 drops of piperidine, and then the mixture was stirred at 50° C. for 2 hours. The solid formed was collected by filtration, and washed with methanol to obtain tert-butyl (Z)-4-({6-hydroxy-2-[(6-methyl-1H-pyrrolo[2,3-b]pyridin-3-yl)methylene]-3-oxo-2,3-dihydrobenzofuran-7-yl}methyl)piperazine-1-carboxylate (0.023 g, 81%).

$^1$H NMR (300 MHz, CD$_3$OD) δ 1.48 (s, 9H), 2.66 (s, 3H), 2.71 (m, 4H), 3.57 (m, 4H), 4.06 (s, 2H), 6.71 (d, J=8.1 Hz, 1H), 7.13 (d, J=8.1 Hz, 1H), 7.21 (s, 1H), 7.65 (d, J=8.1 Hz, 1H), 7.98 (s, 1H), 825 J=8.1 Hz, 1H).

(f) Step 6

A solution of tert-butyl (Z)-4-({6-hydroxy-2-[(6-methyl-1H-pyrrolo[2,3-b]pyridin-3-yl)methylene]-3-oxo-2,3-dihydrobenzofuran-7-yl}methyl)piperazine-1-carboxylate (0.023 g, 0.047 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-[(6-methyl-1H-pyrrolo[2,3-b]pyridin-3-yl)methylene]-7-(piperazin-1-ylmethyl)benzofuran-3(2H)-one trihydrochloride (0.018 g, 77%).

$^1$H NMR (300 MHz, DMSO-d$_6$) δ 2.59 (s, 3H), 3.00-3.75 (m, 8H), 4.55 (br s, 2H), 6.99 (d, J=8.8 Hz, 1H), 7.20 (d, J=8.1 Hz, 1H), 7.26 (s, 1H), 7.75 (d, J=8.8 Hz, 1H), 8.41 (s, 1H), 8.47 (d, J=8.1 Hz, 1H), 12.48 (br s, 1H).

Example A49

(Z)-6-Hydroxy-2-[(6-phenyl-1H-pyrrolo[2,3-b]pyridin-3-yl)methylene]-7-(piperazin-1-ylmethyl)benzofuran-3(2H)-one trihydrochloride (a) Step 1

A solution of 6-bromo-1-benzoyl-1H-pyrrolo[2,3-b]pyridine (0.19 g, 0.64 mmol) obtained in Example A47, Step 1 in 1,2-dimethoxyethane (5.0 mL) was successively added with water (2.0 mL), phenylboronic acid (0.16 g, 0.64 mmol), and sodium carbonate (0.20 g, 1.9 mmol). After the inside of the reaction vessel was replaced with argon, the reaction mixture was added with tetrakis(triphenylphosphine)palladium(0) (0.074 g, 0.064 mmol), and the mixture was stirred overnight at 110° C. in a sealed tube. The reaction mixture was extracted with ethyl acetate, and then the organic layer was washed successively with water and saturated brine, and dried over anhydrous magnesium sulfate. The solvent was evaporated under reduced pressure, and the residue was subjected to silica gel column chromatography (eluted with chloroform/methanol (99:1→99:5)) to obtain 6-phenyl-1H-pyrrolo[2,3-b]pyridine (0.10 g, 80%).

$^1$H NMR (300 MHz, DMSO-d$_6$) δ 6.44-6.50 (m, 1H), 7.38 (m, 1H), 7.43-7.53 (m, 3H), 7.66 (d, J=8.1 Hz, 1H), 8.03 (d, J=8.1 Hz, 1H), 8.10 (d, J=8.1 Hz, 2H), 11.71 (s, 1H).

(b) Step 2

6-Phenyl-1H-pyrrolo[2,3-b]pyridine (0.10 g, 0.52 mmol) was successively added with acetic acid (0.2 mL), water (0.4 mL), and hexamethylenetetramine (0.11 g, 0.77 mmol), and then the mixture was stirred overnight at 120° C. in a sealed tube. The reaction mixture was cooled to room temperature, and then added with saturated aqueous sodium hydrogencarbonate, and the mixture was extracted with ethyl acetate. The organic layer was washed successively with water and saturated brine, and dried over anhydrous magnesium sulfate. The solvent was evaporated under reduced pressure, and the residue was subjected to silica gel column chromatography (eluted with chloroform/methanol (99:1→99:5)) to obtain a solid containing the objective substance. The solid was washed with a mixed solvent of chloroform and methanol to obtain 6-phenyl-1H-pyrrolo[2,3-b]pyridine-3-carboxaldehyde (0.013 g, 11%).

$^1$H NMR (400 MHz, DMSO-d$_6$) δ 7.43 (m, 1H), 7.51 (m, 2H), 7.87 (d, J=8.3 Hz, 1H), 8.12 (d, J=8.3 Hz, 1H), 8.45 (d, J=8.3 Hz, 1H), 8.49 (s, 1H), 8.47 (d, J=8.3 Hz, 1H), 9.91 (s, 1H).

(c) Step 3

A solution of tert-butyl 4-[(6-hydroxy-3-oxo-2,3-dihydrobenzofuran-7-yl)methyl]piperazine-1-carboxylate (0.026 g, 0.075 mmol) obtained in Example A16, Step 1 in methanol (2.0 mL) was added with 6-phenyl-1H-pyrrolo[2,3-b]pyridine-3-carboxaldehyde (0.013 g, 0.059 mmol). Then, the mixture was added with 5 drops of piperidine, and the mixture was stirred overnight at room temperature. The solvent was evaporated under reduced pressure, and then the residue was subjected to silica gel column chromatography (eluted with chloroform/methanol (95:5)) to obtain tert-butyl (Z)-4-({6-hydroxy-3-oxo-2-[(6-phenyl-1H-pyrrolo[2,3-b]pyridin-3-yl)methylene]-2,3-dihydrobenzofuran-7-yl}methyl)piperazine-1-carboxylate (0.019 g, 46%).

$^1$H NMR (300 MHz, CD$_3$OD) δ 1.48 (s, 9H), 2.73 (m, 4H), 3.58 (m, 4H), 4.08 (s, 2H), 6.72 (d, J=8.1 Hz, 1H), 7.25 (s, 1H), 7.36-7.57 (m, 4H), 7.65 (d, J=8.8 Hz, 1H), 7.69 (d, J=8.1 Hz, 1H), 8.01 (d, J=7.3 Hz, 1H), 8.10 (s, 1H), 8.44 (d, J=8.8 Hz, 1H).

(d) Step 4

A solution of tert-butyl (Z)-4-({6-hydroxy-3-oxo-2-[(6-phenyl-1H-pyrrolo[2,3-b]pyridin-3-yl)methylene]-2,3-dihydrobenzofuran-7-yl}methyl)piperazine-1-carboxylate (0.019 g, 0.034 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-6-hydroxy-2-

[(6-phenyl-1H-pyrrolo[2,3-b]pyridin-3-yl)methylene]-7-(piperazin-1-ylmethyl)benzofuran-3(2H)-one trihydrochloride (0.014 g, 74%).

$^1$H NMR (300 MHz, DMSO-d$_6$) δ 2.78-3.78 (m, 8H), 4.61 (br s, 2H), 7.03 (d, J=8.1 Hz, 1H), 7.35 (s, 1H), 7.47 (m, 1H), 7.55 (m, 2H), 7.80 (d, J=8.8 Hz, 1H), 7.94 (d, J=8.1 Hz, 1H), 8.20 (d, J=7.3 Hz, 2H), 8.54 (br s, 1H), 8.67 (d, J=8.8 Hz, 1H), 12.64 (s, 1H).

Example A50

(Z)-2-[(6-Ethynyl-1H-pyrrolo[2,3-b]pyridin-3-yl)methylene]-6-hydroxy-7-(piperazin-1-ylmethyl)benzofuran-3(2H)-one trihydrochloride (a) Step 1

The synthesis was performed with reference to the known literature (Bulletin of the Chemical Society of Japan, Vol. 65, p. 2992, 1992). A solution of 1-benzoyl-6-bromo-1H-pyrrolo[2,3-b]pyridine (0.30 g, 1.0 mmol) in triethylamine (25 mL) was added with dichlorobis(triphenylphosphine)palladium (II) (0.036 g, 0.050 mmol), and copper(I) iodide (0.016 g, 0.085 mmol) under an argon atmosphere. Then, the mixture was slowly added with trimethylsilylacetylene (0.20 g, 2.0 mmol), and then the mixture was stirred at room temperature for 24 hours. Triethylamine was evaporated under reduced pressure, and the residue was dissolved in ethyl acetate, and then the organic layer was washed successively with water and saturated brine, and dried over anhydrous magnesium sulfate. The solvent was evaporated under reduced pressure, and the residue was subjected to silica gel column chromatography (eluted with hexane/ethyl acetate (100:0→90:10)) to obtain 6-[(trimethylsilyl)ethynyl]-1-benzoyl-1H-pyrrolo[2,3-b]pyridine (0.045 g, 14%).

$^1$H NMR (300 MHz, CDCl$_3$) δ 0.23 (s, 9H), 6.61 (d, J=3.7 Hz, 1H), 7.38 (d, J=8.1 Hz, 1H), 7.48 (d, J=7.3 Hz, 1H), 7.51 (d, J=7.3 Hz, 1H), 7.58-7.65 (m, 1H), 7.72 (d, J=3.7 Hz, 1H), 7.80 (m, 2H), 7.84 (d, J=8.1 Hz, 1H).

(b) Step 2

The synthesis was performed with reference to the known literature (Bulletin of Chemical Society of Japan, Vol. 65, p. 2992, 1992). A solution of 6-[(trimethylsilyl)ethynyl]-1-benzoyl-1H-pyrrolo[2,3-b]pyridine (0.039 g, 0.12 mmol) in methanol (2.0 mL) was added with 5 N aqueous sodium hydroxide (1.0 mL), and the mixture was stirred at room temperature for 24 hours. The solvent was evaporated under reduced pressure, the residue was dissolved in ethyl acetate, and then the organic layer was washed successively with water and saturated brine, and dried over anhydrous magnesium sulfate. The solvent was evaporated under reduced pressure, and the residue was washed with a mixed solvent of hexane and ethyl acetate to obtain 6-ethynyl-1H-pyrrolo[2,3-b]pyridine (0.016 g, 90%).

$^1$H NMR (300 MHz, CDCl$_3$) δ 3.18 (s, 1H), 6.53 (m, 1H), 7.33 (d, J=8.1 Hz, 1H), 7.49 (m, 1H), 7.93 (d, J=8.1 Hz, 1H), 11.33 (br s, 1H).

(c) Step 3

6-Ethynyl-1H-pyrrolo[2,3-b]pyridine (0.016 g, 0.11 mmol) was successively added with acetic acid (0.1 mL), water (0.2 mL), and hexamethylenetetramine (0.023 g, 0.17 mmol), and then the mixture was stirred overnight at 120° C. in a sealed tube. The reaction mixture was cooled to room temperature, and then added with saturated aqueous sodium hydrogencarbonate, and the mixture was extracted with ethyl acetate. The organic layer was washed successively with water and saturated brine, and dried over anhydrous magnesium sulfate. The solvent was evaporated under reduced pressure to obtain 6-ethynyl-1H-pyrrolo[2,3-b]pyridine-3-carboxaldehyde (0.016 g, 85%).

$^1$H NMR (300 MHz, DMSO-d$_6$) δ 4.31 (s, 1H), 7.45 (d, J=8.1 Hz, 1H), 8.39 (d, J=8.1 Hz, 1H), 8.58 (s, 1H), 9.93 (s, 1H).

(d) Step 4

A solution of tert-butyl 4-[(6-hydroxy-3-oxo-2,3-dihydrobenzofuran-7-yl)methyl]piperazine-1-carboxylate (0.017 g, 0.049 mmol) obtained in Example A16, Step 1 in methanol (2.0 mL) was added with 6-ethynyl-1H-pyrrolo[2,3-b]pyridine-3-carboxaldehyde (0.007 g, 0.041 mmol). Then, the mixture was added with 5 drops of piperidine, and then the mixture was stirred overnight at room temperature. The solvent was evaporated under reduced pressure, and then the residue was washed with methylene chloride to obtain tert-butyl (Z)-4-({2-[(6-ethynyl-1H-pyrrolo[2,3-b]pyridin-3-yl)methylene]-6-hydroxy-3-oxo-2,3-dihydrobenzofuran-7-yl}methyl)piperazine-1-carboxylate (0.015 g, 60%).

$^1$H NMR (300 MHz, CD$_3$OD) δ 1.48 (s, 9H), 2.71 (m, 4H), 3.33 (s, 1H), 3.57 (m, 4H), 4.05 (s, 2H), 6.71 (d, J=8.8 Hz, 1H), 7.17 (s, 1H), 7.45 (d, J=8.8 Hz, 1H), 7.65 (d, J=8.1 Hz, 1H), 8.12 (s, 1H), 8.31 (d, J=8.1 Hz, 1H).

(e) Step 5

A solution of tert-butyl (Z)-4-({2-[(6-ethynyl-1H-pyrrolo[2,3-b]pyridin-3-yl)methylene]-6-hydroxy-3-oxo-2,3-dihydrobenzofuran-7-yl}methyl)piperazine-1-carboxylate (0.015 g, 0.030 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in methylene chloride and thereby washed to obtain (Z)-2-[(6-ethynyl-1H-pyrrolo[2,3-b]pyridin-3-yl)methylene]-6-hydroxy-7-(piperazin-1-ylmethyl)benzofuran-3(2H)-one trihydrochloride (0.012 g, 78%).

$^1$H NMR (300 MHz, DMSO-d$_6$) δ 2.75-3.75 (m, 8H), 4.30 (s, 1H), 4.53 (br s, 2H), 6.99 (d, J=8.1 Hz, 1H), 7.28 (s, 1H), 7.45 (d, J=8.1 Hz, 1H), 7.75 (d, J=8.8 Hz, 1H), 8.55 (d, J=8.8 Hz, 1H), 8.58 (s, 1H), 2.68 (s, 1H).

Example A51

(Z)-5-Chloro-6-hydroxy-2-[(6-methyl-1H-pyrrolo[2,3-b]pyridin-3-yl)methylene]-7-(piperazin-1-ylmethyl)benzofuran-3(2H)-one trihydrochloride (a) Step 1

A solution of tert-butyl 4-[(5-chloro-6-hydroxy-3-oxo-2,3-dihydrobenzofuran-7-yl)methyl]piperazine-1-carboxylate (0.012 g, 0.031 mmol) obtained in Example A12, Step 2 in methanol (2.0 mL) was added with 6-methyl-1H-pyrrolo[2,3-b]pyridine-3-carboxaldehyde (0.005 g, 0.028 mmol) obtained in Example A48, Step 4. Then, the mixture was added with 5 drops of piperidine, and then the mixture was stirred at 50° C. for 3 hours. The solvent was evaporated under reduced pressure, and then the residue was suspended in diethyl ether and thereby washed to obtain tert-butyl (Z)-4-

({5-chloro-6-hydroxy-2-[(6-methyl-1H-pyrrolo[2,3-b]pyridin-3-yl)methylene]-3-oxo-2,3-dihydrobenzofuran-7-yl}methyl)piperazine-1-carboxylate (0.010 g, 68%).

$^1$H NMR (300 MHz, DMSO-$d_6$) δ 1.41 (s, 9H), 2.56 (s, 3H), 2.92 (m, 4H), 3.51 (m, 4H), 4.24 (s, 2H), 7.04 (s, 1H), 7.11 (d, J=8.1 Hz, 1H), 7.59 (s, 1H), 8.14 (s, 1H), 8.37 (d, J=8.1 Hz, 1H), 12.25 (s, 1H).

(b) Step 2

A solution of tert-butyl (Z)-4-({5-chloro-6-hydroxy-2-[(6-methyl-1H-pyrrolo[2,3-b]pyridin-3-yl)methylene]-3-oxo-2,3-dihydrobenzofuran-7-yl}methyl)piperazine-F carboxylate (0.010 g, 0.019 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-5-chloro-6-hydroxy-2-[(6-methyl-1H-pyrrolo[2,3-b]pyridin-3-yl)methylene]-7-(piperazin-1-ylmethyl)benzofuran-3(2H)-one trihydrochloride (0.008 g, 79%).

$^1$H NMR (300 MHz, DMSO-$d_6$) δ 2.59 (s, 3H), 3.20-3.46 (m, 8H), 4.46 (br s, 2H), 7.19 (d, J=8.1 Hz, 1H), 7.29 (s, 1H), 7.88 (s, 1H), 8.34 (s, 1H), 8.48 (d, J=8.1 Hz, 1H), 12.49 (s, 1H).

Example A52

(Z)-2-[(5-Bromo-1H-pyrrolo[2,3-b]pyridin-3-yl)methylene]-6-hydroxy-7-(piperazin-1-ylmethyl)benzofuran-3(2H)-one trihydrochloride (a) Step 1

5-Bromo-1H-pyrrolo[2,3-b]pyridine (0.087 g, 0.44 mmol) was successively added with acetic acid (0.2 mL), water (0.4 mL), and hexamethylenetetramine (0.087 g, 0.62 mmol), and then the mixture was stirred overnight at 120° C. in a sealed tube. The reaction mixture was added with water, and then the precipitated solid was collected by filtration to obtain 5-bromo-1H-pyrrolo[2,3-b]pyridine-3-carboxaldehyde (0.061 g, 62%).

$^1$H NMR (300 MHz, CDCl$_3$) δ 8.46 (d, J=2.2 Hz, 1H), 8.53 (d, J=2.2 Hz, 1H), 8.54 (s, 1H), 9.93 (s, 1H).

(b) Step 2

A solution of tert-butyl 4-[(6-hydroxy-3-oxo-2,3-dihydrobenzofuran-7-yl)methyl]piperazine-1-carboxylate (0.020 g, 0.058 mmol) obtained in Example A16, Step 1 in methanol (1.0 mL) was added with 5-bromo-1H-pyrrolo[2,3-b]pyridine-3-carboxaldehyde (0.010 g, 0.044 mmol). Then, the mixture was added with 5 drops of piperidine, and the mixture was stirred at 50° C. for 2 hours. The solvent was evaporated under reduced pressure, and then the residue was suspended in methylene chloride and thereby washed to obtain tert-butyl (Z)-4-({2-[(5-bromo-1H-pyrrolo[2,3-b]pyridin-3-yl)methylene]-6-hydroxy-3-oxo-2,3-dihydrobenzofuran-7-yl}methyl)piperazine-1-carboxylate (0.018 g, 56%).

$^1$H NMR (300 MHz, DMSO-$d_6$) δ 1.38 (s, 9H), 2.56 (m, 4H), 3.35 (m, 4H), 3.92 (s, 2H), 6.75 (d, J=8.8 Hz, 1H), 7.21 (s, 1H), 7.56 (d, J=8.8 Hz, 1H), 8.28 (s, 1H), 8.41 (d, J=2.2 Hz, 1H), 8.91 (d, J=2.2 Hz, 1H), 12.72 (s, 1H).

(c) Step 3

A solution of tert-butyl (Z)-4-({2-[(5-bromo-1H-pyrrolo[2,3-b]pyridin-3-yl)methylene]-6-hydroxy-3-oxo-2,3-dihydrobenzofuran-7-yl}methyl)piperazine-1-carboxylate (0.018 g, 0.032 mmol) in methylene chloride (2.0 mL) was added with a 4 M solution of hydrogen chloride in 1,4-dioxane (2.0 mL), and then the mixture was stirred at room temperature for 2 hours. The mixture was azeotroped twice with toluene under reduced pressure, and then the residual solid was suspended in a mixed solvent of methylene chloride and diethyl ether and thereby washed to obtain (Z)-2-[(5-bromo-1H-pyrrolo[2,3-b]pyridin-3-yl)methylene]-6-hydroxy-7-(piperazin-1-ylmethyl)benzofuran-3(2H)-one trihydrochloride (0.014 g, 78%).

$^1$H NMR (300 MHz, DMSO-$d_6$) δ 3.00-3.75 (m, 8H), 4.54 (br s, 2H), 6.99 (d, J=8.1 Hz, 1H), 7.34 (s, 1H), 7.75 (d, J=8.1 Hz, 1H), 8.41 (s, 1H), 8.85 (s, 1H), 8.85 (s, 1H), 12.77 (br s, 1H).

Example A53

(Z)-2-[(1H-Pyrrolo[2,3-b]pyridin-3-yl)methylene]-6-methoxy-7-(piperazin-1-ylmethyl)benzofuran-3(2H)-one (a) Step 1

A solution of tert-butyl 4-[(6-methoxy-3-oxo-2,3-dihydrobenzofuran-7-yl)methyl]piperazine-1-carboxylate (0.107 g, 0.295 mmol) synthesized in Example A40, Step 1 in methanol (1.2 mL) was added with 7-aza-1H-indole-3-carboxaldehyde (0.0517 g, 0.354 mmol) and piperidine (0.00251 g, 0.0295 mmol), and the mixture was stirred at 60° C. for 2 hours. The reaction mixture was cooled to room temperature, and then the precipitated solid was collected by filtration to obtain the objective tert-butyl (Z)-4-({2-[(1H-pyrrolo[2,3-b]pyridin-3-yl)methylene]-6-methoxy-3-oxo-2,3-dihydrobenzofuran-7-yl}methyl)piperazine-1-carboxylate (0.0654 g, 45%).

$^1$H NMR (300 MHz, DMSO-$d_6$) δ 1.36 (s, 9H), 2.46 (m, 4H), 3.30 (m, 4H), 3.76 (s, 2H), 3.96 (s, 3H), 7.03 (d, J=8.8 Hz, 1H), 7.23 (dd, J=4.4 Hz, 8.1 Hz, 1H), 7.24 (s, 1H), 7.74 (d, J=8.8 Hz, 1H), 8.27 (s, 1H), 8.35 (dd, J=1.5 Hz, 4.4 Hz, 1H), 8.67 (dd, J=1.5 Hz, 8.1 Hz, 1H), 12.55 (br s, 1H).

(b) Step 2

A solution of tert-butyl (Z)-4-({2-[(1H-pyrrolo[2,3-b]pyridin-3-yl)methylene]-6-methoxy-3-oxo-2,3-dihydrobenzofuran-7-yl}methyl)piperazine-1-carboxylate (0.0645 g, 0.131 mmol) in methylene chloride (1 mL) was added with trifluoroacetic acid (1 mL), and the mixture was stirred overnight at room temperature. The reaction mixture was concentrated, and then added with saturated aqueous sodium hydrogencarbonate (6 mL), and the mixture was extracted five times with ethyl acetate. The organic layer was dried over anhydrous sodium sulfate, and then the solvent was evaporated to obtain the objective (Z)-2-[(1H-pyrrolo[2,3-b]pyridin-3-yl)methylene]-6-methoxy-7-(piperazin-1-ylmethyl)benzofuran-3(2H)-one (0.0500 g, 97%).

$^1$H NMR (300 MHz, DMSO-$d_6$) δ 2.70 (m, 4H), 3.08 (m, 4H), 3.85 (s, 2H), 3.96 (s, 2H), 7.05 (d, J=8.8 Hz, 1H), 7.25 (dd, J=4.4 Hz, 8.0 Hz, 1H), 7.26 (s, 1H), 7.77 (d, J=8.8 Hz, 1H), 8.28 (d, J=2.9 Hz, 1H), 8.36 (dd, J=1.5 Hz, 4.4 Hz, 1H), 8.67 (d, J=8.0 Hz, 1H), 12.59 (br s, 1H).

Example A54

(Z)-2-[(1H-Pyrrolo[2,3-b]pyridin-3-yl)methylene]-6-methoxy-7-(morpholinomethyl)benzofuran-3(2H)-one A solution of 6-methoxy-7-(morpholinomethyl)benzofuran-3(2H)-one (0.131 g, 0.500 mmol) obtained in Example A41, Step 2 in methanol (1.2 mL) was added with 7-aza-1H-indazole-3-carboxaldehyde (0.0545 g, 0.373 mmol) and piperidine (0.00265 g, 0.0311 mmol), and the mixture was stirred at 60° C. for 2 hours. The reaction mixture was cooled to room temperature, and then added with methanol (2 mL), and the precipitated solid was suspended in methanol and thereby washed to obtain the objective (Z)-2-[(1H-pyrrolo[2,3-b]pyridin-3-yl)methylene]-6-methoxy-7-(morpholinomethyl)benzofuran-3(2H)-one (0.0264 g, 21%).

$^1$H NMR (300 MHz, DMSO-$d_6$) δ 2.50 (m, 4H), 3.56 (m, 4H), 3.74 (s, 2H), 3.95 (s, 3H), 7.02 (d, J=8.1 Hz, 1H), 7.21 (m, 1H), 7.24 (s, 1H), 7.74 (d, J=8.1 Hz, 1H), 8.28 (s, 1H), 8.34 (d, J=5.1 Hz, 1H), 8.67 (d, J=8.1 Hz, 1H), 12.56 (br s, 1H).

Example A55

(Z)-7-[(1,4-Diazepan-1-yl)methyl]-2-[(1H-indol-3-yl)methylene]-6-hydroxybenzofuran-3(2H)-one (a) Step 1

A solution of 6-hydroxybenzofuran-3(2H)-one (0.150 g, 1.00 mmol) in ethanol (1 mL) was added with tert-butyl 1,4-diazepane-1-carboxylate (0.200 g, 1.00 mmol) and paraformaldehyde (0.0300 g, 1.00 mmol) at room temperature, and the mixture was refluxed for 3 hours by heating. The reaction mixture was concentrated, and the resulting residue was purified by silica gel column chromatography (hexane/ethyl acetate) to obtain tert-butyl 4-[(6-hydroxy-3-oxo-2,3-dihydrobenzofuran-7-yl)methyl]-1,4-diazepane-1-carboxylate (0.0583 g, 16%).

$^1$H NMR (300 MHz, CD$_3$OD) δ 1.47 (s, 9H), 1.92 (quin, J=5.9 Hz, 2H), 2.91-2.94 (m, 2H), 2.96-2.99 (m, 2H), 3.47-3.52 (m, 2H), 3.58 (t, J=5.1 Hz, 2H), 4.65 (s, 2H), 4.92 (s, 2H), 6.49 (d, J=8.8 Hz, 1H), 7.42 (d, J=8.8 Hz, 1H).

(b) Step 2

A solution of tert-butyl 4-[(6-hydroxy-3-oxo-2,3-dihydrobenzofuran-7-yl)methyl]-1,4-diazepane-1-carboxylate (0.142 g, 0.392 mmol) in methanol (2 mL) was added with 1H-indole-3-carboxaldehyde (0.0569 g, 0.392 mmol) and piperidine (0.00334 g, 0.0392 mmol), and the mixture was stirred at 60° C. for 2 hours. The reaction mixture was concentrated, and the resulting residue was subjected to silica gel column chromatography (chloroform/methanol). The resulting solid crude product was washed with a mixed solvent of hexane and ethyl acetate to obtain tert-butyl (Z)-4-({2-[(1H-indol-3-yl)methylene]-6-hydroxy-3-oxo-2,3-dihydrobenzofuran-7-yl}methyl)-1,4-diazepane-1-carboxylate (0.141 g, 73%).

$^1$H NMR (300 MHz, CDCl$_3$) δ 1.48 (s, 9H), 1.95 (m, 2H), 2.82-2.89 (m, 4H), 3.51-3.63 (m, 4H), 4.08 (d, J=12.9 Hz, 2H), 6.66 (d, J=6.6 Hz, 1H), 7.23-7.30 (m, 2H), 7.45 (d, J=5.7 Hz, 1H), 7.63 (d, J=6.3 Hz, 1H), 7.89 (d, J=6.0 Hz, 1H), 7.98 (d, J=8.1 Hz, 1H), 9.11 (d, J=5.1 Hz, 1H).

(c) Step 3

A solution of tert-butyl (Z)-4-({2-[(1H-indol-3-yl)methylene]-6-hydroxy-3-oxo-2,3-dihydrobenzofuran-7-yl}methyl)-1,4-diazepane-1-carboxylate (0.141 g, 0.288 mmol) in methylene chloride (1.5 mL) was added with a 4 M solution of hydrogen chloride in 1,4-dioxane (1.5 mL) at room temperature, and the mixture was stirred for 2 hours. The reaction mixture was concentrated, the resulting residue was added with saturated aqueous sodium hydrogencarbonate, and the mixture was extracted with chloroform. The organic layer was washed with saturated brine, and dried over anhydrous sodium sulfate. The solvent was evaporated, and the resulting solid was washed with methylene chloride to obtain (Z)-7-[(1,4-diazepan-1-yl)methyl]-2-[(1H-indol-3-yl)methylene]-6-hydroxybenzofuran-3(2H)-one (0.0843 g, 75%).

$^1$H NMR (300 MHz, DMSO-$d_6$) δ 1.78 (m, 2H), 2.88-2.94 (m, 8H), 4.11 (s, 2H), 6.46 (d, J=6.3 Hz, 1H), 7.04 (s, 1H), 7.15-7.24 (m, 2H), 7.41 (d, J=6.3 Hz, 1H), 7.49 (d, J=5.7 Hz, 1H), 8.03 (d, J=5.7 Hz, 1H), 8.10 (s, 1H).

Example A56

(Z)-2-[(1H-indol-3-yl)methylene]-7-(piperazin-1-ylmethyl)benzofuran-3(2H)-one (a) Step 1

A solution of 2-chloro-1-(2-hydroxy-3-methylphenyl)ethanone (Tetrahedron, Vol. 66, p. 3499, 2010, 6.40 g, 34.7 mmol) in acetonitrile (170 mL) was added with potassium carbonate (14.4 g, 104 mmol), and the mixture was stirred at room temperature for 1 hour, and then filtered. The filtrate was concentrated, and the resulting residue was purified by silica gel column chromatography (hexane/ethyl acetate) to obtain 7-methylbenzofuran-3(2H)-one (2.23 g, 43%).

$^1$H NMR (300 MHz, CDCl$_3$) δ 2.33 (s, 3H), 4.64 (s, 2H), 7.00 (m, 1H), 7.42 (d, J=7.3 Hz, 1H), 7.51 (d, J=8.0 Hz, 1H).

(b) Step 2

A solution of 7-methylbenzofuran-3(2H)-one (0.759 g, 5.12 mol) in carbon tetrachloride (50 mL) was added with N-bromosuccinimide (1.00 g, 5.63 mmol) and benzoyl peroxide (0.0830 g, 0.256 mmol), and the mixture was refluxed for 4 hours by heating. The reaction mixture was cooled to room temperature, and then filtered, and the resulting filtrate was concentrated. The residue was purified by silica gel column chromatography (hexane/ethyl acetate) to obtain 7-bromomethylbenzofuran-3(2H)-one (0.573 g, 49%).

$^1$H NMR (300 MHz, CDCl$_3$) δ 4.58 (s, 2H), 4.73 (s, 2H), 7.10 (t, J=7.3 Hz, 1H), 7.59 (m, 2H).

(c) Step 3

A solution of 7-bromomethylbenzofuran-3(2H)-one (0.573 g, 2.52 mmol) in methylene chloride (20 mL) was added with sodium acetate (0.412 g, 5.03 mmol) and 1-tert-butoxycarbonylpiperazine (0.721 g, 3.87 mmol), and the mixture was stirred at room temperature for 6 hours. The organic layer was washed with water and saturated brine, and then dried over anhydrous magnesium sulfate, and then the solvent was evaporated under reduced pressure. The resulting residue was purified by silica gel column chromatography (hexane/ethyl acetate) to obtain tert-butyl 4-[(3-oxo-2,3-dihydrobenzofuran-7-yl)methyl]piperazine-1-carboxylate (0.391 g, 46%).

$^1$H NMR (300 MHz, CDCl$_3$) δ 1.45 (s, 9H), 2.48 (m, 4H), 3.46 (m, 4H), 3.65 (s, 2H), 4.65 (s, 2H), 7.09 (t, J=7.3 Hz, 1H), 7.61 (d, J=7.3 Hz, 1H), 7.65 (d, J=7.3 Hz, 1H).

(d) Step 4

A solution of tert-butyl 4-[(3-oxo-2,3-dihydrobenzofuran-7-yl)methyl]piperazine-1-carboxylate (0.0251 g, 0.0755 mmol) in methanol (2 mL) was added with 1H-indole-3-carboxaldehyde (0.0115 g, 0.0793 mmol) and piperidine (5 drops), and the mixture was stirred at 50° C. for 2 hours. The reaction mixture was concentrated, and the resulting residue was purified by silica gel column chromatography (chloroform/methanol) to obtain tert-butyl (Z)-4-({2-[(1H-indol-3-yl)methylene]-3-oxo-2,3-dihydrobenzofuran-7-yl}methyl)piperazine-1-carboxylate (0.0305 g, 88%).

$^1$H NMR (300 MHz, CDCl$_3$) δ 1.44 (s, 9H), 2.59 (m, 4H), 3.47 (m, 4H), 3.89 (s, 2H), 7.20-7.31 (m, 3H), 7.48 (s, 1H), 7.46-7.51 (m, 1H), 7.73 (d, J=8.1 Hz, 2H), 7.99-8.06 (m, 1H), 8.23 (s, 1H).

(e) Step 5

A solution of tert-butyl (Z)-4-({2-[(1H-indol-3-yl)methylene]-3-oxo-2,3-dihydrobenzofuran-7-yl}methyl)piperazine-1-carboxylate (0.0305 g, 0.0664 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated to obtain (Z)-2-[(1H-indol-3-yl)methylene-7-(piperazin-1-ylmethyl)benzofuran-3(2H)-one (0.0220 g, 95%).

$^1$H NMR (300 MHz, DMSO-d$_6$) δ 2.48 (m, 4H), 2.76 (m, 4H), 3.79 (s, 2H), 7.15-7.32 (m, 3H), 7.38 (s, 1H), 7.52 (d, J=8.1 Hz, 1H), 7.69 (d, J=8.1 Hz, 2H), 8.19 (d, J=7.3 Hz, 1H), 8.26 (s, 1H), 12.16 (br s, 1H).

Example A57

(Z)-6-Methoxy-7-(piperazin-1-ylmethyl)-2-[(1-tosyl-1H-indol-3-yl)methylene]benzofuran-3(2H)-one (a) Step 1

A solution of tert-butyl 4-[(6-methoxy-3-oxo-2,3-dihydrobenzofuran-7-yl)methyl]piperazine-1-carboxylate (0.488 g, 1.35 mmol) obtained in Example A40, Step 1 in methanol (5 mL) was added with 1-tosyl-1H-indole-3-carboxaldehyde (0.404 g, 1.35 mmol) obtained in Example A33, Step 1 and piperidine (0.0115 g, 0.135 mmol), and the mixture was stirred at 60° C. for 2 hours. The reaction mixture was cooled to room temperature, and then added with methanol (2 mL), and the precipitated solid was suspended in methanol and thereby washed. The reaction mixture was filtered to obtain tert-butyl (Z)-4-({6-methoxy-3-oxo-2-[(1-tosyl-1H-indol-3-yl)methylene]-2,3-dihydrobenzofuran-7-yl}methyl)piperazine-1-carboxylate (0.485 g, 55%).

$^1$H NMR (300 MHz, CDCl$_3$) δ 1.43 (s, 9H), 2.34 (s, 3H), 2.64 (t, J=4.4 Hz, 4H), 3.48 (t, J=4.4 Hz, 4H), 3.86 (s, 2H), 3.98 (s, 3H), 6.82 (d, J=8.0 Hz, 1H), 7.06 (s, 1H), 7.28-7.41 (m, 4H), 7.75-7.82 (m, 4H), 7.99 (d, J=8.0 Hz, 1H), 8.42 (s, 1H).

(b) Step 2

A solution of tert-butyl (Z)-4-({6-methoxy-3-oxo-2-[(1-tosyl-1H-indol-3-yl)methylene]-2,3-dihydrobenzofuran-7-yl}methyl)piperazine-1-carboxylate (0.0400 g, 0.0621 mmol) in methylene chloride (2 mL) was added with a 4 N solution of hydrogen chloride in 1,4-dioxane (2 mL), and the mixture was stirred at room temperature for 11 hours. The reaction mixture was concentrated, the resulting residue was added with saturated aqueous sodium hydrogencarbonate, and the mixture was extracted three times with ethyl acetate. The organic layer was washed with saturated brine, and dried over anhydrous magnesium sulfate, and then the solvent was evaporated to obtain (Z)-6-methoxy-7-(piperazin-1-ylmethyl)-2-[(1-tosyl-1H-indol-3-yl)methylene]benzofuran-3(2H)-one (0.0121 g, 35%).

$^1$H NMR (300 MHz, CDCl$_3$) δ 2.34 (s, 3H), 2.86 (m, 4H), 3.15 (m, 4H), 3.87 (s, 2H), 3.97 (s, 3H), 6.81 (d, J=8.8 Hz, 1H), 7.07 (s, 1H), 7.27-7.37 (m, 4H), 7.76-7.78 (m, 4H), 7.93 (d, J=8.8 Hz, 1H), 8.40 (s, 1H).

Example A58

(Z)-2-[(1H-Pyrrolo[2,3-b]pyridin-3-yl)methylene]-7-(piperazin-1-ylmethyl)benzofuran-3(2H)-one (a) Step 1

A solution of tert-butyl 4-[(3-oxo-2,3-dihydrobenzofuran-7-yl)methyl]piperazine-1-carboxylate (0.0251 g, 0.0755 mmol) obtained in Example A56, Step 3 in methanol (2 mL) was added with 7-azaindole-3-carboxaldehyde (0.0116 g, 0.0793 mmol) and piperidine (5 drops), and the mixture was stirred at 50° C. for 2 hours. The reaction mixture was concentrated, and the resulting residue was purified by silica gel column chromatography (chloroform/methanol) to obtain tert-butyl (Z)-4-({2-[(1H-pyrrolo[2,3-b]pyridin-3-yl)methylene]-3-oxo-2,3-dihydrobenzofuran-7-yl}methyl)piperazine-1-carboxylate (0.0269 g, 77%).

$^1$H NMR (300 MHz, CD$_3$OD) δ 1.43 (s, 9H), 2.56 (t, J=4.4 Hz, 4H), 3.46 (t, J=4.4 Hz, 4H), 3.86 (s, 2H), 7.23-7.29 (m, 2H), 7.34 (s, 1H), 7.69-7.72 (m, 2H), 8.25 (s, 1H), 8.37 (dd, J=1.4 Hz, 5.1 Hz, 1H), 8.55 (dd, J=1.4 Hz, 8.1 Hz, 1H).

(b) Step 2

A solution of tert-butyl (Z)-4-({2-[(1H-pyrrolo[2,3-b]pyridin-3-yl)methylene]-3-oxo-2,3-dihydrobenzofuran-7-yl}methyl)piperazine-1-carboxylate (0.0269 g, 0.0584 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted three times with ethyl acetate. The organic layer was washed with saturated brine, and dried over anhydrous sodium sulfate, and then the solvent was evaporated to obtain (Z)-2-[(1H-pyrrolo[2,3-b]pyridin-3-yl)methylene]-7-(piperazin-1-ylmethyl)benzofuran-3(2H)-one (0.0202 g, 96%).

$^1$H NMR (300 MHz, DMSO-d$_6$) δ 2.46 (m, 4H), 2.74 (m, 4H), 3.77 (s, 2H), 7.23-7.30 (m, 2H), 7.38 (s, 1H), 7.68-7.71 (m, 2H), 8.33 (s, 1H), 8.37 (d, J=4.4 Hz, 1H), 8.71 (d, J=8.1 Hz, 1H).

Example A59

(Z)-2-[(1H-Indol-3-yl)methylene]-6-ethoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.697 g, 2.00 mmol), ethanol (0.140 mL, 2.40 mmol) and triphenylphosphine (0.787 g, 3.00 mmol) in toluene (8 mL) was added with a 40% solution of diethyl azodicarboxylate in toluene (1.31 g, 3.00 mmol), and the mixture was stirred at 110° C. for 5 hours in a sealed tube. The reaction mixture was concentrated, and the resulting residue was subjected to silica gel column chromatography (chloroform/ethyl acetate) to obtain tert-butyl 4-[(6-ethoxy-3-oxo-2,3-dihydrobenzofuran-7-yl)methyl]piperazine-1-carboxylate (0.138 g, 18%).

$^1$H NMR (300 MHz, CDCl$_3$) δ 1.44 (s, 9H), 1.45 (t, J=7.3 Hz, 3H), 2.49 (m, 4H), 3.41 (m, 4H), 3.72 (s, 2H), 4.15 (q, J=7.3 Hz, 2H), 4.64 (s, 2H), 6.67 (d, J=8.8 Hz, 1H), 7.59 (d, J=8.8 Hz, 1H).

(b) Step 2

A solution of tert-butyl 4-[(6-ethoxy-3-oxo-2,3-dihydrobenzofuran-7-yl)methyl]piperazine-1-carboxylate (0.138 g, 0.367 mmol) in methanol (1.5 mL) was added with indole-3-carboxaldehyde (0.0553 g, 0.367 mmol) and piperidine (0.0250 g, 0.294 mmol), and the mixture was stirred at 60° C. for 2 hours. The reaction mixture was cooled to room temperature, and then the precipitated solid was collected by filtration to obtain tert-butyl (Z)-4-({2-[(1H-indol-3-yl)methylene]-6-ethoxy-3-oxo-2,3-dihydrobenzofuran-7-yl}methyl)piperazine-1-carboxylate (0.137 g, 74%).

$^1$H NMR (300 MHz, DMSO-d$_6$) δ 1.36 (s, 9H), 1.39 (t, J=6.6 Hz, 3H), 2.47 (m, 4H), 3.31 (m, 4H), 3.80 (s, 2H), 4.21 (q, J=6.6 Hz, 2H), 6.98 (d, J=8.8 Hz, 1H), 7.17 (t, J=7.3 Hz, 1H), 7.22-7.26 (m, 2H), 7.50 (d, J=8.1 Hz, 1H), 7.70 (d, J=8.8 Hz, 1H), 8.13 (d, J=8.1 Hz, 1H), 8.19 (s, 1H), 12.04 (br s, 1H).

(c) Step 3

A solution of tert-butyl (Z)-4-({2-[(1H-indol-3-yl)methylene]-6-ethoxy-3-oxo-2,3-dihydrobenzofuran-7-yl}methyl)piperazine-1-carboxylate (0.106 g, 0.210 mmol) in methylene chloride (4 mL) was added with a 4 M solution of hydrogen chloride in 1,4-dioxane (4 mL), and the mixture was stirred at room temperature for 2 hours. The reaction mixture was concentrated, the resulting residue was added with saturated aqueous sodium hydrogencarbonate (4 mL), and the precipitated solid was collected by filtration. The resulting solid was washed with water, and then dried under reduced pressure to obtain (Z)-2-[(1H-indol-3-yl)methylene]-6-ethoxy-7-(piperazin-1-ylmethyl)benzofuran-3(2H)-one (0.0653 g, 77%).

$^1$H NMR (300 MHz, DMSO-d$_6$) δ 1.38 (t, J=7.3 Hz, 3H), 2.46 (m, 4H), 2.67 (m, 4H), 3.73 (s, 2H), 4.20 (q, J=7.3 Hz, 2H), 6.97 (d, J=8.8 Hz, 1H), 7.14-7.26 (m, 3H), 7.50 (d, J=8.1 Hz, 1H), 7.68 (d, J=8.8 Hz, 1H), 8.14 (d, J=8.1 Hz, 1H), 8.19 (s, 1H), 12.06 (br s, 1H).

Example A60

(Z)-2-((1H-Indol-3-yl)methylene)-7-(piperazin-1-ylmethyl)-6-propoxybenzofuran-3(2H)-one (a) Step 1

A solution of tert-butyl 4-[(6-hydroxy-3-oxo-2,3-dihydrobenzofuran-7-yl)methyl]piperazine-1-carboxylate (0.522 g, 1.50 mmol), n-propanol (0.135 mL, 1.80 mmol) and triphenylphosphine (0.590 g, 2.25 mmol) in toluene (6 mL) was added with a 40% solution of diethyl azodicarboxylate in toluene (0.980 g, 2.25 mmol), and the mixture was stirred at 110° C. for 5 hours in a sealed tube. The reaction mixture was concentrated, and the resulting residue was subjected to silica gel column chromatography (chloroform/ethyl acetate) to obtain tert-butyl 4-[(3-oxo-6-propoxy-2,3-dihydrobenzofuran-7-yl)methyl]piperazine-1-carboxylate (0.205 g, 35%).

$^1$H NMR (300 MHz, CDCl$_3$) δ 1.07 (t, J=7.3 Hz, 3H), 1.44 (s, 9H), 1.85 (m, 2H), 2.48 (m, 4H), 3.41 (t, J=5.1 Hz, 4H), 3.71 (s, 2H), 4.04 (t, J=6.6 Hz, 2H), 4.64 (s, 2H), 6.67 (d, J=8.8 Hz, 1H), 7.59 (d, J=8.8 Hz, 1H).

(b) Step 2

A solution of tert-butyl 4-[(3-oxo-6-propoxy-2,3-dihydrobenzofuran-7-yl)methyl]piperazine-1-carboxylate (0.163 g, 0.417 mmol) in methanol (1.6 mL) was added with indole-3-carboxaldehyde (0.0605 g, 0.417 mmol) and piperidine (0.0284 g, 0.334 mmol), and the mixture was stirred at 60° C. for 2 hours. The reaction mixture was cooled to room temperature, and then the precipitated yellow solid was collected by filtration (0.147 g). The filtrate was concentrated, and the resulting residue was purified by silica gel column chromatography (chloroform/methanol) to further obtain a yellow solid (0.0190 g). This yellow solid was combined with the yellow solid obtained above (0.147 g) to obtain 0.166 g (77%) of tert-butyl (Z)-4-({2-[(1H-indol-3-yl)methylene]-3-oxo-6-propoxy-2,3-dihydrobenzofuran-7-yl}methyl)piperazine-1-carboxylate.

$^1$H NMR (300 MHz, DMSO-d$_6$) δ 1.04 (t, J=7.3 Hz, 3H), 1.36 (s, 9H), 1.80 (m, 2H), 2.51 (m, 4H), 3.29 (m, 4H), 3.78 (s, 2H), 4.12 (q, J=5.9 Hz, 2H), 6.98 (d, J=8.8 Hz, 1H), 7.17 (t, J=7.3 Hz, 1H), 7.20-7.27 (m, 2H), 7.50 (d, J=7.3 Hz, 1H), 7.69 (d, J=8.8 Hz, 1H), 8.13 (d, J=8.1 Hz, 1H), 8.19 (d, J=2.9 Hz, 1H), 12.03 (br d, J=2.9 Hz, 1H).

(c) Step 3

A solution of tert-butyl (Z)-4-({2-[(1H-indol-3-yl)methylene]-3-oxo-6-propoxy-2,3-dihydrobenzofuran-7-yl}methyl)piperazine-1-carboxylate (0.0705 g, 0.136 mmol) in methylene chloride (7 mL) was added with a 4 M solution of hydrogen chloride in 1,4-dioxane (7 mL), and the mixture was stirred at room temperature for 2 hours. The reaction mixture was concentrated, the resulting residue was added with saturated aqueous sodium hydrogencarbonate (14 mL), and the precipitated solid was collected by filtration. The resulting solid was washed with water, and then further washed with acetonitrile to obtain (Z)-2-[(1H-indol-3-yl)methylene]-7-(piperazin-1-ylmethyl)-6-propoxybenzofuran-3(2H)-one (0.0306 g, 53%).

$^1$H NMR (300 MHz, DMSO-d$_6$) δ 1.05 (t, J=7.3 Hz, 3H), 1.79 (m, 2H), 2.46 (m, 4H), 2.66 (m, 4H), 3.72 (s, 2H), 4.11 (t, J=5.9 Hz, 2H), 6.97 (d, J=8.8 Hz, 1H), 7.17 (t, J=7.3 Hz, 1H), 7.21-7.26 (m, 2H), 7.50 (d, J=8.1 Hz, 1H), 7.68 (d, J=8.8 Hz, 1H), 8.15 (d, J=8.1 Hz, 1H), 8.19 (s, 1H), 12.08 (br s, 1H).

Example A61

(Z)-2-[(1H-Indol-3-yl)methylene]-6-(benzyloxy)-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.522 g, 1.50 mmol), benzyl alcohol (0.186 mL, 1.80 mmol) and triphenylphosphine (0.590 g, 2.25 mmol) in toluene (6 mL) was added with a 40% solution of diethyl azodicarboxylate in toluene (0.980 g, 2.25 mmol), and the mixture was stirred at 110° C. for 5 hours in a sealed tube. The reaction mixture was concentrated, and the resulting residue was subjected to silica gel column chromatography (chloroform/ethyl acetate) to obtain tert-butyl 4-{[6-(benzyloxy)-3-oxo-2,3-dihydrobenzofuran-7-yl]methyl}piperazine-1-carboxylate (0.259 g, 39%).

$^1$H NMR (300 MHz, CDCl$_3$) δ 1.44 (s, 9H), 2.47 (m, 4H), 3.40 (m, 4H), 3.73 (s, 2H), 4.64 (s, 2H), 5.20 (s, 2H), 6.75 (d, J=8.8 Hz, 1H), 7.35-7.45 (m, 5H), 7.60 (d, J=8.8 Hz, 1H).

(b) Step 2

A solution of tert-butyl 4-{[6-(benzyloxy)-3-oxo-2,3-dihydrobenzofuran-7-yl]methyl}piperazine-1-carboxylate (0.198 g, 0.452 mmol) in methanol (1.8 mL) was added with indole-3-carboxaldehyde (0.0656 g, 0.452 mmol) and piperidine (0.0308 g, 0.362 mmol), and the mixture was stirred at 60° C. for 2 hours. The reaction mixture was cooled to room temperature, and then the precipitated yellow solid was collected by filtration to obtain tert-butyl (Z)-4-({2-[(1H-indol-3-yl)methylene]-6-(benzyloxy)-3-oxo-2,3-dihydrobenzofuran-7-yl}methyl)piperazine-1-carboxylate (0.141 g, 55%).

$^1$H NMR (300 MHz, DMSO-d$_6$) δ 1.36 (s, 9H), 2.47 (m, 4H), 3.30 (m, 4H), 3.81 (s, 2H), 5.33 (s, 2H), 7.10 (d, J=8.8 Hz, 1H), 7.17 (t, J=7.3 Hz, 1H), 7.21-7.26 (m, 2H), 7.33-7.45 (m, 3H), 7.49-7.55 (m, 3H), 7.72 (d, J=8.8 Hz, 1H), 8.14 (d, J=8.1 Hz, 1H), 8.20 (d, J=2.9 Hz, 1H), 12.04 (br d, J=2.9 Hz, 1H).

(c) Step 3

A solution of tert-butyl (Z)-4-({2-[(1H-indol-3-yl)methylene]-6-(benzyloxy)-3-oxo-2,3-dihydrobenzofuran-7-yl}methyl)piperazine-1-carboxylate (0.123 g, 0.217 mmol) in methylene chloride (10 mL) was added with a 4 N solution of hydrogen chloride in 1,4-dioxane (10 mL), and the mixture was stirred at room temperature for 2 hours. The reaction mixture was concentrated, the resulting residue was added with saturated aqueous sodium hydrogencarbonate (20 mL), and the precipitated solid was collected by filtration. The resulting solid was washed with water, and then dried under reduced pressure to obtain (Z)-2-[(1H-indol-3-yl)methylene]-6-(benzyloxy)-7-(piperazin-1-ylmethyl)benzofuran-3(2H)-one (0.0720 g, 71%).

$^1$H NMR (300 MHz, DMSO-d$_6$) δ 2.45 (m, 4H), 2.67 (m, 4H), 3.75 (s, 2H), 5.33 (s, 2H), 7.09 (d, J=8.8 Hz, 1H), 7.18 (t, J=7.3 Hz, 1H), 7.21-7.26 (m, 2H), 7.33-7.45 (m, 3H), 7.49-7.55 (m, 3H), 7.70 (d, J=8.8 Hz, 1H), 8.15 (d, J=8.1 Hz, 1H), 8.19 (s, 1H), 12.07 (br s, 1H).

Example B1

(Z)-2-[(1H-Indazol-3-yl)methylene]-6-hydroxy-7-(piperazin-1-ylmethyl)benzofuran-3(2H)-one (a) Step 1

The synthesis was performed with reference to the known literature (Heterocycles, Vol. 53, p. 197, 2000). A solution of 6-hydroxybenzofuran-3(2H)-one (3.00 g, 20.0 mmol) in ethanol (20 mL) was added with 1-tert-butoxycarbonylpiperazine (3.73 g, 20.0 mmol), and 37% aqueous formaldehyde (1.62 g, 20.0 mmol) at room temperature. The reaction mixture was stirred overnight at room temperature, and then subjected to suction filtration, and the filtrate was concentrated. Thr crude product obtained by silica gel column chromatography (hexane/ethyl acetate) was recrystallized from ethyl acetate to obtain the objective tert-butyl 4-[(6-hydroxy-3-oxo-2,3-dihydrobenzofuran-7-yl)methyl]piperazine-1-carboxylate (3.51 g, 50%).

$^1$H NMR (300 MHz, DMSO-d$_6$) δ 1.38 (s, 9H), 2.44 (m, 4H), 3.27 (m, 4H), 3.66 (s, 2H), 4.73 (s, 2H), 6.59 (d, J=8.8 Hz, 1H), 7.40 (d, J=8.8 Hz, 1H).

(b) Step 2

The synthesis was performed with reference to the known literature (Tetrahedron, Vol. 29, p. 359, 1973). A solution of tert-butyl 4-[(6-hydroxy-3-oxo-2,3-dihydrobenzofuran-7-yl)methyl]piperazine-1-carboxylate (0.100 g, 0.287 mmol) in methanol (1.2 mL) was added with 1H-indazole-3-carboxaldehyde (0.0419 g, 0.287 mmol), and piperidine (0.00244 g, 0.0287 mmol) at room temperature, and the mixture was stirred at 60° C. for 3 hours. The solvent was evaporated, and the resulting residue was purified by silica gel column chromatography (chloroform/methanol) to obtain tert-butyl (Z)-4-({2-[(1H-indazol-3-yl)methylene]-6-hydroxy-3-oxo-2,3-dihydrobenzofuran-7-yl}methyl)piperazine-1-carboxylate (0.125 g, 91%).

$^1$H NMR (300 MHz, DMSO-d$_6$) δ 1.37 (s, 9H), 2.52 (m, 4H), 3.33 (m, 4H), 3.82 (s, 2H), 6.79 (d, J=8.0 Hz, 1H), 7.04 (s, 1H), 7.27 (m, 1H), 7.47 (m, 1H), 7.61 (d, J=8.0 Hz, 1H), 7.64 (d, J=8.0 Hz, 1H), 8.55 (d, J=8.0 Hz, 1H), 13.81 (br s, 1H).

(c) Step 3

The synthesis was performed according to the conventional method described in Protective Groups in Organic Synthesis, fourth edition, Wiley Interscience, 2007. A solution of tert-butyl (Z)-4-({2-[(1H-indazol-3-yl)methylene]-6-hydroxy-3-oxo-2,3-dihydrobenzofuran-7-yl}methyl)piperazine-1-carboxylate (0.120 g, 0.252 mmol) in methylene chloride (2 mL) was added with trifluoroacetic acid (2 mL) at room temperature, and the mixture was stirred overnight. The solvent was evaporated, the resulting residue was dissolved in methanol (8 mL), the solution was added with a 5% solution of hydrochloric acid in methanol (2 mL), and the mixture was stirred at room temperature for 2 hours. The precipitated solid was collected by filtration to obtain a hydrochloride (0.0550 g) as a yellow solid. The hydrochloride obtained above was suspended in saturated aqueous sodium hydrogencarbonate, and the suspension was extracted four times with ethyl acetate. The organic layer was dried over anhydrous sodium sulfate, and then the solvent was evaporated to obtain (Z)-2-[(1H-indazol-3-yl)methylene]-6-hydroxy-7-(piperazin-1-ylmethyl)benzofuran-3(2H)-one (0.0265 g, 27%).

$^1$H NMR (300 MHz, DMSO-d$_6$) δ 2.61 (m, 4H), 2.87 (m, 4H), 3.76 (s, 2H), 6.39 (d, J=8.8 Hz, 1H), 6.85 (s, 1H), 7.24 (t, J=7.3 Hz, 1H), 7.39 (d, J=8.1 Hz, 1H), 7.45 (m, 1H), 7.61 (d, J=8.8 Hz, 1H), 8.55 (d, J=8.0 Hz, 1H).

Example B2

(Z)-2-[(1H-Indazol-3-yl)methylene]-7-[cis-3,5-dimethylpiperazin-1-yl)methyl]-6-hydroxybenzofuran-3(2H)-one (a) Step 1

A solution of 6-hydroxybenzofuran-3(2H)-one (0.300 g, 2.00 mmol) in ethanol (2 mL) was added with cis-3,5-dimethylpiperazine (0.288 g, 2.00 mmol), and 37% aqueous formaldehyde (0.162 g, 2.00 mmol) at room temperature. The reaction mixture was stirred overnight at room temperature, and then concentrated. The resulting solid was dissolved in ethyl acetate, and the precipitated solid was removed by filtration. The filtrate was concentrated, and the resulting residue was purified by silica gel column chromatography (hexane/ethyl acetate) to obtain 7-[(cis-3,5-dimethylpiperazin-1-yl)methyl]-6-hydroxybenzofuran-3(2H)-one (0.173 g, 31%).

$^1$H NMR (300 MHz, DMSO-$d_6$) δ 0.942 (d, J=5.9 Hz, 6H), 1.74 (t, J=11.0 Hz, 2H), 2.72-2.81 (m, 4H), 3.72 (s, 2H), 4.70 (s, 2H), 6.48 (d, J=8.8 Hz, 1H), 7.36 (d, J=8.8 Hz, 1H).

(b) Step 2

A solution of 7-[(cis-3,5-dimethylpiperazin-1-yl)methyl]-6-hydroxybenzofuran-3(2H)-one (0.166 g, 0.601 mmol) in methanol (2.4 mL) was added with 1H-indazole-3-carbaldehyde (0.0878 g, 0.601 mmol), and piperidine (0.00512 g, 0.0601 mmol) at room temperature, and the mixture was stirred at 60° C. for 2 hours. The reaction mixture was cooled to room temperature, then added with methanol (8 mL), suspended in methanol, and thereby washed to obtain (Z)-2-[(1H-indazol-3-yl)methylene]-7-[(cis-3,5-dimethylpiperazin-1-yl)methyl]-6-hydroxybenzofuran-3(2H)-one (0.197 g, 81%).

$^1$H NMR (300 MHz, DMSO-$d_6$) δ 0.99 (d, J=6.6 Hz, 6H), 1.91 (t, J=11.0 Hz, 2H), 2.89-2.96 (m, 4H), 3.81 (s, 2H), 6.48 (d, J=8.8 Hz, 1H), 6.90 (s, 1H), 7.24 (m, 1H), 7.42-7.48 (m, 2H), 7.62 (d, J=8.8 Hz, 1H), 8.53 (d, J=8.1 Hz, 1H).

Example B3

(Z)-2-[(1H-Indazol-3-yl)methylene]-6-hydroxy-7-{[2-(S)-methylpiperazin-1-yl]methyl}benzofuran-3(2H)-one (a) Step 1

A solution of 6-hydroxybenzofuran-3(2H)-one (1.50 g, 10.0 mmol) in ethanol (10 mL) was added with 1-tert-butoxycarbonyl-3-(S)-methylpiperazine (2.00 g, 10.0 mmol), and 37% aqueous formaldehyde (0.812 g, 10.0 mmol) at room temperature. The reaction mixture was stirred at 80° C. for 8 hours, and then concentrated. The resulting residue was subjected to silica gel column chromatography (hexane/ethyl acetate) to obtain a crude product (0.602 g).

A solution of the above crude product in methanol (4 mL) was added with 1H-indazole-3-carbaldehyde (0.162 g, 1.11 mmol), and piperidine (0.00945 g, 0.0111 mmol) at room temperature, and the mixture was stirred at 60° C. for 2 hours. The reaction mixture was concentrated, and the residue was purified by silica gel column chromatography (chloroform/methanol) to obtain tert-butyl (Z)-4-({2-[(1H-indazol-3-yl)methylene]-6-hydroxy-3-oxo-2,3-dihydrobenzofuran-7-yl}methyl)-3-(S)-methylpiperazine-1-carboxylate (0.329 g, 6%).

$^1$H NMR (300 MHz, DMSO-$d_6$) δ 1.17 (d, J=6.6 Hz, 3H), 1.38 (s, 9H), 2.34 (m, 1H), 2.70-2.80 (m, 2H), 3.01-3.23 (m, 2H), 3.40-3.55 (m, 2H), 3.74 (d, J=13.2 Hz, 1H), 4.19 (d, J=13.2 Hz, 1H), 6.74 (d, J=8.8 Hz, 1H), 7.06 (s, 1H), 7.28 (m, 1H), 7.46 (m, 1H), 7.60 (d, J=8.8 Hz, 1H), 7.64 (d, J=8.8 Hz, 1H), 8.47 (d, J=8.1 Hz, 1H), 13.82 (br s, 1H).

(b) Step 2

A solution of tert-butyl (Z)-4-({2-[(1H-indazol-3-yl)methylene]-6-hydroxy-3-oxo-2,3-dihydrobenzofuran-7-yl}methyl)-3-(S)-methylpiperazine-1-carboxylate (0.329 g, 0.672 mmol) in methylene chloride (8 mL) was added with trifluoroacetic acid (8 mL) at room temperature, and the mixture was stirred overnight. The reaction mixture was concentrated, then the residue was added with methanol (20 mL) and a 5% solution of hydrogen chloride in methanol (5 mL), and the mixture was stirred at room temperature for 2 hours. The solvent was evaporated, and then the residue was suspended in acetonitrile and thereby washed to obtain orange solid. This solid was dissolved in saturated aqueous sodium hydrogencarbonate, and the solution was extracted three times with ethyl acetate. The organic layer was washed with saturated brine, and then dried over anhydrous magnesium sulfate to obtain the objective (Z)-2-[(1H-indazol-3-yl)methylene]-6-hydroxy-7-{[2-(S)-methylpiperazin-1-yl]methyl}benzofuran-3(2H)-one (0.0460 g, 17%).

$^1$H NMR (300 MHz, DMSO-$d_6$) δ 1.22 (d, J=6.6 Hz, 3H), 2.41-2.59 (m, 2H), 2.69-2.76 (m, 2H), 2.85-2.97 (m, 3H), 3.75 (d, J=13.2 Hz, 1H), 4.24 (d, J=13.2 Hz, 1H), 6.49 (d, J=8.8 Hz, 1H), 6.95 (s, 1H), 7.28 (m, 1H), 7.24-7.46 (m, 2H), 7.62 (d, J=8.8 Hz, 1H), 8.43 (d, J=8.1 Hz, 1H).

Example B4

(Z)-2-[(1H-Indazol-3-yl)methylene]-6-hydroxy-7-[(4-methylpiperazin-1-yl)methyl]benzofuran-3(2H)-one (a) Step 1

A solution of 6-hydroxybenzofuran-3(2H)-one (2.00 g, 13.3 mmol) in ethanol (25 mL) was added with N-methylpiperazine (1.33 g, 13.3 mmol), and 37% aqueous formaldehyde (1.08 g, 13.3 mmol) at room temperature. The mixture was stirred overnight at room temperature, and then subjected to suction filtration, and the filtrate was concentrated. The residue was purified by silica gel column chromatography (chloroform/methanol) to obtain 6-hydroxy-7-[(4-methylpiperazin-1-yl)methyl]benzofuran-3(2H)-one (1.87 g, 54%).

$^1$H NMR (300 MHz, DMSO-$d_6$) δ 2.16 (s, 3H), 2.35 (m, 4H), 2.55 (m, 4H), 3.74 (s, 2H), 4.72 (s, 2H), 6.52 (d, J=8.8 Hz, 1H), 7.38 (d, J=8.8 Hz, 1H).

(b) Step 2

A solution of 6-hydroxy-7-[(4-methylpiperazin-1-yl)methyl]benzofuran-3(2H)-one (0.131 g, 0.500 mmol) in methanol (2 mL) was added with 1H-indazole-3-carbaldehyde (0.0731 g, 0.500 mmol), and piperidine (0.00426 g, 0.0500 mmol) at room temperature, and the mixture was stirred at 60° C. for 2 hours. The reaction mixture was cooled to room temperature, then added with methanol (2 mL), and suspended in methanol and thereby washed to obtain (Z)-2-[(1H-indazol-3-yl)methylene]-6-hydroxy-7-[(4-methylpiperazin-1-yl)methyl]benzofuran-3(2H)-one (0.0731 g, 37%).

$^1$H NMR (300 MHz, DMSO-$d_6$) δ 2.17 (s, 3H), 2.39 (m, 4H), 2.62 (m, 4H), 3.86 (s, 2H), 6.70 (d, J=8.0 Hz, 1H), 7.02 (s, 1H), 7.27 (m, 1H), 7.47 (m, 1H), 7.58 (d, J=8.0 Hz, 1H), 7.64 (d, J=8.0 Hz, 1H), 8.52 (d, J=8.1 Hz, 1H), 13.82 (br s, 1H).

Example B5

(Z)-2-[(1H-Indazol-3-yl)methylene]-6-hydroxy-7-(morpholinomethyl)benzofuran-3(2H)-one (a) Step 1

A solution of 6-hydroxybenzofuran-3(2H)-one (1.50 g, 10.0 mmol) in ethanol (10 mL) was added with morpholine (0.871 g, 10.0 mmol), and 37% aqueous formaldehyde (0.812 g, 10.0 mmol) at room temperature. The mixture was stirred overnight at room temperature, and then the filtrate was concentrated. The resulting residue was purified by silica gel column chromatography (hexane/ethyl acetate) to obtain the objective 6-hydroxy-7-(morpholinomethyl)benzofuran-3 (2H)-one (0.987 g, 40%).

$^1$H NMR (300 MHz, DMSO-$d_6$) δ 2.57 (m, 4H), 3.60 (m, 4H), 3.68 (s, 2H), 4.73 (s, 2H), 6.58 (d, J=8.8 Hz, 1H), 7.40 (d, J=8.8 Hz, 1H).

(b) Step 2

A solution of 6-hydroxy-7-(morpholinomethyl)benzofuran-3(2H)-one (0.125 g, 0.500 mmol) in methanol (2 mL) was added with 1H-indazole-3-carbaldehyde (0.0731 g, 0.500 mmol), and piperidine (0.00426 g, 0.0500 mmol) at room temperature, and the mixture was stirred at 60° C. for 2 hours. The reaction mixture was cooled to room temperature, and then the precipitated solid was collected by filtration to obtain (Z)-2-[(1H-indazol-3-yl)methylene]-6-hydroxy-7-(morpholinomethyl)benzofuran-3(2H)-one (0.119 g, 63%).

$^1$H NMR (300 MHz, DMSO-$d_6$) δ 2.57 (m, 4H), 3.60 (m, 4H), 3.81 (s, 2H), 6.78 (d, J=8.0 Hz, 1H), 7.04 (s, 1H), 7.26 (t, J=7.3 Hz, 1H), 7.47 (m, 1H), 7.60-7.65 (m, 2H), 8.56 (d, J=8.8 Hz, 1H), 13.82 (br s, 1H).

Example B6

(Z)-4-({2-[(1H-Indazol-3-yl)methylene]-6-hydroxy-3-oxo-2,3-dihydrobenzofuran-7-yl}methyl)piperazin-2-one (a) Step 1

A solution of 6-hydroxybenzofuran-3(2H)-one (0.750 g, 5.00 mmol) in ethanol (5 mL) was added with 2-oxopiperazine (0.500 g, 5.00 mmol), and 37% aqueous formaldehyde (0.406 g, 5.00 mmol) at room temperature. The mixture was stirred overnight at room temperature, and then added with 37% aqueous formaldehyde (0.406 g, 5.00 mmol) at room temperature, and the mixture was refluxed for 4 hours by heating. The reaction mixture was cooled to room temperature, and then subjected to suction filtration to obtain 4-[(6-hydroxy-3-oxo-2,3-dihydrobenzofuran-7-yl)-methyl]piperazin-2-one (0.631 g, 48%) as a white solid.

$^1$H NMR (300 MHz, DMSO-$d_6$) δ 2.63 (t, J=5.1 Hz, 2H), 3.00 (s, 2H), 3.13 (m, 2H), 3.64 (s, 2H), 4.74 (s, 2H), 6.64 (d, J=8.8 Hz, 1H), 7.42 (d, J=8.8 Hz, 1H), 7.74 (s, 1H).

(b) Step 2

A solution of 4-[(6-hydroxy-3-oxo-2,3-dihydrobenzofuran-7-yl)methyl]piperazin-2-one (0.131 g, 0.500 mmol) in methanol (2 mL) was added with indazole-3-carbaldehyde (0.0731 g, 0.500 mmol), and piperidine (0.00426 g, 0.0500 mmol) at room temperature, and the mixture was stirred at 60° C. for 2 hours. The reaction mixture was cooled to room temperature, then added with methanol (6 mL), suspended in methanol and thereby washed, and the solid was collected by filtration to obtain (Z)-4-({2-[(1H-indazol-3-yl)methylene]-6-hydroxy-3-oxo-2,3-dihydrobenzofuran-7-yl}methyl)piperazin-2-one (0.122 g, 62%).

$^1$H NMR (300 MHz, DMSO-$d_6$) δ 2.70 (m, 2H), 3.10-3.16 (m, 4H), 3.80 (s, 2H), 6.83 (d, J=8.1 Hz, 1H), 7.04 (s, 1H), 7.29 (t, J=7.3 Hz, 1H), 7.46 (m, 1H). 7.61-7.65 (m, 2H), 7.78 (s, 1H), 8.60 (d, J=8.8 Hz, 1H), 13.83 (br s, 1H).

Example B7

(Z)-2-[(1H-Indazol-3-yl)methylene]-6-hydroxy-7-[1-(piperazin-1-yl)ethyl]benzofuran-3(2H)-one (a) Step 1

The synthesis was performed with reference to the known literature (Journal of the Pharmaceutical Society of Japan (Yakugaku Zasshi), Vol. 88, p. 589, 1968). A suspension of aluminum chloride (3.5 g, 26 mmol) in nitrobenzene (10 mL) was stirred at 0° C. under an argon atmosphere. This suspension was added with chloroacetyl chloride (1.1 g, 9.9 mmol), and then the mixture was added dropwise with a suspension of 2,6-dihydroxyacetophenone (1.0 g, 6.6 mmol) in nitrobenzene (6.0 mL). After completion of the addition, the reaction mixture was stirred at 50° C. for 17 hours. The reaction mixture was added with ethyl acetate and ice water, the mixture was stirred at room temperature for 1 hour, and then the organic layer was separated. The organic layer was extracted with 1 N aqueous sodium hydroxide, and the aqueous layer was made acidic with 3 N hydrochloric acid to precipitate solid. The precipitated solid was collected by filtration and dried to obtain 7-acetyl-6-hydroxybenzofuran-3(2H)-one (0.90 g, 71%).

$^1$H NMR (300 MHz, CDCl$_3$) δ 2.77 (s, 3H), 4.77 (s, 2H), 6.71 (d, J=8.8 Hz, 1H), 7.74 (d, J=8.8 Hz, 1H), 13.99 (s, 1H)

(b) Step 2

A solution of 7-acetyl-6-hydroxybenzofuran-3(2H)-one (0.60 g, 3.1 mmol) in methylene chloride (25 mL) was added with acetic acid (0.25 mL) and N-Boc-piperazine (0.64 g, 3.4 mmol), and the mixture was stirred at room temperature for 10 minutes. The reaction mixture was cooled to 0° C., and then added portionwise with sodium triacetoxyborohydride (0.84 g, 4.1 mmol). After completion of the addition, the ice bath was removed to allow the reaction mixture to warm to room temperature, and the mixture was stirred at the same temperature for 20 hours. The reaction mixture was extracted with methylene chloride, and then the organic layer was successively washed with water, saturated aqueous sodium hydrogencarbonate, and saturated brine, and dried over anhydrous magnesium sulfate. The solvent was evaporated under reduced pressure, and the residue was subjected to silica gel column chromatography (eluted with chloroform/methanol (100:0→97:3)) to obtain tert-butyl 4-[1-(6-hydroxy-3-oxo-2,3-dihydrobenzofuran-7-yl)ethyl]piperazine-1-carboxylate (0.74 g, 90%).

$^1$H NMR (300 MHz, DMSO-$d_6$) δ 1.37 (d, J=6.6 Hz, 3H), 1.39 (s, 9H), 2.38-2.58 (m, 2H), 2.58-2.77 (m, 2H), 3.39 (m, 4H), 3.87-4.08 (m, 1H), 4.74 (s, 2H), 6.53 (d, J=8.1 Hz, 1H), 7.39 (d, J=8.1 Hz, 1H)

(c) Step 3

A solution of tert-butyl 4-[1-(6-hydroxy-3-oxo-2,3-dihydrobenzofuran-7-yl)ethyl]piperazine-1-carboxylate (0.11 g, 0.30 mmol) in methanol (5.0 mL) was added with 1H-indazole-3-carboxaldehyde (0.040 g, 0.27 mmol). Then, the mixture was added with 7 drops of piperidine, and the mixture was stirred at 50° C. for 1 hour. The reaction mixture was added with toluene, then the solvent was evaporated under reduced pressure, and the residue was subjected to silica gel column chromatography (aminopropyl silica was used, eluted with chloroform/methanol (95:5)) to obtain tert-butyl (Z)-4-{1-[2-(1H-indazol-3-yl)methylene-6-hydroxy-3-oxo-2,3-dihydrobenzofuran-7-yl]ethyl}piperazine-1-carboxylate (0.075 g, 51%).

$^1$H NMR (300 MHz, DMSO-d$_6$) δ 1.38 (s, 9H), 1.53 (d, J=7.3 Hz, 3H), 2.41-2.62 (m, 2H), 2.62-2.81 (m, 2H), 3.41 (m, 4H), 4.04-4.19 (m, 1H), 6.71 (d, J=8.1 Hz, 1H), 7.07 (s, 1H), 7.30 (m, 1H), 7.46 (m, 1H), 7.59 (d, J=8.8 Hz, 1H), 7.64 (d, J=8.1 Hz, 1H), 8.46 (d, J=8.1 Hz, 1H), 13.83 (s, 1H)

(d) Step 4

A solution of tert-butyl (Z)-4-{1-[2-(1H-indazol-3-yl)methylene-6-hydroxy-3-oxo-2,3-dihydrobenzofuran-7-yl]ethyl}piperazine-1-carboxylate (0.075 g, 0.15 mmol) in methylene chloride (3.0 mL) was added with a 4 M solution of hydrogen chloride in 1,4-dioxane (3.0 mL), and then the mixture was stirred at room temperature for 2 hours. After completion of the reaction, the mixture was azeotroped twice with toluene under reduced pressure. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate, and then the solvent was evaporated under reduced pressure to obtain (Z)-2-[(1H-indazol-3-yl)methylene]-6-hydroxy-7-[1-(piperazin-1-yl)ethyl]benzofuran-3(2H)-one (0.030 g, 50%).

$^1$H NMR (300 MHz, DMSO-d$_6$) δ 1.51 (d, J=7.3 Hz, 3H), 2.39-2.97 (m, 8H), 4.13 (m, 1H), 6.52 (d, J=81 Hz, 1H), 6.98 (s, 1H), 7.29 (m, 1H), 7.46 (m, 1H), 7.48 (d, J=8.8 Hz, 1H), 7.63 (d, J=8.8 Hz, 1H), 8.43 (d, J=8.1 Hz, 1H).

Example B8

(Z)-6-Hydroxy-7-(piperazin-1-ylmethyl)-2-[(5-fluoro-1H-indazol-3-yl)methylene]benzofuran-3(2H)-one (a) Step 1

The synthesis was performed with reference to the known literature (Tetrahedron Letters, Vol. 48, p. 2457, 2007). Aqueous sodium hydroxide (0.500 g, 12.5 mmol, 11 mL) was heated to 50° C., and added with 5-fluoroisatin (2.00 g, 12.1 mmol). The reaction mixture was stirred at 50° C. for 1 hour, and then cooled on ice. Aqueous sodium nitrite (0.835 g, 12.1 mmol, 4 mL) was cooled on ice, and then added dropwise to the reaction mixture. Then, the mixture was added dropwise with concentrated sulfuric acid (2.31 g, 23.6 mmol) in ice-cooled water (19 mL), and the mixture was stirred for 1 hour under ice cooling. Then, the reaction mixture was added dropwise with an ice-cooled solution of tin(II) chloride dihydrate (6.54 g, 29.0 mmol) in concentrated hydrochloric acid (9.7 mL). The reaction mixture was stirred overnight at room temperature, and then filtered, and the resulting solid was washed with water to obtain a pale brown solid (1.62 g).

A solution of the above solid (1.62 g) in methanol (30 mL) was added with concentrated sulfuric acid (4 mL), and the mixture was refluxed for 3 hours by heating. The reaction mixture was cooled to room temperature, and then poured into water (90 mL), and the precipitated solid was collected by filtration and washed with water to obtain methyl 5-fluoro-1H-indazole-3-carboxylate (1.35 g, 57%).

$^1$H NMR (300 MHz, DMSO-d$_6$) δ 3.92 (s, 3H), 7.37 (ddd, J=2.2, 8.8, 9.5 Hz, 1H), 7.72 (d, J=8.8 Hz, 1H), 7.73 (d, J=9.5 Hz, 1H), 14.08 (br s, 1H).

(b) Step 2

A solution of methyl 5-fluoro-1H-indazole-3-carboxylate (0.582 g, 3.00 mmol) in THF (20 mL) was cooled to −10° C., and added dropwise with a 1 M solution of diisobutylaluminum hydride in toluene (10.8 mL, 10.8 mmol) over 5 minutes. The reaction mixture was stirred at −10° C. for 1 hour, and then overnight at room temperature. The reaction mixture was added dropwise with saturated aqueous sodium sulfate under ice cooling to terminate the reaction, and then filtered through Celite. The filtrate was concentrated, and the resulting residue was purified by silica gel column chromatography (chloroform/methanol) to obtain (5-fluoro-1H-indazol-3-yl)methanol (0.217 g, 43%).

$^1$H NMR (300 MHz, DMSO-d$_6$) δ 4.75 (d, J=5.9 Hz, 2H), 5.23 (t, J=5.9 Hz, 1H), 7.22 (ddd, J=2.2, 8.8, 9.5 Hz, 1H), 7.48-7.57 (m, 2H), 12.89 (s, 1H).

(c) Step 3

A solution of (5-fluoro-1H-indazol-3-yl)methanol (0.215 g, 1.29 mmol) in ethyl acetate (10 mL) was added with manganese dioxide (1.12 g, 12.9 mmol), and the mixture was stirred overnight at room temperature. The reaction mixture was filtered through Celite, then the filtrate was concentrated, and the resulting residue was purified by silica gel column chromatography (chloroform/methanol) to obtain 5-fluoro-1H-indazole-3-carbaldehyde (0.150 g, 70%).

$^1$H NMR (300 MHz, DMSO-d$_6$) δ 7.41 (ddd, J=2.2, 8.8, 9.5 Hz, 1H), 7.75-7.81 (m, 2H), 10.18 (s, 1H), 14.32 (br s, 1H).

(d) Step 4

A solution of tert-butyl 4-[1-(6-hydroxy-3-oxo-2,3-dihydrobenzofuran-7-yl)methyl]piperazine-1-carboxylate (0.100 g, 0.287 mmol) in methanol (1.2 mL) was added with 5-fluoro-1H-indazole-3-carbaldehyde (0.0471 g, 0.287 mmol), and piperidine (0.00244 g, 0.0287 mmol) at room temperature, and the mixture was stirred at 60° C. for 1 hour. The solvent was evaporated, and then the residue was purified by silica gel column chromatography (chloroform/methanol) to obtain a solid (0.164 g).

A solution of the above solid in methylene chloride (4 mL) was added with trifluoroacetic acid (4 mL) at room temperature, and the mixture was stirred overnight. The solvent was evaporated, then the residue was dissolved in methanol (8 mL), the solution was added with a 5% solution of hydrochloric acid in methanol (2 mL), and the mixture was stirred at room temperature for 2 hours. The precipitated solid was collected by filtration to obtain a hydrochloride (0.0700 g) as a yellow solid.

The above hydrochloride was suspended in saturated aqueous sodium hydrogencarbonate (2 mL) and thereby washed, and then the resulting orange solid was washed with water to obtain the objective (Z)-6-hydroxy-7-(piperazin-1-ylmethyl)-2-[(5-fluoro-1H-indazol-3-yl)methylene]benzofuran-3(2H)-one (0.0375 g, 33%).

$^1$H NMR (300 MHz, DMSO-d$_6$) δ 2.61 (m, 4H), 2.88 (m, 4H), 3.76 (s, 2H), 6.37 (d, J=8.8 Hz, 1H), 6.82 (s, 1H), 7.32-7.38 (m, 2H), 7.65 (dd, J=4.4 Hz, 8.8 Hz, 1H), 8.27 (dd, J=1.5 Hz, 10.2 Hz, 1H).

Example B9

(Z)-6-Hydroxy-7-(piperazin-1-ylmethyl)-2-[(5-chloro-1H-indazol-3-yl)methylene]benzofuran-3(2H)-one

(a) Step 1

Aqueous sodium hydroxide (1.13 g, 28.3 mmol, 25 mL) was heated to 50° C., and added with 5-chloroisatin (5.00 g, 27.5 mmol). The mixture was stirred at 50° C. for 1 hour, and then cooled on ice. Aqueous sodium nitrite (1.90 g, 27.5 mmol, 9 mL) was cooled on ice, and then added dropwise to the reaction mixture. Then, the mixture was added dropwise with concentrated sulfuric acid (5.26 g, 53.6 mmol) in ice-cooled water (44 mL), and the mixture was stirred for 1 hour under ice cooling. Then, the reaction mixture was added dropwise with an ice-cooled solution of tin(II) chloride dihydrate (14.9 g, 66.0 mmol) in concentrated hydrochloric acid (22 mL). The mixture was stirred overnight at room temperature, and then filtered, and the resulting solid was washed with water to obtain a pale brown solid (5.10 g).

A solution of the above solid (5.10 g) in methanol (75 mL) was added with concentrated sulfuric acid (10 mL), and the mixture was refluxed for 3 hours by heating. The reaction mixture was cooled to room temperature, and then poured into water (225 mL), and the precipitated solid was collected by filtration, and washed with water to obtain methyl 5-chloro-1H-indazole-3-carboxylate (4.39 g, 75%).

$^1$H NMR (300 MHz, DMSO-$d_6$) δ 3.93 (s, 3H), 7.48 (dd, J=1.5, 8.8 Hz, 1H), 7.72 (d, J=8.8 Hz, 1H), 8.0 (d, J=1.5 Hz, 1H).

(b) Step 2

A solution of methyl 5-chloro-1H-indazole-3-carboxylate (2.11 g, 10.0 mmol) in THF (70 mL) was cooled to −10° C., and added dropwise with a 1 M solution of diisobutylaluminum hydride in toluene (36.0 mL). After completion of the addition, the mixture was stirred at −10° C. for 1 hour, and then stirred overnight at room temperature. The reaction mixture was added dropwise with saturated aqueous sodium sulfate under ice cooling to terminate the reaction, and then the reaction mixture was filtered through Celite. The filtrate was concentrated, and the resulting residue was purified by silica gel column chromatography (chloroform/methanol) to obtain the objective (5-chloro-1H-indazol-3-yl)methanol (0.210 g, 11%).

$^1$H NMR (300 MHz, DMSO-$d_6$) δ 4.76 (d, J=5.9 Hz, 2H), 5.28 (t, J=5.9 Hz, 1H), 7.33 (dd, J=1.5, 8.8 Hz, 1H), 7.52 (d, J=8.8 Hz, 1H), 7.90 (d, J=1.5 Hz, 1H), 12.98 (br s, 1H).

(c) Step 3

A solution of (5-chloro-1H-indazol-3-yl)methanol (0.208 g, 1.14 mmol) in ethyl acetate (10 mL) was added with manganese dioxide (0.991 g, 11.4 mmol), and the mixture was stirred overnight at room temperature. The reaction mixture was filtered through Celite, then the filtrate was concentrated, and the resulting residue was purified by silica gel column chromatography (chloroform/methanol) to obtain 5-chloro-1H-indazole-3-carbaldehyde (0.106 g, 51%).

$^1$H NMR (300 MHz, DMSO-$d_6$) δ 7.53 (dd, J=2.2, 8.8 Hz, 1H), 7.77 (d, J=8.8 Hz, 1H), 8.11 (d, J=2.2 Hz, 1H), 10.18 (s, 1H), 14.36 (br s, 1H).

(d) Step 4

A solution of tert-butyl 4-[1-(6-hydroxy-3-oxo-2,3-dihydrobenzofuran-7-yl)methyl]piperazine-1-carboxylate (0.100 g, 0.287 mmol) in methanol (1.2 mL) was added with 5-chloro-1H-indazole-3-carbaldehyde (0.0518 g, 0.287 mmol), and piperidine (0.00244 g, 0.0287 mmol) at room temperature, and the mixture was stirred at 60° C. for 3 hours. The reaction mixture was added with methanol (4 mL), suspended in methanol and thereby washed, and then the solid was collected by filtration to obtain tert-butyl (Z)-4-({6-hydroxy-3-oxo-2-[(5-chloro-1H-indazol-3-yl)methylene]-2,3-dihydrobenzofuran-7-yl}methyl)piperazine-1-carboxylate (0.0750 g, 51%).

$^1$H NMR (300 MHz, DMSO-$d_6$) δ 1.36 (s, 9H), 2.55 (m, 4H), 3.33 (m, 4H), 3.92 (s, 2H), 6.77 (d, J=8.8 Hz, 1H), 7.02 (s, 1H), 7. (dd, J=2.2, 8.8 Hz, 1H), 7.62 (d, J=8.8 Hz, 1H), 7.68 (d, J=8.8 Hz, 1H), 8.59 (d, J=2.2 Hz, 1H), 13.99 (br s, 1H).

(e) Step 5

A solution of tert-butyl (Z)-4-({6-hydroxy-3-oxo-2-[(5-chloro-1H-indazol-3-yl)methylene]-2,3-dihydrobenzofuran-7-yl}methyl)piperazine-1-carboxylate (0.062 g, 0.121 mmol) in methylene chloride (2 mL) was added with trifluoroacetic acid (2 mL) at room temperature, and the mixture was stirred overnight. The solvent was evaporated, then the residue was dissolved in methanol (4 mL), the solution was added with a 5% solution of hydrochloric acid in methanol (1 mL), and the mixture was stirred at room temperature for 2 hours. The precipitated solid was collected by filtration to obtain a hydrochloride (0.0331 g) as a yellow solid.

The above hydrochloride was suspended in saturated aqueous sodium hydrogencarbonate (2 mL) and thereby washed, and then the resulting orange solid was washed with water to obtain the objective (Z)-6-hydroxy-7-(piperazin-1-ylmethyl)-2-[(5-chloro-1H-indazol-3-yl)methylene]benzofuran-3(2H)-one (0.0146 g, 29%).

$^1$H NMR (300 MHz, DMSO-$d_6$) δ 2.62 (m, 4H), 2.84 (m, 4H), 3.89 (s, 2H), 6.41 (d, J=8.8 Hz, 1H), 6.84 (s, 1H), 7.41 (d, J=8.8 Hz, 1H), 7.47 (d, J=8.8 Hz, 1H), 7.66 (d, J=8.8 Hz, 1H), 8.59 (s, 1H).

Example B10

(Z)-6-Hydroxy-7-(piperazin-1-ylmethyl)-2-[(5-bromo-1H-indazol-3-yl)methylene]benzofuran-3(2H)-one

(a) Step 1

Aqueous sodium hydroxide (1.13 g, 28.3 mmol, 25 mL) was heated to 50° C., and added with 5-bromoisatin (6.22 g, 27.5 mmol). The reaction mixture was stirred at 50° C. for 1 hour, and then cooled on ice. The reaction mixture was added dropwise with ice-cooled aqueous sodium nitrite (1.90 g, 27.5 mmol, 9 mL). Then, the mixture was added dropwise with concentrated sulfuric acid (5.26 g, 53.6 mmol) in ice-cooled water (44 mL), and the mixture was stirred for 1 hour under ice cooling. Then, the reaction mixture was added dropwise with an ice-cooled solution of tin(II) chloride dihydrate (14.9 g, 66.0 mmol) in concentrated hydrochloric acid (22 mL). The mixture was stirred overnight at room temperature, and then filtered, and the resulting solid was washed with water to obtain a pale brown solid (6.21 g).

A solution of the above solid (6.21 g) in methanol (75 mL) was added with concentrated sulfuric acid (10 mL), and the mixture was refluxed for 3 hours by heating. The reaction mixture was cooled to room temperature, and then poured into water (225 mL), and the precipitated solid was collected by filtration, suspended in a mixed solvent of methanol and methylene chloride (20:1) and thereby washed to obtain methyl 5-bromo-1H-indazole-3-carboxylate (2.22 g, 31%).

$^1$H NMR (300 MHz, DMSO-d$_6$) δ 3.93 (s, 3H), 7.58 (dd, J=1.5, 8.8 Hz, 1H), 7.67 (d, J=8.8 Hz, 1H), 8.21 (d, J=1.5 Hz, 1H), 14.14 (br s, 1H).

(b) Step 2

A solution of methyl 5-bromo-1H-indazole-3-carboxylate (2.21 g, 8.66 mmol) in THF (60 mL) was cooled to −10° C., and added dropwise with a 1 M solution of diisobutylaluminum hydride in toluene (36.0 mL, 36.0 mmol). After completion of the addition, the mixture was stirred at −10° C. for 1 hour, and then stirred overnight at room temperature. The reaction mixture was added dropwise with saturated aqueous sodium sulfate under ice cooling to terminate the reaction, and then filtered through Celite. The filtrate was concentrated, and the resulting solid was suspended in methylene chloride and thereby washed to obtain (5-bromo-1H-indazol-3-yl) methanol (0.712 g, 36%).

$^1$H NMR (300 MHz, DMSO-d$_6$) δ 4.76 (d, J=5.9 Hz, 2H), 5.28 (t, J=5.9 Hz, 1H), 7.41-7.49 (m, 2H), 8.05 (s, 1H), 12.98 (br s, 1H).

(c) Step 3

A solution of (5-bromo-1H-indazol-3-yl)-methanol (0.267 g, 1.18 mmol) in ethyl acetate (12 mL) was added with manganese dioxide (1.03 g, 11.8 mmol), and the mixture was stirred overnight at room temperature. The reaction mixture was filtered through Celite, and then the filtrate was concentrated to obtain 5-bromo-1H-indazole-3-carbaldehyde (0.179 g, 67%).

$^1$H NMR (300 MHz, DMSO-d$_6$) δ 7.63 (dd, J=1.5, 8.8 Hz, 1H), 7.71 (d, J=8.8 Hz, 1H), 8.27 (d, J=1.5 Hz, 1H), 10.18 (s, 1H), 14.37 (br s, 1H).

(d) Step 4

A solution of tert-butyl 4-[1-(6-hydroxy-3-oxo-2,3-dihydrobenzofuran-7-yl)methyl]piperazine-1-carboxylate (0.100 g, 0.287 mmol) in methanol (1.2 mL) was added with 5-bromo-1H-indazole-3-carbaldehyde (0.0646 g, 0.287 mmol), and piperidine (0.00244 g, 0.0287 mmol) at room temperature, and the mixture was stirred at 60° C. for 2 hours. The reaction mixture was added with methanol (4 mL), suspended in methanol and thereby washed, and then the solid was collected by filtration to obtain tert-butyl (Z)-4-({6-hydroxy-3-oxo-2-[(5-bromo-1H-indazol-3-yl)methylene]-2,3-dihydrobenzofuran-7-yl}methyl)piperazine-1-carboxylate (0.0700 g, 44%).

$^1$H NMR (300 MHz, DMSO-d$_6$) δ 1.36 (s, 9H), 2.57 (m, 4H), 3.33 (m, 4H), 3.95 (s, 2H), 6.77 (d, J=8.1 Hz, 1H), 7.01 (s, 1H), 7.57-7.65 (m, 3H), 8.74 (s, 1H), 14.00 (br s, 1H).

(e) Step 5

A solution of tert-butyl (Z)-4-({6-hydroxy-3-oxo-2-[(5-bromo-1H-indazol-3-yl)methylene]-2,3-dihydrobenzofuran-7-yl}methyl)piperazine-1-carboxylate (0.058 g, 0.104 mmol) in methylene chloride (2 mL) was added with trifluoroacetic acid (2 mL) at room temperature, and the mixture was stirred overnight. The solvent was evaporated, then the residue was dissolved in methanol (4 mL), the solution was added with a 5% solution of hydrochloric acid in methanol (1 mL), and the mixture was stirred at room temperature for 0.5 hour. The precipitated solid was collected by filtration to obtain a hydrochloride (0.0502 g) as a yellow solid.

The above hydrochloride was dissolved in saturated aqueous sodium hydrogencarbonate (2 mL), and the solution was left overnight at room temperature. The precipitated solid was collected by filtration, and then washed with water to obtain the objective (Z)-6-hydroxy-7-(piperazin-1-ylmethyl)-2-[(5-bromo-1H-indazol-3-yl)methylene]benzofuran-3(2H)-one (0.0205 g, 43%).

$^1$H NMR (300 MHz, DMSO-d$_6$) δ 2.62 (m, 4H), 2.80 (m, 4H), 3.91 (s, 2H), 6.38 (d, J=8.1 Hz, 1H), 6.82 (s, 1H), 7.39 (d, J=8.0 Hz, 1H), 7.55-7.62 (m, 2H), 8.75 (s, 1H).

Example B11

(Z)-6-Hydroxy-7-(piperazin-1-ylmethyl)-2-[(5-methoxy-1H-indazol-3-yl)methylene]benzofuran-3(2H)-one (a) Step 1

Aqueous sodium hydroxide (1.16 g, 29.0 mmol, 25 mL) was heated to 50° C., and added with 5-methoxyisatin (5.00 g, 28.2 mmol). The mixture was stirred at 50° C. for 1 hour, and then cooled on ice. The reaction mixture was added dropwise with ice-cooled aqueous sodium nitrite (1.95 g, 28.2 mmol, 9 mL). Then, the mixture was added dropwise with concentrated sulfuric acid (5.39 g, 55.0 mmol) dissolved in ice-cooled water (45 mL). The mixture was stirred for 1 hour under ice cooling, and then added dropwise with tin(II) chloride dihydrate (15.3 g, 67.7 mmol) dissolved in concentrated hydrochloric acid (22 mL) cooled on ice. The mixture was stirred overnight at room temperature, and then filtered, and the resulting solid was washed with water to obtain a brown solid (3.00 g).

A solution of the above solid (3.00 g) in methanol (45 mL) was added with concentrated sulfuric acid (6 mL), and the mixture was refluxed for 3 hours by heating. The reaction mixture was cooled to room temperature, and then poured into water (140 mL), and the precipitated solid was collected by filtration to obtain a dark reddish-brown solid (1.81 g).

A solution of the above solid (1.81 g) in THF (60 mL) was cooled to −10° C., and added dropwise with a 1 M solution of diisobutylaluminum hydride in toluene (31.6 mL, 31.6 mmol). After completion of the addition, the mixture was stirred at −10° C. for 1 hour, and then at room temperature for 4.5 hours. The reaction mixture was added dropwise with saturated aqueous sodium sulfate under ice cooling to terminate the reaction, and then filtered through Celite. The filtrate was concentrated, and the resulting solid was suspended in methylene chloride and thereby washed to obtain (5-methoxy-1H-indazol-3-yl)methanol (0.369 g, 7%).

$^1$H NMR (300 MHz, DMSO-d$_6$) δ 3.78 (s, 3H), 4.74 (d, J=5.1 Hz, 2H), 5.16 (t, J=5.9 Hz, M), 6.98 (dd, J=2.2, 8.8 Hz, 1H), 7.24 (d, J=2.2 Hz, 1H), 7.37 (d, J=8.8 Hz, 1H), 12.62 (br s, 1H).

(b) Step 2

A solution of (5-methoxy-1H-indazol-3-yl)methanol (0.367 g, 2.06 mmol) in ethyl acetate (20 mL) was added with manganese dioxide (1.79 g, 20.6 mmol), and the mixture was stirred overnight at room temperature. The reaction mixture was filtered through Celite, and then the filtrate was concentrated to obtain 5-methoxy-1H-indazole-3-carbaldehyde (0.254 g, 70%).

¹H NMR (300 MHz, DMSO-d₆) δ 3.83 (s, 3H), 7.13 (dd, J=2.2, 8.8 Hz, 1H), 7.50 (d, J=2.2 Hz, 1H), 7.62 (d, J=8.8 Hz, 1H), 10.16 (s, 1H), 14.09 (br s, 1H).

(c) Step 3

A solution of tert-butyl 4-[1-(6-hydroxy-3-oxo-2,3-dihydrobenzofuran-7-yl)methyl]piperazine-1-carboxylate (0.313 g, 0.898 mmol) in methanol (4 mL) was added with 5-methoxy-1H-indazole-3-carbaldehyde (0.158 g, 0.898 mmol), and piperidine (0.00764 g, 0.0898 mmol) at room temperature, and the mixture was stirred at 60° C. for 2 hours. The reaction mixture was concentrated, and the resulting residue was suspended in acetonitrile and thereby washed to obtain tert-butyl (Z)-4-({6-hydroxy-3-oxo-2-[(5-methoxy-1H-indazol-3-yl)methylene]-2,3-dihydrobenzofuran-7-yl}methyl)piperazine-1-carboxylate (0.318 g, 69%).

¹H NMR (300 MHz, DMSO-d₆) δ 1.36 (s, 9H), 2.51 (m, 4H), 3.33 (m, 4H), 3.89 (s, 3H), 3.94 (s, 2H), 6.75 (d, J=8.8 Hz, 1H), 7.11-7.15 (m, 2H), 7.55 (d, J=8.8 Hz, 1H), 7.60 (d, J=8.8 Hz, 1H), 7.79 (s, 1H), 13.72 (br s, 1H).

(d) Step 4

A solution of tert-butyl (Z)-4-({6-hydroxy-3-oxo-2-[(5-methoxy-1H-indazol-3-yl)methylene]-2,3-dihydrobenzofuran-7-yl}methyl)piperazine-1-carboxylate (0.315 g, 0.622 mmol) in methylene chloride (8 mL) was added with trifluoroacetic acid (8 mL) at room temperature, and the mixture was stirred overnight. The solvent was evaporated, then the residue was dissolved in methanol (12 mL), the solution was added with a 5% solution of hydrochloric acid in methanol (3 mL), and the mixture was stirred at room temperature for 2 hours. The precipitated solid was collected by filtration to obtain a hydrochloride (0.220 g) as a yellow solid.

The above hydrochloride was suspended in saturated aqueous sodium hydrogencarbonate (6 mL) and thereby washed, and then the resulting orange solid was washed with water to obtain the objective (Z)-6-hydroxy-7-(piperazin-1-ylmethyl)-2-[(5-methoxy-1H-indazol-3-yl)methylene]benzofuran-3(2H)-one (0.143 g, 56%).

1H NMR (300 MHz, DMSO-d₆) δ 2.59 (m, 4H), 2.82 (m, 4H), 3.90 (s, 3H), 3.92 (s, 2H), 6.46 (d, J=8.8 Hz, 1H), 6.95 (s, 1H), 7.12 (dd, J=1.5, 8.8 Hz, 1H), 7.44 (d, J=8.8 Hz, 1H), 7.54 (d, J=8.8 Hz, 1H), 7.76 (d, J=1.5 Hz, 1H).

Example B12

(Z)-6-Hydroxy-7-(piperazin-1-ylmethyl)-2-{[5-(trifluoromethoxy)-1H-indazol-3-yl]methylene}benzofuran-3(2H)-one (a) Step 1

Aqueous sodium hydroxide (0.0888 g, 2.22 mmol, 2 mL) was heated to 50° C., and added with 5-trifluoromethoxyisatin (0.500 g, 2.16 mmol). The mixture was stirred at 50° C. for 1 hour, and then cooled on ice. The reaction mixture was added with sodium nitrite (0.149 g, 2.16 mmol), and then added dropwise with a solution of concentrated sulfuric acid (0.413 g, 4.21 mmol) in ice-cooled water (3.5 mL), and the mixture was stirred for 1 hour under ice cooling. Then, the mixture was added dropwise with an ice-cooled solution of tin(II) chloride dihydrate (1.17 g, 5.18 mmol) in concentrated hydrochloric acid (1.7 mL). The mixture was stirred overnight at room temperature, and then filtered to obtain a pale brown solid (0.638 g).

A solution of the above solid (0.638 g) in methanol (6 mL) was added with concentrated sulfuric acid (0.1 mL), and the mixture was refluxed for 3 hours by heating. The reaction mixture was cooled to room temperature, then neutralized with saturated aqueous sodium hydrogencarbonate, and extracted three times with ethyl acetate. The organic layer was dried over anhydrous magnesium sulfate, and then the solvent was evaporated to obtain the objective methyl 5-(trifluoromethoxy)-1H-indazole-3-carboxylate (0.373 g, 66%).

¹H NMR (300 MHz, DMSO-d₆) δ 3.94 (s, 3H), 7.47 (d, J=8.8 Hz, 1H), 7.81 (d, J=8.8 Hz, 1H), 7.96 (s, 1H), 14.23 (br s, 1H).

(b) Step 2

A solution of methyl 5-(trifluoromethoxy)-1H-indazole-3-carboxylate (0.370 g, 1.42 mmol) in THF (10 mL) was cooled to −10° C., and added dropwise with a 1 M solution of diisobutylaluminum hydride in toluene (5.11 mL, 5.11 mmol) over 5 minutes. The reaction mixture was stirred at −10° C. for 1 hour, and then stirred overnight at room temperature. The reaction mixture was added dropwise with saturated aqueous sodium sulfate under ice cooling to terminate the reaction, and then filtered through Celite. The filtrate was concentrated, and the resulting residue was purified by silica gel column chromatography (chloroform/methanol) to obtain the objective [5-(trifluoromethoxy)-1H-indazol-3-yl]methanol (0.133 g, 40%).

¹H NMR (300 MHz, DMSO-d₆) δ 4.79 (d, J=5.9 Hz, 2H), 5.32 (t, J=5.9 Hz, 1H), 7.33 (d, J=8.8 Hz, 1H), 7.60 (d, J=9.5 Hz, 1H), 7.83 (s, 1H), 13.06 (br s, 1H).

(c) Step 3

A solution of [5-(trifluoromethoxy)-1H-indazol-3-yl]methanol (0.109 g, 0.470 mmol) in ethyl acetate (2 mL) was added with manganese dioxide (0.409 g, 4.70 mmol), and the reaction mixture was stirred overnight at room temperature. The reaction mixture was filtered through Celite, then the filtrate was concentrated, and the resulting residue was purified by silica gel column chromatography (chloroform/methanol) to obtain the objective 5-(trifluoromethoxy)-1H-indazole-3-carbaldehyde (0.0710 g, 65%).

¹H NMR (300 MHz, DMSO-d₆) δ 7.52 (d, J=8.8 Hz, 1H), 7.86 (d, J=9.5 Hz, 1H), 8.01 (s, 1H), 10.20 (s, 1H), 14.44 (br s, 1H).

(d) Step 4

A solution of tert-butyl 4-[1-(6-hydroxy-3-oxo-2,3-dihydrobenzofuran-7-yl)methyl]piperazine-1-carboxylate (0.103 g, 0.295 mmol) in methanol (1.2 mL) was added with 5-(trifluoromethoxy)-1H-indazole-3-carbaldehyde (0.0680 g, 0.295 mmol), and piperidine (0.00251 g, 0.0295 mmol) at room temperature, and the mixture was stirred at 60° C. for 3 hours. The solvent was evaporated, and then the residue was purified by silica gel column chromatography (chloroform/methanol) to obtain tert-butyl (Z)-4-[(6-hydroxy-3-oxo-2-{[5-(trifluoromethoxy)-1H-indazol-3-yl]methylene}-2,3-dihydrobenzofuran-7-yl)methyl]piperazine-1-carboxylate (0.0660 g, 40%).

¹H NMR (300 MHz, CDCl₃) δ 1.47 (s, 9H), 2.65 (m, 4H), 3.56 (m, 4H), 4.06 (s, 2H), 6.71 (d, J=8.8 Hz, 1H), 7.24 (s, 1H), 7.37 (d, J=8.8 Hz, 1H), 7.59 (d, J=8.8 Hz, 1H), 7.67 (d, J=8.8 Hz, 1H), 8.30 (s, 1H).

(e) Step 5

A solution of tert-butyl (Z)-4-[(6-hydroxy-3-oxo-2-{[5-(trifluoromethoxy)-1H-indazol-3-yl]methylene}-2,3-dihydrobenzofuran-7-yl)methyl]piperazine-1-carboxylate (0.0560 g, 0.0999 mmol) in methylene chloride (1 mL) was added with trifluoroacetic acid (1 mL) at room temperature, and the mixture was stirred overnight. The solvent was evaporated, then the residue was dissolved in methanol (8 mL), the solution was added with a 5% solution of hydrochloric acid in methanol (2 mL), and the mixture was stirred at room temperature for 2 hours. The precipitated solid was collected by filtration to obtain a hydrochloride as a yellow solid.

The above hydrochloride was added to saturated aqueous sodium hydrogencarbonate (30 mL), and the mixture was extracted three times with ethyl acetate. The organic layer was dried over anhydrous sodium sulfate, and then the solvent was evaporated to obtain the objective (Z)-6-hydroxy-7-(piperazin-1-ylmethyl)-2-{[5-trifluoromethoxy)-1H-indazol-3-yl]methylene}benzofuran-3(2H)-one (0.0430 g, 93%).

$^1$H NMR (300 MHz, DMSO-$d_6$) δ 2.58 (m, 4H), 2.83 (m, 4H), 3.85 (s, 2H), 6.89 (s, 1H), 7.42 (d, J=8.8 Hz, 1H), 7.47 (dd, J=1.5 Hz, 8.8 Hz, 1H), 7.75 (d, J=8.8 Hz, 1H), 8.45 (d, J=1.5 Hz, 1H).

Example B13

(Z)-2-[(1H-Indazol-3-yl)methylene]-5-chloro-6-hydroxy-7-(piperazin-1-ylmethyl)benzofuran-3(2H)-one (a) Step 1

A solution of 4-chlororesorcinol (4.34 g, 30.0 mmol) in nitrobenzene (60 mL) was added with aluminum chloride (10.2 g, 90.0 mmol) at room temperature. Then, the mixture was added with chloroacetyl chloride (2.87 mL, 36.0 mmol) under ice cooling. The reaction mixture was stirred at 40° C. for 2 hours, and then added with 2 N aqueous sodium hydroxide (60 mL), and the aqueous layer was separated. The separated aqueous layer was added with concentrated hydrochloric acid and thereby adjusted to pH 3, and the precipitated solid was collected by filtration to obtain the objective 5-chloro-6-hydroxybenzofuran-3(2H)-one (0.995 g, 17%).

$^1$H NMR (300 MHz, DMSO-$d_6$) δ 4.76 (s, 2H), 6.72 (s, 1H), 7.62 (s, 1H), 11.83 (s, 1H).

(b) Step 2

A solution of 5-chloro-6-hydroxybenzofuran-3(2H)-one (0.185 g, 1.00 mmol) in ethanol (20 mL) was added with 1-tert-butoxycarbonylpiperazine (0.186 g, 1.00 mmol), and 37% aqueous formaldehyde (0.0812 g, 1.00 mmol) at room temperature. The mixture was stirred overnight at room temperature, and then the precipitates formed were collected by filtration, and then washed with ethyl acetate to obtain tert-butyl 4-[(5-chloro-6-hydroxy-3-oxo-2,3-dihydrobenzofuran-7-yl)methyl]piperazine-1-carboxylate (0.216 g, 56%).

$^1$H NMR (300 MHz, DMSO-$d_6$) δ 1.40 (s, 9H), 2.85 (m, 4H), 3.48 (m, 4H), 4.00 (s, 2H), 4.66 (s, 2H), 7.44 (s, 1H).

(c) Step 3

A solution of tert-butyl 4-[(5-chloro-6-hydroxy-3-oxo-2,3-dihydrobenzofuran-7-yl)methyl]piperazine-1-carboxylate (0.100 g, 0.261 mmol) in methanol (1 mL) was added with indazole-3-carbaldehyde (0.0381 g, 0.261 mmol), and piperidine (0.00222 g, 0.0261 mmol) at room temperature, and the mixture was stirred at 60° C. for 3 hours. The reaction mixture was cooled to room temperature, then added with methanol (4 mL), suspended in methanol and thereby washed, and the solid was collected by filtration to obtain tert-butyl (Z)-4-({2-[(1H-indazol-3-yl)methylene]-5-chloro-6-hydroxy-3-oxo-2,3-dihydrobenzofuran-7-yl}methyl)piperazine-1-carboxylate (0.0890 g, 66%).

$^1$H NMR (300 MHz, DMSO-$d_6$) δ 1.39 (s, 9H), 3.01 (m, 4H), 3.52 (m, 4H), 4.19 (s, 2H), 6.90 (s, 1H), 7.29 (m, 1H), 7.44 (m, 1H), 7.59-7.63 (m, 2H), 8.36 (d, J=8.1 Hz, 1H), 13.65 (br s, 1H).

(d) Step 4

A solution of tert-butyl (Z)-4-({2-[(1H-indazol-3-yl)methylene]-5-chloro-6-hydroxy-3-oxo-2,3-dihydrobenzofuran-7-yl}methyl)piperazine-1-carboxylate (0.0750 g, 0.147 mmol) in methylene chloride (1 mL) was added with trifluoroacetic acid (1 mL) at room temperature, and the mixture was stirred overnight. The solvent was evaporated, then the residue was dissolved in methanol (4 mL), the solution was added a 5% solution of hydrochloric acid in methanol (1 mL), and the mixture was stirred at room temperature for 2 hours. The precipitated solid was collected by filtration to obtain a hydrochloride (0.0400 g) as a yellow solid.

The above hydrochloride was suspended in saturated aqueous sodium hydrogencarbonate (1 mL) and thereby washed, and then the resulting yellow solid was washed with water to obtain (Z)-2-[(1H-indazol-3-yl)methylene]-5-chloro-6-hydroxy-7-(piperazin-1-ylmethyl)benzofuran-3(2H)-one (0.0155 g, 25%).

$^1$H NMR (300 MHz, DMSO-$d_6$) δ 2.69 (m, 4H), 3.02 (m, 4H), 3.69 (s, 2H), 6.67 (s, 1H), 7.21 (m, 1H), 7.36 (s, 1H), 7.42 (m, 1H), 7.58 (d, J=8.0 Hz, 1H), 8.58 (d, J=8.1 Hz, 1H), 13.52 (br s, 1H).

Example B14

(Z)-5-Chloro-2-[(5-fluoro-1H-indazol-3-yl)methylene]-6-hydroxy-7-(piperazin-1-ylmethyl)benzofuran-3(2H)-one (a) Step 1

A solution of tert-butyl 4-[(5-chloro-6-hydroxy-3-oxo-2,3-dihydrobenzofuran-7-yl)methyl]piperazine-1-carboxylate (0.100 g, 0.261 mmol) synthesized in Example B13, Step 2 in methanol (1 mL) was added with 5-fluoro-1H-indazole-3-carbaldehyde (0.0428 g, 0.261 mmol) synthesized in Example B8, Step 3, and piperidine (0.00222 g, 0.0261 mmol) at room temperature, and the mixture was stirred at 60° C. for 1 hour. The reaction mixture was cooled to room temperature, then added with methanol (4 mL), and suspended in methanol and thereby washed to obtain tert-butyl (Z)-4-({5-chloro-2-[(5-fluoro-1H-indazol-3-yl)methylene]-6-hydroxy-3-oxo-2,3-dihydrobenzofuran-7-yl}methyl)piperazine-1-carboxylate (0.050 g, 36%).

$^1$H NMR (300 MHz, DMSO-$d_6$) δ 1.41 (s, 9H), 3.04 (m, 4H), 3.56 (m, 4H), 4.20 (s, 2H), 6.90 (s, 1H), 7.34 (m, 1H), 7.61 (s, 1H), 7.66 (m, 1H), 8.12 (d, J=10.2 Hz, 1H), 13.79 (br s, 1H)

(b) Step 2

A solution of tert-butyl (Z)-4-({5-chloro-2-[(5-fluoro-1H-indazol-3-yl)methylene]-6-hydroxy-3-oxo-2,3-dihydrobenzofuran-7-yl}methyl)piperazine-1-carboxylate (0.050 g, 0.0945 mmol) in methylene chloride (2 mL) was added with trifluoroacetic acid (2 mL) at room temperature, and the mixture was stirred overnight. The solvent was evaporated, then the residue was dissolved in methanol (4 mL), the solution was added with a 5% solution of hydrochloric acid in methanol (1 mL), and the mixture was stirred at room temperature for 2 hours. The precipitated solid was collected by filtration to obtain a hydrochloride (0.0410 g) as a yellow solid.

The above hydrochloride was suspended in saturated aqueous sodium hydrogencarbonate (1 mL), and thereby washed, and then the resulting orange solid was washed with water to obtain the objective (Z)-5-chloro-2-[(5-fluoro-1H-indazol-3-yl)methylene]-6-hydroxy-7-(piperazin-1-ylmethyl)benzofuran-3(2H)-one (0.0198 g, 48%).

$^1$H NMR (300 MHz, DMSO-d$_6$) δ 2.58 (m, 4H), 2.89 (m, 4H), 3.63 (s, 2H), 6.63 (s, 1H), 7.32 (m, 1H), 7.34 (s, 1H), 7.62 (dd, J=4.4, 10.2 Hz, 1H), 8.29 (dd, J=2.2 Hz, 10.2 Hz, 1H).

Example B15

(Z)-5-Chloro-2-[(5-chloro-1H-indazol-3-yl)methylene]-6-hydroxy-7-(piperazin-1-ylmethyl)benzofuran-3(2H)-one (a) Step 1

A solution of tert-butyl 4-[(5-chloro-6-hydroxy-3-oxo-2,3-dihydrobenzofuran-7-yl)methyl]piperazine-1-carboxylate (0.100 g, 0.261 mmol) synthesized in Example B13, Step 2 in methanol (1 mL) was added with 5-chloro-1H-indazole-3-carbaldehyde (0.0471 g, 0.261 mmol) synthesized in Example B9, Step 3, and piperidine (0.00222 g, 0.0261 mmol) at room temperature, and the mixture was stirred at 60° C. for 1 hour. The reaction mixture was cooled to room temperature, then added with methanol (4 mL), and suspended in methanol and thereby washed to obtain tert-butyl (Z)-4-({5-chloro-2-[(5-chloro-1H-indazol-3-yl)methylene]-6-hydroxy-3-oxo-2,3-dihydrobenzofuran-7-yl}methyl)piperazine-1-carboxylate (0.050 g, 35%).

$^1$H NMR (300 MHz, DMSO-d$_6$) δ 1.39 (s, 9H), 3.03 (m, 4H), 3.54 (m, 4H), 4.22 (s, 2H), 6.89 (s, 1H), 7.46 (dd, J=1.5, 8.8 Hz, 1H), 7.63 (s, 1H), 7.66 (d, J=8.8 Hz, 1H), 8.47 (s, 1H), 13.87 (br s, 1H)

(b) Step 2

A solution of tert-butyl (Z)-4-({5-chloro-2-[(5-chloro-1H-indazol-3-yl)methylene]-6-hydroxy-3-oxo-2,3-dihydrobenzofuran-7-yl}methyl)piperazine-1-carboxylate (0.039 g, 0.0715 mmol) in methylene chloride (2 mL) was added with trifluoroacetic acid (2 mL) at room temperature, and the mixture was stirred overnight. The solvent was evaporated, then the residue was dissolved in methanol (4 mL), the solution was added with a 5% solution of hydrochloric acid in methanol (1 mL), and the mixture was stirred at room temperature for 2 hours. The precipitated solid was collected by filtration to obtain a hydrochloride (0.0291 g) as a yellow solid.

The above hydrochloride was suspended in saturated aqueous sodium hydrogencarbonate (1 mL), and thereby washed, and then the resulting orange solid was washed with water to obtain the objective (Z)-5-chloro-2-[(5-chloro-1H-indazol-3-yl)methylene]-6-hydroxy-7-(piperazin-1-ylmethyl)benzofuran-3(2H)-one (0.0132 g, 41%).

$^1$H NMR (300 MHz, DMSO-d$_6$) δ 2.67 (m, 4H), 2.98 (m, 4H), 3.76 (s, 2H), 6.65 (s, 1H), 7.38 (s, 1H), 7.45 (dd, J=1.5 Hz, 8.8 Hz, 1H), 7.63 (d, J=8.8 Hz, 1H), 8.58 (d, J=1.5 Hz, 1H).

Example B16

(Z)-5-Chloro-2-[(5-bromo-1H-indazol-3-yl)methylene]-6-hydroxy-7-(piperazin-1-ylmethyl)benzofuran-3(2H)-one (a) Step 1

A solution of tert-butyl 4-[(5-chloro-6-hydroxy-3-oxo-2,3-dihydrobenzofuran-7-yl)methyl]piperazine-1-carboxylate (0.100 g, 0.261 mmol) synthesized in Example B13, Step 2 in methanol (1 mL) was added with 5-bromo-1H-indazole-3-carbaldehyde (0.0587 g, 0.261 mmol) synthesized in Example B10, Step 3, and piperidine (0.00222 g, 0.0261 mmol) at room temperature, and the mixture was stirred at 60° C. for 2 hours. The reaction mixture was cooled to room temperature, then added with methanol (4 mL), and suspended in methanol and thereby washed to obtain tert-butyl (Z)-4-({5-chloro-2-[(5-bromo-1H-indazol-3-yl)methylene]-6-hydroxy-3-oxo-2,3-dihydrobenzofuran-7-yl}methyl)piperazine-1-carboxylate (0.110 g, 71%).

$^1$H NMR (300 MHz, DMSO-d$_6$) δ 1.38 (s, 9H), 3.03 (m, 4H), 3.54 (m, 4H), 4.23 (s, 2H), 6.89 (s, 1H), 7.54-7.63 (m, 3H), 8.63 (s, 1H), 13.88 (br s, 1H)

(b) Step 2

A solution of tert-butyl (Z)-4-({5-chloro-2-[(5-bromo-1H-indazol-3-yl)methylene]-6-hydroxy-3-oxo-2,3-dihydrobenzofuran-7-yl}methyl)piperazine-1-carboxylate (0.095 g, 0.161 mmol) in methylene chloride (4 mL) was added with trifluoroacetic acid (4 mL) at room temperature, and the mixture was stirred overnight. The solvent was evaporated, then the residue was dissolved in methanol (4 mL), the solution was added with a 5% solution of hydrochloric acid in methanol (1 mL), and the mixture was stirred at room temperature for 0.5 hour. The precipitated solid was collected by filtration to obtain a hydrochloride (0.0602 g) as a yellow solid.

The above hydrochloride was suspended in saturated aqueous sodium hydrogencarbonate (1 mL), and thereby washed, and then the resulting orange solid was washed with water to obtain the objective (Z)-5-chloro-2-[(5-bromo-1H-indazol-3-yl)methylene]-6-hydroxy-7-(piperazin-1-ylmethyl)benzofuran-3(2H)-one (0.0339 g, 42%).

$^1$H NMR (300 MHz, DMSO-d$_6$) δ 2.65 (m, 4H), 2.94 (m, 4H), 3.78 (s, 2H), 6.65 (s, 1H), 7.38 (s, 1H), 7.52-7.60 (m, 2H), 8.73 (s, 1H).

Example B17

(Z)-2-[(1H-Indazol-3-yl)methylene]-6-methoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (1.05 g, 3.00 mmol), methanol (0.115 g, 3.60 mmol), and triphenylphosphine (1.18 g, 4.50 mmol) in THF (24 mL) was added with a solution of a 40% solution of diethyl azodicarboxylate in toluene (2.35 g, 5.40 mmol) in THF (12 mL), and the mixture was stirred overnight at room temperature. The reaction mixture was concentrated, and the resulting residue was subjected to silica gel column chromatography (chloroform/methanol) to obtain a crude product (0.712 g) as a white solid.

A solution of the above crude product in methanol (8 mL) was added with 1H-indazole-3-carboxaldehyde (0.288 g, 1.97 mmol) and piperidine (0.0168 mg, 0.197 mmol), and the mixture was stirred at 60° C. for 3 hours. The reaction mixture was concentrated, and the resulting residue was purified by silica gel column chromatography (chloroform/methanol) to obtain tert-butyl (Z)-4-({2-[(1H-indazol-3-yl)methylene]-6-methoxy-3-oxo-2,3-dihydrobenzofuran-7-yl}methyl)piperazine-1-carboxylate (0.206 g, 14%).

$^1$H NMR (300 MHz, DMSO-$d_6$) δ 1.35 (s, 9H), 2.46 (m, 4H), 3.29 (m, 4H), 3.75 (s, 2H), 3.97 (s, 3H), 7.05-7.08 (m, 2H), 7.26 (m, 1H), 7.47 (m, 1H), 7.64 (d, J=8.1 Hz, 1H), 7.81 (d, J=8.8 Hz, 1H), 8.60 (d, J=8.0 Hz, 1H), 13.87 (br s, 1H).

(b) Step 2

A solution of tert-butyl (Z)-4-({2-[(1H-indazol-3-yl)methylene]-6-methoxy-3-oxo-2,3-dihydrobenzofuran-7-yl}methyl)piperazine-1-carboxylate (0.188 g, 0.383 mmol) in methylene chloride (6 mL) was added with trifluoroacetic acid (6 mL) at room temperature, and the mixture was stirred overnight. The solvent was evaporated, then the residue was dissolved in methanol (8 mL), the solution was added with a 5% solution of hydrochloric acid in methanol (2 mL), and the mixture was stirred at room temperature for 2 hours. The precipitated solid was collected by filtration, and added to saturated aqueous sodium hydrogencarbonate, and the mixture was extracted three times with ethyl acetate. The organic layer was dried over anhydrous magnesium sulfate, and then the solvent was evaporated to obtain the objective (Z)-2-[(1H-indazol-3-yl)methylene]-6-methoxy-7-(piperazin-1-ylmethyl)benzofuran-3(2H)-one (0.0130 g, 8%).

$^1$H NMR (300 MHz, DMSO-$d_6$) δ 2.47 (m, 4H), 2.70 (m, 4H), 3.71 (s, 2H), 3.97 (s, 3H), 7.05-7.08 (m, 2H), 7.26 (m, 1H), 7.48 (m, 1H), 7.65 (d, J=8.8 Hz, 1H), 7.80 (d, J=8.8 Hz, 1H), 8.63 (d, J=8.0 Hz, 1H).

Example B18

(Z)-2-[(5-Chloro-1H-indazol-3-yl)methylene]-6-methoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.404 g, 1.16 mmol), methanol (0.0563 mL, 1.39 mmol) and triphenylphosphine (0.456 g, 1.74 mmol) in THF (8 mL) was added with a solution of a 40% solution of diethyl azodicarboxylate in toluene (0.910 g, 2.09 mmol) in THF (4 mL), and the mixture was stirred overnight at room temperature. The reaction mixture was concentrated, and the resulting residue was subjected to silica gel column chromatography (chloroform/ethyl acetate) to obtain a crude product (0.173 g) as a white solid.

A solution of the above crude product in methanol (2 mL) was added with 5-chloro-1H-indazole-3-carboxaldehyde (0.0827 g, 0.458 mmol) and piperidine (0.00390 g, 0.0458 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(5-chloro-1H-indazol-3-yl)methylene]-6-methoxy-3-oxo-2,3-dihydrobenzofuran-7-yl}methyl)piperazine-1-carboxylate (0.0380 g, 6%).

$^1$H NMR (300 MHz, DMSO-$d_6$) δ 1.32 (s, 9H), 2.46 (m, 4H), 3.23 (m, 4H), 3.78 (s, 2H), 3.97 (s, 3H), 7.05-7.08 (m, 2H), 7.47 (dd, J=1.5 Hz, 8.8 Hz, 1H), 7.68 (d, J=8.8 Hz, 1H), 7.81 (d, J=8.8 Hz, 1H), 8.61 (s, 1H), 14.04 (br s, 1H).

(b) Step 2

A solution of tert-butyl (Z)-4-({2-[(5-chloro-1H-indazol-3-yl)methylene]-6-methoxy-3-oxo-2,3-dihydrobenzofuran-7-yl}methyl)piperazine-1-carboxylate (0.0330 g, 0.0629 mmol) in methylene chloride (2 mL) was added with trifluoroacetic acid (2 mL) at room temperature, and the mixture was stirred overnight. The reaction mixture was concentrated, then the residue was added with saturated aqueous sodium hydrogencarbonate (10 mL), and the mixture was extracted three times with ethyl acetate. The organic layer was dried over anhydrous sodium sulfate, and then the solvent was evaporated to obtain (Z)-2-[(5-chloro-1H-indazol-3-yl)methylene]-6-methoxy-7-(piperazin-1-ylmethyl)benzofuran-3(2H)-one (0.0120 g, 44%).

$^1$H NMR (300 MHz, DMSO-$d_6$) δ 2.70 (m, 4H), 3.02 (m, 4H), 3.90 (s, 2H), 3.98 (s, 3H), 7.09-7.12 (m, 2H), 7.50 (d, J=8.8 Hz, 1H), 7.71 (d, J=8.8 Hz, 1H), 7.85 (d, J=8.8 Hz, 1H), 8.58 (s, 1H), 14.06 (br s, 1H).

Example B19

(Z)-2-[(5-Bromo-1H-indazol-3-yl)methylene]-6-methoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (1.68 g, 4.82 mmol), methanol (0.234 mL, 5.78 mmol) and triphenylphosphine (1.90 g, 7.23 mmol) in THF (40 mL) was added with a solution of a 40% solution of diethyl azodicarboxylate in toluene (3.78 g, 8.68 mmol) in THF (20 mL), and the mixture was stirred overnight at room temperature. The reaction mixture was concentrated, and the resulting residue was subjected to silica gel column chromatography (chloroform/methanol) to obtain a crude product (0.818 g) as a white solid.

A solution of the above crude product in methanol (4 mL) was added with 5-bromo-1H-indazole-3-carboxaldehyde (0.176 g, 0.782 mmol) and piperidine (0.00666 g, 0.0782 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(5-bromo-1H-indazol-3-yl)methylene]-6-methoxy-3-oxo-2,3-dihydrobenzofuran-7-yl}methyl)piperazine-1-carboxylate (0.258 g, 9%).

$^1$H NMR (300 MHz, DMSO-$d_6$) δ 1.36 (s, 9H), 2.47 (m, 4H), 3.22 (m, 4H), 3.79 (s, 2H), 3.97 (s, 3H), 7.04-7.06 (m, 2H), 7.55-7.64 (m, 2H), 7.79 (d, J=8.8 Hz, 1H), 8.74 (s, 1H), 14.04 (br s, 1H).

(b) Step 2

A solution of tert-butyl (Z)-4-({2-[(5-bromo-1H-indazol-3-yl)methylene]-6-methoxy-3-oxo-2,3-dihydrobenzofuran-7-yl}methyl)piperazine-1-carboxylate (0.160 g, 0.281 mmol) in methylene chloride (4 mL) was added with trifluoroacetic acid (4 mL) at room temperature, and the mixture was stirred overnight. The reaction mixture was concentrated, and then added with water (10 mL) and saturated aqueous sodium hydrogencarbonate (10 mL), and the mixture was stirred at room temperature for 1 hour. The reaction mixture was filtered, and then the resulting solid was washed with water to obtain the objective (Z)-2-[(5-bromo-1H-indazol-3-yl)methylene]-6-methoxy-7-(piperazin-1-ylmethyl)benzofuran-3(2H)-one (0.0860 g, 65%).

$^1$H NMR (300 MHz, DMSO-d$_6$) δ 2.44 (m, 4H), 2.57 (m, 4H), 3.79 (s, 2H), 3.96 (s, 3H), 7.04 (d, J=8.8 Hz, 1H), 7.10 (s, 1H), 7.50 (d, J=8.8 Hz, 1H), 7.62 (d, J=8.8 Hz, 1H), 7.77 (d, J=8.8 Hz, 1H), 8.75 (s, 1H).

Example B20

(Z)-2-[(1H-Indazol-3-yl)methylene]-6-methoxy-7-[1-(piperazin-1-yl)-ethyl]benzofuran-3(2H)-one (a) Step 1

A solution of tert-butyl 4-[1-(6-hydroxy-3-oxo-2,3-dihydrobenzofuran-7-yl)ethyl]piperazine-1-carboxylate (0.75 g, 2.1 mmol) synthesized in Example B7, Step 2 in tetrahydrofuran (20 mL) was added with methanol (0.20 g, 6.3 mmol), and triphenylphosphine (0.65 g, 2.5 mmol). The reaction mixture was stirred at 0° C. under an argon atmosphere, and added dropwise with a 40% solution of diethyl azodicarboxylate in toluene (1.91 g, 4.4 mmol). After completion of the addition, the mixture was stirred at 40° C. for 20 hours. The solvent was evaporated under reduced pressure, and the residue was subjected to silica gel column chromatography (eluted with hexane/ethyl acetate (85:15→0:100)) to obtain a solid containing the objective substance. The solid was suspended in a mixed solvent of hexane and ethyl acetate and thereby washed, and the insoluble matter was removed by filtration. The filtrate was concentrated, the residue was subjected to silica gel column chromatography (aminopropyl silica was used, eluted with hexane/ethyl acetate (2:1→1:3)) to obtain tert-butyl 4-[1-(6-methoxy-3-oxo-2,3-dihydrobenzofuran-7-yl)ethyl]piperazine-1-carboxylate (0.091 g, 12%).

$^1$H NMR (300 MHz, CDCl$_3$) δ 1.42 (s, 9H), 1.56 (d, J=6.6 Hz, 1H), 2.45 (m, 4H), 3.40 (m, 4H), 3.91 (s, 1H), 4.29 (m, 1H), 4.63 (s, 2H), 6.70 (d, J=8.8 Hz, 1H), 7.60 (d, J=8.8 Hz, 1H).

(b) Step 2

A solution of tert-butyl 4-[1-(6-methoxy-3-oxo-2,3-dihydrobenzofuran-7-yl)-ethyl]piperazine-1-carboxylate (0.091 g, 0.24 mmol) in methanol (3.0 mL) was added with 1H-indazole-3-carboxaldehyde (0.039 g, 0.27 mmol). Then, the mixture was added with 5 drops of piperidine, and then the mixture was stirred at 60° C. for 1 hour. The solvent was evaporated under reduced pressure, and then the residue was subjected to silica gel column chromatography (aminopropyl silica was used, eluted with chloroform/methanol (100:0→97:3)) to obtain tert-butyl (Z)-4-(1-{2-[(1H-indazol-3-yl)methylene]-6-methoxy-3-oxo-2,3-dihydrobenzofuran-7-yl}ethyl)piperazine-1-carboxylate (0.10 g, 85%).

$^1$H NMR (300 MHz, DMSO-d$_6$) δ 1.33 (s, 9H), 1.61 (d, J=6.6 Hz, 3H), 2.44 (m, 4H), 3.30 (m, 4H), 3.96 (s, 3H), 4.21 (m, 1H), 7.06 (d, J=8.8 Hz, 1H), 7.12 (s, 1H), 7.27 (m, 1H), 7.48 (m, 1H), 7.64 (d, J=8.8 Hz, 1H), 7.77 (d, J=8.8 Hz, 1H), 8.70 (d, J=8.1 Hz, 1H), 13.88 (br s, 1H).

(c) Step 3

A solution of tert-butyl (Z)-4-(1-{2-[(1H-indazol-3-yl)methylene]-6-methoxy-3-oxo-2,3-dihydrobenzofuran-7-yl}ethyl)piperazine-1-carboxylate (0.10 g, 0.21 mmol) in methylene chloride (2.0 mL) was added with a 4 M solution of hydrogen chloride in 1,4-dioxane (2.0 mL), and then the mixture was stirred at room temperature for 2 hours. After completion of the reaction, the mixture was azeotroped twice with toluene under reduced pressure. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate, and then the solvent was evaporated under reduced pressure to obtain (Z)-2-[(1H-indazol-3-yl)methylene]-6-methoxy-7-[1-(piperazin-1-yl)ethyl]benzofuran-3(2H)-one (0.080 g, 97%).

$^1$H NMR (300 MHz, DMSO-d$_6$) δ 1.55 (d, J=6.6 Hz, 3H), 2.36 (m, 2H), 2.50 (m, 2H), 2.68 (m, 4H), 3.96 (s, 3H), 4.12 (m, 1H), 7.05 (d, J=8.8 Hz, 1H), 7.10 (s, 1H), 7.26 (m, 1H), 7.47 (m, 1H), 7.63 (d, J=8.8 Hz, 1H), 7.76 (d, J=8.1 Hz, 1H), 8.82 (d, J=8.1 Hz, 1H).

Example B21

(Z)-2-[(1H-Indazol-3-yl)methylene]-6-(2-methoxyethoxy)-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.174 g, 0.500 mmol), methanol (0.457 g, 0.600 mmol) and triphenylphosphine (0.197 g, 0.750 mmol) in THF (4 mL) was added with a solution of a 40% solution of diethyl azodicarboxylate in toluene (2.35 g, 5.40 mmol) in THF (2 mL), and the mixture was stirred overnight at room temperature. The reaction mixture was concentrated, and the resulting residue was purified by silica gel column chromatography to obtain tert-butyl 4-{[6-(2-methoxyethoxy)-3-oxo-2,3-dihydrobenzofuran-7-yl]methyl}piperazine-1-carboxylate (0.203 g, 100%).

$^1$H NMR (300 MHz, CDCl$_3$) δ 1.44 (s, 9H), 2.49 (m, 4H), 3.40 (m, 4H), 3.44 (s, 3H), 3.73 (s, 2H), 3.77 (t, J=5.1 Hz, 2H), 4.23 (t, J=5.1 Hz, 2H), 4.64 (s, 2H), 6.68 (d, J=8.8 Hz, 1H), 7.60 (d, J=8.8 Hz, 1H).

(b) Step 2

A solution of tert-butyl 4-{[6-(2-methoxyethoxy)-3-oxo-2,3-dihydrobenzofuran-7-yl]methyl}piperazine-1-carboxylate (0.203 g, 0.500 mmol) in methanol (2 mL) was added with 1H-indazole-3-carboxaldehyde (0.0730 g, 0.500 mmol) and piperidine (0.00425 g, 0.0500 mmol), and the mixture was stirred at 60° C. for 4 hours. The reaction mixture was concentrated, and the resulting residue was purified by silica gel column chromatography (chloroform/methanol) to obtain a crude product (0.286 g).

A solution of the above crude product in methylene chloride (8 mL) was added with trifluoroacetic acid (8 mL) at room temperature, and the mixture was stirred overnight. The solvent was evaporated, then the residue was dissolved in methanol (8 mL), the solution was added with a 5% solution of hydrochloric acid in methanol (2 mL), and the mixture was stirred at room temperature for 2 hours. The precipitated solid was collected by filtration, and added to saturated aqueous sodium hydrogencarbonate. The mixture was extracted three times with ethyl acetate, the organic layer was dried over anhydrous magnesium sulfate, and the solvent was evaporated to obtain the objective (Z)-2-[(1H-indazol-3-yl)methylene]-6-(2-methoxyethoxy)-7-(piperazin-1-ylmethyl)benzofuran-3(2H)-one (0.0121 g, 5%).

$^1$H NMR (300 MHz, DMSO-d$_6$) δ 2.62 (m, 4H), 2.90 (m, 4H), 3.35 (s, 3H), 3.73 (t, J=4.4 Hz, 2H), 3.78 (s, 2H), 4.32 (t, J=4.4 Hz, 2H), 7.07 (d, J=8.8 Hz, 1H), 7.10 (s, 1H), 7.27 (m, 1H), 7.48 (m, 1H), 7.65 (d, J=8.8 Hz, 1H), 7.79 (d, J=8.8 Hz, 1H), 8.59 (d, J=8.1 Hz, 1H).

Example B22

(Z)-2-[(1H-Indazol-3-yl)methylene]-6-ethoxy-7-(piperazin-1-ylmethyl)benzofuran-3(2H)-one A solution of tert-butyl 4-[(6-hydroxy-3-oxo-2,3-dihydrobenzofuran-7-yl)methyl]piperazine-1-carboxylate (0.174 g, 0.500 mmol), ethanol (0.0276 g, 0.600 mmol) and triphenylphosphine (0.157 g, 0.750 mmol) in THF (4 mL) was added with a solution of a 40% solution of diethyl azodicarboxylate in toluene (0.392 g, 0.900 mmol) in THF (1 mL), and the mixture was stirred at 70° C. for 5 hours in a sealed tube. The reaction mixture was concentrated, and the resulting residue was subjected to silica gel column chromatography (chloroform/ethyl acetate) to obtain a crude product (0.133 g) as a white solid.

A solution of the above crude product in methanol (0.8 mL) was added with 1H-indazole-3-carboxaldehyde (0.0304 g, 0.208 mmol) and piperidine (0.00177 g, 0.0208 mmol), and the mixture was stirred at 60° C. for 2 hours. The reaction mixture was concentrated, and the resulting residue was purified by silica gel column chromatography (chloroform/methanol) to obtain a crude product (0.163 g) as a yellow solid.

A solution of the above crude product in methylene chloride (8 mL) was added with trifluoroacetic acid (8 mL) at room temperature, and the mixture was stirred overnight. The solvent was evaporated, then the residue was dissolved in methanol (20 mL), the solution was added with a 5% solution of hydrochloric acid in methanol (5 mL), and the mixture was stirred at room temperature for 2 hours. The reaction mixture was concentrated, and the resulting solid was suspended in acetonitrile and thereby washed to obtain hydrochloride of the title compound (0.0480 g).

The above hydrochloride was suspended in saturated aqueous sodium hydrogencarbonate, and the suspension was extracted three times with ethyl acetate. The organic layer was washed with saturated brine, and dried over anhydrous magnesium sulfate, and then the solvent was evaporated to obtain the objective (Z)-2-[(1H-indazol-3-yl)methylene]-6-ethoxy-7-(piperazin-1-ylmethyl)benzofuran-3(2H)-one (0.0201 g, 8%).

$^1$H NMR (300 MHz, DMSO-d$_6$) δ 1.40 (t, J=7.3 Hz, 3H), 2.55 (m, 4H), 2.81 (m, 4H), 3.74 (s, 2H), 4.24 (q, J=7.3 Hz, 2H), 7.04 (d, J=8.8 Hz, 1H), 7.08 (s, 1H), 7.26 (t, J=7.3 Hz, 1H), 7.48 (m, 1H), 7.65 (d, J=8.8 Hz, 1H), 7.78 (d, J=8.8 Hz, 1H), 8.61 (d, J=8.8 Hz, 1H).

Example B23

(Z)-2-[(1H-Indazol-3-yl)methylene]-7-(piperazin-1-ylmethyl)-6-propoxybenzofuran-3(2H)-one (a) Step 1

A solution of tert-butyl 4-[(6-hydroxy-3-oxo-2,3-dihydrobenzofuran-7-yl)methyl]piperazine-1-carboxylate (0.174 g, 0.500 mmol), n-propanol (0.0361 g, 0.600 mmol) and triphenylphosphine (0.157 g, 0.750 mmol) in THF (4 mL) was added with a solution of a 40% solution of diethyl azodicarboxylate in toluene (0.392 g, 0.900 mmol) in THF (1 mL), and the mixture was stirred at 70° C. for 5 hours in a sealed tube. The reaction mixture was concentrated, and the resulting residue was subjected to silica gel column chromatography (chloroform/ethyl acetate) to obtain a crude product (0.0882 g) as a white solid.

A solution of the above crude product in methanol (1 mL) was added with 1H-indazole-3-carboxaldehyde (0.0329 g, 0.225 mmol) and piperidine (0.00191 g, 0.0225 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indazol-3-yl)methylene]-3-oxo-6-propoxy-2,3-dihydrobenzofuran-7-yl}methyl)piperazine-1-carboxylate (0.0233 g, 8%).

$^1$H NMR (300 MHz, DMSO-d$_6$) δ 1.04 (t, J=7.3 Hz, 3H), 1.36 (s, 9H), 1.77-1.84 (m, 2H), 2.50 (m, 4H), 3.29 (m, 4H), 3.75 (s, 2H), 4.15 (t, J=5.9 Hz, 2H), 7.04 (d, J=8.8 Hz, 1H), 7.08 (s, 1H), 7.26 (t, J=7.3 Hz, 1H), 7.48 (t, J=7.3 Hz, 1H), 7.65 (d, J=8.8 Hz, 1H), 7.77 (d, J=8.8 Hz, 1H), 8.61 (d, J=8.1 Hz, 1H), 13.86 (br s, 1H).

(b) Step 2

A solution of tert-butyl (Z)-4-({2-[(1H-indazol-3-yl)methylene]-3-oxo-6-propoxy-2,3-dihydrobenzofuran-7-yl}methyl)piperazine-1-carboxylate (0.0210 g, 0.0405 mmol) in methylene chloride (1 mL) was added with trifluoroacetic acid (1 mL) at room temperature, and the mixture was stirred overnight. The reaction mixture was added with saturated aqueous sodium hydrogencarbonate, thereby made basic, and then extracted three times with ethyl acetate. The organic layer was dried over anhydrous sodium sulfate, and then the solvent was evaporated to obtain the objective (Z)-2-[(1H-indazol-3-yl)methylene]-7-(piperazin-1-ylmethyl)-6-propoxybenzofuran-3(2H)-one (0.0160 g, 94%).

$^1$H NMR (300 MHz, DMSO-d$_6$) δ 1.05 (t, J=7.3 Hz, 3H), 1.77-1.98 (m, 2H), 2.56 (m, 4H), 2.83 (m, 4H), 3.74 (s, 2H), 4.14 (t, J=5.9 Hz, 2H), 7.04 (d, J=8.8 Hz, 1H), 7.08 (s, 1H), 7.27 (t, J=7.3 Hz, 1H), 7.48 (t, J=7.3 Hz, 1H), 7.65 (d, J=8.8 Hz, 1H), 7.78 (d, J=8.8 Hz, 1H), 8.62 (d, J=8.1 Hz, 1H).

Example B24

(Z)-2-[(1H-Indazol-3-yl)methylene]-6-butoxy-7-(piperazin-1-ylmethyl)benzofuran-3(2H)-one A solution of tert-butyl 4-[(6-hydroxy-3-oxo-2,3-dihydrobenzofuran-7-yl)methyl]piperazine-1-carboxylate (0.174 g, 0.500 mmol), n-butanol (0.0445 g, 0.600 mmol) and triphenylphosphine (0.157 g, 0.750 mmol) in THF (4 mL) was added with a solution of a 40% solution of diethyl azodicarboxylate in toluene (0.392 g, 0.900 mmol) in THF (1 mL), and the mixture was stirred at 70° C. for 5 hours in a sealed tube. The reaction mixture was concentrated, and the resulting residue was subjected to silica gel column chromatography (chloroform/ethyl acetate) to obtain a crude product (0.135 g) as a white solid.

A solution of the above crude product in methanol (0.5 mL) was added with 1H-indazole-3-carboxaldehyde (0.0239 g, 0.163 mmol) and piperidine (0.00128 g, 0.0163 mmol), and the mixture was stirred at 60° C. for 2 hours. The reaction mixture was concentrated, and the resulting residue was purified by silica gel column chromatography (chloroform/methanol) to obtain a crude product (0.175 g) as a yellow solid.

A solution of the above crude product in a 1 M solution of hydrogen chloride in ethyl acetate (6 mL) was stirred at room temperature for 5 hours. The precipitated solid was collected by filtration to obtain a hydrochloride as a yellow solid.

The above hydrochloride was suspended in saturated aqueous sodium hydrogencarbonate, and the suspension was extracted three times with ethyl acetate. The organic layer was dried over anhydrous magnesium sulfate, and then the solvent was evaporated to obtain the objective (Z)-2-[(1H-indazol-3-yl)methylene]-6-butoxy-7-(piperazin-1-ylmethyl)benzofuran-3(2H)-one (0.0230 g, 10%).

$^1$H NMR (300 MHz, CDCl$_3$) δ 1.00 (t, J=7.3 Hz, 3H), 1.48-1.61 (m, 2H), 1.79-1.88 (m, 2H), 2.68 (m, 4H), 2.97 (m, 4H), 3.87 (s, 2H), 4.12 (t, J=6.6 Hz, 2H), 6.79 (d, J=8.8 Hz, 1H), 7.23 (s, 1H), 7.28 (m, 1H), 7.41 (m, 1H), 7.52 (d, J=8.8 Hz, 1H), 7.76 (d, J=8.8 Hz, 1H), 8.35 (d, J=8.8 Hz, 1H).

Example B25

(Z)-2-[(1H-Indazol-3-yl)methylene]-6-isopropoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.100 g, 0.287 mmol), isopropanol (0.0207 g, 0.344 mmol) and triphenylphosphine (0.113 g, 0.431 mmol) in toluene (2 mL) was added with a solution of a 40% solution of diethyl azodicarboxylate in toluene (0.225 g, 0.517 mmol) in toluene (0.5 mL), and the mixture was stirred at 120° C. for 5 hours in a sealed tube. The reaction mixture was concentrated, and the resulting residue was subjected to silica gel column chromatography (chloroform/ethyl acetate) to obtain a crude product (0.137 g) as a white solid.

A solution of the above crude product in methanol (0.6 mL) was added with 1H-indazole-3-carboxaldehyde (0.0218 g, 0.149 mmol) and piperidine (0.00126 g, 0.0149 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indazol-3-yl)methylene]-6-isopropoxy-3-oxo-2,3-dihydrobenzofuran-7-yl}methyl)piperazine-1-carboxylate (0.0830 g, 55%).

$^1$H NMR (300 MHz, DMSO-d$_6$) δ 1.35 (d, J=7.3 Hz, 6H), 1.36 (s, 9H), 2.50 (m, 4H), 3.30 (m, 4H), 3.74 (s, 2H), 4.89 (m, 1H), 7.05-7.07 (m, 2H), 7.26 (t, J=7.3 Hz, 1H), 7.48 (m, 1H), 7.65 (d, J=8.1 Hz, 1H), 7.75 (d, J=8.8 Hz, 1H), 8.60 (d, J=8.0 Hz, 1H), 13.86 (br s, 1H).

(b) Step 2

A solution of tert-butyl (Z)-4-({2-[(1H-indazol-3-yl)methylene]-6-isopropoxy-3-oxo-2,3-dihydrobenzofuran-7-yl}methyl)piperazine-1-carboxylate (0.0740 g, 0.143 mmol) in methylene chloride (2 mL) was added with trifluoroacetic acid (2 mL) at room temperature, and the mixture was stirred overnight. The reaction mixture was added with water (6 mL) and saturated aqueous sodium hydrogencarbonate (6 mL), and thereby made basic, and then the mixture was stirred at room temperature for 1 hour. The reaction mixture was subjected to suction filtration, and the resulting solid was washed with water to obtain the objective (Z)-2-[(1H-indazol-3-yl)methylene]-6-isopropoxy-7-(piperazin-1-ylmethyl)benzofuran-3(2H)-one (0.0301 g, 50%).

$^1$H NMR (300 MHz, DMSO-d$_6$) δ 1.34 (d, J=5.9 Hz, 6H), 2.46 (m, 4H), 2.66 (m, 4H), 3.68 (s, 2H), 4.88 (m, 1H), 7.05 (d, J=8.8 Hz, 1H), 7.08 (s, 1H), 7.22 (t, J=7.3 Hz, 1H), 7.44 (m, 1H), 7.64 (d, J=8.8 Hz, 1H), 7.73 (d, J=8.8 Hz, 1H), 8.63 (d, J=8.0 Hz, 1H).

Example B26

(Z)-2-[(1H-Indazol-3-yl)methylene]-6-isobutoxy-7-(piperazin-1-ylmethyl)benzofuran-3(2H)-one A solution of tert-butyl 4-[(6-hydroxy-3-oxo-2,3-dihydrobenzofuran-7-yl)methyl]piperazine-1-carboxylate (0.174 g, 0.500 mmol), isobutanol (0.0445 g, 0.600 mmol) and triphenylphosphine (0.157 g, 0.750 mmol) in THF (4 mL) was added with a solution of a 40% solution of diethyl azodicarboxylate in toluene (0.392 g, 0.900 mmol) in THF (1 mL), and the mixture was stirred at 70° C. for 5 hours in a sealed tube. The reaction mixture was concentrated, and the resulting residue was subjected to silica gel column chromatography (chloroform/ethyl acetate) to obtain a crude product (0.232 g) as a white solid.

A solution of the above crude product in methanol (2 mL) was added with 1H-indazole-3-carboxaldehyde (0.0731 g, 0.500 mmol) and piperidine (0.00425 g, 0.0500 mmol), and the mixture was stirred at 60° C. for 2 hours. The reaction mixture was concentrated, and the resulting residue was purified by silica gel column chromatography (chloroform/methanol) to obtain a crude product (0.121 g) as a yellow solid.

A solution of the above crude product in ethyl acetate (1 mL) was added with a 1 M solution of hydrogen chloride in ethyl acetate (6 mL), and the mixture was stirred overnight at room temperature. The precipitated solid was collected by filtration, and suspended in saturated aqueous sodium hydrogencarbonate (6 mL), and the suspension was extracted three times with ethyl acetate. The organic layer was washed with saturated brine, and then dried over anhydrous sodium sulfate, and the solvent was evaporated to obtain the objective (Z)-2-[(1H-indazol-3-yl)methylene]-6-isobutoxy-7-(piperazin-1-ylmethyl)benzofuran-3(2H)-one (0.0160 g, 7%).

$^1$H NMR (300 MHz, CDCl$_3$) δ 1.09 (d, J=6.6 Hz, 6H), 2.17 (m, 1H), 2.72 (m, 4H), 3.01 (m, 4H), 3.88 (s, 2H), 3.89 (d, J=6.6 Hz, 2H), 6.79 (d, J=8.8 Hz, 1H), 7.24 (s, 1H), 7.29 (m, 1H), 7.43 (m, 1H), 7.56 (d, J=8.8 Hz, 1H), 7.76 (d, J=8.8 Hz, 1H), 8.35 (d, J=7.3 Hz, 1H).

Example B27

(Z)-2-[(1H-Indazol-3-yl)methylene]-6-(cyclopropylmethoxy)-7-(piperazin-1-ylmethyl)benzofuran-3(2H)-one A solution of tert-butyl 4-[(6-hydroxy-3-oxo-2,3-dihydrobenzofuran-7-yl)methyl]piperazine-1-carboxylate (0.174 g, 0.500 mmol), cyclopropylmethanol (0.0433 g, 0.600 mmol) and triphenylphosphine (0.157 g, 0.750 mmol) in THF (4 mL) was added with a solution of a 40% solution of diethyl azodicarboxylate in toluene (0.392 g, 0.900 mmol) in THF (1 mL), and the mixture was stirred at 70° C. for 5 hours in a sealed tube. The reaction mixture was concentrated, and the resulting residue was subjected to silica gel column chromatography (chloroform/ethyl acetate) to obtain a crude product (0.0630 g) as a white solid.

A solution of the above crude product in methanol (0.6 mL) was added with 1H-indazole-3-carboxaldehyde (0.0266 g, 0.182 mmol) and piperidine (0.00155 g, 0.0182 mmol), and the mixture was stirred at 60° C. for 2 hours. The reaction mixture was concentrated, and the resulting residue was purified by silica gel column chromatography (chloroform/methanol) to obtain a crude product (0.0703 g) as a yellow solid.

A solution of the above crude product in a 1 M solution of hydrogen chloride in ethyl acetate (2 mL) was stirred at room temperature for 5 hours. The precipitated solid was collected by filtration, and suspended in saturated aqueous sodium hydrogencarbonate (6 mL), and the suspension was extracted three times with ethyl acetate. The organic layer was dried over anhydrous sodium sulfate, and then the solvent was evaporated to obtain the objective (Z)-2-[(1H-indazol-3-yl)methylene]-6-(cyclopropylmethoxy)-7-(piperazin-1-ylmethyl)benzofuran-3(2H)-one (0.0131 g, 6%).

$^1$H NMR (300 MHz, CDCl$_3$) δ 0.37-0.42 (m, 2H), 0.65-0.71 (m, 2H), 0.83-0.92 (m, 2.69 (m, 4H), 2.96 (m, 4H), 3.92 (s, 2H), 3.98 (d, J=6.6 Hz, 2H), 6.75 (d, J=8.8 Hz, 1H), 7.24 (s, 1H), 7.29 (m, 1H), 7.42 (m, 1H), 7.53 (d, J=8.8 Hz, 1H), 7.75 (d, J=8.8 Hz, 1H), 8.37 (d, J=8.0 Hz, 1H).

Example B28

(Z)-2-[(1H-Indazol-3-yl)methylene]-6-(benzyloxy)-7-(piperazin-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.100 g, 0.287 mmol), benzyl alcohol (0.0372 g, 0.344 mmol) and triphenylphosphine (0.113 g, 0.431 mmol) in THF (2 mL) was added with a solution of a 40% solution of diethyl azodicarboxylate in toluene (0.225 g, 0.517 mmol) in THF (0.5 mL), and the mixture was stirred at 70° C. for 2 hours in a sealed tube. The reaction mixture was concentrated, and the resulting residue was subjected to silica gel column chromatography (chloroform/ethyl acetate) to obtain a crude product (0.152 g) as a white solid.

A solution of the above crude product in methanol (1 mL) was added with 1H-indazole-3-carboxaldehyde (0.0281 g, 0.192 mmol) and piperidine (0.00136 g, 0.0160 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indazol-3-yl)methylene]-6-(benzyloxy)-3-oxo-2,3-dihydrobenzofuran-7-yl}methyl)piperazine-1-carboxylate (0.0762 g, 46%).

$^1$H NMR (300 MHz, DMSO-d$_6$) δ 1.36 (s, 9H), 2.49 (m, 4H), 3.29 (m, 4H), 3.78 (s, 2H), 5.36 (s, 2H), 7.09 (s, 1H), 7.15 (d, J=8.8 Hz, 1H), 7.26 (t, J=7.3 Hz, 1H), 7.36-7.55 (m, 6H), 7.65 (d, J=8.8 Hz, 1H), 7.80 (d, J=8.8 Hz, 1H), 8.61 (d, J=8.0 Hz, 1H), 13.87 (br s, 1H).

(b) Step 2

A solution of tert-butyl (Z)-4-({2-[(1H-indazol-3-yl)methylene]-6-(benzyloxy)-3-oxo-2,3-dihydrobenzofuran-7-yl}methyl)piperazine-1-carboxylate (0.0720 g, 0.127 mmol) in methylene chloride (2 mL) was added with trifluoroacetic acid (2 mL) at room temperature, and the mixture was stirred overnight. The reaction mixture was added with water (6 mL) and saturated aqueous sodium hydrogencarbonate (6 mL), and thereby adjusted to pH 8, and then the mixture was stirred at room temperature for 1 hour. The reaction mixture was filtered, and then the resulting solid was washed with water to obtain the objective (Z)-2-[(1H-indazol-3-yl)methylene]-6-(benzyloxy)-7-(piperazin-1-ylmethyl)benzofuran-3(2H)-one (0.0490 g, 82%).

$^1$H NMR (300 MHz, DMSO-d$_6$) δ 2.50 (m, 4H), 2.77 (m, 4H), 3.75 (s, 2H), 5.35 (s, 2H), 7.08 (s, 1H), 7.15 (d, J=8.8 Hz, 1H), 7.27 (m, 1H), 7.36-7.48 (m, 4H), 7.55 (d, J=7.3 Hz, 2H), 7.79 (d, J=8.8 Hz, 1H), 8.63 (d, J=8.8 Hz, 1H).

Example B29

(Z)-2-[(1H-Indazol-3-yl)methylene]-7-(piperazin-1-ylmethyl)-6-(tetrahydro-2H-pyran-4-yloxy)benzofuran-3(2H)-one A solution of tert-butyl 4-[(6-hydroxy-3-oxo-2,3-dihydrobenzofuran-7-yl)methyl]piperazine-1-carboxylate (0.174 g, 0.500 mmol), tetrahydro-4-pyranol (0.0613 g, 0.600 mmol) and triphenylphosphine (0.157 g, 0.750 mmol) in toluene (4 mL) was added with a solution of a 40% solution of diethyl azodicarboxylate in toluene (0.392 g, 0.900 mmol) in toluene (1 mL), and the mixture was stirred at 120° C. for 5 hours in a sealed tube. The reaction mixture was concentrated, and the resulting residue was subjected to silica gel column chromatography (chloroform/ethyl acetate) to obtain a crude product (0.0690 g) as a white solid.

A solution of the above crude product in methanol (1 mL) was added with 1H-indazole-3-carboxaldehyde (0.0233 g, 0.500 mmol) and piperidine (0.00136 g, 0.0160 mmol), and the mixture was stirred at 60° C. for 2 hours. The reaction mixture was concentrated, and the resulting residue was purified by silica gel column chromatography (chloroform/methanol) to obtain a crude product (0.0505 g) as a yellow solid.

A solution of the above crude product in methylene chloride (2 mL) was added with trifluoroacetic acid (2 mL), and the mixture was stirred at room temperature for 1 hour. The reaction mixture was concentrated, and then the resulting residue was dissolved in methanol (4 mL). The solution was added with a 5% solution of hydrogen chloride in methanol (1 mL), the mixture was stirred at room temperature for 1 hour, and then the solvent was evaporated. The residue was added with water (6 mL) and saturated aqueous sodium hydrogencarbonate (6 mL), and the mixture was extracted three times with ethyl acetate. The organic layer was washed with saturated brine, and then dried over anhydrous magnesium sulfate, and the solvent was evaporated to obtain the objective (Z)-2-[(1H-indazol-3-yl)methylene]-7-(piperazin-1-ylmethyl)-6-(tetrahydro-2H-pyran-4-yloxy)benzofuran-3(2H)-one (0.0120 g, 5%).

$^1$H NMR (300 MHz, DMSO-d$_6$) δ 1.66-1.74 (m, 2H), 1.99-2.08 (m, 2H), 2.50 (m, 4H), 2.70 (m, 4H), 3.53-3.61 (m, 2H), 3.86-3.92 (m, 2H), 4.89-4.94 (m, 2H), 7.07 (s, 1H), 7.11 (d, J=8.8 Hz, 1H), 7.26 (m, 1H), 7.48 (m, 1H), 7.65 (d, J=8.8 Hz, 1H), 7.75 (d, J=8.8 Hz, 1H), 8.64 (d, J=8.0 Hz, 1H).

Example B30

(Z)-2-[(1H-Indazol-3-yl)methylene]-6-phenethoxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)-methyl]piperazine-1-carboxylate (0.174 g, 0.500 mmol), 2-phenylethyl alcohol (0.0733 g, 0.600 mmol) and triphenylphosphine (0.157 g, 0.750 mmol) in toluene (4 mL) was added with a solution of a 40% solution of diethyl azodicarboxylate in toluene (0.392 g, 0.900 mmol) in toluene (1 mL), and the mixture was stirred at 120° C. for 3 hours in a sealed tube. The reaction mixture was concentrated, and the resulting residue was subjected to silica gel column chromatography (chloroform/ethyl acetate) to obtain a crude product (0.172 g) as a white solid.

A solution of the above crude product in methanol (1 mL) was added with 1H-indazole-3-carboxaldehyde (0.0428 g, 0.293 mmol) and piperidine (0.00249 g, 0.0293 mmol), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indazol-3-yl)methylene]-3-oxo-6-phenethoxy-2,3-dihydrobenzofuran-7-yl}methyl)piperazine-1-carboxylate (0.0810 g, 27%).

$^1$H NMR (300 MHz, DMSO-d$_6$) δ 1.38 (s, 9H), 2.26 (m, 4H), 3.11 (t, J=5.9 Hz, 2H), 3.19 (m, 4H), 3.64 (s, 2H), 4.44 (t, J=5.9 Hz, 2H), 7.06 (s, 1H), 7.07 (d, J=8.8 Hz, 1H), 7.20-7.49 (m, 7H), 7.63 (d, J=8.1 Hz, 1H), 7.76 (d, J=8.8 Hz, 1H), 8.57 (d, J=8.0 Hz, 1H), 13.86 (br s, 1H).

(b) Step 2

A solution of tert-butyl (Z)-4-({2-[(1H-indazol-3-yl)methylene]-3-oxo-6-phenethoxy-2,3-dihydrobenzofuran-7-yl}methyl)piperazine-1-carboxylate (0.0730 g, 0.126 mmol) in methylene chloride (3 mL) was added with trifluoroacetic acid (3 mL) at room temperature, and the mixture was stirred overnight. The reaction mixture was concentrated, added with methanol (8 mL) and a 5% solution of hydrogen chloride in methanol (2 mL), and thereby made basic, and then the mixture was stirred at room temperature for 2 hours. The reaction mixture was concentrated, and then the residue was suspended in acetonitrile and thereby washed to obtain an orange solid. This solid was suspended in water (4 mL) and saturated aqueous sodium hydrogencarbonate (4 mL), and the suspension was stirred for 1 hour. The reaction mixture was filtered, and then the resulting solid was washed with water to obtain the objective (Z)-2-[(1H-indazol-3-yl)methylene]-6-phenethoxy-7-(piperazin-1-ylmethyl)benzofuran-3(2H)-one (0.0211 g, 34%).

$^1$H NMR (300 MHz, DMSO-d$_6$) δ 2.32 (m, 4H), 2.59 (m, 4H), 3.11 (t, J=5.9 Hz, 2H), 3.64 (s, 2H), 4.41 (t, J=5.9 Hz, 2H), 7.05 (d, J=8.8 Hz, 1H), 7.08 (s, 1H), 7.18-7.62 (m, 7H), 7.63 (d, J=8.1 Hz, 1H), 7.73 (d, J=8.8 Hz, 1H), 8.61 (d, J=8.0 Hz, 1H).

Example B31

(Z)-2-((1H-Indazol-3-yl)methylene)-6-(2-phenoxyethoxy)-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.100 g, 0.287 mmol), 2-phenoxyethanol (0.0475 g, 0.344 mmol) and triphenylphosphine (0.113 g, 0.431 mmol) in THF (2 mL) was added with a solution of a 40% solution of diethyl azodicarboxylate in toluene (0.225 g, 0.517 mmol) in THF (0.5 mL), and the mixture was stirred at 70° C. for 3 hours in a sealed tube. The reaction mixture was concentrated, and the resulting residue was purified by silica gel column chromatography (chloroform/ethyl acetate) to obtain tert-butyl 4-[(3-oxo-6-(2-phenoxyethoxy)-2,3-dihydrobenzofuran-7-yl)methyl]piperazine-1-carboxylate (0.0720 g, 53%).

$^1$H NMR (300 MHz, DMSO-d$_6$) δ 1.43 (s, 9H), 2.47 (m, 4H), 3.38 (m, 4H), 3.72 (s, 2H), 4.34-4.37 (m, 2H), 4.42-4.45 (m, 2H), 4.65 (s, 2H), 6.73 (d, J=8.8 Hz, 1H), 6.92 (d, J=8.1 Hz, 2H), 6.99 (t, J=7.3 Hz, 1H), 7.29-7.34 (m, 2H), 7.62 (d, J=8.8 Hz, 1H).

(b) Step 2

A solution of tert-butyl 4-[(3-oxo-6-(2-phenoxyethoxy)-2,3-dihydrobenzofuran-7-yl)methyl]piperazine-1-carboxylate (0.0720 g, 0.154 mmol) in methanol (1 mL) was added with 1H-indazole-3-carboxaldehyde (0.0225 g, 0.154 mmol) and piperidine (0.00131 g, 0.0154 mmol), and the mixture was stirred at 60° C. for 3 hours. The reaction mixture was concentrated, and the resulting residue was purified by silica gel column chromatography (chloroform/methanol) to obtain tert-butyl (Z)-4-({2-[(1H-indazol-3-yl)methylene]-3-oxo-6-(2-phenoxyethoxy)-2,3-dihydrobenzofuran-7-yl}methyl)piperazine-1-carboxylate (0.0400 g, 43%).

$^1$H NMR (300 MHz, DMSO-d$_6$) δ 1.36 (s, 9H), 2.45 (m, 4H), 3.25 (m, 4H), 3.75 (s, 2H), 4.39-4.42 (m, 2H), 4.52-4.56 (m, 2H), 6.94-7.01 (m, 3H), 7.10-7.14 (m, 2H), 7.23-7.34 (m, 3H), 7.47 (m, 1H), 7.64 (d, J=8.0 Hz, 1H), 7.81 (d, J=8.8 Hz, 1H), 8.57 (d, J=8.0 Hz, 1H).

(c) Step 3

A solution of tert-butyl (Z)-4-({2-[(1H-indazol-3-yl)methylene]-3-oxo-6-(2-phenoxyethoxy)-2,3-dihydrobenzofuran-7-yl}methyl)piperazine-1-carboxylate (0.0380 g, 0.0637 mmol) in methylene chloride (2 mL) was added with trifluoroacetic acid (2 mL) at room temperature, and the mixture was stirred overnight. The reaction mixture was concentrated, and added with water (4 mL) and saturated aqueous sodium hydrogencarbonate (4 mL), and the mixture was stirred for 1 hour. The reaction mixture was filtered, and then the resulting solid was washed with water to obtain the objective (Z)-2-((1H-indazol-3-yl)methylene)-6-(2-phenoxyethoxy)-7-(piperazin-1-ylmethyl)benzofuran-3(2H)-one (0.0280 g, 88%).

$^1$H NMR (300 MHz, DMSO-d$_6$) δ 2.55 (m, 4H), 2.79 (m, 4H), 3.74 (s, 2H), 4.39 (m, 2H), 4.54 (m, 2H), 6.94-7.01 (m, 3H), 7.10-7.14 (m, 2H), 7.23-7.34 (m, 3H), 7.48 (m, 1H), 7.65 (d, J=8.1 Hz, 1H), 7.81 (d, J=8.8 Hz, 1H), 8.57 (d, J=8.1 Hz, 1H).

Example B32

(Z)-2-[(1H-Indazol-3-yl)methylene]-6-methoxy-7-[(4-methylpiperazin-1-yl)methyl]benzofuran-3(2H)-one A solution of 6-hydroxy-7-[(4-methylpiperazin-1-yl)methyl]benzofuran-3(2H)-one (0.438 g, 1.67 mmol), methanol (0.0641 g, 2.00 mmol) and triphenylphosphine (0.658 g, 2.51 mmol) in THF (10 mL) was added with a solution of a 40% solution of diethyl azodicarboxylate in toluene (1.31 g, 3.00 mmol) in THF (6 mL), and the mixture was stirred overnight at room temperature. The reaction mixture was concentrated, and the resulting residue was subjected to silica gel column chromatography (chloroform/methanol) to obtain a crude product (0.199 g) as a white solid.

A solution of the above crude product in methanol (3 mL) was added with 1H-indazole-3-carboxaldehyde (0.105 g, 0.720 mmol) and piperidine (0.00613 g, 0.0720 mmol), and the mixture was stirred at 60° C. for 2 hours, and then concentrated. The residue was subjected to silica gel column chromatography (chloroform/methanol), and the resulting solid was suspended in acetonitrile and thereby washed to obtain the objective (Z)-2-[(1H-indazol-3-yl)methylene]-6-methoxy-7-[(4-methylpiperazin-1-yl)methyl]benzofuran-3 (2H)-one (0.0232 g, 3%).

$^1$H NMR (300 MHz, DMSO-$d_6$) δ 2.09 (s, 3H), 2.29 (m, 4H), 2.51 (m, 4H), 3.71 (s, 2H), 3.97 (s, 3H), 7.05-7.07 (m, 2H), 7.23-7.28 (m, 1H), 7.45-7.51 (m, 1H), 7.65 (d, J=8.8 Hz, 1H), 7.80 (d, J=8.8 Hz, 1H), 8.64 (d, J=8.8 Hz, 1H), 13.88 (br s, 1H).

Example B33

(Z)-2-[(1H-Indazol-3-yl)methylene]-6-methoxy-7-(morpholinomethyl)benzofuran-3(2H)-one

(a) Step 1

A solution of 6-hydroxy-7-(morpholinomethyl)benzofuran-3(2H)-one (0.586 g, 2.35 mmol), methanol (0.0904 g, 2.82 mmol) and triphenylphosphine (0.923 g, 3.52 mmol) in THF (12 mL) was added with a solution of a 40% solution of diethyl azodicarboxylate in toluene (1.84 g, 4.23 mmol) in THF (6 mL), and the mixture was stirred overnight at room temperature. The reaction mixture was concentrated, and the resulting residue was purified by silica gel column chromatography (chloroform/methanol) to obtain 6-methoxy-7-(morpholinomethyl)benzofuran-3(2H)-one (0.509 g, 82%).

$^1$H NMR (300 MHz, DMSO-$d_6$) δ 2.40 (m, 4H), 3.51 (m, 4H), 3.53 (s, 2H), 3.91 (s, 3H), 4.77 (s, 2H), 6.89 (d, J=8.8 Hz, 1H), 7.60 (d, J=8.8 Hz, 1H).

(b) Step 2

A solution of 6-methoxy-7-(morpholinomethyl)benzofuran-3(2H)-one (0.131 g, 0.500 mmol) in methanol (2 mL) was added with 1H-indazole-3-carboxaldehyde (0.0877 g, 0.600 mmol) and piperidine (0.00425 g, 0.0500 mmol), and the mixture was stirred at 60° C. for 2 hours. The reaction mixture was concentrated, and the resulting residue was subjected to silica gel column chromatography (chloroform/methanol), and the resulting crude product was crystallized from ethyl acetate. The precipitated solid was collected by filtration, and then suspended in acetonitrile and thereby washed to obtain the objective (Z)-2-[(1H-indazol-3-yl)methylene]-6-methoxy-7-(morpholinomethyl)benzofuran-3(2H)-one (0.0238 g). Further, the filtrate was concentrated, and the resulting residue was purified again by silica gel column chromatography (chloroform/methanol) to obtain the objective (Z)-2-[(1H-indazol-3-yl)methylene]-6-methoxy-7-(morpholinomethyl)benzofuran-3(2H)-one (0.0254 g) (0.0492 g, 25% in total).

$^1$H NMR (300 MHz, DMSO-$d_6$) δ 3.36 (m, 4H), 3.55 (m, 4H), 3.73 (s, 2H), 3.97 (s, 3H), 7.05-7.08 (m, 2H), 7.24 (t, J=7.3 Hz, 1H), 7.47 (t, J=7.3 Hz, 1H), 7.64 (d, J=8.1 Hz, 1H), 7.80 (d, J=8.1 Hz, 1H), 8.63 (d, J=8.1 Hz, 1H), 13.87 (br s, 1H).

Example B34

(Z)-2-[(1H-Indazol-3-yl)methylene]-6-(2-hydroxyethoxy)-7-(piperazin-1-ylmethyl)benzofuran-3(2H)-one

(a) Step 1

The synthesis was performed with reference to the known literature (Tetrahedron, Vol. 63, p. 419, 2007). A solution of 1H-indazole-3-carboxaldehyde (0.888 g, 6.08 mmol) in methylene chloride (8 mL) was added with 50% aqueous potassium hydroxide (6 mL) and tetrabutylammonium bromide (0.0196 g, 0.0608 mmol), and the mixture was cooled on ice. The reaction mixture was added dropwise with 2-(trimethylsilyl)ethoxymethyl chloride (1.18 mL, 6.67 mmol), and the mixture was stirred for 1 hour under ice cooling, and then at room temperature overnight. The reaction mixture was added with water (30 mL), and the mixture was extracted three times with methylene chloride. The organic layer was dried over magnesium sulfate, and concentrated, and the resulting residue was purified by silica gel column chromatography (hexane/ethyl acetate) to obtain N-{[2-(trimethylsilyl)ethoxy]methyl}-1H-indazole-3-carboxaldehyde.

Positional isomer (1): 1.04 g (61%)

$^1$H NMR (300 MHz, CDCl$_3$) δ −0.06 (s, 9H), 0.90 (t, J=8.8 Hz, 2H), 3.59 (t, J=8.8 Hz, 2H), 5.83 (s, 2H), 7.40 (m, 1H), 7.51 (m, 1H), 7.66 (d, J=8.0 Hz, 1H), 8.32 (d, J=8.1 Hz, 1H), 10.27 (s, 1H).

Positional isomer (2): 0.362 g (21%)

$^1$H NMR (300 MHz, CDCl$_3$) δ −0.04 (s, 9H), 0.93 (t, J=8.8 Hz, 2H), 3.65 (t, J=8.8 Hz, 2H), 6.11 (s, 2H), 7.41-7.45 (m, 2H), 7.85-7.88 (m, 1H), 8.12-8.14 (m, 1H), 10.42 (s, 1H).

(b) Step 2

A solution of the positional isomer (2) of N-{[2-(trimethylsilyl)ethoxy]methyl}-1H-indazole-3-carboxaldehyde (0.354 g, 1.28 mmol) obtained in Step 1 in methanol (5 mL) was added with tert-butyl 4-[(6-hydroxy-3-oxo-2,3-dihydrobenzofuran-7-yl)methyl]piperazine-1-carboxylate (0.446 g, 1.28 mmol) and piperidine (0.0109 g, 0.128 mmol), and the mixture was stirred at 60° C. for 5 hours. The reaction mixture was concentrated, and the resulting residue was purified by silica gel column chromatography (hexane/ethyl acetate) to obtain tert-butyl (Z)-4-({6-hydroxy-3-oxo-2-[(N-{[2-(trimethylsilyl)ethoxy]methyl}-1H-indazol-3-yl)methylene]-2,3-dihydrobenzofuran-7-yl}methyl)piperazine-1-carboxylate (0.419 g, 53%).

$^1$H NMR (300 MHz, CDCl$_3$) δ −0.05 (s, 9H), 0.93 (t, J=8.1 Hz, 2H), 1.47 (s, 9H), 2.47-2.83 (m, 8H), 3.62 (t, J=8.1 Hz, 2H), 3.99 (s, 2H), 5.90 (s, 2H), 6.71 (d, J=8.8 Hz, 1H), 7.21-7.31 (m, 2H), 7.40 (m, 1H), 7.67 (d, J=8.0 Hz, 1H), 7.80 (d, J=8.8 Hz, 1H), 8.28 (d, J=8.8 Hz, 1H).

(c) Step 3

A solution of tert-butyl (Z)-4-({6-hydroxy-3-oxo-2-[(N-{[2-(trimethylsilyl)ethoxy]methyl}-1H-indazol-3-yl)methylene]-2,3-dihydrobenzofuran-7-yl}methyl)piperazine-1-carboxylate (0.416 g, 0.686 mmol) obtained in Step 2 in DMF (6 mL) was added with potassium carbonate (1.42 g, 10.3 mmol), and the mixture was stirred at room temperature for 10 minutes. The reaction mixture was added with 1,3-dioxolan-2-one (0.725 g, 8.23 mmol), and the mixture was stirred at 100° C. for 5 hours. The reaction mixture was cooled to room temperature, and then added with water (60 mL), and the mixture was vigorously stirred at room temperature for 30 minutes. The precipitated solid was collected by filtration to obtain tert-butyl (Z)-4-{[6-(2-hydroxyethoxy)-3-oxo-2-[(N-{[2-(trimethylsilyl)ethoxy]methyl}-1H-indazol-3-yl)methylene]-2,3-dihydrobenzofuran-7-yl]methyl}piperazine-1-carboxylate (0.331 g, 74%).

$^1$H NMR (300 MHz, CDCl$_3$) δ −0.05 (s, 9H), 0.93 (t, J=8.1 Hz, 2H), 1.40 (s, 9H), 2.60 (m, 4H), 3.49 (m, 4H), 3.63 (t, J=8.1 Hz, 2H), 3.79 (s, 2H), 3.83 (t, J=4.4 Hz, 2H), 4.39 (t, J=4.4 Hz, 2H), 5.93 (s, 2H), 6.89 (d, J=8.1 Hz, 1H), 7.29 (m,

1H), 7.34 (s, 1H), 7.41 (m, 1H), 7.81 (d, J=8.8 Hz, 1H), 7.82 (d, J=8.1 Hz, 1H), 8.53 (d, J=8.8 Hz, 1H).

(d) Step 4

A solution of tert-butyl (Z)-4-{[6-(2-hydroxyethoxy)-3-oxo-2-[(N-{[2-(trimethylsilyl)ethoxy]methyl}-1H-indazol-3-yl)methylene]-2,3-dihydrobenzofuran-7-yl]methyl}piperazine-1-carboxylate (0.100 g, 0.154 mmol) obtained in Step 3 in THF (1 mL) was added with a 1 M solution of tetrabutylammonium fluoride in THF (1.54 mL, 1.54 mmol), and the mixture was refluxed for 3 hours by heating. The reaction mixture was cooled to room temperature, and then added with water (20 mL), the mixture was extracted three times with ethyl acetate, and the organic layer was washed with saturated brine. The organic layer was dried over magnesium sulfate, and concentrated, and the resulting residue was purified by silica gel column chromatography (chloroform/methanol) to obtain tert-butyl (Z)-4-({2-[(1H-indazol-3-yl)methylene]-6-(2-hydroxyethoxy)-3-oxo-2,3-dihydrobenzofuran-7-yl}methyl)piperazine-1-carboxylate (0.0440 g, 54%).

$^1$H NMR (300 MHz, CDCl$_3$) δ 1.40 (s, 9H), 2.56 (m, 4H), 3.45 (m, 4H), 3.81-3.84 (m, 4H), 4.39 (t, J=4.4 Hz, 2H), 6.87 (d, J=8.8 Hz, 1H), 7.29-7.34 (m, 1H), 7.30 (s, 1H), 7.47 (m, 1H), 7.57 (d, J=8.0 Hz, 1H), 7.81 (d, J=8.8 Hz, 1H), 8.42 (d, J=8.0 Hz, 1H).

(e) Step 5

A solution of tert-butyl (Z)-4-({2-[(1H-indazol-3-yl)methylene]-6-(2-hydroxyethoxy)-3-oxo-2,3-dihydrobenzofuran-7-yl}methyl)piperazine-1-carboxylate (0.0400 g, 0.0768 mmol) in methylene chloride (1 mL) was added with trifluoroacetic acid (1 mL), and the mixture was stirred overnight at room temperature. The reaction mixture was concentrated, then the residue was added with methanol (4 mL) and a 5% solution of hydrogen chloride in methanol (1 mL), and the mixture was stirred at room temperature for 2 hours. The solvent was evaporated, and the resulting solid was suspended in acetonitrile and thereby washed to obtain a hydrochloride (0.0212 g) as a yellow solid.

The above hydrochloride was suspended in saturated aqueous sodium hydrogencarbonate (0.5 mL) and thereby washed, and then the resulting brown solid was washed with water to obtain the objective (Z)-2-[(1H-indazol-3-yl)methylene]-6-(2-hydroxyethoxy)-7-(piperazin-1-ylmethyl)benzofuran-3(2H)-one (0.00226 g, 6%).

$^1$H NMR (300 MHz, DMSO-d$_6$) δ 2.46 (m, 4H), 2.68 (m, 4H), 3.72-3.80 (m, 4H), 4.23 (m, 2H), 5.09 (br s, 1H), 7.05-7.08 (m, 2H), 7.27 (m, 1H), 7.48 (m, 1H), 7.65 (d, J=8.1 Hz, 1H), 7.77 (d, J=8.1 Hz, 1H), 8.63 (d, J=8.1 Hz, 1H).

Example B35

(Z)-2-[(1H-Indazol-3-yl)methylene]-6-methoxy-7-(piperidin-4-yloxy)benzofuran-3(2H)-one (a) Step 1

Ethyl acetate (5.0 mL) was added with copper(II) bromide (2.2 g, 10 mmol), the mixture was refluxed by heating, and added with a solution of 2',3'-dihydroxy-4'-methoxyacetophenone hydrate (1.0 g, 5.0 mmol) in chloroform (10 mL), and the mixture was refluxed for 20 hours by heating. The reaction mixture was cooled to room temperature, then the solid in the reaction mixture was removed by filtration, and the filtrate was concentrated under reduced pressure.

The residue was dissolved in acetonitrile (25 mL), then the solution was added with potassium carbonate (1.3 g, 10 mmol), and the mixture was stirred at 30° C. for 3 hours. The reaction mixture was added with water, the mixture was extracted with ethyl acetate, and then the organic layer was washed successively with water and saturated brine, and dried over anhydrous magnesium sulfate. The solvent was evaporated under reduced pressure, and then the residual solid was suspended in chloroform and thereby washed, collected by filtration, and dried to obtain 7-hydroxy-6-methoxybenzofuran-3(2H)-one (0.54 g, 59%).

$^1$H NMR (300 MHz, CDCl$_3$) δ 3.89 (s, 3H), 4.76 (s, 2H), 6.85 (d, J=8.8 Hz, 1H), 7.12 (d, J=8.8 Hz, 1H), 9.35 (s, 1H).

(b) Step 2

A solution of 7-hydroxy-6-methoxybenzofuran-3(2H)-one (0.30 g, 1.7 mmol) in DMF (5.0 mL) was added with potassium carbonate (1.0 g, 7.2 mmol), and N-Boc-4-bromopiperidine (0.50 g, 1.9 mmol), and the mixture was stirred at 80° C. for 12 hours. The reaction mixture was added with ethyl acetate, and then the organic layer was washed successively with water and saturated brine, and dried over anhydrous magnesium sulfate. The solvent was evaporated under reduced pressure, and then the residue was subjected to silica gel column chromatography (eluted with hexane/ethyl acetate (1:1)) to obtain tert-butyl 4-(6-methoxy-3-oxo-2,3-dihydrobenzofuran-7-yloxy)piperidine-1-carboxylate (0.019 g, 3%).

$^1$H NMR (300 MHz, CDCl$_3$) δ 1.47 (s, 9H), 1.71-1.96 (m, 4H), 3.19-3.32 (m, 2H), 3.73-3.88 (m, 2H), 3.95 (s, 3H), 4.39-4.50 (m, 1H), 4.66 (s, 2H), 6.72 (d, J=8.8 Hz, 1H), 7.42 (d, J=8.1 Hz, 1H).

(c) Step 3

A solution of tert-butyl 4-(6-methoxy-3-oxo-2,3-dihydrobenzofuran-7-yloxy)piperidine-1-carboxylate (0.019 g, 0.052 mmol) in methanol (2.0 mL) was added with 1H-indazole-3-carboxaldehyde (0.008 g, 0.057 mmol). Then, the mixture was added with 5 drops of piperidine, and the mixture was stirred at room temperature for 2 hours. The reaction mixture was added with toluene, the solvent was evaporated under reduced pressure, and then the residue was purified by silica gel column chromatography (eluted with hexane/ethyl acetate (2:1→1:4)) to obtain tert-butyl (Z)-4-{2-[(1H-indazol-3-yl)methylene]-6-methoxy-3-oxo-2,3-dihydrobenzofuran-7-yloxy}piperidine-1-carboxylate (0.020 g, 79%).

$^1$H NMR (300 MHz, DMSO-d$_6$) δ 1.37 (s, 9H), 1.54-1.76 (m, 2H), 1.86-2.03 (m, 2H), 2.96-3.18 (m, 2H), 3.68-3.85 (m, 2H), 3.98 (s, 3H), 4.59 (m, 1H), 7.09 (d, J=8.8 Hz, 1H), 7.11 (s, 1H), 7.25 (m, 1H), 7.46 (m, 1H), 7.60 (d, J=8.1 Hz, 1H), 7.65 (d, J=8.8 Hz, 1H), 8.56 (d, J=8.1 Hz, 1H), 13.88 (br s, 1H).

(d) Step 4

A solution of tert-butyl (Z)-4-{2-[(1H-indazol-3-yl)methylene]-6-methoxy-3-oxo-2,3-dihydrobenzofuran-7-yloxy}piperidine-1-carboxylate (0.020 g, 0.041 mmol) in methylene chloride (3.0 mL) was added with a 4 M solution of hydrogen chloride in 1,4-dioxane (3.0 mL), and then the mixture was stirred at room temperature for 2 hours. After completion of the reaction, the mixture was azeotroped twice with toluene under reduced pressure. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate, and then the solvent was evaporated under reduced pressure to obtain (Z)-2-[(1H-indazol-3-yl)methylene]-6-methoxy-7-(piperidin-4-yloxy)benzofuran-3(2H)-one (0.016 g, 100%).

$^1$H NMR (300 MHz, DMSO-$d_6$) δ 1.68-1.85 (m, 2H), 1.97-2.11 (m, 2H), 2.74 (m, 2H), 3.10-3.26 (m, 2H), 3.98 (s, 3H), 4.50 (m, 1H), 7.09 (d, J=8.8 Hz, 1H), 7.14 (s, 1H), 7.31 (m, 1H), 7.49 (m, 1H), 7.59 (d, J=8.8 Hz, 1H), 7.66 (d, J=8.1 Hz, 1H), 8.54 (d, J=8.1 Hz, 1H).

Example B36

(Z)-2-[(1H-Indazol-3-yl)methylene]-6-hydroxy-7-(piperazine-1-carbonyl)benzofuran-3(2H)-one (a) Step 1

A suspension of aluminum chloride (2.7 g, 21 mmol) in nitrobenzene (6.0 mL) was cooled to 0° C., and stirred. The suspension was added with chloroacetyl chloride (0.60 g, 6.2 mmol), and then added portionwise with a suspension of 2,6-dihydroxybenzoic acid (0.064 g, 4.1 mmol) in nitrobenzene (6.0 mL). After completion of the addition, the reaction mixture was stirred at 40° C. for 12 hours. The reaction mixture was added with ethyl acetate and ice water, the mixture was stirred at room temperature for 1 hour, and then the organic layer was separated. The organic layer was extracted with 2 N aqueous sodium hydroxide, and the aqueous layer was made acidic with 3 N hydrochloric acid. The precipitated solid was collected by filtration and dried to obtain 6-hydroxy-3-oxo-2,3-dihydrobenzofuran-7-carboxylic acid (0.76 g, 89%).

$^1$H NMR (300 MHz, DMSO-$d_6$) δ 4.85 (s, 2H), 6.70 (d, J=8.8 Hz, 1H), 7.68 (d, J=8.8 Hz, 1H).

(b) Step 2

A solution of 6-hydroxy-3-oxo-2,3-dihydrobenzofuran-7-carboxylic acid (0.060 g, 0.31 mmol) in methylene chloride (2.0 mL) was successively added with 1-hydroxybenzotriazole monohydrate (0.008 g, 0.052 mmol), 1-ethyl-3-(3-dimethylaminopropyl)carbodiimide hydrochloride (0.086 g, 0.45 mmol), and N-Boc-piperazine (0.067 g, 0.36 mmol), and the mixture was stirred at room temperature for 14 hours. The reaction mixture was added with water, the mixture was extracted with ethyl acetate, and the organic layer was washed successively with water and saturated brine, and then dried over anhydrous magnesium sulfate. The solvent was evaporated under reduced pressure, and the residue was subjected to silica gel column chromatography (eluted with chloroform/methanol (99:1→90:10)) to obtain tert-butyl 4-(6-hydroxy-3-oxo-2,3-dihydrobenzofuran-7-carbonyl)piperazine-1-carboxylate (0.072 g, 66%).

$^1$H NMR (300 MHz, CDCl$_3$) δ 1.49 (s, 9H), 3.41-3.82 (m, 8H), 4.67 (s, 2H), 6.77 (d, J=8.8 Hz, 1H), 7.68 (d, J=8.8 Hz, 1H).

(c) Step 3

A solution of tert-butyl 4-(6-hydroxy-3-oxo-2,3-dihydrobenzofuran-7-carbonyl)piperazine-1-carboxylate (0.048 g, 0.13 mmol) in methanol (2.0 mL) was added with 1H-indazole-3-carboxaldehyde (0.025 g, 0.17 mmol). Then, the mixture was added with 7 drops of piperidine, and the mixture was stirred at 50° C. for 4 hours. The solid formed was removed by filtration, the filtrate was concentrated, and then the residue was subjected to silica gel column chromatography (eluted with chloroform/methanol (97:3→90:10)) to obtain tert-butyl (Z)-4-{2-[(1H-indazol-3-yl)methylene]-6-hydroxy-3-oxo-2,3-dihydrobenzofuran-7-carbonyl}piperazine-1-carboxylate (0.054 g, 85%).

$^1$H NMR (300 MHz, DMSO-$d_6$) δ 1.35 (br s, 9H), 3.00-3.59 (m, 6H), 3.68 (m, 1H), 3.83 (m, 1H), 6.85 (d, J=8.8 Hz, 1H), 7.06 (s, 1H), 7.22 (m, 1H), 7.45 (m, 1H), 7.62 (d, J=8.1 Hz, 1H), 7.71 (d, J=8.8 Hz, 1H), 8.38 (d, J=8.8 Hz, 1H), 13.84 (s, 1H).

(d) Step 4

A solution of tert-butyl (Z)-4-{2-[(1H-indazol-3-yl)methylene]-6-hydroxy-3-oxo-2,3-dihydrobenzofuran-7-carbonyl}piperazine-1-carboxylate (0.054 g, 0.11 mmol) in methylene chloride (3.0 mL) was added with a 4 M solution of hydrogen chloride in 1,4-dioxane (3.0 mL), and then the mixture was stirred at room temperature for 2 hours. After completion of the reaction, the mixture was azeotroped twice with toluene under reduced pressure. The residual solid was added with water, and then the mixture was adjusted to pH 9 with saturated aqueous sodium hydrogencarbonate, and the solid was collected by filtration and dried to obtain (Z)-2-[(1H-indazol-3-yl)methylene]-6-hydroxy-7-(piperazine-1-carbonyl)benzofuran-3(2H)-one (0.018 g, 42%).

$^1$H NMR (300 MHz, DMSO-$d_6$) δ 2.75-3.11 (m, 4H), 3.21-3.62 (m, 2H), 3.62-4.10 (m, 2H), 7.05 (d, J=8.8 Hz, 1H), 7.10 (s, 1H), 7.18 (m, 1H), 7.39 (d, J=8.8 Hz, 1H), 7.43 (m, 1H), 7.59 (d, J=8.1 Hz, 1H), 8.48 (d, J=8.1 Hz, 1H), 13.63 (br s, 1H).

Example B37

(Z)-2-[(1H-Indazol-3-yl)methylene]-6-methoxy-7-(piperazine-1-carbonyl)benzofuran-3(2H)-one (a) Step 1

A solution of 6-hydroxy-3-oxo-2,3-dihydrobenzofuran-7-carboxylic acid (0.30 g, 1.6 mmol) in DMF (10 mL) was added with potassium carbonate (0.63 g, 4.6 mmol) and dimethyl sulfate (0.48 g, 3.8 mmol), and the mixture was stirred at room temperature for 1 hour, and at 40° C. for 3 hours. The reaction mixture was added with water, the mixture was extracted with ethyl acetate, and then the organic layer was washed successively with water and saturated brine, and dried over anhydrous magnesium sulfate. The solvent was evaporated under reduced pressure to obtain methyl 6-methoxy-3-oxo-2,3-dihydrobenzofuran-7-carboxylate (0.25 g, 71%).

$^1$H NMR (300 MHz, CDCl$_3$) δ 3.95 (s, 3H), 3.98 (s, 3H), 4.70 (s, 2H), 6.74 (d, J=8.8 Hz, 1H), 7.75 (d, J=8.8 Hz, 1H).

(b) Step 2

A solution of methyl 6-methoxy-3-oxo-2,3-dihydrobenzofuran-7-carboxylate (0.070 g, 0.32 mmol) in methanol (5.0 mL) was added with 1H-indazole-3-carboxaldehyde (0.046 g, 0.32 mmol). Then, the mixture was added with 7 drops of piperidine, then the mixture was stirred at room temperature for 2 hours, and the solid formed was collected by filtration to obtain the objective substance. Further, the filtrate was concentrated, and then the residue was subjected to silica gel column chromatography (eluted with chloroform/methanol (97:3→90:10)) to obtain the objective substance. Two portions of the objective substance was combined to obtain 0.090 g (80%) of methyl (Z)-2-[(1H-indazol-3-yl)methylene]-6-methoxy-3-oxo-2,3-dihydrobenzofuran-7-carboxylate.

$^1$H NMR (300 MHz, DMSO-d$_6$) δ 3.99 (s, 3H), 4.01 (s, 3H), 7.12 (s, 1H), 7.16 (d, J=8.8 Hz, 1H), 7.32 (m, 1H), 7.48 (m, 1H), 7.65 (d, J=8.1 Hz, 1H), 7.99 (d, J=8.8 Hz, 1H), 8.47 (d, J=8.1 Hz, 1H), 13.93 (br s, 1H).

(c) Step 3

Methyl (Z)-2-[(1H-indazol-3-yl)methylene]-6-methoxy-3-oxo-2,3-dihydrobenzofuran-7-carboxylate (0.070 g, 0.20 mmol) was added with methanol (3.0 mL), dimethyl sulfoxide (1.0 mL), and water (0.50 mL), and then added with lithium hydroxide monohydrate (0.025 g, 0.60 mmol), and the mixture was stirred at 30° C. for 10 hours. The reaction mixture was made acidic with 3 N hydrochloric acid, and the solid formed was collected by filtration. The solid was suspended in chloroform/methanol (95:5), then collected by filtration and dried to obtain (Z)-2-[(1H-indazol-3-yl)methylene]-6-methoxy-3-oxo-2,3-dihydrobenzofuran-7-carboxylic acid (0.045 g, 67%).

$^1$H NMR (300 MHz, DMSO-d$_6$) δ 4.00 (s, 3H), 7.12 (s, 1H), 7.13 (d, 1H), 7.30 (m, 1H), 7.48 (m, H), 7.64 (d, J=8.1 Hz, 1H), 7.94 (d, J=8.8 Hz, 1H), 8.65 (d, J=8.1 Hz, 1H), 13.89 (s, 1H).

(d) Step 4

A solution of (Z)-2-[(1H-indazol-3-yl)methylene]-6-methoxy-3-oxo-2,3-dihydrobenzofuran-7-carboxylic acid (0.034 g, 0.10 mmol) in methylene chloride (3.0 mL) was successively added with 1-hydroxybenzotriazole monohydrate (0.004 g, 0.026 mmol), 1-ethyl-3-(3-dimethylaminopropyl)carbodiimide hydrochloride (0.029 g, 0.15 mmol), and N-Boc-piperazine (0.024 g, 0.13 mmol), and the mixture was stirred at 30° C. for 4 hours. The reaction mixture was added with water, the mixture was extracted with methylene chloride, and then the organic layer was successively washed with water, 1 N hydrochloric acid, water, saturated aqueous sodium hydrogencarbonate, and saturated brine, and dried over anhydrous magnesium sulfate.

The solvent was evaporated under reduced pressure, the residue was dissolved in a mixed solvent of methylene chloride (2.0 mL) and methanol (1.0 mL), the solution was added with a 4 M solution of hydrogen chloride in 1,4-dioxane (3.0 mL), and then the mixture was stirred at room temperature for 2 hours. The mixture was azeotroped twice with toluene under reduced pressure to remove the solvent and hydrogen chloride. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate, and then the solvent was evaporated under reduced pressure. The residual solid was suspended in methylene chloride/diethyl ether (1:1) and thereby washed, and then collected by filtration and dried to obtain (Z)-2-[(1H-indazol-3-yl)methylene]-6-methoxy-7-(piperazine-1-carbonyl)benzofuran-3(2H)-one (0.022 g, 54%).

$^1$H NMR (300 MHz, DMSO-d$_6$) δ 2.56 (m, 2H), 2.78 (m, 2H), 3.19 (m, 2H), 3.54-3.71 (m, 1H), 3.71-3.88 (m, 1H), 3.98 (s, 3H), 7.10 (s, 1H), 7.12 (d, J=8.8 Hz, 1H), 7.24 (m, 1H), 7.47 (m, 1H), 7.64 (d, J=8.1 Hz, 1H), 7.90 (d, J=8.8 Hz, 1H), 8.43 (d, J=8.8 Hz, 1H).

Example B38

(Z)-2-[(1H-Indazol-3-yl)methylene]-5,6-dimethoxy-7-(piperazin-1-ylmethyl)benzofuran-3(2H)-one (a) Step 1

A solution of 2'-hydroxy-4',5'-dimethoxyacetophenone (1.0 g, 5.1 mmol) in methylene chloride (20 mL) was added with dichloromethyl methyl ether (1.6 g, 14 mmol) under an argon atmosphere. Then, the mixture was slowly added with titanium(IV) chloride (2.2 mL, 20 mmol) at 0° C., and then the mixture was refluxed for 18 hours by heating. The reaction mixture was added with ice water, the mixture was extracted with ethyl acetate, and the organic layer was washed successively with water and saturated brine, and then dried over anhydrous magnesium sulfate. The organic layer was concentrated under reduced pressure, and then the residue was subjected to silica gel column chromatography (eluted with hexane/ethyl acetate (3:1→1:1)) to obtain 3-acetyl-2-hydroxy-5,6-dimethoxybenzaldehyde (0.12 g, 10%).

$^1$H NMR (300 MHz, CDCl$_3$) δ 2.68 (s, 3H), 3.88 (s, 3H), 4.11 (s, 3H), 7.77 (s, 1H), 10.35 (s, 1H), 12.48 (s, 1H).

(b) Step 2

A solution of 3-acetyl-2-hydroxy-5,6-dimethoxybenzaldehyde (0.14 g, 0.63 mmol) in methylene chloride (5.0 mL) was added with N-Boc-piperazine (0.13 g, 0.70 mmol), and the mixture was stirred at room temperature for 10 minutes. The reaction mixture was cooled to 0° C., and then added portionwise with sodium triacetoxyborohydride (0.16 g, 0.76 mmol). After completion of the addition, the reaction mixture was warmed to room temperature, and stirred for 10 hours. The reaction mixture was added with methylene chloride, and the organic layer was washed successively with water and saturated brine, and then dried over anhydrous magnesium sulfate. The solvent was evaporated under reduced pressure, and the residue was subjected to silica gel column chromatography (eluted with hexane/ethyl acetate (2:1→3:7)) to obtain tert-butyl 4-(3-acetyl-2-hydroxy-5,6-dimethoxybenzyl)piperazine-1-carboxylate (0.20 g, 80%).

$^1$H NMR (300 MHz, CDCl$_3$) δ 1.45 (s, 9H), 2.50 (m, 4H), 2.61 (s, 3H), 3.43 (m, 4H), 3.71 (s, 2H), 3.86 (s, 3H), 3.91 (s, 3H), 7.20 (s, 1H).

(c) Step 3

A solution of tert-butyl 4-(3-acetyl-2-hydroxy-5,6-dimethoxybenzyl)piperazine-1-carboxylate (0.20 g, 0.50 mmol) in pyridine (1.0 mL) was successively added with acetic anhydride (1.0 mL) and 4-dimethylaminopyridine (0.010 g), and the mixture was stirred at room temperature for 15 hours. The reaction mixture was added with ice water, the mixture was extracted with ethyl acetate, and the organic layer was washed successively with water and saturated brine, and then dried over anhydrous magnesium sulfate. The solvent was evaporated under reduced pressure, and then the residue was subjected to silica gel column chromatography (eluted with hexane/ethyl acetate (2:1→3:7)) to obtain tert-butyl 4-(2-acetoxy-3-acetyl-5,6-dimethoxybenzyl)piperazine-1-carboxylate (0.15 g, 70%).

$^1$H NMR (300 MHz, CDCl$_3$) δ 1.44 (s, 9H), 2.31 (s, 3H), 2.36 (m, 4H), 2.52 (s, 3H), 3.33 (m, 4H), 3.50 (s, 2H), 3.90 (s, 3H), 3.91 (s, 3H), 7.32 (s, 1H).

(d) Step 4

A solution of tert-butyl 4-(2-acetoxy-3-acetyl-5,6-dimethoxybenzyl)piperazine-1-carboxylate (0.29 g, 0.67 mmol) in tetrahydrofuran (5.0 mL) was added with trimethylphenylammonium tribromide (0.33 g, 0.87 mmol), and the mixture was stirred at 35° C. for 12 hours. The reaction mixture was added with water, the mixture was extracted with ethyl acetate, and the organic layer was washed successively with water and saturated brine, and then dried over anhydrous magnesium sulfate. The solvent was evaporated under reduced pressure, and then the residue was subjected to silica gel column chromatography (eluted with hexane/ethyl acetate (7:3→3:7)) to obtain a mixture containing a brominated compound.

A solution of the above mixture in methanol (5.0 mL) was added with an excessive amount of sodium acetate, and the mixture was stirred at 50° C. for 30 minutes. The solvent was evaporated under reduced pressure, then the residue was dissolved in ethyl acetate, and the solution was washed successively with water and saturated brine, and then dried over anhydrous magnesium sulfate. The solvent was evaporated under reduced pressure to obtain a residue (0.075 g).

The above residue was dissolved in methanol (4.0 mL), and added with 1H-indazole-3-carboxaldehyde (0.031 g, 0.21 mmol). Then, the mixture was added with 7 drops of piperidine, and the mixture was stirred at room temperature for 12 hours. The reaction mixture was concentrated under reduced pressure, and then the residue was subjected to silica gel column chromatography (eluted with chloroform/methanol (100:0→95:5)) to obtain tert-butyl (Z)-4-({2-[(1H-indazol-3-yl)methylene]-5,6-dimethoxy-3-oxo-2,3-dihydrobenzofuran-7-yl}methyl)piperazine-1-carboxylate (0.026 g, 7%).

$^1$H NMR (300 MHz, DMSO-d$_6$) δ 1.36 (s, 9H), 2.48 (m, 4H), 3.31 (m, 4H), 3.74 (s, 2H), 3.90 (s, 3H), 3.93 (s, 3H), 7.12 (s, 1H), 7.29 (m, 1H), 7.36 (s, 1H), 7.49 (m, 1H), 7.65 (d, J=8.1 Hz, 1H), 8.63 (d, J=8.1 Hz, 1H), 13.91 (s, 1H).

(e) Step 5

A solution of tert-butyl (Z)-4-({2-[(1H-indazol-3-yl)methylene]-5,6-dimethoxy-3-oxo-2,3-dihydrobenzofuran-7-yl}methyl)piperazine-1-carboxylate (0.026 g, 0.050 mmol) in methylene chloride (2.0 mL) was added with a 4 M solution of hydrogen chloride in 1,4-dioxane (2.0 mL), and then the mixture was stirred at room temperature for 2 hours. After completion of the reaction, the mixture was azeotroped twice with toluene under reduced pressure. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate, and then the solvent was evaporated under reduced pressure to obtain (Z)-2-[(1H-indazol-3-yl)methylene]-5,6-dimethoxy-7-(piperazin-1-ylmethyl)benzofuran-3(2H)-one (0.016 g, 76%).

$^1$H NMR (300 MHz, DMSO-d$_6$) δ 2.50 (m, 4H), 2.71 (m, 4H), 3.70 (s, 2H), 3.93 (s, 3.98 (s, 3H), 4.59 (m, 1H), 7.12 (s, 1H), 7.29 (m, 1H), 7.35 (s, 1H), 7.49 (m, 1H), 7.66 (d, J=8.8 Hz, 1H), 8.66 (d, J=8.1 Hz, 1H).

Example B39

(Z)-6-[(1H-Indazol-3-yl)methylene]-4-(piperazin-1-ylmethyl)benzofuro[5,6-d][1,3]dioxol-7(6M-one (a) Step 1

A solution of sesamol (5.6 g, 40 mmol) in acetic anhydride (20 mL) was cooled to 0° C. under an argon atmosphere. The solution was slowly added with boron trifluoride/diethyl ether complex (10 mL), and then the mixture was stirred at 90° C. for 2 hours. The reaction mixture was added to saturated aqueous sodium acetate (50 mL), and the mixture was stirred at room temperature. The solid formed was removed by filtration, and then the reaction mixture was extracted with ethyl acetate, and the organic layer was successively washed with saturated aqueous sodium hydrogencarbonate, water and saturated brine, and then dried over anhydrous magnesium sulfate. The solvent was evaporated under reduced pressure, and the residual solid was suspended in methanol, thereby washed, then collected by filtration and dried to obtain 1-(6-hydroxybenzo[d][1,3]dioxol-5-yl)ethanone (5.9 g, 82%).

$^1$H NMR (300 MHz, CDCl$_3$) δ 2.53 (s, 3H), 5.99 (s, 2H), 6.45 (s, 1H), 7.06 (s, 1H), 13.04 (s, 1H).

(b) Step 2

A solution of 1-(6-hydroxybenzo[d][1,3]dioxol-5-yl)ethanone (1.5 g, 8.3 mmol) in trifluoroacetic acid (15 mL) was added with hexamethylenetetramine (1.7 g, 13 mmol), and the mixture was stirred at 40° C. for 12 hours. The reaction mixture was added with toluene, and then the solvent was evaporated under reduced pressure. The residue was dissolved in ethyl acetate, and the solution was successively washed with water, saturated aqueous sodium hydrogencarbonate, and saturated brine. The organic layer was dried over anhydrous magnesium sulfate, the solvent was concentrated under reduced pressure, and the residue was subjected to silica gel column chromatography (eluted with chloroform/methanol (100:0→97:3)) to obtain 6-acetyl-5-hydroxybenzo[d][1,3]dioxole-4-carboxaldehyde (0.11 g, 6%).

$^1$H NMR (300 MHz, CDCl$_3$) δ 2.57 (s, 3H), 6.17 (s, 2H), 7.28 (s, 1H), 10.43 (s, 1H), 13.79 (s, 1H).

(c) Step 3

A solution of 6-acetyl-5-hydroxybenzo[d][1,3]dioxole-4-carboxaldehyde (0.14 g, 0.67 mmol) in methylene chloride (5.0 mL) was added with N-Boc-piperazine (0.13 g, 0.67 mmol), and the mixture was stirred at room temperature for 10 minutes. The reaction mixture was cooled to 0° C., and then added portionwise with sodium triacetoxyborohydride (0.14 g, 0.67 mmol). After completion of the addition, the mixture was stirred at room temperature for 3 hours. The reaction mixture was added with methylene chloride, and the organic layer was washed successively with water and saturated brine, and then dried over anhydrous magnesium sulfate. The solvent was evaporated under reduced pressure, and the residue was subjected to silica gel column chromatography (eluted with hexane/ethyl acetate (2:1→3:7)) to obtain tert-butyl 4-[(6-acetyl-5-hydroxybenzo[d][1,3]dioxol-4-yl)methyl]piperazine-1-carboxylate (0.18 g, 71%).

$^1$H NMR (300 MHz, CDCl$_3$) δ 1.44 (s, 9H), 2.49 (m, 4H), 2.54 (s, 3H), 3.43 (m, 4H), 3.67 (s, 2H), 6.00 (s, 2H), 7.05 (s, 1H).

(d) Step 4

A solution of tert-butyl 4-[(6-acetyl-5-hydroxybenzo[d][1,3]dioxol-4-yl)methyl]piperazine-1-carboxylate (0.18 g, 0.48 mmol) in pyridine (1.0 mL) was added with acetic anhydride (1.0 mL) and 4-dimethylaminopyridine (0.010 g), and the mixture was stirred at room temperature for 2 hours. The reaction mixture was added with ice water, the mixture was extracted with ethyl acetate, and the organic layer was washed successively with water and saturated brine, and then dried over anhydrous magnesium sulfate. The solvent was evaporated under reduced pressure, and then the residue was subjected to silica gel column chromatography (eluted with hexane/ethyl acetate (7:3→3:7)) to obtain tert-butyl 4-[(5-acetoxy-6-acetylbenzo[d][1,3]dioxol-4-yl)methyl]piperazine-1-carboxylate (0.18 g, 87%).

$^1$H NMR (300 MHz, CDCl$_3$) δ 1.45 (s, 9H), 2.32 (s, 3H), 2.37 (m, 4H), 2.49 (s, 3H), 3.37 (m, 4H), 3.45 (s, 2H), 6.07 (s, 2H), 7.24 (s, 1H).

(e) Step 5

A solution of tert-butyl 4-[(5-acetoxy-6-acetylbenzo[d][1,3]dioxol-4-yl)methyl]piperazine-1-carboxylate (0.12 g, 0.29 mmol) in tetrahydrofuran (5.0 mL) was added with trimethylphenylammonium tribromide (0.14 g, 0.38 mmol), and the mixture was stirred at 35° C. for 11 hours. The reaction mixture was added with ethyl acetate, and the organic layer was washed successively with water and saturated brine, and then dried over anhydrous magnesium sulfate. The solvent was evaporated under reduced pressure, and then the residue was subjected to silica gel column chromatography (eluted with hexane/ethyl acetate (7:3→3:7)) to obtain a mixture containing a brominated compound.

A solution of the above mixture in methanol (5.0 mL) was added with an excessive amount of sodium acetate, and the mixture was stirred at 50° C. for 1 hour. The solvent was evaporated under reduced pressure, then the residue was dissolved in ethyl acetate, and the solution was washed successively with water and saturated brine, and then dried over anhydrous magnesium sulfate. The solvent was evaporated under reduced pressure to obtain a residue (0.025 g).

The above residue was dissolved in methanol (2.0 mL), and added with 1H-indazole-3-carboxaldehyde (0.011 g, 0.073 mmol). Then, the mixture was added with 5 drops of piperidine, and the mixture was stirred at room temperature for 10 hours. The solid formed was collected by filtration to obtain the objective substance.

The filtrate was concentrated under reduced pressure, and the residue was subjected to silica gel column chromatography (eluted with chloroform/methanol (100:0→95:5)) to further obtain the objective substance. Two portions of the objective substance were combined to obtain 0.010 g (7%) of tert-butyl (Z)-4-({6-[(1H-indazol-3-yl)methylene]-7-oxo-6,7-dihydrobenzofuro[5,6-d][1,3]dioxol-4-yl}methyl)piperazine-1-carboxylate.

$^1$H NMR (300 MHz, CD$_3$OD) δ 1.43 (s, 9H), 2.61 (m, 4H), 3.45 (m, 4H), 3.90 (s, 2H), 6.19 (s, 2H), 7.10 (s, 1H), 7.29 (s, 1H), 7.29 (m, 1H), 7.48 (m, 1H), 7.61 (d, J=8.1 Hz, 1H), 8.53 (d, J=8.1 Hz, 1H).

(f) Step 6

A solution of tert-butyl (Z)-4-({6-[(1H-indazol-3-yl)methylene]-7-oxo-6,7-dihydrobenzofuro[5,6-d][1,3]dioxol-4-yl}methyl)piperazine-1-carboxylate (0.019 g, 0.038 mmol) in methylene chloride (2.0 mL) was added with a 4 M solution of hydrogen chloride in 1,4-dioxane (2.0 mL), and then the mixture was stirred at room temperature for 2 hours. The mixture was azeotroped with toluene under reduced pressure to remove the solvent and hydrogen chloride. The residual solid was added with water, and then the mixture was adjusted to pH 9 with saturated aqueous sodium hydrogencarbonate, and extracted with chloroform. The organic layer was washed with saturated brine, and dried over anhydrous sodium sulfate. The solvent was evaporated under reduced pressure, and the residue was subjected to silica gel column chromatography (aminopropyl silica was used, eluted with chloroform/methanol (99:1→95:5)) to obtain (Z)-6-[(1H-indazol-3-yl)methylene]-4-(piperazin-1-ylmethyl)benzofuro[5,6-d][1,3]dioxol-7(6H)-one (0.005 g, 33%).

$^1$H NMR (300 MHz, DMSO-d$_6$) δ 2.46 (m, 4H), 2.70 (m, 4H), 3.66 (s, 2H), 6.24 (s, 2H), 7.08 (s, 1H), 7.18 (s, 1H), 7.26 (m, 1H), 7.48 (m, 1H), 7.65 (d, J=8.1 Hz, 1H), 8.66 (d, J=8.8 Hz, 1H).

Example B40

(Z)-2-[(1H-Indazol-3-yl)methylene]-5-chloro-7-[(4-methylpiperazin-1-yl)methyl]benzofuran-3(2H)-one (a) Step 1

A solution of 5-chloro-2-hydroxybenzoic acid (20 g, 116 mmol) in trifluoroacetic acid (120 mL) was added with hexamethylenetetramine (32 g, 228 mmol), and the mixture was refluxed for 10 hours by heating with stirring. Then, the reaction mixture was added with 1 N hydrochloric acid (800 mL), and refluxed for additional 15 minutes by heating. The reaction mixture was cooled to room temperature, and then the solid formed was collected by filtration, washed with water, dried, and used for the following reaction as it was.

A solution of the above solid in methanol (300 mL) was slowly added with thionyl chloride (20 mL). The reaction mixture was refluxed for 54 hours by heating, and then concentrated, and the solid formed was collected by filtration. The solid was washed with methanol to obtain methyl 5-chloro-3-formyl-2-hydroxybenzoate (10 g, 32%).

$^1$H NMR (300 MHz, CDCl$_3$) δ 4.01 (s, 3H), 7.97 (d, J=2.2 Hz, 1H), 8.06 (d, J=2.2 Hz, 1H), 10.45 (s, 1H), 11.41 (s, 1H).

(b) Step 2

A solution of methyl 5-chloro-3-formyl-2-hydroxybenzoate (6.4 g, 30 mmol) in acetone (50 mL) was added with potassium carbonate (7.4 g, 54 mmol), the mixture was successively added with sodium iodide (0.60 g, 3.0 mmol) and methyl bromoacetate (6.9 g, 45 mmol), and the mixture was stirred at room temperature for 10 hours, and then refluxed for 5 hours by heating. The reaction mixture was cooled to room temperature, and then added with acetone, and the mixture was filtered through Celite. The solvent was evaporated from the filtrate under reduced pressure, the solid formed was suspended in hexane/ethyl acetate (9:1), thereby washed, and then collected by filtration to obtain the objective substance. The filtrate was concentrated under reduced pressure, and the residue was subjected to by silica gel column chromatography (eluted with hexane/ethyl acetate (9:1→1:1)) to further obtain the objective substance. Two portions of the objective substance were combined to obtain 6.5 g (75%) of methyl 5-chloro-3-formyl-2-(2-methoxy-2-oxoethoxy)benzoate.

$^1$H NMR (300 MHz, CDCl$_3$) δ 3.78 (s, 3H), 3.95 (s, 3H), 4.76 (s, 2H), 7.99 (d, J=2.2 Hz, 1H), 8.09 (d, J=2.2 Hz, 1H), 10.54 (s, 1H).

(c) Step 3

A solution of methyl 5-chloro-3-formyl-2-(2-methoxy-2-oxoethoxy)benzoate (0.99 g, 3.5 mmol) in methylene chloride (30 mL) was added with N-methylpiperazine (0.38 g, 3.8 mmol), and the mixture was stirred at room temperature for 10 minutes. The reaction mixture was cooled to 0° C., and then added portionwise with sodium triacetoxyborohydride (0.12 g, 5.5 mmol). After completion of the addition, the reaction mixture was warmed to room temperature, and stirred for 12 hours. The reaction mixture was added with water, the mixture was extracted with ethyl acetate, and the organic layer was successively washed with saturated aqueous sodium hydrogencarbonate, and saturated brine, and then dried over anhydrous magnesium sulfate. The solvent was evaporated under reduced pressure, and the residue was subjected to silica gel column chromatography (eluted with chloroform/methanol (99:1→95:5)) to obtain methyl 5-chloro-2-(2-methoxy-2-oxoethoxy)-3-[(4-methylpiperazin-1-yl) methyl]benzoate (1.2 g, 75%).

$^1$H NMR (300 MHz, CDCl$_3$) δ 2.28 (s, 3H), 2.07-2.77 (m, 8H), 3.55 (s, 2H), 3.83 (s, 3H), 3.89 (s, 3H), 4.78 (s, 2H), 7.49 (d, J=2.2 Hz, 1H), 7.74 (d, J=2.2 Hz, 1H)

(d) Step 4

A solution of methyl 5-chloro-2-(2-methoxy-2-oxoethoxy)-3-[(4-methylpiperazin-1-yl)methyl]benzoate (1.2 g, 3.2 mmol) in methanol (20 mL) was added with water (3.0 mL), and then added with lithium hydroxide monohydrate (0.34 g, 8.1 mmol), and the mixture was stirred at 50° C. for 3 hours. The solvent was evaporated under reduced pressure, then the residue was further added with toluene, and the solvent was evaporated under reduced pressure.

The residue was successively added with acetic acid (6.0 mL), acetic anhydride (10 mL), and sodium acetate (2.0 g), and the mixture was stirred at 110° C. for 5 hours. The solvent was evaporated, then the residue was dissolved in ethyl acetate, and the solution was successively washed with water, saturated aqueous sodium hydrogencarbonate, and saturated brine, and then dried over anhydrous magnesium sulfate. The solvent was evaporated under reduced pressure, and the residue was subjected to silica gel column chromatography (eluted with chloroform/methanol (99:1→93:7)) to obtain 5-chloro-7-[(4-methylpiperazin-1-yl)methyl]benzofuran-3-yl acetate (0.80 g, 77%).

$^1$H NMR (300 MHz, CDCl$_3$) δ 2.29 (s, 3H), 2.38 (s, 3H), 2.03-2.74 (m, 8H), 3.80 (s, 2H), 7.33 (s, 1H), 7.45 (s, 1H), 8.02 (s, 1H).

(e) Step 5

A solution of 5-chloro-7-[(4-methylpiperazin-1-yl)methyl]benzofuran-3-yl acetate (0.12 g, 0.37 mmol) in methanol (8.0 mL) was added with water (2.0 mL) and concentrated hydrochloric acid (0.20 mL), and the mixture was stirred at 80° C. for 4 hours. The solvent was evaporated under reduced pressure, then the residue was dissolved in ethyl acetate, and the solution was successively washed with water, saturated aqueous sodium hydrogencarbonate, and saturated brine, and then dried over anhydrous magnesium sulfate. The solvent was evaporated under reduced pressure, and the residue was purified by silica gel column chromatography (eluted with chloroform/methanol (99:1→95:5)) to obtain 5-chloro-7-[(4-methylpiperazin-1-yl)methyl)]benzofuran-3(2H)-one (0.070 g, 67%).

$^1$H NMR (300 MHz, CDCl$_3$) δ 2.30 (s, 3H), 2.36-2.92 (m, 8H), 3.60 (s, 2H), 4.68 (s, 2H), 7.53 (d, J=2.2 Hz, 1H), 7.62 (d, J=2.2 Hz, 1H).

(f) Step 6

A solution of 5-chloro-7-[(4-methylpiperazin-1-yl)methyl]benzofuran-3(2H)-one (0.12 g, 0.43 mmol) in methanol (5.0 mL) was added with 1H-indazole-3-carboxaldehyde (0.063 g, 0.43 mmol). Then, the mixture was added with 7 drops of piperidine, and then the mixture was stirred at 60° C. for 2 hours. The reaction mixture was concentrated, and then the residue was purified by silica gel column chromatography (eluted with chloroform/methanol (99:1→90:10)) to obtain (Z)-2-[(1H-indazol-3-yl)methylene]-5-chloro-7-[(4-methylpiperazin-1-yl)methyl]benzofuran-3(2H)-one (0.042 g, 24%).

$^1$H NMR (300 MHz, DMSO-d$_6$) δ 2.13 (s, 3H), 2.20-2.75 (m, 8H), 3.76 (s, 2H), 7.23 (s, 1H), 7.29 (m, 1H), 7.50 (m, 1H), 7.67 (d, J=8.1 Hz, 1H), 7.78 (d, J=2.2 Hz, 1H), 7.81 (d, J=2.2 Hz, 1H), 8.60 (d, J=8.1 Hz, 1H), 14.01 (br s, 1H).

Example B41

(Z)-2-[(1H-Indazol-3-yl)methylene]-6-hydroxy-7-{[4-(methylsulfonyl)piperazin-1-yl]methyl}benzofuran-3(2H)-one (a) Step 1

A solution of 6-hydroxybenzofuran-3(2H)-one (0.600 g, 4.00 mmol) in ethanol (4 mL) was added with 1-(methylsulfonyl)piperazine (0.657 g, 4.00 mmol), and 37% aqueous formaldehyde (0.325 g, 4.00 mmol) at room temperature. The reaction mixture was stirred overnight at room temperature, and then concentrated. The resulting residue was purified by silica gel column chromatography (hexane/ethyl acetate) to obtain 6-hydroxy-7-{[4-(methylsulfonyl)piperazin-1-yl]methyl}benzofuran-3(2H)-one (0.169 g, 12%).

$^1$H NMR (300 MHz, DMSO-d$_6$) δ 2.58 (m, 4H), 2.87 (s, 3H), 3.12 (m, 4H), 3.69 (s, 2H), 4.74 (s, 2H), 6.61 (d, J=8.8 Hz, 1H), 7.42 (d, J=8.8 Hz, 1H).

(b) Step 2

A solution of 6-hydroxy-7-{[4-(methylsulfonyl)piperazin-1-yl]methyl}benzofuran-3(2H)-one (0.0681 g, 0.209 mmol) in methanol (0.8 mL) was added with 1H-indazole-3-carboxaldehyde (0.0305 g, 0.209 mmol) and piperidine (0.00178 g, 0.0209 mmol), and the mixture was stirred at 60° C. for 2 hours. The reaction mixture was cooled to room temperature, and then added with methanol (2 mL), and the precipitated solid was suspended in methanol and thereby washed to obtain (Z)-2-[(1H-indazol-3-yl)methylene]-6-hydroxy-7-{[4-(methylsulfonyl)piperazin-1-yl]methyl}benzofuran-3(2H)-one (0.0503 g, 53%).

$^1$H NMR (300 MHz, DMSO-d$_6$) δ 2.66 (m, 4H), 2.82 (s, 3H), 3.13 (m, 4H), 3.83 (s, 2H), 6.81 (d, J=8.8 Hz, 1H), 7.05 (s, 1H), 7.30 (m, 1H), 7.47 (m, 1H), 7.62 (d, J=8.8 Hz, 1H), 7.64 (d, J=8.0 Hz, 1H), 8.56 (d, J=8.1 Hz, 1H), 13.83 (br s, 1H).

Example B42

(Z)-6-Methoxy-2-{[5-(2-morpholinoethoxy)-1H-indazol-3-yl]methylene}-7-(piperazin-1-ylmethyl)benzofuran-3(2H)-one (a) Step 1

A solution of 1H-indol-5-ol (1.33 g, 10.0 mmol) in pyridine (20 mL) was added with acetic anhydride (1.12 g, 11.0 mmol), and the mixture was stirred at room temperature for 16 hours. The reaction mixture was added with water (200 mL), and the precipitated white the solid was collected by filtration (0.543 g). The filtrate was added with 3 N hydrochloric acid, thereby adjusted to pH 2, and then extracted three times with ethyl acetate. The organic layer was washed with saturated aqueous sodium carbonate, dried over anhydrous magnesium sulfate, and then filtered. The filtrate was concentrated, and the resulting residue was purified by silica gel column chromatography (hexane/ethyl acetate) to obtain a white solid (0.714 g). This solid was combined with the white solid obtained above to obtain 1.25 g (71%) of 1H-indol-5-yl acetate.

$^1$H NMR (300 MHz, DMSO-d$_6$) δ 2.25 (s, 3H), 6.41 (s, 1H), 6.81 (dd, J=2.2 Hz, 8.8 HZ, 1H), 7.23 (d, J=2.2 Hz, 1H), 7.35-7.38 (m, 2H), 11.16 (br s, 1H).

(b) Step 2

A solution of 1H-indol-5-yl acetate (0.175 g, 1.00 mmol) in 1,4-dioxane (10 mL) was added with water (120 mL), and the mixture was stirred at room temperature. The reaction mixture was added with sodium nitrite (0.690 g, 10.0 mmol), and the mixture was cooled to 0° C. The reaction mixture was added dropwise with 3 N hydrochloric acid (2.00 mL, 6.00 mmol) at 0° C., and then the mixture was stirred at room temperature for 3 hours. The reaction mixture was filtered, and then the filtrate was extracted three times with ethyl acetate. The organic layer was washed with saturated brine, dried over anhydrous magnesium sulfate, and then filtered. The filtrate was concentrated to obtain 3-formyl-1H-indazol-5-yl acetate (0.100 g, 49%).

$^1$H NMR (300 MHz, DMSO-d$_6$) δ 2.35 (s, 3H), 7.20 (d, J=8.8 Hz, 1H), 7.50 (d, J=8.8 Hz, 1H), 8.01 (s, 1H), 10.24 (s, 1H).

(c) Step 3

A solution of 3-formyl-1H-indazol-5-yl acetate (0.100 g, 0.490 mmol) in methanol (1 mL) was added with potassium carbonate (0.102 g, 0.735 mmol), and the mixture was stirred at room temperature for 30 minutes. The reaction mixture was filtered, and the filtrate was concentrated.

(d) Step 4

A solution of the residue obtained in Step 3 in DMF (1 mL) was added with potassium carbonate (0.285 g, 2.06 mmol) and 4-(2-chloroethyl)morpholine hydrochloride (0.100 g, 0.539 mmol), and the mixture was stirred at room temperature for 12 hours. The reaction mixture was filtered, and the filtrate was added with water. The mixture was extracted three times with ethyl acetate, and the organic layer was washed with saturated brine. The organic layer was dried over anhydrous magnesium sulfate, and concentrated, and the resulting residue was purified by silica gel column chromatography (chloroform/methanol) to obtain 5-(2-morpholinoethoxy)-1H-indazole-3-carboxaldehyde (0.0163 g, 12%).

$^1$H NMR (300 MHz, CDCl$_3$) δ 2.53 (t, J=4.4 Hz, 4H), 2.96 (t, J=6.6 Hz, 2H), 3.67 (m, 4H), 4.56 (t, J=6.6 Hz, 2H), 7.09 (dd, J=2.2 Hz, 8.8 Hz, 1H), 7.38 (d, J=8.8 Hz, 1H), 7.78 (d, J=2.2 Hz, 1H), 10.14 (br s, 1H).

(e) Step 5

A solution of tert-butyl 4-[(6-hydroxy-3-oxo-2,3-dihydrobenzofuran-7-yl)methyl]piperazine-1-carboxylate (3.48 g, 10.0 mmol) in toluene (40 mL) was added with methanol (0.486 mL, 12.0 mmol), triphenylphosphine (3.93 g, 15.0 mmol) and a 40% solution of diethyl azodicarboxylate in toluene (6.53 g, 15.0 mmol), and the mixture was stirred at 110° C. for 5 hours. The reaction mixture was concentrated, and the resulting residue was purified by silica gel column chromatography (chloroform/ethyl acetate) to obtain tert-butyl 4-[(6-methoxy-3-oxo-2,3-dihydrobenzofuran-7-yl)methyl]piperazine-1-carboxylate (1.25 g, 34%).

$^1$H NMR (300 MHz, CDCl$_3$) δ 1.44 (s, 9H), 2.48 (m, 4H), 3.42 (m, 4H), 3.70 (s, 2H), 3.93 (s, 3H), 4.64 (s, 2H), 6.70 (d, J=8.8 Hz, 1H), 7.62 (d, J=8.8 Hz, 1H).

(f) Step 6

A solution of 5-(2-morpholinoethoxy)-1H-indazole-3-carboxaldehyde (0.0163 g, 0.0592 mmol) in methanol (0.5 mL) was added with tert-butyl 4-[(6-methoxy-3-oxo-2,3-dihydrobenzofuran-7-yl)methyl]piperazine-1-carboxylate (0.0172 g, 0.0493 mmol) and piperidine (0.00335 g, 0.0394 mmol), and the mixture was stirred at 60° C. for 3 hours. The reaction mixture was concentrated, and the resulting residue was purified by silica gel column chromatography (chloroform/methanol) to obtain tert-butyl (Z)-4-[(6-methoxy-2-{[5-(2-morpholinoethoxy)-1H-indazol-3-yl]methylene}-3-oxo-2,3-dihydrobenzofuran-7-yl)methyl]piperazine-1-carboxylate (0.0303 g, 99%).

$^1$H NMR (300 MHz, DMSO-d$_6$) δ 1.34 (s, 9H), 2.44 (m, 8H), 2.83 (t, J=6.6 Hz, 2H), 3.24 (t, J=4.4 Hz, 4H), 3.50 (t, J=4.4 Hz, 4H), 3.79 (s, 2H), 3.97 (s, 3H), 4.55 (t, J=6.6 Hz, 2H), 6.99 (s, 1H), 7.03-7.07 (m, 2H), 7.62-7.65 (m, 2H), 7.77 (d, J=8.8 Hz, 1H), 9.41 (br s, 1H).

(g) Step 7

A solution of tert-butyl (Z)-4-[(6-methoxy-2-{[5-(2-morpholinoethoxy)-1H-indazol-3-yl]methylene}-3-oxo-2,3-dihydrobenzofuran-7-yl)methyl]piperazine-1-carboxylate (0.0273 g, 0.0441 mmol) in methylene chloride (2 mL) was added with a 4 M solution of hydrogen chloride in 1,4-dioxane (1 mL), and the mixture was stirred at room temperature for 12 hours. The reaction mixture was concentrated, the resulting residue was added with saturated aqueous sodium hydrogencarbonate, and the mixture was extracted five times with ethyl acetate. The organic layer was washed with saturated brine, and dried over anhydrous sodium sulfate, and then the solvent was evaporated to obtain (Z)-6-methoxy-2-{[5-(2-morpholinoethoxy)-1H-indazol-3-yl]methylene}-7-(piperazin-1-ylmethyl)benzofuran-3(2H)-one (0.0130 g, 56%).

$^1$H NMR (300 MHz, DMSO-d$_6$) δ 2.49 (m, 8H), 2.65 (m, 4H), 2.82 (t, J=6.6 Hz, 2H), 3.50 (t, J=4.4 Hz, 4H), 3.76 (s, 2H), 3.96 (s, 3H), 4.55 (t, J=6.6 Hz, 2H), 6.98 (s, 7.03-7.07 (m, 2H), 7.62-7.65 (m, 2H), 7.77 (d, J=8.0 HZ, 1H).

Example B43

(Z)-6-Methoxy-2-{[5-(methylsulfonyl)-1H-indazol-3-yl]methylene}-7-(piperazin-1-ylmethyl)benzofuran-3(2H)-one (a) Step 1

A solution of 5-(methylsulfonyl)indoline (0.213 g, 1.08 mmol) in chloroform (4 mL) was added with manganese dioxide (0.939 g, 10.8 mmol), and the mixture was stirred at room temperature for 9 hours. The reaction mixture was filtered through Celite, and the resulting filtrate was concentrated to obtain 5-(methylsulfonyl)-1H-indole (0.151 g, 71%).

$^1$H NMR (300 MHz, DMSO-d$_6$) δ 3.08 (s, 3H), 6.71 (t, J=2.2 Hz, 1H), 7.38 (t, J=2.9 Hz, 1H), 7.53 (d, J=8.8 Hz, 1H), 7.72-7.75 (m, 1H), 8.30 (br s, 1H), 8.57 (br s, 1H).

(b) Step 2

A solution of 5-(methylsulfonyl)-1H-indole (0.150 g, 0.768 mmol) in 1,4-dioxane (8 mL) was added with water (96 mL), and the mixture was stirred at room temperature. The reaction mixture was added with sodium nitrite (0.530 g, 7.68 mmol), and the mixture was cooled to 0° C. The reaction mixture was added dropwise with 3 N hydrochloric acid (1.54 mL, 4.62 mmol) at 0° C., and then the mixture was stirred at room temperature for 3 hours. The reaction mixture was extracted three times with ethyl acetate, and then the organic layer was washed with saturated brine, and dried over anhydrous magnesium sulfate. The organic layer was concentrated, and the resulting residue was purified by silica gel column chromatography (chloroform/methanol) to obtain 5-(methylsulfonyl)-1H-indazole-3-carboxaldehyde (0.0433 g, 25%).

$^1$H NMR (300 MHz, DMSO-d$_6$) δ 3.27 (s, 3H), 7.94-8.02 (m, 2H), 8.68 (s, 1H), 10.25 (s, 1H), 14.61 (s, 1H).

(c) Step 3

A solution of 5-(methylsulfonyl)-1H-indazole-3-carboxaldehyde (0.0392 g, 0.175 mmol) in methanol (0.7 mL) was added with tert-butyl 4-[(6-methoxy-3-oxo-2,3-dihydrobenzofuran-7-yl)methyl]piperazine-1-carboxylate (0.0915 g, 0.252 mmol) synthesized in the same manner as that of Example B42, Step 5, and piperidine (0.00149 g, 0.0175 mmol), and the mixture was stirred at 60° C. for 2 hours. The reaction mixture was concentrated, and the resulting residue was purified by silica gel column chromatography (chloroform/methanol) to obtain tert-butyl (Z)-4-[(6-methoxy-2-{[5-(methylsulfonyl)-1H-indazol-3-yl]methylene}-3-oxo-2,3-dihydrobenzofuran-7-yl)methyl]piperazine-1-carboxylate (0.0470 g, 47%).

$^1$H NMR (300 MHz, DMSO-d$_6$) δ 1.29 (s, 9H), 2.39 (m, 4H), 3.16 (m, 4H), 3.25 (s, 3H), 3.90 (s, 2H), 3.98 (s, 3H), 7.07 (d, J=8.8 Hz, 1H), 7.16 (s, 1H), 7.82 (d, J=8.8 Hz, 1H), 7.87 (d, J=8.8 Hz, 1H), 7.97 (dd, J=1.5 Hz, 8.8 Hz, 1H), 9.04 (br s, 1H), 14.29 (br s, 1H).

(d) Step 4

A solution of tert-butyl (Z)-4-[(6-methoxy-2-{[5-(methylsulfonyl)-1H-indazol-3-yl]methylene}-3-oxo-2,3-dihydrobenzofuran-7-yl)methyl]piperazine-1-carboxylate (0.0462 g, 0.0812 mmol) in methylene chloride (1 mL) was added with a 4 M solution of hydrogen chloride in 1,4-dioxane (1 mL), and the mixture was stirred at room temperature for 15 hours. The reaction mixture was concentrated, the resulting residue was added with saturated aqueous sodium hydrogencarbonate, and the mixture was extracted five times with ethyl acetate. The organic layer was dried over anhydrous sodium sulfate, and then the solvent was evaporated to obtain (Z)-6-methoxy-2-{[5-(methylsulfonyl)-1H-indazol-3-yl]methylene}-7-(piperazin-1-ylmethyl)benzofuran-3(2H)-one (0.0277 g, 72%).

$^1$H NMR (300 MHz, DMSO-d$_6$) δ 2.80 (t, J=3.3 Hz, 4H), 3.28 (s, 3H), 3.38 (m, 4H), 3.92 (s, 2H), 3.98 (s, 3H), 7.10 (d, J=6.6 Hz, 1H), 7.17 (s, 1H), 7.84 (d, J=6.6 Hz, 1H), 7.88 (d, J=6.6 Hz, 1H), 7.97 (dd, J=1.1 Hz, 6.6 Hz, 1H), 9.05 (d, J=1.1 Hz, 1H).

Example B44

(Z)-2-[(1H-Indazol-3-yl)methylene]-6-methoxy-7-{[4-(methylsulfonyl)piperazin-1-yl]methyl}benzofuran-3(2H)-one (a) Step 1

A solution of 6-hydroxy-7-{[4-(methylsulfonyl)piperazin-1-yl]methyl}benzofuran-3(2H)-one (0.0900 g, 0.276 mmol) synthesized in Example B41, Step 1 in THF (2 mL) was added with methanol (0.0106 g, 0.331 mmol) and triphenylphosphine (0.109 g, 0.414 mmol), and the mixture was stirred at room temperature. The reaction mixture was added with a solution of a 40% solution of diethyl azodicarboxylate in toluene (0.216 g, 0.497 mmol) in THF (0.5 mL), and the mixture was stirred at room temperature for 14 hours. The reaction mixture was concentrated, and the resulting residue was subjected to silica gel column chromatography (chloroform/methanol) to obtain a solid (0.146 g).

(b) Step 2

A solution of the solid obtained in Step 1 in methanol (1.1 mL) was added with 1H-indazole-3-carboxaldehyde (0.0403 g, 0.276 mmol) and piperidine (0.00235 g, 0.0276 mmol), and the mixture was stirred at 60° C. for 2 hours. The reaction mixture was cooled to room temperature, and then added with methanol (2 mL), and the precipitated solid was suspended in methanol and thereby washed. The solid was collected by filtration to obtain (Z)-2-[(1H-indazol-3-yl)methylene]-6-methoxy-7-{[4-(methylsulfonyl)piperazin-1-yl]methyl}benzofuran-3(2H)-one (0.0294 g, 22%).

$^1$H NMR (300 MHz, DMSO-d$_6$) δ 2.62 (m, 4H), 2.79 (s, 3H), 3.09 (m, 4H), 3.78 (s, 2H), 3.98 (s, 3H), 7.06-7.09 (m, 2H), 7.30 (t, J=7.3 Hz, 1H), 7.48 (t, J=7.3 Hz, 1H), 7.65 (d, J=8.8 Hz, 1H), 7.81 (d, J=8.1 Hz, 1H), 8.60 (d, J=8.0 Hz, 1H), 13.86 (br s, 1H).

Example B45

(Z)-2-[(1H-Indazol-3-yl)methylene]-7-(piperazin-1-ylmethyl)benzofuran-3(2H)-one (a) Step 1

A solution of 2-chloro-1-(2-hydroxy-3-methylphenyl)ethanone (Tetrahedron, Vol. 66, p. 3499, 2010, 6.40 g, 34.7 mmol) in acetonitrile (170 mL) was added with potassium carbonate (14.4 g, 104 mmol), and the mixture was stirred at room temperature for 1 hour, and then filtered. The filtrate was concentrated, and the resulting residue was purified by silica gel column chromatography (hexane/ethyl acetate) to obtain 7-methylbenzofuran-3(2H)-one (2.23 g, 43%).

$^1$H NMR (300 MHz, CDCl$_3$) δ 2.33 (s, 3H), 4.64 (s, 2H), 7.00 (m, 1H), 7.42 (d, J=7.3 Hz, 1H), 7.51 (d, J=8.0 Hz, 1H).

(b) Step 2

A solution of 7-methylbenzofuran-3(2H)-one (0.759 g, 5.12 mol) in carbon tetrachloride (50 mL) was added with N-bromosuccinimide (1.00 g, 5.63 mmol) and benzoyl peroxide (0.0830 g, 0.256 mmol), and the mixture was refluxed for 4 hours by heating. The reaction mixture was cooled to room temperature, and then filtered, and the resulting filtrate was concentrated. The residue was purified by silica gel column chromatography (hexane/ethyl acetate) to obtain 7-bromomethylbenzofuran-3(2H)-one (0.573 g, 49%).

¹H NMR (300 MHz, CDCl₃) δ 4.58 (s, 2H), 4.73 (s, 2H), 7.10 (t, J=7.3 Hz, 1H), 7.59 (m, 2H).

(c) Step 3

A solution of 7-bromomethylbenzofuran-3(2H)-one (0.573 g, 2.52 mmol) in methylene chloride (20 mL) was added with sodium acetate (0.412 g, 5.03 mmol) and 1-tert-butoxycarbonylpiperazine (0.721 g, 3.87 mmol), and the mixture was stirred at room temperature for 6 hours. The organic layer was washed with water and saturated sodium chloride, and then dried over anhydrous magnesium sulfate, and then the solvent was evaporated under reduced pressure. The resulting residue was purified by silica gel column chromatography (hexane/ethyl acetate) to obtain tert-butyl 4-[(3-oxo-2,3-dihydrobenzofuran-7-yl)methyl]piperazine-1-carboxylate (0.391 g, 46%).

¹H NMR (300 MHz, CDCl₃) δ 1.45 (s, 9H), 2.48 (m, 4H), 3.46 (m, 4H), 3.65 (s, 2H), 4.65 (s, 2H), 7.09 (t, J=7.3 Hz, 1H), 7.61 (d, J=7.3 Hz, 1H), 7.65 (d, J=7.3 Hz, 1H).

(d) Step 4

A solution of tert-butyl 4-[(3-oxo-2,3-dihydrobenzofuran-7-yl)methyl]piperazine-1-carboxylate (0.0359 g, 0.108 mmol) in methanol (2 mL) was added with 1H-indazole-3-carboxaldehyde (0.0166 g, 0.113 mmol) and piperidine (5 drops), and the mixture was stirred at 50° C. for 2 hours. The reaction mixture was concentrated, and the resulting residue was purified by silica gel column chromatography (hexane/ethyl acetate) to obtain tert-butyl (Z)-4-({2-[(1H-indazol-3-yl)methylene]-3-oxo-2,3-dihydrobenzofuran-7-yl}methyl)piperazine-1-carboxylate (0.0332 g, 67%).

¹H NMR (300 MHz, CD₃OD) δ 1.43 (s, 9H), 2.58 (m, 4H), 3.44 (m, 4H), 3.90 (s, 2H), 7.27-7.36 (m, 3H), 7.45-7.53 (m, 1H), 7.62 (d, J=8.1 Hz, 1H), 7.75 (d, J=7.3 Hz, 2H), 8.62 (d, J=8.1 Hz, 1H).

(e) Step 5

A solution of tert-butyl (Z)-4-({2-[(1H-indazol-3-yl)methylene]-3-oxo-2,3-dihydrobenzofuran-7-yl}methyl)piperazine-1-carboxylate (0.0301 g, 0.0654 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated to obtain (Z)-2-[(1H-indazol-3-yl)-methylene]-7-(piperazin-1-ylmethyl)benzofuran-3(2H)-one (0.0221 g, 94%).

¹H NMR (300 MHz, DMSO-d₆) δ 2.46 (m, 4H), 2.73 (m, 4H), 3.75 (s, 2H), 7.20 (s, 7.76 (t, J=7.3 Hz, 1H), 7.76 (t, J=7.3 Hz, 1H), 7.49 (m, 1H), 7.67 (d, J=8.1 Hz, 1H), 7.75 (d, J=7.3 Hz, 2H), 8.65 (d, J=8.1 Hz, 1H).

Example B46

(Z)-2-[(1H-Indazol-3-yl)methylene]-6-methoxy-7-[3-(piperazin-1-yl)prop-1-ynyl]benzofuran-3(2H)-one (a) Step 1

A solution of 6-hydroxybenzofuran-3(2H)-one (3.00 g, 20.0 mmol) in ethanol (30 mL) was added with iodine (2.03 g, 8.00 mmol), and the mixture was stirred at room temperature. The reaction mixture was added dropwise with aqueous iodic acid (0.704 g, 4.00 mmol, 18 mL), and then the mixture was stirred at room temperature for 2 hours. The reaction mixture was added with water (250 mL), the mixture was stirred at room temperature for 30 minutes, and the solid was collected by filtration. The resulting solid was washed with saturated aqueous sodium thiosulfate (75 mL), and then washed with water (40 mL). The solid was dried under reduced pressure to obtain 6-hydroxy-7-iodobenzofuran-3(2M-one (4.96 g, 90%).

¹H NMR (400 MHz, DMSO-d₆) δ 4.83 (s, 2H), 6.69 (d, J=8.3 Hz, 1H), 7.44 (d, J=8.3 Hz, 1H), 11.76 (s, 1H)

(b) Step 2

A solution of 6-hydroxy-7-iodobenzofuran-3(2H)-one (2.58 g, 9.35 mmol) in DMF (37 mL) was added with potassium carbonate (1.55 g, 11.2 mmol) and methyl iodide (0.697 mL, 11.2 mmol), and the mixture was stirred at room temperature for 13 hours. The reaction mixture was added with water (400 mL), and the precipitated solid was collected by filtration to obtain 7-iodo-6-methoxybenzofuran-3(2H)-one (1.35 g, 49%).

¹H NMR (300 MHz, CDCl₃) δ 4.02 (s, 3H), 4.74 (s, 2H), 6.65 (d, J=8.1 Hz, 1H), 7.64 (d, J=8.1 Hz, 1H)

(c) Step 3

A solution of propargyl bromide (0.766 g, 6.44 mmol) in acetonitrile (25 mL) was added with 1-tert-butoxycarbonylpiperazine (1.00 g, 5.37 mmol) and potassium carbonate (1.11 g, 8.03 mmol), and the mixture was stirred at 60° C. for 4 hours. The reaction mixture was added with water, and the mixture was extracted with ethyl acetate. The organic layer was washed with saturated brine, then dried over anhydrous magnesium sulfate, and concentrated under reduced pressure. The resulting residue was purified by silica gel column chromatography (hexane/ethyl acetate) to obtain tert-butyl 4-(prop-2-ynyl)piperazine-1-carboxylate (1.01 g, 83%).

¹H NMR (300 MHz, CDCl₃) δ 1.46 (s, 9H), 2.26 (t, J=2.2 Hz, 1H), 2.51 (t, J=5.1 Hz, 4H), 3.32 (d, J=2.2 Hz, 2H), 3.47 (t, J=5.1 Hz, 4H).

(d) Step 4

A solution of tert-butyl 4-(prop-2-ynyl)piperazine-1-carboxylate (0.449 g, 2.00 mmol) in triethylamine (12 mL) was added with 7-iodo-6-methoxybenzofuran-3(2H)-one (0.580 g, 2.00 mmol), dichlorobis(triphenylphosphine)palladium (II) (0.141 g, 0.200 mmol) and copper(I) iodide (0.0381 g, 0.200 mmol), and the mixture was stirred at 50° C. for 4 hours. The reaction mixture was concentrated, then the solid was suspended in a mixed solvent of 50% ethyl acetate in hexane, and the suspension was filtered. The filtrate was concentrated, and the resulting residue was purified by silica gel column chromatography (hexane/ethyl acetate) to obtain tert-butyl 4-[3-(6-methoxy-3-oxo-2,3-dihydrobenzofuran-7-yl)prop-2-ynyl]piperazine-1-carboxylate (0.473 g, 61%).

¹H NMR (300 MHz, CDCl₃) δ 1.46 (s, 9H), 2.62 (m, 4H), 3.51 (m, 4H), 3.67 (s, 2H), 3.98 (s, 3H), 4.69 (s, 2H), 6.68 (d, J=8.8 Hz, 1H), 7.62 (d, J=8.8 Hz, 1H).

(e) Step 5

A solution of tert-butyl 4-[3-(6-methoxy-3-oxo-2,3-dihydrobenzofuran-7-yl)prop-2-ynyl]piperazine-1-carboxylate (0.0500 g, 0.129 mmol) in methanol (3 mL) was added with 1H-indazole-3-carboxaldehyde (0.0198 g, 0.136 mmol) and piperidine (0.0877 g, 0.103 mmol), and the mixture was stirred at 60° C. for 2 hours. The reaction mixture was concentrated, and the resulting residue was purified by silica gel column chromatography (hexane/ethyl acetate) to obtain tert-butyl (Z)-4-(3-{2-[(1H-indazol-3-yl)methylene]-6-methoxy-3-oxo-2,3-dihydrobenzofuran-7-yl}prop-2-ynyl)piperazine-1-carboxylate (0.0625 g, 94%).

$^1$H NMR (300 MHz, DMSO-d$_6$) δ 1.35 (s, 9H), 2.54 (m, 4H), 3.34 (m, 4H), 3.75 (s, 2H), 4.01 (s, 3H), 7.08 (d, J=8.8 Hz, 1H), 7.12 (s, 1H), 7.34 (m, 1H), 7.48 (m, 1H), 7.65 (d, J=8.1 Hz, 1H), 7.83 (d, J=8.1 Hz, 1H), 8.70 (d, J=8.1 Hz, 1H), 13.82 (s, 1H).

(f) Step 6

A solution of tert-butyl (Z)-4-(3-{2-[(1H-indazol-3-yl)methylene]-6-methoxy-3-oxo-2,3-dihydrobenzofuran-7-yl}prop-2-ynyl)piperazine-1-carboxylate (0.0625 g, 0.121 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)-methylene]-6-methoxy-7-[3-(piperazin-1-yl)prop-1-ynyl]benzofuran-3(2H)-one (0.0453 g, 90%).

$^1$H NMR (300 MHz, DMSO-d$_6$) δ 2.56 (m, 4H), 2.74 (m, 4H), 3.69 (s, 2H), 4.02 (s, 3H), 7.07 (d, J=8.8 Hz, 1H), 7.15 (s, 1H), 7.34 (m, 1H), 7.47 (m, 1H), 7.66 (d, J=8.8 Hz, 1H), 7.83 (d, J=8.8 Hz, 1H), 8.66 (d, J=8.1 Hz, 1H).

Example B47

(Z)-2-[(1H-Indazol-3-yl)methylene]-6-methoxy-7-[(Z)-3-(piperizin-1-yl)prop-1-enyl]benzofuran-3(2H)-one (Z)-2-[(1H-Indazol-3-yl)methylene]-6-methoxy-7-[(Z)-3-(piperazin-1-yl)prop-1-enyl]benzofuran-3(2H)-one (a) Step 1

A solution of tert-butyl 4-[3-(6-methoxy-3-oxo-2,3-dihydrobenzofuran-7-yl)prop-2-ynyl]piperazine-1-carboxylate (0.0761 g, 0.196 mmol) obtained in Example B46, Step 4 in ethanol (5 mL) was added with Lindlar's catalyst (0.0700 g), and the mixture was stirred at room temperature for 15 hours under a hydrogen atmosphere. The reaction mixture was filtered through Celite, and then the filtrate was concentrated. The resulting residue was purified by silica gel column chromatography (hexane/ethyl acetate) to obtain tert-butyl (Z)-4-[3-(6-methoxy-3-oxo-2,3-dihydrobenzofuran-7-yl)allyl]piperazine-1-carboxylate (0.0603 g, 79%).

$^1$H NMR (300 MHz, CDCl$_3$) δ 1.43 (s, 9H), 2.33-2.37 (m, 4H), 3.00 (d, J=6.6 Hz, 2H), 3.39-3.42 (m, 4H), 3.93 (s, 3H), 4.64 (s, 2H), 5.97 (dt, J=11.0 Hz, 6.6 Hz, 1H), 6.35 (d, J=11.0 Hz, 1H), 6.71 (d, J=8.1 Hz, 1H), 7.63 (d, J=8.1 Hz, 1H).

(b) Step 2

A solution of tert-butyl (Z)-4-[3-(6-methoxy-3-oxo-2,3-dihydrobenzofuran-7-yl)allyl]piperazine-1-carboxylate (0.0603 g, 0.155 mmol) in methanol (5 mL) was added with 1H-indazole-3-carboxaldehyde (0.0249 g, 0.171 mmol) and piperidine (0.0106 g, 0.124 mmol), and the mixture was stirred at 60° C. for 2 hours. The reaction mixture was concentrated, and then the residue was subjected to silica gel column chromatography (chloroform/methanol). The resulting solid was washed with a mixed solvent of 50% methylene chloride in hexane to obtain tert-butyl 4-((Z)-3-{(Z)-2-[(1H-indazol-3-yl)methylene]-6-methoxy-3-oxo-2,3-dihydrobenzofuran-7-yl}allyl)piperazine-1-carboxylate (0.0303 g, 38%).

$^1$H NMR (300 MHz, DMSO-d$_6$) δ 1.31 (s, 9H), 2.08-2.11 (m, 4H), 3.00-3.01 (m, 2H), 3.09-3.12 (m, 4H), 3.97 (s, 3H), 6.04-6.12 (m, 1H), 6.48 (d, J=11.7 Hz, 1H), 7.06 (d, J=8.8 Hz, 1H), 7.12 (s, 1H), 7.26 (m, 1H), 7.46 (m, 1H), 7.63 (d, J=8.8 Hz, 1H), 7.80 (d, J=8.8 Hz, 1H), 8.38 (d, J=8.1 Hz, 1H), 13.76 (s, 1H).

(c) Step 3

A solution of tert-butyl 4-((Z)-3-{(Z)-2-[1H-indazol-3-yl)methylene]-6-methoxy-3-oxo-2,3-dihydrobenzofuran-7-yl}allyl)piperazine-1-carboxylate (0.0303 g, 0.0587 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[1H-indazol-3-yl)methylene]-6-methoxy-7-[(Z)-3-(piperizin-1-yl)prop-1-enyl]benzofuran-3(2H)-one (Z)-2-[(1H-indazol-3-yl)methylene]-6-methoxy-7-[(Z)-3-(piperazin-1-yl)prop-1-enyl]benzofuran-3(2H)-one (0.0200 g, 83%).

$^1$H NMR (300 MHz, DMSO-d$_6$) δ 2.06 (m, 4H), 2.48 (m, 4H), 2.94 (d, J=5.9 Hz, 2H), 3.97 (s, 3H), 6.03-6.10 (m, 1H), 6.45 (d, J=11.7 Hz, 1H), 7.05 (d, J=8.8 Hz, 1H), 7.12 (s, 1H), 7.25 (m, 1H), 7.45 (m, 1H), 7.63 (d, J=8.8 Hz, 1H), 7.79 (d, J=8.8 Hz, 1H), 8.40 (d, J=8.1 Hz, 1H).

Example B48

(Z)-2-[(1H-Indazol-3-yl)methylene]-6-methoxy-7-[3-(piperazin-1-yl)propyl]benzofuran-3(2H)-one (a) Step 1

A solution of tert-butyl 4-[3-(6-methoxy-3-oxo-2,3-dihydrobenzofuran-7-yl)prop-2-ynyl]piperazine-1-carboxylate (0.0748 g, 0.194 mmol) obtained in Example B46, Step 4 in ethanol (5 mL) was added with 5% palladium/carbon (wetted with 50% water, 0.0700 g), and the mixture was stirred at room temperature for 2 hours under a hydrogen atmosphere. The reaction mixture was filtered through Celite, the filtrate was concentrated, and the resulting residue was purified by silica gel column chromatography (chloroform/methanol) to obtain tert-butyl 4-[3-(6-methoxy-3-oxo-2,3-dihydrobenzofuran-7-yl)propyl]piperazine-1-carboxylate (0.0642 g, 85%).

$^1$H NMR (300 MHz, CDCl$_3$) δ 1.45 (s, 9H), 1.76 (m, 2H), 2.38 (m, 4H), 2.40 (m, 2H), 2.67 (m, 2H), 3.42 (m, 4H), 3.91 (s, 3H), 4.61 (s, 2H), 6.66 (d, J=8.8 Hz, 1H), 7.53 (d, J=8.8 Hz, 1H).

(b) Step 2

A solution of tert-butyl 4-[3-(6-methoxy-3-oxo-2,3-dihydrobenzofuran-7-yl)propyl]piperazine-1-carboxylate (0.0642 g, 0.164 mmol) in methanol (3 mL) was added with 1H-indazole-3-carboxaldehyde (0.0264 g, 0.180 mmol) and piperidine (0.0112 g, 0.131 mmol), and the mixture was stirred at 60° C. for 2 hours. The reaction mixture was concentrated, and then the residue was purified by silica gel column chromatography (chloroform/methanol) to obtain tert-butyl (Z)-4-(3-{2-[(1H-indazol-3-yl)methylene]-6-methoxy-3-oxo-2,3-dihydrobenzofuran-7-yl}propyl)piperazine-1-carboxylate (0.0393 g, 46%).

$^1$H NMR (300 MHz, DMSO-$d_6$) δ 1.36 (s, 9H), 1.80 (m, 2H), 2.24 (m, 4H), 2.40 (t, J=7.4 Hz, 2H), 2.83 (t, J=7.4 Hz, 2H), 3.17 (m, 4H), 3.97 (s, 3H), 7.02 (d, J=8.8 Hz, 1H), 7.07 (s, 1H), 7.31 (m, 1H), 7.48 (m, 1H), 7.65 (d, J=8.8 Hz, 1H), 7.71 (d, J=8.8 Hz, 1H), 8.50 (d, J=8.1 Hz, U).

(c) Step 3

A solution of tert-butyl (Z)-4-(3-{2-[(1H-indazol-3-yl)methylene]-6-methoxy-3-oxo-2,3-dihydrobenzofuran-7-yl}propyl)piperazine-1-carboxylate (0.0393 g, 0.0758 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-[3-(piperazin-1-yl)propyl]benzofuran-3(2H)-one (0.0273 g, 86%).

$^1$H NMR (300 MHz, DMSO-$d_6$) δ 1.79 (m, 2H), 2.23 (m, 4H), 2.38 (m, 2H), 2.58 (m, 4H), 2.82 (m, 2H), 3.97 (s, 3H), 7.02 (d, J=8.8 Hz, 1H), 7.07 (s, 1H), 7.31 (m, 1H), 7.48 (m, 1H), 7.65 (d, J=8.8 Hz, 1H), 7.70 (d, J=8.8 Hz, 1H), 8.52 (d, J=8.1 Hz, 1H).

Example B49

(Z)-2-[(1H-Indazol-3-yl)methylene]-6-methoxy-7-[4-(piperazin-1-yl)but-1-ynyl]benzofuran-3(2H)-one (a) Step 1

A solution of 4-bromo-1-butyne (0.500 g, 3.76 mmol) in acetonitrile (20 mL) was added with 1-tert-butoxycarbonylpiperazine (0.700 g, 3.76 mmol) and potassium carbonate (0.779 g, 5.64 mmol), and the mixture was stirred at 60° C. for 6 hours. The reaction mixture was added with water, and the mixture was extracted with methylene chloride. The organic layer was washed with saturated brine, then dried over anhydrous magnesium sulfate, and concentrated under reduced pressure. The resulting residue was purified by silica gel column chromatography (hexane/ethyl acetate) to obtain tert-butyl 4-(but-3-ynyl)piperazine-1-carboxylate (0.621 g, 69%).

$^1$H NMR (300 MHz, CDCl$_3$) δ 1.46 (s, 9H), 1.98 (m, 1H), 2.29-2.52 (m, 6H), 2.60 (t, J=7.3 Hz, 2H), 3.43 (m, 4H).

(b) Step 2

A solution of tert-butyl 4-(but-3-ynyl)piperazine-1-carboxylate (0.316 g, 1.33 mmol) in triethylamine (5 mL) was added with 7-iodo-6-methoxybenzofuran-3(2H)-one (0.385 g, 1.33 mmol), dichlorobis(triphenylphosphine)palladium (II) (0.0933 g, 0.133 mmol) and copper(I) iodide (0.0127 g, 0.0665 mmol), and the mixture was stirred at 50° C. for 4 hours. The reaction mixture was concentrated, and then added with water, and the mixture was extracted twice with ethyl acetate. The organic layer was washed with saturated brine, then dried over anhydrous magnesium sulfate, and concentrated under reduced pressure. The resulting residue was purified by silica gel column chromatography (hexane/ethyl acetate) to obtain tert-butyl 4-[4-(6-methoxy-3-oxo-2,3-dihydrobenzofuran-7-yl)but-3-ynyl]piperazine-1-carboxylate (0.189 g, 35%).

$^1$H NMR (300 MHz, CDCl$_3$) δ 1.46 (s, 9H), 2.50 (m, 4H), 2.75 (m, 4H), 3.45 (m, 4H), 3.98 (s, 3H), 4.69 (s, 2H), 6.68 (d, J=8.8 Hz, 1H), 7.59 (d, J=8.8 Hz, 1H).

(c) Step 3

A solution of tert-butyl 4-[4-(6-methoxy-3-oxo-2,3-dihydrobenzofuran-7-yl)but-3-ynyl]piperazine-1-carboxylate (0.0394 g, 0.0983 mmol) in methanol (3 mL) was added with 1H-indazole-3-carboxaldehyde (0.0131 g, 0.0894 mmol) and piperidine (5 drops), and the mixture was stirred at 60° C. for 2 hours. The reaction mixture was concentrated, and then the residue was purified by silica gel column chromatography (hexane/ethyl acetate) to obtain tert-butyl (Z)-4-(4-{2-[(1H-indazol-3-yl)methylene]-6-methoxy-3-oxo-2,3-dihydrobenzofuran-7-yl}but-3-ynyl)piperazine-1-carboxylate (0.0315 g, 66%).

$^1$H NMR (300 MHz, DMSO-$d_6$) δ 1.39 (s, 9H), 2.43 (m, 4H), 2.67 (t, J=7.3 Hz, 2H), 2.81 (t, J=7.3 Hz, 2H), 3.30 (m, 4H), 4.00 (s, 3H), 7.06 (d, J=8.8 Hz, 1H), 7.10 (s, 1H), 7.31 (m, 1H), 7.49 (m, 1H), 7.66 (d, J=8.1 Hz, 1H), 7.80 (d, J=8.8 Hz, 1H), 8.74 (d, J=8.8 Hz, 1H), 13.88 (s, 1H).

(d) Step 4

A solution of tert-butyl (Z)-4-(4-{2-[(1H-indazol-3-yl)methylene]-6-methoxy-3-oxo-2,3-dihydrobenzofuran-7-yl}but-3-ynyl)piperazine-1-carboxylate (0.0315 g, 0.0596 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and the solvent was evaporated to obtain (Z)-2-[(1H-indazol-3-yl)methylene]-6-methoxy-7-[4-(piperazin-1-yl)but-1-ynyl]benzofuran-3(2H)-one (0.0120 g, 47%).

$^1$H NMR (300 MHz, DMSO-$d_6$) δ 2.39 (m, 4H), 2.61 (t, J=7.3 Hz, 2H), 2.69 (m, 4H), 2.79 (t, J=7.3 Hz, 2H), 4.00 (s, 3H), 7.06 (d, J=8.8 Hz, 1H), 7.10 (s, 1H), 7.31 (m, 1H), 7.48 (m, 1H), 7.66 (d, J=8.8 Hz, 1H), 7.80 (d, J=8.8 Hz, 1H), 8.75 (d, J=8.1 Hz, 1H).

Example B50

(Z)-2-[(1H-Indazol-3-yl)methylene]-6-methoxy-7-[(Z)-4-(piperazin-1-yl)but-1-enyl]benzofuran-3(2H)-one (a) Step 1

A solution of tert-butyl 4-[4-(6-methoxy-3-oxo-2,3-dihydrobenzofuran-7-yl)but-3-ynyl]piperazine-1-carboxylate (0.0801 g, 0.200 mmol) synthesized in Example B49, Step 2 in ethanol (5 mL) was added with Lindlar's catalyst (0.0800 g), and the mixture was stirred at room temperature for 4 hours under a hydrogen atmosphere. The reaction mixture was filtered through Celite, and then the filtrate was concentrated. The resulting residue was purified by silica gel column chromatography (hexane/ethyl acetate) to obtain tert-butyl (Z)-4-[4-(6-methoxy-3-oxo-2,3-dihydrobenzofuran-7-yl)but-3-enyl]piperazine-1-carboxylate (0.0562 g, 69%).

$^1$H NMR (300 MHz, CDCl$_3$) δ 1.45 (s, 9H), 2.19-2.27 (m, 2H), 2.33-2.37 (m, 4H), 2.44-2.49 (m, 2H), 3.39-3.42 (m, 4H), 3.93 (s, 3H), 4.64 (s, 2H), 5.86-5.94 (m, 1H), 6.24 (d, J=11.0 Hz, 1H), 6.71 (d, J=8.8 Hz, 1H), 7.62 (d, J=8.8 Hz, 1H).

(b) Step 2

A solution of tert-butyl (Z)-4-[4-(6-methoxy-3-oxo-2,3-dihydrobenzofuran-7-yl)but-3-enyl]piperazine1-carboxylate (0.0562 g, 0.139 mmol) in methanol (5 mL) was added with 1H-indazole-3-carboxaldehyde (0.0203 g, 0.139 mmol) and piperidine (7 drops), and the mixture was stirred at 60° C. for 2 hours. The reaction mixture was concentrated, and then the residue was purified by silica gel column chromatography (chloroform/methanol) to obtain tert-butyl 4-((Z)-4-{(Z)-2-[(1H-indazol-3-yl)methylene]-6-methoxy-3-oxo-2,3-dihydrobenzofuran-7-yl}but-3-enyl)piperazine-1-carboxylate (0.0672 g, 91%).

$^1$H NMR (300 MHz, DMSO-d$_6$) δ 1.33 (s, 9H), 1.99 (m, 4H), 2.09-2.14 (m, 2H), 2.22-2.27 (m, 2H), 3.09 (m, 4H), 3.96 (s, 3H), 6.02-6.10 (m, 1H), 6.37 (d, J=11.0 Hz, 1H), 7.06 (d, J=8.8 Hz, 1H), 7.10 (s, 1H), 7.24 (m, 1H), 7.45 (m, 1H), 7.63 (d, J=8.1 Hz, 1H), 7.80 (d, J=8.8 Hz, 1H), 8.43 (d, J=8.1 Hz, 1H), 13.83 (s, 1H).

(c) Step 3

A solution of tert-butyl 4-((Z)-4-{(Z)-2-[(1H-indazol-3-yl)methylene]-6-methoxy-3-oxo-2,3-dihydrobenzofuran-7-yl}but-3-enyl)piperazine-1-carboxylate (0.0672 g, 0.127 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and the solvent was evaporated to obtain (Z)-2-[(1H-indazol-3-yl)methylene]-6-methoxy-7-[(Z)-4-(piperazin-1-yl)but-1-enyl]benzofuran-3(2H)-one (0.0412 g, 75%).

$^1$H NMR (300 MHz, DMSO-d$_6$) δ 1.97 (m, 4H), 2.07-2.12 (m, 2H), 2.16-2.21 (m, 2H), 2.47 (m, 4H), 3.96 (s, 3H), 6.01-6.10 (m, 1H), 6.35 (d, J=11.0 Hz, 1H), 7.06 (d, J=8.8 Hz, 1H), 7.09 (s, 1H), 7.24 (m, 1H), 7.45 (m, 1H), 7.62 (d, J=8.1 Hz, 1H), 7.80 (d, J=8.8 Hz, 1H), 8.44 (d, J=8.1 Hz, 1H).

Example B51

(Z)-2-[(1H-Indazol-3-yl)methylene]-6-methoxy-7-[4-(piperazin-1-yl)butyl]benzofuran-3(2H)-one (a) Step 1

A solution of tert-butyl 4-[4-(6-methoxy-3-oxo-2,3-dihydrobenzofuran-7-yl)but-3-ynyl]piperazine-1-carboxylate (0.0883 g, 0.220 mmol) synthesized in Example B49, Step 2 in ethanol (6 mL) was added with 5% palladium/carbon (wetted with 50% water, 0.100 g), and the mixture was stirred at room temperature for 16 hours under a hydrogen atmosphere. The reaction mixture was filtered through Celite, the filtrate was concentrated, and the resulting residue was purified by silica gel column chromatography (hexane/ethyl acetate) to obtain tert-butyl 4-[4-(6-methoxy-3-oxo-2,3-dihydrobenzofuran-7-yl)butyl]piperazine-1-carboxylate (0.0912 g, quantitative).

$^1$H NMR (300 MHz, CDCl$_3$) δ 1.46 (s, 9H), 1.57 (m, 2H), 1.78 (m, 2H), 2.29-2.46 (m, 6H), 2.67 (m, 2H), 3.43 (m, 4H), 3.91 (s, 3H), 4.61 (s, 2H), 6.66 (d, J=8.8 Hz, 1H), 7.53 (d, J=8.8 Hz, 1H).

(b) Step 2

A solution of tert-butyl 4-[4-(6-methoxy-3-oxo-2,3-dihydrobenzofuran-7-yl)butyl]piperazine-1-carboxylate (0.0860 g, 0.212 mmol) in methanol (5 mL) was added with 1H-indazole-3-carboxaldehyde (0.0282 g, 0.193 mmol) and piperidine (7 drops), and the mixture was stirred at 60° C. for 2 hours. The reaction mixture was concentrated, and then the residue was purified by silica gel column chromatography (chloroform/methanol) to obtain tert-butyl (Z)-4-(4-{2-[(1H-indazol-3-yl)methylene]-6-methoxy-3-oxo-2,3-dihydrobenzofuran-7-yl}butyl)piperazine-1-carboxylate (0.0945 g, 91%).

$^1$H NMR (300 MHz, DMSO-d$_6$) δ 1.37 (s, 9H), 1.45-1.74 (m, 4H), 2.17 (m, 4H), 2.27 (m, 2H), 2.83 (m, 2H), 3.18 (m, 4H), 3.97 (s, 3H), 7.03 (d, J=8.8 Hz, 1H), 7.07 (s, 1H), 7.30 (m, 1H), 7.48 (m, 1H), 7.65 (d, J=8.1 Hz, 1H), 7.71 (d, J=8.8 Hz, 1H), 8.50 (d, J=8.8 Hz, 1H), 13.84 (s, 1H).

(c) Step 3

A solution of tert-butyl (Z)-4-(4-{2-[(1H-indazol-3-yl)methylene]-6-methoxy-3-oxo-2,3-dihydrobenzofuran-7-yl}butyl)piperazine-1-carboxylate (0.0945 g, 0.177 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and the solvent was evaporated to obtain (Z)-2-[(1H-indazol-3-yl)methylene]-6-methoxy-7-[4-(piperazin-1-yl)butyl]benzofuran-3(2H)-one (0.0524 g, 68%).

$^1$H NMR (300 MHz, DMSO-d$_6$) δ 1.51 (m, 2H), 1.63 (m, 2H), 2.14 (m, 4H), 2.20 (m, 2H), 2.56 (m, 4H), 2.82 (m, 2H), 3.97 (s, 3H), 7.02 (d, J=8.8 Hz, 1H), 7.07 (s, 1H), 7.29 (m, 1H), 7.47 (m, 1H), 7.65 (d, J=8.8 Hz, 1H), 7.70 (d, J=8.8 Hz, 1H), 8.50 (d, J=8.1 Hz, 1H).

Example B52

(Z)-2-[(1H-Indazol-3-yl)methylene]-6-methoxy-7-(1,2,3,6-tetrahydropyridin-4-yl)benzofuran-3(2H)-one (a) Step 1

A solution of 7-iodo-6-methoxybenzofuran-3(2H)-one (0.100 g, 0.345 mmol) synthesized in Example B46, Step 2 in 1,4-dioxane (6 mL) was added with tert-butyl 4-(4,4,5,5-tetramethyl-1,3,2-dioxaborolan-2-yl)-5,6-dihydropyridine-1(2H)-carboxylate (0.107 g, 0.345 mmol), dichlorobis(triphenylphosphine)palladium(II) (0.0252 g, 0.0345 mmol) and 2 M aqueous sodium carbonate (0.515 mL, 1.03 mmol), and the mixture was stirred at 150° C. for 30 minutes under irradiation of microwaves. The reaction mixture was poured into water, the mixture was extracted with ethyl acetate, and the organic layer was washed with saturated brine. The organic layer was dried over anhydrous magnesium sulfate, then the solvent was evaporated, and the resulting residue was subjected to silica gel column chromatography (hexane/ethyl acetate). The resulting crude product was purified again by silica gel column chromatography (chloroform/methanol) to obtain tert-butyl 4-(6-methoxy-3-oxo-2,3-dihydrobenzofuran-7-yl)-5,6-dihydropyridine-1(2H)-carboxylate (0.0562 g, 47%).

$^1$H NMR (300 MHz, CDCl$_3$) δ 1.50 (s, 9H), 2.42 (m, 2H), 3.63 (m, 2H), 3.91 (s, 3H), 4.08 (m, 2H), 4.61 (s, 2H), 5.81 (m, 1H), 6.70 (d, J=8.1 Hz, 1H), 7.59 (d, J=8.1 Hz, 1H).

(b) Step 2

A solution of tert-butyl 4-(6-methoxy-3-oxo-2,3-dihydrobenzofuran-7-yl)-5,6-dihydropyridine-1(2H)-carboxylate (0.0402 g, 0.116 mmol) in methanol (3 mL) was added with 1H-indazole-3-carboxaldehyde (0.0170 g, 0.116 mmol) and piperidine (0.100 mL, 1.01 mmol), and the mixture was stirred at 60° C. for 2 hours. The reaction mixture was concentrated, the resulting solid was suspended in 50% ethyl acetate in hexane and thereby washed, and then the solid was collected by filtration. The filtrate was concentrated, and the resulting residue was purified by silica gel column chromatography (hexane/ethyl acetate). The purification product was combined with the solid obtained above to obtain 0.0373 g (68%) of tert-butyl (Z)-4-(2-[1H-indazol-3-yl)methylene]-6-methoxy-3-oxo-2,3-dihydrobenzofuran-7-yl]-3,6-dihydropyridine-1(2H)-carboxylate.

$^1$H NMR (300 MHz, DMSO-d$_6$) δ 1.49 (s, 9H), 2.42 (m, 2H), 3.62 (m, 2H), 3.95 (s, 3H), 4.10 (m, 2H), 5.93 (m, 1H), 7.04 (s, 1H), 7.06 (d, J=8.8 Hz, 1H), 7.22 (m, 1H), 7.42 (m, 1H), 7.63 (d, J=8.8 Hz, 1H), 7.77 (d, J=8.8 Hz, 1H), 8.55 (d, J=8.1 Hz, 1H), 13.83 (s, 1H).

(c) Step 3

A solution of tert-butyl (Z)-4-(2-[1H-indazol-3-yl)methylene]-6-methoxy-3-oxo-2,3-dihydrobenzofuran-7-yl]-3,6-dihydropyridine-1(2H)-carboxylate (0.0373 g, 0.0788 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-(1,2,3,6-tetrahydropyridin-4-yl)benzofuran-3(2H)-one (0.0285 g, 96%).

$^1$H NMR (300 MHz, DMSO-d$_6$) δ 2.40 (m, 2H), 3.10 (m, 2H), 3.57 (m, 2H), 3.95 (s, 3H), 5.97 (m, 1H), 7.05 (s, 1H), 7.06 (d, J=8.8 Hz, 1H), 7.34 (m, 1H), 7.47 (m, 1H), 7.64 (d, J=8.8 Hz, 1H), 7.77 (d, J=8.8 Hz, 1H), 8.61 (d, J=8.1 Hz, 1H).

Example B53

(Z)-2-[(1H-Indazol-3-yl)methylene]-6-methoxy-7-(piperidin-4-yl)benzofuran-3(2H)-one (a) Step 1

A solution of tert-butyl 4-(6-methoxy-3-oxo-2,3-dihydrobenzofuran-7-yl)-5,6-dihydropyridine-1(2H)-carboxylate (0.203 g, 0.587 mmol) synthesized in the same manner as that of Example B52, Step 1 in ethanol (10 mL) was added with 5% palladium/carbon (wetted with 50% water, 0.100 g), and the mixture was stirred at room temperature for 16 hours under a hydrogen atmosphere. The reaction mixture was filtered through Celite, the filtrate was concentrated, and the resulting residue was purified by silica gel column chromatography (hexane/ethyl acetate) to obtain tert-butyl 4-(6-methoxy-3-oxo-2,3-dihydrobenzofuran-7-yl)piperidine-1-carboxylate (0.0263 g, 13%).

$^1$H NMR (300 MHz, CDCl$_3$) δ 1.49 (s, 9H), 1.54-1.59 (m, 2H), 2.11-2.25 (m, 2H), 2.74-2.82 (m, 2H), 3.19-3.30 (m, 1H), 3.91 (s, 3H), 4.20-4.24 (m, 2H), 4.60 (s, 2H), 6.68 (d, J=8.8 Hz, 1H), 7.54 (d, J=8.8 Hz, 1H).

(b) Step 2

A solution of tert-butyl 4-(6-methoxy-3-oxo-2,3-dihydrobenzofuran-7-yl)piperidine-1-carboxylate (0.0341 g, 0.0981 mmol) in methanol (3 mL) was added with 1H-indazole-3-carboxaldehyde (0.0151 g, 0.103 mmol) and piperidine (0.0800 mL, 0.810 mmol), and the mixture was stirred at 60° C. for 2 hours. The reaction mixture was concentrated, and the resulting residue was purified by silica gel column chromatography (chloroform/ethyl acetate) to obtain tert-butyl (Z)-4-{2-[(1H-indazol-3-yl)methylene]-6-methoxy-3-oxo-2,3-dihydrobenzofuran-7-yl}piperidine-1-carboxylate (0.0446 g, 96%).

$^1$H NMR (300 MHz, DMSO-d$_6$) δ 1.46 (s, 9H), 1.66-1.70 (m, 2H), 2.12-2.58 (m, 2H), 2.80 (m, 2H), 3.37 (m, 1H), 3.97 (s, 3H), 4.13-4.17 (m, 2H), 7.05 (d, J=8.8 Hz, 1H), 7.08 (s, 1H), 7.26 (m, 1H), 7.44 (m, 1H), 7.65 (d, J=8.1 Hz, 1H), 7.73 (d, J=8.1 Hz, 1H), 8.48 (d, J=8.1 Hz, 1H), 13.82 (s, 1H).

(c) Step 3

A solution of tert-butyl (Z)-4-{2-[(1H-indazol-3-yl)methylene]-6-methoxy-3-oxo-2,3-dihydrobenzofuran-7-yl}piperidine-1-carboxylate (0.0446 g, 0.0937 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-(piperidin-4-yl)benzofuran-3(2H)-one (0.0312 g, 88%).

$^1$H NMR (300 MHz, DMSO-d$_6$) δ 1.55-1.58 (m, 2.20-2.34 (m, 2H), 2.59-2.66 (m, 2H), 3.08-3.12 (m, 2H), 3.29-3.37 (m, 1H), 3.97 (s, 3H), 7.03 (d, J=8.8 Hz, 1H), 7.09 (s, 1H), 7.37 (m, 1H), 7.49 (m, HA 7.65 (d, J=8.8 Hz, 1H), 7.70 (d, J=8.8 Hz, 1H), 8.56 (d, J=8.1 Hz, 1H).

Example B54

(Z)-2-[(1H-Indazol-3-yl)methylene]-6-methoxy-7-(piperidin-4-ylmethyl)benzofuran-3(2H)-one (a) Step 1

A solution of methyltriphenylphosphonium bromide (2.15 g, 6.02 mmol) in hexane (15 mL) was added with tert-butoxypotassium (0.676 g, 6.02 mmol), and the mixture was stirred at room temperature for 2 hours. The reaction mixture was added portionwise with tert-butyl 4-oxopiperidine-1-carboxylate (1.10 g, 5.52 mmol), and the mixture was stirred overnight at room temperature. The solid was removed by filtration, the concentrated filtrate was added with water, and the mixture was extracted with ethyl acetate. The organic layer was washed with saturated brine, and dried over anhydrous magnesium sulfate. The solvent was evaporated, and the resulting residue was purified by silica gel column chromatography (hexane/ethyl acetate) to obtain tert-butyl 4-methylenepiperidine-1-carboxylate (0.731 g, 67%).

$^1$H NMR (300 MHz, CDCl$_3$) δ 1.47 (s, 9H), 2.18 (t, J=5.9 Hz, 4H), 3.42 (t, J=5.9 Hz, 4H), 4.74 (s, 2H).

(b) Step 2

A solution of tert-butyl 4-methylenepiperidine-1-carboxylate (0.256 g, 1.30 mmol) in THF (2 mL) was added dropwise with a 0.5 M solution of 9-BBN in THF (2.60 mL, 1.30 mmol). The reaction mixture was refluxed for 1 hour by heating, and then cooled to room temperature.

(c) Step 3

A solution of 7-iodo-6-methoxybenzofuran-3(2H)-one (0.290 g, 1.00 mmol) synthesized in Example B46, Step 2 in DMF (6 mL) was added with water (0.6 mL) and potassium carbonate (0.276 g, 2.00 mmol), and the mixture was stirred at room temperature, and added dropwise with the THF solution prepared in Step 2. The reaction mixture was added with [1,1'-bis(diphenylphosphino)ferrocene]dichloropalladium (II) (0.0732 g, 0.100 mmol), and the mixture was stirred at 60° C. for 4 hours. The reaction mixture was filtered through Celite, the filtrate was added with water, and the mixture was extracted with ethyl acetate. The organic layer was washed with saturated brine, and dried over anhydrous magnesium sulfate, and the solvent was evaporated. The resulting residue was purified by silica gel column chromatography (hexane/ethyl acetate) to obtain tert-butyl 4-[(6-methoxy-3-oxo-2,3-dihydrobenzofuran-7-yl)methyl]piperidine-1-carboxylate (0.0263 g, 7%).

$^1$H NMR (300 MHz, CDCl$_3$) δ 1.15-1.29 (m, 2H), 1.45 (s, 9H), 1.56-1.59 (m, 2H), 1.75 (m, 1H), 2.60 (d, J=7.3 Hz, 2H), 2.65-2.69 (m, 2H), 3.91 (s, 3H), 4.03-4.07 (m, 2H), 4.61 (s, 2H), 6.68 (d, J=8.8 Hz, 1H), 7.55 (d, J=8.8 Hz, 1H).

(d) Step 4

A solution of tert-butyl 4-[(6-methoxy-3-oxo-2,3-dihydrobenzofuran-7-yl)methyl]piperidine-1-carboxylate (0.0518 g, 0.143 mmol) in methanol (5 mL) was added with 1H-indazole-3-carboxaldehyde (0.0220 g, 0.151 mmol) and piperidine (0.100 mL, 1.01 mmol), and the mixture was stirred at 60° C. for 2 hours. The reaction mixture was concentrated, and the resulting residue was purified by silica gel column chromatography (chloroform/ethyl acetate) to obtain tert-butyl (Z)-4-({2-[(1H-indazol-3-yl)methylene]-6-methoxy-3-oxo-2,3-dihydrobenzofuran-7-yl}methyl)piperidine-1-carboxylate (0.0525 g, 75%).

$^1$H NMR (300 MHz, DMSO-d$_6$) δ 1.10-1.24 (m, 2H), 1.34 (s, 9H), 1.61-1.64 (m, 2H), 1.88 (m, 1H), 2.64 (m, 2H), 2.76 (d, J=7.3 Hz, 2H), 3.88-3.92 (m, 2H), 3.97 (s, 3H), 7.03 (d, J=8.8 Hz, 1H), 7.06 (s, 1H), 7.24 (m, 1H), 7.46 (m, 1H), 7.65 (d, J=8.8 Hz, 1H), 7.72 (d, J=8.8 Hz, 1H), 8.54 (d, J=8.1 Hz, 1H), 13.84 (s, 1H).

(e) Step 5

A solution of tert-butyl (Z)-4-({2-[(1H-indazol-3-yl)methylene]-6-methoxy-3-oxo-2,3-dihydrobenzofuran-7-yl}methyl)piperidine-1-carboxylate (0.0525 g, 0.107 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was washed with saturated brine, and then dried over anhydrous sodium sulfate. The solvent was evaporated to obtain (Z)-2-[(1H-indazol-3-yl)methylene]-6-methoxy-7-(piperidin-4-ylmethyl)benzofuran-3(2H)-one (0.0384 g, 92%).

$^1$H NMR (300 MHz, DMSO-d$_6$) δ 1.17-1.28 (m, 2H), 1.57-1.61 (m, 2H), 1.79 (m, 1H), 2.34-2.42 (m, 2H), 2.76 (d, J=6.6 Hz, 2H), 2.90-2.94 (m, 2H), 3.97 (s, 3H), 7.04 (d, J=8.8 Hz, 1H), 7.07 (s, 1H), 7.29 (m, 1H), 7.49 (m, 1H), 7.66 (d, J=8.8 Hz, 1H), 7.72 (d, J=8.8 Hz, 1H), 8.57 (d, J=8.1 Hz, 1H).

Example B55

(Z)-2-[(1H-Indazol-3-yl)methylene]-6-methoxy-7-(piperidin-4-ylethynyl)benzofuran-3(2H)-one (a) Step 1

A solution of 7-iodo-6-methoxybenzofuran-3(2H)-one (0.348 g, 1.20 mmol) synthesized in Example B46, Step 2 in triethylamine (10 mL) was added with tert-butyl 4-ethynylpiperidine-1-carboxylate (Journal of Medicinal Chemistry, Vol. 47, p. 3111, 2004, 0.276 g, 1.32 mmol), dichlorobis(triphenylphosphine)palladium(II) (0.0842 g, 0.120 mmol) and copper(I) iodide (0.0229 g, 0.120 mmol), and the mixture was stirred overnight at room temperature. The reaction mixture was concentrated, and the resulting residue was purified by silica gel column chromatography (hexane/ethyl acetate) to obtain tert-butyl 4-[(6-methoxy-3-oxo-2,3-dihydrobenzofuran-7-yl)ethynyl]piperidine-1-carboxylate (0.245 g, 55%).

$^1$H NMR (300 MHz, DMSO-d$_6$) δ 1.41 (s, 9H), 1.48-1.56 (m, 2H), 1.78-1.84 (m, 2H), 2.94 (m, 1H), 3.16-3.22 (m, 2H), 3.58-3.65 (m, 2H), 3.94 (s, 3H), 4.84 (s, 2H), 6.90 (d, J=8.8 Hz, 1H), 7.61 (d, J=8.8 Hz, 1H).

(b) Step 2

A solution of tert-butyl 4-[(6-methoxy-3-oxo-2,3-dihydrobenzofuran-7-yl)ethynyl]piperidine-1-carboxylate (0.103 g, 0.277 mmol) in methanol (5 mL) was added with 1H-indazole-3-carboxaldehyde (0.0386 g, 0.264 mmol) and piperidine (7 drops), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-indazol-3-yl)methylene]-6-methoxy-3-oxo-2,3-dihydrobenzofuran-7-yl}ethynyl)piperidine-1-carboxylate (0.105 g, 80%).

$^1$H NMR (300 MHz, DMSO-d$_6$) δ 1.43 (s, 9H), 1.55-1.67 (m, 2H), 1.90-1.94 (m, 2H), 3.07 (m, 1H), 3.17 (m, 2H), 3.71-3.76 (m, 2H), 4.01 (s, 3H), 7.07 (d, J=8.8 Hz, 1H), 7.11 (s, 1H), 7.25 (m, 1H), 7.46 (m, 1H), 7.66 (d, J=8.8 Hz, 1H), 7.81 (d, J=8.8 Hz, 1H), 8.67 (d, J=8.1 Hz, 1H), 13.89 (s, 1H).

(c) Step 3

A solution of tert-butyl (Z)-4-({2-[(1H-indazol-3-yl)methylene]-6-methoxy-3-oxo-2,3-dihydrobenzofuran-7-yl}ethynyl)piperidine-1-carboxylate (0.0982 g, 0.197 mmol) in methylene chloride (5 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-(piperidin-4-ylethynyl)benzofuran-3(2H)-one (0.0392 g, 50%).

$^1$H NMR (300 MHz, DMSO-d$_6$) δ 1.56-1.68 (m, 2H), 1.87-1.90 (m, 2H), 2.59-2.65 (m, 2H), 2.92 (m, 1H), 2.98-3.02 (m, 2H), 4.00 (s, 3H), 7.07 (d, J=8.8 Hz, 1H), 7.12 (s, 1H), 7.32 (m, 1H), 7.48 (m, 1H), 7.66 (d, J=8.1 Hz, 1H), 7.80 (d, J=8.8 Hz, 1H), 8.69 (d, J=8.1 Hz, 1H).

Example B56

(Z)-2-[(1H-Indazol-3-yl)methylene]-6-methoxy-7-[(Z)-2-(piperidin-4-yl)vinyl]benzofuran-3(2H)-one (a) Step 1

A solution of tert-butyl 4-[(6-methoxy-3-oxo-2,3-dihydrobenzofuran-7-yl)-ethynyl]piperidine-1-carboxylate (0.157 g, 0.423 mmol) synthesized in Example B55, Step 1 in ethyl acetate/ethanol (1:1, 3 mL) was added with 5% palladium/carbon (wetted with 50% water, 0.0500 g), and the mixture was stirred overnight at room temperature under a hydrogen atmosphere. The reaction mixture was filtered through Celite, the filtrate was concentrated, and the resulting residue was purified by silica gel column chromatography (hexane/ethyl acetate) to obtain tert-butyl (Z)-4-[2-(6-methoxy-3-oxo-2,3-dihydrobenzofuran-7-yl)vinyl]piperidine-1-carboxylate (0.0610 g, 39%).

$^1$H NMR (300 MHz, DMSO-d$_6$) δ 1.10-1.24 (m, 2H), 1.38 (s, 9H), 1.53-1.57 (m, 2H), 2.15-2.25 (m, 1H), 2.67 (m, 2H), 3.87 (m, 2H), 3.90 (s, 3H), 4.77 (s, 2H), 5.57-5.64 (m, 1H), 6.03 (d, J=11.0 Hz, 1H), 6.90 (d, J=8.8 Hz, 1H), 7.58 (d, J=8.8 Hz, 1H).

(b) Step 2

A solution of tert-butyl (Z)-4-[2-(6-methoxy-3-oxo-2,3-dihydrobenzofuran-7-yl)vinyl]piperidine-1-carboxylate (0.0374 g, 0.100 mmol) in methanol (3 mL) was added with 1H-indazole-3-carboxaldehyde (0.0146 g, 0.100 mmol) and piperidine (5 drops), and the mixture was stirred at 60° C. for 2 hours. The reaction mixture was concentrated, and the resulting residue was purified by silica gel column chromatography (chloroform/methanol) to obtain tert-butyl 4-((Z)-2-{(Z)-2-[(1H-indazol-3-yl)methylene]-6-methoxy-3-oxo-2,3-dihydrobenzofuran-7-yl}vinyl)piperidine-1-carboxylate (0.0387 g, 77%).

$^1$H NMR (300 MHz, DMSO-d$_6$) δ 1.06-1.19 (m, 2H), 1.32 (s, 9H), 1.55-1.59 (m, 2H), 2.17-2.28 (m, 1H), 2.45 (m, 2H), 3.68-3.71 (m, 2H), 3.96 (s, 3H), 5.80-5.87 (m, 1H), 6.13 (d, J=11.0 Hz, 1H), 7.06 (d, J=8.8 Hz, 1H), 7.10 (s, 1H), 7.23 (m, 1H), 7.45 (m, 1H), 7.63 (d, J=8.1 Hz, 1H), 7.79 (d, J=8.8 Hz, 1H), 8.39 (d, J=8.8 Hz, 1H), 13.81 (s, 1H).

(c) Step 3

A solution of tert-butyl 4-((Z)-2-{(Z)-2-[(1H-indazol-3-yl)methylene]-6-methoxy-3-oxo-2,3-dihydrobenzofuran-7-yl}vinyl)piperidine-1-carboxylate (0.0387 g, 0.0771 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated. The resulting residue was subjected to silica gel column chromatography (aminopropyl silica was used, eluted with chloroform/methanol) to obtain (Z)-2-[(1H-indazol-3-yl-methylene]-6-methoxy-7-[(Z)-2-(piperidin-4-yl)vinyl]benzofuran-3(2H)-one (0.0108 g, 35%).

$^1$H NMR (300 MHz, DMSO-d$_6$) δ 1.18-1.23 (m, 2H), 1.45-1.49 (m, 2H), 2.07-2.20 (m, 3H), 2.67-2.71 (m, 2H), 3.95 (s, 3H), 5.81-5.88 (m, 1H), 6.22 (d, J=11.0 Hz, 1H), 7.07 (d, J=8.8 Hz, 1H), 7.11 (s, 1H), 7.25 (m, 1H), 7.45 (m, 1H), 7.62 (d, J=8.1 Hz, 1H), 7.78 (d, J=8.8 Hz, 1H), 8.45 (d, J=8.8 Hz, 1H).

Example B57

(Z)-2-[(1H-Indazol-3-yl)methylene]-6-methoxy-7-[2-(piperidin-4-yl)ethyl]benzofuran-3(2H)-one (a) Step 1

A solution of tert-butyl 4-[(6-methoxy-3-oxo-2,3-dihydrobenzofuran-7-yl)-ethynyl]piperidine-1-carboxylate (0.0721 g, 0.194 mmol) synthesized in Example B55, Step 1 in ethanol (3 mL) was added with 5% palladium/carbon (wetted with 50% water, 0.0700 g), and the mixture was stirred overnight at room temperature under a hydrogen atmosphere. The reaction mixture was filtered through Celite, and the resulting filtrate was concentrated to obtain tert-butyl 4-[2-(6-methoxy-3-oxo-2,3-dihydrobenzofuran-7-yl)ethyl]piperidine-1-carboxylate (0.0593 g, 81%).

$^1$H NMR (300 MHz, CDCl$_3$) δ 1.07-1.20 (m, 2H), 1.34-1.52 (m, 3H), 1.46 (s, 9H), 1.74-1.78 (m, 2H), 2.64-2.72 (m, 4H), 3.92 (s, 3H), 4.06-4.11 (m, 2H), 4.61 (s, 2H), 6.67 (d, J=8.8 Hz, 1H), 7.54 (d, J=8.8 Hz, 1H).

(b) Step 2

A solution of tert-butyl 4-[2-(6-methoxy-3-oxo-2,3-dihydrobenzofuran-7-yl)ethyl]piperidine-1-carboxylate (0.0542 g, 0.144 mmol) in methanol (3 mL) was added with 1H-indazole-3-carboxaldehyde (0.0211 g, 0.144 mmol) and piperidine (5 drops), and the mixture was stirred at 60° C. for 2 hours. The reaction mixture was concentrated, and the resulting residue was purified by silica gel column chromatography (chloroform/methanol) to obtain tert-butyl (Z)-4-(2-{2-[(1H-indazol-3-yl)methylene]-6-methoxy-3-oxo-2,3-dihydrobenzofuran-7-yl}ethyl)piperidine-1-carboxylate (0.0524 g, 72%).

$^1$H NMR (300 MHz, DMSO-d$_6$) δ 0.93-1.03 (m, 2H), 1.37 (s, 9H), 1.39 (m, 1H), 1.51 (m, 2H), 1.73-1.77 (m, 2H), 2.61 (m, 2H), 2.83 (m, 2H), 3.84-3.89 (m, 2H), 3.97 (s, 3H), 7.02 (d, J=8.8 Hz, 1H), 7.08 (s, 1H), 7.26 (m, 1H), 7.48 (m, 1H), 7.65 (d, J=8.1 Hz, 1H), 7.70 (d, J=8.8 Hz, 1H), 8.45 (d, J=8.8 Hz, 1H), 13.84 (s, 1H).

(c) Step 3

A solution of tert-butyl (Z)-4-(2-{2-[(1H-indazol-3-yl)methylene]-6-methoxy-3-oxo-2,3-dihydrobenzofuran-7-yl}ethyl)piperidine-1-carboxylate (0.0506 g, 0.100 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated. The resulting residue was purified by silica gel column chromatography (aminopropyl silica was used, eluted with chloroform/methanol) to obtain (Z)-2-[(1H-indazol-3-yl)methylene]-6-methoxy-7-[2-(piperidin-4-yl)ethyl]benzofuran-3(2H)-one (0.0172 g, 43%).

$^1$H NMR (300 MHz, DMSO-d$_6$) δ 0.97-1.08 (m, 2H), 1.39 (m, 1H), 1.46-1.54 (m, 1.68-1.72 (m, 2H), 2.36-2.46 (m, 2H), 2.80-2.90 (m, 4H), 3.97 (s, 3H), 7.02 (d, J=8.8 Hz, 1H), 7.09 (s, 1H), 7.26 (m, 1H), 7.48 (m, 1H), 7.65 (d, J=8.1 Hz, 1H), 7.70 (d, J=8.8 Hz, 1H), 8.48 (d, J=8.1 Hz, 1H).

Example B58

(Z)-2-[(1H-Indazol-3-yl)methylene]-6-methoxy-7-[3-(piperidin-4-yl)prop-1-ynyl]benzofuran-3(2H)-one (a) Step 1

A solution of tert-butyl 4-(2-oxoethyl)piperidine-1-carboxylate (0.596 g, 2.62 mmol) in methanol (10 mL) was added with potassium carbonate (0.724 g, 5.24 mmol), and the mixture was stirred at room temperature. The reaction mixture was added with dimethyl (1-diazo-2-oxopropyl)phosphonate (0.500 g, 2.62 mmol), and the mixture was stirred at room temperature for additional 4 hours. The reaction mixture was concentrated, and then added with water, and the mixture was extracted with methylene chloride. The organic layer was washed with saturated brine, and dried over anhydrous magnesium sulfate. The solvent was evaporated, and the resulting residue was purified by silica gel column chromatography (hexane/ethyl acetate) to obtain tert-butyl 4-(prop-2-ynyl)piperidine-1-carboxylate (0.393 g, 67%).

$^1$H NMR (300 MHz, CDCl$_3$) δ 1.13-1.27 (m, 2H), 1.54 (s, 9H), 1.56-1.70 (m, 1H), 1.74-1.78 (m, 2H), 1.98 (t, J=2.9 Hz, 1H), 2.15 (dd, J=6.6 Hz, 2.9 Hz, 2H), 2.65-2.73 (m, 2H), 4.09-4.13 (m, 2H).

(b) Step 2

A solution of 7-iodo-6-methoxybenzofuran-3(2H)-one (0.348 g, 1.20 mmol) synthesized in Example B46, Step 2 in triethylamine (10 mL) was added with tert-butyl 4-(prop-2-ynyl)piperidine-1-carboxylate (0.269 g, 1.20 mmol), dichlorobis(triphenylphosphine)palladium(II) (0.0842 g, 0.120 mmol) and copper(I) iodide (0.0114 g, 0.0600 mmol), and the mixture was stirred overnight at 50° C. The reaction mixture was concentrated, and then added with water, and the mixture was extracted with methylene chloride. The organic layer was washed with saturated brine, and dried over anhydrous magnesium sulfate. The solvent was evaporated, and the resulting residue was purified by silica gel column chromatography (hexane/ethyl acetate) to obtain tert-butyl 4-[3-(6-methoxy-3-oxo-2,3-dihydrobenzofuran-7-yl)prop-2-ynyl]piperidine-1-carboxylate (0.281 g, 61%).

$^1$H NMR (300 MHz, CDCl$_3$) δ 1.25-1.39 (m, 2H), 1.46 (s, 9H), 1.77 (m, 1H), 1.83-1.87 (m, 2H), 2.50 (d, J=6.6 Hz, 2H), 2.69-2.77 (m, 2H), 3.98 (s, 3H), 4.12-4.16 (m, 2H), 4.69 (s, 2H), 6.68 (d, J=8.8 Hz, 1H), 7.59 (d, J=8.8 Hz, 1H).

(c) Step 3

A solution of tert-butyl 4-[3-(6-methoxy-3-oxo-2,3-dihydrobenzofuran-7-yl)prop-2-ynyl]piperidine-1-carboxylate (0.0503 g, 0.130 mmol) in methanol (3 mL) was added with 1H-indazole-3-carboxaldehyde (0.0173 g, 0.119 mmol) and piperidine (5 drops), and the mixture was stirred at 60° C. for 2 hours. The reaction mixture was concentrated, and the resulting residue was purified by silica gel column chromatography (hexane/ethyl acetate) to obtain tert-butyl (Z)-4-(3-{2-[(1H-indazol-3-yl)methylene]-6-methoxy-3-oxo-2,3-dihydrobenzofuran-7-yl}prop-2-ynyl)piperidine-1-carboxylate (0.0293 g, 44%).

$^1$H NMR (300 MHz, DMSO-d$_6$) δ 1.15-1.28 (m, 2H), 1.37 (s, 9H), 1.79-1.82 (m, 3H), 2.63 (d, J=5.9 Hz, 2H), 2.68-2.72 (m, 2H), 3.92-3.95 (m, 2H), 3.90 (s, 3H), 7.06 (d, J=8.8 Hz, 1H), 7.10 (s, 1H), 7.29 (m, 1H), 7.48 (m, 1H), 7.65 (d, J=8.1 Hz, 1H), 7.80 (d, J=8.8 Hz, 1H), 8.73 (d, J=8.8 Hz, 1H), 13.87 (s, 1H).

(d) Step 4

A solution of tert-butyl (Z)-4-(3-{2-[(1H-indazol-3-yl)methylene]-6-methoxy-3-oxo-2,3-dihydrobenzofuran-7-yl}prop-2-ynyl)piperidine-1-carboxylate (0.0293 g, 0.0570 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-[3-(piperidin-4-yl)prop-1-ynyl]benzofuran-3(2H)-one (0.0123 g, 52%).

$^1$H NMR (300 MHz, DMSO-d$_6$) δ 1.21-1.35 (m, 2H), 1.68 (m, 1H), 1.74-1.78 (m, 2H), 2.42-2.46 (m, 2H), 2.59 (d, J=5.9 Hz, 2H), 2.92-2.96 (m, 2H), 4.00 (s, 3H), 7.06 (d, J=8.8 Hz, 1H), 7.12 (s, 1H), 7.28 (m, 1H), 7.48 (m, 1H), 7.66 (d, J=8.8 Hz, 1H), 7.80 (d, J=8.8 Hz, 1H), 8.70 (d, J=8.8 Hz, 1H).

Example B59

(Z)-2-[(1H-Indazol-3-yl)methylene]-6-methoxy-7-[(Z)-3-(piperidin-4-yl)prop-1-enyl]benzofuran-3(2H)-one (a) Step 1

A solution of tert-butyl 4-[3-(6-methoxy-3-oxo-2,3-dihydrobenzofuran-7-yl)prop-2-ynyl]piperidine-1-carboxylate (0.0775 g, 0.201 mmol) synthesized in Example B58, Step 2 in ethanol (5 mL) was added with 5% palladium/carbon (wetted with 50% water, 0.0800 g), and the mixture was stirred overnight at room temperature under a hydrogen atmosphere. The reaction mixture was filtered through Celite, the resulting filtrate was concentrated, and the resulting residue was purified by silica gel column chromatography (hexane/ethyl acetate) to obtain tert-butyl (Z)-4-[3-(6-methoxy-3-oxo-2,3-dihydrobenzofuran-7-yl)allyl]piperidine-1-carboxylate (0.0671 g, 86%).

$^1$H NMR (300 MHz, CD$_3$OD) δ 0.91-1.04 (m, 2H), 1.42 (s, 9H), 1.54 (m, 1H), 1.63-1.67 (m, 2H), 1.93-1.98 (m, 2H), 2.66-2.74 (m, 2H), 3.93 (s, 3H), 3.96-4.00 (m, 2H), 4.68 (s, 2H), 5.81-5.90 (m, 1H), 6.18 (d, J=11.7 Hz, 1H), 6.87 (d, J=8.1 Hz, 1H), 7.60 (d, J=8.1 Hz, 1H).

(b) Step 2

A solution of tert-butyl (Z)-4-(3-(6-methoxy-3-oxo-2,3-dihydrobenzofuran-7-yl)allyl)piperidine-1-carboxylate (0.0802 g, 0.207 mmol) in methanol (5 mL) was added with 1H-indazole-3-carboxaldehyde (0.0302 g, 0.207 mmol) and piperidine (7 drops), and the mixture was stirred at 60° C. for 2 hours. The reaction mixture was concentrated, and the resulting residue was purified by silica gel column chromatography (hexane/ethyl acetate) to obtain tert-butyl 4-((Z)-3-{(Z)-2-[(1H-indazol-3-yl)methylene]-6-methoxy-3-oxo-2,3-dihydrobenzofuran-7-yl}allyl)piperidine-1-carboxylate (0.0724 g, 68%).

$^1$H NMR (300 MHz, DMSO-$d_6$) δ 0.68-0.81 (m, 2H), 1.30 (s, 9H), 1.36 (m, 1H), 1.41-1.45 (m, 2H), 1.87-1.91 (m, 2H), 2.33 (m, 2H), 3.67-3.71 (m, 2H), 3.96 (s, 3H), 6.05-6.13 (m, 1H), 6.37 (d, J=11.0 Hz, 1H), 7.06 (d, J=8.1 Hz, 1H), 7.08 (s, 1H), 7.24 (m, 1H), 7.45 (m, 1H), 7.63 (d, J=8.1 Hz, 1H), 7.80 (d, J=8.1 Hz, 1H), 8.45 (d, J=8.1 Hz, 1H), 13.82 (s, 1H).

(c) Step 3

A solution of tert-butyl 4-((Z)-3-{(Z)-2-[(1H-indazol-3-yl)methylene]-6-methoxy-3-oxo-2,3-dihydrobenzofuran-7-yl}allyl)piperidine-1-carboxylate (0.0724 g, 0.140 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-[(Z)-3-(piperidin-4-yl)prop-1-enyl]benzofuran-3(2H)-one (0.0253 g, 43%).

$^1$H NMR (300 MHz, DMSO-$d_6$) δ 0.74-0.87 (m, 2H), 1.33 (m, 1H), 1.39-1.43 (m, 2H), 1.86-1.90 (m, 2H), 2.13-2.20 (m, 2H), 2.69-2.73 (m, 2H), 3.96 (s, 3H), 6.04-6.13 (m, 1H), 6.36 (d, J=11.0 Hz, 1H), 7.06 (d, J=8.8 Hz, 1H), 7.08 (s, 1H), 7.23 (m, 1H), 7.45 (m, 1H), 7.63 (d, J=8.8 Hz, 1H), 7.79 (d, J=8.8 Hz, 1H), 8.46 (d, J=8.1 Hz, 1H).

Example B60

(Z)-2-[(1H-Indazol-3-yl)methylene]-6-methoxy-7-[3-(piperidin-4-yl)propyl]benzofuran-3(2H)-one (a) Step 1

A solution of tert-butyl 4-[3-(6-methoxy-3-oxo-2,3-dihydrobenzofuran-7-yl)prop-2-ynyl]piperidine-1-carboxylate (0.0332 g, 0.0861 mmol) synthesized in Example B58, Step 2 in ethanol (5 mL) was added with 5% palladium/carbon (wetted with 50% water, 0.0400 g), and the mixture was stirred overnight at 50° C. under a hydrogen atmosphere. The reaction mixture was filtered through Celite, and the resulting filtrate was concentrated to obtain tert-butyl 4-[3-(6-methoxy-3-oxo-2,3-dihydrobenzofuran-7-yl)propyl]piperidine-1-carboxylate (0.0330 g, 96%).

$^1$H NMR (300 MHz, CDCl$_3$) δ 1.00-1.14 (m, 2H), 1.26-1.34 (m, 3H), 1.45 (s, 9H), 1.54-1.66 (m, 4H), 2.60-2.71 (m, 4H), 3.92 (s, 3H), 4.05-4.08 (m, 2H), 4.61 (s, 2H), 6.67 (d, J=8.8 Hz, 1H), 7.53 (d, J=8.8 Hz, 1H).

(b) Step 2

A solution of tert-butyl 4-[3-(6-methoxy-3-oxo-2,3-dihydrobenzofuran-7-yl)propyl]piperidine-1-carboxylate (0.0330 g, 0.0847 mmol) in methanol (3 mL) was added with 1H-indazole-3-carboxaldehyde (0.0124 g, 0.0847 mmol) and piperidine (5 drops), and the mixture was stirred at 60° C. for 2 hours. The reaction mixture was concentrated, and the resulting residue was subjected to silica gel column chromatography (chloroform/methanol). The resulting crude product was further purified by silica gel column chromatography (hexane/ethyl acetate) to obtain tert-butyl (Z)-4-(3-{2-[(1H-indazol-3-yl)methylene]-6-methoxy-3-oxo-2,3-dihydrobenzofuran-7-yl}propyl)piperidine-1-carboxylate (0.0313 g, 71%).

$^1$H NMR (300 MHz, DMSO-$d_6$) δ 0.83-0.95 (m, 2H), 1.22 (m, 2H), 1.31-1.40 (m, 1H), 1.35 (s, 9H), 1.54-1.57 (m, 2H), 1.65 (m, 2H), 2.51 (m, 2H), 2.78-2.83 (m, 2H), 3.79-3.83 (m, 2H), 3.97 (s, 3H), 7.02 (d, J=8.8 Hz, 1H), 7.07 (s, 1H), 7.28 (m, 1H), 7.47 (m, 1H), 7.65 (d, J=8.1 Hz, 1H), 7.71 (d, J=8.1 Hz, 1H), 8.50 (d, J=8.1 Hz, 1H), 13.83 (s, 1H).

(c) Step 3

A solution of tert-butyl (Z)-4-(3-{2-[(1H-indazol-3-yl)methylene]-6-methoxy-3-oxo-2,3-dihydrobenzofuran-7-yl}propyl)piperidine-1-carboxylate (0.0313 g, 0.0605 mmol) in methylene chloride (2 mL) was added with a 4 M solution of hydrogen chloride in 1,4-dioxane (2 mL), and the mixture was stirred at room temperature for 2 hours. The reaction mixture was added with ether, and the precipitated solid was collected by filtration, and washed with ether. The resulting solid was dissolved in a small volume of water, and the solution was adjusted to pH 9 with saturated aqueous sodium hydrogencarbonate. The solution was extracted with ethyl acetate, the organic layer was dried over anhydrous sodium sulfate, and then the solvent was evaporated to obtain (Z)-2-[(1H-indazol-3-yl)methylene]-6-methoxy-7-[3-(piperidin-4-yl)propyl]benzofuran-3(2H)-one (0.0223 g, 88%).

$^1$H NMR (300 MHz, DMSO-$d_6$) δ 0.94-1.07 (m, 2H), 1.32-1.36 (m, 3H), 1.54-1.58 (m, 2H), 1.65 (m, 2H), 2.34-2.41 (m, 2H), 2.78-2.83 (m, 2H), 2.87-2.91 (m, 2H), 3.97 (s, 3H), 7.03 (d, J=8.8 Hz, 1H), 7.08 (s, 1H), 7.28 (m, 1H), 7.49 (m, 1H), 7.66 (d, J=8.8 Hz, 1H), 7.71 (d, J=8.8 Hz, 1H), 8.51 (d, J=8.8 Hz, 1H).

Example B61

(Z)-2-[(1H-Indazol-3-yl)methylene]-6-methoxy-7-[4-(piperidin-4-yl)but-1-ynyl]benzofuran-3(2H)-one (a) Step 1

A solution of tert-butyl 4-(3-hydroxypropyl)piperidine-1-carboxylate (1.00 g, 4.11 mmol) in methylene chloride (20 mL) was cooled to 0° C., and added with the Dess-Martin reagent (2.27 g, 5.34 mmol), and then the mixture was stirred at room temperature for 4 hours. The reaction mixture was filtered, and the filtrate was washed with saturated aqueous sodium hydrogencarbonate, and then further washed with saturated brine. The organic layer was dried over anhydrous magnesium sulfate, then the solvent was evaporated, and the resulting residue was purified by silica gel column chromatography (hexane/ethyl acetate) to obtain tert-butyl 4-(3-oxopropyl)piperidine-1-carboxylate (0.874 g, 88%).

$^1$H NMR (300 MHz, DMSO-$d_6$) δ 0.87-1.00 (m, 2H), 1.34 (m, 1H), 1.38 (s, 9H), 1.42-1.49 (m, 2H), 1.58-1.63 (m, 2H), 2.45 (t, J=7.3 Hz, 2H), 2.64 (m, 2H), 3.89-3.93 (m, 2H), 9.67 (br s, 1H).

(b) Step 2

A solution of tert-butyl 4-(3-oxopropyl)piperidine-1-carboxylate (0.874 g, 3.62 mmol) in methanol (15 mL) was added with potassium carbonate (1.00 g, 7.24 mmol), and the mixture was stirred at room temperature. The reaction mixture was added with dimethyl (1-diazo-2-oxopropyl)phosphonate (0.692 g, 3.62 mmol), and the mixture was stirred at room temperature for additional 3 hours. The reaction mixture was concentrated, and then added with water, and the mixture was extracted with ethyl acetate. The organic layer was washed with saturated brine, and dried over anhydrous magnesium sulfate. The solvent was evaporated, and the resulting residue was purified by silica gel column chromatography (hexane/ethyl acetate) to obtain tert-butyl 4-(but-3-ynyl)piperidine-1-carboxylate (0.670 g, 78%).

$^1$H NMR (300 MHz, DMSO-$d_6$) δ 0.88-1.01 (m, 2H), 1.34-1.42 (m, 2H), 1.38 (s, 9H), 1.45-1.55 (m, 1H), 1.59-1.64 (m, 2H), 2.17 (td, J=7.3 Hz, 2.2 Hz, 2H), 2.61-2.69 (m, 2H), 2.74 (t, J=2.2 Hz, 1H), 3.89-3.93 (m, 2H).

(c) Step 3

A solution of tert-butyl 4-(but-3-ynyl)piperidine-1-carboxylate (0.370 g, 1.56 mmol) in triethylamine (10 mL) was added with 7-iodo-6-methoxybenzofuran-3(2H)-one (0.452 g, 1.56 mmol) synthesized in Example B46, Step 2, dichlorobis(triphenylphosphine)palladium(II) (0.110 g, 0.156 mmol) and copper(I) iodide (0.0297 g, 0.156 mmol), and the mixture was stirred at 50° C. for 6 hours. The reaction mixture was concentrated, and the resulting residue was purified by silica gel column chromatography (chloroform/ethyl acetate) to obtain tert-butyl 4-[4-(6-methoxy-3-oxo-2,3-dihydrobenzofuran-7-yl)but-3-ynyl]piperidine-1-carboxylate (0.338 g, 54%).

$^1$H NMR (300 MHz, CDCl$_3$) δ 1.08-1.20 (m, 2H), 1.46 (s, 9H), 1.63-1.64 (m, 3H), 1.71-1.76 (m, 2H), 2.56-2.60 (m, 2H), 2.67-2.75 (m, 2H), 3.98 (s, 3H), 4.08-4.12 (m, 2H), 4.69 (s, 2H), 6.68 (d, J=8.8 Hz, 1H), 7.59 (d, J=8.8 Hz, 1H).

(d) Step 4

A solution of tert-butyl 4-[4-(6-methoxy-3-oxo-2,3-dihydrobenzofuran-7-yl)but-3-ynyl]piperidine-1-carboxylate (0.0500 g, 0.125 mmol) in methanol (5 mL) was added with 1H-indazole-3-carboxaldehyde (0.0166 g, 0.114 mmol) and piperidine (7 drops), and the mixture was stirred at 60° C. for 2 hours. The reaction mixture was concentrated, and the resulting residue was purified by silica gel column chromatography (chloroform/ethyl acetate) to obtain tert-butyl (Z)-4-(4-{2-[(1H-indazol-3-yl)methylene]-6-methoxy-3-oxo-2,3-dihydrobenzofuran-7-yl}but-3-ynyl)piperidine-1-carboxylate (0.0507 g, 84%).

$^1$H NMR (300 MHz, DMSO-$d_6$) δ 0.96-1.07 (m, 2H), 1.39 (s, 9H), 1.56-1.60 (m, 3H), 1.66-1.70 (m, 2H), 2.64-2.69 (m, 4H), 3.89-3.93 (m, 2H), 4.00 (s, 3H), 7.05 (d, J=8.8 Hz, 1H), 7.09 (s, 1H), 7.27 (m, 1H), 7.48 (m, 1H), 7.65 (d, J=8.8 Hz, 1H), 7.78 (d, J=8.8 Hz, 1H), 8.75 (d, J=8.1 Hz, 1H), 13.87 (s, 1H).

(e) Step 5

A solution of tert-butyl (Z)-4-(4-{2-[(1H-indazol-3-yl)methylene]-6-methoxy-3-oxo-2,3-dihydrobenzofuran-7-yl}but-3-ynyl)piperidine-1-carboxylate (0.0507 g, 0.0961 mmol) in methylene chloride (4 mL) was added with a 4 M solution of hydrogen chloride in 1,4-dioxane (4 mL), and the mixture was stirred at room temperature for 2 hours. The reaction mixture was added with ether, and the precipitated solid was collected by filtration, and washed with ether. The resulting solid was dissolved in a small volume of water, and the solution was adjusted to pH 9 with saturated aqueous sodium hydrogencarbonatewas. The solution was extracted with ethyl acetate, the organic layer was dried over anhydrous sodium sulfate, and then the solvent was evaporated to obtain (Z)-2-[(1H-indazol-3-yl)methylene]-6-methoxy-7-[4-(piperidin-4-yl)but-1-ynyl]benzofuran-3(2H)-one (0.0372 g, 91%).

$^1$H NMR (300 MHz, DMSO-$d_6$) δ 1.05-1.16 (m, 2H), 1.55-1.59 (m, 3H), 1.66-1.71 (m, 2H), 2.46 (m, 2H), 2.63-2.68 (m, 2H), 2.96-3.00 (m, 2H), 4.00 (s, 3H), 7.06 (d, J=8.8 Hz, 1H), 7.10 (s, 1H), 7.27 (m, 1H), 7.48 (m, 1H), 7.66 (d, J=8.8 Hz, 1H), 7.80 (d, J=8.8 Hz, 1H), 8.75 (d, J=8.8 Hz, 1H).

Example B62

(Z)-2-[(1H-Indazol-3-yl)methylene]-6-methoxy-7-[(Z)-4-(piperidin-4-yl)but-1-enyl]benzofuran-3(2H)-one (a) Step 1

A solution of tert-butyl 4-[4-(6-methoxy-3-oxo-2,3-dihydrobenzofuran-7-yl)but-3-ynyl]piperidine-1-carboxylate (0.0902 g, 0.226 mmol) synthesized in Example B61, Step 3 in ethanol (5 mL) was added with Lindlar's catalyst (0.100 g), and the mixture was stirred at room temperature for 16 hours under a hydrogen atmosphere. The reaction mixture was filtered through Celite, and then the filtrate was concentrated. The resulting residue was purified by silica gel column chromatography (hexane/ethyl acetate) to obtain tert-butyl (Z)-4-[4-(6-methoxy-3-oxo-2,3-dihydrobenzofuran-7-yl)but-3-enyl]piperidine-1-carboxylate (0.0265 g, 29%).

$^1$H NMR (300 MHz, CDCl$_3$) δ 0.95-1.08 (m, 2H), 1.34-1.40 (m, 3H), 1.44 (s, 9H), 1.53-1.57 (m, 2H), 2.00-2.07 (m, 2H), 2.57-2.65 (m, 2H), 3.93 (s, 3H), 4.01-4.05 (m, 2H), 4.64 (s, 2H), 5.83-5.91 (m, 1H), 6.17 (d, J=11.0 Hz, 1H), 6.72 (d, J=8.8 Hz, 1H), 7.62 (d, J=8.8 Hz, 1H).

(b) Step 2

A solution of tert-butyl 4-[4-(6-methoxy-3-oxo-2,3-dihydrobenzofuran-7-yl)but-3-enyl]piperidine-1-carboxylate (0.0265 g, 0.0660 mmol) in methanol (3 mL) was added with 1H-indazole-3-carboxaldehyde (0.00964 g, 0.0660 mmol) and piperidine (0.0800 mL, 0.810 mmol), and the mixture was stirred at 60° C. for 2 hours. The reaction mixture was concentrated, and the resulting residue was purified by silica gel column chromatography (chloroform/methanol) to obtain tert-butyl 4-((Z)-4-{(Z)-2-[(1H-indazol-3-yl)methylene]-6-methoxy-3-oxo-2,3-dihydrobenzofuran-7-yl}but-3-enyl)piperidine-1-carboxylate (0.0293 g, 84%).

$^1$H NMR (300 MHz, DMSO-$d_6$) δ 0.58-0.69 (m, 2H), 1.18-1.26 (m, 3H), 1.36-1.39 (m, 2H), 1.31 (s, 9H), 1.95-2.01 (m, 2H), 2.36 (m, 2H), 3.65-3.69 (m, 2H), 3.96 (s, 3H), 5.97-6.06 (m, 1H), 6.34 (d, J=11.7 Hz, 1H), 7.07 (d, J=8.8 Hz, 1H), 7.09 (s, 1H), 7.24 (m, 1H), 7.45 (m, 1H), 7.62 (d, J=8.8 Hz, 1H), 7.80 (d, J=8.1 Hz, 1H), 8.47 (d, J=8.1 Hz, 1H), 13.82 (s, 1H).

(c) Step 3

A solution of tert-butyl 4-((Z)-4-{(Z)-2-[(1H-indazol-3-yl)methylene]-6-methoxy-3-oxo-2,3-dihydrobenzofuran-7-yl}but-3-enyl)piperidine-1-carboxylate (0.0293 g, 0.0553 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-[(Z)-4-(piperidin-4-yl)but-1-enyl]benzofuran-3(2H)-one (0.0173 g, 73%).

$^1$H NMR (300 MHz, DMSO-d$_6$) δ 0.65-0.76 (m, 2H), 1.16-1.28 (m, 5H), 1.94-2.00 (m, 2H), 2.16-2.23 (m, 2H), 2.69-2.73 (m, 2H), 3.96 (s, 3H), 5.97-6.05 (m, 1H), 6.33 (d, J=11.0 Hz, 1H), 7.06 (d, J=8.8 Hz, 1H), 7.09 (s, 1H), 7.24 (m, 1H), 7.45 (m, 1H), 7.63 (d, J=8.8 Hz, 1H), 7.79 (d, J=8.8 Hz, 1H), 8.48 (d, J=8.1 Hz, 1H).

Example B63

(Z)-2-[(1H-Indazol-3-yl)methylene]-6-methoxy-7-[4-(piperidin-4-yl)butyl]benzofuran-3(2H)-one (a) Step 1

A solution of tert-butyl 4-[4-(6-methoxy-3-oxo-2,3-dihydrobenzofuran-7-yl)but-3-ynyl]piperidine-1-carboxylate (0.0302 g, 0.0756 mmol) synthesized in Example B61, Step 3 in ethanol (5 mL) was added with 5% palladium/carbon (wetted with 50% water, 0.100 g), and the mixture was stirred at room temperature for 20 hours under a hydrogen atmosphere. The reaction mixture was filtered through Celite, the filtrate was concentrated, and the resulting residue was purified by silica gel column chromatography (hexane/ethyl acetate) to obtain tert-butyl 4-[4-(6-methoxy-3-oxo-2,3-dihydrobenzofuran-7-yl)butyl]piperidine-1-carboxylate (0.0291 g, 95%).

$^1$H NMR (300 MHz, DMSO-d$_6$) δ 0.85-0.99 (m, 2H), 1.24-1.31 (m, 5H), 1.38 (s, 9H), 1.46-1.51 (m, 2H), 1.57-1.61 (m, 2H), 2.56-2.61 (m, 2H), 2.64 (m, 2H), 3.90 (s, 3H), 3.90 (m, 2H), 4.75 (s, 2H), 6.86 (d, J=8.8 Hz, 1H), 7.49 (d, J=8.8 Hz, 1H).

(b) Step 2

A solution of tert-butyl 4-[4-(6-methoxy-3-oxo-2,3-dihydrobenzofuran-7-yl)butyl]piperidine-1-carboxylate (0.0483 g, 0.119 mmol) in methanol (5 mL) was added with 1H-indazole-3-carboxaldehyde (0.0174 g, 0.119 mmol) and piperidine (5 drops), and the mixture was stirred at 60° C. for 2 hours. The reaction mixture was concentrated, and the resulting residue was subjected to silica gel column chromatography (hexane/ethyl acetate), and the resulting crude product was purified again by silica gel column chromatography (chloroform/methanol) to obtain tert-butyl (Z)-4-(4-{2-[(1H-indazol-3-yl)methylene]-6-methoxy-3-oxo-2,3-dihydrobenzofuran-7-yl}butyl)piperidine-1-carboxylate (0.0454 g, 72%).

$^1$H NMR (300 MHz, DMSO-d$_6$) δ 0.78-0.91 (m, 2H), 1.19-1.24 (m, 3H), 1.32-1.42 (m, 2H), 1.37 (s, 9H), 1.46-1.51 (m, 2H), 1.56-1.66 (m, 2H), 2.55 (m, 2H), 2.80-2.84 (m, 2H), 3.80-3.84 (m, 2H), 3.97 (s, 3H), 7.02 (d, J=8.8 Hz, 1H), 7.07 (s, 1H), 7.27 (m, 1H), 7.48 (m, 1H), 7.65 (d, J=8.1 Hz, 1H), 7.70 (d, J=8.8 Hz, 1H), 8.50 (d, J=8.1 Hz, 1H), 13.83 (s, 1H).

(c) Step 3

A solution of tert-butyl (Z)-4-(4-{2-[(1H-indazol-3-yl)methylene]-6-methoxy-3-oxo-2,3-dihydrobenzofuran-7-yl}butyl)piperidine-1-carboxylate (0.0454 g, 0.0854 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated. The resulting solid was suspended in methylene chloride and thereby washed to obtain (Z)-2-[(1H-indazol-3-yl)methylene]-6-methoxy-7-[4-(piperidin-4-yl)butyl]benzofuran-3(2H)-one (0.0243 g, 66%).

$^1$H NMR (300 MHz, DMSO-d$_6$) δ 0.85-0.98 (m, 2H), 1.18-1.22 (m, 3H), 1.37-1.42 (m, 2H), 1.46-1.50 (m, 2H), 1.56-1.66 (m, 2H), 2.34-2.41 (m, 2H), 2.80-2.89 (m, 4H), 3.97 (s, 3H), 7.03 (d, J=8.8 Hz, 1H), 7.07 (s, 1H), 7.27 (m, 1H), 7.47 (m, 1H), 7.65 (d, J=8.8 Hz, 1H), 7.70 (d, J=8.1 Hz, 1H), 8.51 (d, J=8.8 Hz, 1H).

Example B64

(Z)-2-[(1H-Indazol-3-yl)methylene]-6-methoxy-7-[(E)-2-(piperidin-4-yl)vinyl]benzofuran-3(2H)-one (a) Step 1

A solution of tert-butyl 4-ethynylpiperidine-1-carboxylate (0.414 g, 1.98 mmol) in methylene chloride (1 mL) was added with 4,4,5,5-tetramethyl-1,3,2-dioxaborolane (0.380 g, 2.97 mmol) and triethylamine (0.0201 g, 0.198 mmol), and the mixture was stirred at room temperature. The reaction mixture was added with bis(cyclopentadienyl)zirconium(IV) chloride hydride (0.0766 g, 0.297 mmol), and the mixture was stirred overnight at room temperature. The reaction mixture was concentrated, and the resulting residue was purified by silica gel column chromatography (hexane/ethyl acetate) to obtain tert-butyl (E)-4-[2-(4,4,5,5-tetramethyl-1,3,2-dioxaborolan-2-yl)vinyl]piperidine-1-carboxylate (0.600 g, 89%).

$^1$H NMR (300 MHz, DMSO-d$_6$) δ 1.07-1.16 (m, 2H), 1.19 (s, 12H), 1.39 (s, 9H), 1.62-1.66 (m, 2H), 2.18 (m, 1H), 2.72 (m, 2H), 3.90-3.95 (m, 2H), 5.32 (d, J=18.3 Hz, 1H), 6.44 (dd, J=6.6 Hz, J=18.3 Hz, 1H).

(b) Step 2

A solution of tert-butyl (E)-4-[2-(4,4,5,5-tetramethyl-1,3,2-dioxaborolan-2-yl)vinyl]piperidine-1-carboxylate (0.253 g, 0.750 mmol) in 1,4-dioxane (5 mL) was added with 7-iodo-6-methoxybenzofuran-3(2H)-one (0.198 g, 0.682 mmol) synthesized in Example B46, Step 2, 2 M aqueous sodium carbonate (0.680 mL, 1.36 mmol) and tetrakis(triphenylphosphine)palladium (0.0788 g, 0.0682 mmol), and the mixture was refluxed for 10 hours by heating. The reaction mixture was cooled to room temperature, and then added with water, and the mixture was extracted with ethyl acetate. The organic layer was washed with saturated brine, and dried over anhydrous magnesium sulfate, and then the solvent was evaporated. The residue was subjected to silica gel column chromatography (chloroform/methanol), and the resulting crude product was further purified by silica gel column chromatography (hexane/ethyl acetate) to obtain tert-butyl (E)-4-[2-(6-methoxy-3-oxo-2,3-dihydrobenzofuran-7-yl)vinyl]piperidine-1-carboxylate (0.0692 g, 27%).

$^1$H NMR (300 MHz, DMSO-d$_6$) δ 1.16-1.30 (m, 2H), 1.40 (s, 9H), 1.69-1.73 (m, 2H), 2.28-2.38 (m, 1H), 2.78 (m, 2H), 3.93 (s, 3H), 3.93-3.98 (m, 2H), 4.83 (s, 2H), 6.56 (d, J=16.9 Hz, 1H), 6.64 (dd, J=6.6 Hz, J=16.9 Hz, 1H), 6.89 (d, J=8.8 Hz, 1H), 7.50 (d, J=8.8 Hz, 1H).

(c) Step 3

A solution of tert-butyl (E)-4-[2-(6-methoxy-3-oxo-2,3-dihydrobenzofuran-7-yl)vinyl]piperidine-1-carboxylate (0.0692 g, 0.185 mmol) in methanol (5 mL) was added with 1H-indazole-3-carboxaldehyde (0.0270 g, 0.185 mmol) and piperidine (7 drops), and the mixture was stirred at 60° C. for 2 hours. The reaction mixture was concentrated, and the resulting residue was purified by silica gel column chromatography (chloroform/methanol) to obtain tert-butyl 4-((E)-2-{(Z)-2-[(1H-indazol-3-yl)methylene]-6-methoxy-3-oxo-2,3-dihydrobenzofuran-7-yl}vinyl)piperidine-1-carboxylate (0.0712 g, 77%).

$^1$H NMR (300 MHz, DMSO-$d_6$) δ 1.24-1.36 (m, 2H), 1.43 (s, 9H), 1.79-1.83 (m, 2H), 2.39 (m, 1H), 2.83 (m, 2H), 3.99 (s, 3H), 3.99-4.04 (m, 2H), 6.65 (d, J=16.9 Hz, 1H), 6.99-7.07 (m, 1H), 7.03 (d, J=8.8 Hz, 1H), 7.19 (s, 1H), 7.26 (m, 1H), 7.46 (m, 1H), 7.64-7.72 (m, 2H), 8.28 (d, J=8.1 Hz, 1H), 13.83 (s, 1H).

(d) Step 4

A solution of tert-butyl 4-((E)-2-{(Z)-2-[(1H-indazol-3-yl)methylene]-6-methoxy-3-oxo-2,3-dihydrobenzofuran-7-yl}vinyl)piperidine-1-carboxylate (0.0693 g, 0.138 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was washed with saturated brine, and dried over anhydrous sodium sulfate, and then the solvent was evaporated to obtain (Z)-2-[(1H-indazol-3-yl)methylene]-6-methoxy-7-[(E)-2-(piperidin-4-yl)vinyl]benzofuran-3(2H)-one (0.0473 g, 85%).

$^1$H NMR (300 MHz, DMSO-$d_6$) δ 1.30-1.43 (m, 2H), 1.72-1.76 (m, 2H), 2.25-2.35 (m, 1H), 2.55-2.62 (m, 2H), 3.02-3.06 (m, 2H), 3.99 (s, 3H), 6.62 (d, J=16.9 Hz, 1H), 7.03 (d, J=8.8 Hz, 1H), 7.08 (dd, J=6.6 Hz, J=16.9 Hz, 1H), 7.20 (s, 1H), 7.27 (m, 1H), 7.47 (m, 1H), 7.66 (d, J=8.1 Hz, 1H), 7.68 (d, J=8.8 Hz, 1H), 8.30 (d, J=8.1 Hz, 1H).

Example B65

(Z)-2-[(1H-Indazol-3-yl)methylene]-6-methoxy-7-[(E)-3-(piperidin-4-yl)prop-1-enyl]benzofuran-3(2H)-one (a) Step 1

A solution of tert-butyl 4-(prop-2-ynyl)piperidine-1-carboxylate (0.162 g, 0.725 mmol) synthesized in Example B58, Step 1 in methylene chloride (1 mL) was added with 4,4,5,5-tetramethyl-1,3,2-dioxaborolane (0.139 g, 1.09 mmol) and triethylamine (0.00734 g, 0.0725 mmol), and the mixture was stirred at room temperature. The reaction mixture was added with bis(cyclopentadienyl)zirconium(IV) chloride hydride (0.0281 g, 0.109 mmol), and the mixture was stirred at room temperature for 40 hours. The reaction mixture was concentrated, and the resulting residue was purified by silica gel column chromatography (hexane/ethyl acetate) to obtain tert-butyl (E)-4-[3-(4,4,5,5-tetramethyl-1,3,2-dioxaborolan-2-yl)allyl]piperidine-1-carboxylate (0.132 g, 52%).

$^1$H NMR (300 MHz, CDCl$_3$) δ 1.03-1.16 (m, 2H), 1.27 (s, 12H), 1.45 (s, 9H), 1.53 (m, 1H), 1.64-1.68 (m, 2H), 2.07-2.13 (m, 2H), 2.61-2.71 (m, 2H), 4.04-4.08 (m, 2H), 5.43 (d, J=17.6 Hz, 1H), 6.52-6.62 (m, 1H).

(b) Step 2

A solution of tert-butyl (E)-4-[3-(4,4,5,5-tetramethyl-1,3,2-dioxaborolan-2-yl)allyl]piperidine-1-carboxylate (0.176 g, 0.501 mmol) in 1,4-dioxane (5 mL) was added with 7-iodo-6-methoxybenzofuran-3(2H)-one (0.145 g, 0.501 mmol) synthesized in Example B46, Step 2, 2 M aqueous sodium carbonate (0.750 mL, 1.50 mmol) and tetrakis(triphenylphosphine)palladium (0.0579 g, 0.0501 mmol), and the mixture was refluxed for 12 hours by heating. The reaction mixture was cooled to room temperature, concentrated, and added with water, and then the mixture was extracted with ethyl acetate. The organic layer was washed with saturated brine, and dried over anhydrous magnesium sulfate, and then the solvent was evaporated. The residue was purified by silica gel column chromatography (hexane/ethyl acetate) to obtain tert-butyl (E)-4-[3-(6-methoxy-3-oxo-2,3-dihydrobenzofuran-7-yl)allyl]piperidine-1-carboxylate (0.0313 g, 16%).

$^1$H NMR (300 MHz, DMSO-$d_6$) δ 0.96-1.10 (m, 2H), 1.38 (s, 9H), 1.55 (m, 1H), 1.62-1.67 (m, 2H), 2.14-2.19 (m, 2H), 2.68 (m, 2H), 3.93 (s, 3H), 3.93 (m, 2H), 4.83 (s, 2H), 6.54 (d, J=16.1 Hz, 1H), 6.62-6.72 (m, 1H), 6.89 (d, J=8.8 Hz, 1H), 7.50 (d, J=8.8 Hz, 1H).

(c) Step 3

A solution of tert-butyl (E)-4-[3-(6-methoxy-3-oxo-2,3-dihydrobenzofuran-7-yl)allyl]piperidine-1-carboxylate (0.0313 g, 0.0807 mmol) in methanol (3 mL) was added with 1H-indazole-3-carboxaldehyde (0.0118 g, 0.0807 mmol) and piperidine (0.0800 mL, 0.810 mmol), and the mixture was stirred at 60° C. for 2 hours. The reaction mixture was concentrated, and the resulting residue was purified by silica gel column chromatography (chloroform/methanol) to obtain tert-butyl 4-((E)-3-{(Z)-2-[(1H-indazol-3-yl)methylene]-6-methoxy-3-oxo-2,3-dihydrobenzofuran-7-yl}allyl)piperidine-1-carboxylate (0.0308 g, 74%).

$^1$H NMR (300 MHz, DMSO-$d_6$) δ 1.00-1.12 (m, 2H), 1.36 (s, 9H), 1.57 (m, 1H), 1.65-1.69 (m, 2H), 2.24-2.28 (m, 2H), 2.67 (m, 2H), 3.88-3.93 (m, 2H), 3.99 (s, 3H), 6.64 (d, J=16.1 Hz, 1H), 6.96-7.04 (m, 1H), 7.03 (d, J=8.8 Hz, 1H), 7.19 (s, 1H), 7.27 (m, 1H), 7.47 (m, 1H), 7.66 (d, J=8.8 Hz, 1H), 7.69 (d, J=8.8 Hz, 1H), 8.29 (d, J=8.1 Hz, 1H), 13.76 (s, 1H).

(d) Step 4

A solution of tert-butyl 4-((E)-3-{(Z)-2-[(1H-indazol-3-yl)methylene]-6-methoxy-3-oxo-2,3-dihydrobenzofuran-7-yl}allyl)piperidine-1-carboxylate (0.0308 g, 0.0597 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-6-methoxy-7-[(E)-3-(piperidin-4-yl)prop-1-enyl]benzofuran-3(2H)-one (0.0173 g, 70%).

$^1$H NMR (300 MHz, DMSO-$d_6$) δ 1.62 (m, 5H), 2.37-2.39 (m, 2H), 2.62 (m, 2H), 3.07-3.11 (m, 2H), 3.98 (s, 3H), 6.65 (d, J=16.1 Hz, 1H), 7.01 (d, J=8.8 Hz, 1H), 7.13-7.24 (m, 1H), 7.24 (m, 1H), 7.26 (s, 1H), 7.43 (m, 1H), 7.67 (d, J=8.8 Hz, 1H), 7.70 (d, J=8.8 Hz, 1H), 8.22 (d, J=8.1 Hz, 1H).

Example B66

(Z)-2-[(1H-Indazol-3-yl)methylene]-5-fluoro-6-methoxy-7-[2-(piperidin-4-yl)ethyl]benzofuran-3(2H)-one (a) Step 1

A solution of 4-fluorobenzene-1,3-diol (1.00 g, 7.81 mmol) in nitrobenzene (15 mL) was added with aluminum chloride (3.12 g, 23.4 mmol), and the reaction vessel was cooled to 0° C. The reaction mixture was added dropwise with a solution of chloroacetyl chloride (1.06 g, 9.37 mmol) in nitrobenzene (2 mL), and the mixture was stirred at 40° C. for 6 hours. The reaction mixture was cooled to room temperature, and added with 2 N aqueous sodium hydroxide until the aqueous layer became basic. The aqueous layer was separated, then made acidic with 3 N hydrochloric acid, and extracted with ethyl acetate. The organic layer was washed with saturated brine, and dried over anhydrous magnesium sulfate. The solvent was evaporated, and the resulting residue was purified by silica gel column chromatography (hexane/ethyl acetate) to obtain 5-fluoro-6-hydroxybenzofuran-3 (2H)-one (0.190 g, 14%).

$^1$H NMR (300 MHz, DMSO-d$_6$) δ 4.74 (s, 2H), 6.71 (d, J=6.6 Hz, 1H), 7.41 (d, J=8.8 Hz, 1H), 11.59 (s, 1H).

(b) Step 2

A solution of 5-fluoro-6-hydroxybenzofuran-3(2H)-one (0.190 g, 1.13 mmol) in ethanol (5 mL) was added with iodine (0.115 g, 0.452 mmol) at room temperature. The reaction mixture was added dropwise with a solution of iodic acid (0.0396 g, 0.226 mmol) in water (2 mL), and the mixture was stirred for 2 hours. The reaction mixture was added with water (30 mL), and the precipitated solid was collected by filtration, and dried under reduced pressure to obtain 5-fluoro-6-hydroxy-7-iodobenzofuran-3(2H)-one (0.256 g, 77%).

$^1$H NMR (300 MHz, DMSO-d$_6$) δ 4.85 (s, 2H), 7.48 (d, J=8.8 Hz, 1H).

(c) Step 3

A solution of 5-fluoro-6-hydroxy-7-iodobenzofuran-3 (2H)-one (0.256 g, 0.871 mmol) in DMF (5 mL) was added with potassium carbonate (0.110 g, 0.796 mmol). The mixture was added with dimethyl sulfate (0.0803 g, 0.637 mmol) at room temperature, and the mixture was stirred for 12 hours. The reaction mixture was added with water, the mixture was extracted with ethyl acetate, and the organic layer was washed with saturated brine. The organic layer was dried over anhydrous magnesium sulfate, then the solvent was evaporated, and the resulting residue was purified by silica gel column chromatography (hexane/ethyl acetate) to obtain 5-fluoro-7-iodo-6-methoxybenzofuran-3(2H)-one (0.0582 g, 21%).

$^1$H NMR (300 MHz, DMSO-d$_6$) δ 4.13 (d, J=2.9 Hz, 3H), 4.74 (s, 2H), 7.38 (d, J=9.2 Hz, 1H).

(d) Step 4

A solution of 5-fluoro-7-iodo-6-methoxybenzofuran-3 (2H)-one (0.0582 g, 0.184 mmol) in triethylamine (3 mL) was added with tert-butyl 4-ethynylpiperidine-1-carboxylate (0.0389 g, 0.184 mmol), dichlorobis(triphenylphosphine) palladium(II) (0.0129 g, 0.0184 mmol) and copper(I) iodide (0.00350 g, 0.0184 mmol), and the mixture was stirred at 50° C. for 4 hours. The reaction mixture was concentrated, and the resulting residue was purified by silica gel column chromatography (hexane/ethyl acetate) to obtain tert-butyl 4-[(5-fluoro-6-methoxy-3-oxo-2,3-dihydrobenzofuran-7-yl)ethynyl]piperidine-1-carboxylate (0.0502 g, 70%).

$^1$H NMR (300 MHz, DMSO-d$_6$) δ 1.40 (s, 9H), 1.48-1.59 (m, 2H), 1.79-1.88 (m, 2H), 2.99 (m, 1H), 3.16-3.23 (m, 2H), 3.58-3.66 (m, 2H), 4.10 (d, J=2.2 Hz, 3H), 4.88 (s, 2H), 7.57 (d, J=9.6 Hz, 1H).

(e) Step 5

A solution of tert-butyl 4-[(5-fluoro-6-methoxy-3-oxo-2,3-dihydrobenzofuran-7-371)ethynyl]piperidine-1-carboxylate (0.0403 g, 0.103 mmol) in ethanol (5 mL) was added with 5% palladium/carbon (wetted with 50% water, 0.0500 g), and the mixture was stirred overnight at room temperature under a hydrogen atmosphere. The reaction mixture was filtered through Celite, and the resulting filtrate was concentrated to obtain tert-butyl 4-[2-(5-fluoro-6-methoxy-3-oxo-2,3-dihydrobenzofuran-7-yl)ethyl]piperidine-1-carboxylate (0.0413 g, quantitative).

$^1$H NMR (300 MHz, DMSO-d$_6$) δ 0.92-1.05 (m, 2H), 1.38 (s, 9H), 1.44 (m, 3H), 1.69-1.73 (m, 2H), 2.65 (m, 4H), 3.90 (m, 2H), 3.96 (d, J=2.2 Hz, 3H), 4.83 (s, 2H), 7.41 (d, J=10.2 Hz, 1H).

(f) Step 6

A solution of tert-butyl 4-[2-(5-fluoro-6-methoxy-3-oxo-2,3-dihydrobenzofuran-7-yl)ethyl]piperidine-1-carboxylate (0.0245 g, 0.0623 mmol) in methanol (3 mL) was added with 1H-indazole-3-carboxaldehyde (0.0100 g, 0.0685 mmol) and piperidine (0.100 mL, 1.01 mmol), and the mixture was stirred at 60° C. for 2 hours. The reaction mixture was concentrated, and the resulting residue was purified by silica gel column chromatography (chloroform/methanol) to obtain tert-butyl (Z)-4-(2{-2-[(1H-indazol-3-yl)methylene]-5-fluoro-6-methoxy-3-oxo-2,3-dihydrobenzofuran-7-yl}ethyl)piperidine-1-carboxylate (0.0231 g, 71%).

$^1$H NMR (300 MHz, DMSO-d$_6$) δ 0.93-1.06 (m, 2H), 1.37 (s, 9H), 1.54 (m, 3H), 1.74-1.78 (m, 2H), 2.64 (m, 2H), 2.87 (m, 2H), 3.86-3.90 (m, 2H), 4.04 (d, J=2.9 Hz, 3H), 7.17 (s, 1H), 7.28 (m, 1H), 7.49 (m, 1H), 7.64 (d, J=9.6 Hz, 1H), 7.67 (d, J=8.1 Hz, 1H), 8.43 (d, J=8.1 Hz, 1H), 13.93 (s, 1H).

(g) Step 7

A solution of tert-butyl (Z)-4-(2-{2-[(1H-indazol-3-yl)methylene]-5-fluoro-6-methoxy-3-oxo-2,3-dihydrobenzofuran-7-yl}ethyl)piperidine-1-carboxylate (0.0231 g, 0.0443 mmol) in methylene chloride (3 mL) was added with a 4 M solution of hydrogen chloride in 1,4-dioxane (3 mL), and the mixture was stirred at room temperature for 2 hours. The reaction mixture was concentrated, the resulting residue was added with saturated aqueous sodium hydrogencarbonate, and the precipitated solid was collected by filtration. The solid was washed with water, and then dried under reduced pressure to obtain (Z)-2-[(1H-indazol-3-yl)methylene]-5-fluoro-6-methoxy-7-[2-(piperidin-4-yl)ethyl]benzofuran-3 (2H)-one (0.0152 g, 81%).

$^1$H NMR (300 MHz, DMSO-d$_6$) δ 1.00-1.13 (m, 2H), 1.46 (m, 1H), 1.51-1.58 (m, 2H), 1.71-1.76 (m, 2H), 2.42-2.46 (m, 2H), 2.85-2.95 (m, 4H), 4.03 (d, J=2.2 Hz, 3H), 7.18 (s, 1H), 7.28 (m, 1H), 7.49 (m, 1H), 7.64 (d, J=10.2 Hz, 1H), 7.67 (d, J=8.1 Hz, 1H), 8.45 (d, J=8.1 Hz, 1H), 13.93 (s, 1H).

Example B67

(Z)-2-[(1H-Indazol-3-yl)methylene]-6-methoxy-7-[3-methyl-3-(piperazin-1-yl)but-1-ynyl]benzofuran-3 (2H)-one

(a) Step 1

A solution of 7-iodo-6-methoxybenzofuran-3(2H)-one (0.290 g, 1.00 mmol) synthesized in Example B46, Step 2, dichlorobis(triphenylphosphine)palladium(II) (0.0702 g, 0.100 mmol) and copper(I) iodide (0.0190 g, 0.100 mmol) in triethylamine (4 mL) was added with a solution of tert-butyl 4-(2-methylbut-3-yn-2-yl)piperazine-1-carboxylate (Journal of Medicinal Chemistry, Vol. 47, p. 2833, 2004, 0.252 g, 1.00 mmol) in triethylamine (4 mL), and the mixture was stirred at 50° C. for 7.5 hours. The reaction mixture was concentrated, and the resulting residue was purified by silica gel column chromatography (chloroform/methanol) to obtain tert-butyl 4-[4-(6-methoxy-3-oxo-2,3-dihydrobenzofuran-7-yl)-2-methylbut-3-yn-2-yl]piperazine-1-carboxylate (0.126 g, 30%).

$^1$H NMR (300 MHz, DMSO-$d_6$) δ 1.39 (s, 9H), 1.40 (s, 6H), 2.58 (m, 4H), 3.35 (m, 4H), 3.93 (s, 3H), 4.83 (s, 2H), 6.89 (d, J=8.8 Hz, 1H), 7.61 (d, J=8.8 Hz, 1H).

(b) Step 2

A solution of tert-butyl 4-[4-(6-methoxy-3-oxo-2,3-dihydrobenzofuran-7-yl)-2-methylbut-3-yn-2-yl]piperazine-1-carboxylate (0.113 g, 0.273 mmol) in methanol (1 mL) was added with 1H-indazole-3-carboxaldehyde (0.0399 g, 0.273 mmol) and piperidine (0.0186 g, 0.218 mmol), and the mixture was stirred at 60° C. for 2 hours. The reaction mixture was concentrated, and the resulting residue was purified by silica gel column chromatography (chloroform/methanol) to obtain tert-butyl (Z)-4-(4-{2-[(1H-indazol-3-yl)methylene]-6-methoxy-3-oxo-2,3-dihydrobenzofuran-7-yl}-2-methylbut-3-yn-2-yl)piperazine-1-carboxylate (0.136 g, 91%).

$^1$H NMR (300 MHz, DMSO-$d_6$) δ 1.34 (s, 9H), 1.51 (s, 6H), 2.64 (m, 4H), 3.34 (m, 4H), 3.99 (s, 3H), 7.06 (d, J=8.8 Hz, 1H), 7.12 (s, 1H), 7.30 (t, J=7.3 Hz, 1H), 7.49 (m, 1H), 7.65 (d, J=8.8 Hz, 1H), 7.82 (d, J=8.8 Hz, 1H), 8.56 (d, J=8.8 Hz, 1H) 13.86 (br s, 1H).

(c) Step 3

A solution of tert-butyl (Z)-4-(4-{2-[(1H-indazol-3-yl)methylene]-6-methoxy-3-oxo-2,3-dihydrobenzofuran-7-yl}-2-methylbut-3-yn-2-yl)piperazine-1-carboxylate (0.122 g, 0.225 mmol) in methylene chloride (4 mL) was added with trifluoroacetic acid (4 mL), and the mixture was stirred at room temperature for 2 hours. The reaction mixture was concentrated, and then the residue was dissolved in water (10 mL). The solution was added with saturated aqueous sodium hydrogencarbonate (10 mL), and the precipitated solid was collected by filtration. The solid was washed with water, and then dried under reduced pressure to obtain (Z)-2-[(1H-indazol-3-yl)methylene]-6-methoxy-7-[3-methyl-3-(piperazin-1-yl)but-1-ynyl]benzofuran-3(2H)-one (0.0259 g, 26%).

$^1$H NMR (300 MHz, DMSO-$d_6$) δ 1.50 (s, 6H), 2.77 (br s, 4H), 2.90 (br s, 4H), 4.02 (s, 3H), 7.07 (d, J=8.8 Hz, 1H), 7.16 (s, 1H), 7.30 (t, J=7.3 Hz, 1H), 7.47 (m, 1H), 7.67 (d, J=8.8 Hz, 1H), 7.82 (d, J=8.8 Hz, 1H), 8.49 (d, J=8.8 Hz, 1H).

Example B68

(Z)-2-[(1H-Pyrazolo[3,4-b]pyridin-3-yl)methylene]-6-hydroxy-7-(piperazin-1-ylmethyl)benzofuran-3(2H)-one (a) Step 1

A solution of tert-butyl 4-[(6-hydroxy-3-oxo-2,3-dihydrobenzofuran-7-yl)methyl]piperazine-1-carboxylate (0.0366 g, 0.105 mmol) synthesized in Example B1, Step 1 in methanol (2 mL) was added with 1H-pyrazolo[3,4-b]pyridine-3-carboxaldehyde (International Patent Publication WO2010/051561, 0.0162 g, 0.110 mmol) and piperidine (5 drops), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-pyrazolo[3,4-b]pyridin-3-yl)methylene]-6-hydroxy-3-oxo-2,3-dihydrobenzofuran-7-yl}methyl)piperazine-1-carboxylate (0.0321 g, 64%).

$^1$H NMR (300 MHz, DMSO-$d_6$) δ 1.38 (s, 9H), 2.50 (m, 4H), 3.34 (m, 4H), 3.80 (s, 2H), 6.80 (d, J=8.1 Hz, 1H), 7.00 (s, 1H), 7.36 (dd, J=4.4 Hz, J=8.1 Hz, 1H), 7.62 (d, J=8.1 Hz, 1H), 8.61 (dd, J=1.5 Hz, J=4.4 Hz, 1H), 8.97 (dd, J=1.5 Hz, J=8.1 Hz, 1H).

(b) Step 2

A solution of tert-butyl (Z)-4-({2-[(1H-pyrazolo[3,4-b]pyridin-3-yl)methylene]-6-hydroxy-3-oxo-2,3-dihydrobenzofuran-7-yl}methyl)piperazine-1-carboxylate (0.0321 g, 0.0672 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, and then the solvent was evaporated to obtain (Z)-2-[(1H-pyrazolo[3,4-b]pyridin-3-yl)methylene]-6-hydroxy-7-(piperazin-1-ylmethyl)benzofuran-3(2H)-one (0.0152 g, 60%).

$^1$H NMR (300 MHz, DMSO-$d_6$) δ 2.63 (m, 4H), 2.91 (m, 4H), 3.73 (s, 2H), 6.39 (d, J=8.8 Hz, 1H), 6.79 (s, 1H), 7.32 (ad, J=4.4 Hz, J=8.1 Hz, 1H), 7.38 (d, J=8.8 Hz, 1H), 8.61 (dd, J=1.5 Hz, J=4.4 Hz, 1H), 8.97 (dd, J=1.5 Hz, J=8.1 Hz, 1H).

Example B69

(Z)-2-[(1H-Pyrazolo[3,4-b]pyridin-3-yl)methylene]-6-methoxy-7-(piperazin-1-ylmethyl)benzofuran-3(2H)-one (a) Step 1

A solution of tert-butyl 4-[(6-methoxy-3-oxo-2,3-dihydrobenzofuran-7-yl)methyl]piperazine-1-carboxylate (0.0362 g, 0.100 mmol) in methanol (3 mL) was added with 1H-pyrazolo[3,4-b]pyridine-3-carboxaldehyde (0.0147 g, 0.100 mmol) and piperidine (7 drops), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-pyrazolo[3,4-b]pyridin-3-yl)methylene]-6-methoxy-3-oxo-2,3-dihydrobenzofuran-7-yl}methyl)piperazine-1-carboxylate (0.0352 g, 72%).

$^1$H NMR (300 MHz, DMSO-$d_6$) δ 1.36 (s, 9H), 2.45 (m, 4H), 3.30 (m, 4H), 3.74 (s, 2H), 3.98 (s, 3H), 7.03 (s, 1H), 7.08 (d, J=8.8 Hz, 1H), 7.35 (dd, J=4.4 Hz, J=8.1 Hz, 1H), 7.82 (d, J=8.8 Hz, 1H), 8.64 (dd, J=1.5 Hz, J=4.4 Hz, 1H), 9.00 (dd, J=1.5 Hz, J=8.1 Hz, 1H).

(b) Step 2

A solution of tert-butyl (Z)-4-({2-[(1H-pyrazolo[3,4-b]pyridin-3-yl)methylene]-6-methoxy-3-oxo-2,3-dihydrobenzofuran-7-yl}methyl)piperazine-1-carboxylate (0.0352 g, 0.0716 mmol) in methylene chloride (2 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, then the solvent was evaporated, and the resulting residue was purified by silica gel column chromatography (aminopropyl silica was used, chloroform/methanol) to obtain (Z)-2-[(1H-pyrazolo[3,4-b]pyridin-3-yl)methylene]-6-methoxy-7-(piperazin-1-ylmethyl)benzofuran-3(2H)-one (0.0213 g, 76%).

$^1$H NMR (300 MHz, DMSO-$d_6$) δ 2.43 (m, 4H), 2.68 (m, 4H), 3.69 (s, 2H), 3.98 (s, 3H), 7.03 (s, 1H), 7.07 (d, J=8.8 Hz, 1H), 7.31 (dd, J=4.4 Hz, J=8.1 Hz, 1H), 7.80 (d, J=8.8 Hz, 1H), 8.63 (d, J=4.4 Hz, 1H), 9.03 (d, J=8.1 Hz, 1H).

Example B70

(Z)-2-[(1H-Pyrazolo[3,4-b]pyridin-3-yl)methylene]-7-(piperazin-1-ylmethyl)benzofuran-3(2H)-one (a) Step 1

A solution of tert-butyl 4-[(3-oxo-2,3-dihydrobenzofuran-7-yl)methyl]piperazine-1-carboxylate (0.0442 g, 0.133 mmol) synthesized in Example B45, Step 3 in methanol (3 mL) was added with 1H-pyrazolo[3,4-b]pyridine-3-carboxaldehyde (0.0206 g, 0.140 mmol) and piperidine (7 drops), and the mixture was stirred at 60° C. for 2 hours. The reaction mixture was concentrated, and the resulting residue was purified by silica gel column chromatography (chloroform/methanol) to obtain tert-butyl (Z)-4-({2-[(1H-pyrazolo[3,4-b]pyridin-3-yl)methylene]-3-oxo-2,3-dihydrobenzofuran-7-yl}methyl)piperazine-1-carboxylate (0.0292 g, 48%).

$^1$H NMR (300 MHz, CD$_3$OD) δ 1.43 (s, 9H), 2.56 (m, 4H), 3.44 (m, 4H), 3.87 (s, 2H), 7.23 (s, 1H), 7.32 (t, J=7.3 Hz, 1H), 7.37 (dd, J=4.4 Hz, J=8.1 Hz, 1H), 7.77 (d, J=7.3 Hz, 2H), 8.61 (dd, J=1.5 Hz, J=4.4 Hz, 1H), 9.12 (dd, J=1.5 Hz, J=8.1 Hz, 1H).

(b) Step 2

A solution of tert-butyl (Z)-4-({2-[(1H-pyrazolo[3,4-b]pyridin-3-yl)methylene]-3-oxo-2,3-dihydrobenzofuran-7-yl}methyl)piperazine-1-carboxylate (0.0292 g, 0.0633 mmol) in methylene chloride (3 mL) was added with a 4 M solution of hydrogen chloride in 1,4-dioxane (2 mL), and the mixture was stirred at room temperature for 2 hours. The reaction mixture was concentrated, the resulting residue was added with saturated aqueous sodium hydrogencarbonate, and the mixture was extracted with ethyl acetate. The organic layer was dried over anhydrous sodium sulfate, then the solvent was evaporated, and the resulting residue was purified by silica gel column chromatography (aminopropyl silica was used, chloroform/methanol) to obtain (Z)-2-[(1H-pyrazolo[3,4-b]pyridin-3-yl)methylene]-7-(piperazin-1-ylmethyl)benzofuran-3(2H)-one (0.0132 g, 58%).

$^1$H NMR (300 MHz, DMSO-$d_6$) δ 2.46 (m, 4H), 2.72 (m, 4H), 3.74 (s, 2H), 7.15 (s, 1H), 7.31 (d, J=8.1 Hz, 1H), 7.32-7.38 (m, 1H), 7.76 (d, J=8.1 Hz, 2H), 8.64 (dd, J=1.5 Hz, J=4.4 Hz, 1H), 9.06 (dd, J=1.5 Hz, J=8.1 Hz, 1H).

Example B71

(Z)-2-[(1H-Pyrazolo[3,4-b]pyridin-3-yl)methylene]-6-methoxy-7-(piperidin-4-ylmethyl)benzofuran-3(2H)-one (a) Step 1

A solution of tert-butyl 4-[(6-methoxy-3-oxo-2,3-dihydrobenzofuran-7-yl)methyl]piperidine-1-carboxylate (0.0652 g, 0.180 mmol) synthesized in the same manner as that of Example B54, Step 3 in methanol (5 mL) was added with 1H-pyrazolo[3,4-b]pyridine-3-carboxaldehyde (0.0278 g, 0.189 mmol) and piperidine (0.100 mL, 1.01 mmol), and the mixture was stirred at 60° C. for 2 hours. The reaction mixture was cooled to room temperature, and the precipitated solid was collected by filtration, and washed with methanol to obtain the objective solid (0.0512 g). Then, the filtrate was concentrated, and the residue was purified by silica gel column chromatography (chloroform/methanol) to further obtain solid of the objective substance (0.0133 g). This solid was combined with the solid obtained above to obtain 0.0645 g (73%) of tert-butyl (Z)-4-({2-[(1H-pyrazolo[3,4-b]pyridin-3-yl)methylene]-6-methoxy-3-oxo-2,3-dihydrobenzofuran-7-yl}methyl)piperidine-1-carboxylate.

$^1$H NMR (300 MHz, DMSO-$d_6$) δ 1.09-1.20 (m, 2H), 1.33 (s, 9H), 1.59-1.63 (m, 2H), 1.86 (m, 1H), 2.61 (m, 2H), 2.77 (d, J=7.3 Hz, 2H), 3.86-3.90 (m, 2H), 3.97 (s, 3H), 7.02 (s, 1H), 7.05 (d, J=8.8 Hz, 1H), 7.34 (dd, J=4.4 Hz, J=8.1 Hz, 1H), 7.74 (d, J=8.8 Hz, 1H), 8.63 (d, J=4.4 Hz, 1H), 8.90 (d, J=8.1 Hz, 1H), 14.37 (s, 1H).

(b) Step 2

A solution of tert-butyl (Z)-4-({2-[(1H-pyrazolo[3,4-b]pyridin-3-yl)methylene]-6-methoxy-3-oxo-2,3-dihydrobenzofuran-7-yl}methyl)piperidine-1-carboxylate (0.0645 g, 0.131 mmol) in methylene chloride (3 mL) was added with a 4 M solution of hydrogen chloride in 1,4-dioxane (3 mL), and the mixture was stirred at room temperature for 2 hours. The reaction mixture was concentrated, and then added with saturated aqueous sodium hydrogencarbonate, and the precipitated solid was collected by filtration. The solid was washed with water, and then dried under reduced pressure to obtain (Z)-2-[(1H-pyrazolo[3,4-b]pyridin-3-yl)methylene]-6-methoxy-7-(piperidin-4-ylmethyl)benzofuran-3(2H)-one (0.0395 g, 77%).

$^1$H NMR (300 MHz, DMSO-$d_6$) δ 1.26 (m, 2H), 1.59-1.63 (m, 2H), 1.80 (m, 1H), 2.40-2.44 (m, 2H), 2.76 (d, J=7.3 Hz, 2H), 2.94-2.99 (m, 2H), 3.97 (s, 3H), 7.03 (s, 1H), 7.05 (d, J=8.8 Hz, 1H), 7.36 (dd, J=4.4 Hz, J=8.1 Hz, 1H), 7.73 (d, J=8.8 Hz, 1H), 8.64 (d, J=4.4 Hz, 1H), 8.91 (d, J=8.1 Hz, 1H).

Example B72

(Z)-2-[(1H-Pyrazolo[3,4-b]pyridin-3-yl)methylene]-6-methoxy-7-[2-(piperidin-4-yl)ethyl]benzofuran-3(2H)-one (a) Step 1

A solution of tert-butyl 4-[2-(6-methoxy-3-oxo-2,3-dihydrobenzofuran-7-yl)ethyl]piperidine-1-carboxylate (0.120 g, 0.319 mmol) synthesized in the same manner as that of Example B57, Step 1 in methanol (5 mL) was added with 1H-pyrazolo[3,4-b]pyridine-3-carboxaldehyde (0.0469 g, 0.319 mmol) and piperidine (0.100 mL, 1.01 mmol), and the mixture was stirred at 60° C. for 2 hours. The reaction mixture was cooled to room temperature, and the precipitated solid was collected by filtration. The resulting solid was suspended in 50% ethyl acetate in hexane and thereby washed to obtain tert-butyl (Z)-4-(2-{2-[(1H-pyrazolo[3,4-b]pyridin-3-yl)methylene]-6-methoxy-3-oxo-2,3-dihydrobenzofuran-7-yl}ethyl)piperidine-1-carboxylate (0.0652 g, 41%).

$^1$H NMR (300 MHz, DMSO-$d_6$) δ 0.91-1.02 (m, 2H), 1.37 (s, 9H), 1.49 (m, 3H), 1.71-1.75 (m, 2H), 2.62 (m, 2H), 2.81 (m, 2H), 3.85-3.89 (m, 2H), 3.97 (s, 3H), 7.02 (d, J=8.8 Hz, 1H), 7.03 (s, 1H), 7.33 (dd, J=4.4 Hz, J=8.1 Hz, 1H), 7.70 (d,

J=8.8 Hz, 1H), 8.64 (dd, J=1.5 Hz, J=4.4 Hz, 1H), 8.82 (dd, J=1.5 Hz, J=8.1 Hz, 1H), 14.37 (s, 1H).

(b) Step 2

A solution of tert-butyl (Z)-4-(2-{2-[(1H-pyrazolo[3,4-b]pyridin-3-yl)methylene]-6-methoxy-3-oxo-2,3-dihydrobenzofuran-7-yl}ethyl)piperidine-1-carboxylate (0.0652 g, 0.129 mmol) in methylene chloride (5 mL) was added with a 4 M solution of hydrogen chloride in 1,4-dioxane (3 mL), and the mixture was stirred at room temperature for 2 hours. The reaction mixture was concentrated, and then added with saturated aqueous sodium hydrogencarbonate, and the precipitated solid was collected by filtration. The solid was washed with water, and then dried under reduced pressure to obtain (Z)-2-[(1H-pyrazolo[3,4-b]pyridin-3-yl)methylene]-6-methoxy-7-[2-(piperidin-4-yl)ethyl]benzofuran-3(2H)-one (0.0402 g, 77%).

$^1$H NMR (300 MHz, DMSO-$d_6$) δ 0.99-1.10 (m, 2H), 1.40 (m, 1H), 1.47 (m, 2H), 1.69-1.73 (m, 2H), 2.41-2.45 (m, 2H), 2.81 (m, 2H), 2.90-2.94 (m, 2H), 3.96 (s, 3H), 7.02 (d, J=8.8 Hz, 1H), 7.05 (s, 1H), 7.28 (dd, J=4.4 Hz, J=8.1 Hz, 1H), 7.69 (d, J=8.8 Hz, 1H), 8.61 (d, J=4.4 Hz, 1H), 8.83 (d, J=8.1 Hz, 1H).

Example B73

(Z)-2-[(1H-Indazol-3-yl)methylene]-7-[(3,5-dimethyl-1H-pyrazol-4-yl)methyl]-6-methoxybenzofuran-3(2H)-one (a) Step 1

A solution of aluminum chloride (11.9 g, 89.2 mmol) in nitrobenzene (25 mL) was cooled to 0° C., and added dropwise with chloroacetyl chloride (2.13 mL, 26.7 mmol). Then, the mixture was added dropwise with 2-methylbenzene-1,3-diol (2.21 g, 17.8 mmol), and the mixture was stirred at 50° C. for 4 hours. The reaction mixture was cooled to 0° C., and added with water (100 mL), and the mixture was extracted three times with ethyl acetate. The organic layers were combined, and extracted three times with 2 N aqueous sodium hydroxide, and the aqueous layer was adjusted to pH 7 with 3 N hydrochloric acid. The precipitated solid was collected by filtration, washed with water, and then dried under reduced pressure to obtain a solid (2.35 g).

(b) Step 2

The above solid was dissolved in DMF (22 mL), the solution was added with potassium carbonate (1.52 g, 0.0110 mmol) and methyl iodide (0.822 mL, 0.0132 mmol), and the mixture was stirred at room temperature for 12 hours. The reaction mixture was poured into water (300 mL), and the precipitated solid was collected by filtration. The resulting solid was dried under reduced pressure to obtain 6-methoxy-7-methylbenzofuran-3(2H)-one (1.41 g, 44%).

$^1$H NMR (300 MHz, DMSO-$d_6$) δ 2.07 (s, 3H), 3.32 (s, 3H), 4.76 (s, 2H), 6.86 (d, J=8.8 Hz, 1H), 7.49 (d, J=8.8 Hz, 1H).

(c) Step 3

A solution of 6-methoxy-7-methylbenzofuran-3(2H)-one (0.670 g, 3.76 mmol) in carbon tetrachloride (38 mL) was added with N-bromosuccinimide (0.737 g, 4.14 mmol) and benzoyl peroxide (0.0456 g, 0.188 mmol), and the mixture was refluxed for 4 hours by heating. The reaction mixture was cooled to room temperature, and then filtered, and the filtrate was concentrated. The resulting residue was purified by silica gel column chromatography (chloroform/methanol) to obtain 7-(bromomethyl)-6-methoxybenzofuran-3(2H)-one (0.411 g, 42%).

$^1$H NMR (300 MHz, CDCl$_3$) δ 4.01 (s, 3H), 4.60 (s, 2H), 4.70 (s, 2H), 6.69 (d, J=8.8 Hz, 1H), 7.64 (d, J=8.8 Hz, 1H).

(d) Step 4

A solution of acetylacetone (0.100 g, 1.00 mmol) in THF (2.5 mL) was added with a 1 M solution of tetrabutylammonium fluoride in THF (1.00 mL, 1.00 mmol) and water (1 mL), and the mixture was stirred at room temperature for 10 minutes. The reaction mixture was added with a solution of 7-(bromomethyl)-6-methoxybenzofuran-3(2H)-one (0.257 g, 1.00 mmol) in THF (2 mL), and the mixture was stirred at room temperature for 16 hours. The reaction mixture was added with a 1 M solution of tetrabutylammonium fluoride in THF (1.00 mL, 1.00 mmol), and the mixture was stirred at room temperature for additional 5 hours. The reaction mixture was concentrated, and the resulting residue was purified by silica gel column chromatography (hexane/ethyl acetate) to obtain 3[(6-methoxy-3-oxo-2,3-dihydrobenzofuran-7-yl)methyl]pentane-2,4-dione (0.0533 g, 19%).

$^1$H NMR (300 MHz, CDCl$_3$) δ 2.19 (s, 6H), 3.20 (d, J=7.3 Hz, 2H), 3.92 (s, 3H), 4.02 (t, J=7.3 Hz, 1H), 4.62 (s, 2H), 6.67 (d, J=8.8 Hz, 1H), 7.57 (d, J=8.8 Hz, 1H).

(e) Step 5

A solution of hydrazine monohydrate (0.0102 g, 0.203 mmol) in water (1.25 mL) was cooled to 0° C., and added with a solution of 3-[(6-methoxy-3-oxo-2,3-dihydrobenzofuran-7-yl)methyl]pentane-2,4-dione (0.0533 g, 0.193 mmol) in acetic acid (2 mL), and the mixture was stirred for 18 hours with warming it to room temperature. The reaction mixture was added with saturated aqueous sodium hydrogencarbonate, thereby made basic, and extracted three times with ethyl acetate. The organic layer was washed with saturated brine, and dried over anhydrous magnesium sulfate. The solvent was evaporated, and the residue was purified by silica gel column chromatography (chloroform/methanol) to obtain 7-[(3,5-dimethyl-1H-pyrazol-4-yl)methyl]-6-methoxybenzofuran-3(2H)-one (0.0427 g, 81%).

$^1$H NMR (300 MHz, CDCl$_3$) δ 2.20 (s, 6H), 3.69 (s, 2H), 3.90 (s, 3H), 4.63 (s, 2H), 6.66 (d, J=8.8 Hz, 1H), 7.54 (d, J=8.8 Hz, 1H).

(f) Step 6

A solution of 7-[(3,5-dimethyl-1H-pyrazol-4-yl)methyl]-6-methoxybenzofuran-3(2H)-one (0.0427 g, 0.157 mmol) in methanol (0.6 mL) was added with 1H-indazole-3-carboxaldehyde (0.0229 g, 0.157 mmol) and piperidine (0.0107 g, 0.126 mmol), and the mixture was stirred at 60° C. for 2 hours. The reaction mixture was cooled to room temperature, and the precipitated solid was collected by filtration to obtain (Z)-2-[(1H-indazol-3-yl)methylene]-7-[(3,5-dimethyl-1H-pyrazol-4-yl)methyl]-6-methoxybenzofuran-3(2H)-one (0.0388 g, 61%).

$^1$H NMR (300 MHz, DMSO-$d_6$) δ 2.00 (br s, 3H), 2.06 (br s, 3H), 3.81 (s, 2H), 3.93 (s, 3H), 6.99 (d, J=8.8 Hz, 1H), 7.14 (s, 1H), 7.23 (m, 1H), 7.44 (m, 1H), 7.63 (d, J=8.8 Hz, 1H), 7.73 (d, J=8.8 Hz, 1H), 8.39 (d, J=8.1 Hz, 1H), 11.87 (br s, 1H), 13.85 (br s, 1H).

Test Example 1

Measurement of Pim-1 Kinase Inhibitory Activity

By incubating 1.5 μM of a fluorescent substrate peptide (FAM-RSRHSSYPAGT-NH2), 30 μM of ATP, 0.033 ng/μl of pim-1 kinase, and 0.1 μM of each compound at room temperature for 2 hours, the pim-1 kinase inhibitory activity of the compound was measured. The result of the reaction was determined by quantifying the substrate and the phosphorylated reaction product separated by capillary electrophoresis based on difference in charges of the substances (EZ Reader II, Caliper Life Sciences, was used).

The results are shown in Tables 1 and 2 mentioned below.

TABLE 1

| Compound No. | Pim-1 kinase inhibitory activity (%) |
|---|---|
| A1 | 51 |
| A3 | 47 |
| A4 | 19 |
| A6 | 15 |
| A7 | 81 |
| A8 | 20 |
| A11 | 87 |
| A12 | 81 |
| A13 | 71 |
| A14 | 87 |
| A17 | 82 |
| A18 | 95 |
| A19 | 62 |
| A20 | 62 |
| A21 | 94 |
| A22 | 94 |
| A23 | 56 |
| A24 | 60 |
| A25 | 83 |
| A27 | 29 |
| A28 | 10 |
| A31 | 47 |
| A33 | 94 |
| A34 | 98 |
| A35 | 96 |
| A36 | 99 |
| A37 | 99 |
| A38 | 99 |
| A39 | 99 |
| A40 | 97 |
| A41 | 40 |
| A42 | 96 |
| A43 | 56 |
| A44 | 27 |
| A45 | 83 |
| A46 | 99 |
| A47 | 98 |
| A48 | 97 |
| A49 | 16 |
| A50 | 94 |
| A51 | 94 |
| A52 | 101 |
| A63 | 98 |
| A54 | 72 |
| A55 | 46 |
| A56 | 80 |
| A57 | 28 |
| A58 | 92 |
| A59 | 92 |
| A60 | 84 |
| A61 | 66 |

TABLE 2

| Compound No. | Pim-1 kinase inhibitory activity (%) |
|---|---|
| B1 | 88 |
| B2 | 61 |
| B3 | 79 |
| B4 | 41 |
| B5 | 22 |
| B6 | 49 |
| B7 | 86 |
| B8 | 81 |
| B9 | 93 |
| B10 | 94 |
| B11 | 87 |
| B12 | 90 |
| B13 | 88 |
| B14 | 80 |
| B15 | 90 |
| B16 | 93 |
| B17 | 100 |
| B18 | 95 |
| B19 | 100 |
| B20 | 95 |
| B21 | 97 |
| B22 | 96 |
| B23 | 93 |
| B24 | 88 |
| B25 | 97 |
| B26 | 78 |
| B27 | 91 |
| B28 | 92 |
| B29 | 82 |
| B30 | 89 |
| B31 | 95 |
| B32 | 63 |
| B33 | 39 |
| B34 | 94 |
| B35 | 97 |
| B36 | 31 |
| B37 | 85 |
| B38 | 87 |
| B39 | 95 |
| B40 | 14 |
| B45 | 79 |
| B46 | 86 |
| B47 | 84 |
| B48 | 75 |
| B49 | 63 |
| B50 | 82 |
| B51 | 86 |
| B52 | 50 |
| B53 | 36 |
| B54 | 98 |
| B55 | 84 |
| B56 | 95 |
| B57 | 89 |
| B58 | 90 |
| B59 | 96 |
| B60 | 95 |
| B61 | 70 |
| B62 | 71 |
| B63 | 95 |
| B64 | 81 |
| B65 | 73 |
| B66 | 89 |
| B67 | 46 |
| B68 | 93 |
| B69 | 95 |
| B70 | 94 |
| B71 | 95 |
| B72 | 97 |
| B73 | 49 |

Test Example 2

Measurement of Cell Proliferation-Suppressing Activity (Chromogenic Method)

Human acute myeloid leukemia MV4-11 cells ($10^4$ cells) were inoculated on a 96-well microtiter plate, each compound was added at a final concentration of 1 µM 24 hours afterward, and MTT assay was performed three days after the addition of the compound to measure the cell proliferation-suppressing activity. The results are shown in Tables 3 and 4 mentioned below.

TABLE 3

| Compound No. | Cell proliferation-suppressing activity (%) |
| --- | --- |
| A3 | 41 |
| A7 | 22 |
| A11 | 82 |
| A17 | 73 |
| A22 | 70 |

TABLE 4

| Compound No. | Cell proliferation-suppressing activity (%) |
| --- | --- |
| B2 | 45 |
| B3 | 79 |
| B7 | 88 |
| B17 | 93 |
| B18 | 87 |
| B19 | 94 |
| B21 | 94 |
| B22 | 90 |
| B23 | 90 |
| B24 | 89 |
| B25 | 91 |
| B26 | 86 |
| B27 | 89 |
| B28 | 91 |
| B29 | 90 |
| B30 | 78 |
| B31 | 84 |
| B35 | 95 |
| B37 | 76 |
| B38 | 95 |
| B39 | 92 |

Test Example 3

Measurement of Cell Proliferation-Suppressing Activity (Fluorescence Method)

Each compound was added to a 96-well microtiter plate at a final concentration of 1 µM, then human acute myeloid leukemia MV4.11 cells ($10^4$ cells) were inoculated, and the Alamar Blue assay was performed two days after the inoculation (measurement of fluorescence: Ex. 535 nm, Em. 590 nm) to measure cell proliferation-suppressing activity. The results are shown in Table 5 mentioned below.

TABLE 5

| Compound No. | Cell proliferation-suppressing activity (%) |
| --- | --- |
| A12 | 87 |
| A18 | 71 |
| A25 | 20 |
| A33 | 32 |
| A34 | 58 |
| A35 | 48 |
| A36 | 39 |
| A37 | 55 |
| A38 | 43 |
| A39 | 51 |
| A44 | 46 |
| A45 | 15 |

Test Example 4

Kinase Selectivity

Figure 2:
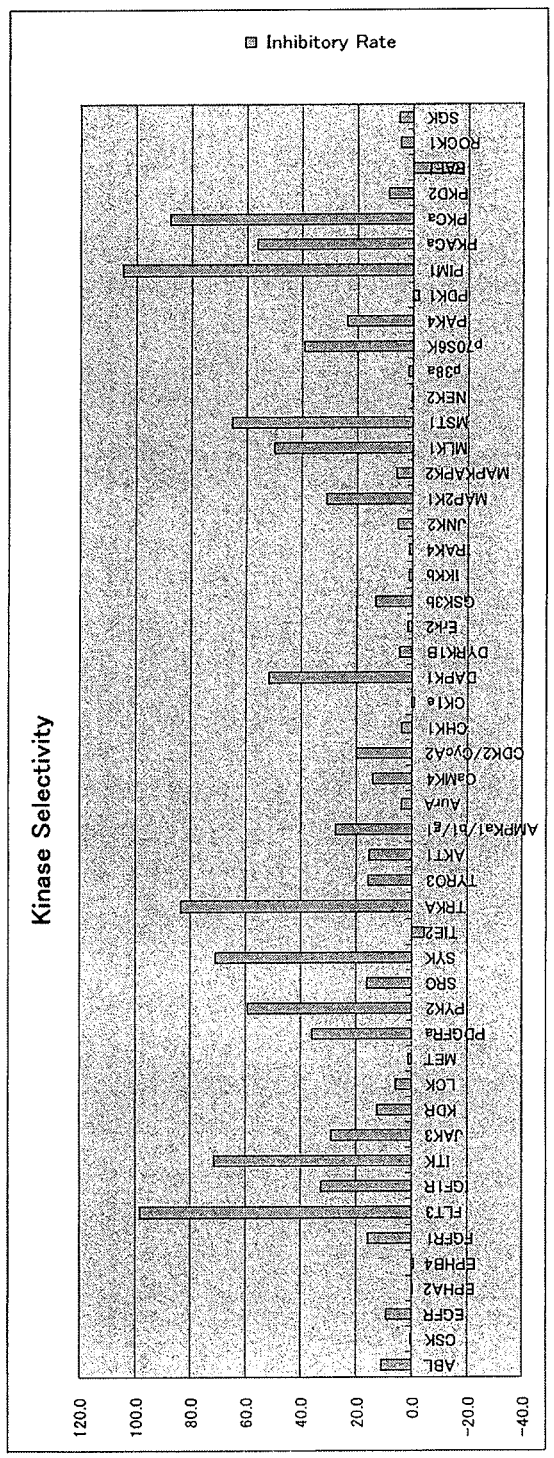
FIG. 2 This figure depicts results of study on inhibitory activity of Compound B17 (concentration of compound: 2 μM) against 50 kinds of kinases including pim-1 kinase.

Kinase inhibitory activities of Compound A42 and Compound B17 (compound concentration: 2 µM) were examined for 50 kinds of kinases including the pim-1 kinase. The results are shown in FIGS. 1 and 2.

Test Example 5

Measurement of Cell Proliferation-Suppressing Activity (Chromogenic Method)

Human acute myeloid leukemia MV4-11 cells ($2 \times 10^4$ cells) are inoculated on a 96-well microtiter plate. Each compound is added at a final concentration of 1 µM on the next day, and the cells are cultured for additional 48 hours. Absorbance is measured at 450 nm by using Cell Counting Kit-8 (Nacalai Tesque) to calculate the cell proliferation-suppressing activity. The results are shown in Tables 6 and 7 mentioned below.

TABLE 6

| Compound No. | Cell proliferation-suppressing activity (%) |
| --- | --- |
| A55 | 79 |
| A56 | 43 |
| A57 | 37 |
| A58 | 72 |
| A59 | 95 |
| A60 | 91 |
| A61 | 58 |

TABLE 7

| Compound No. | Cell proliferation-suppressing activity (%) |
| --- | --- |
| B45 | 28 |
| B46 | 97 |
| B47 | 99 |
| B48 | 96 |
| B49 | 93 |
| B50 | 96 |
| B51 | 94 |
| B52 | 98 |
| B53 | 98 |
| B54 | 97 |

TABLE 7-continued

| Compound No. | Cell proliferation-suppressing activity (%) |
|---|---|
| B55 | 99 |
| B56 | 99 |
| B57 | 99 |
| B58 | 94 |
| B59 | 55 |
| B60 | 98 |
| B61 | 97 |
| B62 | 93 |
| B63 | 95 |
| B64 | 93 |
| B65 | 97 |
| B66 | 88 |
| B67 | 96 |
| B68 | 52 |
| B69 | 100 |
| B70 | 77 |
| B71 | 100 |
| B72 | 93 |
| B73 | 81 |

What is claimed is:

1. A compound represented by formula (IB):

[Formula 3]

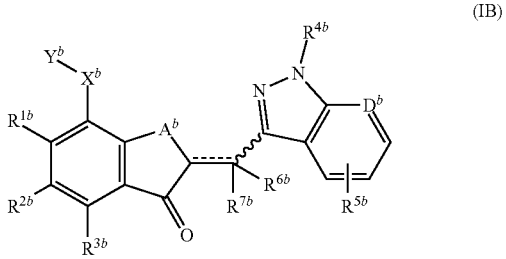

(IB)

wherein, $R^{1b}$ represents a hydrogen atom, a hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group;

$R^{2b}$ represents a hydrogen atom, a halogen atom, a $C_{1-6}$ alkyl group, a $C_{1-6}$ alkoxy group, an aryl group, an amino group, a hydroxyl group, or a heterocyclic group, wherein $R^{1b}$ and $R^{2b}$ may bind together to form a $C_{1-6}$ alkylenedioxy group;

$R^{3b}$ represents a hydrogen atom, a halogen atom, a $C_{1-6}$ alkyl group, a $C_{1-6}$ alkoxy group, an aryl group, an amino group, a hydroxyl group, or a heterocyclic group;

$R^{4b}$ represents a hydrogen atom, a $C_{1-6}$ alkyl group, or sulfonyl group;

$R^{5b}$ represents a hydrogen atom, or one to four substituents substituting on the benzene ring or the pyridine ring selected from the group consisting of a halogen atom, a $C_{1-6}$ alkyl group, a halogen-substituted $C_{1-6}$ alkyl group, a hydroxy-substituted $C_{1-6}$ alkyl group, a hydroxyl group, a $C_{1-6}$ alkoxy group, a halogen-substituted $C_{1-6}$ alkoxy group, an amino group, an aryl group, a sulfonyl group, and a heterocyclic group;

---- represents a single bond or a double bond;

$R^{6b}$ and $R^{7b}$ independently represent a hydrogen atom, a $C_{1-6}$ alkyl group, or a halogen-substituted $C_{1-6}$ alkyl group, wherein when ---- represents a double bond, $R^{7b}$ does not exist;

-$A^b$- represents —O—, —S—, or —$CH_2$—;

-$D^b$= represents —$C(R^{5b})$= or —N=;

—$X^b$— represents a single bond, —O—, —CO—, or a $C_{1-6}$ alkylene group, a $C_{2-6}$ alkenylene group, or a $C_{2-6}$ alkynylene group, wherein the alkylene group, alkenylene group, and alkynylene group may be substituted with a hydroxyl group; and $Y^b$ represents a heterocyclic group or amino group, both of which may have one or more substituents, or a salt thereof.

2. The compound according to claim 1, wherein $R^{1b}$ is a hydrogen atom, a hydroxyl group, a $C_{1-6}$ alkoxy group, an aryl-substituted $C_{1-6}$ alkoxy group, an aryloxy-substituted $C_{1-6}$ alkoxy group, a hydroxy-substituted $C_{1-6}$ alkoxy group, or a $C_{1-6}$ alkoxy-substituted $C_{1-6}$ alkoxy group;

$R^{2b}$ is a hydrogen atom, a halogen atom, or a $C_{1-6}$ alkoxy group, wherein $R^1$ and $R^2$ may bind together to form a $C_{1-6}$ alkylenedioxy group;

$R^{3b}$ is a hydrogen atom, a halogen atom, or a hydroxyl group;

$R^{4b}$ is a hydrogen atom, a $C_{1-6}$ alkyl group, or a sulfonyl group;

$R^{5b}$ is a hydrogen atom, or one to three substituents substituting on the benzene ring or the pyridine ring selected from the group consisting of a halogen atom, a $C_{1-6}$ alkyl group, a halogen-substituted $C_{1-6}$ alkyl group, a hydroxy-substituted $C_{1-6}$ alkyl group, a hydroxyl group, a $C_{1-6}$ alkoxy group, and a halogen-substituted $C_{1-6}$ alkoxy group;

---- is a single bond or a double bond;

$R^{6b}$ and $R^{7b}$ are hydrogen atoms, wherein when ---- represents a double bond, $R^{7b}$ does not exist;

-$A^b$- is —O—, —S—, or —$CH_2$—;

-$D^b$= is —$C(R^{5b})$= or —N=;

—$X^b$— is —O—, —CO—, or a methylene group may be substituted with a $C_{1-6}$ alkyl group or a hydroxyl group; and $Y^b$ is a 5- to 7-membered saturated heterocyclic group containing one to three ring-constituting heteroatoms or an amino group, both of which may have one or more substituents selected from the group consisting of a $C_{1-6}$ alkyl group, a hydroxyl group, an amino group, an alkylsulfonyl group, and an oxo group.

3. The compound or a salt thereof according to claim 2, wherein $Y^b$ is a 1-piperazinyl group, a morpholino group, a 4-piperidinyl group, a 4-tetrahydropyranyl group, a 1-homopiperazinyl group, or 1-pyrrolidinyl group.

4. A pharmaceutical composition comprising the compound according to claim 1 or a physiologically acceptable salt thereof, and at least one pharmaceutically acceptable pharmaceutical additive.

5. The pharmaceutical composition of claim 4, which is for use as a pim-1 kinase inhibitor.

6. A method of inhibiting pim-1 kinase comprising administering an agent comprising the compound according to claim 1.

* * * * *